(12) United States Patent
Orlinger et al.

(10) Patent No.: US 11,407,790 B2
(45) Date of Patent: Aug. 9, 2022

(54) HPV VACCINES

(71) Applicant: Hookipa Biotech GmbH, Vienna (AT)

(72) Inventors: Klaus Orlinger, Vienna (AT); Thomas Monath, Harvard, MA (US); Anders Lilja, Vienna (AT); Sarah Schmidt, Vienna (AT); Ursula Berka, Baden (AT); Michael Schwendinger, Neusiedl am See (AT); Elizabeth Watson, Vienna (AT); Bettina Kiefmann, Vienna (AT); Julia Hinteramskogler, St. Poelten (AT); Gerhard Fuhrmann, Vienna (AT); Andreas Aspöck, Vienna (AT); Katherine Cohen, Vienna (AT)

(73) Assignee: HOOKIPA BIOTECH GMBH, Vienna (AT)

( * ) Notice: Subject to any disclaimer, the term of this patent is extended or adjusted under 35 U.S.C. 154(b) by 0 days.

(21) Appl. No.: 16/863,456

(22) Filed: Apr. 30, 2020

(65) Prior Publication Data

US 2021/0024584 A1 Jan. 28, 2021

Related U.S. Application Data

(62) Division of application No. 15/580,964, filed as application No. PCT/EP2016/063182 on Jun. 9, 2016, now Pat. No. 10,669,315.

(60) Provisional application No. 62/331,158, filed on May 3, 2016, provisional application No. 62/254,410, filed on Nov. 12, 2015, provisional application No. 62/173,805, filed on Jun. 10, 2015.

(51) Int. Cl.
| | |
|---|---|
| *C12N 15/86* | (2006.01) |
| *A61K 39/12* | (2006.01) |
| *C07K 14/005* | (2006.01) |
| *C07K 14/025* | (2006.01) |
| *A61P 35/00* | (2006.01) |
| *A61K 39/00* | (2006.01) |

(52) U.S. Cl.
CPC ............ *C07K 14/005* (2013.01); *A61K 39/12* (2013.01); *A61P 35/00* (2018.01); *C07K 14/025* (2013.01); *A61K 2039/5256* (2013.01); *C12N 2710/20034* (2013.01); *C12N 2760/10043* (2013.01); *C12N 2760/10051* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,057,540 A | 10/1991 | Kensil et al. | |
| 8,592,205 B2 | 11/2013 | Pinschewer et al. | |
| 9,309,289 B2 | 4/2016 | Pinschewer et al. | |
| 9,809,801 B2 | 11/2017 | Belnoue et al. | |
| 9,944,952 B2 | 4/2018 | Pinschewer et al. | |
| 10,111,945 B2 | 10/2018 | Orlinger et al. | |
| 10,655,145 B2 | 5/2020 | Pinschewer et al. | |
| 10,669,315 B2 | 6/2020 | Orlinger et al. | |
| 10,722,564 B2 | 7/2020 | Pinschewer et al. | |
| 11,214,598 B2 | 1/2022 | Monath et al. | |
| 11,266,727 B2 | 3/2022 | Schmidt et al. | |
| 2007/0275003 A1* | 11/2007 | Cassetti ............... | A61K 38/162 424/186.1 |
| 2010/0297172 A1 | 11/2010 | Pinschewer et al. | |
| 2014/0050760 A1 | 2/2014 | Pinschewer et al. | |
| 2016/0024476 A1 | 1/2016 | Belnoue et al. | |
| 2016/0194663 A1 | 7/2016 | Pinschewer et al. | |
| 2016/0206724 A1 | 7/2016 | De la Torre et al. | |
| 2016/0296619 A1 | 10/2016 | Orlinger et al. | |
| 2017/0319673 A1* | 11/2017 | Pinschewer ............... | C12N 7/00 |
| 2018/0179257 A1 | 6/2018 | Orlinger et al. | |
| 2018/0319845 A1 | 11/2018 | Monath et al. | |
| 2018/0344830 A1 | 12/2018 | Schmidt et al. | |
| 2019/0062784 A1 | 2/2019 | Pinschewer et al. | |
| 2019/0135875 A1 | 5/2019 | Bonilla et al. | |
| 2019/0247493 A1 | 8/2019 | Orlinger et al. | |
| 2020/0113995 A1 | 4/2020 | Orlinger et al. | |

(Continued)

FOREIGN PATENT DOCUMENTS

| | | |
|---|---|---|
| CN | 102002105 A * | 4/2011 |
| WO | WO 2007/109812 A2 | 9/2007 |

(Continued)

OTHER PUBLICATIONS

Albarino et al., "Efficient rescue of recombinant Lassa virus reveals the influence of S segment noncoding regions on virus replication and virulence," *J. Virol.*, 85(8):4020-4024 (2011).

Altman et al., "Phenotypic analysis of antigen-specific T lymphocytes" *Science*, 274:94-96 (1996).

Ault, "Epidemiology and Natural History of Human Papillomavirus Infections in the Female Genital Tract," *Infectious Diseases Obstetrics Gynecology*, 2006:1-5 (2006).

Bonilla et al., "Interpretation of lymphocyte proliferation tests," *Ann. Allergy Asthma Immunol.*, 101:101-104 (2008).

(Continued)

*Primary Examiner* — Nianxiang Zou
(74) *Attorney, Agent, or Firm* — Jones Day

(57) ABSTRACT

Provided herein are genetically modified arenaviruses suitable as vaccines against neoplastic diseases or cancer. The invention also relates to pharmaceutical compositions and methods for the prevention or treatment of certain infections causing neoplastic diseases or cancer, such as infections with oncogenic viruses. Specifically, provided herein are pharmaceutical compositions, vaccines, and methods of preventing or treating diseases and conditions caused by and associated with infections with Human Papillomavirus (HPV), such as cervical cancer, anogenital cancer, head and neck cancer and skin cancers. Also provided herein are immunotherapies for the treatment of a neoplastic disease, such as a neoplastic disease caused by infection with oncogenic viruses.

20 Claims, 29 Drawing Sheets

Figure 1A:
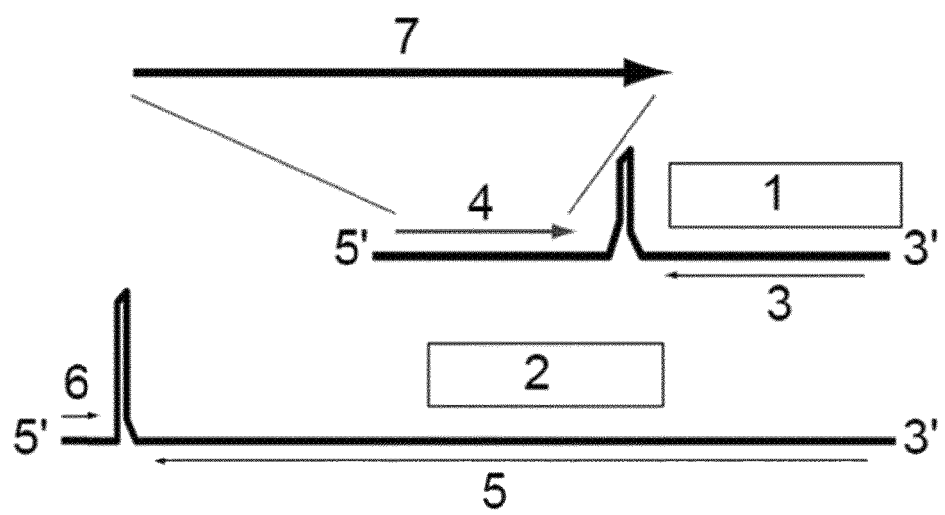

Specification includes a Sequence Listing.

(56) References Cited

U.S. PATENT DOCUMENTS

| | | |
|---|---|---|
| 2020/0206334 A1 | 7/2020 | Schmidt et al. |
| 2021/0071198 A1 | 3/2021 | Pinschewer et al. |
| 2021/0145950 A1 | 5/2021 | Pinschewer et al. |
| 2022/0073568 A1 | 3/2022 | Monath et al. |

FOREIGN PATENT DOCUMENTS

| | | |
|---|---|---|
| WO | WO 2007/109813 A1 | 9/2007 |
| WO | WO 2009/083210 A1 | 7/2009 |
| WO | WO 2012/162428 A1 | 11/2012 |
| WO | WO 2013/112549 A1 | 8/2013 |
| WO | WO 2014/140301 A1 | 9/2014 |
| WO | WO 2014/155076 A1 | 10/2014 |
| WO | WO 2015/082570 A1 | 6/2015 |
| WO | WO 2015/183895 A1 | 12/2015 |
| WO | WO 2016/048949 A1 | 3/2016 |
| WO | WO 2016/071683 A2 | 5/2016 |
| WO | WO 2016/075250 A1 | 5/2016 |
| WO | WO 2016/166285 A1 | 10/2016 |
| WO | WO 2016/198531 A2 | 12/2016 |
| WO | WO 2017/068190 A1 | 4/2017 |
| WO | WO 2017/076988 A1 | 5/2017 |
| WO | WO 2017/080920 A1 | 5/2017 |
| WO | WO 2017/190074 A1 | 11/2017 |
| WO | WO 2017/198726 A1 | 11/2017 |
| WO | WO 2018/083220 A2 | 5/2018 |
| WO | WO 2018/185307 A1 | 10/2018 |
| WO | WO 2021/089853 | 5/2021 |
| WO | WO 2021/239471 | 12/2021 |

OTHER PUBLICATIONS

Bonilla et al., "Practice parameter for the diagnosis and management of primary immunodeficiency," *Ann. Allergy Asthma Immunol.*, 94(5 Suppl 1):S1-63 (2005).

Brandsma et al., "Reversal of papilloma growth in rabbits therapeutically vaccinated against E6 with naked DNA and/or vesicular stomatitis virus vectors," *Vaccine*, 28(52):8345-8351 (2009).

Bzhalava et al., "A systematic review of the prevalence of mucosal and cutaneous human papillomavirus types," *Virology*, 445(1-2):224-231 (2013).

Caruso et al., "Flow cytometric analysis of activation markers on stimulated T cells and their correlation with cell proliferation" *Cytometry*, 27:71-76 (1997).

Cassetti et al., "Antitumor efficacy of Venezuelan equine encephalitis virus replicon particles encoding mutated HPV16 E6 and E7 genes," *Vaccine*, 22:520-527 (2004).

Cheng et al., "Arenavirus Genome Rearrangement for the Development of Live Attenuated Vaccines," J. Virol., 89(14):7373-7384 (2015).

Czerkinsky et al., "A solid-phase enzyme-linked immunospot (ELISPOT) assay for enumeration of specific antibody-secreting cells," *J. Immunol. Methods*, 65:109-121 (1983).

Dhanwani et al., "A Novel Live Pichinde Virus-Based Vaccine Vector Induces Enhanced Humoral and Cellular Immunity after a Booster Dose," J. Virol., 90(5):2551-2560 (2015).

D'Souza et al., "Case-control study of human papillomavirus and oropharyngeal cancer," *N. Engl. J. Med.*, 356(19):1944-1956 (2007).

Emonet et al., "Arenavirus reverse genetics: new approaches for the investigation of arenavirus biology and development of antiviral strategies," Virology, 411(2):416-425 (2011).

Emonet et al., "Generation of recombinant lymphocytic choriomeningitis viruses with trisegmented genomes stably expressing two additional genes of interest," *Proc. Natl. Acad. Sci. USA*, 106(9):3473-3478 (2009).

Emonet et al., "Rescue from cloned cDNAs and in vivo characterization of recombinant pathogenic Romero and live-attenuated Candid # 1 strains of Junin virus, the causative agent of Argentine hemorrhagic fever disease," *J Virol.*, 85(4):1473-1483 (2011).

Fang et al., "An antibody delivery system for regulated expression of therapeutic levels of monoclonal antibodies in vivo," *Mol. Ther.*, 15(6):1153-1159 (2007).

Flatz et al., "Gene-based vaccination with a mismatched envelope protects against simian immunodeficiency virus infection in non-human primates," *J. Virol.*, 86(15):7760-7770 (2012).

Flatz et. al., "Development of replication-defective lymphocytic choriomeningitis virus vectors for the induction of potent CD8+ T cell immunity," *Nat. Med.*, 16(3):339-345 (2010).

Flatz, et al., "Recovery of an arenavirus entirely from RNA polymerase I/II-driven cDNA," *Proc. Natl. Acad. Sci. USA*, 103:4663-4668 (2006).

Flick et al., Transient bicistronic vRNA segments for indirect selection of recombinant influenza viruses, *Virology*, 262(1):93-103 (1999).

Ganguly et al., "Human papillomavirus E6 and E7 oncoproteins as risk factors for tumorigenesis," *J. Biosci.*, 34(1):113-123 (2009).

Garcia-Sastre et al., "Use of a mammalian internal ribosomal entry site element for expression of a foreign protein by a transfectant influenza virus," *J. Virol*, 68(10):6254-6261 (1994).

Ghanekar et al., "Gamma interferon expression in CD8(+) T cells is a marker for circulating cytotoxic T lymphocytes that recognize an HLA A2-restricted epitope of human cytomegalovirus phosphoprotein pp65," *Clin. Diagn. Lab. Immunol.*, 8:628-631 (2001).

Goodwin et al., "Induced senescence in HeLa cervical carcinoma cells containing elevated telomerase activity and extended telomeres," *Cell Growth Differ.*, 12:525-534 (2001).

Goodwin et al., "Repression of human papillomavirus oncogenes in HeLa cervical carcinoma cells causes the orderly reactivation of dormant tumor suppressor pathways," *Proc. Natl. Acad. Sci. USA*, 97:12513-12518 (2000).

Hicks et al., "Age-related changes in mitogen-induced lymphocyte function from birth to old age," *Am. J. Clin. Pathol.*, 80:159-163 (1983).

Hung et al., "Therapeutic human papillomavirus vaccines: current clinical trials and future directions," *Expert Opin. Biol. Ther.*, 8(4):421-439 (2008).

Hutchings et al., "The detection and enumeration of cytokine-secreting cells in mice and man and the clinical application of these assays" *J. Immunol. Methods*, 120:1-8 (1989).

Iwasaki et al., "General Molecular Strategy for Development of Arenavirus Live-Attenuated Vaccines," J. Virol., 89(23):12166-12177 (2015).

Kim et al., "Clearance of persistent HPV infection and cervical lesion by therapeutic DNA vaccine in CIN3 patients," *Nat. Commun.*, 5:5317 (2014).

Liao et al., "Single-Dose, Therapeutic Vaccination of Mice with Vesicular Stomatitis Virus Expressing Human Papillomavirus Type 16 E7 Protein," *Cin. Vaccine Immunol.*, 15(5):817-824 (2008).

Lilja, "Development of novel replication-defective lymphocytic choriomeningitis virus vectors expressing HPV16 antigens for therapeutic vaccination and cancer immunotherapy," *10th Vaccine Congress*, Amsterdam, the Netherlands, pp. 1-16, Sep. 4-7, 2016.

Lilja, "Replication-defective lymphocytic choriomeningitis virus vectors expressing HPV16 antigens for therapeutic vaccination and cancer immunotherapy," *2016 ASV Annual Congress*, Boston, MA, pp. 1-16, Oct. 2-4, 2016.

Lin et al., "Treatment of established tumors with a novel vaccine that enhances major histocompatibility class II presentation of tumor antigen," *Cancer Res.*, 56(1):21-26 (1996).

Machado et al., "Recombinant influenza A viruses harboring optimized dicistronic NA segment with an extended native 5' terminal sequence: induction of heterospecific B and T cell responses in mice," *Virology*, 313(1):235-249 (2003).

Murali-Krishna et al., "Counting antigen-specific CD8 T cells: a reevaluation of bystander activation during viral infection," *Immunity*, 8:177-187 (1998).

Nomura et al., "Optimization of whole blood antigen-specific cytokine assays for CD4(+) T cells," Cytometry; 40:60-68 (2000).

Ortiz-Riano et al., "Arenavirus reverse genetics for vaccine development," *J. Gen. Virol.*, 94:1175-1188 (2013).

Parkin et al., "Global cancer statistics, 2002," *CA Cancer J. Clin.*, 55:74-108 (2005).

Parkin, "The global health burden of infection-associated cancers in the year 2002," *Int. J. Cancer*, 118(12):3030-3044 (2006).

(56) References Cited

OTHER PUBLICATIONS

Peng et al., "Control of HPV-associated tumors by innovative therapeutic HPV DNA vaccine in the absence of CD4+ T cells," *Cell Biosci.*, 4(1):11 (2014).
Percy et al., "Expression of a foreign protein by influenza A virus," *J. Virol.*, 68(7):4486-4492 (1994).
Perez et al., "Characterization of the genomic promoter of the prototypic arenavirus lymphocytic choriomeningitis virus," *J. Virol.*, 77(2):1184-1194 (2003).
Perfetto et al., "Seventeen-colour flow cytometry: unravelling the immune system," *Nat. Rev. Immun.*, 4(8):648-655 (2004).
Popkin et al., "Expanded potential for recombinant trisegmented lymphocytic choriomeningitis viruses: protein production, antibody production, and in vivo assessment of biological function of genes of interest" *J. Virol.*, 85(15):7928-7932 (2011).
Remy-Ziller et al., "Immunological characterization of a modified vaccinia virus Ankara vector expressing the human papillomavirus 16 E1 protein," *Clin. Vaccine Immunol.*, 21(2):147-155 (2014).
Roden et al., "How will HPV vaccines affect cervical cancer?," *Nat. Rev. Cancer*, 6:753-763 (2006).
Sanchez et al., "Rescue of the prototypic Arenavirus LCMV entirely from plasmid," *Virology*, 350:370-380 (2006).
Schiffman et al., "Epidemiologic evidence showing that human papillomavirus infection causes most cervical intraepithelial neoplasia," *J. Natl. Cancer Inst.*, 85:958-964 (1993).
Schiffman et al., "Human papillomavirus and cervical cancer," *Lancet*, 370:890-907 (2007).
Schmidt et al., "Development of Novel Replication-Defective LCMV Vectors Expressing HPV16 Antigens for Immunotherapy," poster, May 10, 2016.
Stern et al., "Therapy of Human Papillomavirus-Related Disease," *Vaccine*, 30:F71-F82 (2012).
Stoute et al., "A preliminary evaluation of a recombinant circumsporozoite protein vaccine against Plasmodium falciparum malaria. RTS,S Malaria Vaccine Evaluation Group" *N. Engl. J. Med.*, 336:86-91 (1997).
Suni et al., "Detection of antigen-specific T cell cytokine expression in whole blood by flow cytometry," *J. Immunol. Methods*, 212:89-98 (1998).
Walboomers et al., "Human papillomavirus is a necessary cause of invasive cervical cancer worldwide," *J. Pathol.*, 189:12-19 (1999).
Zur Hausen et al., "Papillomaviruses and cancer: from basic studies to clinical application," *Nature Rev. Cancer*, 2:342-350 (2002).
International Search Report and Written Opinion dated Nov. 29, 2016 for PCT/EP2016/063182 (16 pages).
Bonilla et al., 2021, "Heterologous arenavirus vector prime-boost overrules self-tolerance for efficient tumor-specific CD8 T cell attack," Cell Reports Medicine, 2(3), 100209. doi: 10.1016/j.xcrm.2021.100209 (34 pages).
Ho et al., 2021, "First report of the safety/tolerability and preliminary antitumor activity of HB-201 and HB-202, an arenavirus-based cancer immunotherapy, in patients with HPV16+ cancers," 2021 ASCO Annual Meeting (15 pages).

* cited by examiner i  wt LCMV ii  r3LCMV-GFP^nat iii  r3LCMV-GFP^art

FIG. 1B

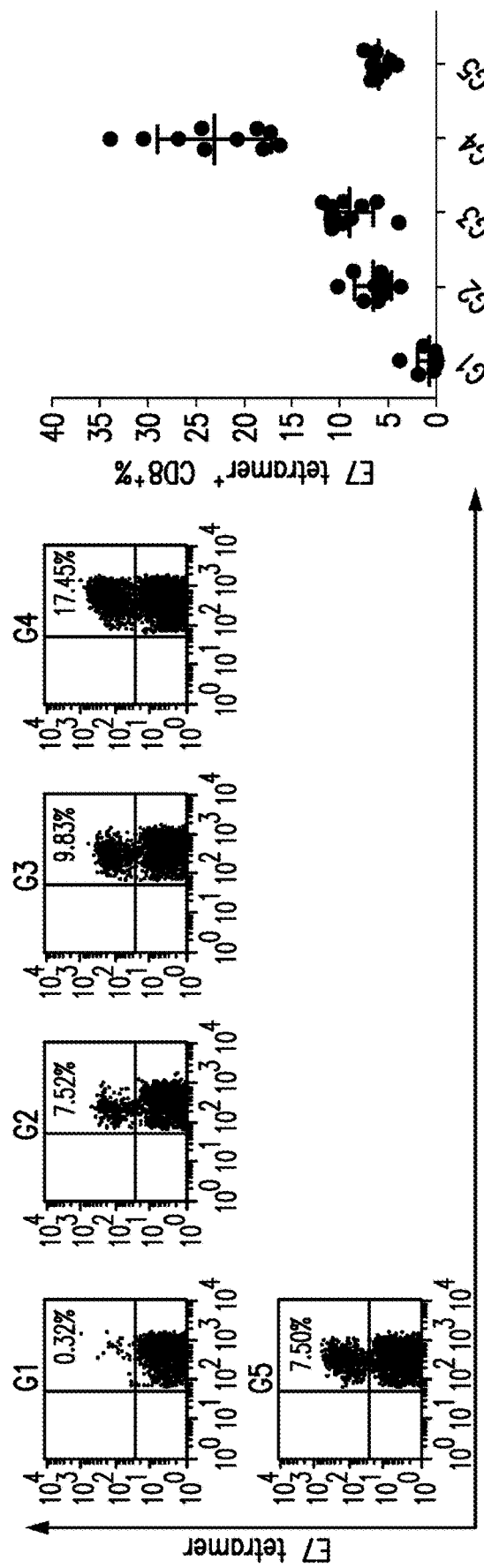

| | Prime day 0 | Boost day 35 |
|---|---|---|
| ■ | r3LCMV-E7E6 | r3JUNV-E7E6 |
| ▲ | r3LCMV-E7E6 | r3LCMV-E7E6 |
| ▼ | r3JUNV-E7E6 | r3JUNV-E7E6 |

HPV VACCINES

This application is a divisional of U.S. patent application Ser. No. 15/580,964, which is a U.S. National Stage Application under 35 U.S.C. § 371 of International Patent Application No. PCT/EP2016/063182, filed Jun. 9, 2016, which claims benefit of priority of U.S. Provisional Application No. 62/331,158, filed on May 3, 2016, U.S. Provisional Application No. 62/254,410, filed on Nov. 12, 2015, and U.S. Provisional Application No. 62/173,805, filed on Jun. 10, 2015, the entire contents of which are incorporated herein by reference.

The instant application contains a Sequence Listing which has been submitted in ASCII format via EFS-Web and is hereby incorporated by reference in its entirety. Said ASCII copy, created on Apr. 29, 2020, is named 13194-057-999_Seq_Listing.txt and is 181, 161 bytes in size.

1. INTRODUCTION

The invention relates to genetically modified arenaviruses suitable as vaccines against neoplastic diseases or cancer. The invention also relates to pharmaceutical compositions and methods for the treatment or prevention of certain infections causing neoplastic diseases or cancer, such as infections with oncogenic viruses. Specifically, provided herein are pharmaceutical compositions, vaccines, and methods of treating or preventing diseases and conditions caused by and associated with infections with Human Papillomavirus (HPV), such as cervical cancer, anogenital cancer, head and neck cancer and skin cancers. Also provided herein are immunotherapies for the treatment of a neoplastic disease, such as a neoplastic disease caused by infection with oncogenic viruses.

2. BACKGROUND 2.1 Medical Need

Neoplastic disease, such as cancer, can be caused by infectious agents, such as viruses, or so-called oncogenic viruses. Oncogenic viruses can be DNA viruses, such as Adenovirus, RNA viruses, such as Hepatitis C virus, or retroviruses, such as Human T-lymphotropic virus.

Human papillomavirus (HPV) is a DNA virus from the papillomavirus family, which has been found to be associated with several types of cancer. Although most HPV infections are subclinical and cause no physical symptoms, subclinical infections can become clinical and cause benign papillomas (such as warts or squamous cell papilloma), or cancers in certain populations. Over 170 HPV types have been identified and are referred to by number (Bzhalava et al., 2013, Virology 445 (1-2): 224-31). There is currently no cure for HPV infections.

About a dozen HPV types (including types 16, 18, 31, and 45) are called "high-risk" types because they can lead to cervical cancer, anal cancer, vulvar cancer, vaginal cancer, and penile cancer (Parkin et al., 2002, CA Cancer J Clin 2005; 55:74-108). It is estimated that 99.7% of all cervical cancers are caused by high-risk oncogenic HPV types (Ault, 2006, Infectious Diseases in Obstetrics and Gynecology 2006: 1-5), including HPV type 16 and HPV type 18, which together account for about 70% of cervical cancers (See World Health Organization's website on HPV and cervical cancer, and the Center for Disease Control's "Pink Book" on HPV). Several types of HPV, in particular type 16, have also been found to be associated with HPV-positive oropharyngeal cancer (OSCC), a form of head and neck cancer (D'Souza et al., 2007, N. Engl. J. Med. 356 (19): 1944-56). Overall, HPV type 16 is the most problematic genotype associated with at least half of all cervical cancers and the great majority (approximately 90%) of the HPV-associated cancers at other anogenital sites and the oral cavity (Peng et al., 2014, Cell Biosci., 4(1):11).

It is estimated that in 2002 about 5.2% of all new cancers worldwide (561,200 new cancer cases) were attributable to HPV, making HPV one of the most important infectious causes of cancer (Parkin, 2006, Int. J. Cancer 118 (12): 3030-44). Cervical cancer is the second most lethal form of cancer in women worldwide, with nearly half a million women diagnosed each year (Parkin et al., 2005, CA Cancer J Clin; 55:74-108).

In developed countries, effective national programs for cytologic (Pap) screening for the precursor lesion, high-grade cervical intraepithelial neoplasia (CIN), have been established. Such cytologic screening is usually followed by ablation of preinvasive lesions by conization or loop electrosurgical excision procedure (LEEP), which has reduced the incidence of cervical cancer by approximately 70-80% in the US, such that there are now approximately 5000 cervical cancer deaths each year (Roden et al., 2006, Nat Rev Cancer; 6:753-763). In cases where cervical cancer has already established, the primary treatment is radical hysterectomy and surgical debulking, followed by chemoradiation therapy. Even after undergoing this conventional therapy, which has significant unwanted side effects, patients with advanced cervical carcinoma still have a poor prognosis. Therefore, novel therapeutics specifically targeting cancerous cells while leaving normal cells unaffected, are still urgently needed for the treatment of established cervical cancer.

In addition, therapeutic vaccines would also be valuable to ensure viral clearance in patients with persistent HPV infection, which presents a necessary, though not sufficient cause of uterine cervical carcinoma, both squamous cell carcinoma and adenocarcinoma (zur Hausen et al., 2002, Nature Rev Cancer 2002; 2:342-350; Schiffman et al., 1993, J Natl Cancer Inst, 85:958-964; Walboomers et al., 1999, J Pathol, 189:12-19). Molecular testing for oncogenic HPV infection has recently been licensed as an adjunct to cytologic screening (Schiffman et al., 2007, Lancet, 370:890-907), and patients tested positive for HPV infection could significantly benefit from therapeutic vaccination.

2.2 HPV Vaccines

Two prophylactic multivalent HPV L1 virus-like particle (VLP) vaccines, i.e., Gardasil® and Cervarix®, preventing oncogenic HPV infection (Roden et al., 2006, Nat Rev Cancer, 6:753-763), HPV related cervical neoplasia, and genital warts, have been approved by the Food and Drug Administration (FDA) and the European Medicines Agency (EMA). These vaccines are believed to prevent HPV related disease by induction of neutralizing antibody responses, but they do not, however, alter the course of pre-existing HPV infections (Hung et al., 2008, Expert Opin Biol Ther., 8(4): 421-439). Thus, there is still a compelling medical need for the development of effective immunotherapeutics that could be used for therapeutic elimination of chronic HPV infection as well as for treatment of established HPV-related cancers.

The HPV early proteins (E1-E7) are expressed throughout the viral life cycle, are only present in infected cells, and are involved in regulation of disease progression. Proteins E6 and E7 are known to act as oncogenes that promote tumor growth and malignant transformation. The expression of these viral oncoproteins has been reported to be necessary to maintain the transformed phenotype of cervical cancer cells (Goodwin et al., 2000, Proc Natl Acad Sci USA 97:12513-12518; Goodwin et al., 2001, Cell Growth Differ., 12:525-534).

2.3 Recombinant LCMV Expressing Genes of Interest

The generation of recombinant negative-stranded RNA viruses expressing foreign genes of interest has been pursued for a long time. Different strategies have been published for other viruses (Garcia-Sastre et al., 1994, J Virol 68(10): 6254-6261; Percy et al., 1994, J Virol 68(7): 4486-4492; Flick and Hobom, 1999, Virology 262(1): 93-103; Machado et al., 2003, Virology 313(1): 235-249). In the past it has been shown that it is possible to introduce additional foreign genes into the genome of bi-segmented LCMV particles (Emonet et al., 2009, PNAS, 106(9):3473-3478). Two foreign genes of interest were inserted into the bi-segmented genome of LCMV, resulting in tri-segmented LCMV particles (r3LCMV) with two S segments and one L segment. In the tri-segmented virus, published by Emonet et al., (2009), both NP and GP were kept in their respective natural position in the S segment and thus were expressed under their natural promoters in the flanking UTR.

2.4 Replication-deficient Arenavirus Vectors

The use of infectious, replication-deficient arenaviruses as vectors for the expression of antigens has been reported (see Flatz et. al., 2010, Nat. Med., 16(3):339-345; Flatz et al., 2012, J. Virol., 86(15), 7760-7770). These infectious, replication-deficient arenaviruses can infect a host cell, i.e., attach to a host cell and release their genetic material into the host cell. However, they are replication-deficient, i.e., the arenavirus is unable to produce further infectious progeny particles in a non-complementing cell, due to a deletion or functional inactivation of an open reading frame (ORF) encoding a viral protein, such as the GP protein. Instead, the ORF is substituted with a nucleotide sequence of an antigen of interest. In Flatz 2010, the authors used infectious, replication-deficient arenaviruses as vectors to express OVA (SIINFEKL epitope). In Flatz 2012, the authors used replication deficient arenaviruses as vectors to express HIV/SIV Env.

Provided herein are infectious arenavirus vectors, including an infectious, replication-deficient arenavirus viral vector, a replication-competent tri-segmented arenavirus viral vector, and a replication-deficient tri-segmented arenavirus viral vector, or an arenavirus genomic segment to treat or prevent a neoplastic disease, such as a neoplastic disease caused by infection with oncogenic viruses.

3. SUMMARY OF THE INVENTION

Provided herein is an arenavirus viral vector having a first nucleotide sequence encoding an antigen of an oncogenic virus, or an antigen of a tumor-associated virus. In certain embodiments, the oncogenic virus or tumor-associated virus is not cytomegalo virus, Hepatitis B virus, or Hepatitis C virus. In certain embodiments, the viral vector is an infectious, replication-deficient arenavirus viral vector, which can be a bi-segmented or a tri-segmented arenavirus viral vector. In certain embodiments, the viral vector is a tri-segmented arenavirus viral vector, which can be replication-competent or replication-deficient. Thus, in certain embodiments, the tri-segmented arenavirus viral vector is a replication-competent tri-segmented arenavirus viral vector. In certain embodiments, the tri-segmented arenavirus viral vector is a replication-deficient tri-segmented arenavirus viral vector.

Also provided herein are arenaviruses with rearrangements of the ORFs in their genomes. In particular, provided herein is an arenavirus genomic segment that has been engineered to carry an arenavirus ORF in a position other than the wild-type position and a first nucleotide sequence encoding an antigen of an oncogenic virus, or an antigen of a tumor-associated virus. In certain embodiments, the oncogenic virus or tumor-associated virus is not cytomegalo virus, Hepatitis B virus, or Hepatitis C virus.

Still further provided herein is an arenavirus viral vector, including an infectious, replication-deficient arenavirus viral vector, a replication-competent tri-segmented arenavirus viral vector, and a replication-deficient tri-segmented arenavirus viral vector, or an arenavirus genomic segment comprising a first nucleotide sequence encoding an oncogenic virus antigen, wherein the oncogenic virus is human papillomavirus (HPV), Kaposi's sarcoma-associated herpesvirus, Epstein-Barr virus, Merkel cell polyomavirus, or human T-lymphotropic virus. In particular, provided herein is an arenavirus viral vector or an arenavirus genomic segment comprising a nucleotide sequence encoding a HPV antigen as described herein, including Section 3.1.

In certain embodiments, an arenavirus viral vector as provided herein is infectious, i.e., is capable of entering into or injecting its genetic material into a host cell. In certain more specific embodiments, an arenavirus viral vector as provided herein is infectious, i.e., is capable of entering into or injecting its genetic material into a host cell followed by amplification and expression of its genetic information inside the host cell. In certain embodiments, the arenavirus viral vector provided herein is an infectious, replication-deficient arenavirus viral vector engineered to contain a genome with the ability to amplify and express its genetic information in infected cells but unable to produce further infectious progeny particles in normal, not genetically engineered cells. In certain embodiments, the infectious arenavirus viral vector is replication-competent and able to produce further infectious progeny particles in normal, not genetically engineered cells.

Also provided herein are immunotherapies for the treatment of a neoplastic disease, such as a neoplastic disease caused by infection with oncogenic viruses, such as those caused by human papillomavirus (HPV), Kaposi's sarcoma-associated herpesvirus, Epstein-Barr virus, Merkel cell polyomavirus, or human T-lymphotropic virus. In certain embodiments, the immunotherapies are for the treatment of neoplastic diseases cause by HPV and/or treatment of an HPV infection. Such immunotherapies include administration of an arenavirus viral vector described herein, a pharmaceutical composition comprising an arenavirus viral vector as described herein, an immunogenic composition comprising an arenavirus viral vector as described herein, or a vaccine comprising an arenavirus viral vector as described herein to a subject.

3.1 Oncogenic Virus Antigens and HPV Antigens

In certain embodiments, an arenavirus viral vector, including an infectious, replication-deficient arenavirus viral vector, a replication-competent tri-segmented arenavirus viral vector, and a replication-deficient tri-segmented arenavirus viral vector, or an arenavirus genomic segment provided herein comprises a first nucleotide sequence encoding a first HPV antigen.

In certain embodiments, the first nucleotide sequence further encodes a second HPV antigen.

In certain embodiments, the arenavirus viral vector or arenavirus genomic segment provided herein further comprises a second nucleotide sequence encoding a second HPV antigen.

In certain embodiments, the first and/or second nucleotide sequence encodes multiple HPV antigens. In a more specific embodiment, the arenavirus viral vector or arenavirus genomic segment comprising a first nucleotide sequence provided herein encodes two, three, four, five, six, seven, eight, nine, ten or more HPV antigens. In another specific embodiment, the arenavirus viral vector or arenavirus genomic segment comprising a second nucleotide sequence provided herein encodes two, three, four, five, six, seven, eight, nine, ten or more HPV antigens. In still another embodiment, the arenavirus viral vector or arenavirus genomic segment comprising a first and a second nucleotide sequence wherein the first nucleotide sequence encodes two, three, four, five, six, seven, eight, nine, ten or more HPV antigens and the second nucleotide sequence encodes two, three, four, five, six, seven, eight, nine, ten or more HPV antigens.

In certain embodiments, the first antigen is selected from the group consisting of HPV protein E1, HPV protein E2, HPV protein E3, HPV protein E4, HPV protein E5, HPV protein E6, HPV protein E7, HPV protein L1 and HPV protein L2.

In certain embodiments, the second antigen is selected from the group consisting of HPV protein E1, HPV protein E2, HPV protein E3, HPV protein E4, HPV protein E5, HPV protein E6, HPV protein E7, HPV protein L1 and HPV protein L2.

In certain embodiments, the first and/or second antigen is an antigen of HPV16, HPV18, HPV31, HPV33, HPV35, HPV39, HPV45, HPV51, HPV52, HPV56, HPV58, HPV59, HPV68, HPV73, or HPV82.

In certain embodiments, the first antigen is an HPV16 antigen, and the second antigen is an HPV18 antigen.

In certain embodiments, the arenavirus viral vector or arenavirus genomic segment provided herein further encodes two, three, four, five or more HPV antigens. In a specific embodiment, the arenavirus viral vector or arenavirus genomic segment encodes one, two, or three HPV16 antigens and one, two or three HPV18 antigens. In an even more specific embodiment, the arenavirus viral vector or arenavirus genomic segment encodes two HPV16 antigens and two HPV18 antigens. In certain embodiments, these HPV antigens are selected from the groups consisting of:
  an HPV16 protein E6, or an antigenic fragment thereof;
  an HPV16 protein E7, or an antigenic fragment thereof;
  an HPV18 protein E6, or an antigenic fragment thereof; and
  an HPV18 protein E7, or an antigenic fragment thereof.

In certain embodiments, the first antigen is selected from the group consisting of:
  an HPV16 protein E6, or an antigenic fragment thereof;
  an HPV16 protein E7, or an antigenic fragment thereof;
  an HPV18 protein E6, or an antigenic fragment thereof; and
  an HPV18 protein E7, or an antigenic fragment thereof.

In certain embodiments, the first and the second antigens are selected from the group consisting of:
  an HPV16 protein E6, or an antigenic fragment thereof;
  an HPV16 protein E7, or an antigenic fragment thereof;
  an HPV18 protein E6, or an antigenic fragment thereof; and
  an HPV18 protein E7, or an antigenic fragment thereof,
wherein the first and the second antigen are not the same.

In certain specific embodiments, the arenavirus viral vector or arenavirus genomic segment provided herein further encodes HPV protein E7 fused to HPV protein E6 fused to HPV protein E6 fused to HPVprotein E7, wherein one HPV protein E7 is from strain HPV16 and the other is from strain HPV18 and one HPV protein E6 is from strain HPV 18 and the other is from strain HPV18.

In certain embodiments, the first or second antigen is HPV protein E7 with a mutation in the Rb binding site.

In certain embodiments, the first or second antigen is HPV protein E7 with mutations in the Rb binding site and the zinc finger motif.

In certain embodiments, the first or second antigen is HPV protein E6 with a mutation in the zinc binding domain.

In certain embodiments, the first or second antigen is HPV protein E6 with mutations in the zinc finger motif.

In certain embodiments, the first and the second antigen are fused directly to each other.

In certain embodiments, the first and the second antigen are fused to each other via a peptide linker.

In certain embodiments, the first and the second antigen are separated from each other via a self-cleaving peptide.

In certain embodiments, the self-cleaving peptide is Porcine teschovirus-1 2A peptide, Thosea asigna virus 2A peptide, or Foot-and-mouth disease virus 2A peptide.

In certain embodiments, the arenavirus viral vector or arenavirus genomic segment provided herein further comprises a third nucleotide sequence encoding an immunomodulatory peptide, polypeptide, or protein.

In certain embodiments, the immunomodulatory peptide, polypeptide, or protein is selected from the group consisting of:
  Calreticulin (CRT), or a fragment thereof;
  Ubiquitin or a fragment thereof;
  Granulocyte-Macrophage Colony-Stimulating Factor (GM-CSF), or a fragment thereof;
  Invariant chain (CD74) or an antigenic fragment thereof;
  Mycobacterium tuberculosis Heat shock protein 70 or an antigenic fragment thereof;
  Herpes simplex virus 1 protein VP22 or an antigenic fragment thereof;
  CD40 ligand or an antigenic fragment thereof;
  Fms-related tyrosine kinase 3 (Flt3) ligand or an antigenic fragment thereof.

In certain embodiments, the immunomodulatory peptide, polypeptide, or protein is selected from the group consisting of:
  Calreticulin (CRT), or a fragment thereof;
  Ubiquitin or a fragment thereof; and
  Granulocyte-Macrophage Colony-Stimulating Factor (GM-CSF), or a fragment thereof.

In certain embodiments, the immunomodulatory peptide, polypeptide, or protein is directly fused to the first antigen, or is fused to the first antigen through a peptide linker.

In certain embodiments, the immunomodulatory peptide, polypeptide, or protein is directly fused to the second antigen, or is fused to the second antigen through a peptide linker.

In certain embodiments, the first antigen and the immunomodulatory peptide, polypeptide, or protein are separated from each other via a self-cleaving peptide.

In certain embodiments, the second antigen and the immunomodulatory peptide, polypeptide, or protein are separated from each other via a self-cleaving peptide.

In certain embodiments, the self-cleaving peptide is Porcine teschovirus-1 2A peptide, Thosea asigna virus 2A peptide, or Foot-and-mouth disease virus 2A peptide.

In certain embodiments, the arenavirus viral vector or arenavirus genomic segment provided herein further comprises a nucleotide sequence encoding a human tyrosinase secretion signal, a human growth hormone secretion signal, or a tissue plasminogen activator signal sequence.

In certain embodiments, the resulting fusion protein is at least 80%, 81%, 82%, 83%, 84%, 85%, 86%, 87%, 88%, 89%, 90%, 91%, 92%, 93%, 94%, 95%, 96%, 97%, 98%, at least 99%, or 100% identical to the amino acid sequence of SEQ ID NO: 10.

In certain embodiments, the resulting fusion protein is at least 80%, 81%, 82%, 83%, 84%, 85%, 86%, 87%, 88%, 89%, 90%, 91%, 92%, 93%, 94%, 95%, 96%, 97%, 98%, at least 99%, or 100% identical to the fusion protein of amino acid sequence of SEQ ID NO: 34.

In certain embodiments, the resulting fusion protein is at least 80%, 81%, 82%, 83%, 84%, 85%, 86%, 87%, 88%, 89%, 90%, 91%, 92%, 93%, 94%, 95%, 96%, 97%, 98%, at least 99%, or 100% identical to the fusion protein of amino acid sequence of SEQ ID NO: 36.

In certain embodiments, the resulting fusion protein is at least 80%, 81%, 82%, 83%, 84%, 85%, 86%, 87%, 88%, 89%, 90%, 91%, 92%, 93%, 94%, 95%, 96%, 97%, 98%, at least 99%, or 100% identical to the fusion protein of amino acid sequence of SEQ ID NO: 38.

In certain embodiments, the arenavirus viral vector or arenavirus genomic segment provided herein comprises a nucleic acid sequence encoding an HPV16 E7/E6 polypeptide that is at least 80%, 81%, 82%, 83%, 84%, 85%, 86%, 87%, 88%, 89%, 90%, 91%, 92%, 93%, 94%, 95%, 96%, 97%, 98%, at least 99%, or 100% identical to the amino acid sequence of SEQ ID NO:10.

In certain embodiments, the arenavirus viral vector or arenavirus genomic segment provided herein comprises a nucleic acid sequence encoding an HPV16 E7/HPV18 E6 polypeptide that is at least 80%, 81%, 82%, 83%, 84%, 85%, 86%, 87%, 88%, 89%, 90%, 91%, 92%, 93%, 94%, 95%, 96%, 97%, 98%, at least 99%, or 100% identical to amino acids 17-263 of the amino acid sequence of SEQ ID NO:34.

In certain embodiments, the arenavirus viral vector or arenavirus genomic segment provided herein comprise a nucleic acid sequence encoding an HPV18 E7/HPV16 E6 polypeptide that is at least 80%, 81%, 82%, 83%, 84%, 85%, 86%, 87%, 88%, 89%, 90%, 91%, 92%, 93%, 94%, 95%, 96%, 97%, 98%, at least 99%, or 100% identical to amino acids 17-270 of the amino acid sequence of SEQ ID NO:36.

In certain embodiments, the arenavirus viral vector or arenavirus genomic segment provided herein comprise a nucleic acid sequence encoding an HPV16 E7/HPV18 E6/HPV16 E6/HPV18 E7 polypeptide that is at least 80%, 81%, 82%, 83%, 84%, 85%, 86%, 87%, 88%, 89%, 90%, 91%, 92%, 93%, 94%, 95%, 96%, 97%, 98%, at least 99%, or 100% identical to amino acids 17-516 of the amino acid sequence of SEQ ID NO:38.

3.2 Replication-Deficient Arenavirus

In certain embodiments, the viral vector provided herein is an infectious, replication-deficient arenavirus viral vector.

In certain embodiments, provided herein is an infectious, replication-deficient arenavirus viral vector comprising a first nucleotide sequence encoding an antigen of an oncogenic virus, or an antigen of a tumor-associated virus, wherein the oncogenic virus or tumor-associated virus is not cytomegalo virus, Hepatitis B virus, or Hepatitis C virus.

In certain embodiments, provided herein is an infectious, replication-deficient arenavirus viral vector comprising a first nucleotide sequence encoding an antigen of an oncogenic virus, wherein the oncogenic virus is human papillomavirus, Kaposi's sarcoma-associated herpesvirus, Epstein-Barr virus, Merkel cell polyomavirus, or human T-lymphotropic virus.

In certain embodiments, provided herein is an infectious, replication-deficient arenavirus viral vector engineered to contain a genome with the ability to amplify and express its genetic information in infected cells but unable to produce further infectious progeny particles in normal, not genetically engineered cells, wherein one arenavirus open reading frame is at least partially removed and replaced by a first nucleotide sequence encoding a first HPV antigen.

In certain embodiments, provided herein is an infectious, replication-deficient arenavirus viral vector engineered to contain a genome with the ability to amplify and express its genetic information in infected cells but unable to produce further infectious progeny particles in normal, not genetically engineered cells, wherein one arenavirus open reading frame is at least partially removed or functionally inactivated and wherein the genome of the arenaviral vector encodes HPV16 E6 or antigenic fragment thereof, HPV16 E7 or antigenic fragment thereof, HPV18 E6 or antigenic fragment thereof, and HPV18 E7 or antigenic fragment thereof.

In certain embodiments, the arenaviral vector encodes an HPV16 E6/E7 fusion protein and an HPV 18 E6/E7 fusion protein. In certain embodiments, the arenaviral vector encodes an HPV16 E7/HPV18 E6 fusion protein. In certain embodiments, the arenaviral vector encodes an HPV18 E7/HPV16 E6 fusion protein. In certain embodiments, the arenaviral vector encodes an HPV16 E7/HPV18 E6/HPV16 E6/HPV18 E7 fusion protein.

In certain embodiments, the HPV16 E6 or antigenic fragment thereof, HPV16 E7 or antigenic fragment thereof, HPV18 E6 or antigenic fragment thereof, and HPV18 E7 or antigenic fragment thereof are encoded by one, two, three, or four heterologous nucleotide sequences.

In certain embodiments, the vector encodes a signal peptide fused to one or more of HPV16 E6 or antigenic fragment thereof, HPV16 E7 or antigenic fragment thereof, HPV18 E6 or antigenic fragment thereof, and HPV18 E7 or antigenic fragment thereof.

In certain embodiments, the vector encodes a peptide linker between two or more of HPV16 E6 or antigenic fragment thereof, HPV16 E7 or antigenic fragment thereof, HPV18 E6 or antigenic fragment thereof, and HPV18 E7 or antigenic fragment thereof.

In certain embodiments, the vector further comprises a nucleotide sequence encoding an immunomodulatory peptide, polypeptide, or protein. In particular, in certain embodiments, the arenavirus comprises a nucleotide sequence encoding a HPV antigen as described herein, including Section 3.1.

In certain embodiments, the vector encodes a peptide linker between an HPV antigen (HPV16 E6, HPV16 E7, HPV18 E6, HPV18 E7) or antigenic fragment thereof as described herein, including Section 3.1 and the immunomodulatory peptide, polypeptide, or protein.

In certain embodiments, the arenavirus is lymphocytic choriomeningitis virus (LCMV) or Junin virus.

In certain embodiments, the genomic information encoding the infectious, replication-deficient arenavirus viral vector is derived from the lymphocytic choriomeningitis virus Clone 13 strain or MP strain.

In certain embodiments, the viral vector is engineered to contain a genome with the ability to amplify and express its genetic information in infected cells but unable to produce further infectious progeny particles in normal, not genetically engineered cells, wherein one arenavirus open reading frame is functionally inactivated.

In certain embodiments, an infectious, replication-deficient arenavirus viral vector provided herein includes a viral vector wherein a viral open reading frame ("ORF") that encodes the glycoprotein ("GP"), nucleoprotein ("NP"), matrix protein Z ("Z protein") or RNA dependent RNA polymerase L ("L protein") of the arenavirus is removed or functionally inactivated.

In certain embodiments, at least one of the four ORFs encoding GP, NP, Z protein, and L protein is removed or functionally inactivated.

In certain embodiments, at least one of the four ORFs encoding GP, NP, Z protein and L protein is removed and replaced with a heterologous ORF from an organism other than an arenavirus. In other embodiments, only one of the four ORFs encoding GP, NP, Z protein and L protein is removed and replaced with a heterologous ORF from an organism other than an arenavirus. In a more specific embodiment, the ORF encoding GP is removed and replaced with a heterologous ORF from an organism other than an arenavirus. In other embodiments, the ORF encoding NP is removed and replaced with a heterologous ORF from an organism other than an arenavirus. In some embodiments, the ORF encoding the Z protein is removed and replaced with a heterologous ORF from an organism other than an arenavirus. In other embodiments, the ORF encoding the L protein is removed and replaced with a heterologous ORF from an organism other than an arenavirus.

In certain embodiments, the heterologous ORF encodes a reporter protein. In some embodiments, the heterologous ORF encodes an antigen derived from an infectious organism, tumor, or allergen. In other embodiments, the heterologous ORF encoding an antigen is selected from human papillomavirus (HPV) antigens, human immunodeficiency virus antigens, hepatitis C virus antigens, hepatitis B surface antigen, varizella zoster virus antigens, cytomegalovirus antigens, *Mycobacterium tuberculosis* antigens, and tumor associated antigens.

In certain embodiments, the growth or infectivity of the infectious, replication-deficient arenavirus viral vector is not affected by the heterologous ORF from an organism other than an arenavirus.

3.3 Arenavirus Genomic Segments

In certain embodiments, provided herein are arenaviruses with rearrangements of the ORFs in their genomes. In particular, provided herein is an arenavirus genomic segment that has been engineered to carry an arenavirus ORF in a position other than the wild-type position and a first nucleotide sequence encoding an antigen of an oncogenic virus, or an antigen of a tumor-associated virus as described herein. In certain embodiments, the oncogenic virus or tumor-associated virus is not cytomegalo virus, Hepatitis B virus, or Hepatitis C virus.

In certain embodiments, provided herein is an arenavirus genomic segment that has been engineered to carry an arenavirus ORF in a position other than the wild-type position and a first nucleotide sequence encoding an oncogenic virus antigen, wherein the oncogenic virus is human papillomavirus (HPV), Kaposi's sarcoma-associated herpesvirus, Epstein-Barr virus, Merkel cell polyomavirus, or human T-lymphotropic virus. In particular, in certain embodiments, the arenavirus genomic segment comprises a nucleotide sequence encoding a HPV antigen as described herein, including Section 3.1.

In certain embodiments, the arenavirus genomic segment is selected from the group consisting of:

(i) an S segment, wherein the ORF encoding the NP is under control of an arenavirus 5' UTR;
(ii) an S segment, wherein the ORF encoding the Z protein is under control of an arenavirus 5' UTR;
(iii) an S segment, wherein the ORF encoding the L protein is under control of an arenavirus 5' UTR;
(iv) an S segment, wherein the ORF encoding the GP is under control of an arenavirus 3' UTR;
(v) an S segment, wherein the ORF encoding the L protein is under control of an arenavirus 3' UTR;
(vi) an S segment, wherein the ORF encoding the Z protein is under control of an arenavirus 3' UTR;
(vii) an L segment, wherein the ORF encoding the GP is under control of an arenavirus 5' UTR;
(viii) an L segment, wherein the ORF encoding the NP is under control of an arenavirus 5' UTR;
(ix) an L segment, wherein the ORF encoding the L protein is under control of an arenavirus 5' UTR;
(x) an L segment, wherein the ORF encoding the GP is under control of an arenavirus 3' UTR;
(xi) an L segment, wherein the ORF encoding the NP is under control of an arenavirus 3' UTR; and
(xii) an L segment, wherein the ORF encoding the Z protein is under control of an arenavirus 3' UTR.

In certain embodiments, the arenavirus 3' UTR is the 3' UTR of the arenavirus S segment or the arenavirus L segment. In certain embodiments, the arenavirus 5' UTR is the 5' UTR of the arenavirus S segment or the arenavirus L segment.

In certain embodiments, the arenavirus genomic segment is derived from lymphocytic choriomeningitis virus ("LCMV") or Junin virus. In particular embodiments, the arenavirus genomic segment is derived from LCMV. The LCMV can be MP strain, Armstrong strain, or Armstrong Clone 13 strain. In particular embodiments, the arenavirus genomic segment is derived from Junin virus. The Junin virus can be Junin virus vaccine Candid #1, or Junin virus vaccine XJ Clone 3 strain.

Also provided herein, is an arenavirus viral vector comprising the arenavirus genomic segment and a second arenavirus genomic segment so that the arenavirus viral vector comprises an S segment and an L segment.

In certain embodiments, the arenavirus viral vector is infectious and replication-competent. In some embodiments, the arenavirus viral vector is attenuated. In other embodiments, the arenavirus viral vector is infectious but unable to produce further infectious progeny in non-complementing cells.

In certain embodiments, the arenavirus viral vector is derived from lymphocytic choriomeningitis virus ("LCMV") or Junin virus. In particular embodiments, the arenavirus viral vector is derived from LCMV. The LCMV can be MP strain, Armstrong strain, or Armstrong Clone 13 strain. In particular embodiments, the arenavirus viral vector is derived from Junin virus. The Junin virus can be Junin virus vaccine Candid #1, or Junin virus vaccine XJ Clone 3 strain.

In certain embodiments, an arenavirus viral vector or an arenavirus genomic segment provided herein includes a viral vector wherein a viral open reading frame ("ORF") that encodes the glycoprotein ("GP"), nucleoprotein ("NP"), matrix protein Z ("Z protein") or RNA dependent RNA polymerase L ("L protein") of the arenavirus is removed or functionally inactivated.

In certain embodiments, at least one of the four ORFs encoding GP, NP, Z protein, and L protein is removed or functionally inactivated.

In certain embodiments, at least one of the four ORFs encoding GP, NP, Z protein and L protein is removed and replaced with a heterologous ORF from an organism other than an arenavirus. In other embodiments, only one of the four ORFs encoding GP, NP, Z protein and L protein is removed and replaced with a heterologous ORF from an organism other than an arenavirus. In a more specific embodiment, the ORF encoding GP is removed and replaced with a heterologous ORF from an organism other than an arenavirus. In other embodiments, the ORF encoding NP is removed and replaced with a heterologous ORF from an organism other than an arenavirus. In some embodiments, the ORF encoding the Z protein is removed and replaced with a heterologous ORF from an organism other than an arenavirus. In other embodiments, the ORF encoding the L protein is removed and replaced with a heterologous ORF from an organism other than an arenavirus.

In certain embodiments, the heterologous ORF encodes a reporter protein. In some embodiments, the heterologous ORF encodes an antigen derived from an infectious organism, tumor, or allergen. In other embodiments, the heterologous ORF encoding an antigen is selected from human papillomavirus (HPV) antigens, human immunodeficiency virus antigens, hepatitis C virus antigens, hepatitis B surface antigen, varizella zoster virus antigens, cytomegalovirus antigens, *Mycobacterium tuberculosis* antigens, and tumor associated antigens.

In certain embodiments, the growth or infectivity of the arenavirus viral vector is not affected by the heterologous ORF from an organism other than an arenavirus.

3.4 Tri-Segmented Arenavirus Viral Vectors

In certain embodiments, the viral vector provided herein is a tri-segmented arenavirus viral vector having a first nucleotide sequence encoding an antigen of an oncogenic virus, or an antigen of a tumor-associated virus. In certain embodiments, the oncogenic virus or tumor-associated virus is not cytomegalo virus, Hepatitis B virus, or Hepatitis C virus. In certain embodiments, the tri-segmented arenavirus viral vector is a replication-competent tri-segmented arenavirus viral vector. In certain embodiments, the tri-segmented arenavirus viral vector is a replication-deficient tri-segmented arenavirus viral vector. The tri-segmented arenavirus viral vector provided herein also includes a first nucleotide sequence encoding an oncogenic virus antigen, wherein the oncogenic virus is human papillomavirus (HPV), Kaposi's sarcoma-associated herpesvirus, Epstein-Barr virus, Merkel cell polyomavirus, or human T-lymphotropic virus. In particular, in certain embodiments, the tri-segmented arenavirus viral vector comprises a nucleotide sequence encoding a HPV antigen as described herein, including Section 3.1.

In particular embodiments, the tri-segmented arenavirus viral vector comprises one L segment and two S segments or two L segments and one S segment that do not recombine into a replication-competent bi-segmented arenavirus particle. The tri-segmented arenavirus viral vectors described herein have improved genetic stability and lasting transgene expression. Accordingly, in certain embodiments, propagation of the tri-segmented arenavirus viral vector does not result in a replication-competent bi-segmented viral viral vector after 70 days of persistent infection in mice lacking type I interferon receptor, type II interferon receptor and recombination activating gene 1 (RAG1) and having been infected with $10^4$ PFU of the tri-segmented arenavirus viral vector. Moreover, in certain embodiments, inter-segmental recombination of the two S segments or two L segments, uniting two arenavirus ORFs on only one instead of two separate segments, abrogates viral promoter activity.

In certain embodiments, provided herein is a tri-segmented arenavirus viral vector comprising one L segment and two S segments and a first nucleotide sequence encoding an antigen of an oncogenic virus, or an antigen of a tumor-associated virus, wherein the oncogenic virus or tumor-associated virus is not cytomegalo virus, Hepatitis B virus, or Hepatitis C virus, and wherein propagation of the tri-segmented arenavirus viral vector does not result in a replication-competent bi-segmented viral vector after 70 days of persistent infection in mice lacking type I interferon receptor, type II interferon receptor and recombination activating gene 1 (RAG1) and having been infected with $10^4$ PFU of the tri-segmented arenavirus viral vector. The tri-segmented arenavirus viral vector also includes a first nucleotide sequence encoding an oncogenic virus antigen, wherein the oncogenic virus is is human papillomavirus (HPV), Kaposi's sarcoma-associated herpesvirus, Epstein-Barr virus, Merkel cell polyomavirus, or human T-lymphotropic virus. In particular, in certain embodiments, the tri-segmented arenavirus viral vector comprises a nucleotide sequence encoding a HPV antigen as described herein, including Section 3.1.

In certain embodiments, provided herein is a tri-segmented arenavirus viral vector comprising two L segments and one S segment and a first nucleotide sequence encoding an antigen of an oncogenic virus, or an antigen of a tumor-associated virus, wherein the oncogenic virus or tumor-associated virus is not cytomegalo virus, Hepatitis B virus, or Hepatitis C virus, and wherein propagation of the tri-segmented arenavirus viral vector does not result in a replication-competent bi-segmented viral vector after 70 days of persistent infection in mice lacking type I interferon receptor, type II interferon receptor and recombination activating gene 1 (RAG1) and having been infected with $10^4$ PFU of the tri-segmented arenavirus viral vector. The tri-segmented arenavirus viral vector also includes a first nucleotide sequence encoding an oncogenic virus antigen, wherein the oncogenic virus is human papillomavirus (HPV), Kaposi's sarcoma-associated herpesvirus, Epstein-Barr virus, Merkel cell polyomavirus, or human T-lymphotropic virus. In particular, in certain embodiments, the tri-segmented arenavirus viral vector comprises a nucleotide sequence encoding a HPV antigen as described herein, including Section 3.1.

Also provided herein is a tri-segmented arenavirus viral vector comprising an arenavirus genomic segment described herein and a second arenavirus genomic segment described herein so that the arenavirus viral vector comprises an S segment and an L segment.

In certain embodiments, the tri-segmented arenavirus viral vector comprising one L segment and two S segments provided herein includes an arenavirus viral vector wherein one of the two S segments is selected from the group consisting of:

(i) an S segment, wherein the ORF encoding the NP is under control of an arenavirus 5' UTR
(ii) an S segment, wherein the ORF encoding the Z protein is under control of an arenavirus 5' UTR;
(iii) an S segment, wherein the ORF encoding the L protein is under control of an arenavirus 5' UTR;
(iv) an S segment, wherein the ORF encoding the GP is under control of an arenavirus 3' UTR;
(v) an S segment, wherein the ORF encoding the L protein is under control of an arenavirus 3' UTR; and
(vi) an S segment, wherein the ORF encoding the Z protein is under control of an arenavirus 3' UTR.

In certain embodiments, the tri-segmented arenavirus viral vector comprising two L segments and one S segment provided herein includes an arenavirus viral vector wherein one of the two L segments is selected from the group consisting of:
  (i) an L segment, wherein the ORF encoding the GP is under control of an arenavirus 5' UTR;
  (ii) an L segment, wherein the ORF encoding the NP is under control of an arenavirus 5' UTR;
  (iii) an L segment, wherein the ORF encoding the L protein is under control of an arenavirus 5' UTR;
  (iv) an L segment, wherein the ORF encoding the GP is under control of an arenavirus 3' UTR;
  (v) an L segment, wherein the ORF encoding the NP is under control of an arenavirus 3' UTR; and
  (vi) an L segment, wherein the ORF encoding the Z protein is under control of an arenavirus 3' UTR.

In certain embodiments, the tri-segmented arenavirus viral vector 3' UTR is the 3' UTR of the arenavirus S segment or the arenavirus L segment. In other embodiments, the tri-segmented arenavirus viral vector 5' UTR is the 5' UTR of the arenavirus S segment or the arenavirus L segment.

In certain embodiments, the two S segments comprise (i) one or two heterologous ORFs from an organism other than an arenavirus; or (ii) one or two duplicated arenavirus ORFs; or (iii) one heterologous ORF from an organism other than an arenavirus and one duplicated arenavirus ORF.

In certain embodiments, the two L segments comprise (i) one or two heterologous ORFs from an organism other than an arenavirus; or (ii) one or two duplicated arenavirus ORFs; or (iii) one heterologous ORF from an organism other than an arenavirus and one duplicated arenavirus ORF.

In certain embodiments, the heterologous ORF encodes an antigen derived from an infectious organism, tumor, or allergen. In other embodiments, the heterologous ORF encoding an antigen is selected from human papillomavirus (HPV) antigens, human immunodeficiency virus antigens, hepatitis C virus antigens, hepatitis B surface antigen, varizella zoster virus antigens, cytomegalovirus antigens, *Mycobacterium tuberculosis* antigens, and tumor associated antigens.

In certain embodiments, at least one heterologous ORF encodes a fluorescent protein. In other embodiments the fluorescent protein is a green fluorescent protein (GFP) or red fluorescent protein (RFP).

In certain embodiments, the tri-segmented arenavirus viral vector comprises all four arenavirus ORFs. In some embodiments the tri-segmented arenavirus viral vector is infectious and replication-competent.

In certain embodiments, the tri-segmented arenavirus viral vector lacks one or more of the four arenavirus ORFs. In other embodiments, the tri-segmented arenavirus viral vector is infectious but unable to produce further infectious progeny in non-complementing cells.

In certain embodiments, the tri-segmented arenavirus viral vector lacks one of the four arenavirus ORFs, wherein the tri-segmented arenavirus viral vector is infectious but unable to produce further infectious progeny in non-complementing cells.

In some embodiments, the tri-segmented arenavirus viral vector lacks the GP ORF.

In a further aspect, provided herein is a tri-segmented arenavirus viral vector comprising one L segment and two S segments. In certain embodiments, a first S segment is engineered to carry an ORF encoding GP in a position under control of an arenavirus 3' UTR and an ORF encoding a first HPV antigen in a position under control of an arenavirus 5' UTR. In some embodiments, a second S segment is engineered to carry an ORF encoding the NP in a position under control of an arenavirus 3' UTR and an ORF encoding a second HPV antigen in a position under control of an arenavirus 5' UTR.

In yet another aspect, provided herein, is a tri-segmented arenavirus viral vector comprising one L segment and two S segments. In certain embodiments, a first S segment is engineered to carry an ORF encoding GP in a position under control of an arenavirus 5' UTR and an ORF encoding a first HPV antigen in a position under control of an arenavirus 3' UTR. In some embodiments, a second S segment is engineered to carry an ORF encoding NP in a position under control of an arenavirus 5' UTR and an ORF encoding a second HPV antigen in a position under control of an arenavirus 3' UTR.

In certain embodiments, the first antigen is an HPV16 antigen, and the second antigen is an HPV18 antigen.

In certain embodiments, the tri-segmented arenavirus viral vector provided herein encodes one, two, or three HPV16 antigens and one, two or three HPV18 antigens.

In certain embodiments, the tri-segmented arenavirus viral vector provided herein encodes two HPV16 antigens and two HPV18 antigens, wherein the antigens are selected from the group consisting of:
  an HPV16 protein E6, or an antigenic fragment thereof;
  an HPV16 protein E7, or an antigenic fragment thereof;
  an HPV18 protein E6, or an antigenic fragment thereof; and
  an HPV18 protein E7, or an antigenic fragment thereof.

In certain embodiments, the first and the second antigens are selected from the group consisting of:
  an HPV16 protein E6, or an antigenic fragment thereof;
  an HPV16 protein E7, or an antigenic fragment thereof;
  an HPV18 protein E6, or an antigenic fragment thereof; and
  an HPV18 protein E7, or an antigenic fragment thereof, and wherein the first and the second antigen are not the same.

In certain embodiments, the first antigen is selected from the group consisting of:
  an HPV16 protein E6, or an antigenic fragment thereof;
  an HPV16 protein E7, or an antigenic fragment thereof;
  an HPV18 protein E6, or an antigenic fragment thereof; and
  an HPV18 protein E7, or an antigenic fragment thereof.

In certain embodiments, the HPV antigen is an HPV16 E7/E6 polypeptide that is at least 80%, 81%, 82%, 83%, 84%, 85%, 86%, 87%, 88%, 89%, 90%, 91%, 92%, 93%, 94%, 95%, 96%, 97%, 98%, at least 99%, or 100% identical to the amino acid sequence of SEQ ID NO:10.

In certain embodiments, the HPV antigen is an HPV16 E7/HPV18 E6 polypeptide that is at least 80%, 81%, 82%, 83%, 84%, 85%, 86%, 87%, 88%, 89%, 90%, 91%, 92%, 93%, 94%, 95%, 96%, 97%, 98%, at least 99%, or 100% identical to amino acids 17-263 of the amino acid sequence of SEQ ID NO:34.

In certain embodiments, the HPV antigen is an HPV18 E7/HPV16 E6 polypeptide that is at least 80%, 81%, 82%, 83%, 84%, 85%, 86%, 87%, 88%, 89%, 90%, 91%, 92%, 93%, 94%, 95%, 96%, 97%, 98%, at least 99%, or 100% identical to amino acids 17-270 of the amino acid sequence of SEQ ID NO:36.

In certain embodiments, the HPV antigen is an HPV16 E7/HPV18 E6/HPV16 E6/HPV18 E7 polypeptide that is at least 80%, 81%, 82%, 83%, 84%, 85%, 86%, 87%, 88%, 89%, 90%, 91%, 92%, 93%, 94%, 95%, 96%, 97%, 98%, at least 99%, or 100% identical to amino acids 17-516 of the amino acid sequence of SEQ ID NO:38.

In certain embodiments, the tri-segmented arenavirus viral vector is infectious and replication-competent. In some embodiments, the arenavirus viral vector is attenuated. In other embodiments, the tri-segmented arenavirus viral vector is infectious but unable to produce further infectious progeny in non-complementing cells.

In certain embodiments, the tri-segmented arenavirus viral vector has the same tropism as the bi-segmented arenavirus particle. In other embodiments, the tri-segmented arenavirus viral vector is replication deficient.

In certain embodiments, the tri-segmented arenavirus viral vector is derived from lymphocytic choriomeningitis virus ("LCMV") or Junin virus. In particular embodiments, the tri-segmented arenavirus viral vector is derived from LCMV. The LCMV can be MP strain, Armstrong strain, or Armstrong Clone 13 strain. In particular embodiments, the tri-segmented arenavirus viral vector is derived from Junin virus. The Junin virus can be Junin virus vaccine Candid #1, or Junin virus vaccine XJ Clone 3 strain.

3.5 Nucleic Acids, Host Cells and Methods of Generating Viral Vectors

In certain embodiments, provided herein is an isolated nucleic acid, including a cDNA, wherein the nucleic acid encodes a viral vector as described above. In certain embodiments, provided herein is an expression vector comprising such a nucleic acid. Also provided herein is a host cell comprising such a nucleic acid or such an expression vector.

In certain embodiments, provided herein is an isolated cDNA of an arenavirus genomic segment provided herein. Also provided herein, is a DNA expression vector comprising the cDNA of an arenavirus genomic segment provided herein.

Still further provided herein is a host cell comprising an arenavirus genomic segment provided herein, a cDNA of the arenavirus genomic segment, or the vector comprising a cDNA of the arenavirus genomic segment.

In certain embodiments, provided herein is a method for generating an infectious, replication-deficient arenavirus viral vector comprising:
 (i) transfecting into a host cell the nucleic acid as described above;
 (ii) maintaining the host cell under conditions suitable for virus formation; and
 (iii) harvesting the infectious, replication-deficient arenavirus viral vector; wherein the host cell expresses the open reading frame that is deleted or functionally inactivated of the genomic segment.

Also provided herein is a method of producing the arenavirus genomic segment. In certain embodiments, the method comprises transcribing the cDNA of the arenavirus genomic segment.

Also provided herein is a method of generating the arenavirus viral vector. In certain embodiments the method of generating the arenavirus viral vector comprises:
 (i) transfecting into a host cell the cDNA of the arenavirus genomic segment;
 (ii) transfecting into the host cell a plasmid comprising the cDNA of the second arenavirus genomic segment;
 (iii) maintaining the host cell under conditions suitable for virus formation; and
 (iv) harvesting the arenavirus viral vector.

In certain embodiments, the transcription of the L segment and the S segment is performed using a bidirectional promoter.

In certain embodiments, the method further comprises transfecting into a host cell one or more nucleic acids encoding an arenavirus polymerase. In yet more specific embodiments, the polymerase is the L protein. In other embodiments, the method further comprises transfecting into the host cell one or more nucleic acids encoding the NP.

In certain embodiments, transcription of the L segment, and the S segment are each under the control of a promoter selected from the group consisting of:
 (i) a RNA polymerase I promoter;
 (ii) a RNA polymerase II promoter; and
 (iii) a T7 promoter.

Also provided herein is a method of generating the tri-segmented arenavirus viral vector. In certain embodiments the method of generating the tri-segmented arenavirus viral vector comprises:
 (i) transfecting into a host cell one or more cDNAs of one L segment and two S segments;
 (ii) maintaining the host cell under conditions suitable for virus formation; and
 (iii) harvesting the arenavirus viral vector.

Also provided herein is a method of generating the tri-segmented arenavirus viral vector. In certain embodiments the method of generating the tri-segmented arenavirus viral vector comprises:
 (vii) transfecting into a host cell one or more cDNAs of two L segments and one S segment;
 (viii) maintaining the host cell under conditions suitable for virus formation; and
 (ix) harvesting the arenavirus viral vector.

In certain embodiments, the transcription of the one L segment and two S segment is performed using a bidirectional promoter. In some embodiments, the transcription of the two L segments and one S segment is performed using a bidirectional promoter.

In certain embodiments, the method further comprises transfecting into a host cell one or more nucleic acids encoding an arenavirus polymerase. In yet more specific embodiments, the polymerase is the L protein. In other embodiments, the method further comprises transfecting into the host cell one or more nucleic acids encoding the NP protein.

In certain embodiments, transcription of the one L segment, and two S segments are each under the control of a promoter selected from the group consisting of:
 (i) a RNA polymerase I promoter;
 (ii) a RNA polymerase II promoter; and
 (iii) a T7 promoter.

In certain embodiments, transcription of the two L segments, and one S segment are each under the control of a promoter selected from the group consisting of:
 (i) a RNA polymerase I promoter;
 (ii) a RNA polymerase II promoter; and
 (iii) a T7 promoter.

3.6 Pharmaceutical Compositions, Vaccines and Methods of Treatment

In certain embodiments, provided herein is a pharmaceutical composition comprising an arenavirus viral vector as described herein and a pharmaceutically acceptable carrier.

In certain embodiments, provided herein is an immunogenic composition comprising an arenavirus viral vector as described herein and a pharmaceutically acceptable carrier.

In certain embodiments, provided herein is a vaccine comprising an arenavirus viral vector as described herein and a pharmaceutically acceptable carrier.

Still further provided herein is a method of treating or preventing a human papillomavirus infection in a patient. In certain embodiments, the method comprises administering to the patient an arenavirus viral vector as described herein, an pharmaceutical composition as described herein, an immunogenic composition as described herein, or a vaccine as described herein.

In certain embodiments, the method results in a reduction of pre-exisiting HPV titer in the patient.

In certain embodiments, the method induces an antigen specific CD8+ T-cell response in the patient.

In certain embodiments, the HPV infection is symptomatic.

In certain embodiments, the HPV infection is asymptomatic.

In certain embodiments, the method reduces the severity or frequency of, or prevents manifestations of the HPV infection.

In certain embodiments, the manifestation is selected from the group consisting of: cervical cancer, anal cancer, vulvar cancer, vaginal cancer, penile cancer, HPV-positive oropharyngeal cancer (OSCC), common warts, plantar warts, subungual or periungual warts, genital warts, condylomata acuminata or venereal warts, respiratory papillomatosis, and epidermodysplasia verruciformis.

In certain embodiments, provided herein is a method of treating or preventing a human papillomavirus infection in a patient, wherein said method comprises administering to the patient a first viral vector as described herein, a first pharmaceutical composition as described herein, a first immunogenic composition as described herein, or a first vaccine as described herein, and administering to the patient a second viral vector as described herein, a second pharmaceutical composition as described herein, a second immunogenic composition as described herein, or a second vaccine as described herein.

In certain embodiments, provided herein is a method of inducing an immune response in a subject. Such a method can comprise administering to the patient a first arenavirus viral vector described herein, and administering to the patient, after a period of time, a second, different arenavirus viral vector as described herein.

In certain embodiments, the first viral vector, the first pharmaceutical composition, the first immunogenic composition, or the first vaccine, and the second viral vector, the second pharmaceutical composition, the second immunogenic composition, or the second vaccine, are homologous (e.g., derived from the same virus).

In certain embodiments, the first viral vector, the first pharmaceutical composition, the first immunogenic composition, or the first vaccine, and the second viral vector, the second pharmaceutical composition, the second immunogenic composition, or the second vaccine, are heterologous (e.g., derived from the different viruses).

In certain embodiments, the first viral vector, the first pharmaceutical composition, the first immunogenic composition, or the first vaccine, is derived from LCMV, and the second viral vector, the second pharmaceutical composition, the second immunogenic composition, or the second vaccine, is derived from Junin virus.

In certain embodiments, the first viral vector, the first pharmaceutical composition, the first immunogenic composition, or the first vaccine, is derived from Junin virus, and the second viral vector, the second pharmaceutical composition, the second immunogenic composition, or the second vaccine, is derived from LCMV.

In certain embodiments, the first arenavirus viral vector and the second arenavirus viral vector express the same antigen. In certain embodiments, the first arenavirus viral vector and the second arenavirus viral vector express different antigens.

3.7 Conventions and Abbreviations

| Abbreviation | Convention |
| --- | --- |
| APC | Antigen presenting cell |
| art | Artificial |
| C-Cell | Complementing Cell |
| CD4 | Cluster of differentiation 4 |
| CD8 | Cluster of Differentiation 8 |
| CD40L | CD40 ligand |
| CMI | Cell-mediated immunity |
| CRT | Calreticulin |
| FFU | Focus Forming Unit |
| Flt3 | Fms-related tyrosine kinase 3 |
| Flt3L | Fms-related tyrosine kinase 3 ligand |
| GFP | Green Fluorescent Protein |
| GM-CSF or GMCSF | Granulocyte Macrophage Colony Stimulation Factor |
| GP | Glycoprotein |
| HK1 constructs (i.e., name includes HK1) | Obtained or derived from LCMV Clone 13 |
| HPV | Human Papillomavirus |
| IGR | Intergenic region |
| li | invariant chain |
| L protein | RNA-dependent RNA polymerase |
| L segment | Long segment |
| LCMV | Lymphocytic choriomeningitis virus |
| MHC | Major Histocompatibility Complex |
| MOI | Multiplicity of Infection |
| nat | Natural |
| NP | Nucleoprotein |
| ORF | Open Reading Frame |
| OSCC | oropharyngeal squamous cell carcinoma |
| r2LCMV | Recombinant bi-segmented LCMV |
| r3LCMV | Recombinant tri-segmented LCMV |
| r3JUNV | Recombinant tri-segmented Junin virus |
| RFP | Red fluorescent protein |
| S segment | Short segment |
| rJUNV | Recombinant Junin virus |
| rLCMV | Recombinant LCMV |
| TAA | Tumor Associated Antigen |
| Ub | Ubiquitin |
| UTR | Untranslated region |
| VP22 | Herpes simplex virus 1 protein VP22 |
| VSV | Vesicular Stomatitis Virus |
| Z protein | Matrix protein Z |

4. DESCRIPTION OF THE SEQUENCE LISTING

SEQ ID NO: 1 Lymphocytic choriomeningitis virus segment S, complete sequence. The genomic segment is RNA, the sequence in SEQ ID NO:1 is sh SEQ ID NO: 5 Lymphocytic choriomeningitis strain MP segment S, complete sequence. The genomic segment is RNA, the sequence in SEQ ID NO: 5 is shown for DNA; however, exchanging all thymidines ("T") in SEQ ID NO:5 for uridines ("U") provides the RNA sequence.

SEQ ID NO: 6 Amino acid sequence of the NP protein of the MP strain of LCMV.

SEQ ID NO: 7 Amino acid sequence of the GP protein of the MP strain of LCMV.

SEQ ID NO: 8 Amino acid sequence of the L protein of the MP strain of LCMV.

SEQ ID NO: 9 Amino acid sequence of the Z protein of the MP strain of LCMV.

SEQ ID NO: 10 Amino acid sequence of HPV16 E7/E6 fusion protein with mutations in Rb binding site and zinc finger motifs.

SEQ ID NO: 11 Amino acid sequence of HPV16 E7/E6 fusion protein with mutations in Rb binding site and zinc finger motifs, linked to mouse Calreticulin.

SEQ ID NO: 12 Amino acid sequence of HPV16 E7/E6 fusion protein with mutations in Rb binding site and zinc finger motifs, linked to mouse Ubiquitin.

SEQ ID NO: 13 Amino acid sequence of HPV16 E7/E6 fusion protein with mutations in Rb binding site and zinc finger motifs, co-expressed with mouse GM-CSF, separated by a nucleotide sequence that encodes a self-cleaving peptide (2A peptide).

SEQ ID NO: 14 Nucleotide sequence encoding HPV16 E7/E6 fusion protein with mutations in Rb binding site and zinc finger motifs.

SEQ ID NO: 15 Nucleotide sequence encoding HPV16 E7/E6 fusion protein with mutations in Rb binding site and zinc finger motifs, linked to mouse Calreticulin.

SEQ ID NO: 16 Nucleotide sequence encoding HPV16 E7/E6 fusion protein with mutations in Rb binding site and zinc finger motifs, linked to mouse Ubiquitin.

SEQ ID NO: 17 Nucleotide sequence encoding HPV16 E7/E6 fusion protein with mutations in Rb binding site and zinc finger motifs, co-expressed with mouse GM-CSF, separated by a nucleotide sequence that encodes a self-cleaving peptide (2A peptide).

SEQ ID NO: 18 GSG.

SEQ ID NO: 19 Junin virus Candid #1 L segment.

SEQ ID NO: 20 Junin virus Candid #1 S segment.

SEQ ID NO: 21 Nucleotide sequence of HK1-E7E6-GMCSF

SEQ ID NO: 22 Amino acid sequence of E7E6-GMCSF antigen

SEQ ID NO: 23 Nucleotide sequence of HK1-E7E6-VP22

SEQ ID NO: 24 Amino acid sequence of E7E6-VP22 antigen

SEQ ID NO: 25 Nucleotide sequence of HK1-E7E6-CD40L

SEQ ID NO: 26 Amino acid sequence of E7E6-CD40L antigen

SEQ ID NO: 27 Nucleotide sequence of HK1-Flt3L-E7E6

SEQ ID NO: 28 Amino acid sequence of Flt3L-E7E6 antigen

SEQ ID NO: 29 Nucleotide sequence of HK1-Flt3L-E7E6shuffle

SEQ ID NO: 30 Amino acid sequence of Flt3L-E7E6shuffle antigen

SEQ ID NO: 31 Nucleotide sequence of HK1-li-E7E6

SEQ ID NO: 32 Amino acid sequence of li-E7E6 antigen

SEQ ID NO: 33 Nucleotide sequence encoding a HPV16E7-HPV18E6 fusion protein having an N-terminal VSVG signal sequence and a C-terminal GSG linker followed by a self-cleaving peptide (2A peptide from Porcine Teschovirus) and the CDS for human GM-CSF.

SEQ ID NO: 34 Amino acid sequence of a HPV16E7-HPV18E6 fusion protein having an N-terminal VSVG signal sequence and a C-terminal GSG linker followed by a self-cleaving peptide (2A peptide from Porcine Teschovirus) and the CDS for human GM-CSF.

SEQ ID NO: 35 Nucleotide sequence encoding a HPV18E7-HPV16E6 fusion protein having an N-terminal VSVG signal sequence and a C-terminal GSG linker followed by a self-cleaving peptide (2A peptide from Porcine Teschovirus) and the CDS for human GM-CSF.

SEQ ID NO: 36 Amino acid sequence of a HPV18E7-HPV16E6 fusion protein having an N-terminal VSVG signal sequence and a C-terminal GSG linker followed by a self-cleaving peptide (2A peptide from Porcine Teschovirus) and the CDS for human GM-CSF SEQ ID NO: 37 Nucleotide sequence encoding a HPV16E7-HPV18E6 HPV16E6-HPV18E7 fusion protein having an N-terminal VSVG signal sequence and a C-terminal GSG linker followed by a self-cleaving peptide (2A peptide from Porcine Teschovirus) and the CDS for human GM-CSF.

SEQ ID NO: 38 Amino acid sequence of a HPV16E7-HPV18E6 HPV16E6-HPV18E7 fusion protein having an N-terminal VSVG signal sequence and a C-terminal GSG linker followed by a self-cleaving peptide (2A peptide from Porcine Teschovirus) and the CDS for human GM-CSF.

SEQ ID NO: 39 Nucleotide sequence of a tri-segmented r3LCMVart-based vector expressing HPV16 E7E6 fusion protein: S segment 1 (containing GP).

SEQ ID NO: 40 Nucleotide sequence of a tri-segmented r3LCMVart-based vector expressing HPV16 E7E6 fusion protein: S segment 2 (containing GP).

SEQ ID NO: 41 Nucleotide sequence of a tri-segmented r3LCMVart-based vector expressing HPV16 E7E6 fusion protein: L segment.

SEQ ID NO: 42 Nucleotide sequence of a tri-segmented r3JUNVart-based vector expressing the HPV16 E7E6 fusion protein: S segment 1 (containing NP).

SEQ ID NO: 43 Nucleotide sequence of a tri-segmented r3JUNVart-based vector expressing the HPV16 E7E6 fusion protein: S segment 2 (containing GP).

SEQ ID NO: 44 Nucleotide sequence of a tri-segmented r3JUNVart-based vector expressing the HPV16 E7E6 fusion protein: L segment.

5. BRIEF DESCRIPTION OF THE FIGURES

FIG. 1A: The genome of wild type arenaviruses consists of a short (1; ~3.4 kb) and a large (2; ~7.2 kb) RNA segment. The short segment carries open reading frames encoding the nucleoprotein (3) and glycoprotein (4). The large segment encodes the RNA-dependent RNA polymerase L (5) and the matrix protein Z (6). Wild type arenaviruses can be rendered replication-deficient vaccine vectors by deleting the glycoprotein gene and inserting, instead of the glycoprotein gene, antigens of choice (7) against which immune responses are to be induced.

Figure 1B:
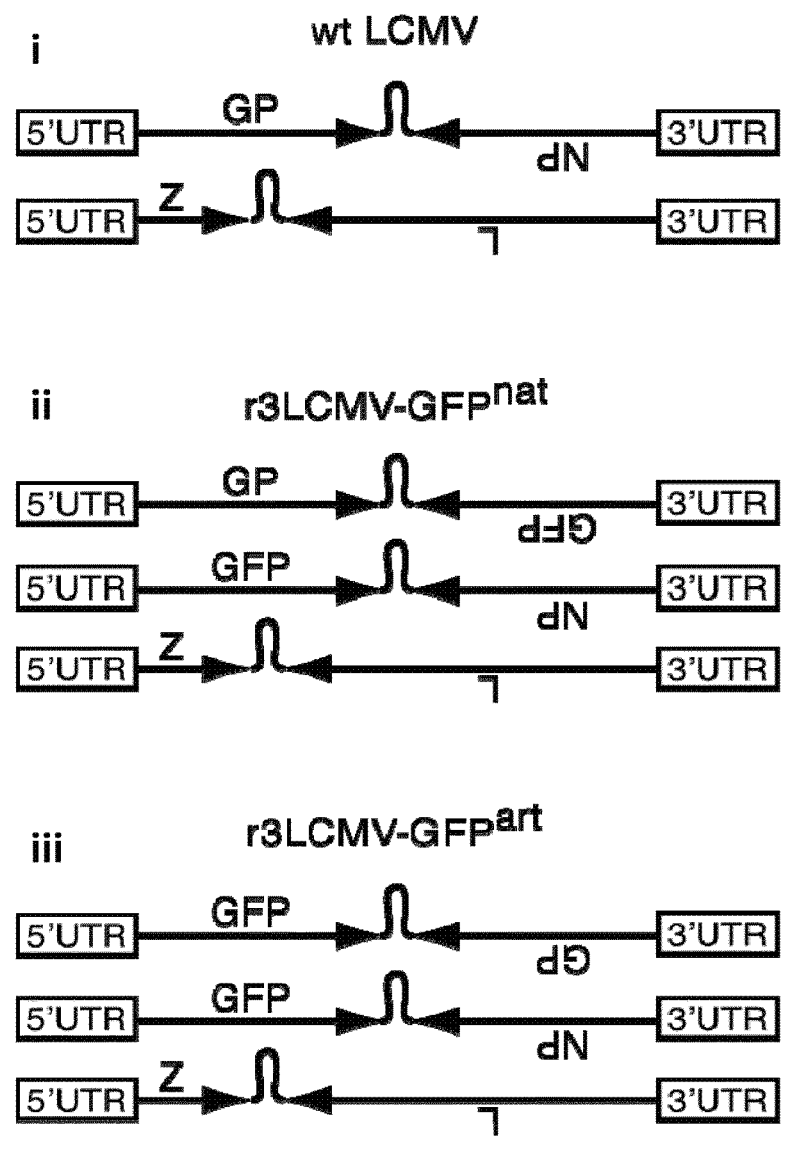

FIG. 1B: Schematic representation of the genomic organization of bi- and tri-segmented LCMV. The bi-segmented genome of wild-type LCMV consists of one S segment encoding the GP and NP and one L segment encoding the Z protein and the L protein (i). Both segments are flanked by the respective 5' and 3' UTRs. The genome of recombinant tri-segmented LCMVs (r3LCMV) consists of one L and two S segments with one position where to insert a gene of interest (here GFP) into each one of the S segments. r3LCMV-GFP$^{natural}$ (nat) has all viral genes in their natural position (ii), whereas the GP ORF in r3LCMV-GFP$^{artificial}$ (art) is artificially juxtaposed to and expressed under control of the 3' UTR (iii).

Figure 2A:
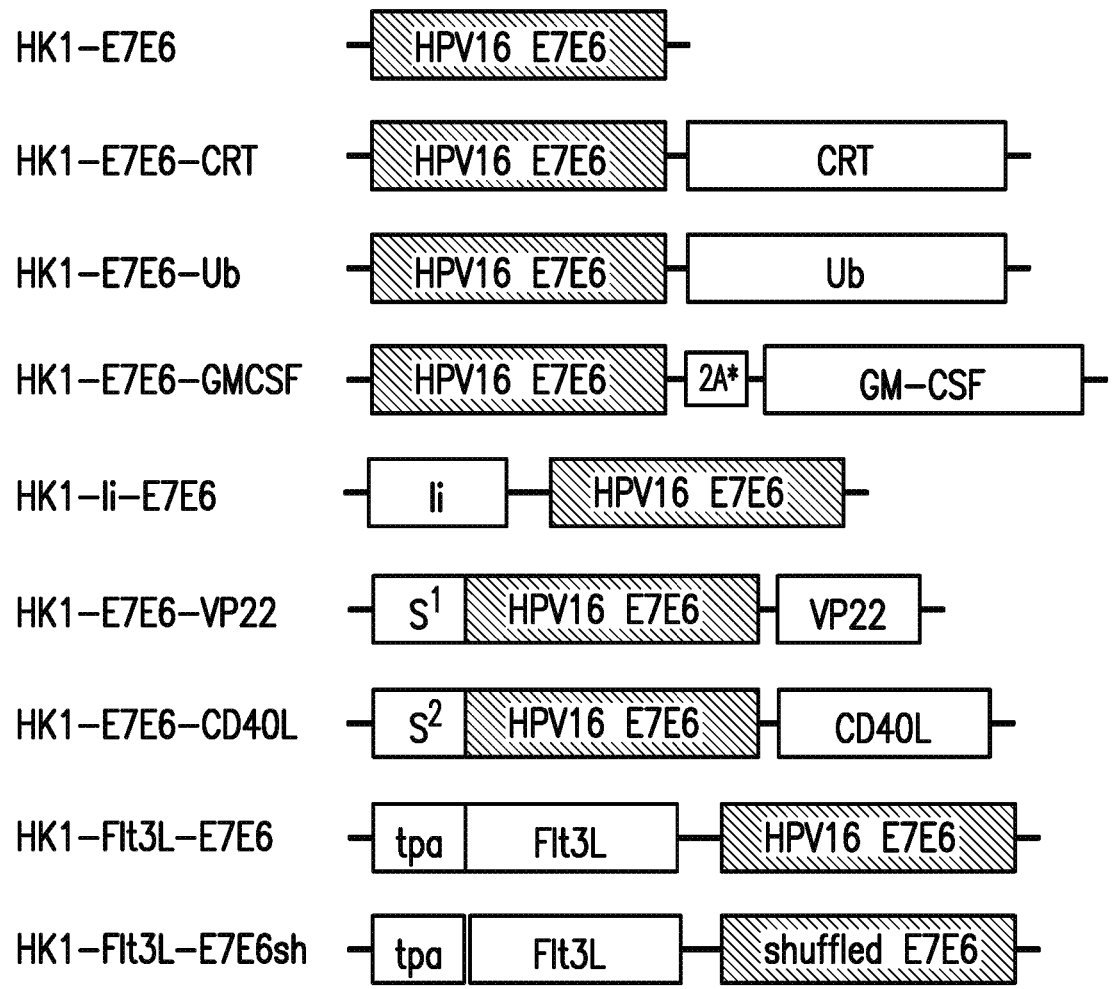
Figure 2B:
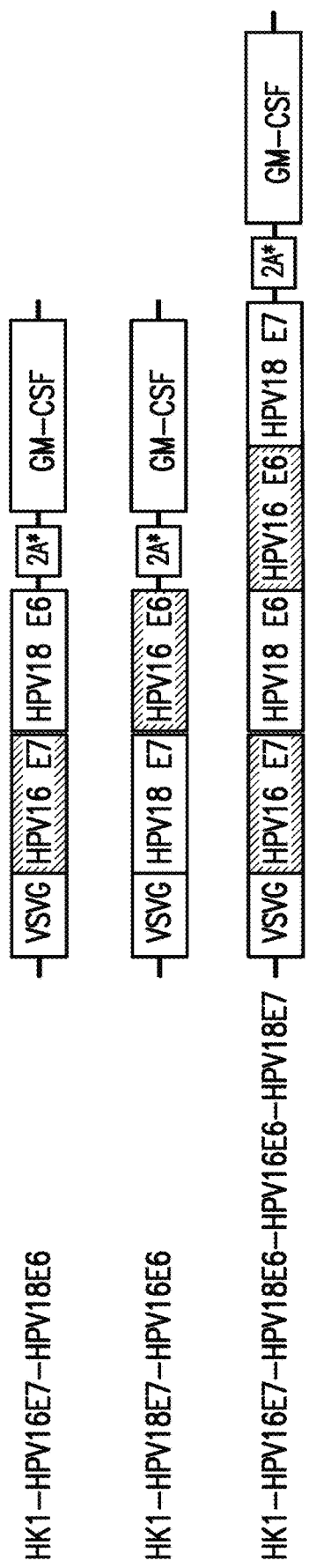

FIGS. 2A and 2B: Different vector constructs are generated for the expression of HPV antigens and combinations of HPV antigens, alone or in combination with various immunomodulatory peptides, polypeptides, or proteins. CRT: Calreticulin; Ub: Ubiquitin; GM-CSF: Granulocyte-macrophage colony-stimulating factor; Ii: invariant chain; S$^1$: secretion signal from human tyrosinase; VP22: Herpes simplex virus 1 protein VP22; S$^2$: secretion signal from human growth hormone; CD40L: CD40 ligand; tpa: signal sequence of tissue plasminogen activator, Flt3L: Fms-related tyrosine kinase 3 ligand; sh: shuffled E7E6 sequence according to Kim et al., *Nat. Commun.* 2014; VSVG: signal sequence of Vesicular Stomatitis Virus G glycoprotein.

Figure 3:
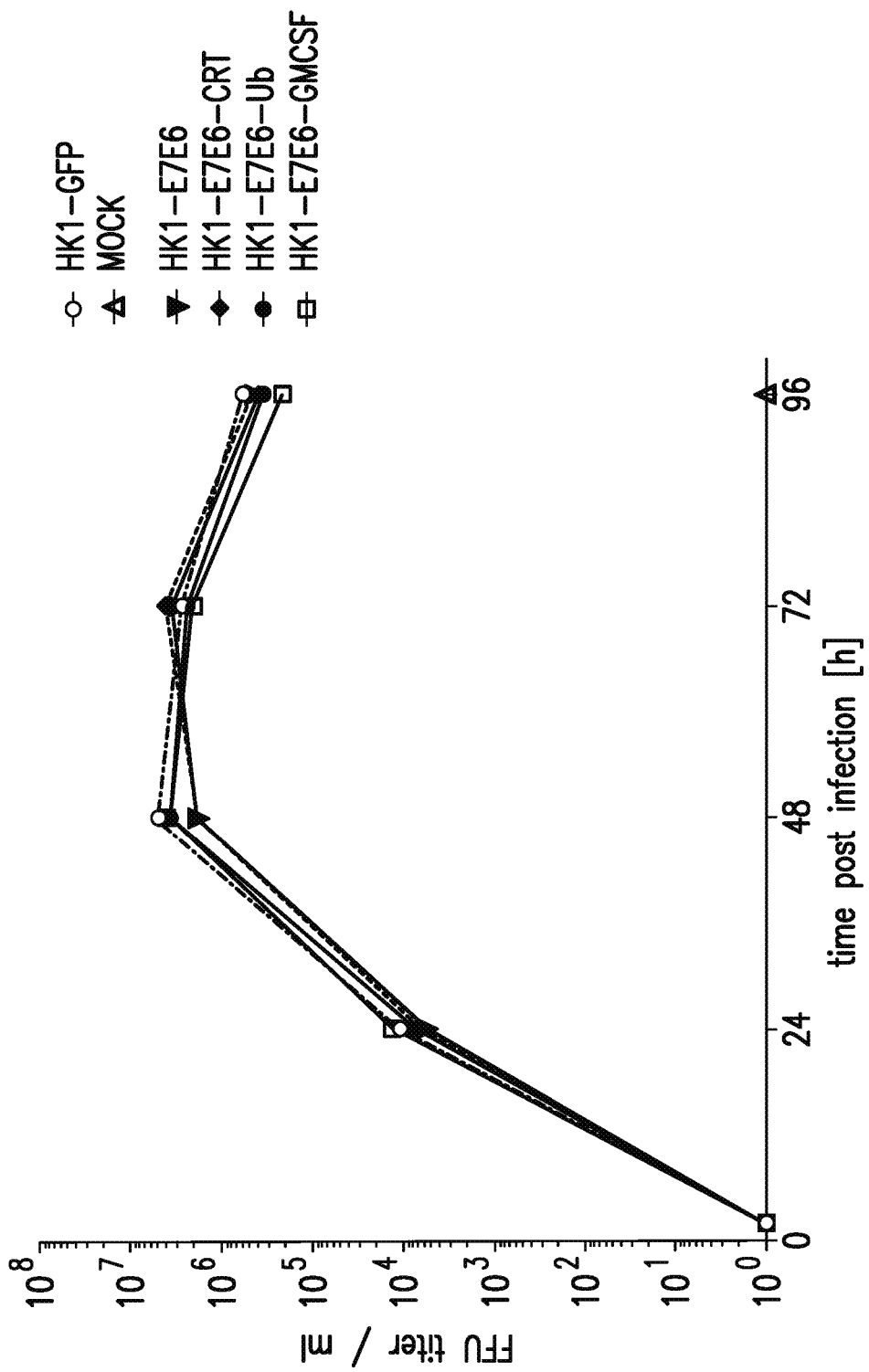

FIG. 3: In order to analyze vector replication, growth curves were performed using suspension 293 cells expressing LCMV GP. Respective cells were seeded with cell density of 3×10$^5$ cells/ml and infected with individual vectors (HK1-E7E6, HK1-E7E6-CRT, HK1-E7E6-Ub and HK1-E7E6-GMCSF) at MOI of 0.001. A corresponding rLCMV vector expressing the green-fluorescent-protein (HK1-GFP) was used as control. Samples were drawn every 24 hours and analyzed by Focus Forming Units assay. All tested vectors exhibited similar growth kinetics and peak titers compared to HK1-GFP indicating that the individual E7E6 transgenes did not interfere with vector replication to a greater extent than the reporter gene GFP.

Figure 4:
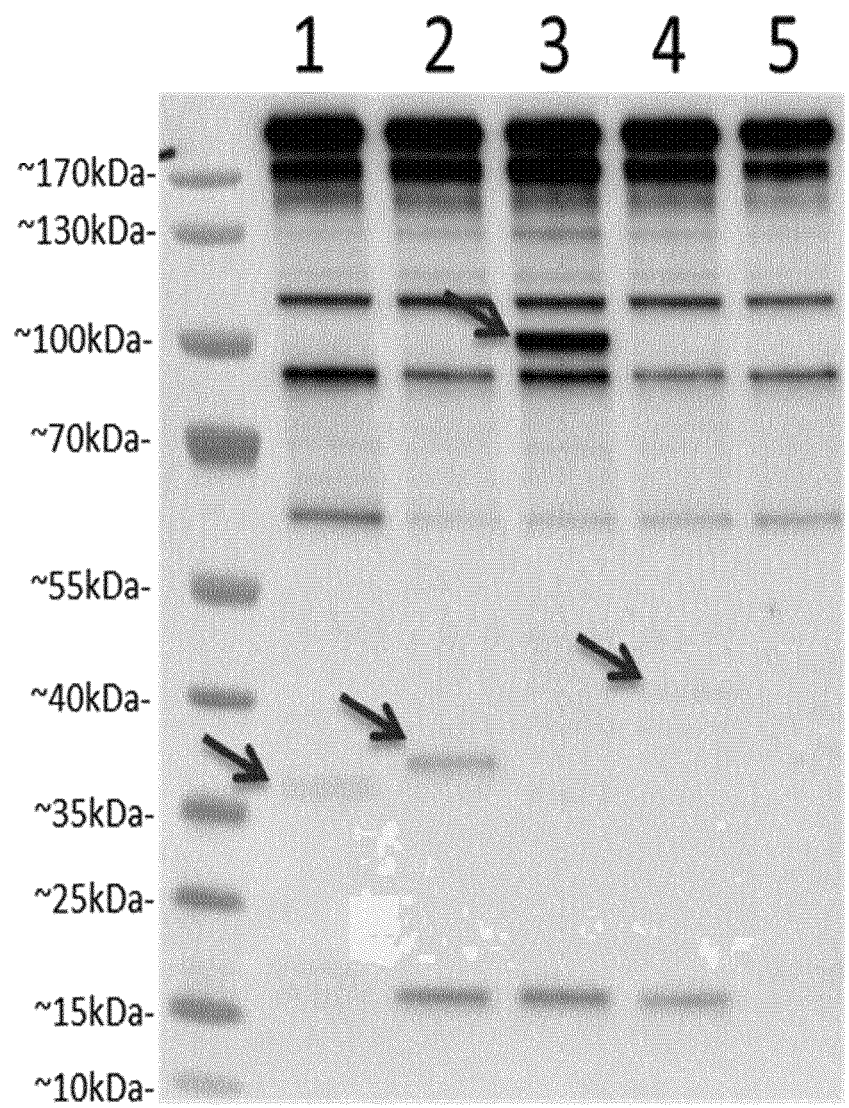

FIG. 4: HEK 293 cells expressing LCMV GP were infected with individual constructs (HK1-E7E6 (group 1), HK1-E7E6-GMCSF (group 2), HK1-E7E6-CRT (group 3) and HK1-E7E6-Ub (group 4)) at a multiplicity of infection (MOI) of 0.001 or a HK1-GFP control vector (group 5). Cells were analyzed 96 h post infection. Proteins were separated on SDS gels, transferred to nitrocellulose membranes and HPV E7 protein expression was detected with anti HPV E7 antibody and appropriate secondary antibody. Expected sizes of transgenes were calculated based on the Science Gateway Protein Molecular Weight Calculator (HK1-E7E6: ~30 kDa; HK1-mE7E6-GMCSF: ~48 kDa/30 kDa; HK1-mE7E6-CRT: ~78 kDa; HK1-mE7E6-Ub: ~38 kDa). Specific bands, indicated by red arrows, were detected for all tested constructs, however, significantly different expression levels were observed, with HK1-E7E6 and HK1-E7E6-Ub-infected cells exhibiting the lowest antigen levels.

Figure 5:
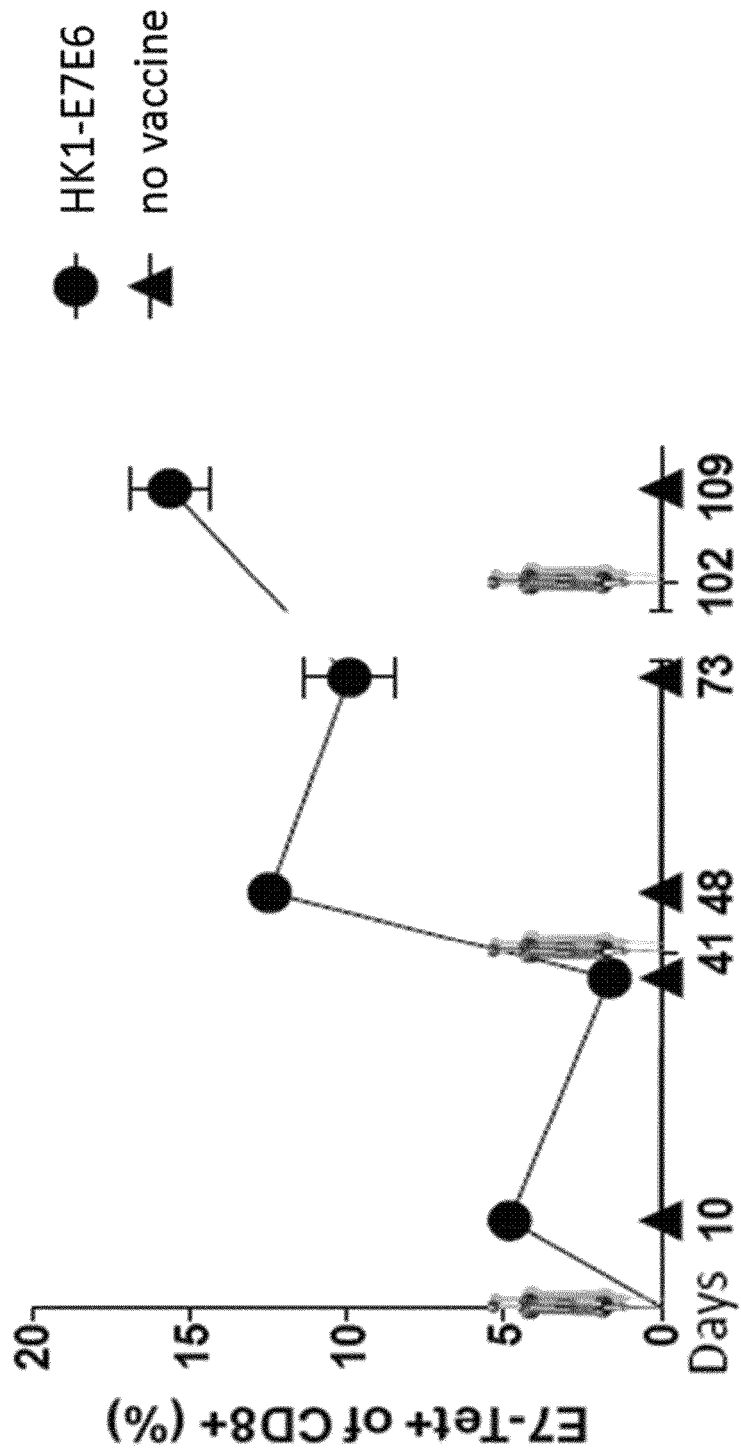

FIG. 5: C57BL/6 mice (n=5 per group) were immunized three times on days 0, 41 and 102 by intravenous injection of 2-8×10$^5$ FFU (prime: 2×10$^5$, boost: 8×10$^5$) of HK1-E7E6. E7-specific CD8+ T cell responses were subsequently analyzed by tetramer staining (H-2Db/HPV16 E7 49-57 (RAHYNIVTF)) from blood on days 10, 38, 48, 73 and 109 of the experiment. The percentage of tetramer-binding CD8+ T cells is expressed as a percentage of the total CD8+ T cell pool. Symbols show the mean+/−SEM of five mice.

Figure 6:
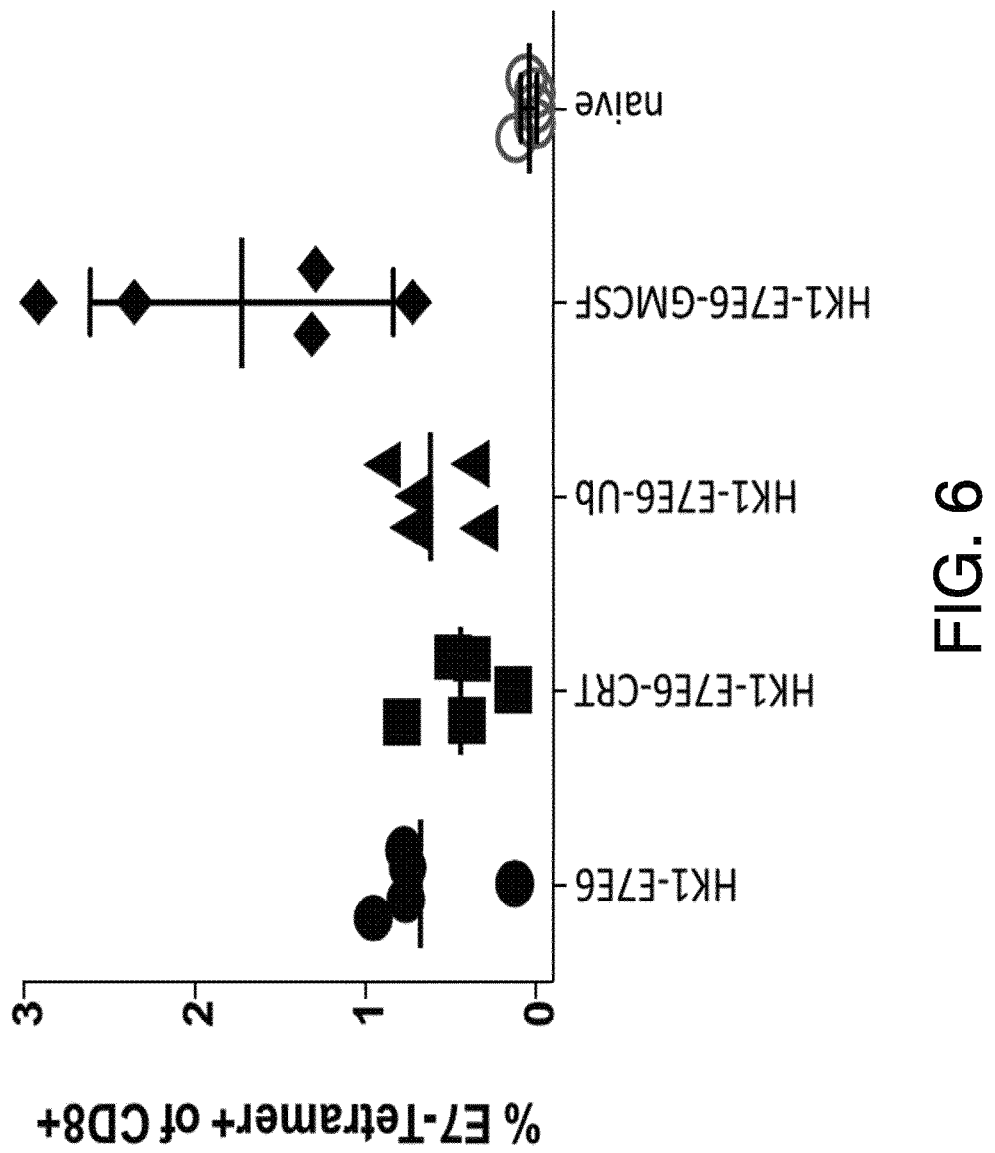

FIG. 6: C57BL/6 mice (n=5 per group) were immunized once by intravenous injection of 1×10$^4$ FFU of HK1-E7E6, HK1-E7E6-CRT, HK1-E7E6-Ub and HK1-E7E6-GMCSF. Naïve mice were used as control. E7-specific CD8+ T cell responses were subsequently analyzed by tetramer staining (H-2Db/HPV16 E7 49-57 (RAHYNIVTF)) on day 9 after immunization. The percentage of tetramer-binding CD8+ T cells is expressed as a percentage of the total CD8+ T cell pool.

Figure 7A:
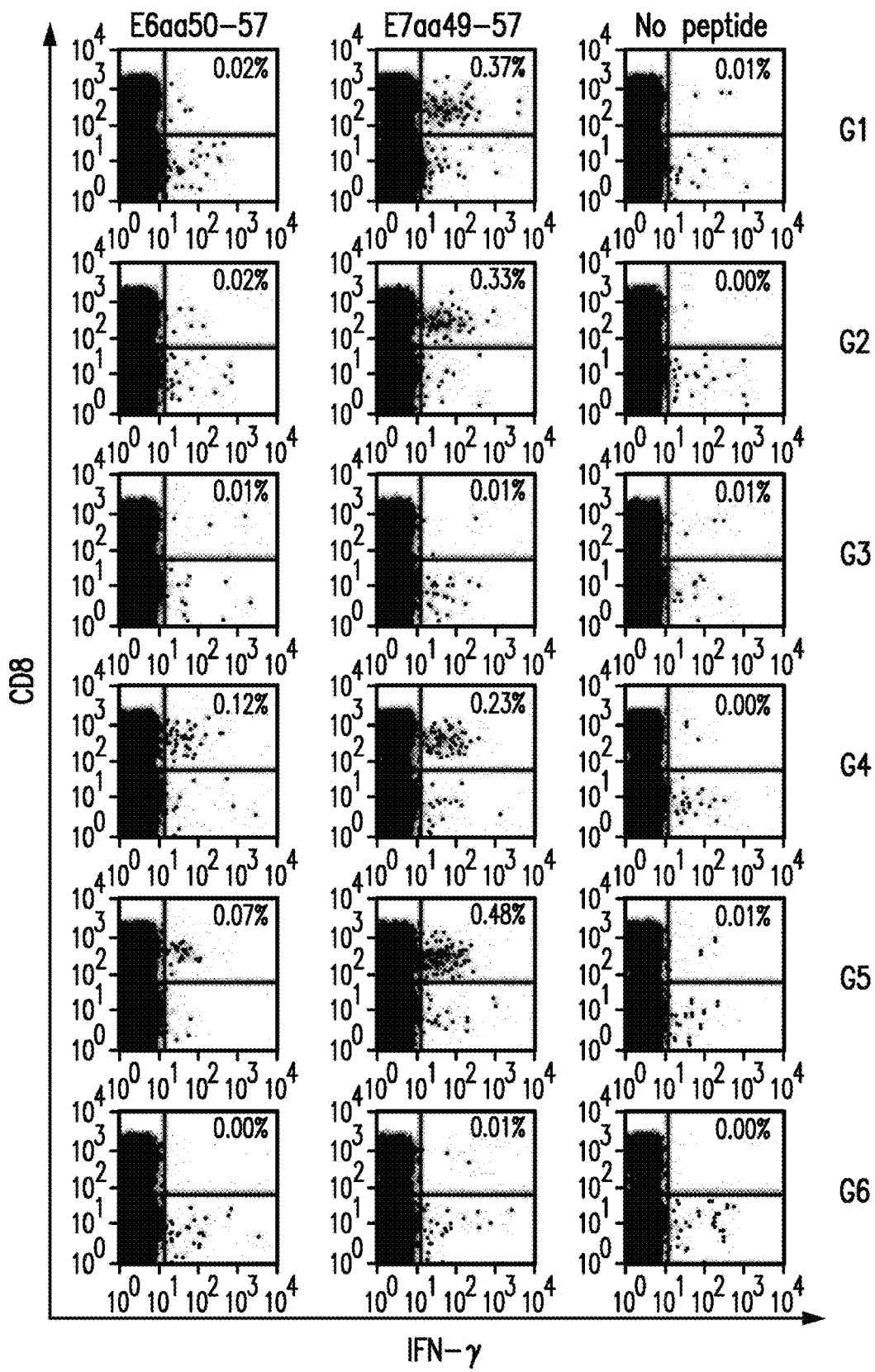
Figure 7B:
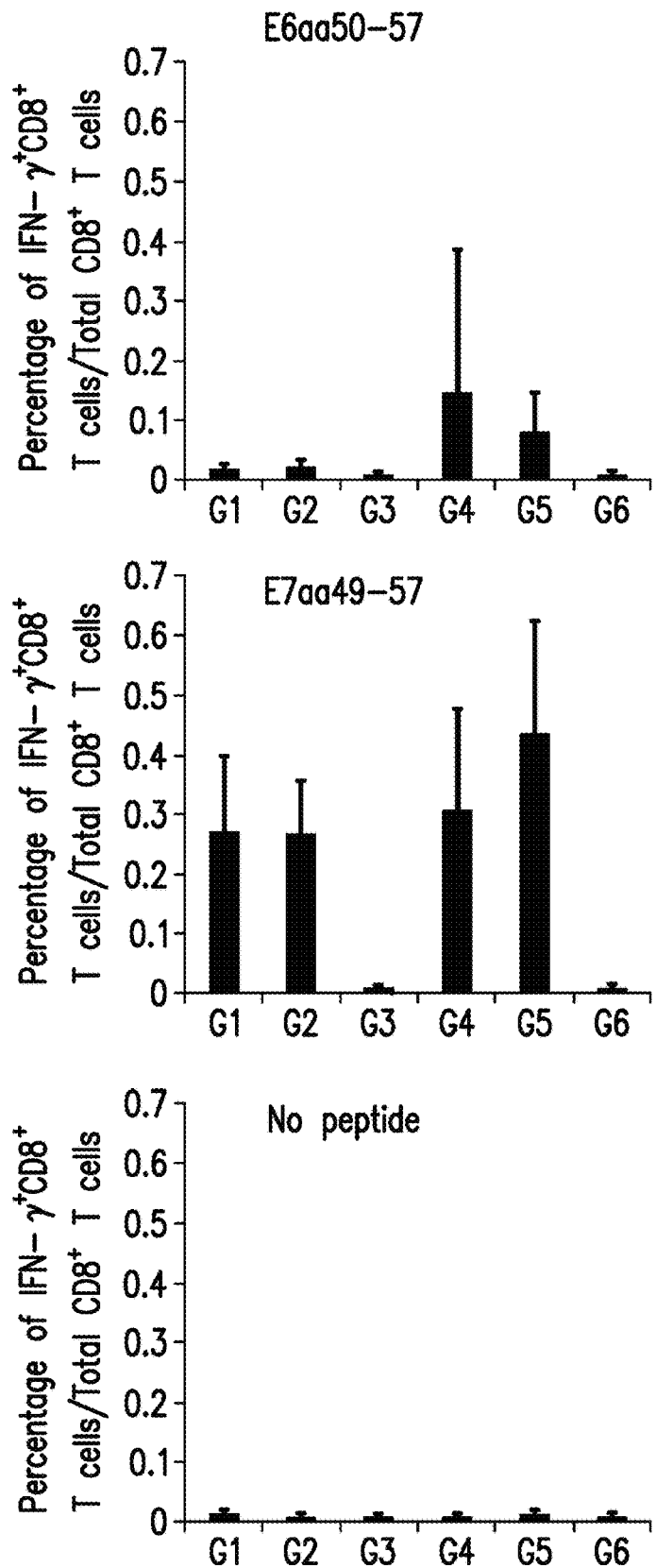

FIGS. 7A and 7B: C57BL/6 mice (n=5 per group) were immunized twice on days 0 and 28 by intramuscular injection of 1×10$^5$ FFU of HK1-E7E6 (groups 1 and 2), HK1-GFP (group 3), or HK1-E7E6-GMCSF (group 5), or 1×10$^7$ PFU of Ad5-E7E6 (group 4). Control mice (group 6) received two injections of 0.9% NaCl on days 0 and 28. 7 days after the last vaccination, splenocytes from immunized mice were isolated and stimulated with either HPV16 E6aa50-57 peptide or E7aa49-57 peptide (all at 1 µg/ml) at the presence of GolgiPlug (1 µl/ml) at 37° C. overnight. The cells were stained with PE-conjugated anti-mouse CD8a antibody, washed, permeabilized and fixed with CytoFix/CytoPerm. Subsequently, cells were washed and intracellularly stained with FITC-conjugated anti-mouse IFN-γ antibody. After wash, cells were acquired with FACSCalibur and analyzed with CellQuest software. FIG. 7A. Representative flow cytometry images. FIG. 7B. Summary of the flow cytometry data.

Figure 8:
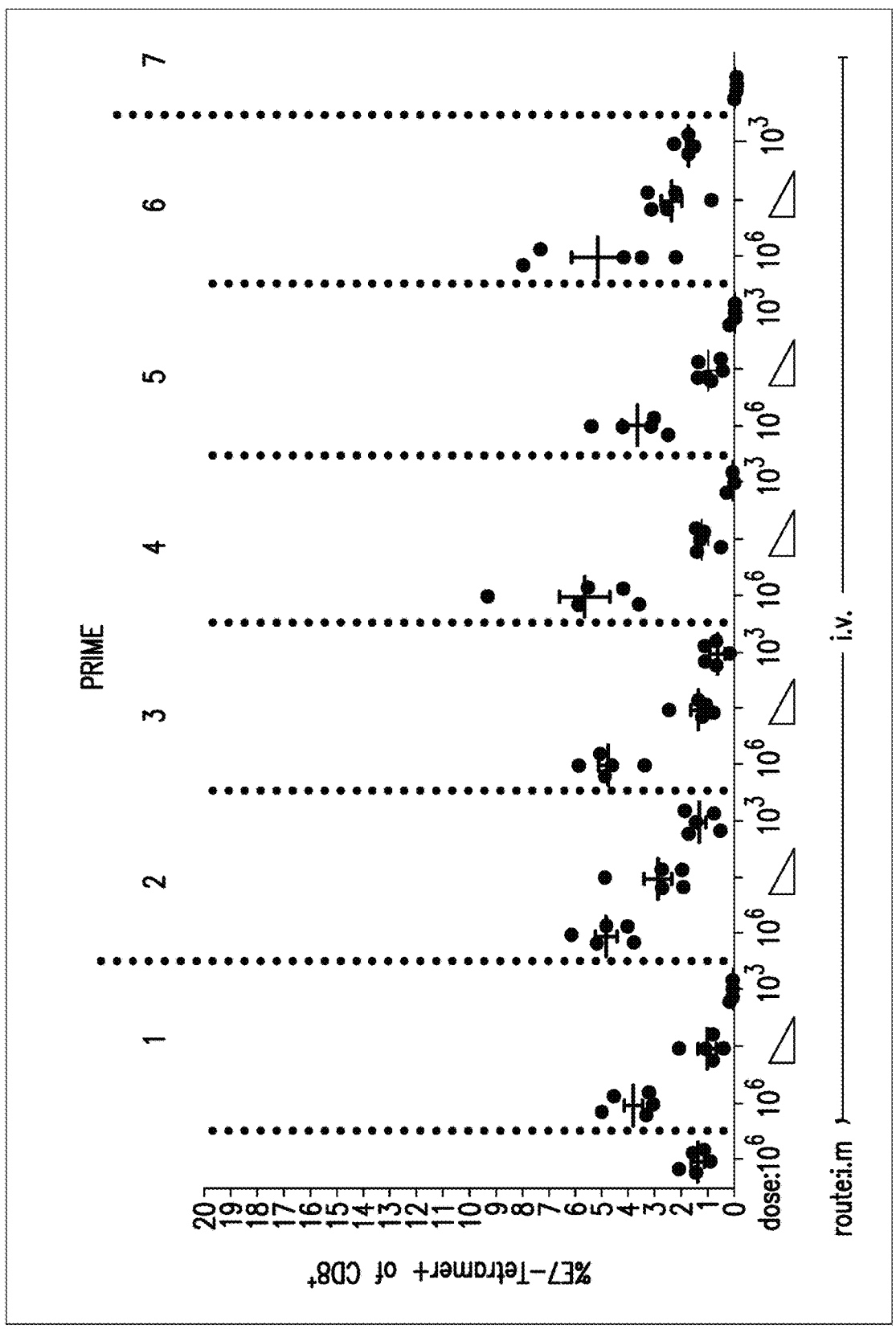
Figure 8:
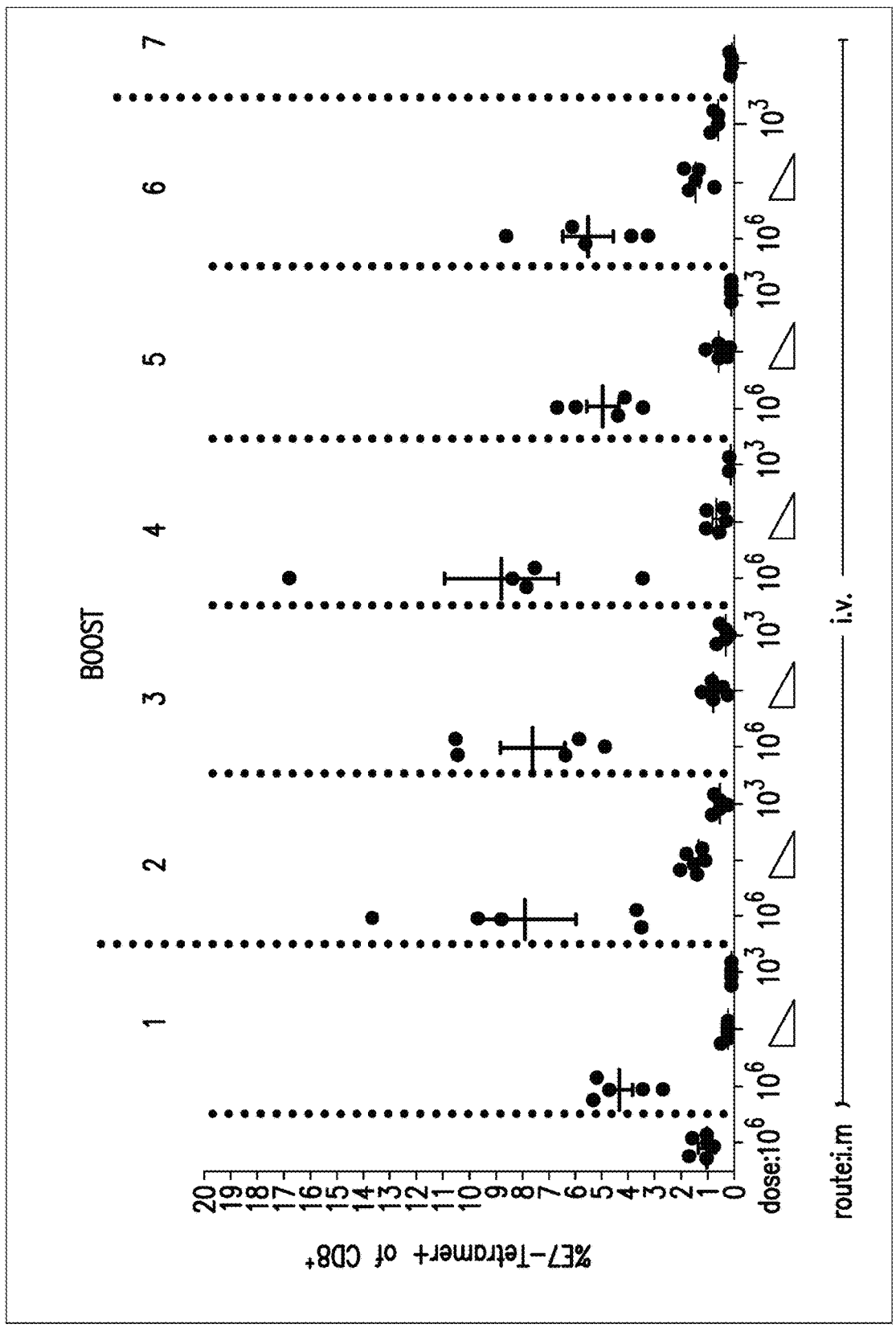

FIG. 8: C57BL/6 mice were immunized twice on days 0 and 10 by intravenous (i.v.) or intramuscular (i.m.) injection (as indicated) using different doses (10$^3$, 3×10$^4$, 10$^6$ FFU) of HK1-E7E6-GMCSF (1), HK1-E7E6-VP22 (2), HK1-E7E6-CD40L (3), HK1-Flt3L-E7E6 (4), HK1-Flt3L-E7E6shuffle (5), HK1-li-E7E6 (6), or formulation buffer (mock infected) (7). E7-specific CD8+ T cell responses were subsequently analyzed by tetramer staining (H-2Db/HPV16 E7 49-57 (RAHYNIVTF)) on days 8 and 18 of the experiment. The percentage of tetramer-binding CD8+ T cells is expressed as a percentage of the total CD8+ T cell pool.

Figure 9A:
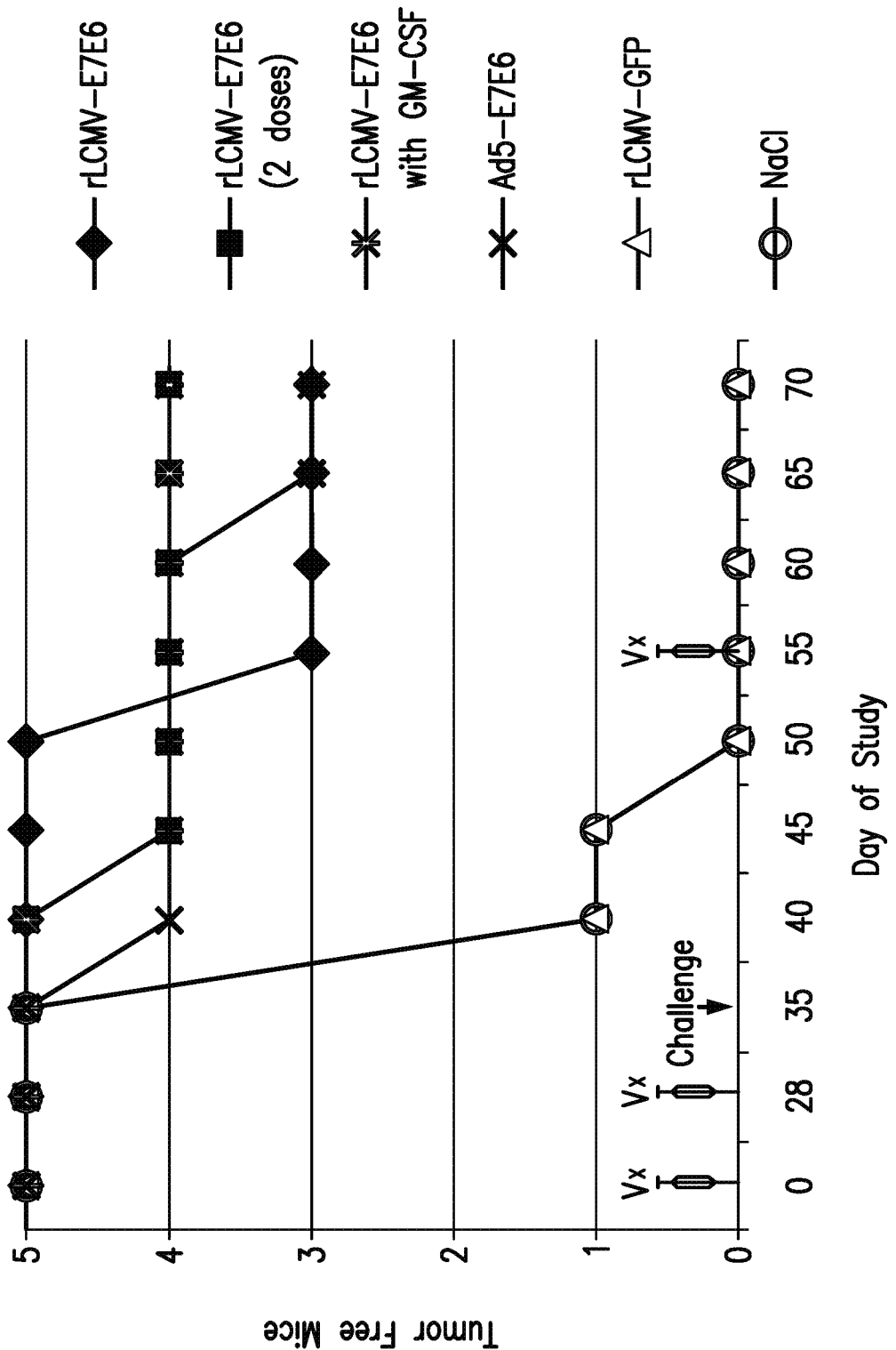
Figure 9B:
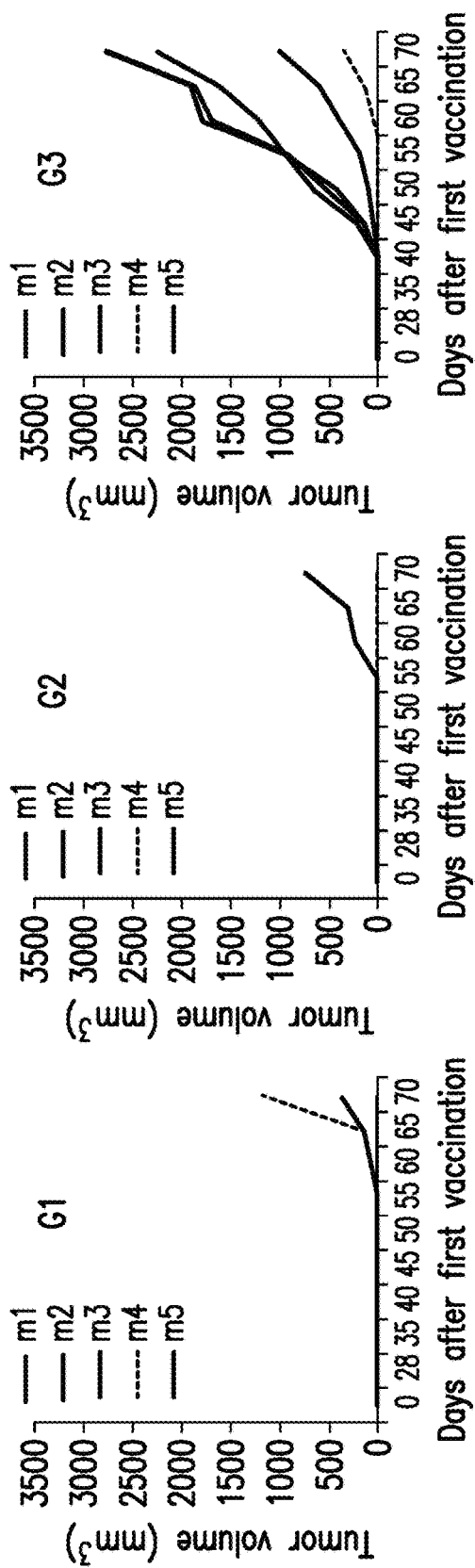
Figure 9B:
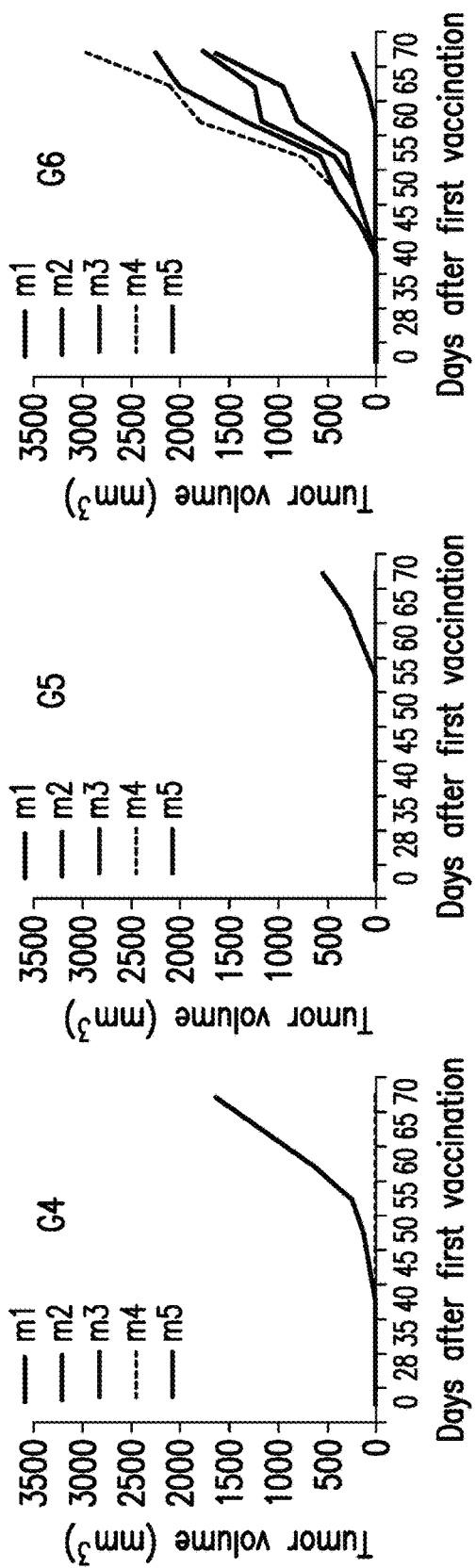

FIGS. 9A and 9B: C57BL/6 mice (n=5 per group) were immunized twice on days 0 and 28 by intramuscular injection with 1×10$^5$ FFU of HK1-E7E6 (groups 1 and 2), HK1-GFP (group 3), or HK1-E7E6-GMCSF (group 5), or 1×10$^7$ PFU of Ad5-E7E6 (group 4). Control mice (group 6) received two injections of 0.9% NaCl on days 0 and 28. On day 55, mice from groups 1, 3, 4, 5 and 6 were further boosted with the same regimen. On day 35, the mice were injected with 5×10$^4$ of TC-1 tumor cells subcutaneously. Tumor growth was monitored by palpitation twice a week. FIG. 9A. Number of tumor free animals. FIG. 9B. Tumor size measured with a digital caliper. Tumor volume was calculated with the following formula: [largest diameter× (perpendicular diameter)$^2$]×3.14/6.

Figures 10A, 10B:
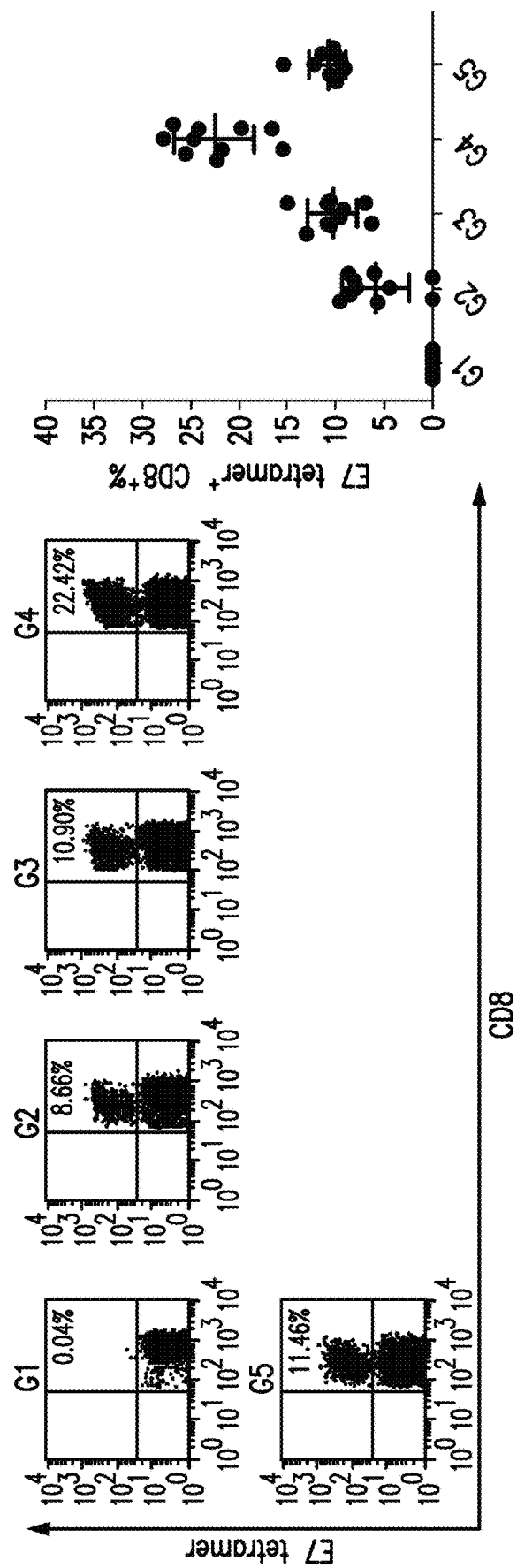

FIGS. 10A-10D: Analysis of E7-specific CD8+ T cells in peripheral blood of TC-1 tumor-bearing mice after vaccination. 5~8 weeks old female C57BL/6 mice (10 mice/group) were injected with 1×10$^5$ of TC-1 tumor cells on day 1. The tumor-bearing mice were then vaccinated intravenously via the retro-orbital route on days 4 and 14 with PBS (G1), 10$^6$ FFU HK1-E7E6 (G2), 10$^6$ FFU HK1-E7E6-GMCSF (G3), 10$^6$ FFU HK1-E7E6-CD40L (G4), 10$^5$ FFU r3LCMV-E7E6 (G5). On day 13 and 23, PBMCs were harvested from blood sampled via the tail vein and E7-specific CD8+ T cell responses were analyzed by tetramer staining (HPV16 E7aa49-57 peptide loaded H-2D$^b$ tetramer). FIG. 10A. Representative flow cytometry image of HPV16 E7 tetramer staining of day 13 PBMCs. FIG. 10B. Summary of HPV16 E7 tetramer (+) CD8(+) T cells in the day 13 peripheral blood. FIG. 10C. Representative flow cytometry image of HPV16 E7 tetramer staining of day 23 PBMCs. FIG. 10D. Summary of HPV16 E7 tetramer (+) CD8(+) T cells in the day 23 peripheral blood.

Figures 11A, 11B:
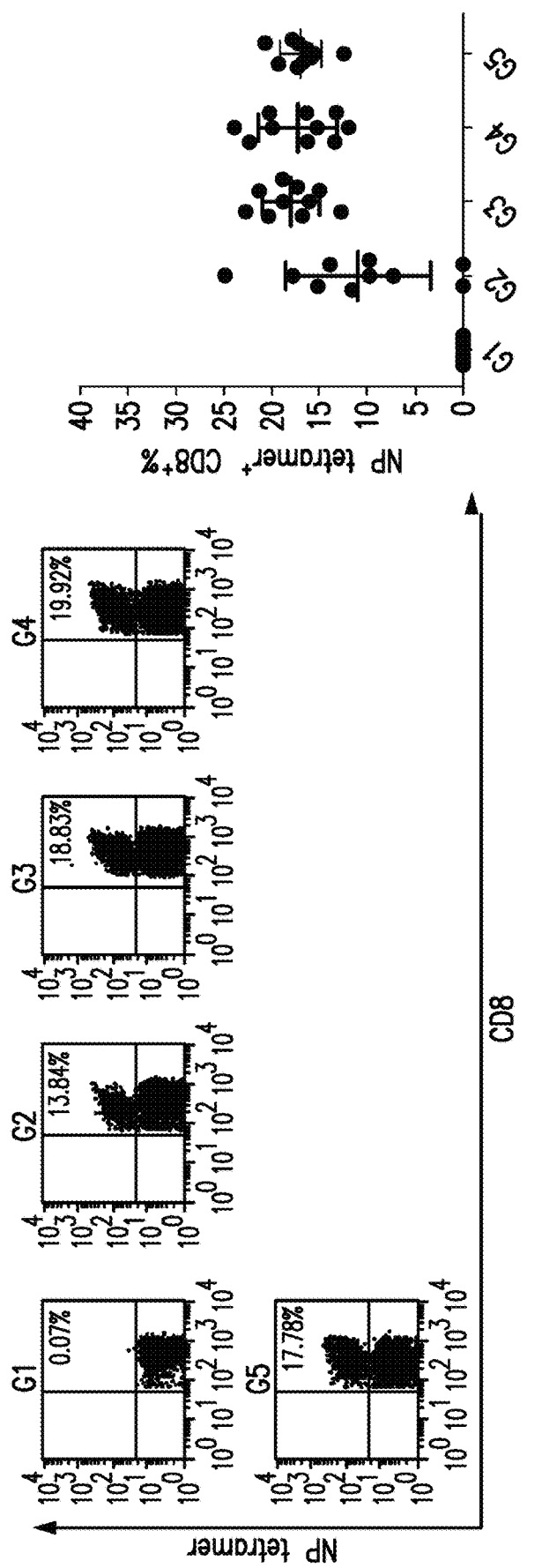
Figures 11C, 11D:
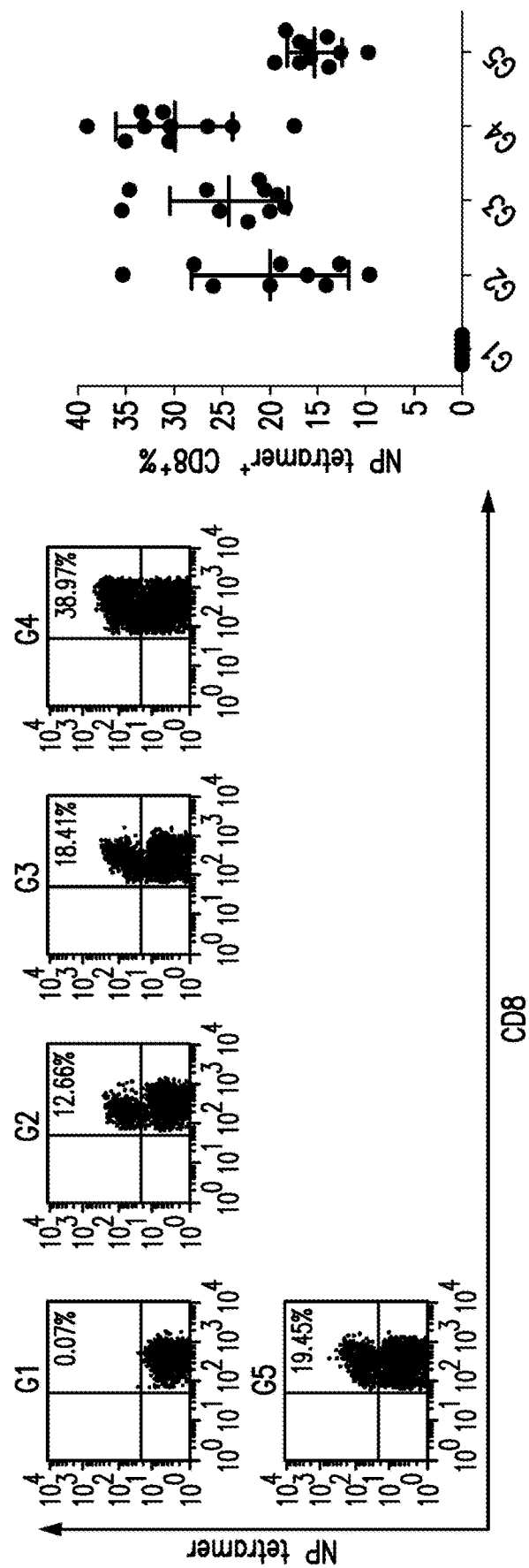

FIGS. 11A-11D: Analysis of NP-specific CD8+ T cells in peripheral blood of TC-1 tumor-bearing mice after vaccination. 5~8 weeks old female C57BL/6 mice (10 mice/group) were injected with 1×10$^5$ of TC-1 tumor cells on day 1. The tumor-bearing mice were then vaccinated intravenously via the retro-orbital route on days 4 and 14 with PBS (G1), $10^6$ FFU HK1-E7E6 (G2), $10^6$ FFU HK1-E7E6-GMCSF (G3), $10^6$ FFU HK1-E7E6-CD40L (G4), $10^5$ FFU r3LCMV-E7E6 (G5). On day 13 and 23, PBMCs were harvested blood sampled via the from tail vein and LCMV NP-specific CD8+ T cell responses were analyzed by tetramer staining (LCMV NP peptide loaded H-2D$^b$ tetramer). FIG. 11A. Representative flow cytometry image of LCMV NP tetramer staining of day 13 PBMCs. FIG. 11B. Summary of LCMV NP tetramer (+) CD8(+) T cells in the day 13 peripheral blood. FIG. 11C. Representative flow cytometry image of LCMV NP tetramer staining of day 23 PBMCs. FIG. 11D. Summary of LCMV NP tetramer (+) CD8(+) T cells in the day 23 peripheral blood.

Figure 12A:
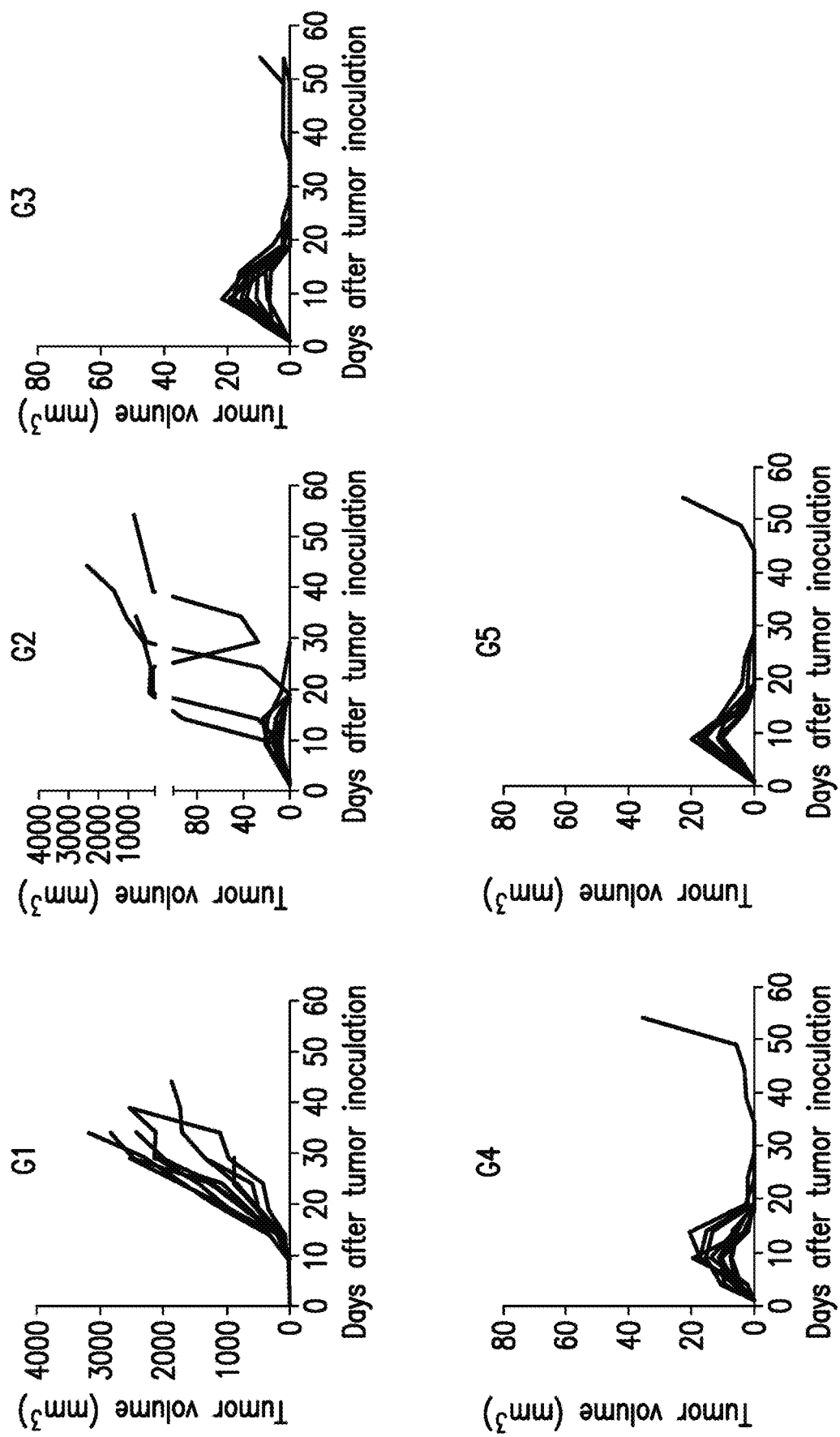
Figure 12B:
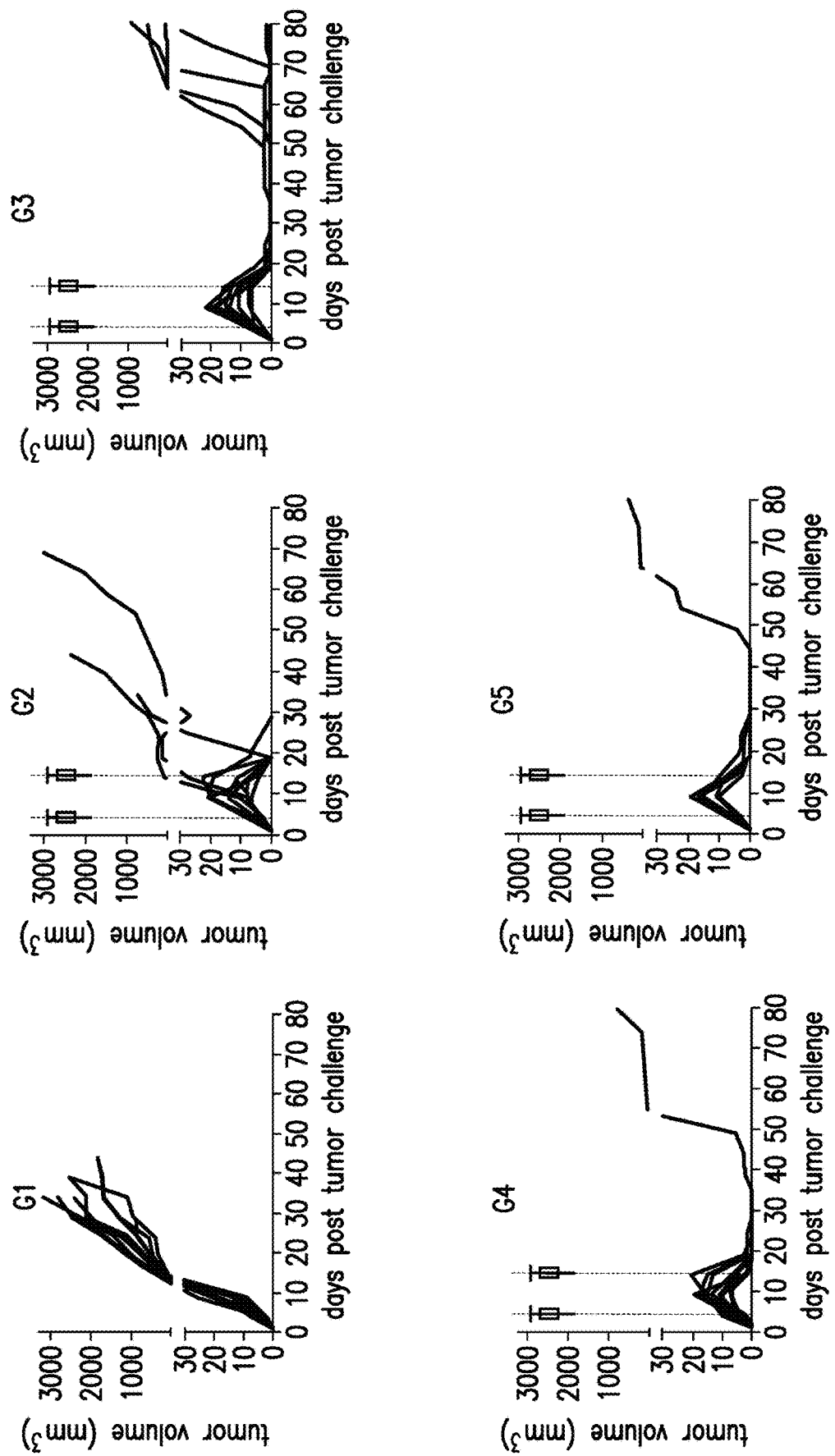
Figure 12C:
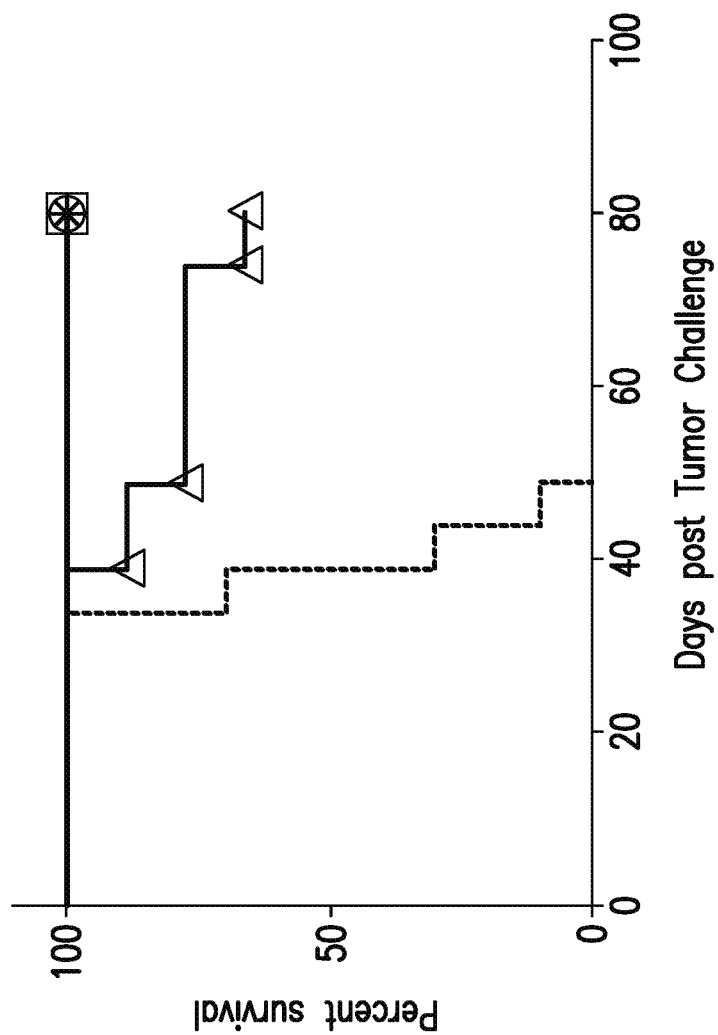

FIGS. 12A-12C: 5~8 weeks old female C57BL/6 mice (10 mice/group) were injected with $1 \times 10^5$ of TC-1 tumor cells on day 1. The tumor-bearing mice were then vaccinated intravenously via the retro-orbital route on days 4 and 14 with PBS (G1), $10^6$ FFU HK1-E7E6 (G2), $10^6$ FFU HK1-E7E6-GMCSF (G3), $10^6$ FFU HK1-E7E6-CD40L (G4), $10^5$ FFU r3LCMV-E7E6 (G5). FIGS. 12A and 12B show the size of the tumor as measured with a digital caliper on the indicated date. Tumor volume was calculated with the following formula: [largest diameter×(perpendicular diameter)$^2$]×3.14/6. FIG. 12C shows the survival of the mice following vaccination.

Figure 13B:
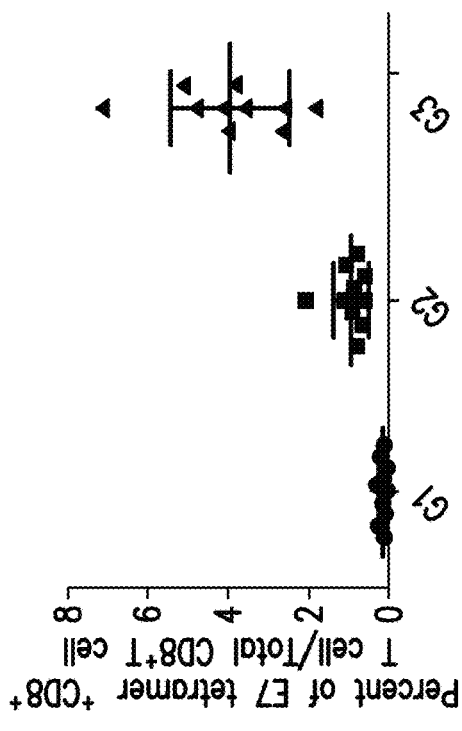
Figure 13D:
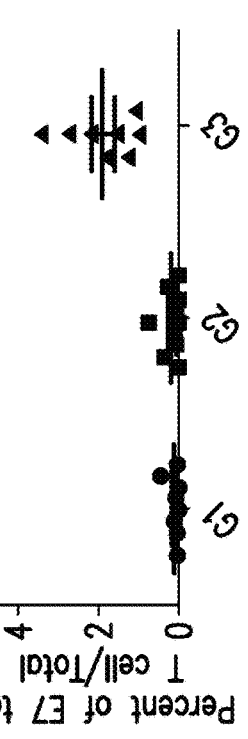
Figure 13A:
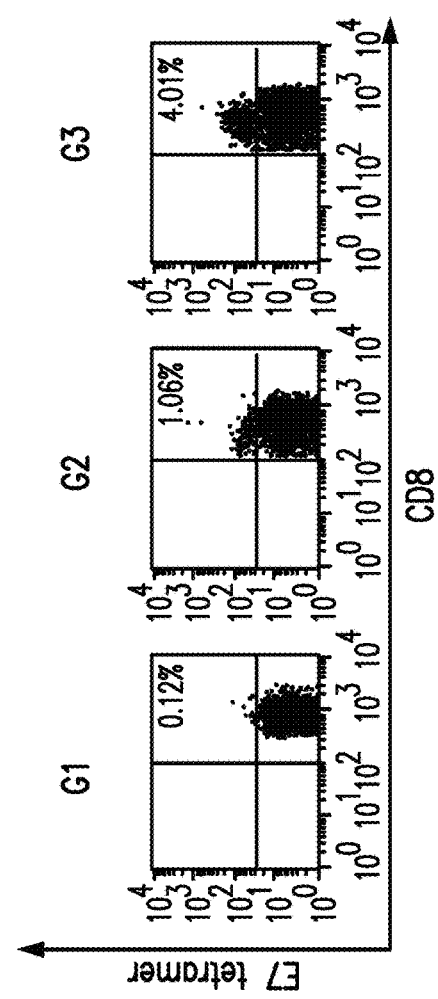
Figure 13C:
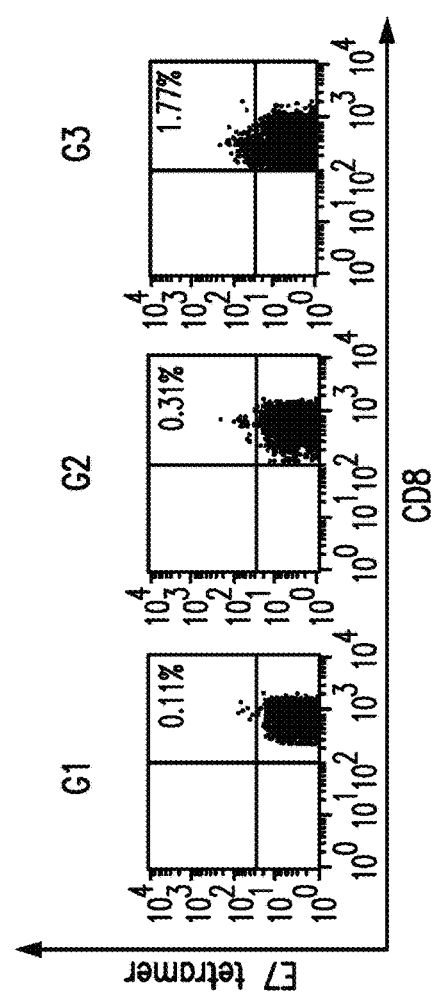

FIGS. 13A-13D: Analysis of E7-specific CD8+ T cells in peripheral blood of TC-1 tumor-bearing mice after vaccination. 5~8 weeks old female C57BL/6 mice (10 mice/group) were injected with $1 \times 10^5$ of TC-1 tumor cells on day 1. The tumor-bearing mice were then vaccinated intravenously via the retro-orbital route on days 4 and 14 with PBS (G1), $1 \times 10^7$ PFU of Ad5-E7E6 (G2), $10^6$ FFU HK1-E7E6 (G3). On day 14 and 24, PBMCs were harvested from blood sampled via the tail vein and E7-specific CD8+ T cell responses were analyzed by tetramer staining (HPV16 E7aa49-57 peptide loaded H-2Db tetramer). FIG. 13A. Representative flow cytometry image of HPV16 E7 tetramer staining of day 14 PBMCs. FIG. 13B. Summary of HPV16 E7 tetramer (+) CD8(+) T cells in the day 14 peripheral blood. FIG. 13C. Representative flow cytometry image of HPV16 E7 tetramer staining of day 24 PBMCs. FIG. 13D. Summary of HPV16 E7 tetramer (+) CD8(+) T cells in the day 24 peripheral blood.

Figure 14A:
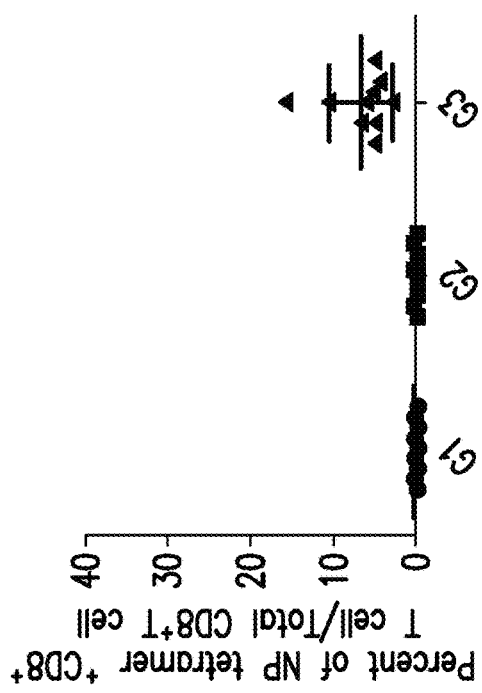
Figure 14B:
Figure 14C:
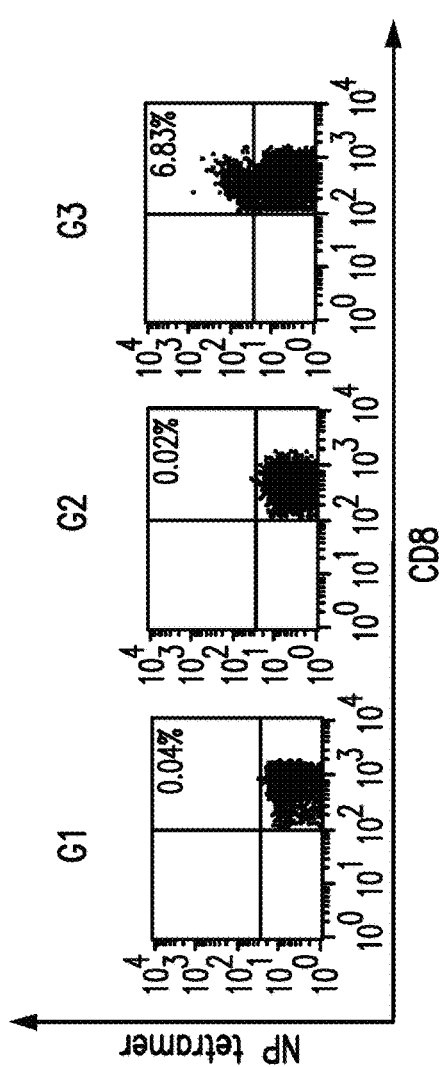
Figure 14D:
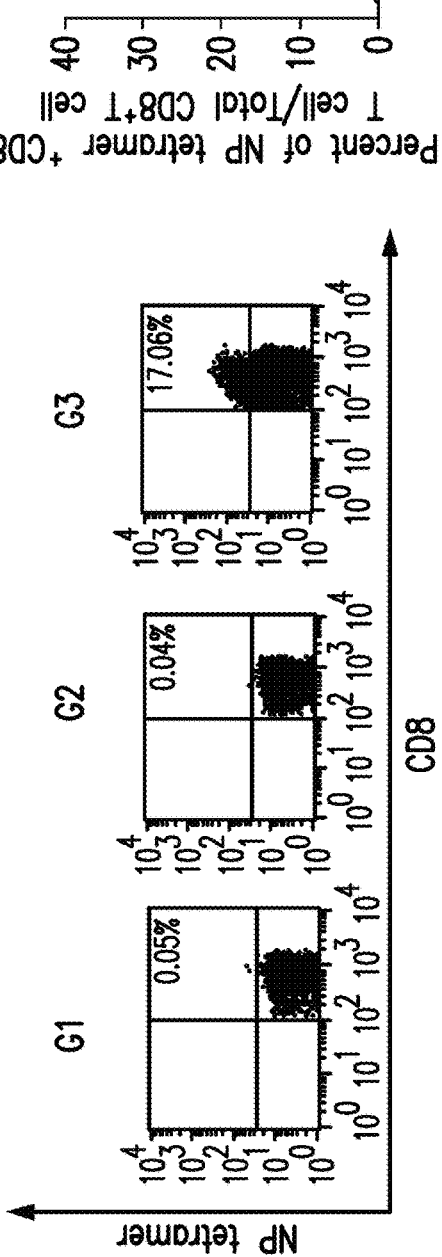

FIGS. 14A-14D: Analysis of NP-specific CD8+ T cells in peripheral blood of TC-1 tumor-bearing mice after vaccination. 5~8 weeks old female C57BL/6 mice (10 mice/group) were injected with $1 \times 10^5$ of TC-1 tumor cells on day 1. The tumor-bearing mice were then vaccinated intravenously via the retro-orbital route on days 4 and 14 with PBS (G1), $1 \times 10^7$ PFU of Ad5-E7E6 (G2) and $10^6$ FFU HK1-E7E6 (G3). On day 14 and 24, PBMCs were harvested from blood sampled via the tail vein and NP-specific CD8+ T cell responses were analyzed by tetramer staining (LCMV NP peptide loaded H-2D$^b$ tetramer). FIG. 14A. Representative flow cytometry image of LCMV NP tetramer staining of day 14 PBMCs. FIG. 14B. Summary of LCMV NP tetramer (+) CD8(+) T cells in the day 14 peripheral blood. FIG. 14C. Representative flow cytometry image of LCMV NP tetramer staining of day 43 PBMCs. FIG. 14D. Summary of LCMV NP tetramer (+) CD8(+) T cells in the day 24 peripheral blood.

Figure 15A:
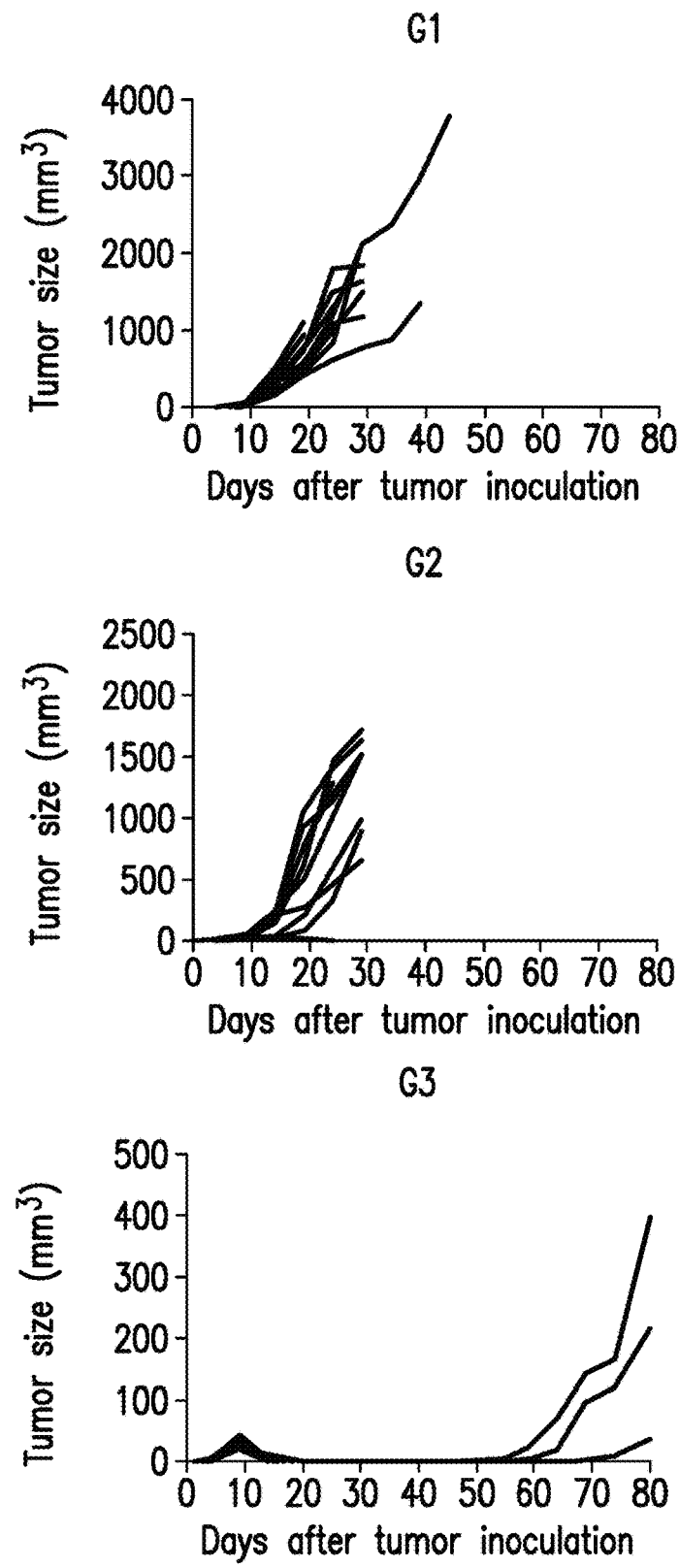
Figure 15B:
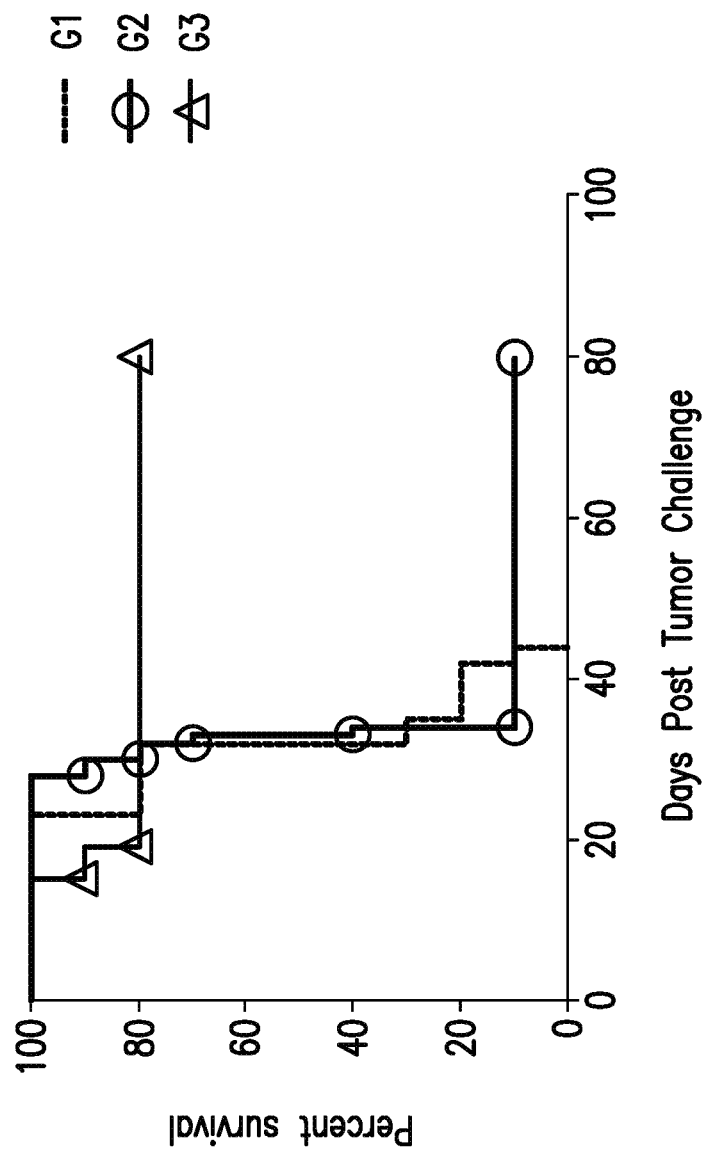

FIGS. 15A and 15B: 5~8 weeks old female C57BL/6 mice (10 mice/group) were injected with $1 \times 10^5$ of TC-1 tumor cells on day 1. The tumor-bearing mice were then vaccinated intravenously via the retro-orbital route on days 4 and 14 with PBS (G1), $1 \times 10^7$ PFU of Ad5-E7E6 (G2) and $10^6$ FFU HK1-E7E6 (G3). FIG. 15A shows the size of the tumor as measured with a digital caliper on the indicated date. Tumor volume was calculated with the following formula: [largest diameter×(perpendicular diameter)$^2$]×3.14/6. FIG. 15B shows the survival of the mice following vaccination.

Figure 16:
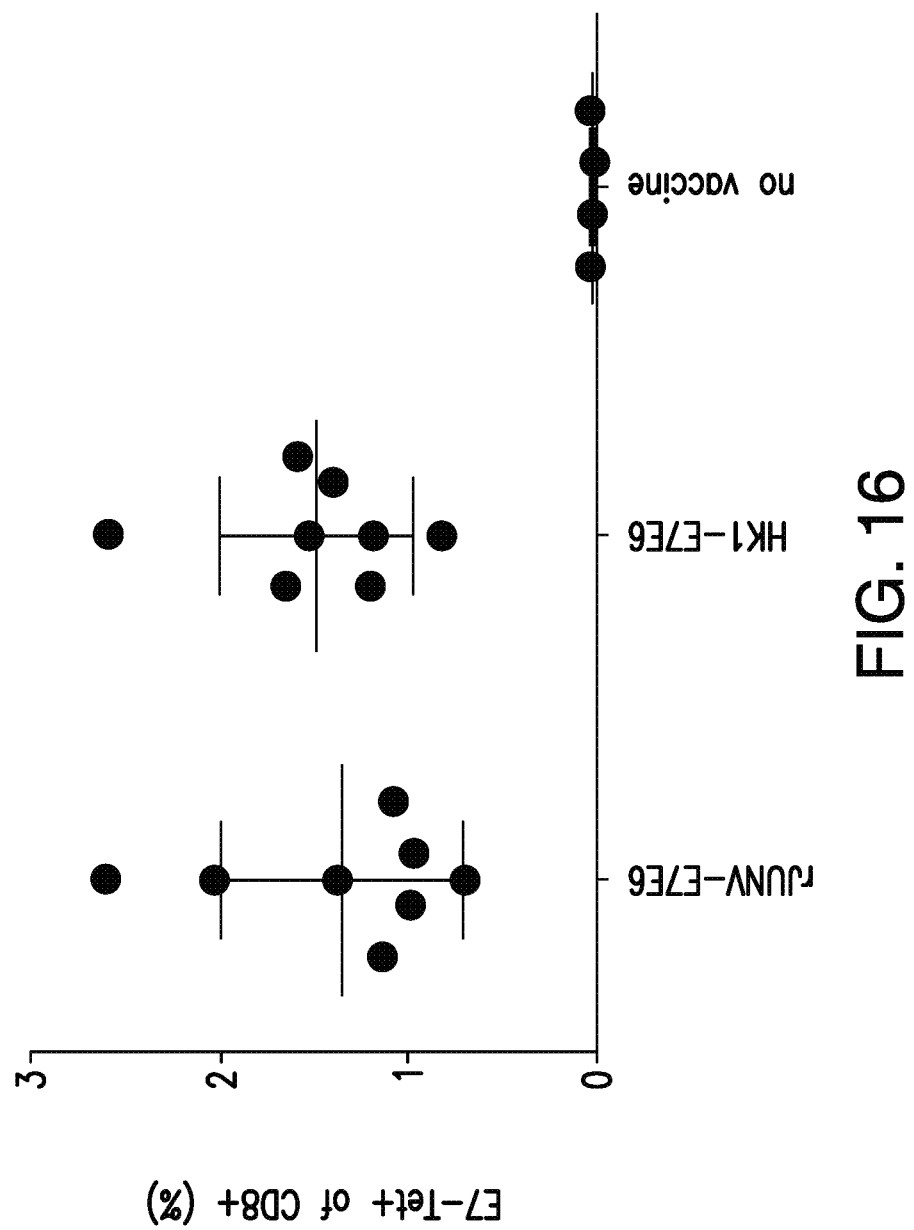

FIG. 16: C57BL/6 mice were immunized on day 0 by intravenous injection of $10^5$ FFU of HK1-E7E6 or rJUNV-E7E6. E7-specific CD8+ T cell responses were subsequently analyzed by tetramer staining (H-2Db/HPV16 E7 49-57 (RAHYNIVTF)) on day 8 after immunization. The percentage of tetramer-binding CD8+ T cells is expressed as a percentage of the total CD8+ T cell pool. Symbols show individual mice.

Figure 17A:
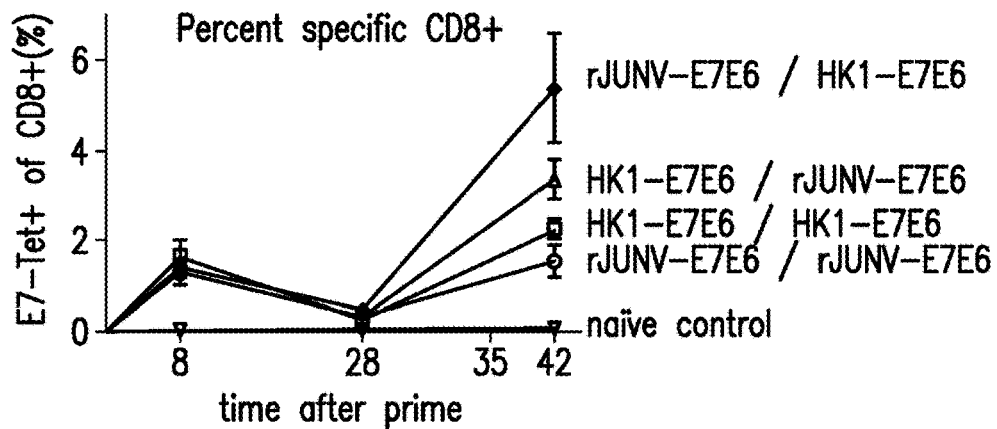
Figure 17B:
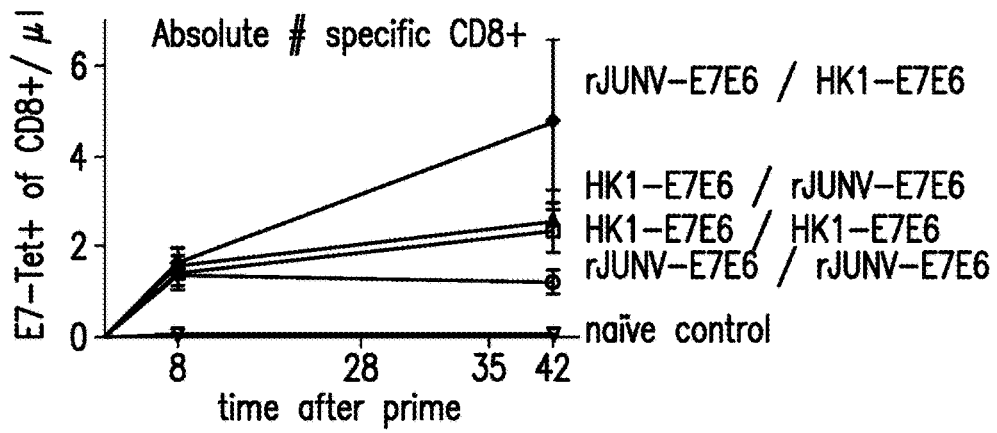
Figure 17C:
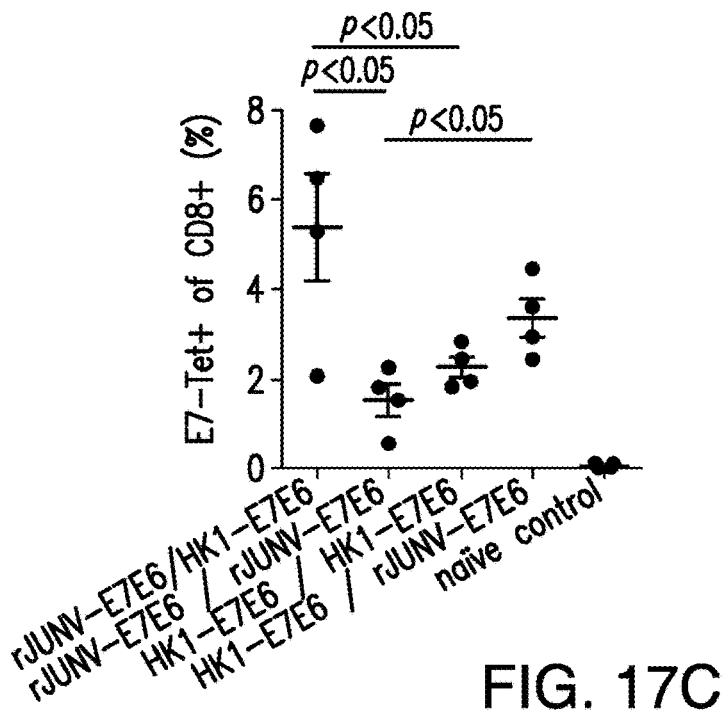

FIGS. 17A-17C: C57BL/6 mice (n=4 per group) were immunized on day 0 by intravenous injection of $10^5$ FFU of HK1-E7E6 or rJUNV-E7E6. Mice were subsequently boosted intravenously on day 35 with $10^5$ FFU of the homologous or the heterologous vector by the same route. E7-specific CD8+ T cell responses were analyzed by tetramer staining (H-2Db/HPV16 E7 49-57 (RAHYNIVTF)) on days 8, 28 and 42 of the experiment. The percentage (FIG. 17A) as well as absolute counts (FIG. 17B) of antigen-specific CD8+ T cells in the blood of vaccinated mice is shown. Symbols represent the mean+/−SEM of four mice per group. (FIG. 17C) Comparison of day 42 (day 7 post boost) frequencies by multiple student's t-tests.

Figure 18:
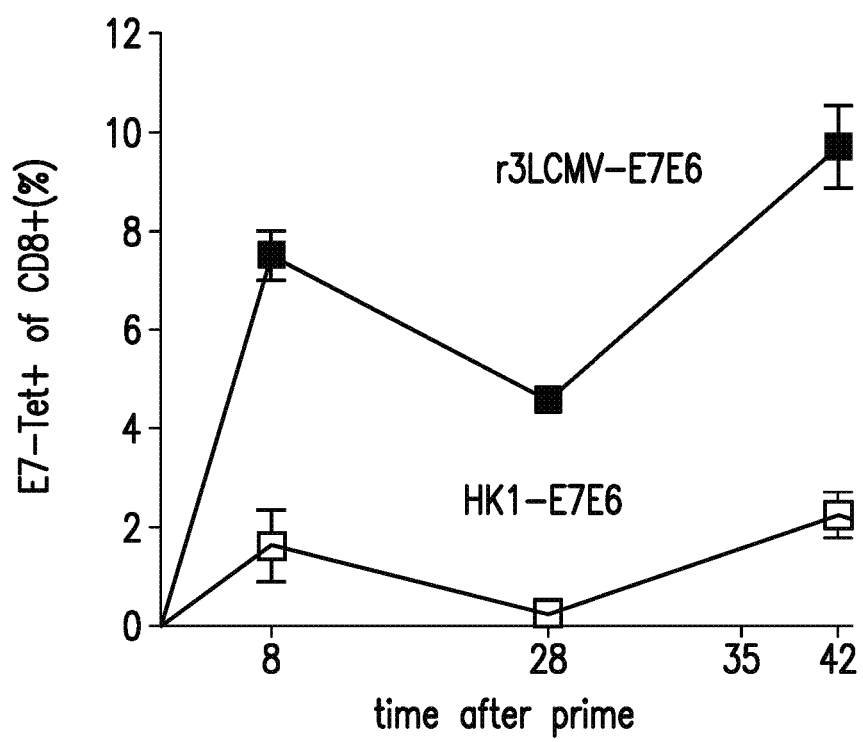

FIG. 18: C57BL/6 mice were immunized intravenously on days 0 and 35 of the experiment with $10^5$ FFU of a replicating vector expressing E7E6 (r3LCMV-E7E6) or with $10^5$ FFU of a non-replicating vector expressing E7E6 (HK1-E7E6). Epitope-specific CD8+ T cells were stained using E7 epitope-loaded MHC class I tetramers in combination with anti-CD8a antibody. The frequency of E7-tetramer-binding cells within the CD8+ T cell compartment in peripheral blood was calculated.

Figure 19A:
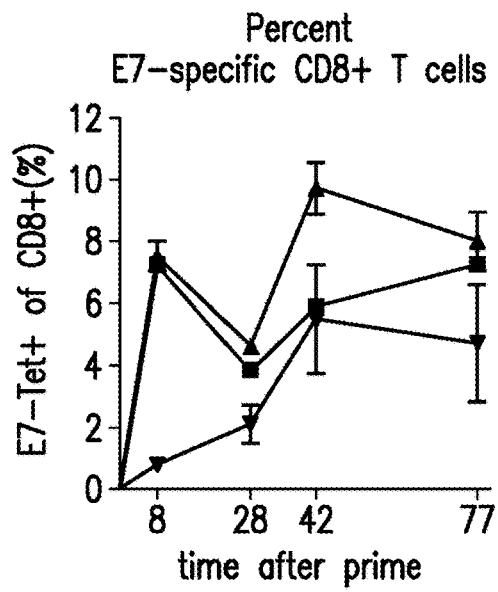
Figure 19B:
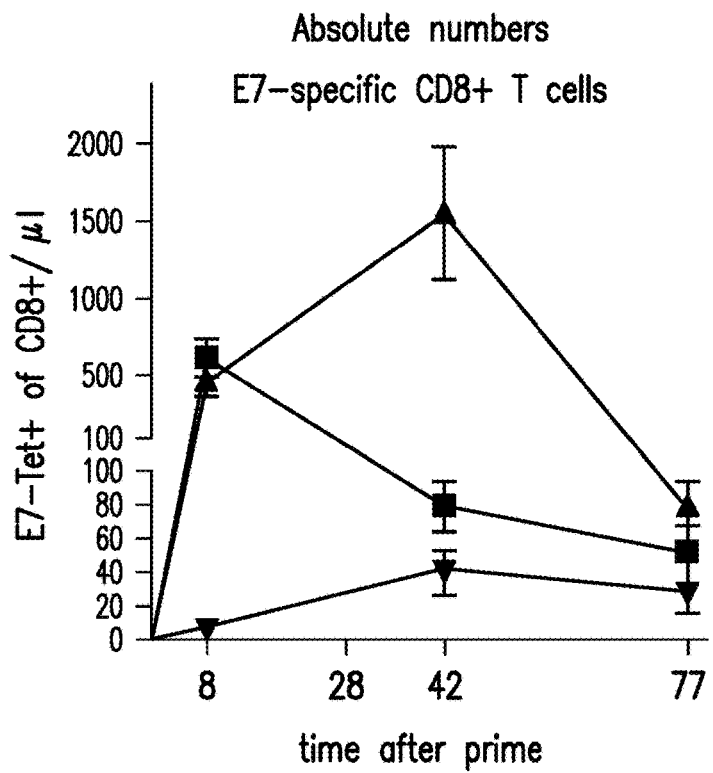

FIGS. 19A-19B: C57BL/6 mice (4 animals per group) were immunized on day 0 by intravenous injection of either $8.5 \times 10^4$ FFU of r3LCMV-E7E6 or $1.5 \times 10^5$ FFU of an analogous replication-competent vector based on Junin Candid #1 virus (r3JUNV-E7E6). Mice were subsequently boosted intravenously on day 35 with the homologous or heterologous vector as indicated in the chart. Epitope-specific CD8+ T cell responses were analyzed by tetramer staining using E7 epitope-loaded MHC class I tetramers in combination with anti-CD8a antibody. The frequency of E7-tetramer-binding cells within the CD8+ T cell compartment in peripheral blood (FIG. 19A) and the absolute number of E7 tetramer-binding CD8+ T cells per microliter of peripheral blood (FIG. 19B) was calculated. Symbols represent the mean+/−SEM of 4 mice per group and time point.

6. DETAILED DESCRIPTION OF THE INVENTION

Provided herein are methods and compositions for the prevention or treatment of diseases and conditions associated with neoplastic disease, such as cancer. Provided herein are methods and compositions for the treatment or prevention of diseases and conditions associated with neoplastic disease, such as cancer, using vaccines. Specifically, provided herein are arenavirus viral vectors, including an infectious, replication-deficient arenavirus viral vector, a replication-competent tri-segmented arenavirus viral vector, and a replication-deficient tri-segmented arenavirus viral vector, or an arenavirus genomic segment, for use as vaccines for the prevention or treatment of diseases and conditions caused by tumor-associated viruses. Such vaccines can be an infectious, replication-deficient arenavirus, a replication-competent tri-segmented arenavirus viral vector, a replication-deficient tri-segmented arenavirus viral vector, or an arenavirus genomic segment expressing an antigen of a tumor-associated virus.

Provided herein are methods and compositions for the prevention or treatment of neoplastic disease, such as cancer. Provided herein are methods and compositions for the treatment or prevention of neoplastic disease, such as cancer, using vaccines. Specifically, provided herein are infectious, replication-deficient arenavirus viral vectors, replication-competent tri-segmented arenavirus viral vectors, replication-deficient tri-segmented arenavirus viral vectors, or arenavirus genomic segments for use as vaccines for the prevention or treatment of neoplastic disease, such as cancer. More specifically, these vaccines can be used for the prevention or treatment of cancer caused by infection with oncogenic viruses, such as human papillomavirus (HPV). Such vaccines can be infectious, replication-deficient arenaviruses, replication-competent tri-segmented arenavirus viral vectors, replication-deficient tri-segmented arenavirus viral vectors, or arenavirus genomic segments expressing an antigen of an oncogenic virus, such as HPV.

In certain specific embodiments, provided herein is a genetically modified arenavirus, wherein the arenavirus:
  i) is infectious;
  ii) cannot form infectious progeny virus in a non-complementary cell (i.e., a cell that does not express the functionality that is missing from the replication-deficient arenavirus and causes it to be replication-deficient);
  iii) is capable of replicating its genome and expressing its genetic information; and
  iv) encodes an antigen of an oncogenic virus, such as an HPV virus, or a fragment thereof, alone or in combination with an immunomodulatory peptide, polypeptide, or protein.

In certain specific embodiments, the arenavirus for use with the methods and compositions provided is a genetically engineered lymphocytic choriomeningitis virus (LCMV) or is a genetically engineered Junin virus. In certain specific embodiments, an LCMV or a Junin virus is genetically modified by a functional inactivation (e.g., deletion) of an open reading frame (ORF) such that the resulting virus cannot produce further infectious progeny virus particles in non-complementing cells, i.e., a cell that does not provide the functionally inactivated ORF in trans. The resulting infectious replication-deficient LCMV or Junin virus can be used as a vector to express an antigen of an oncogenic virus, such as HPV. The generation and propagation of arenavirus vectors for use with the compositions and methods provided herein is described in more detail in Sections 6.1, 6.2, 6.3 and 6.4.

The arenavirus vectors provided herein are genetically engineered to comprise a heterologous nucleotide sequence, which expresses a heterologous peptide or protein. In certain embodiments, the heterologous sequence encodes a tumor antigen. In certain embodiments, the heterologous sequence encodes an antigen of an oncogenic virus. In certain specific embodiments, the heterologous sequence encodes an HPV antigen. In certain specific embodiments, the heterologous sequence encodes two, three, four or more antigens of one or more oncogenic viruses. In certain embodiments, an arenavirus vector for use with the present methods encodes also an immunomodulatory peptide or protein. In certain embodiments, the arenavirus vector also encodes a signal peptide or protein. Without being bound by theory, such a signal peptide facilitates the transport of a protein (e.g., an HPV antigen and/or an immunomodulatory protein or peptide) outside the cell in which the antigen and/or immunomodulatory protein or peptide was expressed. The heterologous sequences for use with the compositions and methods provided herein are described in more detail in Section 6.5.

Pharmaceutical compositions, immunogenic compositions, and vaccines comprising the arenavirus vectors provided herein are described in Section 6.6.

Methods of use of the arenavirus vectors for the prevention or treatment of neoplastic disease, e.g., non-malignant neoplasm or cancer, are provided herein. Specifically, provided herein are methods for preventing or treating cancer in a subject comprising administering to the subject one or more arenaviruses expressing an HPV antigen or a fragment thereof. In a specific embodiment, provided herein are methods for preventing or treating cancer in a subject comprising administering to the subject one or more arenaviruses expressing an HPV antigen or a fragment thereof, alone or in combination with one or more of an immunomodulatory peptide, polypeptide, or protein, a linker, or a signal sequence. In certain embodiments, immunization with an arenavirus that expresses an HPV antigen or a fragment thereof, as described herein provides a cytotoxic T-cell response. In certain embodiments, a second or third immunization can be administered for a boosting effect. In certain embodiments, the second or third immunization utilizes a homologous vector. In certain embodiments, the second or third immunization utilizes a heterologous vector. In certain embodiments, the first immunization utilizes an Old World arenavirus vector, and the second immunization utilizes an Old World arenavirus vector. In certain embodiments, the first immunization utilizes an Old World arenavirus vector, and the second immunization utilizes an New World arenavirus vector. In certain embodiments, the first immunization utilizes an New World arenavirus vector, and the second immunization utilizes an Old World arenavirus vector. In certain embodiments, the first immunization utilizes an New World arenavirus vector, and the second immunization utilizes an New World arenavirus vector. A more detailed description of methods of treatment and/or prevention of neoplastic disease using an arenavirus as described herein is provided in Section 6.7.

6.1 Replication Defective Arenavirus Vectors

Infectious, replication-deficient viruses as described herein can be produced as described in International Patent Application Publication No. WO 2009/083210 (application number PCT/EP2008/010994), which is incorporated by reference herein in its entirety.

Arenaviruses for use with the methods and compositions provided herein can be Old World viruses, for example Lassa virus, Lymphocytic choriomeningitis virus (LCMV), Mobala virus, Mopeia virus, or Ippy virus, or New World viruses, for example Amapari virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, Bear Canyon virus, or Whitewater Arroyo virus.

A genetically modified arenavirus described herein is infectious, i.e., it can attach to a host cell and release its genetic material into the host cell. A genetically modified arenavirus described herein is replication-deficient, i.e., the arenavirus is unable to produce further infectious progeny particles in a non-complementing cell. In particular, the genome of the arenavirus is modified (e.g., by deletion or functional inactivation of an open reading frame or another genetic element of the virus genome that is required for the generation of an infectious particle) such that a virus carrying the modified genome can no longer produce infectious progeny viruses in a non-complementing cell. A non-complementing cell is a cell that does not provide the functionality that has been eliminated from the replication-deficient arenavirus by modification of its genome. For example, if the open reading frame encoding the GP protein has been deleted or functionally inactivated, a non-complementing cell does not provide the GP protein. However, a genetically modified arenavirus as provided herein is capable of producing infectious progeny viruses in complementing cells. Complementing cells are cells that provide the functionality that has been eliminated from the replication-deficient arenavirus by modification of its genome. For example, if the open reading frame encoding the GP protein is deleted or functionally inactivated, a complementing cell does provide the GP protein. Expression of the complementing functionality (e.g., the GP protein) can be accomplished by any method known to the skilled artisan (e.g., transient or stable transfection, using a suitable expression vector).

A genetically modified arenavirus as described herein can amplify and express its genetic information in a cell that has been infected by the virus. Specifically, as described herein, the genetically modified arenavirus can amplify and express its genetic information in a complementing cell or a non-complementing cell. A genetically modified infectious, replication-deficient arenavirus as provided herein comprises a heterologous nucleotide sequence that encodes antigens of interest, an immunomodulatory peptide, polypeptide, or protein, a signal sequence, and/or a linker. Such sequences and their arrangement are described in Section 6.5.

In certain embodiments, the open reading frame (ORF) that encodes the glycoprotein (GP) gene of the arenavirus is deleted to generate a replication-deficient arenavirus for use with the compositions and methods provided herein. A heterologous nucleotide sequence (Section 6.5) is inserted in place of the deleted ORF. Thus, in certain embodiments, a genetically modified arenavirus viral vector provided herein comprises a genomic segment that a) has a deletion or functional inactivation of an open reading frame that is present in the wild type form of the genomic segment; and b) encodes one or more antigens of an oncogenic virus (e.g., HPV E6, HPV E7, and/or HPV E6/E7 fusion protein), and/or an immunomodulatory peptide, polypeptide, or protein.

Generally, arenavirus viral vectors can be recombinantly produced by standard reverse genetic techniques as described for LCMV (Flatz, et al., 2006, Proc Natl Acad Sci USA 103:4663-4668; Sanchez et al., 2006, Virology 350: 370; Ortiz-Riano, et al., 2013 J Gen Virol. 94:1175-88). Infectious, replication-deficient virus vectors as described herein can be produced as described in International Patent Application Publication No. WO 2009/083210 (application number PCT/EP2008/010994), which is incorporated by reference herein in its entirety. The genome of the rescued virus is modified as described in Section 6.5. These modifications can be: i) one or more, e.g., two, three or four, of the four arenavirus open reading frames (glycoprotein (GP); nucleoprotein (NP); matrix protein Z; RNA-dependent RNA polymerase L) are removed or functionally inactivated to prevent formation of infectious particles in non-complementing cells, albeit still allowing gene expression in arenavirus vector-infected host cells; and ii) a nucleic acid that encodes one or more of an heterologous antigen, an immunomodulatory peptide, polypeptide, or protein, a signal sequence, or a linker can be introduced.

Owing to the removal or functional inactivation of one or more of the viral genes in arenavirus vectors (here, deletion of the glycoprotein, GP, will be taken as an example), arenavirus vectors can be generated and expanded in cells providing in trans the deleted viral gene(s), e.g., the GP in the present example. Such a complementing cell line, henceforth referred to as C-cells, is generated by transfecting a mammalian cell line such as BHK-21, HEK293, VERO or other (here HEK293 will be taken as an example) with one or more plasmid(s) for expression of the viral gene(s) of interest (complementation plasmid, referred to as C-plasmid). The C-plasmid(s) express the viral gene(s) deleted in the arenavirus vector to be generated under control of one or more expression cassettes suitable for expression in mammalian cells, e.g., a mammalian polymerase II promoter such as the CMV or EF1 alpha promoter with a polyadenylation signal. In addition, the complementation plasmid features a mammalian selection marker, e.g., puromycin resistance, under control of an expression cassette suitable for gene expression in mammalian cells, e.g., polymerase II expression cassette as above, or the viral gene transcript(s) are followed by an internal ribosome entry site, such as the one of encephalomyocarditis virus, followed by the mammalian resistance marker. For production in *E. coli*, the plasmid additionally features a bacterial selection marker, such as an ampicillin resistance cassette.

For generation of C-cells, cells that can be used, e.g., BHK-21, HEK293, MC57G, are kept in culture and are transfected with the C-plasmid(s) using any of the commonly used strategies such as calcium-phosphate, liposome-based protocols, or electroporation. A few days later, the suitable selection agent, e.g., puromycin, is added in titrated concentrations. Surviving clones are isolated and subcloned following standard procedures, and high-expressing C-cell clones are identified using Western blot or flow cytometry procedures with antibodies directed against the viral protein(s) of interest. As an alternative to the use of stably transfected C-cells, transient transfection of normal cells can complement the missing viral gene(s) in each of the steps where C-cells will be used below. In addition, a helper virus can be used to provide the missing functionality in trans. In other certain embodiments, other methods known in the art can be used for the generation of stable cell lines e.g., lentivirus transduction.

For generation of arenavirus vectors, plasmids that can be used can be of two types: i) Two plasmids, referred to as TF-plasmids for expressing intracellularly in C-cells the minimal transacting factors of the arenavirus, the vector is derived from e.g., NP and L proteins of LCMV or Junin virus in the present example; and ii) Plasmids, referred to as GS-plasmids, for expressing intracellularly in C-cells the arenavirus vector genome segments, e.g., the segments with designed modifications. TF-plasmids express the NP and L proteins of the respective arenavirus vector under control of an expression cassette suitable for protein expression in mammalian cells, typically e.g., a mammalian polymerase II promoter such as the CMV or EF1alpha promoter, either one of them preferentially in combination with a polyadenylation signal. From the GS-plasmids the small (S) and the large (L) genome segments of the vector are transcribed. Typically, polymerase I-driven expression cassettes or T7 bacteriophage RNA polymerase (T7-) driven expression cassettes can be used, the latter preferentially with a 3'-terminal ribozyme for processing of the primary transcript to yield the correct end. In the case of using a T7-based system, expression of T7 in C-cells must be provided by either including in the recovery process an additional expression plasmid, constructed analogously to TF-plasmids, providing T7, or C-cells are constructed to additionally express T7 in a stable manner. In certain embodiments, TF and GS plasmids can be the same, i.e. the genome sequence and transacting factors can be transcribed by T7, polI and polII promoters from one plasmid.

For recovering of the arenavirus vector, the following procedures can be used. First day: C-cells, typically 80% confluent in M6-well plates, are transfected with a mixture of the two TF-plasmids plus the two GS-plasmids. In certain embodiments, the TF and GS plasmids can be the same, i.e., the genome sequence and transacting factors can be transcribed by T7, polI and polII promoters from one plasmid. For this one can exploit any of the commonly used strategies such as calcium-phosphate, liposome-based protocols or electroporation. In another embodiment, C-cells, e.g., P5A3 cells, can also be cultured in suspension and transfected at a defined cell density.

3-5 days later: The culture supernatant (arenavirus vector preparation) is harvested, aliquoted and stored at 4° C., −20° C. or −80° C. depending on how long the arenavirus vector should be stored prior to use. Then the arenavirus vector preparation's infectious titer is assessed by an immunofocus assay on C-cells. In another embodiment, 3-5 days later, the transfected cells and supernatant are transferred to a larger culture flask. 3 days later, the culture supernatant (arenavirus vector preparation) is harvested, aliquoted and stored at 4° C., −20° C. or at −80° C. depending on how long the arenavirus vector should be stored prior to use. Then, the arenavirus vector preparation's infectious titer is assessed by an immunofocus assay on C-cells.

Once generated from cDNA, the infectious, replication-deficient arenaviruses provided herein can be propagated in complementing cells. Complementing cells are cells that provide the functionality that has been eliminated from the infectious, replication-deficient arenavirus by modification of its genome (e.g., if the open reading frame encoding the GP protein is deleted or functionally inactivated, a complementing cell does provide the GP protein).

Provided herein are compositions and methods for the expression of a heterologous antigen in a cell culture wherein the cell culture is infected with an infectious, replication-deficient arenavirus expressing a heterologous sequence. When used for expression of a heterologous sequence in cultured cells, the following two procedures can be used:

i) The cell type of interest is infected with the arenavirus vector preparation described herein at a multiplicity of infection (MOI) of one or more, e.g., two, three or four, resulting in production of the heterologous sequence in all cells already shortly after infection.

ii) Alternatively, a lower MOI can be used and individual cell clones can be selected for their level of virally driven heterologous sequence expression. Subsequently individual clones can be expanded infinitely owing to the non-cytolytic nature of arenavirus vectors. Irrespective of the approach, the heterologous sequence can subsequently be collected (and purified) either from the culture supernatant or from the cells themselves, depending on the properties of the heterologous sequence produced. However, the compositions and methods provided herein are not limited to these two strategies, and other ways of driving expression of heterologous sequence using infectious, replication-deficient arenaviruses as vectors may be considered.

Alternatively, a rescue system consisting of three plasmids can be used: (1) the first plasmid expresses the protein NP by transcription via Polymerase II and subsequent translation in transfected cells; (2) the second plasmid gives rise to the (negative-stranded) L-Segment of the LCMV genome by transcription via Polymerase I as well as the L protein by transcription via Polymerase II from the same template in the opposite direction of the Polymerase I promoter; (3) the third plasmid gives rise to the S-segment of the LCMV genome (encoding the antigen coding sequence instead of the LCMV glycoprotein) via transcription by Polymerase I. 3 μg of each plasmid is used for electroporation of C-cells, followed by seeding of cells in 6-well plates and incubation at 37° C. After incubation, cells and supernatant from transfections are combined with freshly seeded C-cells, and vectors are harvested and cleared from cells & debris at a defined timepoint post infection. Once the vector has been generated, a nucleic acid encoding an antigen of an oncogenic virus and/or an immunomodulatory peptide, polypeptide, or protein (see Section 6.5) can be inserted into a plasmid from which a genomic segment of an infectious replication-deficient vector is transcribed by any technique known to the skilled artisan.

Owing to the removal or functional inactivation of one or more of the viral genes in arenavirus vectors (here deletion of the glycoprotein, GP, will be taken as an example) arenavirus vectors can be generated and expanded in cells that provide the deleted or functionally inactivated viral gene(s) (e.g., the GP) in trans. The resulting virus itself is infectious but is unable to produce further infectious progeny particles in non-complementing cells due to the lack of the deleted or functionally inactivated viral gene(s) (e.g., the GP). The complementing cell can provide the missing functionality either by stable transfection, transient transfection, or by infection with a helper virus that expresses the missing functionality.

In certain embodiments, the complementing cell provides the viral gene that has been deleted or functionally inactivated from the arenavirus vector genome. In a specific embodiment, the complementing cell provides the viral gene from a viral strain that is the same as the viral strain that was used to generate the genome of the arenavirus vector. In another embodiment, the complementing cell provides the viral gene from a viral strain that is different from the viral strain that was used to generate the genome of the arenavirus vector. For example, the viral gene provided in the complementing cell is obtained from the MP strain of LCMV and encodes a protein having the amino acid sequence of SEQ ID NO: 6, 7, 8, or 9.

In a specific embodiment, the complementing cell provides the GP of the MP strain of LCMV and the arenavirus vector comprises an ORF of a human HPV antigen as described herein in place of the ORF encoding the GP protein. In an even more specific embodiment, the complementing cell provides the GP of the MP strain of LCMV and the arenavirus vector is obtained from LCMV Clone 13 and comprises an ORF of a human HPV antigen as described herein in place of the ORF encoding the GP protein. In an even more specific embodiment, the GP protein is at least 90%, 91%, 92%, 93%, 94%, 95%, 96%, 97%, 98%, at least 99%, or 100% identical to the amino acid sequence of SEQ ID NO: 7.

6.2 Arenaviruses with an Open Reading Frame in a Non-natural Position

Provided herein are arenaviruses with rearrangements of their ORFs. In certain embodiments, such arenaviruses are replication-competent and infectious. In certain embodiments, such arenaviruses are replication-deficient and infectious. Genomic sequences of such arenaviruses are provided herein. In one aspect, provided herein is an arenavirus genomic segment, wherein the arenavirus genomic segment is engineered to carry an arenavirus ORF in a position other than the position in which the respective gene is found in viruses isolated from the wild. In one embodiment, the arenavirus viral vector is LCMV. In another aspect, an arenavirus genomic segment as provided herein comprises a heterologous nucleotide sequence that encodes antigens of interest, an immunomodulatory peptide, polypeptide, or protein, a signal sequence, and/or a linker. Such sequences and their arrangement are described in Section 6.5.

The wild-type arenavirus genomic segments and ORFs are known in the art. In particular, the arenavirus genome consists of an S segment and an L segment. The S segment carries the ORFs encoding the GP and the NP. The L segment encodes the L protein and the Z protein. Both segments are flanked by the respective 5' and 3' UTRs.

In certain embodiments, an arenavirus genomic segment can be engineered to carry two or more arenavirus ORFs in a position other than the wild-type position. In other embodiments, the arenavirus genomic segment can be engineered to carry two arenavirus ORFs, or three arenavirus ORFs, or four arenavirus ORFs in a position other than the wild-type position.

In certain embodiments, the open reading frame (ORF) that encodes the glycoprotein ("GP"), nucleoprotein ("NP"), matrix protein Z ("Z protein") or RNA dependent RNA polymerase L ("L protein") of the arenavirus is removed (e.g. deleted) to generate a replication-deficient arenavirus for use with the compositions and methods provided herein. A heterologous nucleotide sequence (Section 6.5) can be inserted in place of the deleted arenavirus ORF. Thus, in certain embodiments, an arenavirus genomic segment provided herein comprises a genomic segment that a) has a deletion or functional inactivation of an open reading frame that is present in the wild type form of the genomic segment; and b) encodes one or more antigens of an oncogenic virus (e.g., HPV E6, HPV E7, and/or HPV E6/E7 fusion protein), and/or an immunomodulatory peptide, polypeptide, or protein.

In certain embodiments, an arenavirus genomic segment provided herein can be:
  (i) an arenavirus S segment, wherein the ORF encoding the NP is under control of an arenavirus 5' UTR;
  (ii) an arenavirus S segment, wherein the ORF encoding the Z protein is under control of an arenavirus 5' UTR;
  (iii) an arenavirus S segment, wherein the ORF encoding the L protein is under control of an arenavirus 5' UTR;
  (iv) an arenavirus S segment, wherein the ORF encoding the GP is under control of an arenavirus 3' UTR;
  (v) an arenavirus S segment, wherein the ORF encoding the L protein is under control of an arenavirus 3' UTR;
  (vi) an arenavirus S segment, wherein the ORF encoding the Z protein is under control of an arenavirus 3' UTR;
  (vii) an arenavirus L segment, wherein the ORF encoding the GP is under control of an arenavirus 5' UTR;
  (viii) an arenavirus L segment, wherein the ORF encoding the NP is under control of an arenavirus 5' UTR;
  (ix) an arenavirus L segment, wherein the ORF encoding the L protein is under control of an arenavirus 5' UTR;
  (x) an arenavirus L segment, wherein the ORF encoding the GP is under control of an arenavirus 3' UTR;
  (xi) an arenavirus L segment, wherein the ORF encoding the NP is under control of an arenavirus 3' UTR; and
  (xii) an arenavirus L segment, wherein the ORF encoding the Z protein is under control of an arenavirus 3' UTR.

In certain embodiments, the ORF that is in the non-natural position of the arenavirus genomic segment described herein can be under the control of an arenavirus 3' UTR or an arenavirus 5' UTR. In more specific embodiments, the arenavirus 3' UTR is the 3' UTR of the arenavirus S segment. In another specific embodiment, the arenavirus 3' UTR is the 3'UTR of the arenavirus L segment. In more specific embodiments, the arenavirus 5' UTR is the 5' UTR of the arenavirus S segment. In other specific embodiments, the 5' UTR is the 5' UTR of the L segment.

In other embodiments, the ORF that is in the non-natural position of the arenavirus genomic segment described herein can be under the control of the arenavirus conserved terminal sequence element (the 5'- and 3'-terminal 19-20-nt regions) (see e.g., Perez & de la Torre, 2003, J Virol. 77(2): 1184-1194).

In certain embodiments, the ORF that is in the non-natural position of the arenavirus genomic segment can be under the control of the promoter element of the 5' UTR (see e.g., Albarino et al., 2011, J Virol., 85(8):4020-4). In another embodiment, the ORF that is in the non-natural position of the arenavirus genomic segment can be under the control of the promoter element of the 3' UTR (see e.g., Albarino et al., 2011, J Virol., 85(8):4020-4). In more specific embodiments, the promoter element of the 5' UTR is the 5' UTR promoter element of the S segment or the L segment. In another specific embodiment, the promoter element of the 3' UTR is the 3' UTR the promoter element of the S segment or the L segment.

In certain embodiments, the ORF that is in the non-natural position of the arenavirus genomic segment can be under the control of a truncated arenavirus 3' UTR or a truncated arenavirus 5' UTR (see e.g., Perez & de la Torre, 2003, J Virol. 77(2): 1184-1194; Albarino et al., 2011, J Virol., 85(8):4020-4). In more specific embodiments, the truncated 3' UTR is the 3' UTR of the arenavirus S segment or L segment. In more specific embodiments, the truncated 5' UTR is the 5' UTR of the arenavirus S segment or L segment.

Also provided herein, is an arenavirus viral vector comprising a first genomic segment that has been engineered to carry an ORF in a position other than the wild-type position of the ORF and a second arenavirus genomic segment so that the arenavirus viral vector comprises an S segment and an L segment. In specific embodiments, the ORF in a position other than the wild-type position of the ORF is one of the arenavirus ORFs.

In certain specific embodiments, the arenavirus viral vector can comprise a full complement of all four arenavirus ORFs. In specific embodiments, the second arenavirus genomic segment has been engineered to carry an ORF in a position other than the wild-type position of the ORF. In another specific embodiment, the second arenavirus genomic segment can be the wild-type genomic segment (i.e., comprises the ORFs on the segment in the wild-type position).

In certain embodiments, the first arenavirus genomic segment is an L segment and the second arenavirus genomic segment is an S segment. In other embodiments, the first arenavirus genomic segment is an S segment and the second arenavirus genomic segment is an L segment.

Non-limiting examples of the arenavirus viral vector comprising a genomic segment with an ORF in a position other than the wild-type position of the ORF and a second genomic segment are illustrated in Table 1

TABLE 1

Arenavirus viral vector

| Position 1 | Position 2 | Position 3 | Position 4 |
|---|---|---|---|
| GP | NP | L | Z |
| GP | Z | L | NP |
| GP | Z | NP | L |
| GP | L | NP | Z |
| GP | L | Z | NP |
| NP | GP | L | Z |
| NP | GP | Z | L |
| NP | L | GP | Z |
| NP | L | Z | GP |
| NP | Z | GP | L |
| NP | Z | L | GP |
| Z | GP | L | NP |
| Z | GP | NP | L |
| Z | NP | GP | L |
| Z | NP | L | GP |
| Z | L | NP | GP |
| Z | L | GP | NP |
| L | NP | GP | Z |
| L | NP | Z | GP |
| L | GP | Z | NP |
| L | GP | NP | Z |
| L | Z | NP | GP |
| L | Z | GP | NP |

*Position 1 is under the control of an arenavirus S segment 5' UTR; Position 2 is under the control of an arenavirus S segment 3' UTR; Position 3 is under the control of an arenavirus L segment 5' UTR; Position 4 is under the control of an arenavirus L segment 3' UTR.

In certain embodiments, provided herein is an arenavirus genomic segment that can be suitable for use as a vaccine and methods of using such arenavirus genomic segment in a vaccination and treatment or prevention of, for example, infections and cancers. For example, in certain embodiments, an arenavirus genomic segment provided herein with a heterologous nucleotide sequence that encodes antigens of interest, an immunomodulatory peptide, polypeptide, or protein, a signal sequence, and/or a linker can be used as a vaccine in the methods provided herein or as a component of compositions provided herein. More detailed description of the methods of using the arenavirus genomic segment described herein is provided in Section 6.7.

In certain embodiments, provided herein is an arenavirus genomic segment that can be suitable for use as a pharmaceutical composition and methods of using such arenavirus genomic segment in a vaccination and treatment or prevention of, for example, infections or cancers. For example, in certain embodiments, an arenavirus genomic segment provided herein with a heterologous nucleotide sequence that encodes antigens of interest, an immunomodulatory peptide, polypeptide, or protein, a signal sequence, and/or a linker can be used in the methods provided herein or as a component of compositions provided herein. More detailed description of the methods of using the arenavirus genomic segment described herein is provided in Section 6.7.

Also provided herein, is a cDNA of the arenavirus genomic segment engineered to carry an ORF in a position other than the wild-type position of the ORF. In more specific embodiments, provided herein is a cDNA or a set of cDNAs of an arenavirus genome as set forth in Table 1.

In certain embodiments, a cDNA of the arenavirus genomic segment that is engineered to carry an ORF in a position other than the wild-type position of the ORF is part of or incorporated into a DNA expression vector. In a specific embodiment, a cDNA of the arenavirus genomic segment that is engineered to carry an ORF in a position other than the wild-type position of the ORF is part of or incorporated into a DNA expression vector that facilitates production of an arenavirus genomic segment as described herein. In another embodiment, a cDNA described herein can be incorporated into a plasmid. More detailed description of the cDNAs or nucleic acids and expression systems are provided is Section 6.8 Techniques for the production of a cDNA are routine and conventional techniques of molecular biology and DNA manipulation and production. Any cloning technique known to the skilled artesian can be used. Such techniques are well known and are available to the skilled artesian in laboratory manuals such as, Sambrook and Russell, Molecular Cloning: A laboratory Manual, 3$^{rd}$ edition, Cold Spring Harbor Laboratory N.Y. (2001).

In certain embodiments, the cDNA of the arenavirus genomic segment that is engineered to carry an ORF in a position other than the wild-type position of the ORF is introduced (e.g., transfected) into a host cell. Thus, in some embodiments provided herein, is a host cell comprising a cDNA of the arenavirus genomic segment that is engineered to carry an ORF in a position other than the wild-type position of the ORF (i.e., a cDNA of the genomic segment). In other embodiments, the cDNA described herein is part of or can be incorporated into a DNA expression vector and introduced into a host cell. Thus, in some embodiments provided herein is a host cell comprising a cDNA described herein that is incorporated into a vector. In other embodiments, the arenavirus genomic segment described herein is introduced into a host cell.

In certain embodiments, described herein is a method of producing the arenavirus genomic segment, wherein the method comprises transcribing the cDNA of the arenavirus genomic segment. In certain embodiments, a viral polymerase protein can be present during transcription of the arenavirus genomic segment in vitro or in vivo.

In certain embodiments, transcription of the arenavirus genomic segment is performed using a bi-directional promoter. In other embodiments, transcription of the arenavirus genomic segment is performed using a bi-directional expression cassette (see e.g., Ortiz-Riaño et al., 2013, J Gen Virol., 94(Pt 6): 1175-1188). In more specific embodiments the bi-directional expression cassette comprises both a polymerase I and a polymerase II promoter reading from opposite sides into the two termini of the inserted arenavirus genomic segment, respectively. In yet more specific embodiments the bi-directional expression cassette with pol-I and pol-II promoters read from opposite sides into the L segment and S segment In other embodiments, transcription of the cDNA of the arenavirus genomic segment described herein comprises a promoter. Specific examples of promoters include an RNA polymerase I promoter, an RNA polymerase II promoter, an RNA polymerase III promoter, a T7 promoter, an SP6 promoter or a T3 promoter.

In certain embodiments, the method of producing the arenavirus genomic segment can further comprise introducing into a host cell the cDNA of the arenavirus genomic segment. In certain embodiments, the method of producing the arenavirus genomic segment can further comprise introducing into a host cell the cDNA of the arenavirus genomic segment, wherein the host cell expresses all other components for production of the arenavirus genomic segment; and purifying the arenavirus genomic segment from the supernatant of the host cell. Such methods are well-known to those skilled in the art.

Provided herein are cell lines, cultures and methods of culturing cells infected with nucleic acids, vectors, and compositions provided herein. More detailed description of nucleic acids, vector systems and cell lines described herein is provided in Section 6.8.

In certain embodiments, the arenavirus viral vector as described herein results in an infectious and replication-competent arenavirus viral vector. In specific embodiments, the arenavirus viral vector described herein is attenuated. In a particular embodiment, the arenavirus viral vector is attenuated such that the virus remains, at least partially, able to spread and can replicate in vivo, but can only generate low viral loads resulting in subclinical levels of infection that are non-pathogenic. Such attenuated viruses can be used as an immunogenic composition. Provided herein, are immunogenic compositions that comprise an arenavirus with an ORF in a non-natural position as described in Section 6.6.

In certain embodiments, provided herein is an arenavirus viral vector that can be suitable for use as a vaccine and methods of using such arenavirus viral vector in a vaccination and treatment or prevention of, for example, infections and cancers. For example, in certain embodiments, an arenavirus viral vector provided herein with a heterologous nucleotide sequence that encodes antigens of interest, an immunomodulatory peptide, polypeptide, or protein, a signal sequence, and/or a linker can be used as a vaccine in the methods provided herein or as a component of compositions provided herein. More detailed description of the methods of using the arenavirus viral vector described herein is provided in Section 6.7.

In certain embodiments, provided herein is an arenavirus viral vector that can be suitable for use as a pharmaceutical composition and methods of using such arenavirus viral vector in a vaccination and treatment or prevention of, for example, infections or cancers. For example, in certain embodiments, an arenavirus viral vector provided herein with a heterologous nucleotide sequence that encodes antigens of interest, an immunomodulatory peptide, polypeptide, or protein, a signal sequence, and/or a linker can be used in the methods provided herein or as a component of compositions provided herein. More detailed description of the methods of using the arenavirus viral vector described herein is provided in Section 6.7.

(a) Replication-Deficient Arenavirus Particle with an Open Reading Frame in a Non-Natural Position In certain embodiments, provided herein is an arenavirus viral vector in which (i) an ORF is in a position other than the wild-type position of the ORF; and (ii) an ORF encoding GP, NP, Z protein, and L protein has been removed (e.g., deleted) or functionally inactivated such that the resulting virus cannot produce further infectious progeny virus particles. An arenavirus viral vector comprising a genetically modified genome in which one or more ORFs has been deleted or functionally inactivated can be produced in complementing cells (i.e., cells that express the arenavirus ORF that has been deleted or functionally inactivated). The genetic material of the resulting arenavirus viral vector can be transferred upon infection of a host cell into the host cell, wherein the genetic material can be expressed and amplified. In addition, the genome of the genetically modified arenavirus viral vector described herein can encode a heterologous ORF from an organism other than an arenavirus viral vector.

In certain embodiments, at least one of the four ORFs encoding GP, NP, Z protein, and L protein is removed and replaced with a heterologous ORF from an organism other than an arenavirus. In another embodiment, at least one ORF, at least two ORFs, at least three ORFs, or at least four ORFs encoding GP, NP, Z protein and L protein can be removed and replaced with a heterologous ORF from an organism other than an arenavirus, including a heterologous ORF as described in Section 6.5. In specific embodiments, only one of the four ORFs encoding GP, NP, Z protein, and L protein is removed and replaced with a heterologous ORF from an organism other than an arenavirus viral vector, including a heterologous ORF as described in Section 6.5. In more specific embodiments, the ORF that encodes GP of the arenavirus genomic segment is removed. In another specific embodiment, the ORF that encodes the NP of the arenavirus genomic segment is removed. In more specific embodiments, the ORF that encodes the Z protein of the arenavirus genomic segment is removed. In yet another specific embodiment, the ORF encoding the L protein is removed.

Thus, in certain embodiments, the arenavirus viral vector provided herein comprises a genomic segment that (i) is engineered to carry an arenavirus ORF in a non-natural position; (ii) an ORF encoding GP, NP, Z protein, or L protein is removed; (iii) the ORF that is removed is replaced with a heterologous ORF from an organism other than an arenavirus, including a heterologous ORF as described in Section 6.5.

In certain embodiments, the heterologous ORF is 8 to 100 nucleotides in length, 15 to 100 nucleotides in length, 25 to 100 nucleotides in length, 50 to 200 nucleotide in length, 50 to 400 nucleotide in length, 200 to 500 nucleotide in length, or 400 to 600 nucleotides in length, 500 to 800 nucleotide in length. In other embodiments, the heterologous ORF is 750 to 900 nucleotides in length, 800 to 1000 nucleotides in length, 850 to 1000 nucleotides in length, 900 to 1200 nucleotides in length, 1000 to 1200 nucleotides in length, 1000 to 1500 nucleotides or 1200 to 1500 nucleotides in length, 1500 to 2000 nucleotides in length, 1700 to 2000 nucleotides in length, 2000 to 2300 nucleotides in length, 2200 to 2500 nucleotides in length, 2500 to 3000 nucleotides in length, 3000 to 3200 nucleotides in length, 3000 to 3500 nucleotides in length, 3200 to 3600 nucleotides in length, 3300 to 3800 nucleotides in length, 4000 nucleotides to 4400 nucleotides in length, 4200 to 4700 nucleotides in length, 4800 to 5000 nucleotides in length, 5000 to 5200 nucleotides in length, 5200 to 5500 nucleotides in length, 5500 to 5800 nucleotides in length, 5800 to 6000 nucleotides in length, 6000 to 6400 nucleotides in length, 6200 to 6800 nucleotides in length, 6600 to 7000 nucleotides in length, 7000 to 7200 nucleotides in lengths, 7200 to 7500 nucleotides in length, or 7500 nucleotides or more in length. In some embodiments, the heterologous ORF encodes a peptide or polypeptide that is 5 to 10 amino acids in length, 10 to 25 amino acids in length, 25 to 50 amino acids in length, 50 to 100 amino acids in length, 100 to 150 amino acids in length, 150 to 200 amino acids in length, 200 to 250 amino acids in length, 250 to 300 amino acids in length, 300 to 400 amino acids in length, 400 to 500 amino acids in length, 500 to 750 amino acids in length, 750 to 1000 amino acids in length, 1000 to 1250 amino acids in length 1250 to 1500 amino acids in length, 1500 to 1750 amino acids in length, 1750 to 2000 amino acids in length, 2000 to 2500 amino acids in length, or more than 2500 or more amino acids in length. In some embodiments, the heterologous ORF encodes a polypeptide that does not exceed 2500 amino acids in length. In specific embodiments the heterologous ORF does not contain a stop codon. In certain embodiments, the heterologous ORF is codon-optimized. In certain embodiments the nucleotide composition, nucleotide pair composition or both can be optimized. Techniques for such optimizations are known in the art and can be applied to optimize a heterologous ORF.

Any heterologous ORF from an organism other than an arenavirus may be included in an arenavirus genomic segment. In one embodiment, the heterologous ORF encodes a reporter protein. More detailed description of reporter proteins are described in Section 6.5. In another embodiment, the heterologous ORF encodes an antigen for an infectious pathogen or an antigen associated with any disease that is capable of eliciting an immune response. In specific embodiments the antigen is derived from an infectious organism, a tumor (i.e., cancer), or an allergen. More detailed description on heterologous ORFs is described in Section 6.5.

In certain embodiments, the growth and infectivity of the arenavirus viral vector is not affected by the heterologous ORF from an organism other than an arenavirus.

Techniques known to one skilled in the art may be used to produce an arenavirus viral vector comprising an arenavirus genomic segment engineered to carry an arenavirus ORF in a position other than the wild-type position. For example, reverse genetics techniques may be used to generate such arenavirus viral vector. In other embodiments, the replication-deficient arenavirus viral vector (i.e., the arenavirus genomic segment engineered to carry an arenavirus ORF in a position other than the wild-type position, wherein an ORF encoding GP, NP, Z protein, L protein, has been deleted) can be produced in a complementing cell.

In certain embodiments, the arenavirus genomic segment or the arenavirus viral vector using according to the present application can be Old World Viruses, for example, LCMV.

In certain embodiments, the present application relates to the arenavirus viral vector as described herein suitable for use as a vaccine and methods of using such arenavirus viral vector in a vaccination and treatment or prevention of, for example, infections or cancers. More detailed description of the methods of using the arenavirus viral vector described herein is provided in Section 6.7.

In certain embodiments, provided herein is a kit comprising, in one or more containers, one or more cDNAs described herein. In a specific embodiment, a kit comprises, in one or two or more containers, an arenavirus genomic segment or an arenavirus viral vector as described herein. The kit may further comprise one or more of the following: a host cell suitable for rescue of the arenavirus genomic segment or the arenavirus viral vector, reagents suitable for transfecting plasmid cDNA into a host cell, a helper virus, plasmids encoding viral proteins and/or one or more primers specific for an modified arenavirus genomic segment or arenavirus viral vector or cDNAs of the same.

In certain embodiments, the present application relates to the arenavirus viral vector as described herein suitable for use as a pharmaceutical composition and methods of using such arenavirus viral vector in a vaccination and treatment or prevention of, for example, infections and cancers. More detailed description of the methods of using the arenavirus viral vector described herein is provided in Section 6.7.

6.3 Tri-Segmented Arenavirus Viral Vector

Provided herein are tri-segmented arenavirus viral vectors with rearrangements of their ORFs.

In one aspect, the tri-segmented arenavirus viral vector as provided herein comprises a heterologous nucleotide sequence that encodes antigens of interest, an immunomodulatory peptide, polypeptide, or protein, a signal sequence, and/or a linker. Such sequences and their arrangement are described in Section 6.5.

In another aspect, provided herein is a tri-segmented arenavirus viral vector comprising one L segment and two S segments or two L segments and one S segment. In certain embodiments, the tri-segmented arenavirus viral vector does not recombine into a replication-competent bi-segmented arenavirus particle. In specific embodiments, the tri-segmented arenavirus viral vector comprises an ORF in a position other than the wild-type position of the ORF. In yet another specific embodiment, the tri-segmented arenavirus viral vector comprises all four arenavirus ORFs. Thus, in certain embodiments, the tri-segmented arenavirus viral vector is replication-competent and infectious. In other embodiments, the tri-segmented arenavirus viral vector lacks one of the four arenavirus ORFs. Thus, in certain embodiments, the tri-segmented arenavirus viral vector is infectious but is replication-deficient (i.e., unable to produce further infectious progeny in non-complementing cells).

In certain embodiments, the ORF encoding GP, NP, Z protein, or the L protein of the tri-segmented arenavirus viral vector described herein can be under the control of an arenavirus 3' UTR or an arenavirus 5' UTR. In more specific embodiments, the tri-segmented arenavirus 3' UTR is the 3' UTR of an arenavirus S segment(s). In another specific embodiment, the tri-segmented arenavirus 3' UTR is the 3' UTR of a tri-segmented arenavirus L segment(s). In more specific embodiments, the tri-segmented arenavirus 5' UTR is the 5' UTR of an arenavirus S segment(s). In other specific embodiments, the 5' UTR is the 5' UTR of the L segment(s).

In other embodiments, the ORF encoding GP, NP, Z protein, or the L protein of tri-segmented arenavirus viral vector described herein can be under the control of the arenavirus conserved terminal sequence element (the 5'- and 3'-terminal 19-20-nt regions) (see e.g., Perez & de la Torre, 2003, J Virol. 77(2): 1184-1194).

In certain embodiments, the ORF encoding GP, NP, Z protein or the L protein of the tri-segmented arenavirus viral vector can be under the control of the promoter element of the 5' UTR (see e.g., Albarino et al., 2011, J Virol., 85(8): 4020-4). In another embodiment, the ORF encoding GP, NP Z protein, L protein of the tri-segmented arenavirus viral vector can be under the control of the promoter element of the 3' UTR (see e.g., Albarino et al., 2011, J Virol., 85(8): 4020-4). In more specific embodiments, the promoter element of the 5' UTR is the 5' UTR promoter element of the S segment(s) or the L segment(s). In another specific embodiment, the promoter element of the 3' UTR is the 3' UTR the promoter element of the S segment(s) or the L segment(s).

In certain embodiments, the ORF that encoding GP, NP, Z protein or the L protein of the tri-segmented arenavirus viral vector can be under the control of a truncated arenavirus 3' UTR or a truncated arenavirus 5' UTR (see e.g., Perez & de la Torre, 2003, J Virol. 77(2): 1184-1194; Albarino et al., 2011, J Virol., 85(8):4020-4). In more specific embodiments, the truncated 3' UTR is the 3' UTR of the arenavirus S segment or L segment. In more specific embodiments, the truncated 5' UTR is the 5' UTR of the arenavirus S segment(s) or L segment(s).

Also provided herein, is a cDNA of the tri-segmented arenavirus viral vector. In more specific embodiments, provided herein is a DNA nucleotide sequence or a set of DNA nucleotide sequences encoding a tri-segmented arenavirus viral vector as set forth in Table 2 or Table 3.

In certain embodiments, the nucleic acids encoding the tri-segmented arenavirus genome are part of or incorporated into one or more DNA expression vectors. In a specific embodiment, nucleic acids encoding the genome of the tri-segmented arenavirus viral vector are part of or incorporated into one or more DNA expression vectors that facilitate production of a tri-segmented arenavirus viral vector as described herein. In another embodiment, a cDNA described herein can be incorporated into a plasmid. More detailed description of the cDNAs and expression systems are provided is Section 6.8. Techniques for the production of a cDNA routine and conventional techniques of molecular biology and DNA manipulation and production. Any cloning technique known to the skilled artesian can be used. Such techniques are well known and are available to the skilled artesian in laboratory manuals such as, Sambrook and Russell, Molecular Cloning: A laboratory Manual, $3^{rd}$ edition, Cold Spring Harbor Laboratory N.Y. (2001).

In certain embodiments, the cDNA of the tri-segmented arenavirus is introduced (e.g., transfected) into a host cell. Thus, in some embodiments provided herein, is a host cell comprising a cDNA of the tri-segmented arenavirus viral vector (i.e., a cDNA of the genomic segments of the tri-segmented arenavirus viral vector). In other embodiments, the cDNA described herein that is part of or can be incorporated into a DNA expression vector and introduced into a host cell. Thus, in some embodiments provided herein is a host cell comprising a cDNA described herein that is incorporated into a vector. In other embodiments, the tri-segmented arenavirus genomic segments (i.e., the L segment and/or S segment or segments) described herein is introduced into a host cell.

In certain embodiments, described herein is a method of producing the tri-segmented arenavirus viral vector, wherein the method comprises transcribing the cDNA of the tri-segmented arenavirus viral vector. In certain embodiments, a viral polymerase protein can be present during transcription of the tri-segmented arenavirus viral vector in vitro or in vivo. In certain embodiments, transcription of the arenavirus genomic segment is performed using a bi-directional promoter.

In other embodiments, transcription of the arenavirus genomic segment is performed using a bi-directional expression cassette (see e.g., Ortiz-Riaño et al., 2013, J Gen Virol., 94(Pt 6): 1175-1188). In more specific embodiments the bi-directional expression cassette comprises both a polymerase I and a polymerase II promoter reading from opposite sides into the two termini of the inserted arenavirus genomic segment, respectively.

In other embodiments, transcription of the cDNA of the arenavirus genomic segment described herein comprises a promoter. Specific examples of promoters include an RNA polymerase I promoter, an RNA polymerase II promoter, an RNA polymerase III promoter, a T7 promoter, an SP6 promoter, or a T3 promoter.

In certain embodiments, the method of producing the tri-segmented arenavirus viral vector can further comprise introducing into a host cell the cDNA of the tri-segmented arenavirus viral vector. In certain embodiments, the method of producing the tri-segmented arenavirus viral vector can further comprise introducing into a host cell the cDNA of the tri-segmented arenavirus viral vector, wherein the host cell expresses all other components for production of the tri-segmented arenavirus viral vector; and purifying the tri-segmented arenavirus viral vector from the supernatant of the host cell. Such methods are well-known to those skilled in the art.

Provided herein are cell lines, cultures and methods of culturing cells infected with nucleic acids, vectors, and compositions provided herein. More detailed description of nucleic acids, vector systems and cell lines described herein is provided in Section 6.8.

In certain embodiments, the tri-segmented arenavirus viral vector as described herein results in a infectious and replication-competent arenavirus viral vector. In specific embodiments, the arenavirus viral vector described herein is attenuated. In a particular embodiment, the tri-segmented arenavirus viral vector is attenuated such that the virus remains, at least partially, replication-competent and can replicate in vivo, but can only generate low viral loads resulting in subclinical levels of infection that are non-pathogenic. Such attenuated viruses can be used as an immunogenic composition.

In certain embodiments, the tri-segmented arenavirus viral vector has the same tropism as the bi-segmented arenavirus particle.

Also provided herein is a kit comprising, in one or more containers, one or more cDNAs described herein. In a specific embodiment, a kit comprises, in one or two or more containers a tri-segmented arenavirus viral vector as described herein. The kit may further comprise one or more of the following: a host cell suitable for rescue of the tri-segmented arenavirus viral vector, reagents suitable for transfecting plasmid cDNA into a host cell, a helper virus, plasmids encoding viral proteins and/or one or more oligonucleotide primers specific for a modified arenavirus genomic segment or arenavirus viral vector or nucleic acids encoding the same.

Also provided herein, are immunogenic compositions that comprise the tri-segmented arenavirus viral vector as described in Section 6.6.

In certain embodiments, provided herein is a tri-segmented arenavirus viral vector that can be suitable for use as a vaccine and methods of using such arenavirus viral vector in a vaccination and treatment or prevention of, for example, infections and cancers. For example, in certain embodiments, a tri-segmented arenavirus viral vector provided herein with rearrangements of it ORF's and a heterologous nucleotide sequence that encodes antigens of interest, an immunomodulatory peptide, polypeptide, or protein, a signal sequence, and/or a linker can be used as a vaccine in the methods provided herein or as a component of compositions provided herein. More detailed description of the methods of using the tri-segmented arenavirus viral vector described herein is provided in Section 6.7.

In certain embodiments, provided herein is a tri-segmented arenavirus viral vector that can be suitable for use as a pharmaceutical composition and methods of using such arenavirus viral vector in a vaccination and treatment or prevention of, for example, infections or cancers. For example, in certain embodiments, a tri-segmented arenavirus viral vector provided herein with rearrangements of it ORF's and a heterologous nucleotide sequence that encodes antigens of interest, an immunomodulatory peptide, polypeptide, or protein, a signal sequence, and/or a linker can be used in the methods provided herein or as a component of compositions provided herein. More detailed description of the methods of using the arenavirus viral vector described herein is provided in Section 6.7.

(a) Tri-Segmented Arenavirus Viral Vector Comprising One L Segment and Two S Segments In one aspect, provided herein is a tri-segmented arenavirus viral vector comprising one L segment and two S segments. In certain embodiments, propagation of the tri-segmented arenavirus viral vector comprising one L segment and two S segments does not result in a replication-competent bi-segmented viral vector. In specific embodiments, propagation of the tri-segmented arenavirus viral vector comprising one L segment and two S segments does not result in a replication-competent bi-segmented viral particle after at least 10 days, at least 20 days, at least 30 days, at least 40 days, at least 50 days, at least 60 days, at least 70 days, at least 80 days, at least 90 days, or at least 100 days of persistent infection in mice lacking type I interferon receptor, type II interferon receptor and recombination activating gene (RAG1), and having been infected with $10^4$ PFU of the tri-segmented arenavirus viral vector. In other embodiments, propagation of the tri-segmented arenavirus viral vector comprising one L segment and two S segments does not result in a replication-competent bi-segmented viral vector after at least 10 passages, at least 20 passages, at least 30 passages, at least 40 passages, or at least 50 passages.

In one aspect, the tri-segmented arenavirus viral vector comprising one L segment and two S segments further comprises a heterologous nucleotide sequence that encodes antigens of interest, an immunomodulatory peptide, polypeptide, or protein, a signal sequence, and/or a linker. Such sequences and their arrangement are described in Section 6.5.

The tri-segmented arenavirus viral vector with all viral genes in their respective wild-type position is known in the art (e.g., Emonet et al., 2011 J. Virol., 85(4):1473; Popkin et al., 2011, J. Virol, 85(15):7928). In particular, the tri-segmented arenavirus genome consists of one L segment and two S segments, in which a heterologous ORF (Section 6.5) is inserted into one position on each S segment. More specifically, one S segment encodes GP and an HPV antigen, respectively. The other S segment encodes an HPV antigen and NP, respectively. The L segment encodes the L protein and Z protein. All segments are flanked by the respective 5' and 3' UTRs.

In certain embodiments, inter-segmental recombination of the two S segments of the tri-segmented arenavirus viral vector, provided herein, that unities the two arenaviral ORFs on one instead of two separate segments results in a non functional promoter (i.e., a genomic segment of the structure: 5' UTR-5' UTR or a 3' UTR-3' UTR), wherein each UTR forming one end of the genome is an inverted repeat sequence of the other end of the same genome.

In certain embodiments, the tri-segmented arenavirus viral vector comprising one L segment and two S segments has been engineered to carry an arenavirus ORF in a position other than the wild-type position of the ORF. In other embodiments, the tri-segmented arenavirus viral vector comprising one L segment and two S segments has been engineered to carry two arenavirus ORFs, or three arenavirus ORFs, or four arenavirus ORFs, or five arenavirus ORFs, or six arenavirus ORFs in a position other than the wild-type position. In specific embodiments, the tri-segmented arenavirus viral vector comprising one L segment and two S segments comprises a full complement of all four arenavirus ORFs. Thus, in some embodiments, the tri-segmented arenavirus viral vector is an infectious and replication-competent tri-segmented arenavirus viral vector. In specific embodiments, the two S segments of the tri-segmented arenavirus viral vector have been engineered to carry one of their ORFs in a position other than the wild-type position. In more specific embodiments, the two S segments comprise a full complement of the S segment ORF's. In certain specific embodiments, the L segment has been engineered to carry an ORF in a position other than the wild-type position or the L segment can be the wild-type genomic segment.

In certain embodiments, one of the two S segments can be:
 (i) an arenavirus S segment, wherein the ORF encoding the Z protein is under control of an arenavirus 5' UTR;
 (ii) an arenavirus S segment, wherein the ORF encoding the L protein is under control of an arenavirus 5' UTR;
 (iii) an arenavirus S segment, wherein the ORF encoding the NP is under control of an arenavirus 5' UTR;
 (iv) an arenavirus S segment, wherein the ORF encoding the GP is under control of an arenavirus 3' UTR;
 (v) an arenavirus S segment, wherein the ORF encoding the L is under control of an arenavirus 3' UTR; and
 (vi) an arenavirus S segment, wherein the ORF encoding the Z protein is under control of an arenavirus 3' UTR.

In certain embodiments, the tri-segmented arenavirus viral vector comprising one L segment and two S segments can comprise a duplicate ORF (i.e., two wild-type S segment ORFs e.g., GP or NP). In specific embodiments, the tri-segmented arenavirus viral vector comprising one L segment and two S segments can comprise one duplicate ORF (e.g., (GP, GP)) or two duplicate ORFs (e.g., (GP, GP) and (NP, NP)).

Table 2A, below, is an illustration of the genome organization of a tri-segmented arenavirus viral vector comprising one L segment and two S segments, wherein intersegmental recombination of the two S segments in the tri-segmented arenavirus genome does not result in a replication-competent bi-segmented viral vector and abrogates arenaviral promoter activity (i.e., the resulting recombed S segment is made up of two 3'UTRs instead of a 3' UTR and a 5' UTR).

TABLE 2A

Tri-segmented arenavirus viral vector comprising one L segment and two S segments

| Position 1 | Position 2 | Position 3 | Position 4 | Position 5 | Position 6 |
|---|---|---|---|---|---|
| *ORF | GP | *ORF | NP | Z | L |
| *ORF | NP | *ORF | GP | Z | L |
| *ORF | NP | *ORF | GP | L | Z |
| *ORF | NP | *ORF | Z | L | GP |
| *ORF | NP | Z | GP | *ORF | Z |
| *ORF | NP | Z | GP | Z | *ORF |
| *ORF | NP | *ORF | L | Z | GP |
| *ORF | L | *ORF | NP | Z | GP |
| *ORF | L | Z | NP | *ORF | GP |
| *ORF | L | *ORF | GP | Z | NP |
| *ORF | L | Z | GP | *ORF | NP |
| *ORF | Z | L | NP | *ORF | GP |
| *ORF | Z | *ORF | GP | L | NP |
| *ORF | Z | L | GP | *ORF | NP |
| L | GP | *ORF | NP | *ORF | Z |
| L | GP | *ORF | *ORF | Z | NP |
| L | GP | *ORF | Z | *ORF | NP |
| L | *ORF | Z | GP | *ORF | NP |
| L | GP | *ORF | NP | *ORF | Z |
| L | GP | *ORF | Z | *ORF | NP |
| L | GP | Z | NP | *ORF | *ORF |
| L | GP | Z | NP | *ORF | *ORF |
| L | *ORF | Z | NP | *ORF | GP |
| L | NP | *ORF | Z | *ORF | GP |
| L | NP | Z | *ORF | GP | *ORF |
| L | *ORF | Z | *ORF | GP | NP |
| L | NP | Z | GP | *ORF | *ORF |
| L | NP | *ORF | Z | *ORF | GP |
| L | *ORF | Z | NP | *ORF | GP |
| L | Z | *ORF | GP | *ORF | NP |
| L | Z | *ORF | NP | *ORF | GP |
| Z | GP | *ORF | NP | *ORF | L |
| Z | GP | *ORF | *ORF | L | NP |
| Z | GP | *ORF | L | *ORF | NP |
| Z | *ORF | L | GP | *ORF | NP |
| Z | GP | *ORF | NP | *ORF | L |
| Z | GP | *ORF | L | *ORF | NP |
| Z | GP | L | NP | *ORF | *ORF |
| Z | GP | L | NP | *ORF | *ORF |
| Z | *ORF | L | NP | *ORF | GP |
| Z | NP | *ORF | *ORF | L | GP |
| Z | NP | *ORF | GP | *ORF | L |
| Z | NP | *ORF | *ORF | L | GP |
| Z | NP | *ORF | L | *ORF | GP |

TABLE 2A-continued

Tri-segmented arenavirus viral vector comprising one
L segment and two S segments

| Position 1 | Position 2 | Position 3 | Position 4 | Position 5 | Position 6 |
|---|---|---|---|---|---|
| Z | NP | L | GP | *ORF | *ORF |
| Z | *ORF | L | GP | *ORF | NP |
| Z | NP | *ORF | GP | *ORF | L |
| Z | NP | *ORF | L | *ORF | GP |
| Z | *ORF | L | NP | *ORF | GP |
| Z | L | *ORF | GP | *ORF | NP |

Position 1 is under the control of an arenavirus S segment 5' UTR; Position 2 is under the control of an arenavirus S segment 3' UTR; Position 3 is under the control of an arenavirus S segment 5' UTR; Position 4 under the control of an arenavirus S segment 3' UTR; Position 5 is under the control of an arenavirus L segment 5' UTR; Position 6 is under the control of an arenavirus L segment 3' UTR.
*ORF indicates that a heterologous ORF has been inserted.

In certain embodiments, the IGR between position one and position two can be an arenavirus S segment or L segment IGR; the IGR between position two and three can be an arenavirus S segment or L segment IGR; and the IGR between the position five and six can be an arenavirus L segment IGR. In a specific embodiment, the IGR between position one and position two can be an arenavirus S segment IGR; the IGR between position two and three can be an arenavirus S segment IGR; and the IGR between the position five and six can be an arenavirus L segment IGR. In certain embodiments, other combinations are also possible. For example, a tri-segmented arenavirus viral vector comprising one L segment and two S segments, wherein intersegmental recombination of the two S segments in the tri-segmented arenavirus genome does not result in a replication-competent bi-segmented viral vector and abrogates arenaviral promoter activity (i.e., the resulting recombined S segment is made up of two 5'UTRs instead of a 3' UTR and a 5' UTR).

In certain embodiments, intersegmental recombination of an S segment and an L segment in the tri-segmented arenavirus viral vector comprising one L segment and two S segments, restores a functional segment with two viral genes on only one segment instead of two separate segments. In other embodiments, intersegmental recombination of an S segment and an L segment in the tri-segmented arenavirus viral vector comprising one L segment and two S segments does not result in a replication-competent bi-segmented viral particle.

Table 2B, below, is an illustration of the genome organization of a tri-segmented arenavirus viral vector comprising one L segment and two S segments, wherein intersegmental recombination of an S segment and an L segment in the tri-segmented arenavirus genome does not result in a replication-competent bi-segmented viral particle and abrogates arenaviral promoter activity (i.e., the resulting recombined segment is made up of two 3'UTRs instead of a 3' UTR and a 5' UTR).

TABLE 2B

Tri-segmented arenavirus viral vector comprising one L
segment and two S segments

| Position 1 | Position 2 | Position 3 | Position 4 | Position 5 | Position 6 |
|---|---|---|---|---|---|
| L | GP | *ORF | NP | Z | *ORF |
| L | GP | Z | *ORF | *ORF | NP |
| L | GP | *ORF | NP | Z | *ORF |
| L | GP | Z | *ORF | *ORF | NP |
| L | NP | *ORF | GP | Z | *ORF |
| L | NP | Z | *ORF | *ORF | GP |

TABLE 2B-continued

Tri-segmented arenavirus viral vector comprising one L
segment and two S segments

| Position 1 | Position 2 | Position 3 | Position 4 | Position 5 | Position 6 |
|---|---|---|---|---|---|
| L | NP | *ORF | GP | Z | *ORF |
| L | NP | Z | *ORF | *ORF | GP |
| Z | GP | *ORF | NP | L | *ORF |
| Z | GP | L | *ORF | *ORF | NP |
| Z | GP | *ORF | NP | L | *ORF |
| Z | NP | L | *ORF | *ORF | GP |
| Z | NP | *ORF | GP | L | *ORF |
| Z | NP | L | *ORF | *ORF | GP |

Position 1 is under the control of an arenavirus S segment 5' UTR; Position 2 is under the control of an arenavirus S segment 3' UTR; Position 3 is under the control of an arenavirus S segment 5' UTR; Position 4 under the control of an arenavirus S segment 3' UTR; Position 5 is under the control of an arenavirus L segment 5' UTR; Position 6 is under the control of an arenavirus L segment 3' UTR.
*ORF indicates that a heterologous ORF has been inserted.

In certain embodiments, the IGR between position one and position two can be an arenavirus S segment or L segment IGR; the IGR between position two and three can be an arenavirus S segment or L segment IGR; and the IGR between the position five and six can be an arenavirus L segment IGR. In a specific embodiment, the IGR between position one and position two can be an arenavirus S segment IGR; the IGR between position two and three can be an arenavirus S segment IGR; and the IGR between the position five and six can be an arenavirus L segment IGR. In certain embodiments, other combinations are also possible. For example, a tri-segmented arenavirus viral vector comprising one L segment and two S segments, wherein intersegmental recombination of the two S segments in the tri-segmented arenavirus genome does not result in a replication-competent bi-segmented viral particle and abrogates arenaviral promoter activity (i.e., the resulting recombined S segment is made up of two 5'UTRs instead of a 3' UTR and a 5' UTR).

In certain embodiments, one skilled in the art could construct an arenavirus genome with an organization as illustrated in Table 2A or 2B and as described herein, and then use an assay as described in Section 6.9 to determine whether the tri-segmented arenavirus viral vector is genetically stable, i.e., does not result in a replication-competent bi-segmented viral particle as discussed herein.

(b) Tri-Segmented Arenavirus Viral Vector Comprising Two L Segments and One S Segment In one aspect, provided herein is a tri-segmented arenavirus viral vector comprising two L segments and one S segment. In certain embodiments, propagation of the tri-segmented arenavirus viral vector comprising two L segments and one S segment does not result in a replication-competent bi-segmented viral particle. In specific embodiments, propagation of the tri-segmented arenavirus viral vector comprising two L segments and one S segment does not result in a replication-competent bi-segmented viral particle after at least 10 days, at least 20 days, at least 30 days, at least 40 days, or at least 50 days, at least 60 days, at least 70 days, at least 80 days, at least 90 days, at least 100 days of persistent in mice lacking type I interferon receptor, type II interferon receptor and recombination activating gene (RAG1), and having been infected with $10^4$ PFU of the tri-segmented arenavirus viral vector. In other embodiments, propagation of the tri-segmented arenavirus viral vector comprising two L segments and one S segment does not result in a replication-competent bi-segmented viral particle after at least 10 passages, 20 passages, 30 passages, 40 passages, or 50 passages.

In one aspect, the tri-segmented arenavirus viral vector comprising two L segments and one S segment further comprises a heterologous nucleotide sequence that encodes antigens of interest, an immunomodulatory peptide, polypeptide, or protein, a signal sequence, and/or a linker. Such sequences and their arrangement are described in Section 6.5.

In certain embodiments, inter-segmental recombination of the two L segments of the tri-segmented arenavirus viral vector, provided herein, that unities the two arenaviral ORFs on one instead of two separate segments results in a non functional promoter (i.e., a genomic segment of the structure: 5' UTR-5' UTR or a 3' UTR-3' UTR), wherein each UTR forming one end of the genome is an inverted repeat sequence of the other end of the same genome.

In certain embodiments, the tri-segmented arenavirus viral vector comprising two L segments and one S segment has been engineered to carry an arenavirus ORF in a position other than the wild-type position of the ORF. In other embodiments, the tri-segmented arenavirus viral vector comprising two L segments and one S segment has been engineered to carry two arenavirus ORFs, or three arenavirus ORFs, or four arenavirus ORFs, or five arenavirus ORFs, or six arenavirus ORFs in a position other than the wild-type position. In specific embodiments, the tri-segmented arenavirus viral vector comprising two L segments and one S segment comprises a full complement of all four arenavirus ORFs. Thus, in some embodiments, the tri-segmented arenavirus viral vector is an infectious and replication-competent tri-segmented arenavirus viral vector. In specific embodiments, the two L segments of the tri-segmented arenavirus viral vector have been engineered to carry one of their ORFs in a position other than the wild-type position. In more specific embodiments, the two L segments comprise a full complement of the L segment ORF's. In certain specific embodiments, the S segment has been engineered to carry one of their ORFs in a position other than the wild-type position or the S segment can be the wild-type genomic segment.

In certain embodiments, one of the two L segments can be:
  (i) an L segment, wherein the ORF encoding the GP is under control of an arenavirus 5' UTR;
  (ii) an L segment, wherein the ORF encoding NP is under control of an arenavirus 5' UTR;
  (iii) an L segment, wherein the ORF encoding the L protein is under control of an arenavirus 5' UTR;
  (iv) an L segment, wherein the ORF encoding the GP is under control of an arenavirus 3' UTR;
  (v) an L segment, wherein the ORF encoding the NP is under control of an arenavirus 3' UTR; and
  (vi) an L segment, wherein the ORF encoding the Z protein is under control of an arenavirus 3' UTR.

In certain embodiments, the tri-segmented arenavirus viral vector comprising two L segments and one S segment can comprise a duplicate ORF (i.e., two wild-type L segment ORFs e.g., Z protein or L protein). In specific embodiments, the tri-segmented arenavirus viral vector comprising two L segments and one S segment can comprise one duplicate ORF (e.g., (Z protein, Z protein)) or two duplicate ORFs (e.g., (Z protein, Z protein) and (L protein, L protein)).

Table 3, below, is an illustration of the genome organization of a tri-segmented arenavirus viral vector comprising two L segments and one S segment, wherein intersegmental recombination of the two L segments in the tri-segmented arenavirus genome does not result in a replication-competent bi-segmented viral vector and abrogates arenaviral promoter activity (i.e., the putatively resulting recombinant L segment would be made up of two 3'UTRs instead of a 3' UTR and a 5' UTR). Based on Table 3 similar combinations could be predicted for generating an arenavirus viral vector made up of two 5' UTRs instead of a 3' UTR and a 5' UTR.

TABLE 3

Tri-segmented arenavirus viral vector comprising two L segments and one S segment

| Position 1 | Position 2 | Position 3 | Position 4 | Position 5 | Position 6 |
|---|---|---|---|---|---|
| ORF* | Z | ORF* | L | NP | GP |
| ORF* | Z | ORF* | L | GP | NP |
| ORF* | Z | GP | L | ORF* | NP |
| ORF* | Z | ORF* | GP | NP | L |
| ORF* | Z | GP | ORF* | NP | L |
| ORF* | Z | NP | ORF* | GP | L |
| ORF* | ORF* | NP | Z | GP | L |
| ORF* | Z | GP | NP | ORF* | L |
| ORF* | Z | NP | GP | ORF* | L |
| ORF* | L | ORF* | Z | NP | GP |
| ORF* | L | ORF* | Z | GP | NP |
| ORF* | L | ORF* | GP | NP | Z |
| ORF* | L | GP | Z | ORF* | NP |
| ORF* | L | ORF* | GP | NP | Z |
| ORF* | L | NP | Z | ORF* | GP |
| ORF* | L | GP | NP | ORF* | Z |
| ORF* | L | NP | GP | ORF* | Z |
| ORF* | GP | ORF* | L | NP | Z |
| ORF* | GP | NP | L | ORF* | Z |
| ORF* | GP | ORF* | Z | NP | L |
| ORF* | GP | NP | Z | ORF* | L |
| ORF* | NP | ORF* | L | GP | Z |
| ORF* | NP | GP | L | ORF* | Z |
| ORF* | NP | GP | Z | ORF* | L |
| ORF* | NP | ORF* | Z | GP | L |
| ORF* | L | ORF* | Z | NP | GP |
| ORF* | L | ORF* | Z | GP | NP |
| ORF* | L | ORF* | NP | GP | Z |
| ORF* | L | ORF* | GP | NP | Z |
| ORF* | L | NP | Z | ORF* | GP |
| ORF* | Z | ORF* | GP | NP | L |
| ORF* | Z | GP | L | ORF* | NP |
| ORF* | Z | NP | GP | ORF* | L |
| ORF* | Z | GP | NP | ORF* | L |
| ORF* | GP | ORF* | L | NP | Z |
| ORF* | GP | ORF* | L | Z | NP |
| ORF* | GP | ORF* | Z | GP | L |
| ORF* | GP | NP | L | ORF* | Z |
| GP | L | ORF* | Z | ORF* | NP |
| GP | L | ORF* | NP | ORF* | Z |
| GP | Z | ORF* | L | ORF* | NP |
| GP | Z | ORF* | L | ORF* | NP |
| GP | Z | ORF* | NP | ORF* | L |
| GP | NP | ORF* | Z | ORF* | L |
| NP | L | ORF* | Z | ORF* | GP |
| NP | L | ORF* | GP | ORF* | Z |
| NP | L | ORF* | Z | ORF* | GP |

*Position 1 is under the control of an arenavirus L segment 5' UTR; position 2 is under the control of an arenavirus L segment 3' UTR; position 3 is under the control of an arenavirus L segment 5' UTR; position 4 is under the control of an arenavirus L segment 3' UTR; position 5 is under the control of an arenavirus S segment 5' UTR; position 6 is under the control of an arenavirus S segment 3' UTR.
*ORF indicates that a heterologous ORF has been inserted.

In certain embodiments, the IGR between position one and position two can be an arenavirus S segment or L segment IGR; the IGR between position two and three can be an arenavirus S segment or L segment IGR; and the IGR between the position five and six can be an arenavirus S or L segment IGR. In a specific embodiment, the IGR between position one and position two can be an arenavirus L segment IGR; the IGR between position two and three can be an arenavirus L segment IGR; and the IGR between the position five and six can be an arenavirus S segment IGR. In certain embodiments, other combinations are also possible.

In certain embodiments, intersegmental recombination of an L segment and an S segment from the tri-segmented arenavirus viral vector comprising two L segments and one S segment restores a functional segment with two viral genes on only one segment instead of two separate segments. In other embodiments, intersegmental recombination of an L segment and an S segment in the tri-segmented arenavirus viral vector comprising two L segments and one S segment does not result in a replication-competent bi-segmented viral particle.

Table 3B, below, is an illustration of the genome organization of a tri-segmented arenavirus viral vector comprising two L segments and one S segment, wherein intersegmental recombination of an L segment and an S segment in the tri-segmented arenavirus genome does not result in a replication-competent bi-segmented viral particle and abrogates arenaviral promoter activity (i.e., the resulting recombined segment is made up of two 3'UTRs instead of a 3' UTR and a 5' UTR).

TABLE 3B

Tri-segmented arenavirus viral vector comprising two L segments and one S segment

| Position 1 | Position 2 | Position 3 | Position 4 | Position 5 | Position 6 |
|---|---|---|---|---|---|
| NP | Z | *ORF | GP | L | *ORF |
| NP | Z | GP | *ORF | *ORF | L |
| NP | Z | *ORF | GP | L | *ORF |
| NP | Z | GP | *ORF | *ORF | L |
| NP | L | *ORF | GP | Z | *ORF |
| NP | L | GP | *ORF | *ORF | Z |
| NP | L | *ORF | GP | Z | *ORF |
| NP | L | GP | *ORF | *ORF | Z |
| GP | Z | *ORF | NP | L | *ORF |
| GP | Z | NP | *ORF | *ORF | L |
| GP | Z | *ORF | NP | L | *ORF |
| GP | L | NP | *ORF | *ORF | Z |
| GP | L | *ORF | NP | Z | *ORF |
| GP | L | NP | *ORF | *ORF | Z |

*Position 1 is under the control of an arenavirus L segment 5' UTR; position 2 is under the control of an arenavirus L segment 3' UTR; position 3 is under the control of an arenavirus L segment 5' UTR; position 4 is under the control of an arenavirus L segment 3' UTR; position 5 is under the control of an arenavirus S segment 5' UTR; position 6 is under the control of an arenavirus S segment 3' UTR.
*ORF indicates that a heterologous ORF has been inserted.

In certain embodiments, the IGR between position one and position two can be an arenavirus S segment or L segment IGR; the IGR between position two and three can be an arenavirus S segment or L segment IGR; and the IGR between the position five and six can be an arenavirus S segment or L segment IGR. In a specific embodiment, the IGR between position one and position two can be an arenavirus L segment IGR; the IGR between position two and three can be an arenavirus L segment IGR; and the IGR between the position five and six can be an arenavirus S segment IGR. In certain embodiments, other combinations are also possible.

In certain embodiments, one skilled in the art could construct an arenavirus genome with an organization as illustrated in Table 3A or 3B and as described herein, and then use an assay as described in Section 6.9 to determine whether the tri-segmented arenavirus viral vector is genetically stable, i.e., does not result in a replication-competent bi-segmented viral vector as discussed herein.

(c) Replication-Deficient Tri-Segmented Arenavirus Viral Vector

In certain embodiments, provided herein is a tri-segmented arenavirus viral vector in which (i) an ORF is in a position other than the wild-type position of the ORF; and (ii) an ORF encoding GP, NP, Z protein, or L protein has been removed or functionally inactivated such that the resulting virus cannot produce further infectious progeny virus particles (i.e., is replication defective). In certain embodiments, the third arenavirus segment can be an S segment. In other embodiments, the third arenavirus segment can be an L segment. In more specific embodiments, the third arenavirus segment can be engineered to carry an ORF in a position other than the wild-type position of the ORF or the third arenavirus segment can be the wild-type arenavirus genomic segment. In yet more specific embodiments, the third arenavirus segment lacks an arenavirus ORF encoding GP, NP, Z protein, or the L protein.

In one aspect, the replication-deficient tri-segmented arenavirus viral vector provided herein further comprises a heterologous nucleotide sequence that encodes antigens of interest, an immunomodulatory peptide, polypeptide, or protein, a signal sequence, and/or a linker. Such sequences and their arrangement are described in Section 6.5.

In certain embodiments, a tri-segmented genomic segment could be a S or a L segment hybrid (i.e., a genomic segment that can be a combination of the S segment and the L segment). In other embodiments, the hybrid segment is an S segment comprising an L segment IGR. In another embodiment, the hybrid segment is an L segment comprising an S segment IGR. In other embodiments, the hybrid segment is an S segment UTR with an L segment IGR. In another embodiment, the hybrid segment is an L segment UTR with an S segment IGR. In specific embodiments, the hybrid segment is an S segment 5' UTR with an L segment IGR or an S segment 3' UTR with an L segment IGR. In other specific embodiments, the hybrid segment is an L segment 5' UTR with an S segment IGR or an L segment 3' UTR with an S segment IGR.

A tri-segmented arenavirus viral vector comprising a genetically modified genome in which one or more ORFs has been removed (e.g., deleted) or functionally inactivated can be produced in complementing cells (i.e., cells that express the arenavirus ORF that has been removed or functionally inactivated). The genetic material of the resulting arenavirus viral vector can be transferred upon infection of a host cell into the host cell, wherein the genetic material can be expressed and amplified. In addition, the genome of the genetically modified arenavirus viral vector described herein can encode a heterologous ORF from an organism other than an arenavirus viral vector.

In certain embodiments, at least one of the four ORFs encoding GP, NP, Z protein, and L protein is removed and replaced with a heterologous ORF from an organism other than an arenavirus. In another embodiment, at least one ORF, at least two ORFs, at least three ORFs, or at least four ORFs encoding GP, NP, Z protein and L protein can be removed and replaced with a heterologous ORF from an organism other than an arenavirus. In specific embodiments, only one of the four ORFs encoding GP, NP, Z protein, and L protein is removed and replaced with a heterologous ORF from an organism other than an arenavirus viral vector. In more specific embodiments, the ORF that encodes GP of the arenavirus genomic segment is removed. In another specific embodiment, the ORF that encodes the NP of the arenavirus genomic segment is removed. In more specific embodiments, the ORF that encodes the Z protein of the arenavirus genomic segment is removed. In yet another specific embodiment, the ORF encoding the L protein is removed.

In certain embodiments, provided herein is a tri-segmented arenavirus viral vector comprising one L segment and two S segments in which (i) an ORF is in a position other than the wild-type position of the ORF; and (ii) an ORF encoding GP or NP has been removed or functionally inactivated, such that the resulting virus is replication-deficient and not infectious. In a specific embodiment, one ORF is removed and replaced with a heterologous ORF from an organism other than an arenavirus. In another specific embodiment, two ORFs are removed and replaced with heterologous ORFs from an organism other than an arenavirus. In other specific embodiments, three ORFs are removed and replaced with heterologous ORFs from an organism other than an arenavirus. In specific embodiments, the ORF encoding GP is removed and replaced with a heterologous ORF from an organism other than an arenavirus. In other specific embodiments, the ORF encoding NP is removed and replaced with a heterologous ORF from an organism other than an arenavirus. In yet more specific embodiments, the ORF encoding NP and the ORF encoding GP are removed and replaced with one or two heterologous ORFs from an organism other than an arenavirus viral vector. Thus, in certain embodiments the tri-segmented arenavirus viral vector comprises (i) one L segment and two S segments; (ii) an ORF in a position other than the wild-type position of the ORF; (iii) one or more heterologous ORFs from an organism other than an arenavirus.

In certain embodiments, provided herein is a tri-segmented arenavirus viral vector comprising two L segments and one S segment in which (i) an ORF is in a position other than the wild-type position of the ORF; and (ii) an ORF encoding the Z protein, and/or the L protein has been removed or functionally inactivated, such that the resulting virus replication-deficient and not infectious. In a specific embodiment, one ORF is removed and replaced with a heterologous ORF from an organism other than an arenavirus. In another specific embodiment, two ORFs are removed and replaced with a heterologous ORF from an organism other than an arenavirus. In specific embodiments, the ORF encoding the Z protein is removed and replaced with a heterologous ORF from an organism other than an arenavirus. In other specific embodiments, the ORF encoding the L protein is removed and replaced with a heterologous ORF from an organism other than an arenavirus. In yet more specific embodiments, the ORF encoding the Z protein and the ORF encoding the L protein is removed and replaced with a heterologous ORF from an organism other than an arenavirus viral vector. Thus, in certain embodiments the tri-segmented arenavirus viral vector comprises (i) two L segments and one S segment; (ii) an ORF in a position other than the wild-type position of the ORF; (iii) a heterologous ORF from an organism other than an arenavirus.

Thus, in certain embodiments, the tri-segmented arenavirus viral vector provided herein comprises a tri-segmented arenavirus viral vector (i.e., one L segment and two S segments or two L segments and one S segment) that i) is engineered to carry an ORF in a non-natural position; ii) an ORF encoding GP, NP, Z protein, or L protein is removed); and iii) the ORF that is removed is replaced with one or more heterologous ORFs from an organism other than an arenavirus (Section 6.5).

In certain embodiments, the heterologous ORF is 8 to 100 nucleotides in length, 15 to 100 nucleotides in length, 25 to 100 nucleotides in length, 50 to 200 nucleotide in length, 50 to 400 nucleotide in length, 200 to 500 nucleotide in length, or 400 to 600 nucleotides in length, 500 to 800 nucleotide in length. In other embodiments, the heterologous ORF is 750 to 900 nucleotides in length, 800 to 100 nucleotides in length, 850 to 1000 nucleotides in length, 900 to 1200 nucleotides in length, 1000 to 1200 nucleotides in length, 1000 to 1500 nucleotides or 1200 to 1500 nucleotides in length, 1500 to 2000 nucleotides in length, 1700 to 2000 nucleotides in length, 2000 to 2300 nucleotides in length, 2200 to 2500 nucleotides in length, 2500 to 3000 nucleotides in length, 3000 to 3200 nucleotides in length, 3000 to 3500 nucleotides in length, 3200 to 3600 nucleotides in length, 3300 to 3800 nucleotides in length, 4000 nucleotides to 4400 nucleotides in length, 4200 to 4700 nucleotides in length, 4800 to 5000 nucleotides in length, 5000 to 5200 nucleotides in length, 5200 to 5500 nucleotides in length, 5500 to 5800 nucleotides in length, 5800 to 6000 nucleotides in length, 6000 to 6400 nucleotides in length, 6200 to 6800 nucleotides in length, 6600 to 7000 nucleotides in length, 7000 to 7200 nucleotides in lengths, 7200 to 7500 nucleotides in length, or 7500 nucleotides or more in length. In some embodiments, the heterologous ORF encodes a peptide or polypeptide that is 5 to 10 amino acids in length, 10 to 25 amino acids in length, 25 to 50 amino acids in length, 50 to 100 amino acids in length, 100 to 150 amino acids in length, 150 to 200 amino acids in length, 200 to 250 amino acids in length, 250 to 300 amino acids in length, 300 to 400 amino acids in length, 400 to 500 amino acids in length, 500 to 750 amino acids in length, 750 to 1000 amino acids in length, 1000 to 1250 amino acids in length 1250 to 1500 amino acids in length, 1500 to 1750 amino acids in length, 1750 to 2000 amino acids in length, 2000 to 2500 amino acids in length, or more than 2500 amino acids in length. In some embodiments, the heterologous ORF encodes a polypeptide that does not exceed 2500 amino acids in length. In specific embodiments the heterologous ORF does not contain a stop codon. In certain embodiments, the heterologous ORF is codon-optimized. In certain embodiments the nucleotide composition, nucleotide pair composition or both can be optimized. Techniques for such optimizations are known in the art and can be applied to optimize a heterologous ORF.

Any heterologous ORF from an organism other than an arenavirus may be included in the tri-segmented arenavirus viral vector. Thus, in certain embodiments, a tri-segmented arenavirus viral vector provided herein comprises a) a deletion or functional inactivation of an open reading frame that is present in the wild type arenavirus; and b) encodes one or more antigens of an oncogenic virus (e.g., HPV E6, HPV E7, and/or HPV E6/E7 fusion protein), and/or an immunomodulatory peptide, polypeptide, or protein. More detailed description on heterologous ORFs is described in Section 6.5.

In one embodiment, the heterologous ORF encodes a reporter protein. More detailed description of reporter proteins are described in Section 6.5.

In certain embodiments, the growth and infectivity of the arenavirus viral vector is not affected by the heterologous ORF from an organism other than an arenavirus.

Techniques known to one skilled in the art may be used to produce an arenavirus viral vector comprising an arenavirus genomic segment engineered to carry an arenavirus ORF in a position other than the wild-type position. For example, reverse genetics techniques may be used to generate such arenavirus viral vector. In other embodiments, the replication-deficient arenavirus viral vector (i.e., the arenavirus genomic segment engineered to carry an arenavirus ORF in a position other than the wild-type position, wherein an ORF encoding GP, NP, Z protein, L protein, has been deleted) can be produced in a complementing cell.

In certain embodiments, the tri-segmented arenavirus viral vector used according to the present application can be Old World viruses, for example, LCMV.

6.4 Generation of an Arenavirus Viral Vector and a Tri-Segmented Arenavirus Viral Vector Generally, arenavirus viral vectors can be recombinantly produced by standard reverse genetic techniques as described for LCMV (see Flatz et al., 2006, Proc Natl Acad Sci USA 103:4663-4668; Sanchez et al., 2006, Virology 350:370; Ortiz-Riano et al., 2013, J Gen Virol. 94:1175-88, which are incorporated by reference herein). To generate the arenavirus viral vectors provided herein, these techniques can be applied as described below. The genome of the viruses can be modified as described in Sections 6.2 or 6.3.

(a) Non-Natural Position Open Reading Frame

The generation of an arenavirus viral vector comprising a genomic segment that has been engineered to carry a viral ORF in a position other than the wild-type position of the ORF can be recombinantly produced by any reverse genetic techniques known to one skilled in the art.

(i) Infectious and Replication-Competent Arenavirus Viral Vector

In certain embodiments, the method of generating the arenavirus viral vector comprises (i) transfecting into a host cell the cDNA of the first arenavirus genomic segment; (ii) transfecting into a host cell the cDNA of the second arenavirus genomic segment; (iii) transfecting into a host cell plasmids expressing the arenavirus' minimal trans-acting factors NP and L; (iv) maintaining the host cell under conditions suitable for virus formation; and (v) harvesting the arenavirus viral vector. In certain more specific embodiments, the cDNA is comprised in a plasmid.

Once generated from cDNA, arenavirus viral vectors (i.e., infectious and replication-competent) can be propagated. In certain embodiments, the arenavirus viral vector can be propagated in any host cell that allows the virus to grow to titers that permit the uses of the virus as described herein. In one embodiment, the host cell allows the arenavirus viral vector to grow to titers comparable to those determined for the corresponding wild-type.

In certain embodiments, the arenavirus viral vector may be propagated in host cells. Specific examples of host cells that can be used include BHK-21, HEK 293, VERO or other. In a specific embodiment, the arenavirus viral vector may be propagated in a cell line.

In certain embodiments, the host cells are kept in culture and are transfected with one or more plasmid(s). The plasmid(s) express the arenavirus genomic segment(s) to be generated under control of one or more expression cassettes suitable for expression in mammalian cells, e.g., consisting of a polymerase I promoter and terminator.

Plasmids that can be used for the generation of the arenavirus viral vector can include: i) a plasmid encoding the S genomic segment e.g., pol-I S, ii) a plasmid encoding the L genomic segment e.g., pol-I L. In certain embodiments, the plasmid encoding an arenavirus polymerase that direct intracellular synthesis of the viral L and S segments can be incorporated into the transfection mixture. For example, a plasmid encoding the L protein and/or a plasmid encoding NP (pC-L and pC-NP, respectively) can be present. The L protein and NP are the minimal trans-acting factors necessary for viral RNA transcription and replication. Alternatively, intracellular synthesis of viral L and S segments, together with NP and L protein can be performed using an expression cassette with pol-I and pol-II promoters reading from opposite sides into the L and S segment cDNAs of two separate plasmids, respectively.

In certain embodiments, the arenavirus genomic segments are under the control of a promoter. Typically, RNA polymerase I-driven expression cassettes, RNA polymerase II-driven cassettes or T7 bacteriophage RNA polymerase driven cassettes can be used. In certain embodiments, the plasmid(s) encoding the arenavirus genomic segments can be the same, i.e., the genome sequence and transacting factors can be transcribed by a promoter from one plasmid. Specific examples of promoters include an RNA polymerase I promoter, an RNA polymerase II promoter, an RNA polymerase III promoter, a T7 promoter, an SP6 promoter or a T3 promoter.

In addition, the plasmid(s) can feature a mammalian selection marker, e.g., puromycin resistance, under control of an expression cassette suitable for gene expression in mammalian cells, e.g., polymerase II expression cassette as above, or the viral gene transcript(s) are followed by an internal ribosome entry site, such as the one of encephalomyocarditis virus, followed by the mammalian resistance marker. For production in *E. coli*, the plasmid additionally features a bacterial selection marker, such as an ampicillin resistance cassette.

Transfection of a host cell with a plasmid(s) can be performed using any of the commonly used strategies such as calcium-phosphate, liposome-based protocols or electroporation. A few days later the suitable selection agent, e.g., puromycin, is added in titrated concentrations. Surviving clones are isolated and subcloned following standard procedures, and high-expressing clones are identified using Western blot or flow cytometry procedures with antibodies directed against the viral protein(s) of interest.

For recovering the arenavirus viral vector described herein, the following procedures are envisaged. First day: cells, typically 80% confluent in M6-well plates, are transfected with a mixture of the plasmids, as described above. For this one can exploit any commonly used strategies such as calcium-phosphate, liposome-based protocols or electroporation.

3-5 days later: The cultured supernatant (arenavirus vector preparation) is harvested, aliquoted and stored at 4° C., −20° C., or −80° C., depending on how long the arenavirus vector should be stored prior use. The arenavirus vector preparation's infectious titer is assessed by an immunofocus assay. Alternatively, the transfected cells and supernatant may be passaged to a larger vessel (e.g., a T75 tissue culture flask) on day 3-5 after transfection, and culture supernatant is harvested up to five days after passage.

The present application furthermore provides expression of a heterologous ORF, wherein a plasmid encoding the genomic segment is modified to incorporate a heterologous ORF. More detailed description on heterologous ORFs is described in Section 6.5. The heterologous ORF can be incorporated into the plasmid using restriction enzymes.

(ii) Infectious, Replication-Deficient Arenavirus Viral Vector

Infectious, replication-deficient arenavirus viral vectors can be rescued as described above. However, once generated from cDNA, the infectious, replication-deficient arenaviruses provided herein can be propagated in complementing cells. Complementing cells are cells that provide the functionality that has been eliminated from the replication-deficient arenavirus by modification of its genome (e.g., if the ORF encoding the GP protein is deleted or functionally inactivated, a complementing cell does provide the GP protein).

Owing to the removal or functional inactivation of one or more of the ORFs in arenavirus vectors (here deletion of the glycoprotein, GP, will be taken as an example), arenavirus vectors can be generated and expanded in cells providing in trans the deleted viral gene(s), e.g., the GP in the present example. Such a complementing cell line, henceforth referred to as C-cells, is generated by transfecting a cell line such as BHK-21, HEK 293, VERO or other with one or more plasmid(s) for expression of the viral gene(s) of interest (complementation plasmid, referred to as C-plasmid). The C-plasmid(s) express the viral gene(s) deleted in the arenavirus vector to be generated under control of one or more expression cassettes suitable for expression in mammalian cells, e.g., a mammalian polymerase II promoter such as the EF1alpha promoter with a polyadenylation signal. In addition, the complementation plasmid features a mammalian selection marker, e.g., puromycin resistance, under control of an expression cassette suitable for gene expression in mammalian cells, e.g., polymerase II expression cassette as above, or the viral gene transcript(s) are followed by an internal ribosome entry site, such as the one of encephalomyocarditis virus, followed by the mammalian resistance marker. For production in E. coli, the plasmid additionally features a bacterial selection marker, such as an ampicillin resistance cassette.

Cells that can be used, e.g., BHK-21, HEK 293, MC57G or other, are kept in culture and are transfected with the complementation plasmid(s) using any of the commonly used strategies such as calcium-phosphate, liposome-based protocols or electroporation. A few days later the suitable selection agent, e.g., puromycin, is added in titrated concentrations. Surviving clones are isolated and subcloned following standard procedures, and high-expressing C-cell clones are identified using Western blot or flow cytometry procedures with antibodies directed against the viral protein(s) of interest. As an alternative to the use of stably transfected C-cells transient transfection of normal cells can complement the missing viral gene(s) in each of the steps where C-cells will be used below. In addition, a helper virus can be used to provide the missing functionality in trans.

Plasmids can be of two types: i) two plasmids, referred to as TF-plasmids for expressing intracellularly in C-cells the minimal transacting factors of the arenavirus, is derived from e.g., NP and L proteins of LCMV in the present example; and ii) plasmids, referred to as GS-plasmids, for expressing intracellularly in C-cells the arenavirus vector genome segments, e.g., the segments with designed modifications. TF-plasmids express the NP and L proteins of the respective arenavirus vector under control of an expression cassette suitable for protein expression in mammalian cells, typically e.g., a mammalian polymerase II promoter such as the CMV or EF1 alpha promoter, either one of them preferentially in combination with a polyadenylation signal. GS-plasmids express the small (S) and the large (L) genome segments of the vector. Typically, polymerase I-driven expression cassettes or T7 bacteriophage RNA polymerase (T7-) driven expression cassettes can be used, the latter preferentially with a 3'-terminal ribozyme for processing of the primary transcript to yield the correct end. In the case of using a T7-based system, expression of T7 in C-cells must be provided by either including in the recovery process an additional expression plasmid, constructed analogously to TF-plasmids, providing T7, or C-cells are constructed to additionally express T7 in a stable manner. In certain embodiments, TF and GS plasmids can be the same, i.e., the genome sequence and transacting factors can be transcribed by T7, polI and polII promoters from one plasmid.

For recovering of the arenavirus vector, the following procedures can be used. First day: C-cells, typically 80% confluent in M6-well plates, are transfected with a mixture of the two TF-plasmids plus the two GS-plasmids. In certain embodiments, the TF and GS plasmids can be the same, i.e., the genome sequence and transacting factors can be transcribed by T7, polI and polII promoters from one plasmid. For this one can exploit any of the commonly used strategies such as calcium-phosphate, liposome-based protocols or electroporation.

3-5 days later: The culture supernatant (arenavirus vector preparation) is harvested, aliquoted and stored at 4° C., −20° C. or −80° C. depending on how long the arenavirus vector should be stored prior to use. Then the arenavirus vector preparation's infectious titer is assessed by an immunofocus assay on C-cells. Alternatively, the transfected cells and supernatant may be passaged to a larger vessel (e.g., a T75 tissue culture flask) on day 3-5 after transfection, and culture supernatant is harvested up to five days after passage.

Also provided herein is expression of an antigen in a cell culture, wherein the cell culture is infected with an infectious, replication-deficient arenavirus expressing an antigen. When used for expression of an antigen in cultured cells, the following two procedures can be used:

i) The cell type of interest is infected with the arenavirus vector preparation described herein at a multiplicity of infection (MOI) of one or more, e.g., two, three or four, resulting in production of the antigen in all cells already shortly after infection.

ii) Alternatively, a lower MOI can be used and individual cell clones can be selected for their level of virally driven antigen expression. Subsequently individual clones can be expanded infinitely owing to the non-cytolytic nature of arenavirus vectors. Irrespective of the approach, the antigen can subsequently be collected (and purified) either from the culture supernatant or from the cells themselves, depending on the properties of the antigen produced. However, the invention is not limited to these two strategies, and other ways of driving expression of antigen using infectious, replication-deficient arenaviruses as vectors may be considered.

(b) Generation of a Tri-Segmented Arenavirus Viral Vector

A tri-segmented arenavirus viral vector can be recombinantly produced by reverse genetic techniques known in the art, for example as described by Emonet et al., 2008, PNAS, 106(9):3473-3478; Popkin et al., 2011, J. Virol., 85 (15): 7928-7932, which are incorporated by reference herein. The generation of the tri-segmented arenavirus viral vector provided herein can be modified as described in Section 6.3.

(i) Infectious and Replication-Competent Tri-Segmented Arenavirus Viral Vector

In certain embodiments, the method of generating the tri-segmented arenavirus viral vector comprises (i) transfecting into a host cell the cDNAs of the one L segment and two S segments or two L segments and one S segment; (ii) transfecting into a host cell plasmids expressing the arenavirus' minimal trans-acting factors NP and L; (iii) maintaining the host cell under conditions suitable for virus formation; and (iv) harvesting the arenavirus viral vector.

Once generated from cDNA, the tri-segmented arenavirus viral vector (i.e., infectious and replication-competent) can be propagated. In certain embodiments tri-segmented arenavirus viral vector can be propagated in any host cell that allows the virus to grow to titers that permit the uses of the virus as described herein. In one embodiment, the host cell allows the tri-segmented arenavirus viral vector to grow to titers comparable to those determined for the corresponding wild-type.

In certain embodiments, the tri-segmented arenavirus viral vector may be propagated in host cells. Specific examples of host cells that can be used include BHK-21, HEK 293, VERO or other. In a specific embodiment, the tri-segmented arenavirus viral vector may be propagated in a cell line.

In certain embodiments, the host cells are kept in culture and are transfected with one or more plasmid(s). The plasmid(s) express the arenavirus genomic segment(s) to be generated under control of one or more expression cassettes suitable for expression in mammalian cells, e.g., consisting of a polymerase I promoter and terminator.

In specific embodiments, the host cells are kept in culture and are transfected with one or more plasmid(s). The plasmid(s) express the viral gene(s) to be generated under control of one or more expression cassettes suitable for expression in mammalian cells, e.g., consisting of a polymerase I promoter and terminator.

Plasmids that can be used for generating the tri-segmented arenavirus comprising one L segment and two S segments can include: i) two plasmids each encoding the S genome segment e.g., pol-I S, ii) a plasmid encoding the L genome segment e.g., pol-I L. Plasmids needed for the tri-segmented arenavirus comprising two L segments and one S segments are: i) two plasmids each encoding the L genome segment e.g., pol-L, ii) a plasmid encoding the S genome segment e.g., pol-I S.

In certain embodiments, plasmids encoding an arenavirus polymerase that direct intracellular synthesis of the viral L and S segments can be incorporated into the transfection mixture. For example, a plasmid encoding the L protein and a plasmid encoding NP (pC-L and pC-NP, respectively). The L protein and NP are the minimal trans-acting factors necessary for viral RNA transcription and replication. Alternatively, intracellular synthesis of viral L and S segments, together with NP and L protein can be performed using an expression cassette with pol-I and pol-II promoters reading from opposite sides into the L and S segment cDNAs of two separate plasmids, respectively.

In addition, the plasmid(s) features a mammalian selection marker, e.g., puromycin resistance, under control of an expression cassette suitable for gene expression in mammalian cells, e.g., polymerase II expression cassette as above, or the viral gene transcript(s) are followed by an internal ribosome entry site, such as the one of encephalomyocarditis virus, followed by the mammalian resistance marker. For production in *E. coli*, the plasmid additionally features a bacterial selection marker, such as an ampicillin resistance cassette.

Transfection of BHK-21 cells with a plasmid(s) can be performed using any of the commonly used strategies such as calcium-phosphate, liposome-based protocols or electroporation. A few days later the suitable selection agent, e.g., puromycin, is added in titrated concentrations. Surviving clones are isolated and subcloned following standard procedures, and high-expressing clones are identified using Western blot or flow cytometry procedures with antibodies directed against the viral protein(s) of interest.

Typically, RNA polymerase I-driven expression cassettes, RNA polymerase II-driven cassettes or T7 bacteriophage RNA polymerase driven cassettes can be used, the latter preferentially with a 3'-terminal ribozyme for processing of the primary transcript to yield the correct end. In certain embodiments, the plasmids encoding the arenavirus genomic segments can be the same, i.e., the genome sequence and transacting factors can be transcribed by T7, polI and polII promoters from one plasmid.

For recovering the arenavirus the tri-segmented arenavirus vector, the following procedures are envisaged. First day: cells, typically 80% confluent in M6-well plates, are transfected with a mixture of the plasmids, as described above. For this one can exploit any commonly used strategies such as calcium-phosphate, liposome-based protocols or electroporation.

3-5 days later: The cultured supernatant (arenavirus vector preparation) is harvested, aliquoted and stored at 4° C., −20° C., or −80° C., depending on how long the arenavirus vector should be stored prior use. The arenavirus vector preparation's infectious titer is assessed by an immunofocus assay. Alternatively, the transfected cells and supernatant may be passaged to a larger vessel (e.g., a T75 tissue culture flask) on day 3-5 after transfection, and culture supernatant is harvested up to five days after passage.

The present application furthermore relates to expression of a heterologous ORF, wherein a plasmid encoding the genomic segment is modified to incorporated a heterologous ORF. More detailed description on heterologous ORFs is described in Section 6.5. The heterologous ORF can be incorporated into the plasmid using restriction enzymes.

(ii) Infectious, Replication-Deficient Tri-Segmented Arenavirus Viral Vector

Infectious, replication-deficient tri-segmented arenavirus viral vectors can be rescued as described above. However, once generated from cDNA, the infectious, replication-deficient arenaviruses provided herein can be propagated in complementing cells. Complementing cells are cells that provide the functionality that has been eliminated from the replication-deficient arenavirus by modification of its genome (e.g., if the ORF encoding the GP protein is deleted or functionally inactivated, a complementing cell does provide the GP protein).

Owing to the removal or functional inactivation of one or more of the ORFs in arenavirus vectors (here deletion of the glycoprotein, GP, will be taken as an example), arenavirus vectors can be generated and expanded in cells providing in trans the deleted viral gene(s), e.g., the GP in the present example. Such a complementing cell line, henceforth referred to as C-cells, is generated by transfecting a mammalian cell line such as BHK-21, HEK 293, VERO or other (here BHK-21 will be taken as an example) with one or more plasmid(s) for expression of the viral gene(s) of interest (complementation plasmid, referred to as C-plasmid). The C-plasmid(s) express the viral gene(s) deleted in the arenavirus vector to be generated under control of one or more expression cassettes suitable for expression in mammalian cells, e.g., a mammalian polymerase II promoter such as the CMV or EF1alpha promoter with a polyadenylation signal. In addition, the complementation plasmid features a mammalian selection marker, e.g., puromycin resistance, under control of an expression cassette suitable for gene expression in mammalian cells, e.g., polymerase II expression cassette as above, or the viral gene transcript(s) are followed by an internal ribosome entry site, such as the one of encephalomyocarditis virus, followed by the mammalian resistance marker. For production in *E. coli*, the plasmid additionally features a bacterial selection marker, such as an ampicillin resistance cassette.

Cells that can be used, e.g., BHK-21, HEK 293, MC57G or other, are kept in culture and are transfected with the complementation plasmid(s) using any of the commonly used strategies such as calcium-phosphate, liposome-based protocols or electroporation. A few days later the suitable selection agent, e.g., puromycin, is added in titrated concentrations. Surviving clones are isolated and subcloned following standard procedures, and high-expressing C-cell clones are identified using Western blot or flow cytometry procedures with antibodies directed against the viral protein(s) of interest. As an alternative to the use of stably transfected C-cells transient transfection of normal cells can complement the missing viral gene(s) in each of the steps where C-cells will be used below. In addition, a helper virus can be used to provide the missing functionality in trans.

Plasmids of two types can be used: i) two plasmids, referred to as TF-plasmids for expressing intracellularly in C-cells the minimal transacting factors of the arenavirus, is derived from e.g., NP and L proteins of LCMV in the present example; and ii) plasmids, referred to as GS-plasmids, for expressing intracellularly in C-cells the arenavirus vector genome segments, e.g., the segments with designed modifications. TF-plasmids express the NP and L proteins of the respective arenavirus vector under control of an expression cassette suitable for protein expression in mammalian cells, typically e.g., a mammalian polymerase II promoter such as the CMV or EF1 alpha promoter, either one of them preferentially in combination with a polyadenylation signal. GS-plasmids express the small (S) and the large (L) genome segments of the vector. Typically, polymerase I-driven expression cassettes or T7 bacteriophage RNA polymerase (T7-) driven expression cassettes can be used, the latter preferentially with a 3'-terminal ribozyme for processing of the primary transcript to yield the correct end. In the case of using a T7-based system, expression of T7 in C-cells must be provided by either including in the recovery process an additional expression plasmid, constructed analogously to TF-plasmids, providing T7, or C-cells are constructed to additionally express T7 in a stable manner. In certain embodiments, TF and GS plasmids can be the same, i.e., the genome sequence and transacting factors can be transcribed by T7, polI and polII promoters from one plasmid.

For recovering of the arenavirus vector, the following procedures can be used. First day: C-cells, typically 80% confluent in M6-well plates, are transfected with a mixture of the two TF-plasmids plus the two GS-plasmids. In certain embodiments, the TF and GS plasmids can be the same, i.e., the genome sequence and transacting factors can be transcribed by T7, polI and polII promoters from one plasmid. For this one can exploit any of the commonly used strategies such as calcium-phosphate, liposome-based protocols or electroporation.

3-5 days later: The culture supernatant (arenavirus vector preparation) is harvested, aliquoted and stored at 4° C., −20° C. or −80° C. depending on how long the arenavirus vector should be stored prior to use. Then the arenavirus vector preparation's infectious titer is assessed by an immunofocus assay on C-cells. Alternatively, the transfected cells and supernatant may be passaged to a larger vessel (e.g., a T75 tissue culture flask) on day 3-5 after transfection, and culture supernatant is harvested up to five days after passage.

The invention furthermore relates to expression of an antigen in a cell culture wherein the cell culture is infected with an infectious, replication-deficient tri-segmented arenavirus expressing a antigen. When used for expression of a CMV antigen in cultured cells, the following two procedures can be used:

i) The cell type of interest is infected with the arenavirus vector preparation described herein at a multiplicity of infection (MOI) of one or more, e.g., two, three or four, resulting in production of the antigen in all cells already shortly after infection.

ii) Alternatively, a lower MOI can be used and individual cell clones can be selected for their level of virally driven antigen expression. Subsequently individual clones can be expanded infinitely owing to the non-cytolytic nature of arenavirus vectors. Irrespective of the approach, the antigen can subsequently be collected (and purified) either from the culture supernatant or from the cells themselves, depending on the properties of the antigen produced. However, the invention is not limited to these two strategies, and other ways of driving expression of CMV antigen using infectious, replication-deficient arenaviruses as vectors may be considered.

6.5 Heterologous Sequences (a) Oncogenic Virus Antigens and HPV Antigens

In certain embodiments, a heterologous sequence encompassed by an arenavirus viral vector described herein encodes an antigen. In certain embodiments, an oncogenic virus antigen for use with the methods and compositions described herein is an antigen of a DNA virus, an RNA virus or of a retrovirus. In certain, more specific embodiments, the antigen itself is oncogenic.

In certain embodiments, the heterologous nucleotide sequence is derived from an oncogenic virus.

In certain embodiments, an antigen for use with the methods and compositions described herein can be an antigen of any oncogenic virus excluding Hepatitis B virus antigen and Hepatitis C virus antigen.

In certain embodiments, oncogenic virus antigens are antigens of human papillomavirus, antigens of Kaposi's sarcoma-associated herpesvirus, such as latency-associated nuclear antigen, antigens of Epstein-Barr virus, such as EBV-EA, EBV-MA, or EBV-VCA, antigens of Merkel cell polyomavirus, such as MCV T antigen, or antigens of human T-lymphotropic virus, such as HTLV-1 Tax antigen.

In certain specific embodiments, antigens for use with the methods and compositions described herein are HPV antigens.

In certain embodiments, any strain of human HPV or any clinical isolate of human HPV can be used to obtain the heterologous sequence for generation of the arenaviruses for the use with the compositions and methods described herein. In certain embodiments, the heterologous sequence is obtained from, and encodes an antigen of, an HPV strain, such as strains including HPV genotype 1 (HPV1), HPV genotype 2 (HPV2), HPV genotype 3 (HPV3), HPV genotype 4 (HPV4), HPV genotype 6 (HPV6), HPV genotype 7 (HPV7), HPV genotype 8 (HPV8), HPV genotype 10 (HPV10), HPV genotype 11 (HPV11), HPV genotype 13 (HPV13), HPV genotype 16 (HPV16), HPV genotype 18 (HPV18), HPV genotype 22 (HPV22), HPV genotype 26 (HPV26), HPV genotype 31 (HPV31), HPV genotype 32 (HPV32), HPV genotype 33 (HPV33), HPV genotype 35 (HPV35), HPV genotype 39 (HPV39), HPV genotype 42 (HPV42), HPV genotype 44 (HPV44), HPV genotype 45 (HPV45), HPV genotype 51 (HPV51), HPV genotype 52 (HPV52), HPV genotype 53 (HPV53), HPV genotype 56 (HPV56), HPV genotype 58 (HPV58), HPV genotype 59 (HPV59), HPV genotype 60 (HPV60), HPV genotype 63 (HPV63), HPV genotype 66 (HPV66), HPV genotype 68 (HPV68), HPV genotype 73 (HPV73), or HPV genotype 82 (HPV82), or other genotypes. In certain embodiments, strains include "high-risk" genotypes of HPV, such as HPV16, HPV18, HPV31, HPV33, HPV35, HPV39, HPV45, HPV51, HPV52, HPV56, HPV58, HPV59, HPV68, HPV73, and HPV82.

In certain embodiments, the antigen can be a papillomavirus antigen ortholog, e.g., a mammalian (i.e., non-human primate, pig, dog, cat, or horse) papillomavirus antigen.

In certain embodiments, an open reading frame (ORF) of an arenavirus is deleted and replaced with a heterologous sequence encoding an antigen of an oncogenic virus.

More specifically, one or more, e.g., two, three, or four, of the four arenavirus ORFs (glycoprotein (GP); nucleoprotein (NP); matrix protein Z; RNA-dependent RNA polymerase L) are removed or mutated to prevent formation of infectious particles in normal cells, albeit still allowing gene expression in arenavirus vector-infected cells. A heterologous sequence, such as foreign nucleic acids coding for one or more proteins can be introduced. These foreign nucleic acids are transcribed from one or more, e.g., two or three of the four arenavirus promoters 5' UTR and 3' UTR of the S segment, and 5' UTR and 3' UTR of the L segment, or from additionally introduced promoter sequences that can be read by the viral RNA-dependent RNA polymerase, by cellular RNA polymerase I, RNA polymerase II, or RNA polymerase III, such as duplications of viral promoter sequences that are naturally found in the viral UTRs, the 28S ribosomal RNA promoter, the beta-actin promoter, or the 5S ribosomal RNA promoter, respectively. The ribonucleic acids coding for proteins or modulating host gene expression are transcribed and translated either by themselves or as read-through by fusion to arenavirus protein ORFs. Expression of proteins in the host cell may be enhanced by introducing in the viral transcript sequence at the appropriate place(s) one or more, e.g., two, three or four, internal ribosome entry sites.

In certain embodiments, an ORF of an arenavirus is deleted and replaced with a heterologous sequence encoding a DNA virus antigen, an RNA virus antigen, or a retrovirus antigen.

In certain, more specific embodiments, an ORF of an arenavirus is deleted and replaced with a heterologous sequence encoding any oncogenic virus antigen excluding Hepatitis B virus antigens and Hepatitis C virus antigens.

In certain embodiments, an ORF of an arenavirus is deleted and replaced with a heterologous sequence encoding an antigen of an oncogenic virus, such as antigens of human papillomavirus, antigens of Kaposi's sarcoma-associated herpesvirus, such as latency-associated nuclear antigen, antigens of Epstein-Barr virus, such as EBV-EA, EBV-MA, or EBV-VCA, antigens of Merkel cell polyomavirus, such as MCV T antigen, or antigens of human T-lymphotropic virus, such as HTLV-1 Tax antigen.

In certain embodiments, an ORF of an arenavirus is deleted and replaced with a heterologous sequence encoding one or more HPV antigens.

In certain embodiments, an ORF of an arenavirus is deleted and replaced with a heterologous sequence encoding an antigen of any strain of HPV or any clinical isolate of HPV. Such strains include HPV genotype 1 (HPV1), HPV genotype 2 (HPV2), HPV genotype 3 (HPV3), HPV genotype 4 (HPV4), HPV genotype 6 (HPV6), HPV genotype 7 (HPV7), HPV genotype 8 (HPV8), HPV genotype 10 (HPV10), HPV genotype 11 (HPV11), HPV genotype 13 (HPV13), HPV genotype 16 (HPV16), HPV genotype 18 (HPV18), HPV genotype 22 (HPV22), HPV genotype 26 (HPV26), HPV genotype 31 (HPV31), HPV genotype 32 (HPV32), HPV genotype 33 (HPV33), HPV genotype 35 (HPV35), HPV genotype 39 (HPV39), HPV genotype 42 (HPV42), HPV genotype 44 (HPV44), HPV genotype 45 (HPV45), HPV genotype 51 (HPV51), HPV genotype 52 (HPV52), HPV genotype 53 (HPV53), HPV genotype 56 (HPV56), HPV genotype 58 (HPV58), HPV genotype 59 (HPV59), HPV genotype 60 (HPV60), HPV genotype 63 (HPV63), HPV genotype 66 (HPV66), HPV genotype 68 (HPV68), HPV genotype 73 (HPV73), or HPV genotype 82 (HPV82), or other genotypes. In certain embodiments, strains include "high-risk" genotypes of HPV, such as HPV16, HPV18, HPV31, HPV33, HPV35, HPV39, HPV45, HPV51, HPV52, HPV56, HPV58, HPV59, HPV68, HPV73, or HPV82.

In certain embodiments, an ORF of an arenavirus is deleted and replaced with a heterologous sequence encoding an antigen of any strain of HPV or any clinical isolate of HPV, wherein the amino acid sequence of the antigen is 80%, 81%, 82%, 83%, 84%, 85%, 86%, 87%, 88%, 89%, 90%, 91%, 92%, 93%, 94%, 95%, 96%, 97%, 98%, 99%, or 100% identical to the amino acid sequence of an antigen, for example E6 and/or E7 antigen of HPV genotype 1 (HPV1), HPV genotype 2 (HPV2), HPV genotype 3 (HPV3), HPV genotype 4 (HPV4), HPV genotype 6 (HPV6), HPV genotype 7 (HPV7), HPV genotype 8 (HPV8), HPV genotype 10 (HPV10), HPV genotype 11 (HPV11), HPV genotype 13 (HPV13), HPV genotype 16 (HPV16), HPV genotype 18 (HPV18), HPV genotype 22 (HPV22), HPV genotype 26 (HPV26), HPV genotype 31 (HPV31), HPV genotype 32 (HPV32), HPV genotype 33 (HPV33), HPV genotype 35 (HPV35), HPV genotype 39 (HPV39), HPV genotype 42 (HPV42), HPV genotype 44 (HPV44), HPV genotype 45 (HPV45), HPV genotype 51 (HPV51), HPV genotype 52 (HPV52), HPV genotype 53 (HPV53), HPV genotype 56 (HPV56), HPV genotype 58 (HPV58), HPV genotype 59 (HPV59), HPV genotype 60 (HPV60), HPV genotype 63 (HPV63), HPV genotype 66 (HPV66), HPV genotype 68 (HPV68), HPV genotype 73 (HPV73), or HPV genotype 82 (HPV82), or other genotypes. In certain embodiments, strains include "high-risk" genotypes of HPV, such as HPV16, HPV18, HPV31, HPV33, HPV35, HPV39, HPV45, HPV51, HPV52, HPV56, HPV58, HPV59, HPV68, HPV73, or HPV82.

In certain embodiments, an ORF of an arenavirus is deleted and replaced with a heterologous sequence encoding one or more HPV antigens. In certain embodiments, an ORF of an arenavirus is deleted and replaced with a heterologous sequence encoding an early (E) or late (L) protein of HPV. In certain embodiments, an ORF of an arenavirus is deleted and replaced with a heterologous sequence encoding an HPV protein E1, HPV protein E2, HPV protein E3, HPV protein E4, HPV protein E5, HPV protein E6, HPV protein E7, HPV protein L1 or HPV protein L2. In certain embodiments, an ORF of an arenavirus is deleted and replaced with a heterologous sequence encoding a fusion protein of two, three, four, five, or more of HPV protein E1, HPV protein E2, HPV protein E3, HPV protein E4, HPV protein E5, HPV protein E6, HPV protein E7, HPV protein L1 or HPV protein L2. In certain specific embodiments, the heterologous sequence is HPV protein E6 fused to HPV protein E7. In certain specific embodiments, the heterologous sequence is HPV protein E7 fused to HPV protein E6 fused to HPV protein E6 fused to HPVprotein E7, wherein one HPV protein E7 is from strain HPV16 and the other is from strain HPV18 and one HPV protein E6 is from strain HPV 18 and the other is from strain HPV18. In certain specific embodiments, the heterologous sequence is a shuffled sequence of HPV protein E6 fused to HPV protein E7. In certain specific embodiments, the sequence of HPV protein E6 fused to HPV protein E7 is expressed with protein E7 upstream of protein E6. In certain specific embodiments, the sequence of HPV protein E6 fused to HPV protein E7 is expressed with protein E6 upstream of protein E7. In certain embodiments, the E7 protein has mutations in the Rb binding site and the zinc finger motif. In certain embodiments, the E6 protein has mutations in the zinc finger motifs.

In certain embodiments, an ORF of an arenavirus is deleted and replaced with a heterologous sequence encoding an antigen that is 80%, 81%, 82%, 83%, 84%, 85%, 86%, 87%, 88%, 89%, 90%, 91%, 92%, 93%, 94%, 95%, 96%, 97%, 98%, 99%, or 100% identical to the amino acid sequence of an antigen of a HPV protein E1, HPV protein E2, HPV protein E3, HPV protein E4, HPV protein E5, HPV protein E6, HPV protein E7, HPV protein L1 or HPV protein L2. In certain embodiments, an ORF of an arenavirus is deleted and replaced with a heterologous sequence encoding an antigen that is 80%, 81%, 82%, 83%, 84%, 85%, 86%, 87%, 88%, 89%, 90%, 91%, 92%, 93%, 94%, 95%, 96%, 97%, 98%, 99%, or 100% identical to the amino acid sequence of HPV protein E6 fused to HPV protein E7. In certain embodiments, an ORF of an arenavirus is deleted and replaced with a heterologous sequence encoding an antigen that is 80%, 81%, 82%, 83%, 84%, 85%, 86%, 87%, 88%, 89%, 90%, 91%, 92%, 93%, 94%, 95%, 96%, 97%, 98%, 99%, or 100% identical to the amino acid sequence of a shuffled sequence of HPV protein E6 fused to HPV protein E7. In certain specific embodiments, the HPV protein E6 sequence fused to HPV protein E7 sequence is expressed with protein E7 sequence upstream of protein E6 sequence. In certain specific embodiments, the HPV protein E6 sequence fused to HPV protein E7 sequence is expressed with the protein E6 sequence upstream of the protein E7 sequence. In certain embodiments, the E7 protein sequence has mutations in the Rb binding site and the zinc finger motif. In certain embodiments, the E6 protein sequence has mutations in the zinc finger motifs.

In certain embodiments, an ORF of an arenavirus is deleted and replaced with a heterologous nucleotide sequence encoding an antigen, for example an HPV protein E6 and/or E7 antigen. HPV protein E6 is an oncoprotein. For example, it has been reported that protein E6 binds to tumor suppressor p53 and causes proteasomal degradation of p53 (Ganguly et al., 2009, J. Biosci. 34(1), 113-123). HPV protein E7 is also an oncoprotein. For example, it has been shown that E7 binds to the retinoblastoma protein (pRb), which is a tumor suppressor protein, and inactivates its function (Ganguly et al., 2009, J. Biosci. 34(1), 113-123).

In certain embodiments, an ORF of an arenavirus is deleted and replaced with a heterologous nucleotide sequence encoding an antigen, for example an HPV protein E6 and/or E7 antigen, or a fragment thereof. In certain embodiments, the E6 protein fragment is an N-terminal truncated fragment. In certain embodiments, the E6 protein fragment is a C-terminal truncated fragment. In certain embodiments, the E6 protein fragment is at least 10, 20, 30, 40, 50, 60, 70, 80, 90, 100, 110, 120, 130, 140, 150, or 158 amino acids in length. In certain embodiments, the E7 protein fragment is an N-terminal truncated fragment. In certain embodiments, the E7 protein fragment is an C-terminal truncated fragment. In certain embodiments, the E7 protein fragment is at least 10, 20, 30, 40, 50, 60, 70, 80, 90, or 98 amino acids in length. In certain embodiments, the E7 protein fragment has mutations in the Rb binding site and the zinc finger motif. In certain embodiments, the E6 protein fragment has mutations in the zinc finger motifs.

In certain embodiments, an ORF of an arenavirus is deleted and replaced with a heterologous nucleotide sequence encoding HPV16 protein E6, HPV16 protein E7, HPV18 protein E6, and HPV18 protein E7. In certain embodiments, an ORF of an arenavirus is deleted and replaced with a heterologous nucleotide sequence encoding HPV16 protein E6 or an antigenic fragment thereof, HPV16 protein E7 or an antigenic fragment thereof, HPV18 protein E6 or an antigenic fragment thereof, and HPV18 protein E7 or an antigenic fragment thereof. In certain embodiments, one, two, three or all four of HPV16 protein E6 or antigenic fragment thereof, HPV16 protein E7 or antigenic fragment thereof, HPV18 protein E6 or antigenic fragment thereof, and HPV18 protein E7 or antigenic fragment thereof, can be shuffled sequences. Each one of HPV16 protein E6 or antigenic fragment thereof, HPV16 protein E7 or antigenic fragment thereof, HPV18 protein E6 or antigenic fragment thereof, and HPV18 protein E7 or antigenic fragment thereof, can be directly fused to one or two different sequences of HPV16 protein E6 or antigenic fragment thereof, HPV16 protein E7 or antigenic fragment thereof, HPV18 protein E6 or antigenic fragment thereof, and HPV18 protein E7 or antigenic fragment thereof. Each one of HPV16 protein E6 or antigenic fragment thereof, HPV16 protein E7 or antigenic fragment thereof, HPV18 protein E6 or antigenic fragment thereof, and HPV18 protein E7 or antigenic fragment thereof, can be fused to one or two different sequences of HPV16 protein E6 or antigenic fragment thereof, HPV16 protein E7 or antigenic fragment thereof, HPV18 protein E6 or antigenic fragment thereof, and HPV18 protein E7 or antigenic fragment thereof, via a linker or self-cleaving peptide. Each one of HPV16 protein E6 or antigenic fragment thereof, HPV16 protein E7 or antigenic fragment thereof, HPV18 protein E6 or antigenic fragment thereof, and HPV18 protein E7 or antigenic fragment thereof, can be fused to one or two different sequences of HPV16 protein E6 or antigenic fragment thereof, HPV16 protein E7 or antigenic fragment thereof, HPV18 protein E6 or antigenic fragment thereof, and HPV18 protein E7 or antigenic fragment thereof. The sequence of HPV16 protein E6 or antigenic fragment thereof, HPV16 protein E7 or antigenic fragment thereof, HPV18 protein E6 or antigenic fragment thereof, and HPV18 protein E7 or antigenic fragment thereof, can be arranged in any manner known to the skilled artisan, e.g., each one of HPV16 protein E6 or antigenic fragment thereof, HPV16 protein E7 or antigenic fragment thereof, HPV18 protein E6 or antigenic fragment thereof, and HPV18 protein E7 or antigenic fragment thereof, can be upstream or downstream of a different one of HPV16 protein E6 or antigenic fragment thereof, HPV16 protein E7 or antigenic fragment thereof, HPV18 protein E6 or antigenic fragment thereof, and HPV18 protein E7 or antigenic fragment thereof. Each one of HPV16 protein E6 or antigenic fragment thereof, HPV16 protein E7 or antigenic fragment thereof, HPV18 protein E6 or antigenic fragment thereof, and HPV18 protein E7 or antigenic fragment thereof, can be fused to a signal peptide. In certain more specific embodiments, an ORF of an arenavirus is deleted and replaced with a heterologous nucleotide sequence encoding an HPV16 E6/HPV16 E7 fusion protein or antigenic fragment thereof, or an HPV16 E6/HPV18 E6 fusion protein or antigenic fragment thereof, or an HPV16 E6/HPV18 E7 fusion protein or antigenic fragment thereof, or an HPV16 E7/HPV18 E6 fusion protein or antigenic fragment thereof, or an HPV16 E7/HPV18 E7 fusion protein or antigenic fragment thereof, or an HPV18 E6/HPV18 E7 fusion protein or antigenic fragment thereof. In certain more specific embodiments, an ORF of an arenavirus is deleted and replaced with a heterologous nucleotide sequence encoding two fusion proteins, wherein the first fusion protein is an HPV16 E6/HPV16 E7 fusion protein or antigenic fragment thereof, or an HPV16 E6/HPV18 E6 fusion protein or antigenic fragment thereof, HPV16 E6/HPV18 E7 fusion protein or antigenic fragment thereof, or an HPV16 E7/HPV18 E6 fusion protein or antigenic fragment thereof, HPV16 E7/HPV18 E7 fusion protein or antigenic fragment thereof, or an HPV18 E6/HPV18 E7 fusion protein or antigenic fragment thereof, and the second fusion protein is a different fusion protein selected from an HPV16 E6/HPV16 E7 fusion protein or antigenic fragment thereof, or an HPV16 E6/HPV18 E6 fusion protein or antigenic fragment thereof, HPV16 E6/HPV18 E7 fusion protein or antigenic fragment thereof, or an HPV16 E7/HPV18 E6 fusion protein or antigenic fragment thereof, HPV16 E7/HPV18 E7 fusion protein or antigenic fragment thereof, or an HPV18 E6/HPV18 E7 fusion protein or antigenic fragment thereof. In certain specific embodiments, the heterologous nucleotide sequence further encodes an immunomodulatory peptide, polypeptide, or protein. In certain specific embodiments, the heterologous nucleotide sequence further encodes a signal sequence (e.g. derived from VSVG).

In certain embodiments, an ORF of an arenavirus is deleted and replaced with a heterologous nucleotide sequence encoding an HPV16 E6/E7 fusion protein and an HPV18 E6/E7 fusion protein. In certain embodiments, an ORF of an arenavirus is deleted and replaced with a heterologous nucleotide sequence encoding shuffled sequence of an HPV16 E6/E7 fusion protein and a shuffled sequence of an HPV18 E6/E7 fusion protein. In certain specific embodiments, the heterologous nucleotide sequence encodes an HPV16 E6/E7 fusion protein and an HPV18 E6/E7 fusion protein that are directly fused to each other. In certain specific embodiments, the heterologous sequence encodes an HPV16 E6/E7 fusion protein and an HPV18 E6/E7 fusion protein that are fused to each other via a peptide linker or self-cleaving peptide. In certain specific embodiments, the heterologous sequence encodes an HPV16 E6/E7 fusion protein located upstream of the HPV18 E6/E7 fusion protein. In certain specific embodiments, the heterologous nucleotide sequence encodes an HPV16 E6/E7 fusion protein located downstream of the HPV18 E6/E7 fusion protein. In certain specific embodiments, the heterologous nucleotide sequence encodes an HPV16 E6/E7 fusion protein fused to a signal peptide. In certain specific embodiments, the heterologous nucleotide sequence encodes an HPV18 E6/E7 fusion protein fused to a signal peptide. In certain specific embodiments, the heterologous nucleotide sequence further encodes an immunomodulatory peptide, polypeptide, or protein.

In certain embodiments, an ORF of an arenavirus is deleted and replaced with a heterologous sequence encoding an antigen that is 80%, 81%, 82%, 83%, 84%, 85%, 86%, 87%, 88%, 89%, 90%, 91%, 92%, 93%, 94%, 95%, 96%, 97%, 98%, 99%, or 100% identical to the amino acid sequence of HPV16 E6/E7 fusion protein and an antigen that is 80%, 81%, 82%, 83%, 84%, 85%, 86%, 87%, 88%, 89%, 90%, 91%, 92%, 93%, 94%, 95%, 96%, 97%, 98%, 99%, or 100% identical to the amino acid sequence of HPV18 E6/E7 fusion protein.

In certain embodiments, an ORF of an arenavirus is deleted and replaced with a heterologous sequence encoding an antigen that is 80%, 81%, 82%, 83%, 84%, 85%, 86%, 87%, 88%, 89%, 90%, 91%, 92%, 93%, 94%, 95%, 96%, 97%, 98%, 99%, or 100% identical to the amino acid sequence of a shuffled sequence of an HPV16 E6/E7 fusion protein. In certain embodiments, an ORF of an arenavirus is deleted and replaced with a heterologous sequence encoding an antigen that is 80%, 81%, 82%, 83%, 84%, 85%, 86%, 87%, 88%, 89%, 90%, 91%, 92%, 93%, 94%, 95%, 96%, 97%, 98%, 99%, or 100% identical to the amino acid sequence of a shuffled sequence of an HPV18 E6/E7 fusion protein.

In certain specific embodiments, the E6 protein fragment of the HPV16 E6/E7 fusion protein or the HPV18 E6/E7 fusion protein is an N-terminal truncated fragment. In certain embodiments, the E6 protein fragment is a C-terminal truncated fragment. In certain embodiments, the E6 protein fragment is at least 10, 20, 30, 40, 50, 60, 70, 80, 90, 100, 110, 120, 130, 140, 150, or 158 amino acids in length. In certain embodiments, the E7 protein fragment of the HPV16 E6/E7 fusion or the HPV18 E6/E7 fusion is an N-terminal truncated fragment. In certain embodiments, the E7 protein fragment is an C-terminal truncated fragment. In certain embodiments, the E7 protein fragment is at least 10, 20, 30, 40, 50, 60, 70, 80, 90, or 98 amino acids in length.

In certain embodiments, the heterologous nucleotide sequence encoding the HPV16 E6/E7 fusion protein and the heterologous nucleotide sequence encoding the HPV18 E6/E7 fusion protein are on the same position of the viral genome. In certain embodiments, the heterologous nucleotide sequence encoding the HPV16 E6/E7 fusion protein and the heterologous nucleotide sequence encoding the HPV18 E6/E7 fusion protein are on different positions of the viral genome. In certain embodiments, the heterologous nucleotide sequence encoding the HPV16 E6/E7 fusion protein and the heterologous nucleotide sequence encoding the HPV18 E6/E7 fusion protein are expressed on the same virus. In certain embodiments, the heterologous nucleotide sequence encoding the HPV16 E6/E7 fusion protein and the heterologous nucleotide sequence encoding the HPV18 E6/E7 fusion protein are expressed on different viruses.

In certain specific embodiments, the heterologous nucleotide sequence of HPV16 protein E6 fused to protein E7 is expressed with protein E7 upstream of protein E6. In certain specific embodiments, the heterologous nucleotide sequence of HPV18 protein E6 fused to protein E7 is expressed with protein E6 upstream of protein E7. In certain embodiments, the E7 protein of the HPV16 E6/E7 fusion protein or the HPV18 E6/E7 fusion protein has mutations in the Rb binding site and the zinc finger motif. In certain embodiments, the E6 protein of the HPV16 E6/E7 fusion protein or the HPV18 E6/E7 fusion protein has mutations in the zinc finger motifs.

In certain embodiments, the heterologous sequence encoding the antigen of an oncogenic virus further encodes a signal peptide. More specifically, the heterologous sequence encodes an antigen that is fused to the signal peptide such that the resulting expression product is secreted from the cell in which it is expressed. Such a signal peptide can be fused to the N-terminus or the C-terminus of the antigen. Any signal peptide known to the skilled artisan can be used with the compositions and methods provided herein. Specifically, the signal peptide is a signal peptide of a human secreted protein. More specifically, the signal peptide is a human tyrosinase secretion signal, a human growth hormone secretion signal, a human tissue plasminogen activator signal sequence, or a VSVG signal sequence.

The heterologous nucleotide sequence can encode more than one antigen. In certain embodiments, the heterologous nucleotide sequence encodes two, three, four, five, or more antigens of one or more different oncogenic viruses. Specifically, the heterologous nucleotide sequence can encode a first antigen of one strain of HPV and a second antigen that is the analogous antigen from a different strain of HPV. For example, the heterologous nucleotide sequence can encode protein E6 from one strain of HPV (e.g., strain HPV 16), and protein E6 from another strain (e.g., strain HPV 18), and/or protein E7 from one strain of HPV (e.g., strain HPV 16), and protein E7 from another strain (e.g., strain HPV 18). In certain embodiments, the heterologous nucleotide sequence encodes two, three, four, five, or more different antigens of the same oncogenic virus, or of one or more different oncogenic viruses. Specifically, the heterologous nucleotide sequence can encode a first antigen of one strain of HPV and a second different antigen that is the analogous antigen from the same strain or a different strain of HPV. For example, the heterologous nucleotide sequence can encode protein E6 from one strain of HPV (e.g., strain HPV 16), and protein E7 from the same strain or another strain (e.g., strain HPV 18). As another example, the heterologous nucleotide sequence can encode protein E6 from two strains of HPV (e.g., strain HPV 16 and 18), and protein E7 from the two strains (e.g., strain HPV 16 and 18).

In certain embodiments, the heterologous sequence encoding the antigen of an oncogenic virus further encodes a linker or a self-cleaving peptide. The linker or self-cleaving peptide is useful for the simultaneous expression of two or more genes. More specifically, the heterologous sequence encodes an antigen that is fused to another antigen or an immunomodulatory peptide, polypeptide, or protein, either directly or fused through a linker sequence. In another specific embodiment, the heterologous sequence encodes an antigen linked to another antigen or an immunomodulatory peptide, polypeptide, or protein, through a self-cleaving peptide. Such a linker or self-cleaving peptide can be fused to the N-terminus or the C-terminus of the antigen. Any linker peptide or self-cleaving peptide known to the skilled artisan can be used with the compositions and methods provided herein. Any number of antigens or immunomodulatory peptides, polypeptides, or proteins can be fused or linked in this manner. For example, in one specific embodiment, the first HPV antigen is directly fused to a second HPV antigen, or is fused to the second antigen through a peptide linker. In another specific embodiment, the second HPV antigen is directly fused to a third HPV antigen, or is fused to the third antigen through a peptide linker. In another specific embodiment, the first HPV antigen and the second HPV antigen are separated from each other via a self-cleaving peptide. In another specific embodiment, the second HPV antigen and the third HPV antigen are separated from each other via a self-cleaving peptide.

In certain embodiments, the ORFs encoding two, three, four, or more HPV antigens described herein are transcribed as a single transcript. In certain embodiments, the ORFs encoding the HPV antigens on that transcript are separated by a nucleic acid encoding a self-cleaving peptide or a ribosome-skipping sequence. In certain embodiments, the self-cleaving peptide can be obtained from a 2A protein from a member of the virus family Picornaviridae. In certain specific embodiments, the self-cleaving peptide is obtained from (or derived from) Porcine teschovirus-1 2A, Thosea asigna virus 2A, Foot-and-mouth disease virus 2A peptide, or equine rhinitis A virus 2A peptide. In certain specific embodiments, the 2A peptide obtained from (or derived from) the porcine teschovirus-1 2A has the highest cleavage efficiency. In certain embodiments, the 2A peptide has a high cleavage efficiency in combination with the HPV antigens described herein upstream or downstream of the 2A peptide.

In certain embodiments, the ORFs encoding two, three, four, or more HPV antigens are separated by a ribosome-skipping sequence. In more specific embodiments, the ribosome-skipping sequence is a cis-acting hydrolase element sequence.

In certain embodiments, the ORFs encoding two, three, four, or more HPV antigens are separated by a self-cleaving protease obtained from (or derived from) tobacco etch viruses (TEVs) of the Potyviridae family.

In certain embodiments, a Gly-Ser-Gly, NDAQAPKS or a SDRYLNRRA linker is inserted at the N-terminus and/or C-terminus of the 2A peptide. In more specific embodiments, the Gly-Ser-Gly, NDAQAPKS or a SDRYLNRRA linker is inserted at the N-terminus of the 2A peptide. In more specific embodiments, the Gly-Ser-Gly, NDAQAPKS or a SDRYLNRRA linker is inserted at the C-terminus of the 2A peptide. In certain embodiments, the Gly-Ser-Gly, NDAQAPKS or a SDRYLNRRA linker improves the efficiency of cleavage by the 2A peptide.

In certain embodiments, the ORFs encoding two, three, four, or more HPV antigens are separated by an internal ribosome entry site. In certain embodiments, the internal ribosome entry site functions under the control of an upstream promoter. In certain embodiments the internal ribosome entry site is obtained from (or derived from) the encephalomyocarditis virus.

In certain embodiments, the ORFs encoding two, three, four, or more HPV antigens are separated by a 2A peptide and a furin cleavage site. In certain embodiments, the 2A peptide is flanked by a furin cleavage site. In certain embodiments, the furin cleavage site is located between an ORF encoding an HPV antigen and the 2A peptide. In certain embodiments, the furin cleavage site is added upstream of the 2A peptide. In certain embodiments, the furin cleavage site is added downstream of the 2A peptide. In certain embodiments, the furin cleavage site is located in the vector with the ORFs encoding two, three, or four, or more HPV antigens, a self-cleaving peptide, and combinations thereof. In certain embodiments, the furin cleavage site consensus sequence is R—X—K—/R—R. In a more specific embodiment the furin cleavage site is cleaved by the furin protein in the trans golgi network. In another embodiment, the furin cleavage site removes the 2A peptide sequence. In yet another embodiment, the furin cleavage site removes the self-cleaving peptide sequence at the C-terminus. For example, see Fang et al., 2007, Molecular Therapy 15(6):1153-1159.

In certain embodiments, the ORFs encoding two, three, or four, or more HPV antigens are separated by the 2A peptide and a tag. In certain embodiments, the tag is linked to the 2A peptide. In certain embodiments, the tag is located between the 2A peptide and the furin cleavage site. In certain embodiments, the tag is located at the C-terminus or N-terminus of the downstream ORF encoding the HPV antigen. In certain embodiments, the tag is located at the C-terminus or N-terminus of the upstream ORF encoding the HPV antigen. In certain embodiments the tag is located in the vector with the ORFs encoding two, three, four, or more HPV antigens, a 2A peptide, a furin cleavage site, or a combination thereof. In certain embodiments the tag is a peptide tag. In more specific embodiments the tag is a V5 amino acid tag.

In certain embodiments, the ORFs encoding two, three, four, or five or more HPV antigens are separated by the 2A peptide and a spacer sequence. In certain embodiments, the spacer sequence is located upstream of the 2A peptide. In certain embodiments, the spacer sequence is located between the ORFs encoding the HPV antigens. In certain embodiments, the spacer sequence is located between the upstream of the 2A peptide and the tag. In certain embodiments, the spacer sequence is located between the upstream 2A peptide and the downstream furin cleavage site. In certain embodiments the spacer sequence is located in the vector with the ORFs encoding HPV antigens, a self-cleaving peptide, a furin cleavage site, a tag or a combination thereof. In certain embodiments, the spacer sequence increases cleavage efficiency.

In certain embodiments, an ORF of an arenavirus is deleted and replaced with a heterologous sequence encoding one, two, three, or four, or more HPV antigens.

(b) Immunomodulatory Sequences

In certain embodiments, antigens for use with the methods and compositions described herein are administered together with an immunomodulatory element, e.g., an immunomodulatory peptide, polypeptide, or protein.

In certain embodiments, the heterologous nucleotide sequence encompassed by an infectious replication-deficient arenavirus further encodes an immunomodulatory peptide, polypeptide, or protein. The immunomodulatory peptide, polypeptide, or protein can be Calreticulin (CRT), or a fragment thereof, Ubiquitin or a fragment thereof, Granulocyte-Macrophage Colony-Stimulating Factor (GM-CSF), or a fragment thereof, Invariant chain (CD74) or an antigenic fragment thereof, Mycobacterium tuberculosis Heat shock protein 70 or an antigenic fragment thereof, Herpes simplex virus 1 protein VP22 or an antigenic fragment thereof; CD40 ligand or an antigenic fragment thereof; or Fms-related tyrosine kinase 3 (Flt3) ligand or an antigenic fragment thereof.

In certain embodiments, the sequence encoding the immunomodulatory peptide, polypeptide, or protein and the sequence encoding an antigen are on the same position of the viral genome. For example, the sequence encoding the immunomodulatory peptide, polypeptide, or protein and the sequence encoding an antigen are located in place of the functionally inactivated, e.g., deleted, ORF of the infectious, replication-deficient arenavirus. In certain embodiments, the sequence encoding the immunomodulatory peptide, polypeptide, or protein and the sequence encoding an antigen are on different positions of the viral genome. In certain embodiments, the sequence encoding the immunomodulatory peptide, polypeptide, or protein and the sequence encoding a first antigen are located on different genomic segments of the infectious, replication-deficient arenavirus.

In certain embodiments, an ORF of an arenavirus is deleted and replaced with a heterologous sequence encoding one, two, three, or four, or more HPV antigens and an immunomodulatory peptide, polypeptide, or protein.

In certain embodiments, the heterologous sequence encoding the immunomodulatory peptide, polypeptide, or protein, further encodes a signal peptide. More specifically, the heterologous sequence encodes an immunomodulatory peptide, polypeptide, or protein that is fused to the signal peptide such that the resulting expression product is secreted from the cell in which it is expressed. Such a signal peptide can be fused to the N-terminus or the C-terminus of the immunomodulatory peptide, polypeptide, or protein. Any signal peptide known to the skilled artisan can be used with the compositions and methods provided herein. Specifically, the signal peptide is a signal peptide of a human secreted protein. More specifically, the signal peptide is a human tyrosinase secretion signal, a human growth hormone secretion signal, or a tissue plasminogen activator signal sequence.

In certain embodiments, the heterologous sequence encoding the immunomodulatory peptide, polypeptide, or protein, further encodes a linker or a self-cleaving peptide. More specifically, the heterologous sequence encodes an immunomodulatory peptide, polypeptide, or protein, which is fused to an antigen or another immunomodulatory peptide, polypeptide, or protein, either directly or fused through a linker sequence. In another specific embodiment, the heterologous sequence encodes an immunomodulatory peptide, polypeptide, or protein, linked to an antigen or another immunomodulatory peptide, polypeptide, or protein, through a self-cleaving peptide. Such a linker or self-cleaving peptide can be fused to the N-terminus or the C-terminus of the immunomodulatory peptide, polypeptide, or protein. Any linker peptide or self-cleaving peptide known to the skilled artisan can be used with the compositions and methods provided herein. Any number of immunomodulatory peptides, polypeptides, or proteins, can be fused or linked in this manner to an antigen or another immunomodulatory peptide, polypeptide, or protein. For example, in one specific embodiment, the immunomodulatory peptide, polypeptide, or protein is directly fused to a first antigen, or is fused to the first antigen through a peptide linker. In another specific embodiment, the immunomodulatory peptide, polypeptide, or protein is directly fused to a second antigen, or is fused to the second antigen through a peptide linker. In another specific embodiment, the first antigen and the immunomodulatory peptide, polypeptide, or protein are separated from each other via a self-cleaving peptide. In another specific embodiment, the second antigen and the immunomodulatory peptide, polypeptide, or protein are separated from each other via a self-cleaving peptide.

In certain embodiments, the ORFs encoding two, three, or four, or more HPV antigens and the immunomodulatory peptide, polypeptide, or protein are transcribed as a single transcript. In certain embodiments, the ORFs encoding the HPV antigens and the immunomodulatory sequence on that transcript are separated by a nucleic acid encoding a self-cleaving peptide or a ribosome-skipping sequence. In certain embodiments, the self-cleaving peptide can be obtained from a 2A protein from a member of the virus family Picornaviridae. In certain specific embodiments, the self-cleaving peptide is obtained from (or derived from) Porcine teschovirus-1 2A peptide, Thoseaasignavirus 2A peptide, Foot-and-mouth disease virus 2A peptide, or equine rhinitis A virus 2A peptide. In certain specific embodiments, the 2A peptide obtained from (or derived from) the porcine teschovirus-1 2A has the highest cleavage efficiency. In certain embodiments, the 2A peptide has a high cleavage efficiency in combination with the HPV antigens described herein upstream or downstream of the 2A peptide.

In certain embodiments, the ORFs encoding two, three, or four, or more HPV antigens and the immunomodulatory peptide, polypeptide, or protein are separated by a ribosome-skipping sequence. In more specific embodiments, the ribosome-skipping sequence is a cis-acting hydrolase element sequence.

In certain embodiments, the ORFs encoding two, three, or four, or more HPV antigens and the immunomodulatory peptide, polypeptide, or protein are separated by a self-cleaving protease obtained from (or derived from) tobacco etch viruses (TEVs) of the Potyviridae family.

In certain embodiments, a Gly-Ser-Gly, NDAQAPKS or a SDRYLNRRA linker is inserted at the N-terminus and/or C-terminus of the 2A peptide. In more specific embodiments, the Gly-Ser-Gly, NDAQAPKS or a SDRYLNRRA linker is inserted at the N-terminus of the 2A peptide. In more specific embodiments, the Gly-Ser-Gly, NDAQAPKS or a SDRYLNRRA linker is inserted at the C-terminus of the 2A peptide. In certain embodiments, the Gly-Ser-Gly, NDAQAPKS or a SDRYLNRRA linker improves the efficiency of cleavage by the 2A peptide.

In certain embodiments, the ORFs encoding two, three, or four, or more HPV antigens and the immunomodulatory peptide, polypeptide, or protein are separated by an internal ribosome entry site. In certain embodiments, the internal ribosome entry site functions under the control of an upstream promoter. In certain embodiments the internal ribosome entry site is obtained from (or derived from) the encephalomyocarditis virus.

In certain embodiments the ORFs encoding two, three, or four, or more HPV antigens and the immunomodulatory peptide, polypeptide, or protein are separated by a 2A peptide and a furin cleavage site. In certain embodiments, the 2A peptide is flanked by a furin cleavage site. In certain embodiments, the furin cleavage site is located between an ORF encoding an HPV antigen and the 2A peptide. In certain embodiments the furin cleavage site is added upstream of the 2A peptide. In certain embodiments the furin cleavage site is added downstream of the 2A peptide. In certain embodiments, the furin cleavage site is located in the vector with the ORFs encoding two, three, or four, or more HPV antigens, a self-cleaving peptide, and combinations thereof. In certain embodiments, the furin cleavage site consensus sequence is R—X—K—/R—R. In a more specific embodiment the furin cleavage site is cleaved by the furin protein in the trans golgi network. In another embodiment the furin cleavage site removes the 2A peptide sequence. In yet another embodiment the furin cleavage site removes the self-cleaving peptide sequence at the C-terminus. For example, see Fang et al., Molecular Therapy, 2007; 15(6):1153-1159.

In certain embodiments, the ORFs encoding two, three, or four, or more HPV antigens and the immunomodulatory peptide, polypeptide, or protein are separated by the 2A peptide and a tag. In certain embodiments, the tag is linked to the 2A peptide. In certain embodiments, the tag is located between the 2A peptide and the furin cleavage site. In certain embodiments the tag is located at the C-terminus or N-terminus of the downstream ORF encoding the HPV antigen. In certain embodiments the tag is located at the C-terminus or N-terminus of the upstream ORF encoding the HPV antigen. In certain embodiments the tag is located in the vector with the ORFs encoding two, three, four, or more HPV antigens, a 2A peptide, a furin cleavage site, or a combination thereof. In certain embodiments the tag is a peptide tag. In more specific embodiments the tag is a V5 amino acid tag.

In certain embodiments, the ORFs encoding two, three, four, or five or more HPV antigens and the immunomodulatory peptide, polypeptide, or protein are separated by the 2A peptide and a spacer sequence. In certain embodiments, the spacer sequence is located upstream of the 2A peptide. In certain embodiments, the spacer sequence is located between the ORFs encoding the HPV antigens. In certain embodiments, the spacer sequence is located between the upstream of the 2A peptide and the tag. In certain embodiments, the spacer sequence is located between the upstream 2A peptide and the downstream furin cleavage site. In certain embodiments the spacer sequence is located in the vector with the ORFs encoding HPV antigens, a self-cleaving peptide, a furin cleavage site, a tag or a combination thereof. In certain embodiments, the spacer sequence increases cleavage efficiency.

In certain embodiments, the ORFs encoding two, three, four, or five, or more HPV antigens and the immunomodulatory peptide, polypeptide, or protein are separated by a nucleotide sequence that encodes: a self-cleaving peptide, an amino acid sequence that leads to release of the upstream amino acid sequence by "ribosome skipping," or a sequence element leading to binding of the ribosome and translation of the downstream sequence such as "internal ribosome entry sites" (IRES).

(c) Illustrative Insertions

In certain embodiments, the ORF that encodes the glycoprotein of the arenavirus is substituted by a nucleic acid sequence encoding one, two, three, or four, or more HPV antigens described herein and an immunomodulatory peptide, polypeptide, or protein. In certain embodiments, the ORF that encodes the glycoprotein of the arenavirus is substituted by a nucleic acid sequence encoding two, three, or four, or more HPV antigens described herein, separated from the immunomodulatory peptide, polypeptide, or protein by self-cleaving peptides or ribosome-skipping sequences. In certain embodiments, the self-cleaving peptide (or the ribosome-skipping sequence) can be obtained from a 2A protein from a member of the virus family Picornaviridae. In certain specific embodiments, the self-cleaving peptide (or the ribosome-skipping sequence) is obtained from (or derived from) Porcine teschovirus-1 2A, Thoseaasignavirus 2A, or Foot-and-mouth disease virus 2A peptide.

In certain embodiments, the heterologous nucleotide sequence encodes one or more of:
an HPV antigen or an antigenic fragment thereof;
an HPV16 protein E6, or an antigenic fragment thereof;
an HPV16 protein E7, or an antigenic fragment thereof;
an HPV18 protein E6, or an antigenic fragment thereof;
an HPV18 protein E7, or an antigenic fragment thereof;
an HPV16 protein E6/protein E7 fusion protein or an antigenic fragment thereof;
a shuffled HPV16 protein E6/protein E7 fusion protein or an antigenic fragment thereof;
an HPV16 protein E6/HPV18 protein E7 fusion protein or an antigenic fragment thereof;
an HPV16 protein E7/HPV18 protein E6 fusion protein or an antigenic fragment thereof;
an HPV18 protein E6/HPV16 protein E7 fusion protein or an antigenic fragment thereof; or
an HPV18 protein E7/HPV16 protein E6 fusion protein or an antigenic fragment thereof.

In certain embodiments, the heterologous nucleotide sequence further encodes, or the infectious, replication deficient arenavirus genome further comprises a second heterologous nucleotide sequence that encodes
Calreticulin (CRT), or a fragment thereof;
Ubiquitin or a fragment thereof;
Granulocyte-Macrophage Colony-Stimulating Factor (GM-CSF), or a fragment thereof;
Invariant chain (CD74) or an antigenic fragment thereof;
Mycobacterium tuberculosis Heat shock protein 70 or an antigenic fragment thereof;
Herpes simplex virus 1 protein VP22 or an antigenic fragment thereof;
CD40 ligand or an antigenic fragment thereof; or
Fms-related tyrosine kinase 3 (Flt3) ligand or an antigenic fragment thereof.

In certain embodiments, the Calreticulin protein fragment is an N-terminal truncated fragment. In certain embodiments, the Calreticulin protein fragment is a C-terminal truncated fragment. In certain embodiments, the Calreticulin protein fragment is at least 20, 40, 60, 80, 100, 120, 140, 160, 180, 200, 220, 240, 260, 280, 300, 320, 340, 360, 380, 400, or 417 amino acids in length. In certain embodiments, the Ubiquitin protein fragment is an N-terminal truncated fragment. In certain embodiments, the Ubiquitin protein fragment is a C-terminal truncated fragment. In certain embodiments, the Ubiquitin protein fragment is at least 10, 20, 30, 40, 50, 60, 70, or 76 amino acids in length. In certain embodiments, the GM-CSF protein fragment is an N-terminal truncated fragment. In certain embodiments, the GM-CSF protein fragment is a C-terminal truncated fragment. In certain embodiments, the GM-CSF protein fragment is at least 10, 20, 30, 40, 50, 60, 70, 80, 90, 100, 110, 120, or 127 amino acids in length. In certain embodiments, the Invariant chain (CD74) protein fragment is an N-terminal truncated fragment. In certain embodiments, the Invariant chain (CD74) protein fragment is a C-terminal truncated fragment. In certain embodiments, the Invariant chain (CD74) protein fragment is at least 20, 40, 60, 80, 100, 120, 140, 160, 180, 200, 220, or 232 amino acids in length. In certain embodiments, the Mycobacterium tuberculosis Heat shock protein 70 protein fragment is an N-terminal truncated fragment. In certain embodiments, the Mycobacterium tuberculosis Heat shock protein 70 protein fragment is a C-terminal truncated fragment. In certain embodiments, the Mycobacterium tuberculosis Heat shock protein 70 protein fragment is at least 20, 40, 60, 80, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, or 701 amino acids in length. In certain embodiments, the Herpes simplex virus 1 protein VP22 protein fragment is an N-terminal truncated fragment. In certain embodiments, the Herpes simplex virus 1 protein VP22 protein fragment is a C-terminal truncated fragment. In certain embodiments, the Herpes simplex virus 1 protein VP22 protein fragment is at least 20, 40, 60, 80, 100, 120, 140, 160, 180, 200, 220, 240, 260, 280, 300, or 301 amino acids in length. In certain embodiments, the CD40 ligand protein fragment is an N-terminal truncated fragment. In certain embodiments, the CD40 ligand protein fragment is a C-terminal truncated fragment. In certain embodiments, the CD40 ligand protein fragment is at least 20, 40, 60, 80, 100, 120, 140, 160, 180, 200, 220, 240, 260, or 261 amino acids in length. In certain embodiments, the Fms-related tyrosine kinase 3 (Flt3) ligand protein fragment is an N-terminal truncated fragment. In certain embodiments, the Fms-related tyrosine kinase 3 (Flt3) ligand protein fragment is a C-terminal truncated fragment. In certain embodiments, the Fms-related tyrosine kinase 3 (Flt3) ligand protein fragment is at least 10, 20, 30, 40, 50, 60, 70, 80, 90, 100, 110, 120, 130, 140, 150, or 153 amino acids in length.

In specific embodiments, the heterologous nucleotide sequence encodes HPV 16 protein E6, or a fragment thereof. In more specific embodiments, the antigen encoded by the heterologous nucleotide sequence is the HPV 16 protein E6 with one or more mutation(s) in the zinc finger motif(s). A mutation in the zinc finger motif prevents binding to Tumor protein p53. Tumor protein p53 has an anticancer function, because it can activate DNA repair proteins when DNA has sustained damage, because it can arrest growth by holding the cell cycle at the G1/S regulation point on DNA damage recognition, and because it can initiate apoptosis if DNA damage proves to be irreparable. In specific embodiments, the antigen is the HPV 16 protein E7, or a fragment thereof. In more specific embodiments, the antigen is the HPV 16 protein E7 with one or more mutation(s) in the Rb binding site and the zinc finger motif. The mutation prevents binding to retinoblastoma protein (pRb). Oncogenic proteins bind and inactivate pRb, which can lead to cancer because one function of pRb is to prevent excessive cell growth by inhibiting cell cycle progression until a cell is ready to divide. In specific embodiments, the antigen is the HPV 18 protein E6, or a fragment thereof. In more specific embodiments, the antigen is the HPV 18 protein E6 with one or more mutation(s) in the zinc finger motif. In specific embodiments, the antigen is the HPV 18 protein E7, or a fragment thereof. In more specific embodiments, the antigen is the HPV 18 protein E7 with one or more mutation(s) in the Rb binding site and the zinc finger motif.

In certain embodiments, the antigen is an HPV16 protein E7/E6 fusion protein, an HPV18 protein E7/E6 fusion protein, an HPV16 protein E7/HPV18 protein E6 fusion protein, or an HPV18 protein E7/HPV 16 protein E6 fusion protein, wherein the E6 protein has one or more mutation(s) in the zinc finger motif, and the protein E7 has one or more mutation(s) in the Rb binding site and the zinc finger motif.

In certain embodiments, the antigen is the HPV16 protein E7/E6 fusion protein, HPV18 protein E7/E6 fusion protein, HPV16 protein E7/HPV18 protein E6 fusion protein, or HPV18 protein E7/HPV 16 protein E6 fusion protein, expressed together with an immunomodulatory peptide, polypeptide, or protein, wherein the immunomodulatory peptide, polypeptide, or protein is Calreticulin (CRT), or a fragment thereof; Ubiquitin or a fragment thereof; Granulocyte-Macrophage Colony-Stimulating Factor (GM-CSF), or a fragment thereof; Invariant chain (CD74) or an antigenic fragment thereof; Mycobacterium tuberculosis Heat shock protein 70 or an antigenic fragment thereof; Herpes simplex virus 1 protein VP22 or an antigenic fragment thereof; CD40 ligand or an antigenic fragment thereof; or Fms-related tyrosine kinase 3 (Flt3) ligand or an antigenic fragment thereof, wherein the E6 protein has one or more mutation(s) in the zinc finger motif and the protein E7 has one or more mutation(s) in the Rb binding site and the zinc finger motif.

In one embodiment, the ORF that encodes the glycoprotein of the arenavirus is substituted by nucleic acid sequences encoding an HPV antigen. In certain embodiments, the ORF that encodes the glycoprotein of the arenavirus is substituted by nucleic acid sequences encoding antigen that is a fragment of at least at least 10, 20, 30, 40, 50, 60, 70, 80, 90, 100, 110, 120, 130, 140, 150, or 158 amino acids of a gene product of a gene of HPV 16 protein E6 or a fragment thereof. In certain embodiments, the ORF that encodes the glycoprotein of the arenavirus is substituted by nucleic acid sequences encoding antigen that is a fragment of at least at least 10, 20, 30, 40, 50, 60, 70, 80, 90, or 98 amino acids of a gene product of a gene of HPV 16 protein E7 or a fragment thereof. In certain embodiments, the ORF that encodes the glycoprotein of the arenavirus is substituted by nucleic acid sequences encoding antigen that is a fragment of at least at least 10, 20, 30, 40, 50, 60, 70, 80, 90, 100, 110, 120, 130, 140, 150, or 158 amino acids of a gene product of a gene of HPV 18 protein E6 or a fragment thereof. In certain embodiments, the ORF that encodes the glycoprotein of the arenavirus is substituted by nucleic acid sequences encoding antigen that is a fragment of at least at least 10, 20, 30, 40, 50, 60, 70, 80, 90, or 98 amino acids of a gene product of a gene of HPV 18 protein E7 or a fragment thereof.

In certain embodiments, the ORF that encodes the glycoprotein of the arenavirus is substituted by nucleic acid sequences encoding an antigen that is a fusion protein between HPV 16 protein E6 and HPV 16 protein E7. In certain embodiments, the ORF that encodes the glycoprotein of the arenavirus is substituted by nucleic acid sequences encoding an antigen that is a fusion protein between HPV 16 protein E7 and HPV 18 protein E6. In certain embodiments, the ORF that encodes the glycoprotein of the arenavirus is substituted by nucleic acid sequences encoding an antigen that is a fusion protein between HPV 18 protein E7 and HPV 16 protein E6. In certain embodiments, the ORF that encodes the glycoprotein of the arenavirus is substituted by nucleic acid sequences encoding an antigen that is a fusion protein between HPV 18 protein E6 and HPV 18 protein E7. In certain embodiments, the ORF that encodes the glycoprotein of the arenavirus is substituted by nucleic acid sequences encoding an antigen that is a fusion protein of HPV16 E7, HPV18 E6, HPV16 E6 and HPV18 E7. In certain embodiments, the ORF that encodes the glycoprotein of the arenavirus is substituted by nucleic acid sequences encoding an antigen that is at least 10, 15, 20, 25, 50, 75, 100, 150, 200, 250, 300, 350, 400, 450, 500, 1000 or more amino acids long. In certain embodiments, the ORF that encodes the glycoprotein of the arenavirus is substituted by nucleic acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 14.

In certain embodiments, the ORF that encodes the glycoprotein of the arenavirus is substituted by nucleic acid sequences encoding an antigen that is a fusion protein between HPV 16 protein E6 and HPV16 protein E7, and Calreticulin. In certain embodiments, the ORF that encodes the glycoprotein of the arenavirus is substituted by nucleic acid sequences encoding an antigen that is at least 10, 15, 20, 25, 50, 75, 100, 150, 200, 250, 300, 350, 400, 500, 600, or at least 676 amino acids long. In certain embodiments, the ORF that encodes the glycoprotein of the arenavirus is substituted by nucleic acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:15.

In certain embodiments, the ORF that encodes the glycoprotein of the arenavirus is substituted by nucleic acid sequences encoding an antigen that is a fusion protein between HPV 16 protein E6 and HPV 16 protein E7, and Ubiquitin. In certain embodiments, the ORF that encodes the glycoprotein of the arenavirus is substituted by nucleic acid sequences encoding an antigen that is at least 10, 15, 20, 25, 50, 75, 100, 150, 200, 250, 300, or at least 332 amino acids long. In certain embodiments, the ORF that encodes the glycoprotein of the arenavirus is substituted by nucleic acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:16.

In certain embodiments, the ORF that encodes the glycoprotein of the arenavirus is substituted by nucleic acid sequences encoding an antigen that is a fusion protein between HPV 16 protein E6 and HPV 16 protein E7, and GM-CSF, separated by a nucleotide sequence that encodes a self-cleaving peptide (2A peptide). In certain embodiments, the ORF that encodes the glycoprotein of the arenavirus is substituted by nucleic acid sequences encoding an antigen that is at least 10, 15, 20, 25, 50, 75, 100, 150, 200, 250, 300, 350, or at least 383 amino acids long. In certain embodiments, the ORF that encodes the glycoprotein of the arenavirus is substituted by nucleic acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:17.

In certain embodiments, the ORF that encodes the glycoprotein of the arenavirus is substituted by nucleic acid sequences encoding an antigen that is a fusion protein between HPV 16 protein E7 and HPV 18 protein E6, having an N-terminal VSVG signal sequence and a C-terminal peptide linker followed by a nucleotide sequence that encodes a self-cleaving peptide (2A peptide) and GM-CSF. In certain embodiments, the ORF that encodes the glycoprotein of the arenavirus is substituted by nucleic acid sequences encoding an antigen that is at least 10, 15, 20, 25, 50, 75, 100, 150, 200, 250, 300, 350, 400, or at least 428 amino acids long. In certain embodiments, the ORF that encodes the glycoprotein of the arenavirus is substituted by nucleic acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:33.

In certain embodiments, the ORF that encodes the glycoprotein of the arenavirus is substituted by nucleic acid sequences encoding an antigen that is a fusion protein between HPV 18 protein E7 and HPV 16 protein E6, having an N-terminal VSVG signal sequence and a C-terminal peptide linker followed by a nucleotide sequence that encodes a self-cleaving peptide (2A peptide) and GM-CSF. In certain embodiments, the ORF that encodes the glycoprotein of the arenavirus is substituted by nucleic acid sequences encoding an antigen that is at least 10, 15, 20, 25, 50, 75, 100, 150, 200, 250, 300, 350, 400, or at least 435 amino acids long. In certain embodiments, the ORF that encodes the glycoprotein of the arenavirus is substituted by nucleic acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:35.

In certain embodiments, the ORF that encodes the glycoprotein of the arenavirus is substituted by nucleic acid sequences encoding an antigen that is a fusion protein between HPV 16 protein E7, HPV 18 protein E6, HPV 16 protein E6 and HPV 18 protein E7, having an N-terminal VSVG signal sequence and a C-terminal peptide linker followed by a nucleotide sequence that encodes a self-cleaving peptide (2A peptide) and GM-CSF. In certain embodiments, the ORF that encodes the glycoprotein of the arenavirus is substituted by nucleic acid sequences encoding an antigen that is at least 10, 15, 20, 25, 50, 75, 100, 150, 200, 250, 300, 350, 400, 450, 500, 550, 600, 650, or at least 681 amino acids long. In certain embodiments, the ORF that encodes the glycoprotein of the arenavirus is substituted by nucleic acid sequence that is 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:37.

The immunomodulatory peptides, polypeptides, or proteins presented in these illustrative examples are murine sequences. Analogous constructs encoding the human sequences would be generated for human vaccine development.

In other embodiments, the arenavirus genomic segment or arenavirus viral vector described herein further comprises a reporter protein. The reporter protein is capable of expression at the same time as the antigen described herein. Ideally, expression is visible in normal light or other wavelengths of light. In certain embodiments, the intensity of the effect created by the reporter protein can be used to directly measure and monitor the arenavirus particle or tri-segmented arenavirus particle.

Reporter genes would be readily recognized by one skilled in the art. In certain embodiments, the arenavirus particle is a fluorescent protein. In other embodiments, the reporter gene is GFP. GFP emits bright green light when exposed to UV or blue like. Non-limiting examples of reporter proteins include various enzymes, such as, but not to β-galactosidase, chloramphenicol acetyltransferase, neomycin phosphotransferase, luciferase or RFP.

6.6 Immunogenic Compositions and Vaccines

Provided herein are vaccines, immunogenic compositions, and pharmaceutical compositions comprising an arenavirus viral vector as described herein, including an infectious, replication-deficient arenavirus viral vector, a replication-competent tri-segmented arenavirus viral vector, a replication-deficient tri-segmented arenavirus viral vector, or an arenavirus genomic segment as described herein. Such vaccines and pharmaceutical compositions can be formulated according to standard procedures in the art. Such compositions can be used in methods of treatment and prevention of disease.

In a specific embodiment, the compositions described herein are used in the treatment of subjects infected with, or susceptible to, an infection with HPV or reactivation of HPV. In another specific embodiment, the compositions provided herein can be used to induce an immune response in a host to whom the composition is administered. The immunogenic compositions described herein can be used as vaccines and can accordingly be formulated as pharmaceutical compositions. In a specific embodiment, the immunogenic compositions described herein are used in the prevention or treatment of infection of subjects (e.g., human subjects) by HPV or reactivation of HPV in subjects (e.g., human subjects).

In certain embodiments, the compositions provided herein further comprise a pharmaceutically acceptable excipient. In certain embodiments, such an immunogenic composition further comprises an adjuvant. An adjuvant can also be administered in combination with, but separate from, an arenavirus viral vector as described herein (including an infectious, replication-deficient arenavirus viral vector, a replication-competent tri-segmented arenavirus viral vector, a replication-deficient tri-segmented arenavirus viral vector, or an arenavirus genomic segment as described herein) before, concomitantly with, or after administration of said arenavirus viral vector. In some embodiments, the term "adjuvant" refers to a compound that when administered in conjunction with or as part of a composition described herein augments, enhances and/or boosts the immune response to an arenavirus viral vector as described herein, but when the compound is administered alone does not generate an immune response to the arenavirus viral vector. In some embodiments, the adjuvant generates an immune response to the arenavirus viral vector and does not produce an allergy or other adverse reaction. Adjuvants can enhance an immune response by several mechanisms including, e.g., lymphocyte recruitment, stimulation of B and/or T cells, and stimulation of macrophages. When a vaccine or immunogenic composition as provided herein comprises adjuvants or is administered together with one or more adjuvants, the adjuvants that can be used include, but are not limited to, mineral salt adjuvants or mineral salt gel adjuvants, particulate adjuvants, microparticulate adjuvants, mucosal adjuvants, and immunostimulatory adjuvants. Examples of adjuvants include, but are not limited to, aluminum salts (alum) (such as aluminum hydroxide, aluminum phosphate, and aluminum sulfate), 3 De-O-acylated monophosphoryl lipid A (MPL) (see GB 2220211), MF59 (Novartis), AS03 (GlaxoSmithKline), AS04 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al., in Vaccine Design: The Subunit and Adjuvant Approach (eds. Powell & Newman, Plenum Press, N.Y., 1995)); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., 1997, N. Engl. J. Med. 336, 86-91).

The compositions comprise an arenavirus described herein, including an infectious, replication-deficient arenavirus viral vector, a replication-competent tri-segmented arenavirus viral vector, and a replication-deficient tri-segmented arenavirus viral vector, or an arenavirus genomic segment described herein, alone or together with a pharmaceutically acceptable carrier. Suspensions or dispersions of genetically engineered arenaviruses, especially isotonic aqueous suspensions or dispersions, can be used. The pharmaceutical compositions may be sterilized and/or may comprise excipients, e.g., preservatives, stabilizers, wetting agents and/or emulsifiers, solubilizers, salts for regulating osmotic pressure and/or buffers and are prepared in a manner known per se, for example by means of conventional dispersing and suspending processes. In certain embodiments, such dispersions or suspensions may comprise viscosity-regulating agents. The suspensions or dispersions are kept at temperatures around 2-8° C., or preferentially for longer storage may be frozen and then thawed shortly before use. For injection, the vaccine or immunogenic preparations may be formulated in aqueous solutions, preferably in physiologically compatible buffers. The solution may contain formulatory agents such as suspending, stabilizing and/or dispersing agents.

In certain embodiments, the compositions described herein additionally comprise a preservative. In other embodiments, the pharmaceutical compositions described herein do not comprise a preservative.

The pharmaceutical compositions comprise from about $10^3$ to about $10^{11}$ focus forming units of the genetically engineered arenaviruses. Unit dose forms for parenteral administration are, for example, ampoules or vials, e.g., vials containing from about $10^3$ to $10^{10}$ focus forming units (e.g., focus forming units in a complementing cell line) or $10^5$ to $10^{15}$ physical particles of genetically engineered arenaviruses.

In another embodiment, a vaccine or immunogenic composition provided herein is formulated suitable for administration to a subject by, including but not limited to, oral, intradermal, intramuscular, intraperitoneal, intravenous, topical, subcutaneous, percutaneous, intranasal and inhalation routes, and via scarification (scratching through the top layers of skin, e.g., using a bifurcated needle). Specifically, subcutaneous, intramuscular or intravenous routes can be used. In one aspect, the vaccine or immunogenic composition is formulated for intravenous administration to a subject.

For administration intranasally or by inhalation, the preparation for use provided herein can be conveniently formulated in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflators may be formulated containing a powder mix of the compound and a suitable powder base such as lactose or starch.

The dosage of the active ingredient depends upon the type of vaccination and upon the subject, and their age, weight, individual condition, the individual pharmacokinetic data, and the mode of administration.

Provided herein is also a process and a use of genetically engineered arenaviruses for the manufacture of vaccines in the form of pharmaceutical preparations, which comprise genetically engineered arenaviruses as active ingredient. The pharmaceutical compositions as provided herein are prepared in a manner known per se, for example by means of conventional mixing and/or dispersing processes.

6.7 Methods of Treatment

Provided herein are methods for the treatment and/or prevention of neoplastic disease, such as cancer. These methods comprise administration to a subject in need of treatment and/or prevention of neoplastic disease, such as cancer, an effective amount of an arenavirus as described herein (see Sections 6.1, 6.2, 6.3 and 6.4). Also provided herein are methods for the treatment and/or prevention of an infection with an oncogenic virus, wherein the method comprises administration to a subject in need of treatment and/or prevention of an infection with an oncogenic virus an effective amount of an arenavirus that expresses at least one antigen of the oncogenic virus. Such oncogenic viruses can be human papillomavirus, Kaposi's sarcoma-associated herpesvirus, Epstein-Barr virus, Merkel cell polyomavirus, or human T-lymphotropic virus. Such antigens of oncogenic viruses can be antigens of human papillomavirus, Kaposi's sarcoma-associated herpesvirus, Epstein-Barr virus, Merkel cell polyomavirus, or human T-lymphotropic virus.

In one embodiment, provided herein are methods of treating and/or preventing an HPV infection in a subject comprising administering to the subject an arenavirus expressing an HPV antigen as described herein (see Sections 6.1, 6.2, 6.3, 6.4 and 6.5). In a specific embodiment, a method for treating and/or preventing an HPV infection comprises administering to a subject in need thereof an effective amount of an arenavirus viral vector, including an infectious, replication-deficient arenavirus viral vector, a replication-competent tri-segmented arenavirus viral vector, and a replication-deficient tri-segmented arenavirus viral vector, or an arenavirus genomic segment, expressing at least one HPV antigen described herein. The subject can be a mammal, such as, but not limited to a human being, a mouse, a rat, a guinea pig, a domesticated animal, such as, but not limited to, a cow, a horse, a sheep, a pig, a goat, a cat, a dog, a hamster, a donkey. In a specific embodiment, the subject is a human.

In another embodiment, provided herein are methods for inducing an immune response against HPV infection or its manifestation in a subject comprising administering to the subject an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen or a composition thereof.

In another embodiment, the subjects to whom an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen described herein or a composition thereof is administered have, are susceptible to, or are at risk for an HPV infection or reactivation. In another specific embodiment, the subjects to whom an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen described herein or a composition thereof is administered are infected with, are susceptible to, or are at risk for, an infection with HPV or reactivation with HPV.

In another embodiment, the subjects to whom an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen described herein or a composition thereof is administered are suffering from, are susceptible to, or are at risk for, an infection with HPV in the keratinocytes of the skin or the mucous membrane. In a specific embodiment, the subjects to whom an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen described herein or a composition thereof is administered are suffering from, are susceptible to, or are at risk for, an infection with HPV in one or more organs of the body, including but not limited to the skin, uterus, genitalia, areas of the respiratory tract.

In another embodiment, the subjects to whom an arenavirus viral vector, including an infectious, replication-deficient arenavirus viral vector, a replication-competent tri-segmented arenavirus viral vector, an replication-deficient tri-segmented arenavirus viral vector, or an arenavirus genomic segment, expressing an HPV antigen described herein or a composition thereof is administered to are suffering from symptoms including but not limited to cervical cancer, anal cancer, vulvar cancer, vaginal cancer, penile cancer, HPV-positive oropharyngeal cancer (OSCC), common warts, plantar warts, subungual or periungual warts, genital warts, condylomata acuminata or venereal warts, respiratory papillomatosis, and epidermodysplasia verruciformis.

In another embodiment, an arenavirus viral vector, including an infectious, replication-deficient arenavirus viral vector, a replication-competent tri-segmented arenavirus viral vector, an replication-deficient tri-segmented arenavirus viral vector, or an arenavirus genomic segment, expressing an HPV antigen as described herein or a composition thereof is administered to a subject of any age group suffering from, are susceptible to, or are at risk for, an infection with HPV. In a specific embodiment, an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen as described herein or a composition thereof is administered to a subject with a compromised immune system, a pregnant subject, a subject undergoing an organ or bone marrow transplant, a subject taking immunosuppressive drugs, a subject undergoing hemodialysis, a subject who has cancer, or a subject who is suffering from, is susceptible to, or is at risk for, an infection with HPV or reactivation of HPV. In a more specific embodiment, an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen as described herein or a composition thereof is administered to a subject with a compromised immune system due to HIV infection, who is suffering from, is susceptible to, or is at risk for, an infection with HPV or reactivation of HPV.

In another embodiment, an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen described herein or a composition thereof is administered to subjects with a heightened risk of disseminated HPV infection.

In another embodiment, an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen as described herein or a composition thereof is administered to a subject having a dormant infection with HPV. In a specific embodiment, an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment expressing an HPV antigen described herein or a composition thereof is administered to a subject having a dormant infection with HPV, which can reactivate upon immune system compromise. Thus, provided herein is a method for preventing reactivation of HPV.

In another embodiment, an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen described herein or a composition thereof is administered to subjects infected with, or at risk of infection with, one or more genotypes of HPV. In certain embodiments, one or more of those genotypes include HPV genotype 1 (HPV1), HPV genotype 2 (HPV2), HPV genotype 3 (HPV3), HPV genotype 4 (HPV4), HPV genotype 6 (HPV6), HPV genotype 7 (HPV7), HPV genotype 8 (HPV8), HPV genotype 10 (HPV10), HPV genotype 11 (HPV11), HPV genotype 13 (HPV13), HPV genotype 16 (HPV16), HPV genotype 18 (HPV18), HPV genotype 22 (HPV22), HPV genotype 26 (HPV26), HPV genotype 31 (HPV31), HPV genotype 32 (HPV32), HPV genotype 33 (HPV33), HPV genotype 35 (HPV35), HPV genotype 39 (HPV39), HPV genotype 42 (HPV42), HPV genotype 44 (HPV44), HPV genotype 45 (HPV45), HPV genotype 51 (HPV51), HPV genotype 52 (HPV52), HPV genotype 53 (HPV53), HPV genotype 56 (HPV56), HPV genotype 58 (HPV58), HPV genotype 59 (HPV59), HPV genotype 60 (HPV60), HPV genotype 63 (HPV63), HPV genotype 66 (HPV66), HPV genotype 68 (HPV68), HPV genotype 73 (HPV73), or HPV genotype 82 (HPV82), or other genotypes.

In another embodiment, an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen described herein or a composition thereof is administered to subjects infected with, or at risk of infection with, one or more "high-risk" genotypes of HPV, such as HPV16, HPV18, HPV31, HPV33, HPV35, HPV39, HPV45, HPV51, HPV52, HPV56, HPV58, HPV59, HPV68, HPV73, and HPV82.

In another embodiment, administering an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen as described herein or a composition thereof to subjects confer cell-mediated immunity (CMI) against an infection with HPV or reactivation of HPV. Without being bound by theory, in another embodiment, an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen as described herein or a composition thereof infects and expresses antigens of interest in antigen presenting cells (APC) of the host (e.g., macrophages) for direct presentation of antigens on Major Histocompatibility Complex (MHC) class I. In another embodiment, administering an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen as described herein or a composition thereof to subjects induces IFN-γ and CD8+ T cell responses (IFN-γ is produced by CD8+ T cells) of high magnitude to treat or prevent an infection with HPV or reactivation of HPV.

In another embodiment, administering an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen described herein or a composition thereof reduces the risk that an individual will develop an infection with HPV or reactivation of HPV by at least about 10%, at least about 20%, at least about 25%, at least about 30%, at least about 35%, at least about 40%, at least about 50%, at least about 60%, at least about 70%, at least about 80%, at least about 90%, or more, compared to the risk of developing an infection with HPV or reactivation of HPV in the absence of such treatment.

In another embodiment, administering an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen described herein or a composition thereof reduces the symptoms or manifestations of an infection with HPV or reactivation of HPV by at least about 10%, at least about 20%, at least about 25%, at least about 30%, at least about 35%, at least about 40%, at least about 50%, at least about 60%, at least about 70%, at least about 80%, at least about 90%, or more, compared to the manifestation of the symptoms of an infection HPV or reactivation of HPV in the absence of such treatment.

Manifestations of HPV infections include but are not limited to cervical cancer, anal cancer, vulvar cancer, vaginal cancer, penile cancer, HPV-positive oropharyngeal cancer (OSCC), common warts, plantar warts, subungual or periungual warts, genital warts, condylomata acuminata or venereal warts, respiratory papillomatosis, and epidermodysplasia verruciformis.

In another embodiment, administering an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen described herein or a composition thereof in subjects with immature neonatal immune system induces cell-mediated immunity (CMI) response against an infection with HPV or reactivation of HPV by at least about 10%, at least about 20%, at least about 25%, at least about 30%, at least about 35%, at least about 40%, at least about 50%, at least about 60%, at least about 70%, at least about 80%, at least about 90%, or more, compared to CMI response against an infection with HPV or reactivation of HPV in the absence of such a treatment.

In another embodiment, administering an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen described herein or a composition thereof in subjects induces an HPV antigen specific immune response resulting in an increased amount of antigen-specific CD8+ T cells detected in peripheral blood. In certain embodiments, administering an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen described herein or a composition thereof in subjects induces an increase of HPV antigen specific CD8+ T-cells, wherein the HPV antigen specific CD8+ T-cells comprise approximately 1%, 2%, 3%, 4%, 5%, 6%, 7%, 8%, 9%, 10%, 15%, 20%, 30%, 40% or 50% of the total CD8+ T-cell population. In certain embodiments, the percentage of HPV antigen specific CD8+ T-cells can be determined through any method known to the skilled artisan, such as through a tetramer staining assay.

Changes in cell-mediated immunity (CMI) response function against an infection with HPV or reactivation of HPV induced by administering an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen described herein or a composition thereof in subjects can be measured by any assay known to the skilled artisan including, but not limited to flow cytometry (see, e.g., Perfetto et al., 2004, Nat Rev Immun., 4(8):648-55), lymphocyte proliferation assays (see, e.g., Bonilla et al., 2008, Ann Allergy Asthma Immunol., 101:101-4; and Hicks et al., 1983, Am J Clin Pathol., 80:159-63), assays to measure lymphocyte activation including determining changes in surface marker expression following activation of measurement of cytokines of T lymphocytes (see, e.g., Caruso et al., 1997, Cytometry, 27:71-6), ELISPOT assays (see, e.g., Czerkinsky et al., 1983, J Immunol Methods., 65:109-121; and Hutchings et al., 1989, J Immunol Methods, 120:1-8), or Natural killer cell cytotoxicity assays (see, e.g., Bonilla et al., 2005, Ann Allergy Asthma Immunol. May; 94 (5 Suppl 1):S1-63).

(a) Combination Therapy

In one embodiment, provided herein are methods of treating and/or preventing an HPV infection in a subject comprising administering to the subject two or more arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen as described herein. See Sections 6.1 to 6.5. In specific embodiments, a method for treating and/or preventing an HPV infection comprises administering a first arenavirus viral vector, including an infectious, replication-deficient arenavirus viral vector, a replication-competent tri-segmented arenavirus viral vector, and a replication-deficient tri-segmented arenavirus viral vector, or an arenavirus genomic segment, expressing an HPV antigen as described herein, e.g., in which the ORF encoding the GP of the S genomic segment is substituted with a nucleotide sequence encoding the HPV antigen, wherein the HPV antigen can be but is not limited to:

an HPV16 protein E6, or an antigenic fragment thereof;
an HPV16 protein E7, or an antigenic fragment thereof;
an HPV18 protein E6, or an antigenic fragment thereof; or
an HPV18 protein E7, or an antigenic fragment thereof.

and a second arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing a HPV antigen as described herein, e.g., in which the ORF encoding the GP of the S genomic segment is substituted with a nucleotide sequence encoding the HPV antigen, wherein the HPV antigen can be but is not limited to:

an HPV16 protein E6, or an antigenic fragment thereof;
an HPV16 protein E7, or an antigenic fragment thereof;
an HPV18 protein E6, or an antigenic fragment thereof; or
an HPV18 protein E7, or an antigenic fragment thereof.

In certain embodiments, provided herein are methods for treating and/or preventing an infection comprising administering two arenavirus viral vector constructs, or two arenavirus genomic segments, expressing an HPV antigen as described herein. In a specific embodiment, the two arenavirus viral vectors, including an infectious, replication-deficient arenavirus viral vector, a replication-competent tri-segmented arenavirus viral vector, or replication-deficient tri-segmented arenavirus viral vector, or an arenavirus genomic segment, express a different HPV antigen. In other embodiments, the two arenavirus viral vector constructs, or arenavirus genomic segments, have different arenaviral backbones. In yet other embodiments, the two arenavirus viral vector constructs, or arenavirus genomic segments, express different HPV antigens and have different arenaviral backbones.

In certain embodiments, provided herein are methods for treating and/or preventing an HPV infection comprising administering three or more arenavirus viral vector constructs, or arenavirus genomic segments, expressing an HPV antigen as described herein. In another embodiment, provided herein are methods for treating/and or preventing an infection comprising administering four or more arenavirus viral vector constructs or arenavirus genomic segments, five or more arenavirus viral vector constructs or arenavirus genomic segments, six or more arenavirus viral vector constructs or arenavirus genomic segments, or seven arenavirus viral vector constructs or arenavirus genomic segments, each expressing an HPV antigen as described herein. In certain embodiments, each of the different arenavirus viral vectors expresses a different HPV antigen as described herein. In certain embodiments, the arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, is derived from LCMV. In certain embodiments, the arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, is derived from Junin virus. In certain embodiments, the arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, is derived from a combination of LCMV and Junin virus.

In certain specific embodiments, administration of an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing HPV16 protein E7/E6 fusion protein and an immunomodulatory peptide, polypeptide, or protein elicits a greater antigen specific CD8+ T-cell response than administration of an arenavirus viral vector, including an infectious, replication-deficient arenavirus arenavirus viral vector, a replication-competent tri-segmented arenavirus viral vector, a replication-deficient tri-segmented arenavirus viral vector, or an arenavirus genomic segment, expressing an HPV16 protein E7/E6 fusion protein alone. In certain specific embodiments, administration of an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing HPV16 protein E7/E6 fusion protein and GM-CSF elicits a greater antigen specific CD8+ T-cell response than administration of an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing HPV16 protein E7/E6 fusion protein alone. In certain specific embodiments, administration of an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing HPV16 protein E7/E6 fusion protein and GM-CSF elicits an antigen specific CD8+ T-cell response that is 10%, 50%, 100%, 150%, or 200% greater than the antigen specific CD8+ T-cell response to administration of an arenavirus viral vector, including infectious, replication-deficient arenavirus viral vector, a replication-competent tri-segmented arenavirus viral vector, a replication-deficient tri-segmented arenavirus viral vector, or an arenavirus genomic segment, expressing HPV16 protein E7/E6 fusion protein alone.

In certain specific embodiments, administration of an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing HPV16 E7/HPV18 E6 fusion protein and an immunomodulatory peptide, polypeptide, or protein elicits a greater antigen specific CD8+ T-cell response than administration of an arenavirus viral vector, including an infectious, replication-deficient arenavirus arenavirus viral vector, a replication-competent tri-segmented arenavirus viral vector, a replication-deficient tri-segmented arenavirus viral vector, or an arenavirus genomic segment, expressing an HPV16 E7/HPV18 E6 fusion protein alone. In certain specific embodiments, administration of an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing HPV16 E7/HPV18 E6 fusion protein and GM-CSF elicits a greater antigen specific CD8+ T-cell response than administration of an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing HPV16 E7/HPV18 E6 fusion protein alone. In certain specific embodiments, administration of an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing HPV16 E7/HPV18 E6 fusion protein and GM-CSF elicits an antigen specific CD8+ T-cell response that is 10%, 50%, 100%, 150%, or 200% greater than the antigen specific CD8+ T-cell response to administration of an arenavirus viral vector, including infectious, replication-deficient arenavirus viral vector, a replication-competent tri-segmented arenavirus viral vector, a replication-deficient tri-segmented arenavirus viral vector, or an arenavirus genomic segment, expressing HPV16 E7/HPV18 E6 fusion protein alone In certain specific embodiments, administration of an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing HPV18 E7/HPV16 E6 fusion protein and an immunomodulatory peptide, polypeptide, or protein elicits a greater antigen specific CD8+ T-cell response than administration of an arenavirus viral vector, including an infectious, replication-deficient arenavirus arenavirus viral vector, a replication-competent tri-segmented arenavirus viral vector, a replication-deficient tri-segmented arenavirus viral vector, or an arenavirus genomic segment, expressing an HPV18 E7/HPV16 E6 fusion protein alone. In certain specific embodiments, administration of an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing HPV18 E7/HPV16 E6 fusion protein and GM-CSF elicits a greater antigen specific CD8+ T-cell response than administration of an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing HPV18 E7/HPV16 E6 fusion protein alone. In certain specific embodiments, administration of an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing HPV18 E7/HPV16 E6 fusion protein and GM-CSF elicits an antigen specific CD8+ T-cell response that is 10%, 50%, 100%, 150%, or 200% greater than the antigen specific CD8+ T-cell response to administration of an arenavirus viral vector, including infectious, replication-deficient arenavirus viral vector, a replication-competent tri-segmented arenavirus viral vector, a replication-deficient tri-segmented arenavirus viral vector, or an arenavirus genomic segment, expressing HPV18 E7/HPV16 E6 fusion protein alone In certain specific embodiments, administration of an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing HPV16 E7/HPV18 E6/HPV16 E6/HPV18 E7 fusion protein and an immunomodulatory peptide, polypeptide, or protein elicits a greater antigen specific CD8+ T-cell response than administration of an arenavirus viral vector, including an infectious, replication-deficient arenavirus arenavirus viral vector, a replication-competent tri-segmented arenavirus viral vector, a replication-deficient tri-segmented arenavirus viral vector, or an arenavirus genomic segment, expressing an HPV16 E7/HPV18 E6/HPV16 E6/HPV18 E7 fusion protein alone. In certain specific embodiments, administration of an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing HPV16 E7/HPV18 E6/HPV16 E6/HPV18 E7 fusion protein and GM-CSF elicits a greater antigen specific CD8+ T-cell response than administration of an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing HPV16 E7/HPV18 E6/HPV16 E6/HPV18 E7 fusion protein alone. In certain specific embodiments, administration of an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing HPV16 E7/HPV18 E6/HPV16 E6/HPV18 E7 fusion protein and GM-CSF elicits an antigen specific CD8+ T-cell response that is 10%, 50%, 100%, 150%, or 200% greater than the antigen specific CD8+ T-cell response to administration of an arenavirus viral vector, including infectious, replication-deficient arenavirus viral vector, a replication-competent tri-segmented arenavirus viral vector, a replication-deficient tri-segmented arenavirus viral vector, or an arenavirus genomic segment, expressing HPV16 E7/HPV18 E6/HPV16 E6/HPV18 E7 fusion protein alone In specific embodiments, the HPV antigens as described herein are expressed together with signal peptides and/or linkers as described herein. In specific embodiments the HPV antigens and immunomodulatory peptides, polypeptides, or proteins as described herein are expressed together with signal peptides and/or linkers as described herein.

In another embodiment, the vector generated to encode one or more HPV antigens as described herein of the first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, may be based on LCMV Clone 13 or LCMV MP strain. (See, e.g., Section 6.8).

In another embodiment, the vector generated to encode one or more HPV antigens as described herein of the second arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, may be based on LCMV Clone 13 or LCMV MP strain. (See, e.g., Section 6.8).

In another embodiment, the vector generated to encode one or more HPV antigens as described herein of the first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, may be based on Junin virus.

In another embodiment, the vector generated to encode one or more HPV antigens as described herein of the second arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, may be based on Junin virus.

(b) Treatment Regimens

The HPV antigens can be any HPV antigen as described herein. Without being limited by theory, administration of a first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, and subsequently of a second arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, results in a prime-boost effect.

In certain embodiments, provided herein are methods for treating and/or preventing an infection comprising administering two or more arenavirus vector constructs each expressing the same or a different HPV antigen sequentially. The time interval between each administration can be about 1 week, about 2 weeks, about 3 week, about 4 weeks, about 5 weeks, about 6 weeks, about 7 weeks, about 8 weeks, about 3 months, about 4 months, about 5 months, about 6 months, about 7 months, about 8 months, about 9 months, about 10 months, about 11 months, about 12 months, about 18 months, or about 24 months.

In certain embodiments, the first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, and the second arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, are homologous. In certain embodiments, the first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, and the second arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, are heterologous.

In certain specific embodiments, the first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, is an Old World arenavirus, and the second arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, is an Old World arenavirus. In certain specific embodiments, the first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, is an Old World arenavirus, and the second arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, is a New World arenavirus. In certain specific embodiments, the first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, is a New World arenavirus, and the second arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, is an New World arenavirus. In certain specific embodiments, the first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, is an New World arenavirus, and the second arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, is an Old World arenavirus.

In certain specific embodiments, the first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, is derived from LCMV, and the second arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, is derived from LCMV. In certain specific embodiments, the first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, is derived from LCMV, and the second arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, is derived from Junin virus. In certain specific embodiments, the first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, is derived from Junin virus, and the second arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, is derived from Junin virus. In certain specific embodiments, the first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, arenavirus is derived from Junin virus, and the second arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, is derived from LCMV.

In certain embodiments, provided herein is a method of treating and/or preventing, a neoplastic disease, such as cancer, wherein a first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, is administered first as a "prime," and a second arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, is administered as a "boost." The first and the second arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, can express the same or different tumor antigens. The tumor antigen can be an antigen of human papillomavirus, antigen of Kaposi's sarcoma-associated herpesvirus, such as latency-associated nuclear antigen, antigen of Epstein-Barr virus, such as EBV-EA, EBV-MA, or EBV-VCA, antigen of Merkel cell polyomavirus, such as MCV T antigen, or antigen of human T-lymphotropic virus, such as HTLV-1 Tax antigen. The tumor antigen can also be Alphafetoprotein (AFP), Carcinoembryonic antigen (CEA), CA-125, MUC-1, Epithelial tumor antigen (ETA), Tyrosinase, Melanoma-associated antigen (MAGE), or abnormal products of ras, and p53. The neoplastic disease can be a disease associated with benign neoplasms, such as uterine fibroids and melanocytic nevi, potentially malignant neoplasms, such as carcinoma in situ, or malignant neoplasms, such as cancer. In certain specific embodiments, the "prime" administration is performed with an arenavirus viral vector, including an infectious, replication-deficient arenavirus viral vector, a replication-competent tri-segmented arenavirus viral vector, and a replication-deficient tri-segmented arenavirus viral vector, or an arenavirus genomic segment, derived from LCMV, and the "boost" is performed with an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, derived from Junin virus. In certain specific embodiments, the "prime" administration is performed with an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, derived from Junin virus, and the "boost" is performed with an arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, derived from LCMV.

In certain embodiments, administering a first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen or a fragment thereof, followed by administering a second arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen or a fragment thereof results in a greater antigen specific CD8+ T cell response than administering a single arenavirus viral vector expressing an HPV antigen or a fragment thereof. In certain specific embodiments, administering a first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV16 E7/E6 fusion protein, followed by administering a second arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV16 E7/E6 fusion protein results in a greater antigen specific CD8+ T cell response than administering a single arenavirus viral vector, including an infectious, replication-deficient arenavirus viral vector, a replication-competent tri-segmented arenavirus viral vector, and a replication-deficient tri-segmented arenavirus viral vector, or an arenavirus genomic segment, expressing an HPV16 E7/E6 fusion protein. In certain embodiments, the antigen specific CD8+ T cell count increases by 50%, 100%, 150% or 200% after the second administration compared to the first administration. In certain embodiments, administering a third arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV16 E7/E6 fusion protein results in a greater antigen specific CD8+ T cell response than administering two consecutive arenavirus viral vectors expressing an HPV16 E7/E6 fusion protein. In certain embodiments, the antigen specific CD8+ T cell count increases by about 50%, about 100%, about 150%, about 200% or about 250% after the third administration compared to the first administration (See FIG. 5).

In certain embodiments, provided herein are methods for treating and/or preventing an infection comprising administering two or more arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, wherein the two or more arenavirus viral vectors are homologous, and wherein the time interval between each administration is about 1 week, about 2 weeks, about 3 week, about 4 weeks, about 5 weeks, about 6 weeks, about 7 weeks, about 8 weeks, about 3 months, about 4 months, about 5 months, about 6 months, about 7 months, about 8 months, about 9 months, about 10 months, about 11 months, about 12 months, about 18 months, or about 24 months.

In certain embodiments, administering a first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen or a fragment thereof and a second, heterologous, arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen or a fragment thereof elicits a greater CD8+ T cell response than administering a first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen or a fragment thereof and a second, homologous, arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen or a fragment thereof.

In certain specific embodiments, the first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV16 E7/E6 fusion protein, an HPV16 E7/HPV18 E6 fusion protein, an HPV18 E7/HPV16 E6 fusion protein or an HPV16 E7/HPV18 E6/HPV16 E6/HPV18 E7 fusion protein is LCMV, and the second, homologous, arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV16 E7/E6 fusion protein, an HPV16 E7/HPV18 E6 fusion protein, an HPV18 E7/HPV16 E6 fusion protein or an HPV16 E7/HPV18 E6/HPV16 E6/HPV18 E7 fusion protein is LCMV. In certain specific embodiments, the first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV16 E7/E6 fusion protein, an HPV16 E7/HPV18 E6 fusion protein, an HPV18 E7/HPV16 E6 fusion protein or an HPV16 E7/HPV18 E6/HPV16 E6/HPV18 E7 fusion protein is Junin virus, and the second, homologous, arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV16 E7/E6 fusion protein, an HPV16 E7/HPV18 E6 fusion protein, an HPV18 E7/HPV16 E6 fusion protein or an HPV16 E7/HPV18 E6/HPV16 E6/HPV18 E7 fusion protein is Junin virus.

In certain specific embodiments, the first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV16 E7/E6 fusion protein, an HPV16 E7/HPV18 E6 fusion protein, an HPV18 E7/HPV16 E6 fusion protein or an HPV16 E7/HPV18 E6/HPV16

E6/HPV18 E7 fusion protein is LCMV, and the second, heterologous, arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV16 E7/E6 fusion protein, an HPV16 E7/HPV18 E6 fusion protein, an HPV18 E7/HPV16 E6 fusion protein or an HPV16 E7/HPV18 E6/HPV16 E6/HPV18 E7 fusion protein is Junin virus. In certain specific embodiments, the first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV16 E7/E6 fusion protein, an HPV16 E7/HPV18 E6 fusion protein, an HPV18 E7/HPV16 E6 fusion protein or an HPV16 E7/HPV18 E6/HPV16 E6/HPV18 E7 fusion protein is Junin virus, and the second, heterologous, arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV16 E7/E6 fusion protein, an HPV16 E7/HPV18 E6 fusion protein, an HPV18 E7/HPV16 E6 fusion protein or an HPV16 E7/HPV18 E6/HPV16 E6/HPV18 E7 fusion protein is LCMV.

In certain specific embodiments, administering a first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV16 E7/E6 fusion protein, an HPV16 E7/HPV18 E6 fusion protein, an HPV18 E7/HPV16 E6 fusion protein or an HPV16 E7/HPV18 E6/HPV16 E6/HPV18 E7 fusion protein and a second, heterologous, arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV16 E7/E6 fusion protein, an HPV16 E7/HPV18 E6 fusion protein, an HPV18 E7/HPV16 E6 fusion protein or an HPV16 E7/HPV18 E6/HPV16 E6/HPV18 E7 fusion protein thereof elicits a greater CD8+ T cell response than administering a first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, arenavirus expressing an HPV16 E7/E6 fusion protein, an HPV16 E7/HPV18 E6 fusion protein, an HPV18 E7/HPV16 E6 fusion protein or an HPV16 E7/HPV18 E6/HPV16 E6/HPV18 E7 fusion protein and a second, homologous, arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV16 E7/E6 fusion protein, an HPV16 E7/HPV18 E6 fusion protein, an HPV18 E7/HPV16 E6 fusion protein or an HPV16 E7/HPV18 E6/HPV16 E6/HPV18 E7 fusion protein. In certain specific embodiments, administering a first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV16 E7/E6 fusion protein, an HPV16 E7/HPV18 E6 fusion protein, an HPV18 E7/HPV16 E6 fusion protein or an HPV16 E7/HPV18 E6/HPV16 E6/HPV18 E7 fusion protein and a second, heterologous, arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV16 E7/E6 fusion protein, an HPV16 E7/HPV18 E6 fusion protein, an HPV18 E7/HPV16 E6 fusion protein or an HPV16 E7/HPV18 E6/HPV16 E6/HPV18 E7 fusion protein thereof elicits a CD8+ T cell response that is about 20%, about 40%, about 60%, about 80%, about 100%, about 120%, about 140%, about 160%, about 180%, or about 200% greater than administering a first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV16 E7/E6 fusion protein, an HPV16 E7/HPV18 E6 fusion protein, an HPV18 E7/HPV16 E6 fusion protein or an HPV16 E7/HPV18 E6/HPV16 E6/HPV18 E7 fusion protein and a second, homologous, arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV16 E7/E6 fusion protein, an HPV16 E7/HPV18 E6 fusion protein, an HPV18 E7/HPV16 E6 fusion protein or an HPV16 E7/HPV18 E6/HPV16 E6/HPV18 E7 fusion protein (See FIGS. 14A-14D).

In certain embodiments, provided herein are methods for treating and/or preventing an infection comprising administering two or more arenavirus vector constructs, wherein the two or more arenavirus vector constructs are heterologous, and wherein the time interval between each administration is about 1 week, about 2 weeks, about 3 week, about 4 weeks, about 5 weeks, about 6 weeks, about 7 weeks, about 8 weeks, about 3 months, about 4 months, about 5 months, about 6 months, about 7 months, about 8 months, about 9 months, about 10 months, about 11 months, about 12 months, about 18 months, or about 24 months.

In yet another embodiment, provided herein is the combined use of the arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen described herein and one or more replication-deficient virus vectors. In a more specific embodiment the replication-deficient virus vector is selected from the group comprising of poxviruses, adenoviruses, alphaviruses, herpes simplex viruses, paramyxoviruses, rhabdoviruses, poliovirus, adeno-associated virus, and sendai virus, and mixtures thereof. In a specific embodiment, the poxvirus is a modified vaccine Ankara.

In yet another embodiment, provided herein is the combined use of the arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen described herein and one or more replication-deficient virus vectors expressing an HPV antigen. In a more specific embodiment the replication-deficient virus vector is selected from the group comprising of poxviruses, adenoviruses, alphaviruses, herpes simplex viruses, paramyxoviruses, rhabdoviruses, poliovirus, adeno-associated virus, and sendai virus, and mixtures thereof. In a specific embodiment, the poxvirus is a modified vaccine Ankara.

In another embodiment, the first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen as described herein is administered before or after the second arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen as described herein. For example the first arenavirus viral vector expressing an HPV antigen is administered around 30-60 minutes before or after the first administration of the second arenavirus viral vector.

In another embodiment, the first arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing a vaccine antigen is administered before the second arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing a vaccine antigen. In certain embodiments there is a period of about 1 hour, 2 hours, 3 hours, 6 hours, 12 hours, 1 day, 2 days, 3 days, 5 days, 1 week, 2 weeks, 1 month, 2 months, 3 months, 4 months, 5 months, 6 months, 7 months, 8 months, 9 months, 10 months, 11 months, 1 year between the administration of the first arenavirus viral vector and the second arenavirus viral vector.

In another embodiment, two arenavirus viral vectors, including an infectious, replication-deficient arenavirus viral vector, a replication-competent tri-segmented arenavirus viral vector, a replication-deficient tri-segmented arenavirus viral vector, or two arenavirus genomic segments, are administered in a treatment regime at molar ratios ranging from about 1:1 to 1:1000, in particular including: 1:1 ratio, 1:2 ratio, 1:5 ratio, 1:10 ratio, 1:20 ratio, 1:50 ratio, 1:100 ratio, 1:200 ratio, 1:300 ratio, 1:400 ratio, 1:500 ratio, 1:600 ratio, 1:700 ratio, 1:800 ratio, 1:900 ratio, 1:1000 ratio.

In another embodiment, the subjects to whom two or more arenavirus viral vectors, including an infectious, replication-deficient arenavirus viral vector, a replication-competent tri-segmented arenavirus viral vector, a replication-deficient tri-segmented arenavirus viral vector, or two or more arenavirus genomic segments, expressing an HPV antigen described herein are administered have, are susceptible to, or are at risk for an HPV infection or reactivation. In another embodiment, the subjects to whom two or more arenavirus viral vectors, including an infectious, replication-deficient arenavirus viral vector, a replication-competent tri-segmented arenavirus viral vector, a replication-deficient tri-segmented arenavirus viral vector, or two or more arenavirus genomic segments, expressing an HPV antigen described herein are administered are infected with, are susceptible to, or are at risk for, an infection with HPV or reactivation with HPV.

The subjects who can be treated with the methods provided herein are susceptible to, or are at risk for an HPV infection or reactivation.

In another embodiment, said two or more arenavirus viral vector, including an infectious, replication-deficient arenavirus viral vector, a replication-competent tri-segmented arenavirus viral vector, a replication-deficient tri-segmented arenavirus viral vector, or an arenavirus genomic segment, expressing an HPV antigen as described herein further express at least another immunostimulatory peptide, polypeptide or protein. In certain embodiments, the immunostimulatory peptide, polypeptide or protein is Calreticulin (CRT), or a fragment thereof; Ubiquitin or a fragment thereof; Granulocyte-Macrophage Colony-Stimulating Factor (GM-CSF), or a fragment thereof; Invariant chain (CD74) or an antigenic fragment thereof; Mycobacterium tuberculosis Heat shock protein 70 or an antigenic fragment thereof; Herpes simplex virus 1 protein VP22 or an antigenic fragment thereof, CD40 ligand or an antigenic fragment thereof; or Fms-related tyrosine kinase 3 (Flt3) ligand or an antigenic fragment thereof.

Heterologous prime-boost methods with arenavirus viral vectors, including an infectious, replication-deficient arenavirus viral vector, a replication-competent tri-segmented arenavirus viral vector, a replication-deficient tri-segmented arenavirus viral vector, or an arenavirus genomic segments, wherein the two arenavirus viral vectors are derived from different arenaviruses (e.g., LCMV and Junin virus) are also provided. These arenavirus viral vectors can express an antigen, such as an antigen of an oncogenic virus, or an antigen of a tumor-associated virus. In specific embodiments, the oncogenic virus is human papillomavirus, Kaposi's sarcoma-associated herpesvirus, Epstein-Barr virus, Merkel cell polyomavirus, or human T-lymphotropic virus.

6.8 Nucleic Acids, Vector Systems and Cell Lines

In one embodiment, described herein is a nucleic acid sequence encoding the large genomic segment (L segment) of an arenavirus viral vector, including an infectious, replication-deficient arenavirus viral vector, a replication-competent tri-segmented arenavirus viral vector, and a replication-deficient tri-segmented arenavirus viral vector, or an arenavirus genomic segment, described herein, in which one ORF of the genomic segment is deleted or functionally inactivated, and the genomic segment comprises a heterologous nucleotide sequence as described in Section 6.5, such as a heterologous nucleotide sequence encoding an HPV antigen.

In one embodiment, described herein is a nucleic acid sequence that encodes the short genomic segment (S segment) of an arenavirus viral vector, including an infectious, replication-deficient arenavirus viral vector, a replication-competent tri-segmented arenavirus viral vector, and a replication-deficient tri-segmented arenavirus viral vector, or an arenavirus genomic segment, described herein, in which one ORF of the genomic segment is deleted or functionally inactivated and wherein the short genomic segment comprises a nucleotide sequence encoding an HPV antigen. In another embodiment, described herein is a nucleic acid sequence that encodes the short genomic segment (S segment) of an arenavirus viral vector, including an infectious, replication-deficient arenavirus viral vector, a replication-competent tri-segmented arenavirus viral vector, and a replication-deficient tri-segmented arenavirus viral vector, or an arenavirus genomic segment, described herein, in which the ORF of the glycoprotein gene is deleted or functionally inactivated and wherein the short genomic segment comprises a heterologous nucleotide sequence encoding an HPV antigen. In certain, more specific embodiments, the HPV antigen is an antigen as described in Section 6.5.

In certain embodiments, the nucleic acid sequences provided herein can be derived from a particular strain of LCMV. Strains of LCMV include Clone 13, MP strain, Arm CA 1371, Arm E-250, WE, UBC, Traub, Pasteur, 810885, CH-5692, Marseille #12, HP65-2009, 200501927, 810362, 811316, 810316, 810366, 20112714, Douglas, GR01, SN05, CABN and their derivatives. In specific embodiments, the nucleic acid is derived from LCMV Clone 13. In other specific embodiments, the nucleic acid is derived from LCMV MP strain or Junin virus.

In a more specific embodiment, provided herein is a nucleic acid encoding an arenavirus genomic segment comprising a sequence that is at least 90%, 91%, 92%, 93%, 94%, 95%, 96%, 97%, 98%, at least 99%, or 100% identical to the sequence of SEQ ID NO: 14, SEQ ID NO: 15, SEQ ID NO: 16, or SEQ ID NO: 17. In another embodiment, provided herein is a nucleic acid that encodes an arenavirus genomic segment comprising (i) a nucleotide sequence that is at least 90%, 91%, 92%, 93%, 94%, 95%, 96%, 97%, 98%, at least 99%, or 100% identical to the sequence of nucleotide 1639 to 3315 of SEQ ID NO: 1; and (ii) a heterologous nucleotide sequence encoding an HPV antigen.

In another embodiment, provided herein is a nucleic acid that encodes an arenavirus genomic segment comprising (i) a nucleotide sequence that is at least 90%, 91%, 92%, 93%, 94%, 95%, 96%, 97%, 98%, at least 99%, or 100% identical to the sequence of nucleotide 1639 to 3315 of SEQ ID NO: 1; (ii) a heterologous nucleotide sequence encoding an HPV antigen; and (iii) a heterologous nucleotide sequence encoding an immunomodulatory peptide, polypeptide, or protein.

In another embodiment, provided herein is a nucleic acid that encodes an arenavirus genomic segment comprising (i) a nucleotide sequence encoding an expression product whose amino acid sequence is at least 90%, 91%, 92%, 93%, 94%, 95%, 96%, 97%, 98%, at least 99%, or 100% identical to the amino acid sequence encoded by 1639 to 3315 of SEQ ID NO: 1; and (ii) a heterologous nucleotide sequence encoding an HPV antigen.

In another embodiment, provided herein is a nucleic acid that encodes an arenavirus genomic segment comprising (i) a nucleotide sequence encoding an expression product whose amino acid sequence is at least 90%, 91%, 92%, 93%, 94%, 95%, 96%, 97%, 98%, at least 99%, or 100% identical to the amino acid sequence encoded by 1639 to 3315 of SEQ ID NO: 1; (ii) a heterologous nucleotide sequence encoding an HPV antigen; and (iii) a heterologous nucleotide sequence encoding an immunomodulatory peptide, polypeptide, or protein.

In another embodiment, provided herein is a nucleic acid that encodes an arenavirus genomic segment comprising (i) a nucleotide sequence that is at least 90%, 91%, 92%, 93%, 94%, 95%, 96%, 97%, 98%, at least 99%, or 100% identical to the sequence of nucleotide 1640 to 3316 of SEQ ID NO: 2; and (ii) a heterologous nucleotide sequence encoding an HPV antigen.

In another embodiment, provided herein is a nucleic acid that encodes an arenavirus genomic segment comprising (i) a nucleotide sequence that is at least 90%, 91%, 92%, 93%, 94%, 95%, 96%, 97%, 98%, at least 99%, or 100% identical to the sequence of nucleotide 1640 to 3316 of SEQ ID NO: 2; and (ii) a heterologous nucleotide sequence encoding an HPV antigen; and (iii) a heterologous nucleotide sequence encoding an immunomodulatory peptide, polypeptide, or protein.

In another embodiment, provided herein is a nucleic acid that encodes an arenavirus genomic segment comprising (i) a nucleotide sequence encoding an expression product whose amino acid sequence is at least 90%, 91%, 92%, 93%, 94%, 95%, 96%, 97%, 98%, at least 99%, or 100% identical to the amino acid sequence encoded by 1640 to 3316 of SEQ ID NO: 2; and (ii) a heterologous nucleotide sequence encoding an HPV antigen.

In another embodiment, provided herein is a nucleic acid that encodes an arenavirus genomic segment comprising (i) a nucleotide sequence encoding an expression product whose amino acid sequence is at least 90%, 91%, 92%, 93%, 94%, 95%, 96%, 97%, 98%, at least 99%, or 100% identical to the amino acid sequence encoded by 1640 to 3316 of SEQ ID NO: 2; (ii) a heterologous nucleotide sequence encoding an HPV antigen, and (iii) a heterologous nucleotide sequence encoding an immunomodulatory peptide, polypeptide, or protein.

In another embodiment, provided herein are nucleic acids that encode an arenavirus genomic segment comprising (i) a nucleotide sequence encoding at least one self-cleaving peptide or ribosome-skipping sequence; and (ii) a nucleotide sequence encoding two, three, or four, or more HPV antigens. In specific embodiments, the nucleotide sequence encoding a self-cleaving peptide encodes Teschovirus 2A. In certain embodiments, provided herein are nucleic acids that encode two, three, four, or more HPV antigens separated by one or more nucleotide sequences encoding self-cleaving peptides or ribosome-skipping sequences (e.g., T2A). In certain embodiments, provided herein are nucleic acids that encode a HPV16 E6/E7 fusion protein and a HPV18 E6/E7 fusion protein, separated by one or more nucleotide sequences encoding self-cleaving peptides or ribosome-skipping sequences.

In another embodiment, provided herein are nucleic acids that encode an arenavirus genomic segment comprising (i) a nucleotide sequence encoding at least one self-cleaving peptide or ribosome-skipping sequence; (ii) a heterologous nucleotide sequence encoding two, three, or four, or more HPV antigens; and (iii) a heterologous nucleotide sequence encoding an immunomodulatory peptide, polypeptide, or protein. In specific embodiments, the nucleotide sequence encoding a self-cleaving peptide encodes Teschovirus 2A. In certain embodiments, provided herein are nucleic acids that encode two, three, four, or five HPV antigens separated by one or more nucleotide sequences encoding self-cleaving peptides or ribosome-skipping sequences (e.g., T2A). In certain embodiments, provided herein are nucleic acids that encode HPV16 E6/E7 fusion protein and HPV18 E6/E7 fusion protein, and one or more immunomodulatory peptides, polypeptides, or proteins, separated from the HPV16 E6/E7 fusion protein by one or more nucleotide sequences encoding self-cleaving peptides or ribosome-skipping sequences. In other embodiments, provided herein are nucleic acids that encode HPV16 E6/E7 fusion protein and HPV18 E6/E7 fusion protein, and one or more immunomodulatory peptides, polypeptides, or proteins, separated from the HPV18 E6/E7 fusion protein by one or more nucleotide sequences encoding self-cleaving peptides or ribosome-skipping sequences. In certain embodiments, provided herein are nucleic acids that encode an HPV16 E7/HPV18 E6 fusion protein, and one or more immunomodulatory peptides, polypeptides, or proteins, separated from the HPV16 E7/HPV18 E6 fusion protein by one or more nucleotide sequences encoding self-cleaving peptides or ribosome-skipping sequences. In other embodiments, provided herein are nucleic acids that encode a HPV16 E7/HPV18 E6 fusion protein, and one or more immunomodulatory peptides, polypeptides, or proteins, separated from the HPV16 E7/HPV18 E6 fusion protein by one or more nucleotide sequences encoding self-cleaving peptides or ribosome-skipping sequences. In certain embodiments, provided herein are nucleic acids that encode a HPV18 E7/HPV16 E6 fusion protein, and one or more immunomodulatory peptides, polypeptides, or proteins, separated from the HPV18 E7/HPV16 E6 fusion protein by one or more nucleotide sequences encoding self-cleaving peptides or ribosome-skipping sequences. In other embodiments, provided herein are nucleic acids that encode a HPV18 E7/HPV16 E6 fusion protein, and one or more immunomodulatory peptides, polypeptides, or proteins, separated from the HPV18 E7/HPV16 E6 fusion protein by one or more nucleotide sequences encoding self-cleaving peptides or ribosome-skipping sequences. In certain embodiments, provided herein are nucleic acids that encode a HPV16 E7/HPV18 E6/HPV16 E6/HPV18 E7 fusion protein, and one or more immunomodulatory peptides, polypeptides, or proteins, separated from the HPV16 E7/HPV18 E6/HPV16 E6/HPV18 E7 fusion protein by one or more nucleotide sequences encoding self-cleaving peptides or ribosome-skipping sequences. In other embodiments, provided herein are nucleic acids that encode HPV16 E7/HPV18 E6/HPV16 E6/HPV18 E7 fusion protein, and one or more immunomodulatory peptides, polypeptides, or proteins, separated from the HPV16 E7/HPV18 E6 HPV16 E6/HPV18 E7 fusion protein by one or more nucleotide sequences encoding self-cleaving peptides or ribosome-skipping sequences.

In another embodiment, provided herein are nucleic acids that encode an arenavirus genomic segment comprising (i) a nucleotide sequence encoding at least one self-cleaving peptide (or ribosome-skipping sequence); (ii) a heterologous nucleotide sequence encoding two, three, or four, or more HPV antigens; (iii) a heterologous nucleotide sequence encoding an immunomodulatory peptide, polypeptide, or protein, and (iv) a nucleotide sequence encoding a signaling sequence including a secretion signal from human tyrosinase, including a secretion signal from human growth hormone, signal sequence of tissue plasminogen activator.

In one embodiment, described herein is a vector system comprising one or more vectors that together encode the genome of an infectious, replication-deficient arenavirus particle described herein. Specifically, provided herein is a vector system wherein one or more vectors encode two arenavirus genomic segments, namely an L segment and an S segment, of an infectious, replication-deficient arenavirus described herein. Such a vector system can encode (on one or more separate DNA molecules):

an arenavirus S genomic segment that is modified such that an arenavirus particle carrying this modified S genomic segment cannot produce infectious progeny virus particles and an arenavirus L genomic segment that comprises a nucleotide sequence encoding (in sense or antisense) an HPV antigen;

an arenavirus L genomic segment that is modified such that an arenavirus particle carrying this modified L genomic segment cannot produce infectious progeny virus particles and an arenavirus S genomic segment that comprises a nucleotide sequence encoding (in sense or antisense) an HPV antigen;

an arenavirus S genomic segment that is modified such that an arenavirus particle carrying this modified S genomic segment cannot produce infectious progeny virus particles and wherein the arenavirus S genomic segment comprises a heterologous nucleotide sequence encoding (in sense or antisense) an HPV antigen and a wild type arenavirus L genomic segment; or an arenavirus L genomic segment that is modified such that an arenavirus particle carrying this modified L genomic segment cannot produce infectious progeny virus particles and wherein the arenavirus L genomic segment comprises a heterologous nucleotide sequence encoding (in sense or antisense) an HPV antigen and a wild type arenavirus S genomic segment.

In certain embodiments, described herein is cDNA of an arenavirus (e.g., LCMV or Junin virus) genomic segment in which the ORF encoding the GP of the S genomic segment is substituted with a heterologous nucleotide sequence encoding:

an HPV16 protein E6, or an antigenic fragment thereof;
an HPV16 protein E7, or an antigenic fragment thereof;
an HPV18 protein E6, or an antigenic fragment thereof;
an HPV18 protein E7, or an antigenic fragment thereof;
an HPV16 protein E6/protein E7 fusion protein or an antigenic fragment thereof;
a shuffled HPV16 protein E6/protein E7 fusion protein or an antigenic fragment thereof;
an HPV18 protein E6/protein E7 fusion protein or an antigenic fragment thereof; or
a shuffled HPV18 protein E6/protein E7 fusion protein or an antigenic fragment thereof.

In certain embodiments, described herein is cDNA of an arenavirus (e.g., LCMV or Junin virus) genomic segment in which the ORF encoding the GP of the S genomic segment is substituted with a heterologous nucleotide sequence encoding:

an HPV16 protein E6, or an antigenic fragment thereof;
an HPV16 protein E7, or an antigenic fragment thereof;
an HPV18 protein E6, or an antigenic fragment thereof;
an HPV18 protein E7, or an antigenic fragment thereof;
an HPV16 protein E6/protein E7 fusion protein or an antigenic fragment thereof;
a shuffled HPV16 protein E6/protein E7 fusion protein or an antigenic fragment thereof;
an HPV18 protein E6/protein E7 fusion protein or an antigenic fragment thereof; or
a shuffled HPV18 protein E6/protein E7 fusion protein or an antigenic fragment thereof
and an immunomodulatory peptide, polypeptide, or protein, or a fragment thereof.

In certain embodiments, the heterologous nucleotide sequence further encodes, or the infectious, replication deficient arenavirus genome further comprises a second heterologous nucleotide sequence that encodes Calreticulin (CRT), or a fragment thereof;
Ubiquitin or a fragment thereof;
Granulocyte-Macrophage Colony-Stimulating Factor (GM-CSF), or a fragment thereof;
Invariant chain (CD74) or an antigenic fragment thereof;
Mycobacterium tuberculosis Heat shock protein 70 or an antigenic fragment thereof;
Herpes simplex virus 1 protein VP22 or an antigenic fragment thereof;
CD40 ligand or an antigenic fragment thereof; or
Fms-related tyrosine kinase 3 (Flt3) ligand or an antigenic fragment thereof.

In certain embodiments, described herein is a nucleic acid sequence encoding an arenavirus (e.g., LCMV or Junin virus) genomic segment in which the ORF encoding the GP of the S genomic segment is substituted with a heterologous nucleotide sequence encoding one or more HPV antigen sequences (e.g., one or more of those listed in the above paragraph), separated by nucleotide sequences encoding a self-cleaving peptide (or ribosome-skipping sequences). In specific embodiments, the nucleotide sequences encoding a self-cleaving peptide encode Teschovirus 2A.

In another embodiment, provided herein is a cell wherein the cell comprises a nucleic acid or a vector system described above in this section. Cell lines derived from such cells, cultures comprising such cells, and methods of culturing such cells infected are also provided herein. In certain embodiments, provided herein is a cell wherein the cell comprises a nucleic acid encoding the large genomic segment (L segment) of an infectious, replication-deficient arenavirus described herein, in which one ORF of the genomic segment is deleted or functionally inactivated, and the genomic segment comprises a nucleotide sequence encoding an HPV antigen.

In other embodiments, provided herein is a cell wherein the cell comprises a nucleic acid sequence that encodes the short genomic segment (S segment) of an infectious, replication-deficient arenavirus described herein, in which one ORF of the genomic segment is deleted or functionally inactivated and wherein the short genomic segment comprises a heterologous nucleotide sequence encoding HPV 16 protein E6 or an antigenic fragment thereof.

In other embodiments, provided herein is a cell wherein the cell comprises a nucleic acid sequence that encodes the short genomic segment (S segment) of an infectious, replication-deficient arenavirus described herein, in which one ORF of the genomic segment is deleted or functionally inactivated and wherein the short genomic segment comprises a heterologous nucleotide sequence encoding HPV 16 protein E7 or an antigenic fragment thereof.

In other embodiments, provided herein is a cell wherein the cell comprises a nucleic acid sequence that encodes the short genomic segment (S segment) of an infectious, replication-deficient arenavirus described herein, in which one ORF of the genomic segment is deleted or functionally inactivated and wherein the short genomic segment comprises a heterologous nucleotide sequence encoding HPV 18 protein E6 or an antigenic fragment thereof.

In other embodiments, provided herein is a cell wherein the cell comprises a nucleic acid sequence that encodes the short genomic segment (S segment) of an infectious, replication-deficient arenavirus described herein, in which one ORF of the genomic segment is deleted or functionally inactivated and wherein the short genomic segment comprises a heterologous nucleotide sequence encoding HPV 18 protein E7 or an antigenic fragment thereof.

In other embodiments, provided herein is a cell wherein the cell comprises a nucleic acid sequence that encodes the short genomic segment (S segment) of an infectious, replication-deficient arenavirus described herein, in which one ORF of the genomic segment is deleted or functionally inactivated and wherein the short genomic segment comprises a heterologous nucleotide sequence encoding an HPV16 E7/E6 fusion protein or an antigenic fragment thereof.

In other embodiments, provided herein is a cell wherein the cell comprises a nucleic acid sequence that encodes the short genomic segment (S segment) of an infectious, replication-deficient arenavirus described herein, in which one ORF of the genomic segment is deleted or functionally inactivated and wherein the short genomic segment comprises a heterologous nucleotide sequence encoding an HPV18 E7/E6 fusion protein or an antigenic fragment thereof.

In other embodiments, provided herein is a cell wherein the cell comprises a nucleic acid sequence that encodes the short genomic segment (S segment) of an infectious, replication-deficient arenavirus described herein, in which one ORF of the genomic segment is deleted or functionally inactivated and wherein the short genomic segment comprises a heterologous nucleotide sequence encoding an HPV16 E7/E6 fusion protein or an antigenic fragment thereof, and an HPV18 E7/E6 fusion protein or an antigenic fragment thereof.

In other embodiments, provided herein is a cell wherein the cell comprises a nucleic acid sequence that encodes the short genomic segment (S segment) of an infectious, replication-deficient arenavirus described herein, in which one ORF of the genomic segment is deleted or functionally inactivated and wherein the short genomic segment comprises a heterologous nucleotide sequence encoding an HPV16 E7/E6 fusion protein or an antigenic fragment thereof and encoding Calreticulin, or an immunomodulatory fragment thereof.

In other embodiments, provided herein is a cell wherein the cell comprises a nucleic acid sequence that encodes the short genomic segment (S segment) of an infectious, replication-deficient arenavirus described herein, in which one ORF of the genomic segment is deleted or functionally inactivated and wherein the short genomic segment comprises a heterologous nucleotide sequence encoding an HPV16 E7/E6 fusion protein or an antigenic fragment thereof, and an HPV18 E7/E6 fusion protein or an antigenic fragment thereof, and encoding Calreticulin, or an immunomodulatory fragment thereof.

In other embodiments, provided herein is a cell wherein the cell comprises a nucleic acid sequence that encodes the short genomic segment (S segment) of an infectious, replication-deficient arenavirus described herein, in which one ORF of the genomic segment is deleted or functionally inactivated and wherein the short genomic segment comprises a heterologous nucleotide sequence encoding an HPV16 E7/E6 fusion protein or an antigenic fragment thereof and encoding Ubiquitin, or an immunomodulatory fragment thereof.

In other embodiments, provided herein is a cell wherein the cell comprises a nucleic acid sequence that encodes the short genomic segment (S segment) of an infectious, replication-deficient arenavirus described herein, in which one ORF of the genomic segment is deleted or functionally inactivated and wherein the short genomic segment comprises a heterologous nucleotide sequence encoding an HPV16 E7/E6 fusion protein or an antigenic fragment thereof, and an HPV18 E7/E6 fusion protein or an antigenic fragment thereof, and encoding Ubiquitin, or an immunomodulatory fragment thereof.

In other embodiments, provided herein is a cell wherein the cell comprises a nucleic acid sequence that encodes the short genomic segment (S segment) of an infectious, replication-deficient arenavirus described herein, in which one ORF of the genomic segment is deleted or functionally inactivated and wherein the short genomic segment comprises a heterologous nucleotide sequence encoding an HPV16 E7/E6 fusion protein or an antigenic fragment thereof and encoding GM-CSF, or an immunomodulatory fragment thereof. In other, more specific embodiments, the short genomic segment comprises a heterologous nucleotide sequence encoding an HPV16 E7/E6 fusion protein, GM-CSF, and a self-cleaving peptide. In certain embodiments, the self-cleaving peptide is 2A peptide.

In other embodiments, provided herein is a cell wherein the cell comprises a nucleic acid sequence that encodes HPV16 protein E6, HPV16 protein E7, HPV18 protein E6, and HPV18 protein E7. In other embodiments, provided herein is a cell wherein the cell comprises a nucleic acid sequence that encodes HPV16 protein E6 or an antigenic fragment thereof, HPV16 protein E7 or an antigenic fragment thereof, HPV18 protein E6 or an antigenic fragment thereof, and HPV18 protein E7 or an antigenic fragment thereof. In certain embodiments, one, two, three or all four of HPV16 protein E6 or antigenic fragment thereof, HPV16 protein E7 or antigenic fragment thereof, HPV18 protein E6 or antigenic fragment thereof, and HPV18 protein E7 or antigenic fragment thereof, can be shuffled sequences. Each one of HPV16 protein E6 or antigenic fragment thereof, HPV16 protein E7 or antigenic fragment thereof, HPV18 protein E6 or antigenic fragment thereof, and HPV18 protein E7 or antigenic fragment thereof, can be directly fused to one or two different sequences of HPV16 protein E6 or antigenic fragment thereof, HPV16 protein E7 or antigenic fragment thereof, HPV18 protein E6 or antigenic fragment thereof, and HPV18 protein E7 or antigenic fragment thereof. Each one of HPV16 protein E6 or antigenic fragment thereof, HPV16 protein E7 or antigenic fragment thereof, HPV18 protein E6 or antigenic fragment thereof, and HPV18 protein E7 or antigenic fragment thereof, can be fused to one or two different sequences of HPV16 protein E6 or antigenic fragment thereof, HPV16 protein E7 or antigenic fragment thereof, HPV18 protein E6 or antigenic fragment thereof, and HPV18 protein E7 or antigenic fragment thereof, via a linker or self-cleaving peptide. Each one of HPV16 protein E6 or antigenic fragment thereof, HPV16 protein E7 or antigenic fragment thereof, HPV18 protein E6 or antigenic fragment thereof, and HPV18 protein E7 or antigenic fragment thereof, can be fused to one or two different sequences of HPV16 protein E6 or antigenic fragment thereof, HPV16 protein E7 or antigenic fragment thereof, HPV18 protein E6 or antigenic fragment thereof, and HPV18 protein E7 or antigenic fragment thereof. The sequence of HPV16 protein E6 or antigenic fragment thereof, HPV16 protein E7 or antigenic fragment thereof, HPV18 protein E6 or antigenic fragment thereof, and HPV18 protein E7 or antigenic fragment thereof, can be arranged in any manner known to the skilled artisan, e.g., each one of HPV16 protein E6 or antigenic fragment thereof, HPV16 protein E7 or antigenic fragment thereof, HPV18 protein E6 or antigenic fragment thereof, and HPV18 protein E7 or antigenic fragment thereof, can be upstream or downstream of a different one of HPV16 protein E6 or antigenic fragment thereof, HPV16 protein E7 or antigenic fragment thereof, HPV18 protein E6 or antigenic fragment thereof, and HPV18 protein E7 or antigenic fragment thereof. Each one of HPV16 protein E6 or antigenic fragment thereof, HPV16 protein E7 or antigenic fragment thereof, HPV18 protein E6 or antigenic fragment thereof, and HPV18 protein E7 or antigenic fragment thereof, can be fused to a signal peptide. In certain other embodiments, provided herein is a cell wherein the cell comprises a nucleic acid sequence that encodes HPV16 E6/HPV16 E7 fusion protein or antigenic fragment thereof, or an HPV16 E6/HPV18 E6 fusion protein or antigenic fragment thereof, HPV16 E6/HPV18 E7 fusion protein or antigenic fragment thereof, or an HPV16 E7/HPV18 E6 fusion protein or antigenic fragment thereof, HPV16 E6/HPV18 E7 fusion protein or antigenic fragment thereof, or an HPV18 E6/HPV18 E7 fusion protein or antigenic fragment thereof. In certain other embodiments, provided herein is a cell wherein the cell comprises a nucleic acid sequence that encodes two fusion proteins, wherein the first fusion protein is an HPV16 E6/HPV16 E7 fusion protein or antigenic fragment thereof, or an HPV16 E6/HPV18 E6 fusion protein or antigenic fragment thereof, HPV16 E6/HPV18 E7 fusion protein or antigenic fragment thereof, or an HPV16 E7/HPV18 E6 fusion protein or antigenic fragment thereof, HPV16 E6/HPV18 E7 fusion protein or antigenic fragment thereof, or an HPV18 E6/HPV18 E7 fusion protein or antigenic fragment thereof, and the second fusion protein is a different fusion protein selected from an HPV16 E6/HPV16 E7 fusion protein or antigenic fragment thereof, or an HPV16 E6/HPV18 E6 fusion protein or antigenic fragment thereof, HPV16 E6/HPV18 E7 fusion protein or antigenic fragment thereof, or an HPV16 E7/HPV18 E6 fusion protein or antigenic fragment thereof, HPV16 E6/HPV18 E7 fusion protein or antigenic fragment thereof, or an HPV18 E6/HPV18 E7 fusion protein or antigenic fragment thereof. In certain other embodiments, provided herein is a cell wherein the cell comprises a nucleic acid sequence that further encodes an immunomodulatory peptide, polypeptide, or protein.

In other embodiments, provided herein is a cell wherein the cell comprises a nucleic acid sequence that encodes an HPV16 E6/E7 fusion protein and an HPV18 E6/E7 fusion protein. In other embodiments, provided herein is a cell wherein the cell comprises a nucleic acid sequence that encodes a shuffled sequence of an HPV16 E6/E7 fusion protein and a shuffled sequence of an HPV18 E6/E7 fusion protein. In other embodiments, provided herein is a cell wherein the cell comprises a nucleic acid sequence that encodes an HPV16 E6/E7 fusion protein and an HPV18 E6/E7 fusion protein that are directly fused to each other. In other embodiments, provided herein is a cell wherein the cell comprises a nucleic acid sequence that encodes an HPV16 E6/E7 fusion protein and an HPV18 E6/E7 fusion protein that are fused to each other via a peptide linker or self-cleaving peptide. In other embodiments, provided herein is a cell wherein the cell comprises a nucleic acid sequence that encodes an HPV16 E6/E7 fusion protein located upstream of the HPV18 E6/E7 fusion protein. In other embodiments, provided herein is a cell wherein the cell comprises a nucleic acid sequence that encodes HPV16 E6/E7 fusion protein located downstream of the HPV18 E6/E7 fusion protein. In other embodiments, provided herein is a cell wherein the cell comprises a nucleic acid sequence that encodes an HPV16 E6/E7 fusion protein that is fused to a signal peptide. In other embodiments, provided herein is a cell wherein the cell comprises a nucleic acid sequence that encodes HPV18 E6/E7 fusion protein fused to a signal peptide. In certain specific embodiments, the heterologous nucleotide sequence further encodes an immunomodulatory peptide, polypeptide, or protein.

In other embodiments, provided herein is a cell wherein the cell comprises a nucleic acid sequence that encodes the short genomic segment (S segment) of an infectious, replication-deficient arenavirus described herein, in which one ORF of the genomic segment is deleted or functionally inactivated and wherein the short genomic segment comprises a heterologous nucleotide sequence encoding an HPV16 E7/E6 fusion protein or an antigenic fragment thereof, and an HPV18 E7/E6 fusion protein or an antigenic fragment thereof, and encoding GM-CSF, or an immunomodulatory fragment thereof. In other, more specific embodiments, the short genomic segment comprises a heterologous nucleotide sequence encoding an HPV16 E7/E6 fusion protein or an antigenic fragment thereof, and an HPV18 E7/E6 fusion protein or an antigenic fragment thereof, and encoding GM-CSF, and a self-cleaving peptide. In certain embodiments, the self-cleaving peptide is 2A peptide.

In other embodiments, provided herein is a cell wherein the cell comprises a nucleic acid sequence that encodes the short genomic segment (S segment) of an infectious, replication-deficient arenavirus described herein, in which one ORF of the genomic segment is deleted or functionally inactivated and wherein the short genomic segment comprises a heterologous nucleotide sequence encoding one or more of HPV antigens separated by one or more self-cleaving peptides (or ribosome-skipping sequences). In specific embodiments, the one or more self-cleaving peptides are T2A peptides.

In another embodiment, provided herein is a cell wherein the cell comprises two nucleic acids or a vector system described herein. Cell lines derived from such cells, cultures comprising such cells, and methods of culturing such cells infected are also provided herein.

In certain embodiments, provided herein is a nucleic acid comprising a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 4 or SEQ ID NO: 5. In certain embodiments, provided herein is an expression vector comprising a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 4 or SEQ ID NO: 5. In certain embodiments, provided herein is a host cell comprising a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 4 or SEQ ID NO: 5.

In certain embodiments, provided herein is a nucleic acid comprising a nucleotide sequence encoding an amino acid sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 6, 7, 8, or 9. In certain embodiments, provided herein is an expression vector comprising a nucleotide sequence encoding an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 6, 7, 8, or 9. In certain embodiments, provided herein is a host cell comprising a nucleotide sequence that encodes an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 6, 7, 8, or 9.

In certain embodiments, provided herein is an isolated protein comprising an amino acid sequence at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 6, 7, 8, or 9. In certain embodiments, provided herein is a host cell that expresses a protein comprising an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 6, 7, 8, or 9. In certain embodiments, the host cell is cultured in cell culture medium.

In certain embodiments, provided herein is a nucleic acid comprising a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 2 or SEQ ID NO: 3. In certain embodiments, provided herein is an expression vector comprising a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 2 or SEQ ID NO: 3. In certain embodiments, provided herein is a host cell comprising a nucleotide sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 2 or SEQ ID NO: 3.

In certain embodiments, provided herein are cDNAs comprising or consisting of the arenavirus genomic segment or the tri-segmented arenavirus viral vector as described in Section 6.2 and Section 6.3, respectively.

(a) Non-Natural Position Open Reading Frame

In one embodiment, provided herein are nucleic acids that encode an arenavirus genomic segment as described in Section 6.2. In more specific embodiments, provided herein is a DNA nucleotide sequence or a set of DNA nucleotide sequences as set forth in Table 1. Host cells that comprise such nucleic acids are also provided Section 6.2.

In specific embodiments, provided herein is a cDNA of the arenavirus genomic segment engineered to carry an ORF in a position other than the wild-type position of the ORF, wherein the arenavirus genomic segment encodes a heterologous ORF as described in Section 6.5.

In one embodiment, provided herein is a DNA expression vector system that encodes the arenavirus genomic segment engineered to carry an ORF in a position other than the wild-type position of the ORF. Specifically, provided herein is a DNA expression vector system wherein one or more vectors encodes two arenavirus genomic segments, namely, an L segment and an S segment, of an arenavirus viral vector described herein. Such a vector system can encode (one or more separate DNA molecules).

In another embodiment, provided herein is a cDNA of the arenavirus S segment that has been engineered to carry an ORF in a position other than the wild-type position is part of or incorporated into a DNA expression system. In other embodiments, a cDNA of the arenavirus L segment that has been engineered to carry an ORF in a position other than the wild-type position is part of or incorporated into a DNA expression system. In certain embodiments, is a cDNA of the arenavirus genomic segment that has been engineered to carry (i) an ORF in a position other than the wild-type position of the ORF; and (ii) and ORF encoding GP, NP, Z protein, or L protein has been removed and replaced with a heterologous ORF from an organism other than an arenavirus.

In certain embodiments, the cDNA provided herein can be derived from a particular strain of LCMV. Strains of LCMV include Clone 13, MP strain, Arm CA 1371, Arm E-250, WE, UBC, Traub, Pasteur, 810885, CH-5692, Marseille #12, HP65-2009, 200501927, 810362, 811316, 810316, 810366, 20112714, Douglas, GR01, SN05, CABN and their derivatives. In specific embodiments, the cDNA is derived from LCMV Clone 13. In other specific embodiments, the cDNA is derived from LCMV MP strain.

In certain embodiments, the vector generated to encode an arenavirus viral vector or a tri-segmented arenavirus viral vector as described herein may be based on a specific strain of LCMV. Strains of LCMV include Clone 13, MP strain, Arm CA 1371, Arm E-250, WE, UBC, Traub, Pasteur, 810885, CH-5692, Marseille #12, HP65-2009, 200501927, 810362, 811316, 810316, 810366, 20112714, Douglas, GR01, SN05, CABN and their derivatives. In certain embodiments, an arenavirus viral vector or a tri-segmented arenavirus viral vector as described herein may be based on LCMV Clone 13. In other embodiments, the vector generated to encode an arenavirus viral vector or a tri-segmented arenavirus viral vector as described herein LCMV MP strain. The sequence of the S segment of LCMV Clone 13 is listed as SEQ ID NO: 2. In certain embodiments, the sequence of the S segment of LCMV Clone 13 is the sequence set forth in SEQ ID NO: 1. The sequence of the L segment of LCMV Clone 13 is listed as SEQ ID NO: 5. The sequence of the S segment of LCMV strain MP is listed as SEQ ID NO: 53. The sequence of the L segment of LCMV strain MP is listed as SEQ ID NO: 4.

In another embodiment, provided herein is a cell, wherein the cell comprises a cDNA or a vector system described above in this section. Cell lines derived from such cells, cultures comprising such cells, methods of culturing such cells infected are also provided herein. In certain embodiments, provided herein is a cell, wherein the cell comprises a cDNA of the arenavirus genomic segment that has been engineered to carry an ORF in a position other than the wild-type position of the ORF. In some embodiments, the cell comprises the S segment and/or the L segment.

(b) Tri-Segmented Arenavirus Viral Vector

In one embodiment, provided herein are nucleic acids that encode a tri-segmented arenavirus viral vector as described in Section 6.3. In more specific embodiments, provided herein is a DNA nucleotide sequence or a set of DNA nucleotide sequences, for example, as set forth in Table 2 or Table 3. Host cells that comprise such nucleic acids are also provided Section 6.3. In specific embodiments, provided herein are nucleic acids that encode a tri-segmented arenavirus viral vector as described, wherein the tri-segmented arenavirus viral vector encodes a heterologous ORF as described in Section 6.5.

In specific embodiments, provided herein is a cDNA consisting of a cDNA of the tri-segmented arenavirus viral vector that has been engineered to carry an ORF in a position other than the wild-type position of the ORF. In other embodiments, is a cDNA of the tri-segmented arenavirus viral vector that has been engineered to (i) carry an arenavirus ORF in a position other than the wild-type position of the ORF; and (ii) wherein the tri-segmented arenavirus viral vector encodes a heterologous ORF as described in Section 6.3.

In one embodiment, provided herein is a DNA expression vector system that together encodes the tri-segmented arenavirus viral vector as described herein. Specifically, provided herein is a DNA expression vector system wherein one or more vectors encode three arenavirus genomic segments, namely, one L segment and two S segments or two L segments and one S segment of a tri-segmented arenavirus viral vector described herein. Such a vector system can encode (one or more separate DNA molecules).

In another embodiment, provided herein is a cDNA of the arenavirus S segment(s) that has been engineered to carry an ORF in a position other than the wild-type position, and is part of or incorporated into a DNA expression system. In other embodiments, a cDNA of the arenavirus L segment(s) that has been engineered to carry an ORF in a position other than the wild-type position is part of or incorporated into a DNA expression system. In certain embodiments, is a cDNA of the tri-segmented arenavirus viral vector that has been engineered to carry (i) an ORF in a position other than the wild-type position of the ORF; and (ii) an ORF encoding GP, NP, Z protein, or L protein has been removed and replaced with a heterologous ORF from an organism other than an arenavirus.

In certain embodiments, the cDNA provided herein can be derived from a particular strain of LCMV. Strains of LCMV include Clone 13, MP strain, Arm CA 1371, Arm E-250, WE, UBC, Traub, Pasteur, 810885, CH-5692, Marseille #12, HP65-2009, 200501927, 810362, 811316, 810316, 810366, 20112714, Douglas, GR01, SN05, CABN and their derivatives. In specific embodiments, the cDNA is derived from LCMV Clone 13. In other specific embodiments, the cDNA is derived from LCMV MP strain.

In certain embodiments, the vector generated to encode an arenavirus viral vector or a tri-segmented arenavirus viral vector as described herein may be based on a specific strain of LCMV. Strains of LCMV include Clone 13, MP strain, Arm CA 1371, Arm E-250, WE, UBC, Traub, Pasteur, 810885, CH-5692, Marseille #12, HP65-2009, 200501927, 810362, 811316, 810316, 810366, 20112714, Douglas, GR01, SN05, CABN and their derivatives. In certain embodiments, an arenavirus viral vector or a tri-segmented arenavirus viral vector as described herein may be based on LCMV Clone 13. In other embodiments, the vector generated to encode an arenavirus viral vector or a tri-segmented arenavirus viral vector as described herein LCMV MP strain. The sequence of the S segment of LCMV Clone 13 is listed as SEQ ID NO: 2. In certain embodiments, the sequence of the S segment of LCMV Clone 13 is the sequence set forth in SEQ ID NO: 1. The sequence of the L segment of LCMV Clone 13 is listed as SEQ ID NO: 5. The sequence of the S segment of LCMV strain MP is listed as SEQ ID NO: 53. The sequence of the L segment of LCMV strain MP is listed as SEQ ID NO: 4.

In another embodiment, provided herein is a cell, wherein the cell comprises a cDNA or a vector system described above in this section. Cell lines derived from such cells, cultures comprising such cells, methods of culturing such cells infected are also provided herein. In certain embodiments, provided herein is a cell, wherein the cell comprises a cDNA of the tri-segmented arenavirus viral vector. In some embodiments, the cell comprises the S segment and/or the L segment.

6.9 Assays

Assay for Measuring Arenavirus Vector Infectivity: Any assay known to the skilled artisan can be used for measuring the infectivity of an arenavirus vector preparation. For example, determination of the virus/vector titer can be done by a "focus forming unit assay" (FFU assay). In brief, complementing cells, e.g., HEK 293 cells expressing LCMV GP protein, are plated and inoculated with different dilutions of a virus/vector sample. After an incubation period, to allow cells to form a monolayer and virus to attach to cells, the monolayer is covered with Methylcellulose. When the plates are further incubated, the original infected cells release viral progeny. Due to the Methylcellulose overlay the spread of the new viruses is restricted to neighboring cells. Consequently, each infectious particle produces a circular zone of infected cells called a Focus. Such Foci can be made visible and by that countable using antibodies against LCMV-NP and a HRP-based color reaction. The titer of a virus/vector can be calculated in focus-forming units per milliliter (FFU/mL).

To determine the infectious titer (FFU/mL) of transgene-carrying vectors this assay is modified by the use of the respective transgene-specific antibody instead of anti-LCMV-NP antibody.

Serum ELISA: Determination of the humoral immune response upon vaccination of animals (e.g., mice, guinea pigs) can be done by antigen-specific serum ELISA's (enzyme-linked immunosorbent assays). In brief, plates are coated with antigen (e.g., recombinant protein), blocked to avoid unspecific binding of antibodies and incubated with serial dilutions of sera. After incubation, bound serum-antibodies can be detected, e.g., using an enzyme-coupled anti-species (e.g., mouse, guinea pig)-specific antibody (detecting total IgG or IgG subclasses) and subsequent color reaction. Antibody titers can be determined as, e.g., endpoint geometric mean titer.

Neutralizing Assay in ARPE-19 cells: Determination of the neutralizing activity of induced antibodies in sera is performed with the following cell assay using ARPE-19 cells from ATCC and a GFP-tagged virus. In addition supplemental guinea pig serum as a source of exogenous complement is used. The assay is started with seeding of $6.5 \times 10^3$ cells/well (50 µl/well) in a 384 well plate one or two days before using for neutralization. The neutralization is done in 96-well sterile tissue culture plates without cells for 1 h at 37° C. After the neutralization incubation step the mixture is added to the cells and incubated for additional 4 days for GFP-detection with a plate reader. A positive neutralizing human sera is used as assay positive control on each plate to check the reliability of all results. Titers (EC50) are determined using a 4 parameter logistic curve fitting. As additional testing the wells are checked with a fluorescence microscope.

Plaque Reduction Assay: In brief, plaque reduction (neutralization) assays for guinea pig cytomegalovirus are performed by use of an isolate of GPCMV tagged with green fluorescent protein, 5% rabbit serum was used as a source of exogenous complement, and plaques were enumerated by fluorescence microscopy. Neutralization titers were defined as the highest dilution of serum that resulted in a 50% reduction in plaques, compared with that in control (pre-immune) serum samples.

Neutralization Assay in guinea pig lung fibroblast (GPL) cells: In brief, serial dilutions of test and control (pre-vaccination) sera were prepared in GPL complete media with supplemental rabbit serum (1%) as a source of exogenous complement. The dilution series spanned 1:40 through 1:5120. Serum dilutions were incubated with eGFP tagged virus (100-200 pfu per well) for 30 min at 37° C., and then transferred to 12-well plates containing confluent GPL cells. Samples were processed in triplicate. After 2 hours incubation at 37° C. the cells were washed with PBS, re-fed with GPL complete media and incubated at 37° C./5% CO2 for 5 days. Plaques were visualized by fluorescence microscopy, counted, and compared to control wells. That serum dilution resulting in a 50% reduction in plaque number compared to controls was designated as the neutralizing titer.

qPCR: LCMV RNA genomes are isolated using QIAamp Viral RNA mini Kit (QIAGEN), according to the protocol provided by the manufacturer. LCMV RNA genome equivalents are detected by quantitative PCR carried out on an StepOnePlus Real Time PCR System (Applied Biosystems) with SuperScript® III Platinum® One-Step qRT-PCR Kit (Invitrogen) and primers and probes (FAM reporter and NFQ-MGB Quencher) specific for part of the LCMV NP coding region. The temperature profile of the reaction is: 30 min at 60° C., 2 min at 95° C., followed by 45 cycles of 15 s at 95° C., 30 s at 56° C. RNA is quantified by comparison of the sample results to a standard curve prepared from a log10 dilution series of a spectrophotometrically quantified, in vitro-transcribed RNA fragment, corresponding to a fragment of the LCMV NP coding sequence containing the primer and probe binding sites.

Western Blotting: Infected cells grown in tissue culture flasks or in suspension are lysed at indicated timepoints post infection using RIPA buffer (Thermo Scientific) or used directly without cell-lysis. Samples are heated to 99° C. for 10 minutes with reducing agent and NuPage LDS Sample buffer (NOVEX) and chilled to room temperature before loading on 4-12% SDS-gels for electrophoresis. Proteins are blotted onto membranes using Invitrogens iBlot Gel transfer Device and visualized by Ponceau staining. Finally, the preparations are probed with an primary antibodies directed against proteins of interest and alkaline phosphatase conjugated secondary antibodies followed by staining with 1-Step NBT/BCIP solution (INVITROGEN).

MHC-Peptide Multimer Staining Assay for Detection of Antigen-Specific CD8+ T-cell proliferation: Any assay known to the skilled artisan can be used to test antigen-specific CD8+ T-cell responses. For example, the MHC-peptide tetramer staining assay can be used (see, e.g., Altman et al., 1996, Science; 274:94-96; and Murali-Krishna et al., 1998, Immunity, 8:177-187). Briefly, the assay comprises the following steps, a tetramer assay is used to detect the presence of antigen specific T-cells. In order for a T-cell to detect the peptide to which it is specific, it must both recognize the peptide and the tetramer of MHC molecules custom made for an antigen specific T-cell (typically fluorescently labeled). The tetramer is then detected by flow cytometry via the fluorescent label.

ELISPOT Assay for Detection of Antigen-Specific CD4+ T-cell Proliferation: Any assay known to the skilled artisan can be used to test antigen-specific CD4+ T-cell responses. For example, the ELISPOT assay can be used (see, e.g., Czerkinsky et al., 1983, J Immunol Methods.; 65:109-121; and Hutchings et al., 1989, J Immunol Methods.; 120:1-8). Briefly, the assay comprises the following steps: An immunospot plate is coated with an anti-cytokine antibody. Cells are incubated in the immunospot plate. Cells secrete cytokines and are then washed off. Plates are then coated with a second biotyinlated-anticytokine antibody and visualized with an avidin-HRP system.

Intracellular Cytokine Assay for Detection of Functionality of CD8+ and CD4+ T-cell Responses: Any assay known to the skilled artisan can be used to test the functionality of CD8+ and CD4+ T cell responses. For example, the intracellular cytokine assay combined with flow cytometry can be used (see, e.g., Suni et al., 1998, J Immunol Methods.; 212:89-98; Nomura et al., 2000, Cytometry; 40:60-68; and Ghanekar et al., 2001, Clinical and Diagnostic Laboratory Immunology; 8:628-63). Briefly, the assay comprises the following steps: activation of cells via specific peptides or protein, an inhibition of protein transport (e.g., brefeldin A) is added to retain the cytokines within the cell. After washing, antibodies to other cellular markers can be added to the cells. Cells are then fixed and permeabilized. The anti-cytokine antibody is added and the cells can be analyzed by flow cytometry.

Assay for Confirming Replication-Deficiency of Viral Vectors: Any assay known to the skilled artisan that determines concentration of infectious and replication-competent virus particles can also be used as a to measure replication-deficient viral particles in a sample. For example, FFU assays with non-complementing cells can be used for this purpose.

Furthermore, plaque-based assays are the standard method used to determine virus concentration in terms of plaque forming units (PFU) in a virus sample. Specifically, a confluent monolayer of non-complementing host cells is infected with the virus at varying dilutions and covered with a semi-solid medium, such as agar to prevent the virus infection from spreading indiscriminately. A viral plaque is formed when a virus successfully infects and replicates itself in a cell within the fixed cell monolayer (see, e.g., Kaufmann, S. H.; Kabelitz, D. (2002). Methods in Microbiology Vol. 32:Immunology of Infection. Academic Press. ISBN 0-12-521532-0). Plaque formation can take 3-14 days, depending on the virus being analyzed. Plaques are generally counted manually and the results, in combination with the dilution factor used to prepare the plate, are used to calculate the number of plaque forming units per sample unit volume (PFU/mL). The PFU/mL result represents the number of infective replication-competent particles within the sample.

Assay for Expression of Viral Antigen Any assay known to the skilled artisan can be used for measuring expression of viral antigens. For example, FFU assays can be performed. For detection, mono- or polyclonal antibody preparation(s) against respective viral antigens are used (transgene-specific FFU). Furthermore, Western Blotting can be performed.

Animal Models The safety, tolerance and immunogenic effectiveness of vaccines comprising of an infectious, replication-deficient arenavirus expressing an HPV antigen described herein or a composition thereof can be tested in animals models. In certain embodiments, the animal models that can be used to test the safety, tolerance and immunogenic effectiveness of the vaccines and compositions thereof used herein include mouse, guinea pig, rat, and monkey. In a preferred embodiment, the animal models that can be used to test the safety, tolerance and immunogenic effectiveness of the vaccines and compositions thereof used herein include mouse.

7. EXAMPLES

These examples demonstrate that arenavirus-based vector technology can be successfully used to develop new vaccines against infection with HPV by including antigens into the arenavirus vector, and that administration of such vaccines can induce antigen-specific CD8+ T cell responses of high magnitude to control HPV infection.

7.1 Design of Arenavirus Vector Genome

Referring to established approaches (U.S. Patent Application Publication No. US 2010/0297172 A1; and Flatz et al., 2010, Nat Med. March; 16(3): 339-345), rLCMV and rJUNV vaccine vectors were designed that express a fusion of proteins E6 and E7 of HPV type 16, a major oncogenic genotype of HPV, including mutations (Cassetti et al, 2004, Vaccine 22:520-527) to eliminate the oncogenic potential of the antigen. As the epitopes required to generate T-cell immunity targeting HPV infected cells are linear in both HPV E6 and E7, the two tumor associated antigens (TAAs) could be incorporated as a fusion protein in a single vector.

FIG. 1A shows the genome of wild type arenaviruses consisting of a short (1; ~3.4 kb) and a large (2; ~7.2 kb) RNA segment. The short segment carries open reading frames encoding the nucleoprotein (3) and glycoprotein (4). The large segment encodes the RNA-dependent RNA polymerase L (5) and the matrix protein Z (6). Wild type arenaviruses can be rendered replication-deficient vaccine vectors by deleting the glycoprotein gene and inserting, instead of the glycoprotein gene, antigens of choice (7) against which immune responses are to be induced.

Design of rLCMV vectors expressing E7E6: For generation of rLCMV vaccine vectors expressing the E7/E6 fusion protein alone or fused to a immunomodulatory peptide, polypeptide, or protein, various rLCMV vector constructs were designed. FIGS. 2A and 2B show the different vector constructs generated for the expression of an HPV 16 E7 and E6 fusion protein alone or in combination with various immunomodulatory peptides, polypeptides, or proteins.

The following sequences are illustrative amino acid sequences and nucleotide sequences that can be used with the methods and compositions described herein. In some instances a DNA sequence is used to describe the RNA sequence of a viral genomic segment. The RNA sequence can be readily deduced from the DNA sequence. Exemplary sequences are:

Recombinant LCMV encoding HPV16 E7/E6 fusion protein with mutations in Rb binding site and zinc finger motifs (HK1-E7E6, SEQ ID NO: 10), Recombinant LCMV encoding HPV16 E7/E6 fusion protein with mutations in Rb binding site and zinc finger motifs, linked to heat shock protein Calreticulin (HK1-E7E6-CRT, SEQ ID NO: 11), Recombinant LCMV encoding HPV16 E7/E6 fusion protein with mutations in Rb binding site and zinc finger motifs, linked to Ubiquitin (HK1-E7E6-Ub, SEQ ID NO: 12), Recombinant LCMV encoding HPV16 E7/E6 fusion protein with mutations in Rb binding site and zinc finger motifs, co-expressed with Granulocyte Macrophage Colony Stimulation Factor GM-CSF, separated by a nucleotide sequence that encodes a self-cleaving peptide (2A peptide) (HK1-E7E6-GMCSF, SEQ ID NO: 13), 7.2 Vector Characterization In order to analyze replication of the generated vectors, growth curves were performed using suspension HEK 293 cells expressing LCMV GP. Respective cells were infected with individual E7/E6 vectors (HK1-E7E6, HK1-E7E6-CRT, HK1-E7E6-Ub and HK1-E7E6-GMCSF) at multiplicity of infection (MOI) of 0.001, or a control vector expressing the green-fluorescent-protein (HK1-GFP). Samples were drawn every 24 hours and analyzed by Focus Forming Units (FFU) Assay. As shown in FIG. 3, respective results demonstrated that all tested vectors exhibited similar growth kinetics and peak titers compared to HK1-GFP indicating that the individual E7/E6 transgenes did not interfere with vector replication to a greater extent than the reporter gene GFP.

(a) Transgene Expression

Western blot experiments confirmed presence of the HPV E7E6 antigen for all tested constructs. As shown in FIG. 4, HEK 293 cells expressing LCMV GP were infected with individual constructs (HK1-E7E6 (group 1), HK1-E7E6-GMCSF (group 2), HK1-E7E6-CRT (group 3) and HK1-E7E6-Ub (group 4)) at a MOI of 0.001 or a HK1-GFP control vector (group 5). Cells were analyzed 96 h post infection. Proteins were separated on SDS gels, transferred to nitrocellulose membranes, and HPV E7 protein expression was detected with anti HPV E7 antibody and appropriate secondary antibody. Expected sizes of transgenes were calculated based on the Science Gateway Protein Molecular Weight Calculator (HK1-E7E6: ~30 kDa; HK1-mE7E6-GMCSF: ~48 kDa/30 kDa; HK1-mE7E6-CRT: ~78 kDa; HK1-mE7E6-Ub: ~38 kDa). Specific bands, indicated by arrows, were detected for all tested constructs. Significantly different expression levels, however, were observed, with HK1-E7E6- and HK1-E7E6-Ub-infected cells exhibiting the lowest antigen levels.

(b) Immunogenicity

To investigate the ability of HK1-E7E6 to induce CD8+ T cell responses in a homologous prime-boost setting, C57BL/6 mice were vaccinated three times on days 0, 41 and 102 with HK1-E7/E6. Antigen (E7) specific CD8+ T cell responses were subsequently analyzed by tetramer staining on days 10, 38, 48, 73 and 109 of the experiment. The data obtained (FIG. 5) indicate that significant antigen-specific CD8+ T cell responses are induced after single immunization with HK1-E7E6. These immune responses are considerably augmented, i.e. boosted, upon re-administration of the same vaccine vector, which can be done repeatedly.

The immunogenicity of different test vaccines was subsequently compared by evaluating the induction of antigen-specific CD8+ T cell frequencies in mice upon intravenous immunization with HK1-E7E6, HK1-E7E6-CRT, HK1-E7E6-Ub and HK1-E7E6-GMCSF. A suboptimal vector dose ($1\times10^4$ FFU) was used to allow for differentiation of constructs. Naive mice were used as control.

Antigen-(E7-) specific CD8+ T cell responses were subsequently analyzed by tetramer staining. FIG. 6 shows results for C57BL/6 mice (n=5 per group) immunized once by intravenous injection of $1\times10^4$ FFU of HK1-E7E6, HK1-E7E6-CRT, HK1-E7E6-Ub and HK1-E7E6-GMCSF. Naïve mice were used as control. E7-specific CD8+ T cell responses were subsequently analyzed by tetramer staining (H-2Db/HPV16 E7 49-57 (RAHYNIVTF)) on day 9 after immunization. The percentage of tetramer-binding CD8+ T cells is expressed as a percentage of the total CD8+ T cell pool. This data indicate that HK1-E7E6-GMCSF induces considerably higher antigen-specific CD8+ T cell responses compared to the other tested vector constructs.

The immunogenicity of selected test vaccines was subsequently further analyzed and compared by evaluating the induction of antigen-specific CD8+ T cell responses in mice upon vaccination. C57BL/6 mice were immunized with HK1-E7E6, HK1-E7E6-GMCSF or HK1-GFP as an irrelevant negative control vector. Ad5-E7E6, a recombinant Adenovirus 5 (Ad5) vector expressing the HPV16 E7E6 fusion protein (with mutations in Rb binding site and E6 zinc binding domains), was used as a benchmark vector. Control mice received injections of 0.9% NaCl. Seven days after the second injection, splenocytes from vaccinated mice were isolated and stimulated with HPV16 E6 or HPV16 E7 peptides. The percentage of IFN-γ-producing CD8+ T cells was subsequently analyzed by double immunofluorescence assay.

FIGS. 7A-7B shows the detection of peptide-specific CD8+ T cell responses induced by vaccines. C57BL/6 mice (n=5 per group) were immunized twice on days 0 and 28 by intramuscular injection of $1\times10^5$ FFU of HK1-E7E6 (groups 1 and 2), HK1-GFP (group 3), or HK1-E7E6-GMCSF (group 5), or $1\times10^7$ PFU of Ad5-E7E6 (group 4). Control mice (group 6) received two injections of 0.9% NaCl on days 0 and 28. 7 days after the last vaccination, splenocytes from immunized mice were isolated and stimulated with either HPV16 E6aa50-57 peptide or E7aa49-57 peptide (all at 1 µg/ml) in the presence of GolgiPlug (1 µl/ml) at 37° C. overnight. The cells were stained with PE-conjugated anti-mouse CD8a antibody, washed, permeabilized and fixed with CytoFix/CytoPerm. Subsequently, cells were washed and intracellularly stained with FITC-conjugated anti-mouse IFN-γ antibody. After wash, cells were acquired with FACSCalibur and analyzed with CellQuest software.

This data indicated strong HPV16 E7-specific CD8+ T cell responses in groups 1, 2, 4 and 5, i.e., a strong response in mice vaccinated with HK1-E7E6, HK1-E7E6-GMCSF or Ad5-E7/E6. Weak HPV16 E6-specific CD8+ T cell responses were observed in mice immunized with HK1-E7E6-GMCSF or Ad5-E7E6, indicating weaker immunogenicity of E6 compared to E7.

To further investigate and compare the immunogenicity of test vectors encoding different immunostimulating sequences, the induction of antigen-specific CD8+ T cell frequencies was analyzed upon intravenous injection of HK1-E7E6-GMCSF, HK1-E7E6-VP22, HK1-E7E6-CD40L, HK1-Flt3L-E7E6, HK1-Flt3L-E7E6shuffle or HK1-li-E7E6 constructs. Moreover, different vector doses were used to further investigate the dose dependency of the induced responses. Mock infected mice were used as controls. To analyze the effect of different immunization routes, one control group was injected intramuscularly with $10^6$ FFU of HK1-E7E6-GMCSF. Frequencies of E7-specific CD8+ T cells circulating in blood were subsequently analyzed by tetramer staining (H-2Db/HPV16 E7 49-57 (RAHYNIVTF)) on days 8 and 18 of the experiment. The percentage of tetramer-binding CD8+ T cells is expressed as a percentage of the total CD8+ T cells in the test sample.

FIG. 8 shows the results of the above experiments, which indicate that, at a dose of $10^6$ FFU, E7 specific CD8+ frequencies in the range of ~4%-11% can be achieved with all tested constructs. The results further demonstrate that significantly higher CD8+ T cell responses can be induced by intravenous immunization compared to intramuscular injection.

(c) Protective Efficacy

The protective efficacy of the vaccine candidates was subsequently investigated in the TC-1 model (Lin et al, 1996, Cancer Res.; 56(1):21-6), which is one of the most commonly used models for developing therapeutic HPV vaccines. TC-1 tumor cells derived from mouse primary epithelial cells, co-transformed with HPV-16 E6 and E7 and c-Ha-ras oncogenes, were used in this experiment. Immunized mice were challenged by subcutaneous injection of TC-1 tumor cells after the second vaccination. A third vaccination was administered to certain treatment groups after challenge to further boost immunity. Protective efficacy was assessed by evaluating the number of tumor-free mice as well as measuring the tumor volume in the animals every 5 days. Mean tumor volumes in vaccinated animals and unvaccinated control animals were compared.

FIGS. 9A and 9B show the results for C57BL/6 mice (n=5 per group) immunized twice on days 0 and 28 by intramuscular injection with $1\times10^5$ FFU of HK1-E7E6 (groups 1 and 2), HK1-GFP (group 3), or HK1-E7E6-GMCSF (group 5), or $1\times10^7$ PFU of Ad5-E7E6 (group 4). Control mice (group 6) received two injections of 0.9% NaCl on days 0 and 28. On day 55, mice from groups 1, 3, 4, 5 and 6 were further boosted with the same regimen. On day 35, the mice were injected with $5\times10^4$ of TC-1 tumor cells subcutaneously. Tumor growth was monitored by palpitation twice a week.

The results indicated that the observed induction of E7-specific CD8+ T cell responses correlates well with antitumor effects in the vaccinated mice. Immunization with HK1-E7E6 or HK1-E7E6-GMCSF significantly reduced the mean tumor volumes as well as the percentage of tumor-bearing mice within the experimental group. Observed results were comparable to the effects seen after vaccination with Ad5-E7E6.

(d) Therapeutic Efficacy

To further evaluate the therapeutic efficacy of the vaccine candidates, TC-1 tumor-bearing mice were vaccinated with the test vectors and frequencies of E7-specific CD8+ T cells circulating in blood were subsequently analyzed. FIGS. 10A-10D show the results for C57BL/6 mice injected with $1\times10^5$ of TC-1 tumor cells on day 1 and subsequently vaccinated on days 4 and 14 with buffer (G1), $10^6$ FFU HK1-E7E6 (G2), $10^6$ FFU HK1-E7E6-GMCSF (G3), $10^6$ FFU HK1-E7E6-CD40L (G4), or $10^5$ FFU r3LCMV-E7E6. E7-specific CD8+ T cells were analyzed by tetramer staining on days 13 (A, B) and 23 (C, D). The results demonstrate a high frequency of E7 specific CD8+ T cells after intravenous immunization with all tested vector constructs.

To also investigate the induction of anti-vector immune responses, LCMV NP specific CD8+ T cell frequencies was analyzed in the tumor-bearing mice after vaccination with the indicated test vectors. The results of this analysis are shown in FIGS. 11A-11D, which demonstrate a high frequency of NP specific CD8+ T cells after intravenous immunization with all vector constructs.

To analyze the impact of E7-specific CD8+ T cell responses on tumor control, the body weight of the vaccinated mice (data not shown) as well as the tumor volume and overall survival in the respective animals were monitored. FIG. 12A shows the tumor volume results out to about 55 days post tumor inoculation for C57BL/6 mice injected with $1 \times 10^5$ of TC-1 tumor cells on day 1 and subsequently vaccinated with PBS (G1), $10^6$ FFU HK1-E7E6 (G2), $10^6$ FFU HK1-E7E6-GMCSF (G3), $10^6$ FFU HK1-E7E6-CD40L (G4), or $10^5$ FFU r3LCMV-E7E6 (G5) on days 4 and 14. FIG. 12B shows the tumor volume results of the same C57BL/6 mice with extended observations out to 80 days post tumor inoculation. FIG. 12C shows the overall survival of the mice following vaccination. Respective results indicate that tumor growth was controlled in all groups vaccinated with LCMV vectors expressing HPV E7E6 and that mice injected with these vectors had better overall survival. However, the protection conferred by immunization with HK1-E7E6 (G2) was somewhat less than the other tested constructs.

As a further investigation into the anti-vector immune responses, using the same methods described above, formation of E7-specific CD8+ T cells and LCMV NP specific CD8+ T cells in peripheral blood of TC-1 tumor-bearing mice were analyzed following vaccination with PBS (G1), $1 \times 10^7$ PFU of Ad5-E7E6 (G2) and $10^6$ FFU HK1-E7E6 (G3). The results of this analysis are shown in FIGS. 13A-13D and 14A-14D, which again demonstrate a high frequency of E7-specific CD8+ T cells and LCMV NP specific CD8+ T cells after intravenous immunization with HK1-E7E6 LCMV vector. Additionally, the LCMV vector expressing HPV E7E6 showed an even higher percentage of E7-specific CD8+ T cells following immunization than the adeno-based vector expressing HPV E7E6.

Tumor volume and overall survival were also monitored in the mice vaccinated with PBS (G1), $1 \times 10^7$ PFU of Ad5-E7E6 (G2) and $10^6$ FFU HK1-E7E6 (G3). FIG. 15A shows the tumor volume results out to 80 days post tumor inoculation. FIG. 15B shows the overall survival of the mice following vaccination. These results show that an LCMV vector expressing HPV E7E6 was able to control tumor growth and resulted in better overall survival in comparison to the adeno-based vector expressing HPV E7E6.

7.3 Prime-Boost Immunization

Owing to the race against tumor growth, rapid induction of strong anti-tumor immune responses is an important challenge for successful development of cancer immunotherapies. Repeated prime-boost immunization strategies are likely necessary in order to achieve these goals. Although it has been shown that replication-deficient LCMV vectors can efficiently be re-administered in homologous prime-boost vaccination, heterologous prime-boost immunization regimens may offer distinct advantages such as to allow for shorter intervals between vaccinations, or to result in even higher efficacy. Vaccine vectors based on replication-deficient forms of various other members of the arenavirus family such as Junin virus or Mopeia virus can be used.

To investigate the ability of respective vectors to induce CD8+ T cell responses against HPV antigens, a replication-deficient glycoprotein-deficient vector based on Junin virus vaccine strain Candid #1, encoding HPV16 E7E6 fusion protein with mutations in Rb binding site and E6 zinc binding domains, was generated (rJUNV-E7E6). C57BL/6 mice were vaccinated once by intravenous injection of $10^5$ FFU of rJUNV-E7E6 or HK1-E7E6. Eight days after immunization the induction of antigen-(E7 epitope-) specific CD8+ T cell responses was analyzed by tetramer staining from blood. Results shown in FIG. 16 demonstrate that rJUNV-E7E6 induced CD8+ T cell responses of similar magnitude as the rLCMV-based HK1-E7E6 vaccine To investigate the effect of homologous versus heterologous prime-boost immunization on the induction of antigen-specific CD8+ T cell responses, C57BL/6 mice were vaccinated on day 0 by intravenous injection of $10^5$ FFU of either HK1-E7E6 or rJUNV-E7E6. 35 days later mice were either boosted with the respective homologous or heterologous vector ($10^5$ FFU i.v.). The induction of antigen-(E7 epitope-) specific CD8+ T cell responses was analyzed by tetramer staining on days 8, 28 and 42 of the experiment. Results in FIGS. 17A-17C demonstrate that heterologous rJUNV-E7E6 prime—HK1-E7E6 boost induces significantly higher E7-specific CD8+ T cell frequencies than homologous prime-boost immunization with HK1-E7E6 ($p<0.05$ by unpaired two-tailed student's t test). Further, the data show that rJUNV-E7E6 vectors (pseudotyped with LCMV-GP from producer cells) can efficiently be re-administered in homologous prime-boost vaccination, similarly to rLCMV vectors, which were pseudotyped with the same glycoprotein (compare FIG. 5).

7.4 Replication-Competent Tri-Segmented Arenavirus Viral Vectors

In an attempt to induce even stronger effector T cell responses due to the inflammation elicited by a replicating infection, replication-competent tri-segmented LCMV vectors expressing a fusion of proteins E6 and E7 of HPV type 16 were generated. The immunogenicity of the non-replicating bi-segmented vector (HK1-E7E6) and the analogous replicating, tri-segmented vector (r3LCMV-E7E6) was compared by evaluating the induction of antigen-specific CD8+ T cell responses in mice upon intravenous injection with the respective vectors. C57BL/6 mice were immunized on days 0 and 35 of the experiment with $10^5$ FFU of r3LCMV-E7E6 or HK1-E7E6. Epitope-specific CD8+ T cells were stained using E7 epitope-loaded MHC class I tetramers in combination with anti-CD8a antibody. The frequency of E7-tetramer-binding cells within the CD8+ T cell compartment in peripheral blood was calculated. FIG. 18 shows the results of these experiments, which demonstrate that 4-5 fold higher frequencies of E7 specific CD8+ can be induced by replicating vectors compared to non-replicating vectors.

To investigate the effect of homologous versus heterologous prime-boost immunization using replication-competent vectors, the induction of antigen-specific CD8+ T cell responses was analyzed in mice after vaccination with r3LCMV-E7E6 and an analogous replication-competent vector based on Junin Candid #1 virus (r3JUNV-E7E6) in homologous or heterologous combinations. FIGS. 19A-19B shows the results of these experiments, which demonstrate that both homologous and heterologous prime-boost combinations of replication-competent tri-segmented LCMV- and JUNV-based vaccine vectors induce strong HPV E7-specific CD8+ T cells responses.

TABLE 1

Sequences

| SEQ ID No. | Description | Sequence |
|---|---|---|
| 1 | Lymphocytic choriomeningitis virus segment S, complete sequence. The genomic segment is RNA, the sequence in SEQ ID NO: 1 is shown for DNA; however, exchanging all thymidines ("T") in SEQ ID NO: 1 for uridines ("U") provides the RNA sequence. | cgcaccgggg atcctaggct ttttggattg cgctttcctc tagatcaact gggtgtcagg ccctatccta cagaaggatg ggtcagattg tgacaatgtt tgaggctctg cctcacatca tcgatgaggt gatcaacatt gtcattattg tgcttatcgt gatcacgggt atcaaggctg tctacaattt tgccacctgt gggatattcg cattgatcag tttcctactt ctggctggca ggtcctgtgg catgtacggt cttaagggac ccgacattta caaaggagtt taccaattta agtcagtgga gtttgatatg tcacatctga acctgaccat gcccaacgca tgttcagcca acaactccca ccattacatc agtatgggga cttctggact agaattgacc ttcaccaatg attccatcat cagtcacaac ttttgcaatc tgacctctgc cttcaacaaa aagacctttg accacacact catgagtata gtttcgagcc tacacctcag tatcagaggg aactccaact ataaggcagt atcctgcgac ttcaacaatg cataaccat ccaatacaac ttgacattct cagatcgaca aagtgctcag agccagtgta gaaccttcag aggtagagtc ctagatatgt ttagaactgc cttcgggggg aaatacatga ggagtggctg gggctggaca ggctcagatg gcaagaccac ctggtgtagc cagacgagtt accaatacct gattatacaa aatagaacct gggaaaacca ctgcacatat gcaggtcctt ttgggatgtc caggattctc cttcccaag agaagactaa gttcttcact aggagactag cgggcacatt cacctggact ttgtcagact cttcagggt ggagaatcca ggtggttatt gcctgaccaa atggatgatt cttgctgcag agcttaagtg tttcgggaac acagcagttg cgaatgcaa tgtaaatcat gatgccgaat tctgtgacat gctgcgacta attgactaca caaggctgc tttgagtaag ttcaaagagg acgtagaatc tgccttgcac ttattcaaaa caacagtgaa ttctttgatt tcagatcaac tactgatgag gaaccacttg agagatctga tgggggtgcc atattgcaat tactcaaagt tttggtacct agaacatgca aagaccggcg aaactagtgt ccccaagtgc tggcttgtca ccaatggttc ttacttaaat gagacccact tcagtgatca aatcgaacag gaagccgata acatgattac agagatgttg aggaaggatt acataaagag gcagggagt accccctag cattgatgga ccttctgatg ttttccacat ctgcatatct agtcagcatc ttcctgcacc ttgtcaaaat accaacacac aggcacataa aaggtggctc atgtccaaag ccacaccgat taaccaacaa aggaatttgt agttgtggtg catttaaggt gcctggtgta aaaaccgtct ggaaaagacg ctgaagaaca gcgcctccct gactctccac ctcgaaagag gtggagagtc agggaggccc agagggtctt agagtgtcac aacatttggg cctctaaaaa ttaggtcatg tggcagaatg ttgtgaacag ttttcagatc tgggagcctt gctttggagg cgctttcaaa aatgatcag tccatgagtg cacagtgcgg ggtgatctct ttcttctttt tgtcccttac tattccagta tgcatcttac acaaccagcc atatttgtcc cacactttgt cttcatactc cctcgaagct tccctggtca tttcaacatc gataagctta atgtccttcc tattctgtga gtccagaagc tttctgatgt catcggagcc ttgacagctt agaaccatcc cctgcggaag agcacctata actgacgagg tcaacccggg ttgcgcattg aagaggtcgg caagatccat gccgtgtgag tacttggaat cttgcttgaa ttgttttga tcaacgggtt ccctgtaaaa gtgtatgaac tgcccgttct gtggttggaa aattgctatt tccactggat cattaaatct accctcaatg tcaatccatg taggagcgtt ggggtcaatt cctcccatga ggtcttttaa |

TABLE 1-continued

Sequences

| SEQ ID No. | Description | Sequence |
|---|---|---|
| | | aagcattgtc tggctgtagc ttaagcccac ctgaggtgga cctgctgctc caggcgctgg cctgggtgaa ttgactgcag gtttctcgct tgtgagatca attgttgtgt tttcccatgc tctccccaca atcgatgttc tacaagctat gtatggccat ccttcacctg aaaggcaaac tttatagagg atgttttcat aagggttcct gtccccaact tggtctgaaa caaacatgtt gagttttctc ttggccccga gaactgcctt caagaggtcc tcgctgttgc ttggcttgat caaaattgac tctaacatgt taccccccatc caacagggct gccccctgcct tcacggcagc accaagacta aagtatagc cagaaatgtt gatgctggac tgctgttcag tgatgacccc cagaactggg tgcttgtctt tcagcctttc aagatcatta agatttggat acttgactgt gtaaagcaag ccaaggtctg tgagcgcttg tacaacgtca ttgagcggag tctgtgactg tttggccata caagccatag ttagacttgg cattgtgcca aattgattgt tcaaaagtga tgagtctttc acatcccaaa ctcttaccac accacttgca ccctgctgag gctttctcat cccaactatc tgtaggatct gagatctttg gtctagttgc tgtgttgtta agttccccat atatacccct gaagcctggg gcctttcaga cctcatgatc ttggccttca gcttctcaag gtcagccgca agagacatca gttcttctgc actgagcctc cccactttca aaacattctt ctttgatgtt gactttaaat ccacaagaga atgtacagtc tggttgagac ttctgagtct ctgtaggtct ttgtcatctc tcttttcctt cctcatgatc ctctgaacat tgctgacctc agagaagtcc aacccattca gaaggttggt tgcatcctta atgacagcag ccttcacatc tgatgtgaag ctctgcaatt ctcttctcaa tgcttgcgtc cattggaagc tcttaacttc cttagacaag gacatcttgt tgctcaatgg tttctcaaga caaatgcgca atcaaatgcc taggatccac tgtgcg |
| 2 | Lymphocytic choriomeningitis virus clone 13 segment S, complete sequence (GenBank: DQ361065.2). The genomic segment is RNA, the sequence in SEQ ID NO: 2 is shown for DNA; however, exchanging all thymidines ("T") in SEQ ID NO: 2 for uridines ("U") provides the RNA sequence. | gcgcaccggg gatcctaggc tttttggatt gcgctttcct ctagatcaac tgggtgtcag gccctatcct acagaaggat gggtcagatt gtgacaatgt ttgaggctct gcctcacatc atcgatgagg tgatcaacat tgtcattatt gtgcttatcg tgatcacggg tatcaaggct gtctacaatt ttgccacctg tgggatattc gcattgatca gtttcctact tctggctggc aggtcctgtg gcatgtacgg tcttaaggga cccgacattt acaaaggagt ttaccaattt aagtcagtgg agtttgatat gtcacatctg aacctgacca tgcccaacgc atgttcagcc aacaactccc accattacat cagtatgggg acttctggac tagaattgac cttcaccaat gattccatca tcagtcacaa cttttgcaat ctgacctctg ccttcaacaa aaagaccttt gaccacacac tcatgagtat agtttcgagc ctacacctca gtatcagagg gaactccaac tataaggcag tatcctgcga cttcaacaat ggcataacca tccaatacaa cttgacattc tcagatgcac aaagtgctca gagccagtgt agaaccttca gaggtagagt cctagatatg tttagaactg ccttcggggg gaaatacatg aggagtggct ggggctggac aggctcagat ggcaagacca cctggtgtag ccagacgagt taccaatacc tgattataca aaatagaacc tgggaaaacc actgcacata tgcaggtcct tttgggatgt ccaggattct cctttcccaa gagaagacta agttcctcac taggagacta gcgggcacat tcacctggac tttgtcagac tcttcagggg tggagaatcc aggtggttat tgcctgacca aatggatgat tcttgctgca gagcttaagt gtttcgggaa cacagcagtt gcgaaatgca atgtaaatca tgatgaagaa |

TABLE 1-continued

Sequences

| SEQ ID No. | Description | Sequence |
|---|---|---|
| | | ttctgtgaca tgctgcgact aattgactac aacaaggctg ctttgagtaa gttcaaagag gacgtagaat ctgccttgca cttattcaaa acaacagtga attctttgat ttcagatcaa ctactgatga ggaaccactt gagagatctg atgggggtgc catattgcaa ttactcaaag ttttggtacc tagaacatgc aaagaccggc gaaactagtg tccccaagtg ctggcttgtc accaatggtt cttacttaaa tgagacccac ttcagtgacc aaatcgaaca ggaagccgat aacatgatta cagagatgtt gaggaaggat tacataaaga ggcagggag tacccccta gcattgatgg accttctgat gttttccaca tctgcatatc tagtcagcat cttcctgcac cttgtcaaaa taccaacaca caggcacata aaaggtggct catgtccaaa gccacaccga ttaaccaaca aaggaatttg tagttgtggt gcatttaagg tgcctggtgt aaaaaccgtc tggaaaagac gctgaagaac agcgcctccc tgactctcca cctcgaaaga ggtggagagt cagggaggcc cagagggtct tagagtgtca caacatttgg gcctctaaaa attaggtcat gtggcagaat gttgtgaaca gttttcagat ctgggagcct tgctttggag gcgctttcaa aaatgatgca gtccatgagt gcacagtgcg gggtgatctc tttcttcttt ttgtcccta ctattccagt atgcatctta cacaaccagc catatttgtc ccacacttg tcttcatact ccctcgaagc ttccctggtc atttcaacat cgataagctt aatgtccttc ctattctgtg agtccagaag ctttctgatg tcatcggagc cttgacagct tagaaccatc ccctgcggaa gagcacctat aactgacgag gtcaacccgg gttgcgcatt gaagaggtcg gcaagatcca tgccgtgtga gtacttggaa tcttgcttga attgttttg atcaacgggt tccctgtaaa agtgtatgaa ctgcccgttc tgtggttgga aaattgctat ttccactgga tcattaaatc taccctcaat gtcaatccat gtaggagcgt tggggtcaat tcctcccatg aggtctttta aaagcattgt ctggctgtag cttaagccca cctgaggtgg acctgctgct ccaggcgctg gcctgggtga attgactgca ggtttctcgc ttgtgagatc aattgttgtg ttttcccatg ctctccccac aatcgatgtt ctacaagcta tgtatggcca tccttcacct gaaaggcaaa ctttatagag gatgttttca taagggttcc tgtccccaac ttggtctgaa acaaacatgt tgagttttct cttggcccg agaactgcct tcaagaggtc ctcgctgttg cttggcttga tcaaaattga ctctaacatg ttaccccat ccaacagggc tgcccctgcc ttcacggcag caccaagact aaagttatag ccagaaatgt tgatgctgga ctgctgttca gtgatgaccc ccagaactgg gtgcttgtct ttcagccttt caagatcatt aagatttgga tacttgactg tgtaaagcaa gccaaggtct gtgagcgctt gtacaacgtc attgagcgga gtctgtgact gtttggccat acaagccata gttagacttg gcattgtgcc aaattgattg ttcaaaagtg atgagtcttt cacatcccaa actcttacca caccacttgc accctgctga ggctttctca tcccaactat ctgtaggatc tgagatcttt ggtctagttg ctgtgttgtt aagttcccca tatataccc tgaagcctgg ggcctttcag acctcatgat cttggccttc agcttctcaa ggtcagccgc aagagacatc agttcttctg cactgagcct ccccactttc aaaacattct tctttgatgt tgactttaaa tccacaagag aatgtacagt ctggttgaga cttctgagtc tctgtaggtc tttgtcatct ctcttttcct tcctcatgat cctctgaaca ttgctgacct cagagaagtc caacccattc agaaggttgg ttgcatcctt aatgacagca gccttcacat |

TABLE 1-continued

Sequences

| SEQ ID No. | Description | Sequence |
|---|---|---|
| | | ctgatgtgaa gctctgcaat tctcttctca atgcttgcgt ccattggaag ctcttaactt ccttagacaa ggacatcttg ttgctcaatg gtttctcaag acaaatgcgc aatcaaatgc ctaggatcca ctgtgcg |
| 3 | Lymphocytic choriomeningitis virus clone 13 segment L, complete sequence (GenBank: DQ361066.1). The genomic segment is RNA, the sequence in SEQ ID NO: 3 is shown for DNA; however, exchanging all thymidines ("T") in SEQ ID NO: 3 for uridines ("U") provides the RNA sequence. | gcgcaccggg gatcctaggc gtttagttgc gctgtttggt tgcacaactt tcttcgtgag gctgtcagaa gtggacctgg ctgatagcga tgggtcaagg caagtccaga gaggagaaag gcaccaatag tacaaacagg gccgaaatcc taccagatac cacctatctt ggccctttaa gctgcaaatc ttgctggcag aaatttgaca gcttggtaag atgccatgac cactaccttt gcaggcactg tttaaacctt ctgctgtcag tatccgacag gtgtcctctt tgtaaatatc cattaccaac cagattgaag atatcaacag ccccaagctc tccacctccc tacgaagagt aacaccgtcc ggccccggcc ccgacaaaca gcccagcaca agggaaccgc acgtcaccca acgcacacag acacagcacc caacacagaa cacgcacaca cacacacaca cacacccaca cgcacgcgcc cccaccaccg ggggcgccc ccccccgggg ggcggccccc cgggagcccg ggcggagccc cacggagatg cccatcagtc gatgtcctcg gccaccgacc cgcccagcca atcgtcgcag gacctcccct tgagtctaaa cctgccccc actgtttcat acatcaaagt gctcctagat ttgctaaaac aaagtctgca atccttaaag gcgaaccagt ctggcaaaag cgacagtgga atcagcagaa tagatctgtc tatacatagt tcctggagga ttacacttat ctctgaaccc aacaaatgtt caccagttct gaatcgatgc aggaagaggt tcccaaggac atcactaatc ttttcatagc cctcaagtcc tgctagaaag actttcatgt ccttggtctc cagcttcaca atgatatttt ggacaaggtt tcttccttca aaaagggcac ccatctttac agtcagtggc acaggctccc actcaggtcc aactctctca aagtcaatag atctaatccc atccagtatt cttttggagc ccaacaactc aagctcaaga gaatcaccaa gtatcaaggg atcttccatg taatcctcaa actcttcaga tctgatatca aagacaccat cgttcacctt gaagacagag tctgtcctca gtaagtggag gcattcatcc aacattcttc tatctatctc acccttaaag aggtgagagc atgataaaag ttcagccaca cctggattct gtaattggca cctaaccaag aatatcaatg aaaatttcct taaacagtca gtattattct gattgtgcgt aaagtccact gaaattgaaa actccaatac ccttttgtg tagttgagca tgtagtccca cagatccttt aaggatttaa atgcctttgg gtttgtcagg ccctgcctaa tcaacatggc agcattacac acaacatctc ccattcggta agagaaccac ccaaaaccaa actgcaaatc attcctaaac ataggcctct ccacattttt gttcaccacc tttgagacaa atgattgaaa ggggcccagt gcctcagcac catcttcaga tggcatcatt tctttatgag ggaaccatga aaaattgcct aatgtcctgg ttgttgcaac aaattctcga acaaatgatt caaaatacac ctgttttaag aagttcttgc agacatccct cgtgctaaca acaaattcat caaccagact ggagtcagat cgctgatgag aattggcaag gtcagaaaac agaacagtgt aatgttcatc cctttccac ttaacaacat gagaaatgag tgacaaggat tctgagttaa tatcaattaa aacacagagg tcaaggaatt taattctggg actccacctc atgtttttg agctcatgtc agacataaat ggaagaagct gatcctcaaa gatcttggga tatagccgcc tcacagattg aatcacttgg ttcaaaattca ctttgtcctc cagtagcctt gagctctcag gctttcttgc |

TABLE 1-continued

Sequences

| SEQ ID No. | Description | Sequence |
|---|---|---|
| | | tacataatca catgggttta agtgcttaag agttaggttc tcactgttat tcttcccttt ggtcggttct gctaggaccc aaacacccaa ctcaaaagag ttgctcaatg aaatacaaat gtagtcccaa agaagaggcc ttaaaaggca tatatgatca cggtgggctt ctggatgaga ctgtttgtca caaatgtaca gcgttatacc atcccgattg caaactcttg tcacatgatc atctgtggtt agatcctcaa gcagcttttt gatatacaga tttcccctat ttttgtttct cacacacctg cttcctagag ttttgcaaag gcctataaag ccagatgaga tacaactctg gaaagctgac ttgttgattg cttctgacag cagcttctgt gcacccttg tgaatttact acaaagtttg ttctggagtg tcttgatcaa tgatgggatt ctttcctctt ggaaagtcat cactgatgga taaaccacct tttgtcttaa aaccatcctt aatgggaaca tttcattcaa attcaaccag ttaacatctg ctaactgatt cagatcttct tcaagaccga ggaggtctcc caattgaaga atggcctcct ttttatctct gttaaatagg tctaagaaaa attcttcatt aaattcacca tttttgagct tatgatgcag tttccttaca agcttttctta caacctttgt ttcattagga cacagttcct caatgagtct ttgtattctg taacctctag aaccatccag ccaatctttc acatcagtgt tggtattcag tagaaatgga tccaaaggga aattggcata ctttaggagg tccagtgttc tcctttggat actattaact agggagactg ggacgccatt tgcgatggct tgatctgcaa ttgtatctat tgtttcacaa agttgatgtg gctctttaca cttgacattg tgtagcgctg cagatacaaa ctttgtgaga agagggactt cctccccca tacatagaat ctagatttaa attctgcagc gaacctccca gccacacttt ttgggctgat aaatttgttt aacaagccgc tcagatgaga ttggaattcc aacaggacaa ggacttcctc cggatcactt acaaccaggt cactcagcct cctatcaaat aaagtgatct gatcatcact tgatgtgtaa gcctctggtc tttcgccaaa gataacacca atgcagtagt tgatgaacct ctcgctaagc aaaccataga agtcagaagc attatgcaag attccctgcc ccatatcaat aaggctggat atatgggatg gcactatccc catttcaaaa tattgtctga aaattctctc agtaacagtt gtttctgaac ccctgagaag ttttagcttc gacttgacat atgatttcat cattgcattc acaacaggaa aggggacctc gacaagctta tgcatgtgcc aagttaacaa agtgctaaca tgatctttcc cggaacgcac atactggtca tcacctagtt tgagattttg tagaaacatt aagaacaaaa atgggcacat cattggtccc catttgctgt gatccatact atagtttaag aacccttccc gcacattgat agtcattgac aagattgcat tttcaaattc cttatcattg tttaaacagg agcctgaaaa gaaacttgaa aaagactcaa aataatcttc tattaacctt gtgaacattt ttgtcctcaa atctccaata tagagttctc tatttccccc aacctgctct ttataagata gtgcaaattt cagccttcca gagtcaggac ctactgaggt gtatgatgtt ggtgattctt ctgagtagaa gcacagattt ttcaaagcag cactcataca ttgtgtcaac gacagagctt tactaaggga ctcagaatta ctttccctct cactgattct cacgtcttct tccagtttgt cccagtcaaa tttgaaattc aagccttgcc tttgcatatg cctgtatttc cctgagtacg catttgcatt catttgcaac agaatcatct tcatgcaaga aaaccaatca ttctcagaaa agaactttct acaaaggttt tttgccatct catcgaggcc acactgatct ttaatgactg aggtgaaata caaaggtgac agctctgtgg aaccctcaac |

TABLE 1-continued

Sequences

| SEQ ID No. | Description | Sequence |
|---|---|---|
| | | agcctcacag ataaatttca tgtcatcatt ggttagacat |
| | | gatgggtcaa agtcttctac |
| | | taaatggaaa gatatttctg acaagataac ttttcttaag |
| | | tgagccatct tccctgttag |
| | | aataagctgt aaatgatgta gtccttttgt atttgtaagt |
| | | ttttctccat ctcctttgtc |
| | | attggccctc ctacctcttc tgtaccgtgc tattgtggtg |
| | | ttgacctttt cttcgagact |
| | | tttgaagaag cttgtctctt cttctccatc aaaacatatt |
| | | tctgccaggt tgtcttccga |
| | | tctccctgtc tcttctccct tggaaccgat gaccaatcta |
| | | gagactaact tggaaacttt |
| | | atattcatag tctgagtggc tcaacttata cttttgtttt |
| | | cttacgaaac tctccgtaat |
| | | ttgactcaca gcactaacaa gcaatttgtt aaagtcatat |
| | | tccagaagtc gttctccatt |
| | | tagatgctta ttaaccacca cacttttgtt actagcaaga |
| | | tctaatgctg tcgcacatcc |
| | | agagttagtc atgggatcta ggctgtttag cttcttctct |
| | | cctttgaaaa ttaaagtgcc |
| | | gttgttaaat gaagacacca ttaggctaaa ggcttccaga |
| | | ttaacacctg gagttgtatg |
| | | ctgacagtca atttctttac tagtgaatct cttcatttgc |
| | | tcatagaaca cacattcttc |
| | | ctcaggagtg attgcttcct tggggttgac aaaaaaacca |
| | | aattgactttt tgggctcaaa |
| | | gaacttttca aaacatttta tctgatctgt tagcctgtca |
| | | ggggtctcct ttgtgatcaa |
| | | atgacacagg tatgacacat tcaacataaa tttaaatttt |
| | | gcactcaaca acaccttctc |
| | | accagtacca aaaatagttt ttattaggaa tctaagcagc |
| | | ttatacacca ccttctcagc |
| | | aggtgtgatc agatcctccc tcaacttatc cattaatgat |
| | | gtagatgaaa aatctgacac |
| | | tattgccatc accaaatatc tgacactctg tacctgcttt |
| | | tgatttctct ttgttgggtt |
| | | ggtgagcatt agcaacaata gggtcctcag tgcaacctca |
| | | atgtcggtga gacagtcttt |
| | | caaatcagga catgatctaa tccatgaaat catgatgtct |
| | | atcatattgt ataagacctc |
| | | atctgaaaaa attggtaaaa agaaccttt aggatctgca |
| | | tagaaggaaa ttaaatgacc |
| | | atccgggcct tgtatggagt agcaccttga agattctcca |
| | | gtcttctggt ataataggtg |
| | | gtattcttca gagtccagtt ttattacttg gcaaaacact |
| | | tcttttgcatt ctaccacttg |
| | | atatctcaca gaccctattt gattttgcct tagtctagca |
| | | actgagctag ttttcatact |
| | | gtttgttaag gccagacaaa cagatgataa tcttctcagg |
| | | ctctgtatgt tcttcagctg |
| | | ctctgtgctg ggttggaaat tgtaatcttc aaacttcgta |
| | | taatacatta tcgggtgagc |
| | | tccaattttc ataaagttct caaattcagt gaatggtatg |
| | | tggcattctt gctcaaggtg |
| | | ttcagacagt ccgtaatgct cgaaactcag tcccaccact |
| | | aacaggcatt tttgaatttt |
| | | tgcaatgaac tcactaatag atgccctaaa caattcctca |
| | | aaagacacct ttctaaacac |
| | | ctttgacttt tttctattcc tcaaagtct aatgaactcc |
| | | tctttagtgc tgtgaaagct |
| | | taccagccta tcattcacac tactatagca acaacccacc |
| | | cagtgtttat catttttaa |
| | | cccttttgaat ttcgactgtt ttatcaatga ggaaagacac |
| | | aaaacatcca gatttaacaa |
| | | ctgtctcctt ctagtattca acagtttcaa actcttgact |
| | | ttgtttaaca tagagaggag |
| | | cctctcatat tcagtgctag tctcacttcc cctttcgtgc |
| | | ccatgggtct ctgcagttat |
| | | gaatctcatc aaaggacagg attcgactgc ctccctgctt |
| | | aatgttaaga tatcatcact |
| | | atcagcaagg ttttcataga gctcagagaa ttccttgatc |
| | | aagccttcag ggtttacttt |
| | | ctgaaagttt ctctttaatt tcccactttc taaatctctt |
| | | ctaaacctgc tgaaaagaga |

TABLE 1-continued

Sequences

| SEQ ID No. | Description | Sequence |
|---|---|---|
| | | gtttattcca aaaaccacat catcacagct catgttgggg ttgatgcctt cgtggcacat cctcataatt tcatcattgt gagttgacct cgcatctttc agaattttca tagagtccat accggagcgc ttgtcgatag tagtcttcag ggactcacag agtctaaaat attcagactc ttcaaagact ttctcatttt ggttagaata ctccaaaagt ttgaataaaa ggtctctaaa tttgaagttt gcccactctg gcataaaact attatcataa tcacaacgac catctactat tggaactaat gtgacacccg caacagcaag gtcttccctg atgcatgcca atttgttagt gtcctctata aatttcttct caaaactggc tggagtgctc ctaacaaaac actcaagaag aatgagagaa ttgtctatca gcttgtaacc atcaggaatg ataagtggta gtcctgggca tacaattcca gactccacca aaattgtttc cacagactta tcgtcgtggt tgtgtgtgca gccactcttg tctgcactgt ctatttcaat gcagcgtgac agcaacttga gtccctcaat cagaaccatt ctgggttccc tttgtcccag aaagttgagt ttctgccttg acaacctctc atcctgttct atatagttta aacataactc tctcaattct gagatgattt catccattgc gcatcaaaaa gcctaggatc ctcggtgcg |
| 4 | Lymphocytic choriomeningitis strain MP segment L, complete sequence. The genomic segment is RNA, the sequence in SEQ ID NO: 4 is shown for DNA; however, exchanging all thymidines ("T") in SEQ ID NO: 4 for uridines ("U") provides the RNA sequence. | gcgcaccggg gatcctaggc attttttgttg cgcattttgt tgtgttattt gttgcacagc ccttcatcgt gggaccttca caaacaaacc aaaccaccag ccatgggcca aggcaagtcc aaagagggaa gggatgccag caatacgagc agagctgaaa ttctgccaga caccacctat ctcggacctc tgaactgcaa gtcatgctgg cagagatttg acagtttagt cagatgccat gaccactatc tctgcagaca ctgcctgaac ctcctgctgt cagtctccga caggtgccct ctctgcaaac atccattgcc aaccaaactg aaaatatcca cggccccaag ctctccaccc ccttacgagg agtgacgccc cgagccccaa caccgacaca aggaggccac caacacaacg cccaacacgg aacacacaca cacacaccca cacacacatc cacacacacg cgccccaca acggggggcgc cccccccgggg gtggcccccc gggtgctcgg gcggagcccc acggagaggc caattagtcg atctcctcga ccaccgactt ggtcagccag tcatcacagg acttgccctt aagtctgtac ttgcccacaa ctgtttcata catccacgtg ttctttgact tactgaaaca tagcctacag tcttttgaaag tgaaccagtc aggcacaagt gacagcggta ccagtagaat ggatctatct atacacaact cttggagaat tgtgctaatt tccgacccct gtagatgctc accagttctg aatcgatgta gaagaaggct cccaaggacg tcatcaaaat ttccataacc ctcgagctct gccaagaaaa ctctcatatc cttggtctcc agtttcacaa cgatgttctg aacaaggctt cttccctcaa aaagagcacc cattctcaca gtcaagggca caggctccca ttcaggccca atcctctcaa aatcaaggga tctgatcccg tccagtattt tccttgagcc tatcagctca agctcaagag agtcaccgag tatcaggggg tcctccatat agtcctcaaa ctcttcagac ctaatgtcaa aaacaccatc gttcaccttg aagatagagt ctgatctcaa caggtggagg cattcgtcca agaaccttct gtccacctca cctttaaaga ggtgagagca tgataggaac tcagctacac ctggaccttg taactggcac ttcactaaaa agatcaatga aaacttcctc aaacaatcag tgttattctg gttgtgagtg aaatctactg taattgagaa ctctagcact ccctctgtat tatttatcat gtaatcccac aagtttctca aagacttgaa tgcctttgga tttgtcaagc cttgtttgat tagcatggca gcattgcaca caatatctcc |

TABLE 1-continued

Sequences

| SEQ ID No. | Description | Sequence |
|---|---|---| caatcggtaa gagaaccatc caaatccaaa ttgcaagtca
ttcctaaaca tgggcctctc
catatttttg ttcactactt ttaagatgaa tgattggaaa
ggccccaatg cttcagcgcc
atcttcagat ggcatcatgt ctttatgagg gaaccatgaa
aaacttccta gagttctgct
tgttgctaca aattctcgta caaatgactc aaaatacact
tgttttaaaa agtttttgca
gacatccctt gtactaacga caaattcatc aacaaggctt
gagtcagagc gctgatggga
atttacaaga tcagaaaata gaacagtgta gtgttcgtcc
ctcttccact taactacatg
agaaatgagc gataaagatt ctgaattgat atcgatcaat
acgcaaaggt caaggaattt
gattctggga ctccatctca tgtttttga gctcatatca
gacatgaagg gaagcagctg
atcttcatag attttagggt acaatcgcct cacagattgg
attacatggt ttaaacttat
cttgtcctcc agtagccttg aactctcagg cttccttgct
acataatcac atgggttcaa
gtgcttgagg cttgagcttc cctcattctt ccctttcaca
ggttcagcta agacccaaac
acccaactca aaggaattac tcagtgagat gcaaatatag
tcccaaagga ggggcctcaa
gagactgatg tggtcgcagt gagcttctgg atgactttgc
ctgtcacaaa tgtacaacat
tatgccatca tgtctgtgga ttgctgtcac atgcgcatcc
atagctagat cctcaagcac
ttttctaatg tatagattgt ccctatttt atttctcaca
catctacttc ccaaagtttt
gcaaagacct ataaagcctg atgagatgca actttgaaag
gctgacttat tgattgcttc
tgacagcaac ttctgtgcac ctcttgtgaa cttactgcag
agcttgttct ggagtgtctt
gattaatgat gggattcttt cctcttggaa agtcattact
gatggataaa ccactttctg
cctcaagacc attcttaatg ggaacaactc attcaaattc
agccaattta tgtttgccaa
ttgacttaga tcctcttcga ggccaaggat gtttcccaac
tgaagaatgg cttccttttt
atccctattg aagaggtcta agaagaattc ttcattgaac
tcaccattct tgagcttatg
atgtagtctc cttacaagcc ttctcatgac cttcgtttca
ctaggacaca attcttcaat
aagcctttgg attctgtaac ctctagagcc atccaaccaa
tccttgacat cagtattagt
gttaagcaaa aatgggtcca agggaaagtt ggcatatttt
aagaggtcta atgttctctt
ctggatgcag tttaccaatg aaactggaac accatttgca
acagcttgat cggcaattgt
atctattgtt tcacagagtt ggtgtggctc tttacactta
acgttgtgta atgctgctga
cacaaatttt gttaaaagtg ggacctcttc cccccacaca
taaaatctgg atttaaattc
tgcagcaaat cgccccacca cactttcgg actgatgaac
ttgttaagca agccactcaa
atgagaatga aattccagca atacaaggac ttcctcaggg
tcactatcaa ccagttcact
caatctccta tcaaataagg tgatctgatc atcacttgat
gtgtaagatt ctggtctctc
accaaaaatg acaccgatac aataattaat gaatctctca
ctgattaagc cgtaaaagtc
agaggcatta tgtaagattc cctgtcccat gtcaatgaga
ctgcttatat gggaaggcac
tattcctaat tcaaaatatt ctcgaaagat tctttcagtc
acagttgtct ctgaacccct
aagaagtttc agctttgatt tgatatatga tttcatcatt
gcattcacaa caggaaaagg
gacctcaaca agtttgtgca tgtgccaagt taataaggtg
ctgatatgat cctttccgga
acgcacatac tggtcatcac ccagtttgag attttgaagg
agcattaaaa acaaaaatgg
gcacatcatt ggcccccatt tgctatgatc catactgtag
ttcaacaacc cctctcgcac

TABLE 1-continued

Sequences

| SEQ ID No. | Description | Sequence |
|---|---|---|
| | | attgatggtc attgatagaa ttgcattttc aaattctttg tcattgttta agcatgaacc tgagaagaag ctagaaaaag actcaaaata atcctctatc aatcttgtaa acattttgt tctcaaatcc ccaatataaa gttctctgtt tcctccaacc tgctctttgt atgataacgc aaacttcaac cttccggaat caggaccaac tgaagtgtat gacgttggtg actcctctga gtaaaaacat aaattcttta aagcagcact catgcatttt gtcaatgata gagccttact tagagactca gaattacttt ccctttcact aattctaaca tcttcttcta gtttgtccca gtcaaacttg aaattcagac cttgtctttg catgtgcctg tatttccctg agtatgcatt tgcattcatt tgcagtagaa tcattttcat acacgaaaac caatcaccct ctgaaaaaaa cttcctgcag aggttttttg ccatttcatc cagaccacat tgttctttga cagctgaagt gaaatacaat ggtgacagtt ctgtagaagt ttcaatagcc tcacagataa atttcatgtc atcattggtg agacaagatg ggtcaaaatc ttccacaaga tgaaaagaaa tttctgataa gatgaccttc cttaaatatg ccattttacc tgacaatata gtctgaaggt gatgcaatcc ttttgtattt tcaaacccca cctcattttc cccttcattg gtcttcttgc ttctttcata ccgcttttatt gtggagttga ccttatcttc taaattcttg aagaaacttg tctcttcttc cccatcaaag catatgtctg ctgagtcacc ttctagtttc ccagcttctg tttctttaga gccgataacc aatctagaga ccaactttga aaccttgtac tcgtaatctg agtggttcaa tttgtacttc tgctttctca tgaagctctc tgtgatctga ctcacagcac taacaagcaa tttgttaaaa tcatactcta ggagccgttc cccatttaaa tgtttgttaa caaccacact tttgttgctg gcaaggtcta atgctgttgc acacccagag ttagtcatgg gatccaagct attgagcctc ttctcccctt tgaaaatcaa agtgccattg ttgaatgagg acaccatcat gctaaaggcc tccagattga cacctggggt tgtgcgctga cagtcaactt cttttcccagt gaacttcttc atttggtcat aaaaaacaca ctcttcctca ggggtgattg actctttagg gttaacaaag aagccaaact cacttttagg ctcaaagaat ttctcaaagc atttaatttg atctgtcagc ctatcagggg tttcctttgt gattaaatga cacaggtatg acacattcaa catgaacttg aactttgcgc tcaacagtac cttttcacca gtcccaaaaa cagttttgat caaaaatctg agcaatttgt acactacttt ctcagcaggt gtgatcaaat cctccttcaa cttgtccatc aatgatgtgg atgagaagtc tgagacaatg gccatcacta aatacctaat gttttgaacc tgttttgat tcctctttgt tgggttggtg agcatgagta ataatagggt tctcaatgca atctcaacat catcaatgct gtccttcaag tcaggacatg atctgatcca tgagatcatg gtgtcaatca tgttgtgcaa cacttcatct gagaagattg gtaaaagaa ccttttggg tctgcataaa aagagattag atggccattg ggaccttgta tagaataaca ccttgaggat tctccagtct tttgatacag caggtgatat tcctcagagt ccaatttat cacttggcaa aatacctctt tacattccac cacttgatac cttacagagc ccaattggtt ttgtcttaat ctagcaactg aacttgtttt catactgttt gtcaaagcta gacagacaga tgacaatctt ttcaaactat gcatgttcct taattgttcc gtattaggct ggaaatcata atcttcaaac tttgtataat acattatagg atgagttccg gacctcatga aattctcaaa ctcaataaat ggtatgtggc actcatgctc aagatgttca gacagaccat agtgcccaaa |

TABLE 1-continued

Sequences

| SEQ ID No. | Description | Sequence |
|---|---|---|
| | | actaagtccc accactgaca agcacctttg aacttttaaa atgaactcat ttatggatgt tctaaacaaa tcctcaagag atacctttct atacgccttt gactttctcc tgttccttag aagtctgatg aactcttcct tggtgctatg aaagctcacc aacctatcat tcacactccc atagcaacaa ccaacccagt gcttatcatt ttttgaccct ttgagtttag actgtttgat caacgaagag agacacaaga catccaaatt cagtaactgt ctccttctgg tgttcaataa ttttaaactt ttaactttgt tcaacataga gaggagcctc tcatactcag tgctagtctc acttcctctc tcataaccat gggtatctgc tgtgataaat ctcatcaaag gacaggattc aactgcctcc ttgcttagtg ctgaaatgtc atcactgtca gcaagagtct cataaagctc agagaattcc ttaattaaat ttccggggtt gattttctga aaactcctct tgagcttccc agtttccaag tctcttctaa acctgctgta aagggagttt atgccaagaa ccacatcatc gcagttcatg tttgggttga caccatcatg gcacattttc ataatttcat cattgtgaaa tgatcttgca tctttcaaga ttttcataga gtctataccg gaacgcttat caacagtggt cttgagagat tcgcaaagtc tgaagtactc agattcctca aagactttct catcttggct agaatactct aaaagtttaa acagaaggtc tctgaacttg aaattcaccc actctggcat aaagctgtta tcataatcac accgaccatc cactattggg accaatgtga tacccgcaat ggcaaggtct tctttgatac aggctagttt attggtgtcc tctataaatt tcttctcaaa actagctggt gtgcttctaa cgaagcactc aagaagaatg agggaattgt caatcagttt ataaccatca ggaatgatca aaggcagtcc cgggcacaca atcccagact ctattagaat tgcctcaaca gatttatcat catggttgtg tatgcagccg ctcttgtcag cactgtctat ctctatacaa cgcgacaaaa gtttgagtcc ctctatcaat accattctgg gttctctttg ccctaaaaag ttgagcttct gccttgacaa cctctcatct tgttctatgt ggtttaagca caactctctc aactccgaaa tagcctcatc cattgcgcat caaaaagcct aggatcctcg gtgcg |
| 5 | Lymphocytic choriomeningitis strain MP segment S, complete sequence. The genomic segment is RNA, the sequence in SEQ ID NO: 5 is shown for DNA; however, exchanging all thymidines ("T") in SEQ ID NO: 5 for uridines ("U") provides the RNA sequence. | cgcaccgggg atcctaggct ttttggattg cgctttcctc agctccgtct tgtgggagaa tgggtcaaat tgtgacgatg tttgaggctc tgcctcacat cattgatgag gtcattaaca ttgtcattat cgtgcttatt atcatcacga gcatcaaagc tgtgtacaat ttcgccacct gcgggatact tgcattgatc agctttcttt ttctggctgg caggtcctgt ggaatgtatg gtcttgatgg gcctgacatt tacaaagggg tttaccgatt caagtcagtg gagtttgaca tgtcttacct taacctgacg atgcccaatg catgttcggc aaacaactcc catcattata taagtatggg gacttctgga ttggagttaa ccttcacaaa tgactccatc atcacccaca acttttgtaa tctgacttcc gccctcaaca agaggacttt tgaccacaca cttatgagta tagtctcaag tctgcacctc agcattagag gggtccccag ctacaaagca gtgtcctgtg attttaacaa tggcatcact attcaataca acctgtcatt ttctaatgca cagagcgctc tgagtcaatg taagcacttc aggggggagag tcctggatat gttcagaact gcttttggag gaaagtacat gaggagtggc tggggctgga caggttcaga tggcaagact acttggtgca gccagacaaa ctaccaatat ctgattatac aaaacaggac ttgggaaaac cactgcaggt acgcaggccc tttcggaatg tctagaattc tcttcgctca agaaaagaca aggtttctaa |

TABLE 1-continued

Sequences

| SEQ ID No. | Description | Sequence |
|---|---|---|
| | | ctagaaggct tgcaggcaca ttcacttgga ctttatcaga ctcatcagga gtggagaatc caggtggtta ctgcttgacc aagtggatga tcctcgctgc agagctcaag tgttttggga acacagctgt tgcaaagtgc aatgtaaatc atgatgaaga gttctgtgat atgctacgac tgattgatta caacaaggct gctttgagta aattcaaaga agatgtagaa tccgctctac atctgttcaa gacaacagtg aattctttga tttctgatca gcttttgatg agaaatcacc taagagactt gatgggagtg ccatactgca attactcgaa attctggtat ctagagcatg caaagactgg tgagactagt gtccccaagt gctggcttgt cagcaatggt tcttatttga atgaaaccca tttcagcgac caaattgagc aggaagcaga taatatgatc acagaaatgc tgagaaagga ctacataaaa aggcaaggga gtaccctct agccttgatg gatctattga tgttttctac atcagcatat ttgatcagca tctttctgca tcttgtgagg ataccaacac acagacacat aaagggcggc tcatgcccaa aaccacatcg gttaaccagc aagggaatct gtagttgtgg tgcatttaaa gtaccaggtg tggaaaccac ctggaaaaga cgctgaacag cagcgcctcc ctgactcacc acctcgaaag aggtggtgag tcagggaggc ccagagggtc ttagagtgtt acgacatttg gacctctgaa gattaggtca tgtggtagga tattgtggac agttttcagg tcggggagcc ttgccttgga ggcgctttca aagatgatac agtccatgag tgcacagtgt ggggtgacct cttctttt cttgtccctc actattccag tgtgcatctt gcatagccag ccatatttgt cccagacttt gtcctcatat tctcttgaag cttctttagt catctcaaca tcgatgagct taatgtctct tctgttttgt gaatctagga gtttcctgat gtcatcagat ccctgacaac ttaggaccat tccctgtgga agagcaccta ttactgaaga tgtcagccca ggttgtgcat tgaagaggtc agcaaggtcc atgccatgtg agtatttgga gtcctgcttg aattgttttt gatcagtggg ttctctatag aaatgtatgt actgcccatt ctgtggctga aatattgcta tttctaccgg gtcattaaat ctgccctcaa tgtcaatcca tgtaggagcg ttagggtcaa tacctcccat gaggtccttc agcaacattg tttggctgta gcttaagccc acctgaggtg ggcccgctgc cccaggcgct ggtttgggtg agttggccat aggcctctca tttgtcagat caattgttgt gttctcccat gctctcccta caactgatgt tctacaagct atgtatggcc acccctcccc tgaaagacag actttgtaga ggatgttctc gtaaggattc ctgtctccaa cctgatcaga aacaaacatg ttgagtttct tcttggcccc aagaactgct ttcaggagat cctcactgtt gcttggctta attaagatgg attccaacat gttaccccca tctaacaagg ctgccctgc tttcacagca gcaccgagac tgaaattgta gccagatatg ttgatgctag actgctgctc agtgatgact cccaagactg ggtgcttgtc tttcagcctt tcaaggtcac ttaggttcgg gtacttgact gtgtaaagca gcccaaggtc tgtgagtgct tgcacaacgt cattgagtga ggtttgtgat tgtttggcca tacaagccat tgttaagctt ggcattgtgc cgaattgatt gttcagaagt gatgagtcct tcacatccca gaccctcacc acaccatttg cactctgctg aggtctcctc attccaacca tttgcagaat ctgagatctt tggtcaagct gttgtgctgt taagttcccc atgtagactc cagaagttag aggcctttca gacctcatga ttttagcctt cagtttttca aggtcagctg caagggacat cagttcttct gcactaagcc tccctacttt tagaacattc ttttttgatg ttgactttag |

TABLE 1-continued

Sequences

| SEQ ID No. | Description | Sequence |
|---|---|---|
| | | gtccacaagg gaatacacag tttggttgag gcttctgagt ctctgtaaat ctttgtcatc cctcttctct ttcctcatga tcctctgaac attgctcacc tcagagaagt ctaatccatt cagaaggctg gtggcatcct tgatcacagc agctttcaca tctgatgtga agccttgaag ctctctcctc aatgcctggg tccattgaaa gcttttaact tctttggaca gagacatttt gtcactcagt ggatttccaa gtcaaatgcg caatcaaaat gcctaggatc cactgtgcg |
| 6 | Amino acid sequence of the NP protein of the MP strain of LCMV | Met Ser Leu Ser Lys Glu Val Lys Ser Phe Gln Trp Thr Gln Ala Leu Arg Arg Glu Leu Gln Gly Phe Thr Ser Asp Val Lys Ala Ala Val Ile Lys Asp Ala Thr Ser Leu Leu Asn Gly Leu Asp Phe Ser Glu Val Ser Asn Val Gln Arg Ile Met Arg Lys Glu Lys Arg Asp Asp Lys Asp Leu Gln Arg Leu Arg Ser Leu Asn Gln Thr Val Tyr Ser Leu Val Asp Leu Lys Ser Thr Ser Lys Lys Asn Val Leu Lys Val Gly Arg Leu Ser Ala Glu Glu Leu Met Ser Leu Ala Ala Asp Leu Glu Lys Leu Lys Ala Lys Ile Met Arg Ser Glu Arg Pro Leu Thr Ser Gly Val Tyr Met Gly Asn Leu Thr Ala Gln Gln Leu Asp Gln Arg Ser Gln Ile Leu Gln Met Val Gly Met Arg Arg Pro Gln Gln Ser Ala Asn Gly Val Val Arg Val Trp Asp Val Lys Asp Ser Ser Leu Leu Asn Asn Gln Phe Gly Thr Met Pro Ser Leu Thr Met Ala Cys Met Ala Lys Gln Ser Gln Thr Ser Leu Asn Asp Val Val Gln Ala Leu Thr Asp Leu Gly Leu Leu Tyr Thr Val Lys Tyr Pro Asn Leu Ser Asp Leu Glu Arg Leu Lys Asp Lys His Pro Val Leu Gly Val Ile Thr Glu Gln Gln Ser Ser Ile Asn Ile Ser Gly Tyr Asn Phe Ser Leu Gly Ala Ala Val Lys Ala Gly Ala Ala Leu Leu Asp Gly Gly Asn Met Leu Glu Ser Ile Leu Ile Lys Pro Ser Asn Ser Glu Asp Leu Leu Lys Ala Val Leu Gly Ala Lys Lys Lys Leu Asn Met Phe Val Ser Asp Gln Val Gly Asp Arg Asn Pro Tyr Glu Asn Ile Leu Tyr Lys Val Cys Leu Ser Gly Glu Gly Trp Pro Tyr Ile Ala Cys Arg Thr Ser Val Val Gly Arg Ala Trp Glu Asn Thr Thr Ile Asp Leu Thr Asn Glu Arg Pro Met Ala Asn Ser Pro Lys Pro Ala Pro Gly Ala Ala Gly Pro Pro Gln Val Gly Leu Ser Tyr Ser Gln Thr Met Leu Leu Lys Asp Leu Met Gly Gly Ile Asp Pro Asn Ala Pro Thr Trp Ile Asp Ile Glu Gly Arg Phe Asn Asp Pro Val Glu Ile Ala Ile Phe Gln Pro Gln Asn Gly Gln Tyr Ile His Phe Tyr Arg Glu Pro Thr Asp Gln Lys Gln Phe Lys Gln Asp Ser Lys Tyr Ser His Gly Met Asp Leu Ala Asp Leu Phe Asn Ala Gln Pro Gly Leu Thr Ser Ser Val Ile Gly Ala Leu Pro Gln Gly Met Val Leu Ser Cys Gln Gly Ser Asp Asp Ile Arg Lys Leu Leu Asp Ser Gln Asn Arg Arg Asp Ile Lys Leu Ile Asp Val Glu Met Thr Lys Glu Ala Ser Arg Glu Tyr Glu Asp Lys Val Trp Asp Lys Tyr Gly Trp Leu Cys Lys Met His Thr Gly Ile Val Arg Asp |

TABLE 1-continued

Sequences

| SEQ ID No. | Description | Sequence |
|---|---|---|
| | | Lys Lys Lys Lys |
| | | Glu Val Thr Pro His Cys Ala Leu Met Asp Cys Ile |
| | | Ile Phe Glu Ser |
| | | Ala Ser Lys Ala Arg Leu Pro Asp Leu Lys Thr Val |
| | | His Asn Ile Leu |
| | | Pro His Asp Leu Ile Phe Arg Gly Pro Asn Val Val |
| | | Thr Leu |
| 7 | Amino acid sequence of the GP protein of the MP strain of LCMV. | Met Gly Gln Ile Val Thr Met Phe Glu Ala Leu Pro His Ile Ile Asp |
| | | Glu Val Ile Asn Ile Val Ile Ile Val Leu Ile Ile Ile Thr Ser Ile |
| | | Lys Ala Val Tyr Asn Phe Ala Thr Cys Gly Ile Leu Ala Leu Ile Ser |
| | | Phe Leu Phe Leu Ala Gly Arg Ser Cys Gly Met Tyr Gly Leu Asp Gly |
| | | Pro Asp Ile Tyr Lys Gly Val Tyr Arg Phe Lys Ser Val Glu Phe Asp |
| | | Met Ser Tyr Leu Asn Leu Thr Met Pro Asn Ala Cys Ser Ala Asn Asn |
| | | Ser His His Tyr Ile Ser Met Gly Thr Ser Gly Leu Glu Leu Thr Phe |
| | | Thr Asn Asp Ser Ile Ile Thr His Asn Phe Cys Asn Leu Thr Ser Ala |
| | | Leu Asn Lys Arg Thr Phe Asp His Thr Leu Met Ser Ile Val Ser Ser |
| | | Leu His Leu Ser Ile Arg Gly Val Pro Ser Tyr Lys Ala Val Ser Cys |
| | | Asp Phe Asn Asn Gly Ile Thr Ile Gln Tyr Asn Leu Ser Phe Ser Asn |
| | | Ala Gln Ser Ala Leu Ser Gln Cys Lys Thr Phe Arg Gly Arg Val Leu |
| | | Asp Met Phe Arg Thr Ala Phe Gly Gly Lys Tyr Met Arg Ser Gly Trp |
| | | Gly Trp Thr Gly Ser Asp Gly Lys Thr Thr Trp Cys Ser Gln Thr Asn |
| | | Tyr Gln Tyr Leu Ile Ile Gln Asn Arg Thr Trp Glu Asn His Cys Arg |
| | | Tyr Ala Gly Pro Phe Gly Met Ser Arg Ile Leu Phe Ala Gln Glu Lys |
| | | Thr Arg Phe Leu Thr Arg Arg Leu Ala Gly Thr Phe Thr Trp Thr Leu |
| | | Ser Asp Ser Ser Gly Val Glu Asn Pro Gly Gly Tyr Cys Leu Thr Lys |
| | | Trp Met Ile Leu Ala Ala Glu Leu Lys Cys Phe Gly Asn Thr Ala Val |
| | | Ala Lys Cys Asn Val Asn His Asp Glu Glu Phe Cys Asp Met Leu Arg |
| | | Leu Ile Asp Tyr Asn Lys Ala Ala Leu Ser Lys Phe Lys Glu Asp Val |
| | | Glu Ser Ala Leu His Leu Phe Lys Thr Thr Val Asn Ser Leu Ile Ser |
| | | Asp Gln Leu Leu Met Arg Asn His Leu Arg Asp Leu Met Gly Val Pro |
| | | Tyr Cys Asn Tyr Ser Lys Phe Trp Tyr Leu Glu His Ala Lys Thr Gly |
| | | Glu Thr Ser Val Pro Lys Cys Trp Leu Val Ser Asn Gly Ser Tyr Leu |
| | | Asn Glu Thr His Phe Ser Asp Gln Ile Glu Gln Glu Ala Asp Asn Met |
| | | Ile Thr Glu Met Leu Arg Lys Asp Tyr Ile Lys Arg Gln Gly Ser Thr |
| | | Pro Leu Ala Leu Met Asp Leu Leu Met Phe Ser Thr Ser Ala Tyr Leu |
| | | Ile Ser Ile Phe Leu His Leu Val Arg Ile Pro Thr His Arg His Ile |
| | | Lys Gly Gly Ser Cys Pro Lys Pro His Arg Leu Thr Ser Lys Gly Ile |
| | | Cys Ser Cys Gly Ala Phe Lys Val Pro Gly Val Glu Thr Thr Trp Lys |
| | | Arg Arg |

TABLE 1-continued

Sequences

| SEQ ID No. | Description | Sequence |
|---|---|---|
| 8 | Amino acid sequence of the L protein of the MPstrain of LCMV. | Met Asp Glu Ala Ile Ser Glu Leu Arg Glu Leu Cys Leu Asn His Ile Glu Gln Asp Glu Arg Leu Ser Arg Gln Lys Leu Asn Phe Leu Gly Gln Arg Glu Pro Arg Met Val Leu Ile Glu Gly Leu Lys Leu Leu Ser Arg Cys Ile Glu Ile Asp Ser Ala Asp Lys Ser Gly Cys Ile His Asn His Asp Asp Lys Ser Val Glu Ala Ile Leu Ile Glu Ser Gly Ile Val Cys Pro Gly Leu Pro Leu Ile Ile Pro Asp Gly Tyr Lys Leu Ile Asp Asn Ser Leu Ile Leu Leu Glu Cys Phe Val Arg Ser Thr Pro Ala Ser Phe Glu Lys Lys Phe Ile Glu Asp Thr Asn Lys Leu Ala Cys Ile Lys Glu Asp Leu Ala Ile Ala Gly Ile Thr Leu Val Pro Ile Val Asp Gly Arg Cys Asp Tyr Asp Asn Ser Phe Met Pro Glu Trp Val Asn Phe Lys Phe Arg Asp Leu Leu Phe Lys Leu Leu Glu Tyr Ser Ser Gln Asp Glu Lys Val Phe Glu Glu Ser Glu Tyr Phe Arg Leu Cys Glu Ser Leu Lys Thr Thr Val Asp Lys Arg Ser Gly Ile Asp Ser Met Lys Ile Leu Lys Asp Ala Arg Ser Phe His Asn Asp Glu Ile Met Lys Met Cys His Asp Gly Val Asn Pro Asn Met Asn Cys Asp Asp Val Val Leu Gly Ile Asn Ser Leu Tyr Ser Arg Phe Arg Arg Asp Leu Glu Thr Gly Lys Leu Lys Arg Ser Phe Gln Lys Ile Asn Pro Gly Asn Leu Ile Lys Glu Phe Ser Glu Leu Tyr Glu Thr Leu Ala Asp Ser Asp Asp Ile Ser Ala Leu Ser Lys Glu Ala Val Glu Ser Cys Pro Leu Met Arg Phe Ile Thr Ala Asp Thr His Gly Tyr Glu Arg Gly Ser Glu Thr Ser Thr Glu Tyr Glu Arg Leu Leu Ser Met Leu Asn Lys Val Lys Ser Leu Lys Leu Leu Asn Thr Arg Arg Arg Gln Leu Leu Asn Leu Asp Val Leu Cys Leu Ser Ser Leu Ile Lys Gln Ser Lys Leu Lys Gly Ser Lys Asn Asp Lys His Trp Val Gly Cys Cys Tyr Gly Ser Val Asn Asp Arg Leu Val Ser Phe His Ser Thr Lys Glu Glu Phe Ile Arg Leu Leu Arg Asn Arg Arg Lys Ser Lys Ala Tyr Arg Lys Val Ser Leu Glu Asp Leu Phe Arg Thr Ser Ile Asn Glu Phe Ile Leu Lys Val Gln Arg Cys Leu Ser Val Val Gly Leu Ser Phe Gly His Tyr Gly Leu Ser Glu His Leu Glu His Glu Cys His Ile Pro Phe Ile Glu Phe Glu Asn Phe Met Arg Ser Gly Thr His Pro Ile Met Tyr Tyr Thr Lys Phe Glu Asp Tyr Asp Phe Gln Pro Asn Thr Glu Gln Leu Arg Asn Met His Ser Leu Lys Arg Leu Ser Ser Val Cys Leu Ala Leu Thr Asn Ser Met Lys Thr Ser Ser Val Ala Arg Leu Arg Gln Asn Gln Leu Gly Ser Val Arg Tyr Gln Val Val Glu Cys Lys Glu Val Phe Cys Gln Val Ile Lys Leu Asp Ser Glu Glu Tyr His Leu Leu Tyr Gln Lys Thr Gly Glu Ser Ser Arg Cys Tyr Ser Ile Gln Gly Pro Asn Gly His Leu Ile Ser Phe Tyr Ala Asp Pro Lys Arg Phe Phe Leu Pro Ile Phe Ser Asp Glu Val Leu His Asn Met Ile Asp Thr |

TABLE 1-continued

Sequences

| SEQ ID No. | Description | Sequence |
|---|---|---|
| | | Met Ile Ser Trp
Ile Arg Ser Cys Pro Asp Leu Lys Asp Ser Ile Asp
Asp Val Glu Ile
Ala Leu Arg Thr Leu Leu Leu Leu Met Leu Thr Asn
Pro Thr Lys Arg
Asn Gln Lys Gln Val Gln Asn Ile Arg Tyr Leu Val
Met Ala Ile Val
Ser Asp Phe Ser Ser Thr Ser Leu Met Asp Lys Leu
Lys Glu Asp Leu
Ile Thr Pro Ala Glu Lys Val Val Tyr Lys Leu Leu
Arg Phe Leu Ile
Lys Thr Val Phe Gly Thr Gly Glu Lys Val Leu Leu
Ser Ala Lys Phe
Lys Phe Met Leu Asn Val Ser Tyr Leu Cys His Leu
Ile Thr Lys Glu
Thr Pro Asp Arg Leu Thr Asp Gln Ile Lys Cys Phe
Glu Lys Phe Phe
Glu Pro Lys Ser Glu Phe Gly Phe Phe Val Asn Pro
Lys Glu Ser Ile
Thr Pro Glu Glu Glu Cys Val Phe Tyr Asp Gln Met
Lys Lys Phe Thr
Gly Lys Glu Val Asp Cys Gln Arg Thr Thr Pro Gly
Val Asn Leu Glu
Ala Phe Ser Met Met Val Ser Ser Phe Asn Asn Gly
Thr Leu Ile Phe
Lys Gly Glu Lys Arg Leu Asn Ser Leu Asp Pro Met
Thr Asn Ser Gly
Cys Ala Thr Ala Leu Asp Leu Ala Ser Asn Lys Ser
Val Val Val Asn
Lys His Leu Asn Gly Glu Arg Leu Leu Glu Tyr Asp
Phe Asn Lys Leu
Leu Val Ser Ala Val Ser Gln Ile Thr Glu Ser Phe
Met Arg Lys Gln
Lys Tyr Lys Leu Asn His Ser Asp Tyr Glu Tyr Lys
Val Ser Lys Leu
Val Ser Arg Leu Val Ile Gly Ser Lys Glu Thr Glu
Ala Gly Lys Leu
Glu Gly Asp Ser Ala Asp Ile Cys Phe Asp Gly Glu
Glu Glu Thr Ser
Phe Phe Lys Asn Leu Glu Asp Lys Val Asn Ser Thr
Ile Lys Arg Tyr
Glu Arg Ser Lys Lys Thr Asn Glu Gly Glu Asn Glu
Val Gly Phe Glu
Asn Thr Lys Gly Leu His His Leu Gln Thr Ile Leu
Ser Gly Lys Met
Ala Tyr Leu Arg Lys Val Ile Leu Ser Glu Ile Ser
Phe His Leu Val
Glu Asp Phe Asp Pro Ser Cys Leu Thr Asn Asp Asp
Met Lys Phe Ile
Cys Glu Ala Ile Glu Thr Ser Thr Glu Leu Ser Pro
Leu Tyr Phe Thr
Ser Ala Val Lys Glu Gln Cys Gly Leu Asp Glu Met
Ala Lys Asn Leu
Cys Arg Lys Phe Phe Ser Glu Gly Asp Trp Phe Ser
Cys Met Lys
Met Ile Leu Leu Gln Met Asn Ala Asn Ala Tyr Ser
Gly Lys Tyr
Arg His Met Gln Arg Gln Gly Leu Asn Phe Lys Phe
Asp Trp Asp
Lys Leu Glu Glu Asp Val Arg Ile Ser Glu Arg Glu
Ser Asn Ser
Glu Ser Leu Ser Lys Ala Leu Ser Leu Thr Lys Cys
Met Ser Ala
Ala Leu Lys Asn Leu Cys Phe Tyr Ser Glu Glu Ser
Pro Thr Ser
Tyr Thr Ser Val Gly Pro Asp Ser Gly Arg Leu Lys
Phe Ala Leu
Ser Tyr Lys Glu Gln Val Gly Gly Asn Arg Glu Leu
Tyr Ile Gly
Asp Leu Arg Thr Lys Met Phe Thr Arg Leu Ile Glu
Asp Tyr Phe
Glu Ser Phe Ser Ser Phe Phe Ser Gly Ser Cys Leu
Asn Asn Asp
Lys Glu Phe Glu Asn Ala Ile Leu Ser Met Thr Ile |

TABLE 1-continued

Sequences

| SEQ ID No. | Description | Sequence |
|---|---|---|
| | | Asn Val Arg
Glu Gly Leu Leu Asn Tyr Ser Met Asp His Ser Lys Trp Gly Pro
Met Met Cys Pro Phe Leu Phe Leu Met Leu Leu Gln Asn Leu Lys
Leu Gly Asp Asp Gln Tyr Val Arg Ser Gly Lys Asp His Ile Ser
Thr Leu Leu Thr Trp His Met His Lys Leu Val Glu Val Pro Phe
Pro Val Val Asn Ala Met Met Lys Ser Tyr Ile Lys Ser Lys Leu
Lys Leu Leu Arg Gly Ser Glu Thr Thr Val Thr Glu Arg Ile Phe
Arg Glu Tyr Phe Glu Leu Gly Ile Val Pro Ser His Ile Ser Ser
Leu Ile Asp Met Gly Gln Gly Ile Leu His Asn Ala Ser Asp Phe
Tyr Gly Leu Ile Ser Glu Arg Phe Ile Asn Tyr Cys Ile Gly Val
Ile Phe Gly Glu Arg Pro Glu Ser Tyr Thr Ser Ser Asp Asp Gln
Ile Thr Leu Phe Asp Arg Arg Leu Ser Glu Leu Val Asp Ser Asp
Pro Glu Glu Val Leu Val Leu Leu Glu Phe His Ser His Leu Ser
Gly Leu Leu Asn Lys Phe Ile Ser Pro Lys Ser Val Val Gly Arg
Phe Ala Ala Glu Phe Lys Ser Arg Phe Tyr Val Trp Gly Glu Glu
Val Pro Leu Leu Thr Lys Phe Val Ser Ala Ala Leu His Asn Val
Lys Cys Lys Glu Pro His Gln Leu Cys Glu Thr Ile Asp Thr Ile
Ala Asp Gln Ala Val Ala Asn Gly Val Pro Val Ser Leu Val Asn
Cys Ile Gln Lys Arg Thr Leu Asp Leu Leu Lys Tyr Ala Asn Phe
Pro Leu Asp Pro Phe Leu Leu Asn Thr Asn Thr Asp Val Lys Asp
Trp Leu Asp Gly Ser Arg Gly Tyr Arg Ile Gln Arg Leu Ile Glu
Glu Leu Cys Pro Ser Glu Thr Lys Val Met Arg Arg Leu Val Arg
Arg Leu His His Lys Leu Lys Asn Gly Glu Phe Asn Glu Glu Phe
Phe Leu Asp Leu Phe Asn Arg Asp Lys Lys Glu Ala Ile Leu Gln
Leu Gly Asn Ile Leu Gly Leu Glu Glu Asp Leu Ser Gln Leu Ala
Asn Ile Asn Trp Leu Asn Leu Asn Glu Leu Phe Pro Leu Arg Met
Val Leu Arg Gln Lys Val Val Tyr Pro Ser Val Met Thr Phe Gln
Glu Glu Arg Ile Pro Ser Leu Ile Lys Thr Leu Gln Asn Lys Leu
Cys Ser Lys Phe Thr Arg Gly Ala Gln Lys Leu Leu Ser Glu Ala
Ile Asn Lys Ser Ala Phe Gln Ser Cys Ile Ser Ser Gly Phe Ile
Gly Leu Cys Lys Thr Leu Gly Ser Arg Cys Val Arg Asn Lys Asn
Arg Asp Asn Leu Tyr Ile Arg Lys Val Leu Glu Asp Leu Ala Met
Asp Ala His Val Thr Ala Ile His Arg His Asp Gly Ile Met Leu
Tyr Ile Cys Asp Arg Gln Ser His Pro Glu Ala His Cys Asp His
Ile Ser Leu Leu Arg Pro Leu Leu Trp Asp Tyr Ile Cys Ile Ser
Leu Ser Asn Ser Phe Glu Leu Gly Val Trp Val Leu Ala Glu Pro
Val Lys Gly Lys Asn Glu Gly Ser Ser Leu Lys His Leu Asn
Pro Cys Asp Tyr Val Ala Arg Lys Pro Glu Ser Ser |

TABLE 1-continued

Sequences

| SEQ ID No. | Description | Sequence |
|---|---|---|
| | | Arg Leu Leu<br>Glu Asp Lys Ile Ser Leu Asn His Val Ile Gln Ser<br>Val Arg Arg<br>Leu Tyr Pro Lys Ile Tyr Glu Asp Gln Leu Leu Pro<br>Phe Met Ser<br>Asp Met Ser Ser Lys Asn Met Arg Trp Ser Pro Arg<br>Ile Lys Phe<br>Leu Asp Leu Cys Val Leu Ile Asp Ile Asn Ser Glu<br>Ser Leu Ser<br>Leu Ile Ser His Val Val Lys Trp Lys Arg Asp Glu<br>His Tyr Thr<br>Val Leu Phe Ser Asp Leu Val Asn Ser His Gln Arg<br>Ser Asp Ser<br>Ser Leu Val Asp Glu Phe Val Val Ser Thr Arg Asp<br>Val Cys Lys<br>Asn Phe Leu Lys Gln Val Tyr Phe Glu Ser Phe Val<br>Arg Glu Phe<br>Val Ala Thr Ser Arg Thr Leu Gly Ser Phe Ser Trp<br>Phe Pro His<br>Lys Asp Met Met Pro Ser Glu Asp Gly Ala Glu Ala<br>Leu Gly Pro<br>Phe Gln Ser Phe Ile Leu Lys Val Val Asn Lys Asn<br>Met Glu Arg<br>Pro Met Phe Arg Asn Asp Leu Gln Phe Gly Phe Gly<br>Trp Phe Ser<br>Tyr Arg Leu Gly Asp Ile Val Cys Asn Ala Ala Met<br>Leu Ile Lys<br>Gln Gly Leu Thr Asn Pro Lys Ala Phe Lys Ser Leu<br>Arg Asn Leu<br>Trp Asp Tyr Met Ile Asn Asn Thr Glu Gly Val Leu<br>Glu Phe Ser<br>Ile Thr Val Asp Phe Thr His Asn Gln Asn Asn Thr<br>Asp Cys Leu<br>Arg Lys Phe Ser Leu Ile Phe Leu Val Lys Cys Gln<br>Leu Gln Gly<br>Pro Gly Val Ala Glu Phe Leu Ser Cys Ser His Leu<br>Phe Lys Gly<br>Glu Val Asp Arg Arg Phe Leu Asp Glu Cys Leu His<br>Leu Leu Arg<br>Ser Asp Ser Ile Phe Lys Val Asn Asp Gly Val Phe<br>Asp Ile Arg<br>Ser Glu Glu Phe Glu Asp Tyr Met Glu Asp Pro Leu<br>Ile Leu Gly<br>Asp Ser Leu Glu Leu Glu Leu Ile Gly Ser Arg Lys<br>Ile Leu Asp<br>Gly Ile Arg Ser Leu Asp Phe Glu Arg Ile Gly Pro<br>Glu Trp Glu<br>Pro Val Pro Leu Thr Val Arg Met Gly Ala Leu Phe<br>Glu Gly Arg<br>Ser Leu Val Gln Asn Ile Val Val Lys Leu Glu Thr<br>Lys Asp Met<br>Arg Val Phe Leu Ala Glu Leu Glu Gly Tyr Gly Asn<br>Phe Asp Asp<br>Val Leu Gly Ser Leu Leu His Arg Phe Arg Thr<br>Gly Glu His<br>Leu Gln Gly Ser Glu Ile Ser Thr Ile Leu Gln Glu<br>Leu Cys Ile<br>Asp Arg Ser Ile Leu Leu Val Pro Leu Ser Leu Val<br>Pro Asp Trp<br>Phe Thr Phe Lys Asp Cys Arg Leu Cys Phe Ser Lys<br>Ser Lys Asn<br>Thr Val Met Tyr Glu Thr Val Val Gly Lys Tyr Arg<br>Leu Lys Gly<br>Lys Ser Cys Asp Asp Trp Leu Thr Lys Ser Val Val<br>Glu Glu Ile<br>Asp |
| 9 | Amino acid sequence of the Z protein of the MP strain of LCMV. | Met Gly Gln Gly Lys Ser Lys Glu Gly Arg Asp Ala<br>Ser Asn Thr Ser<br>Arg Ala Glu Ile Leu Pro Asp Thr Thr Tyr Leu Gly<br>Pro Leu Asn Cys<br>Lys Ser Cys Trp Gln Arg Phe Asp Ser Leu Val Arg<br>Cys His Asp His<br>Tyr Leu Cys Arg His Cys Leu Asn Leu Leu Leu Ser |

TABLE 1-continued

Sequences

| SEQ ID No. | Description | Sequence |
|---|---|---|
| | | Val Ser Asp Arg<br>Cys Pro Leu Cys Lys His Pro Leu Pro Thr Lys Leu<br>Lys Ile Ser Thr<br>Ala Pro Ser Ser Pro Pro Pro Tyr Glu Glu |
| 10 | Amino acid sequence of HPV16 E7/E6 fusion protein with mutations in Rb binding site and zinc finger motifs. | MHGDTPTLHEYMLDLQPETTDLYGYGQLNDSSEEEDEIDGPAGQAEPDRA<br>HYNIVTFCCKCDSTLRLCVQSTHVDIRTLEDLLMGTLGIVGPICSQKPHQ<br>KRTAMFQDPQERPRKLPQLCTELQTTIHDIILECVYCKQQLLRREVYDFA<br>FRDLCIVYRDGNPYAVGDKCLKFYSKISEYRHYCYSLYGTTLEQQYNKPL<br>CDLLIRCINGQKPLCPEEKQRHLDKKQR<br>FHNIRGRWTGRCMSCCRSSRTRRETQL |
| 11 | Amino acid sequence of HPV16 E7/E6 fusion protein with mutations in Rb binding site and zinc finger motifs, linked to mouse Calreticulin | MHGDTPTLHEYMLDLQPETTDLYGYGQLNDSSEEEDEIDGPAGQAEPDRA<br>HYNIVTFCCKCDSTLRLCVQSTHVDIRTLEDLLMGTLGIVGPICSQKPHQ<br>KRTAMFQDPQERPRKLPQLCTELQTTIHDIILECVYCKQQLLRREVYDFA<br>FRDLCIVYRDGNPYAVGDKCLKFYSKISEYRHYCYSLYGTTLEQQYNKPL<br>CDLLIRCINGQKPLCPEEKQRHLDKKQRFHNIRGRWTGRCMSCCRSSRTR<br>RETQLLLSVPLLLGLLGLAAADPAIYFKEQFLDGDAWTNRWVESKHKSDF<br>GKFVLSSGKFYGDLEKDKGLQTSQDARFYALSAKFEPFSNKGQTLVVQFT<br>VKHEQNIDCGGGYVKLFPSGLDQKDMHGDSEYNIMFGPDICGPGTKKVHV<br>IFNYKGKNVLINKDIRCKDDEFTHLYTLIVRPDNTYEVKIDNSQVESGSL<br>EDDWDFLPPKKIKDPDAAKPEDWDERAKIDDPTDSKPEDWDKPEHIPDPD<br>AKKPEDWDEEMDGEWEPPVIQNPEYKGEWKPRQIDNPDYKGTWIHPEIDN<br>PEYSPDANIYAYDSFAVLGLDLWQVKSGTIFDNFLITNDEAYAEEFGNET<br>WGVTKAAEKQMKDKQDEEQRLKEEEEDKKRKEEEEAEDKEDDDDRDEDED<br>EEDEKEEDEEESPGQAKDEL |
| 12 | Amino acid sequence of HPV16 E7/E6 fusion protein with mutations in Rb binding site and zinc finger motifs, linked to mouse Ubiquitin | MHGDTPTLHEYMLDLQPETTDLYGYGQLNDSSEEEDEIDGPAGQAEPDRA<br>HYNIVTFCCKCDSTLRLCVQSTHVDIRTLEDLLMGTLGIVGPICSQKPHQ<br>KRTAMFQDPQERPRKLPQLCTELQTTIHDIILECVYCKQQLLRREVYDFA<br>FRDLCIVYRDGNPYAVGDKCLKFYSKISEYRHYCYSLYGTTLEQQYNKPL<br>CDLLIRCINGQKPLCPEEKQRHLDKKQRFHNIRGRWTGRCMSCCRSSRTR<br>RETQLQIFVKTLTGKTITLEVEPSDTIENVKAKIQDKEGIPPDQQRLIFA<br>GKQLEDGRTLSDYNIQKESTLHLVLRLRGA |
| 13 | Amino acid sequence of HPV16 E7/E6 fusion protein with mutations in Rb binding site and zinc finger motifs, co-expressed with mouse GM-CSF, separated by a nucleotide sequence that encodes a self-cleaving peptide (2A peptide) | MHGDTPTLHEYMLDLQPETTDLYGYGQLNDSSEEEDEIDGPAGQAEPDRA<br>HYNIVTFCCKCDSTLRLCVQSTHVDIRTLEDLLMGTLGIVGPICSQKPHQ<br>KRTAMFQDPQERPRKLPQLCTELQTTIHDIILECVYCKQQLLRREVYDFA<br>FRDLCIVYRDGNPYAVGDKCLKFYSKISEYRHYCYSLYGTTLEQQYNKPL<br>CDLLIRCINGQKPLCPEEKQRHLDKKQRFHNIRGRWTGRCMSCCRSSRTR<br>RETQLGSGATNFSLLKQAGDVEENPGPWLQNLLFLGIVVYSLSAPTRSPI<br>TVTRPWKHVEAIKEALNLLDDMPVTLNEEVEVVSNEFSFKKLTCVQTRLK<br>IFEQGLRGNFTKLKGALNMTASYYQTYCPPTPETDCETQVTTYADFIDSL<br>KTFLTDIPFECKKPVQK |
| 14 | Nucleotide sequence encoding HPV16 E7/E6 fusion protein with mutations in Rb binding site and zinc finger motifs | ATGCACGGCGACACCCCTACCCTGCACGAGTACATGCTGGACCTGCAGCC<br>CGAGACAACCGACCTGTACGGCTACGGCCAGCTGAACGACAGCAGCGAGG<br>AAGAGGACGAGATCGACGGCCCTGCTGGACAGGCCGAACCTGACAGAGCC<br>CACTACAACATCGTGACATTCTGCTGCAAGTGCGACAGCACCCTGAGACT<br>GTGCGTGCAGAGCACCCACGTGGACATCAGAACCCTGGAAGATCTGCTGA<br>TGGGCACCCTGGGCATCGTGGGCCCTATCTGCTCTCAGAAGCCCCACCAG<br>AAAAAGAACCGCCATGTTCCAGGACCCCCAGGAAAGACCCAGAAAGCTGCC<br>CCAGCTGTGCACCGAGCTGCAGACCACCATCCACGACATCATCCTGGAAT<br>GCGTGTACTGCAAGCAGCAGCTGCTGAGAAGAGAGGTGTACGACTTCGCC<br>TTCCGGGACCTGTGCATCGTGTACAGGGACGGCAACCCTTACGCCGTGGG<br>CGACAAGTGCCTGAAGTTCTACAGCAAGATCAGCGAGTACCGGCACTACT<br>GCTACAGCCTGTACGGAACCACCCTGGAACAGCAGTACAACAAGCCCCTG<br>TGCGACCTGCTGATCAGATGCATCAACGGCCAGAAACCCTGTGCCCCGA<br>GGAAAAGCAGAGACACCTGGACAAGAAGCAGCGGTTCCACAACATCGAG<br>GCAGATGGACCGGCAGATGCATGAGCTGTTGCAGAAGCAGCAGAACCAGA<br>CGCGAGACTCAGCTGTGA |
| 15 | Nucleotide sequence encoding HPV16 E7/E6 fusion protein with mutations in Rb binding site and zinc finger motifs, linked to mouse Calreticulin | ATGCACGGCGACACCCCTACCCTGCACGAGTACATGCTGGACCTGCAGCC<br>CGAGACAACCGACCTGTACGGCTACGGCCAGCTGAACGACAGCAGCGAGG<br>AAGAGGACGAGATCGACGGCCCTGCTGGACAGGCCGAACCTGACAGAGCC<br>CACTACAACATCGTGACATTCTGCTGCAAGTGCGACAGCACCCTGAGACT<br>GTGCGTGCAGAGCACCCACGTGGACATCAGAACCCTGGAAGATCTGCTGA<br>TGGGCACCCTGGGCATCGTGGGCCCTATCTGCTCTCAGAAGCCCCACCAG<br>AAAAAGAACCGCCATGTTCCAGGACCCCCAGGAAAGACCCAGAAAGCTGCC<br>CCAGCTGTGCACCGAGCTGCAGACCACCATCCACGACATCATCCTGGAAT<br>GCGTGTACTGCAAGCAGCAGCTGCTGAGAAGAGAGGTGTACGACTTCGCC<br>TTCCGGGACCTGTGCATCGTGTACAGGGACGGCAACCCTTACGCCGTGGG |

TABLE 1-continued

Sequences

| SEQ ID No. | Description | Sequence |
|---|---|---|
| | | CGACAAGTGCCTGAAGTTCTACAGCAAGATCAGCGAGTACCGGCACTACT<br>GCTACAGCCTGTACGGAACCACCCTGGAACAGCAGTACAACAAGCCCCTG<br>TGCGACCTGCTGATCAGATGCATCAACGGCCAGAAACCCCTGTGCCCCGA<br>GGAAAAGCAGAGACACCTGGACAAGAAGCAGCGGTTCCACAACATCAGAG<br>GCAGATGGACCGGCAGATGCATGAGCTGTTGCAGAAGCAGCAGAACCAGA<br>AGAGAGAGACACAGCTGCTGCTGTCCGTGCCCCTGCTGCTGGGCCTGCTGGG<br>ACTGGCTGCTGCAGATCCCGCCATCTACTTCAAAGAGCAGTTCCTGGACG<br>GCGACGCCTGGACCAACAGATGGGTGGAAAGCAAGCACAAGAGCGACTTC<br>GGCAAGTTCGTGCTGAGCAGCGGCAAGTTTTACGGCGACCTGGAAAAGGA<br>CAAGGGCCTGCAGACAAGCCAGGACGCCAGATTCTACGCCCTGAGCGCCA<br>AGTTCGAGCCCTTCAGCAACAAGGGCCAGACCCTGGTGGTGCAGTTCACC<br>GTGAAGCACGAGCAGAACATCGACTGCGGCGGAGGCTACGTGAAGCTGTT<br>CCCTAGCGGCCTGGATCAGAAAGACATGCACGGGGACTCCGAGTACAACA<br>TCATGTTCGGCCCCGACATCTGCGGCCCTGGCACCAAGAAAGTGCACGTG<br>ATCTTCAACTACAAGGGCAAGAACGTGCTGATCAACAAGGACATCAGGTG<br>CAAGGACGACGAGTTCACCCACCTGTACACCCTGATCGTGCGGCCCGACA<br>ACACCTACGAAGTGAAGATCGACAACAGCCAGGTGGAATCCGGCTCTCTG<br>GAAGATGACTGGGACTTCCTGCCCCCCAAGAAGATCAAGGACCCCGACGC<br>CGCCAAGCCCGAGGACTGGGATGAGAGAGCCAAGATCGACGACCCCACCG<br>ACAGCAAGCCTGAAGATTGGGACAAGCCTGAGCACATCCCCGACCCAGAC<br>GCCAAGAAGCCAGAGGATTGGGACGAAGAGATGGACGGGGAGTGGGAGCC<br>CCCCGTGATCCAGAACCCAGAGTACAAGGGCGAGTGGAAGCCCAGACAGA<br>TCGATAACCCCGACTATAAGGGCACCTGGATCCACCCCGAAATCGACAAC<br>CCTGAGTACTCCCCTGACGCCAACATCTACGCCTACGACAGCTTCGCCGT<br>GCTGGGGCTGGATCTGTGGCAAGTGAAGTCCGGAACAATTCTTCGACAACT<br>TCCTGATCACCAACGACGAGGCCTACGCCGAGGAATTCGGCAACGAGACA<br>TGGGGCGTGACCAAGGCCGCCGAGAAGCAGATGAAGGACAAGCAGGATGA<br>GGAACAGCGCCTGAAAGAGGAAGAAGAGGATAAGAAGCGCAAAGAAGAGG<br>AAGAGGCCGAGGACAAAGAGGACGACGACGACAGGGACGAGGACGAGGAT<br>GAAGAAGATGAGAAAGAAGAGGACGAAGAAGAGTCCCCAGGCCAGGCCAA<br>GGACGAGCTGTGATGA |
| 16 | Nucleotide sequence encoding HPV16 E7/E6 fusion protein with mutations in Rb binding site and zinc finger motifs, linked to mouse Ubiquitin | ATGCACGGCGACACCCCTACCCTGCACGAGTACATGCTGGACCTGCAGCC<br>CGAGACAACCGACCTGTACGGCTACGGCCAGCTGAACGACAGCAGCGAGG<br>AAGAGGACGAGATCGACGGCCCTGCTGGACAGGCCGAACCTGACAGAGCC<br>CACTACAACATCGTGACATTCTGCTGCAAGTGCGACAGCACCCTGAGACT<br>GTGCGTGCAGAGCACCCACGTGGACATCAGAACCCTGGAAGATCTGCTGA<br>TGGGCACCCTGGGCATCGTGGGCCCTATCTGCTCTCAGAAGCCCCACCAG<br>AAAAGAACCGCCATGTTCCAGGACCCCCAGGAAAGACCCAGAAAGCTGCC<br>CCAGCTGTGCACCGAGCTGCAGACCACCATCCACGACATCATCCTGGAAT<br>GCGTGTACTGCAAGCAGCAGCTGCTGAGAAGAGAGGTGTACGACTTCGCC<br>TTCCGGGACCTGTGCATCGTGTACAGGGACGGCAACCCTTACGCCGTGGG<br>CGACAAGTGCCTGAAGTTCTACAGCAAGATCAGCGAGTACCGGCACTACT<br>GCTACAGCCTGTACGGAACCACCCTGGAACAGCAGTACAACAAGCCCCTG<br>TGCGACCTGCTGATCAGATGCATCAACGGCCAGAAACCCCTGTGCCCCGA<br>GGAAAAGCAGAGACACCTGGACAAGAAGCAGCGGTTCCACAACATCAGAG<br>GCAGATGGACCGGCAGATGCATGAGCTGTTGCAGAAGCAGCAGAACCAGA<br>AGAGAGAGACACAGCTGCAGATCTTTGTGAAAACCCTGACCGGCAAGACCAT<br>CACACTGGAAGTGGAACCCAGCGACACCATCGAGAACGTGAAGGCCAAGA<br>TCCAGGACAAAGAGGGCATCCCCCCCGACCAGCAGAGACTGATCTTCGCC<br>GGGAAAGCAGCTGGAAGATGGCAGGACCCTGAGCGATTACAACATCCAGAA<br>AGAGTCCACCCTGCACCTGGTGCTGAGACTGAGAGGCGCCTGA |
| 17 | Nucleotide sequence encoding HPV16 E7/E6 fusion protein with mutations in Rb binding site and zinc finger motifs, co-expressed with mouse GM-CSF, separated by a nucleotide sequence that encodes a self-cleaving peptide (2A peptide) | ATGCACGGCGACACCCCTACCCTGCACGAGTACATGCTGGACCTGCAGCC<br>CGAGACAACCGACCTGTACGGCTACGGCCAGCTGAACGACAGCAGCGAGG<br>AAGAGGACGAGATCGACGGCCCTGCTGGACAGGCCGAACCTGACAGAGCC<br>CACTACAACATCGTGACATTCTGCTGCAAGTGCGACAGCACCCTGAGACT<br>GTGCGTGCAGAGCACCCACGTGGACATCAGAACCCTGGAAGATCTGCTGA<br>TGGGCACCCTGGGCATCGTGGGCCCTATCTGCTCTCAGAAGCCCCACCAG<br>AAAAGAACCGCCATGTTCCAGGACCCCCAGGAAAGACCCAGAAAGCTGCC<br>CCAGCTGTGCACCGAGCTGCAGACCACCATCCACGACATCATCCTGGAAT<br>GCGTGTACTGCAAGCAGCAGCTGCTGAGAAGAGAGGTGTACGACTTCGCC<br>TTCCGGGACCTGTGCATCGTGTACAGGGACGGCAACCCTTACGCCGTGGG<br>CGACAAGTGCCTGAAGTTCTACAGCAAGATCAGCGAGTACCGGCACTACT<br>GCTACAGCCTGTACGGAACCACCCTGGAACAGCAGTACAACAAGCCCCTG<br>TGCGACCTGCTGATCAGATGCATCAACGGCCAGAAACCCCTGTGCCCCGA<br>GGAAAAGCAGAGACACCTGGACAAGAAGCAGCGGTTCCACAACATCAGAG<br>GCAGATGGACCGGCAGATGCATGAGCTGTTGCAGAAGCAGCAGAACCAGA<br>AGAGAGACTCAGCTGGGCAGCGGCGCCACCAACTTCAGCCTGCTGAAACA<br>GGCCGGCGACGTGGAAGAGAACCCAGGCCCTTGGCTGCAGAACCTGCTGT<br>TTCTGGGAATCGTGGTGTACAGCCTGAGCGCCCCTACCAGATCCCCCATC<br>ACCGTGACCAGACCTTGGAAGCACGTGGAAGCCATCAAAGAGGCCCTGAA<br>TCTGCTGGACGACATGCCCGTGACCCTGAACGAAGAGGTGGAAGTGGTGT<br>CCAACGAGTTCAGCTTCAAGAAACTGACCTGTGTGCAGACCCGGCTGAAG |

TABLE 1-continued

Sequences

| SEQ ID No. | Description | Sequence |
|---|---|---|
| | | ATCTTTGAGCAGGGCCTGAGAGGCAACTTCACCAAGCTGAAGGGCGCTCT GAACATGACCGCCAGCTACTACCAGACCTACTGCCCCCCCACCCCCGAGA CAGATTGCGAGACACAAGTGACCACCTACGCCGACTTCATCGACAGCCTG AAAACCTTCCTGACCGACATCCCCTTCGAGTGCAAGAAACCCGTGCAGAA GTGA |
| 18 | GSG | Gly Ser Gly |
| 19 | Junin virus Candid#1 L segment | gcgcaccggggatcctaggcgtaacttcatcattaaaatctcagattctg ctctgagtgtgacttactgcgaagaggcagacaaatgggcaactgcaacg gggcatccaagtctaaccagccagactcctcaagagccacacagccagcc gcagaaatttaggagggtagctcacagcagtctatatggtagatataactg taagtgctgctggtttgctgataccaatttgataacctgtaatgatcact acctttgtttaaggtgccatcagggtatgttaaggaattcagatctctgc aatatctgctggaagcccct gcccaccacaatcacagtaccggtggagccaacagcaccaccaccatagg cagactgcacagggtcagacccgacccccggggggcccccatggggacc ccccgtggggaaccccgggggtgatgcgccattagtcaatgtctttgat ctcgactttgtgcttcagtggcctgcatgtcaccccttcaatctgaact gcccttggggatctgatatcagcaggtcatttaaagatct gctgaatgccaccttgaaatttgagaattccaaccagtcaccaaatttat caagtgaacggatcaactgctctttgtgta gatcataaacgaggacaaagtcctcttgctgaaataatattgtttgtgat gttgtttttagataaggccatagttggctt aataaggtttccacactatcaatgtcctctagtgctccaattgccttgac tatgacatccccagacaactcaactctata tgttgacaacctttcattacctctgtaaaagataccctctttcaagacaa gaggttctcctgggttatctggcccaatga ggtcatatgcatacttgttacttagttcagaataaaagtcaccaaagttg aacttaacatggctcagaatattgtcatca tttgtcgcagcgtagcctgcatcaataaacaagccagctaggtcaaagct ctcatggcctgtgaacaatggtaggctagc gataaccagtgcaccatccaacaatgagtggcttccctcagacccagaaa cacattgactcattgcatccacattcagct ctaattcaggggtaccgacatcatccactcctagtgaactgacaatggtg taactgtacaccatctttcttctaagttta aattttgtcgaaactcgtgtgtgttctacttgaatgatcaattttagttt cacagcttcttggcaagcaacattgcgcaa cacagtgtgcaggtccatcatgtcttcctgaggcaacaaggagatgttgt caacagagacaccctcaaggaaaaccttga tattatcaaagctagaaactacataacccattgcaatgtcttcaacaaac attgctcttgatactttattattcctaact gacaaggtaaaatctgtgagttcagctagatctacttgactgtcatcttc tagatctagaacttcattgaaccaaaagaa ggatttgagacacgatgttgacatgactagtgggtttatcatcgaagata agacaacttgcaccatgaagttcctgcaaa cttgctgtgggctgatgccaacttcccaatttgtatactctgactgtcta acatgggctgaagcgcaatcactctgtttc acaatataaacattattatctcttacttttcaataagtgacttataatccc taagttttcattcatcatgtctagagccac acagacatctagaaacttgagtcttccactatccaaagatctgttcactt gaagatcattcataaagggtgccaaatgtt cttcaaatagtttggggtaatttcttcgtatagaatgcaatacatggttc atgcctaattggtcttctatctgtcgtact gctttgggtttaacagcccagaagaaattcttattacataagaccagagg ggcctgtggactcttaatagcagaaaacac ccactcccctaactcacaggcatttgtcagcaccaaagagaagtaatccc acaaaattggtttagaaaattggttaactt cttaagtgatttttgacagtaaataactttaggctttctctcacaaatt ccacaaagacatggcattattcgagtaaat atgtccttatatacagaaatccgcctttaccatccctaacacacttact ccccatactcttacaaaacccaatgaagcc tgaggcaacagaagactgaaatgcagatttgttgattgactctgccaaga tcttcttcacgccttttgtgaaatttcttg acagcctggactgtattgtccttatcaatgttggcatctcttctttctct aacactcttcgacttgtcatgagtttggtc ctcaagaccaacctcaagtccccaaagctcgctaaattgacccatctgta gtctagagtttgtctgatttcatcttcact acaccggcatattgcaggaatccggataaagcctcatcccctcccctgc ttatcaagttgataaggttttcctcaaaga ttttgcctctcttaatgtcattgaacactttcctcgcgcagttccttata aacattgtctcctatcatcagaaaaaata gcttcaattttcctctgtagacggtaccctctagacccatcaacccagtc tttgacatcttgttcttcaatagctccaaa |

TABLE 1-continued

Sequences

| SEQ ID No. | Description | Sequence |
|---|---|---|
| | | cggagtctctctgtatccagagtatctaatcaattggttgactctaatgg aaatctttgacactatatgagtgctaaccc cattagcaatacattgatcacaaattgtgtctatggtctctgacagttgt gttggagttttacacttaacgttgtgtaga gcagcagacacaaacttggtgagtaaaggagtctcttcacccatgacaaa aaatcttgacttaaactcagcaacaaaagttcctatcacactctttgggc tgataaacttgtttaatttagaagataagaattcatggaagcacaccatt ccagcagtt ctgtcctgtcttgaaacttttcatcactaaggcaaggaatttttataagg ctaacctggtcatcgctggaggtataagtg acaggtatcacatcatacaataagtcaagtgcataacacagaaattgttc agtaattagcccatataaatctgatgtgtt gtgcaagattccctggcccatgtccaagacagacattatatggctgggga cctggtcccttgactgcagatactggtgaa aaaactcttcaccaacactagtacagtcacaacccattaaacctaaagat ctcttcaatttccctacacagtaggcttct gcaacattaattggaacttcaacgaccttatgaagatgccatttgagaat gttcattactggttcaagattcacctttgt tctatctctgggattcttcaattctaatgtgtacaaaaaagaaaggaaaa gtgctgggctcatagttggtccccatttgg agtggtcatatgaacaggacaagtcaccattgttaacagccatttttcata tcacagattgcacgttcgaattccttttct gaattcaagcatgtgtatttcattgaactacccacagcttctgagaagtc ttcaactaacctggtcatcagcttagtgtt gaggtctcccacatacagttctctatttgagccaacctgctccttataac ttagtccaaatttcaagttccctgtatttg agctgatgcttgtgaactctgtaggagagtcgtctgaatagaaacataaa ttccgtagggctgcatttgtaaaataactt ttgtctagcttatcagcaatggcttcagaattgctttccctggtactaag ccgaacctcatcctttagtctcagaacttc actggaaaagcccaatctagatctacttctatgctcataactacccaatt tctgatcataatgtccttgaattaaaagat acttgaagcattcaaagaattcatcttcttggtaggctattgttgtcaaa ttttttaataacaaacccaaagggcagatg tcctgcggtgcttcaagaaaataagtcaatttaaatggagatagataaac agcatcacataactctttatacacatcaga cctgagcacatctggatcaaaatccttcacctcatgcattgacacctctg cttaatctctctcaacactccaaaagggg cccacaatgactcaagagactctcgctcatcaacagatggattttttgat ttcaacttggtgatctcaacttttgtcccc tcactattagccatcttggctagtgtcatttgtacgtcatttctaatacc ctcaaaggcccttacttgatcctctgttaa actctcatacatcactgataattcttcttgattggttctggttcttgaac cggtgctcacaagaccgttagattttta atattaagtagtccatggaatcaggatcaagattatacctgccttttgtt ttaaacctctcagccatagtagaaacgcat gttgaaacaagtttctccttatcataaacagaaagaatatttccaagttc gtcgagcttggggattaccacacttttatt gcttgacagatccagagctgtgctagtgatgttaggcctgtagggattgc ttttcagttcacctgtaactttaagtcttc ctctattgaagagagaaatgcagaaggacaaaatctctttacacactcct ggaatttgagtatctgaggaagtcttagcc tctttggaaaagaatctgtccaatcctcttatcatggtgtcctcttgttc cagtgttagactcccacttagaggggggtt tacaacaacacaatcaaacttgactttgggctcaataaacttctcaaaac actttatttgatctgtcaggcgatcaggtg tctctttggttaccaagtgacacagataactaacatttaatagatattta aaccttcttgcaaagtaaagatctgcatct tccccttcacccaaaattgtctggaaaagttccacagccatcctctgaat cagcacctctgatccagacatgcagtcgac ccttaactttgacatcaaatccacatgatggatttgatttgcatatgcca tcaagaaatatcttagaccttgtaaaaatg tctggttccttttggaagggaacagagtacagctaacactaacaatctt aatattggccttgtcattgtcatgagttcg tggctaaaatccaaccagctggtcatttcctcacacatttcaattaacac atcctccgaaaatataggcaggaaaaatct cttttggatcacagtaaaaagagccttgttcttccaatacccccattgatgg atagatagataatagcaccttgacttct cacctgttttttggtaaaacaagagaccaaatgtattctttgtcagatga aatctttgtacataacactctcttagtcta acattcccaaaatatctagaatactctcttcattgattaacaatcggga ggaaaatgatgtcttcatcgagttgaccaa tgcaagggaaatggaggacaaaatcctaaataatttcttctgctccacctt ccactaagctgctgaatggctgatgtctac |

TABLE 1-continued

Sequences

| SEQ ID No. | Description | Sequence |
|---|---|---|
| | | agattttctcaaattccttgttaatagtatatctcatcactggtctgtca gaaacaagtgcctgagctaaaatcatcaag ctatccatatcagggtgttttattagtttttccagctgtgaccagagatc ttgatgagagttcttcaatgttctggaaca cgcttgaacccacttgggctggtcatcaatttcttccttattagtttaa tcgcctccagaatatctagaagtctgtcat tgactaacattaacatttgtccaacaactattcccgcatttcttaaccttt acaattgcatcatcatgcgttttgaaaaga tcacaaagtaaattgagtaaaactaagtccagaaacagtaaagtgtttct cctggtgttgaaaacttttagaccttttcac tttgttacacacggaaagggcttgaagataacacctctctacagcatcaa tagatatagaattctcatctgactggcttt ccatgttgacttcatctattggatgcaatgcgatagagtagactacatcc atcaacttgtttgcacaaaaagggcagctg ggcacatcactgtctttgtggcttcctaataagatcaagtcatttataag cttagacttttgtgaaaatttgaatttccc caactgcttgtcaaaaatctccttcttaaaccaaaaccttaacttttatga gttcttctcttatgacagattctctaatgt ctcctctaaccccaacaaagagggattcatttaacctctcatcataaccc aaagaattctttttcaagcattcgatgttt tctaatcccaagctctggttttttgtgttggacaaactatggatcaatcg ctggtattcttgttcttcaatattaatctc ttgcataaattttgatttctttaggatgtcgatcagcaaccaccgaactc tttcaacaacccaatcagcaaggaatctat tgctgtagctagatctgccatcaaccacaggaaccaacgtaatccctgcc cttagtaggtcggactttaggtttaagagc tttgacatgtcactcttccattttctctcaaactcatcaggattgaccct aacaaaggtttccaataggatgagtgtttt ccctgtgagtttgaagccatccggaatgacttttggaagggtgggacata gtatgccatagtcagacaggatcacatcaa caaacttctgatctgaattgatctgacaggcgtgtgcctcacaggactca agctctactaaacttgacagaagtttgaac ccttccaacaacagagagctggggtgatgttgagataaaaagatgtccct ttggtatgctagctcctgtctttctggaaa atgctttctaataaggcttttatttcatttactgattcctccatgctca agtgccgcctaggatcctcggtgcg |
| 20 | Junin virus Candid#1 S segment | gcgcaccggggatcctaggcgattttggttacgctataattgtaactgtt ttctgtttggacaacatcaaaaacatccattgcacaatggggcagttcat tagcttcatgcaagaaataccaacctttttgcaggaggctctgaacattg ctcttgttgc agtcagtctcattgccatcattaagggtatagtgaacttgtacaaaagtg gtttattccaattctttgtattcctagcgc ttgcaggaagatcctgcacagaagaagctttcaaaatcggactgcacact gagttccagactgtgtccttctcaatggtg ggtctcttttccaacaatccacatgacctaccttttgttgtgtaccttaaa caagagccatctttacattaagggggggcaa tgcttcatttcagatcagctttgatgatattgcagtattgttgccacagt atgatgttataatacaacatccagcagata tgagctggtgttccaaaagtgatgatcaaatttggttgtctcagtggttc atgaatgctgtgggacatgattggcatcta gacccaccatttctgtgtaggaaccgtgcaaagacagaaggcttcatctt tcaagtcaacacctccaagactggtgtcaa tggaaattatgctaagaagtttaagactggcatgcatcatttatatagag aatatcctgacccttgcttgaatggcaaac tgtgcttaatgaaggcacaacctaccagttggcctctccaatgtccactc gaccacgttaacacattacacttccttaca agaggtaaaaacattcaacttccaaggaggtccttgaaagcattcttctc ctggtctttgacagactcatccggcaagga taccctggaggctattgtctagaagagtggatgctcgtagcagccaaaa tgaagtgttttggcaatactgctgtagcaa aatgcaatttgaatcatgactctgaattctgtgacatgttgaggctcttt gattacaacaaaaatgctatcaaaaccta aatgatgaaactaagaaacaagtaaatctgatggggcagacaatcaatgc cctgatatctgacaatttattgatgaaaaa caaaattagggaactgatgagtgtcccttactgcaattacacaaaatttt ggtatgtcaaccacacactttcaggacaac actcattaccaaggtgctggttaataaaaaacaacagctatttgaacatc tctgacttccgtaatgactggatattagaa agtgacttcttaatttctgaaatgctaagcaaagagtattcggacaggca gggtaaaactcctttgactttagttgacat ctgtatttggagcacagtattcttcacagcgtcactcttccttcacttgg tgggtatacctcccacagacacatcaggg gcgaagcatgccctttgccacacaggttgaacagcttgggtggttgcaga |

TABLE 1-continued

Sequences

| SEQ ID No. | Description | Sequence |
|---|---|---|
| | | tgtggtaagtaccccaatctaaagaaacca<br>acagtttggcgtagaggacactaagacctcctgagggtccccaccagccc<br>gggcactgcccgggctggtgtggcccccagtccgcggcctggccgcgga<br>ctggggaggcactgcttacagtgcataggctgccttcgggaggaacagca<br>agctcggtggtaatagaggtgtaggttcctcctcatagagcttcccatct<br>agcactgactgaaacattatgcagtctagcagagcacagtgtggttcact<br>ggaggccaacttgaagggagtatcctttcctctttttcttattgacaa<br>ccactccattgtgatatttg<br>cataagtgaccatatttctcccagacctgttgatcaaactgcctggcttg<br>ttcagatgtgagcttaacatcaaccagttt<br>aagatctcttcttccatggaggtcaaacaacttcctgatgtcatcggatc<br>cttgagtagtcacaaccatgtctggaggca<br>gcaagccgatcacgtaactaagaactcctggcattgcatcttctatgtcc<br>ttcattaagatgccgtgagagtgtctgcta<br>ccatttttaaacccttttctcatcatgtggttttctgaagcagtgaatgta<br>ctgcttacctgcaggttggaataatgccat<br>ctcaacagggtcagtggctggtccttcaatgtcgagccaaagggtgttgg<br>tggggtcgagtttccccactgcctctctga<br>tgacagcttcttgtatctctgtcaagttagccaatctcaaattctgaccg<br>tttttttccggctgtctaggaccagcaact<br>ggtttccttgtcagatcaatacttgtgttgtcccatgacctgcctgtgat<br>ttgtgatctagaaccaatataaggccaacc<br>atcgccagaaagacaaagtttgtacaaaaggttttcataaggatttctat<br>tgcctggtttctcatcaataaacatgcctt<br>ctcttcgtttaacctgaatggttgattttatgagggaagagaagtttct<br>ggggtgactctgattgtttccaacatgttt<br>ccaccatcaagaatagatgctccagcctttactgcagctgaaagactgaa<br>gttgtaaccagaaatattgatggagcttc<br>atctttagtcacaatctgaaggcagtcatgttcctgagtcagtctgtcaa<br>ggtcacttaagtttggatacttcacagtgt<br>atagaagcccaagtgaggttaaagcttgtatgacactgttcattgtctca<br>cctccttgaacagtcatgcatgcaattgtc<br>aatgcaggaacagagccaaactgattgtttagctttgaagggtctttaac<br>atcccatatcctcaccacaccatttccccc<br>agtcccttgctgttgaaatcccagtgttctcaatatctctgatcttttag<br>caagttgtgactgggacaagttacccatgt<br>aaaccccctgagagcctgtctctgctcttcttatcttgttttttaatttc<br>tcaaggtcagacgccaactccatcagttca<br>tccctccccagatctcccaccttgaaaactgtgtttcgttgaacactcct<br>catggacatgagtctgtcaacctctttatt<br>caggtccctcaacttgttgaggtcttcttccccctttttagtcttttctga<br>gtgcccgctgcacctgtgccacttggttga<br>agtcgatgctgtcagcaattagcttggcgtccttcaaaacatctgacttg<br>acagtctgagtgaattggctcaaacctctc<br>cttaaggactgagtccatctaaagcttggaacctccttggagtgtgccat<br>gccagaagttctggtgattttgatctagaa<br>tagagttgctcagtgaaagtgttagacactatgcctaggatccactgtgc<br>g |
| 21 | Nucleotide sequence of HK1-E7E6-GMCSF | ATGCACGGCGACACCCCTACCCTGCACGAGTACATGCTGGACCTGCAGCC<br>CGAGACAACCGACCTGTACGGCTACGGCCAGCTGAACGACAGCAGCGAGG<br>AAGAGGACGAGATCGACGGCCCTGCTGGACAGGCCGAACCTGACAGAGCC<br>CACTCACAACATCGTGACATTCTGCTGCAAGTGCGACAGCACCCTGAGACT<br>GTGCGTGCAGAGCACCCACGTGGACATCAGAACCCTGGAAGATCTGCTGA<br>TGGGCACCCTGGGCATCGTGGGCCCTATCTGCTCTCAGAAGCCCCACCAG<br>AAAAGAACCGCCATGTTCCAGGACCCCCAGGAAAGACCCAGAAAGCTGCC<br>CCAGCTGTGCACCGAGCTGCAGACCACCATCCACGACATCATCCTGGAAT<br>GCGTGTACTGCAAGCAGCAGCTGCTGAGAAGAGAGGTGTACGACTTCGCC<br>TTCCGGGACCTGTGCATCGTGTACAGGGACGGCAACCCTTACGCCGTGGG<br>CGACAAGTGCCTGAAGTTCTACAGCAAGATCAGCGAGTACCGGCACTACT<br>GCTACAGCCTGTACGGAACCACCCTGGAACAGCAGTACAACAAGCCCCTG<br>TGCGACCTGCTGATCAGATGCATCAACGGCCAGAAACCCTGTGCCCCGA<br>GGAAAAGCAGAGACACCTGGACAAGAAGCAGCGGTTCCACAACATCAGAG<br>GCAGATGGACCGGCAGATGCATGAGCTGTTGCAGAAGCAGCAGAACCAGA<br>AGAGAGACTCAGCTGGGCAGCGGCGCCACCAACTTCAGCCTGCTGAAACA<br>GGCCGGCGACGTGGAAGAGAACCCAGGCCCTTGGCTGCAGAACCTGCTGT<br>TTCTGGGAATCGTGGTGTACAGCCTGAGCGCCCCTACCAGATCCCCCATC<br>ACCGTGACCAGACCTTGGAAGCACGTGGAAGCCATCAAAGAGGCCCTGAA<br>TCTGCTGGACGACATGCCCGTGACCCTGAACGAAGAGGTGGAAGTGGTGT<br>CCAACGAGTTCAGCTTCAAGAAACTGACCTGTGTGCAGACCCGGCTGAAG<br>ATCTTTGAGCAGGGCCTGAGAGGCAACTTCACCAAGCTGAAGGGCGCTCT<br>GAACATGACCGCCAGCTACTACCAGACCTACTGCCCCCCCACCCCCGAGA<br>CAGATTGCGAGACACAAGTGACCACCTACGCCGACTTCATCGACAGCCTG |

TABLE 1-continued

Sequences

| SEQ ID No. | Description | Sequence |
|---|---|---|
| | | AAAACCTTCCTGACCGACATCCCCTTCGAGTGCAAGAAACCCGTGCAGAAGTGA |
| 22 | Amino acid sequence of E7E6-GMCSF antigen | MHGDTPTLHEYMLDLQPETTDLYGYGQLNDSSEEEDEIDGPAGQAEPDRAHYNIVTFCCKCDSTLRLCVQSTHVDIRTLEDLLMGTLGIVGPICSQKPHQKRTAMFQDPQERPRKLPQLCTELQTTIHDIILECVYCKQQLLRREVYDFAFRDLCIVYRDGNPYAVGDKCLKFYSKISEYRHYCYSLYGTTLEQQYNKPLCDLLIRCINGQKPLCPEEKQRHLDKKQRFHNIRGRWTGRCMSCCRSSRTRRETQLGSGATNFSLLKQAGDVEENPGPWLQNLLFLGIVVYSLSAPTRSPITVTRPWKHVEAIKEALNLLDDMPVTLNEEVEVVSNEFSFKKLTCVQTRLKIFEQGLRGNFTKLKGALNMTASYYQTYCPPTPETDCETQVTTYADFIDSLKTFLTDIPFECKKPVQK |
| 23 | Nucleotide sequence of HK1-E7E6-VP22 | ATGCATGGTGACACCCCAACCCTGCATGAGTACATGCTGGACCTGCAGCCAGAGACAACAGACCTGTATGGCTATGGCCAGCTGAATGACAGCAGTGAGGAAGAGGATGAGATTGATGGCCCTGCTGGACAGGCAGAACCTGACAGAGCCCACTACAACATTGTGACATTCTGCTGCAAGTGTGACAGCACCCTGAGACTGTGTGTGCAGAGCACCCATGTGGACATCAGAACCCTGGAAGATCTGCTGATGGGCACCCTGGGCATTGTGGGCCCCATCTGCTCTCAGAAGCCCCACCAGAAAAGAACAGCCATGTTCCAGGACCCCCAGGAAAGACCCAGAAAGCTGCCCCAGCTGTGCACTGAGCTGCAGACCACCATCCATGACATCATCCTGGAATGTGTGTACTGCAAGCAGCAGCTGCTGAGAAGAGAGGTGTATGACTTTGCCTTCAGGGACCTGTGCATTGTGTACAGGGATGGCAACCCTTATGCAGTGGGAGACAAGTGCCTGAAGTTCTACAGCAAGATCAGTGAGTACAGGCACTACTGCTACAGCCTGTATGGAACCACCCTGGAACAGCAGTACAACAAGCCCCTGTGTGACCTGCTGATCAGATGCATCAATGGCCAGAAACCCCTGTGCCCTGAGGAAAAGCAGAGACACCTGGACAAGAAGCAGAGGTTCCACAACATCAGAGGCAGATGGACTGGCAGATGCATGAGCTGTTGCAGAAGCAGCAGAACCAGAAGGGAGACTCAGCTGGGATCAGGAATGACCTCAAGGAGGTCAGTGAAGTCTGGTCCAAGGGAGGTTCCCAGAGATGAGTATGAGGATCTGTACTACACCCCTTCTTCATGCATGGCCAGTCCTGACAGTCCCCCTGACACCTCCAGAAGAGGTGCCCTGCAGACAAGAGCCAGACCAAGGGGGGAGGTCAGATTTGTCCAGTATGATGAGTCAGATTATGCCCTCTATGGGGGCTCATCATCTGAAGATGATGAACACCCAGAGGTCCCCAGGACCAGGAGACCTGTTTCAGGGGCTGTTTTGTCAGCCCCAGGGCCTGCAAGGGCCCCTCCCCCCCCTGCTGGGTCAGGAGGGGCAGGAAGAACACCCACCACTGCCCCCAGGGCCCCCAGAACCCAGAGGGTGGCCACCAAGGCCCCTGCAGCCCCTGCAGCAGAGACCACCAGGGGCAGGAAATCAGCCCAGCCAGAATCAGCAGCACTCCCAGATGCCCCAGCATCAACAGCTCCAACCAGATCCAAGACACCAGCACAGGGGCTGGCCAGAAAGCTGCACTTCAGCACAGCCCCCCCAAACCCTGATGCCCCATGGACCCCCAGGGTGGCAGGCTTCAACAAGAGGGTCTTCTGTGCTGCAGTTGGGAGGCTGGCAGCCATGCATGCCAGGATGGCAGCTGTCCAGCTCTGGGACATGTCAAGACCAAGGACAGATGAAGACCTCAATGAACTCCTTGGCATCACCACCATCAGGGTGACTGTCTGTGAGGGCAAAAACCTGATTCAGAGGGCCAATGAGTTGGTGAATCCAGATGTGGTGCAGGATGTTGATGCTGCCACTGCAACTAGAGGGAGGTCTGCTGCCTCAAGACCCACTGAGAGACCAAGAGCCCCAGCCAGGTCTGCTTCCAGACCCAGAAGGCCAGTGGAGTGA |
| 24 | Amino acid sequence of E7E6-VP22 antigen | MHGDTPTLHEYMLDLQPETTDLYGYGQLNDSSEEEDEIDGPAGQAEPDRAHYNIVTFCCKCDSTLRLCVQSTHVDIRTLEDLLMGTLGIVGPICSQKPHQKRTAMFQDPQERPRKLPQLCTELQTTIHDIILECVYCKQQLLRREVYDFAFRDLCIVYRDGNPYAVGDKCLKFYSKISEYRHYCYSLYGTTLEQQYNKPLCDLLIRCINGQKPLCPEEKQRHLDKKQRFHNIRGRWTGRCMSCCRSSRTRRETQLGSGMTSRRSVKSGPREVPRDEYEDLYYTPSSCMASPDSPPDTSRRGALQTRARPRGEVRFVQYDESDYALYGGSSSEDDEHPEVPRTRRPVSGAVLSAPGPARAPPPPAGSGGAGRTPTTAPRAPRTQRVATKAPAAPAAETTRGRKSAQPESAALPDAPASTAPTRSKTPAQGLARKLHFSTAPPNPDAPWTPRVAGFNKRVFCAAVGRLAAMHARMAAVQLWDMSRPRTDEDLNELLGITTIRVTVCEGKNLIQRANELVNPDVVQDVDAATATRGRSAASRPTERPRAPARSASRPRRPVE |
| 25 | Nucleotide sequence of HK1-E7E6-CD40L | ATGCATGGTGACACCCCTACCCTGCATGAGTACATGCTGGACCTGCAGCCAGAGACAACAGACCTGTATGGCTATGGCCAGCTGAATGACAGCAGTGAGGAAGAGGATGAGATTGATGGCCCTGCTGGACAGGCTGAACCTGACAGAGCCCACTACAACATTGTGACATTCTGCTGCAAGTGTGACAGCACCCTGAGACTGTGTGTGCAGAGCACCCATGTGGACATCAGAACCCTGGAAGATCTGCTGATGGGCACCCTGGGCATTGTGGGCCCCATCTGCTCTCAGAAGCCCCACCAGAAAAGAACAGCCATGTTCCAGGACCCCCAGGAAAGACCCAGAAAGCTGCCCCAGCTGTGCACAGAGCTGCAGACCACCATCCATGACATCATCCTGGAATGTGTGTACTGCAAGCAGCAGCTGCTGAGAAGAGAGGTGTATGACTTTGCCTTCAGGGACCTGTGCATAGTGTACAGGGATGGCAACCCTTATGCTGTGGGGACAAGTGCCTGAAGTTCTACAGCAAGATCAGTGAGTACAGGCACTACTGCTACAGCCTGTATGGAACCACCCTGGAACAGCAGTACAACAAGCCCCTGTGTGACCTGCTGATCAGATGCATCAATGGCCAGAAACCCCTGTGCCCTGA |

TABLE 1-continued

Sequences

| SEQ ID No. | Description | Sequence |
|---|---|---|
| | | GGAAAAGCAGAGACACCTGGACAAGAAGCAGAGGTTCCACAACATCAGAG<br>GCAGATGGACAGGCAGATGCATGAGCTGTTGCAGAAGCAGCAGAACCAGA<br>AGAGAGACTCAGCTGAATGATGCACAGGCACCAAAGAGTGTGGAAGAGGA<br>AGTCAACCTTCATGAAGATTTTGTTTTCATCAAAAAGCTCAAGAGATGCA<br>ACAAAGGAGAAGGATCTTTGTCCTTGCTGAACTGTGAGGAGATGAGAAGG<br>CAATTTGAAGACCTTGTCAAGGACATCACTTTGAACAAAGAAGAGAAAA<br>AGAAAACAGCTTTGAAATGCAAGAGGTGATGAGGATCCTCAAATTGCAG<br>CACATGTTGTCAGTGAAGCCAACAGCAATGCAGCATCTGTTCTGCAGTGG<br>GCCAAGAAAGGATATTACACCATGAAAAGCAACTTGGTCATGCTTGAAAA<br>TGGGAAACAGCTGACTGTGAAAAGAGAAGGACTCTATTATGTCTACACTC<br>AAGTCACCTTCTGCTCAAACAGGGAGCCTTCAAGTCAAAGACCATTCATT<br>GTGGGCCTCTGGCTGAAGCCCAGCAGTGGATCTGAGAGAATCTTGCTCAA<br>GGCAGCAAACACCCACAGTTCCTCCCAGCTTTGTGAGCAGCAGTCTGTTC<br>ACTTGGGAGGAGTGTTTGAATTGCAAGCTGGTGCTTCTGTGTTTGTCAAT<br>GTGACTGAAGCAAGCCAAGTGATCCACAGAGTTGGCTTCTCATCTTTTGG<br>CTTGCTCAAACTCTGA |
| 26 | Amino acid sequence of E7E6-CD40L antigen | MHGDTPTLHEYMLDLQPETTDLYGYGQLNDSSEEEDEIDGPAGQAEPDRA<br>HYNIVTFCCKCDSTLRLCVQSTHVDIRTLEDLLMGTLGIVGPICSQKPHQ<br>KRTAMFQDPQERPRKLPQLCTELQTTIHDIILECVYCKQQLLRREVYDFA<br>FRDLCIVYRDGNPYAVGDKCLKFYSKISEYRHYCYSLYGTTLEQQYNKPL<br>CDLLIRCINGQKPLCPEEKQRHLDKKQRFHNIRGRWTGRCMSCCRSSRTR<br>RETQLNDAQAPKSVEEEVNLHEDFVFIKKLKRCNKGEGSISLLNCEEMRR<br>QFEDLVKDITLNKEEKKENSFEMQRGDEDPQIAAHVVSEANSNAASVLQW<br>AKKGYYTMKSNLVMLENGKQLTVKREGLYYVYTQVTFCSNREPSSQRPFI<br>VGLWLKPSSGSERILLKAANTHSSSQLCEQQSVHLGGVFELQAGASVFVN |
| 27 | Nucleotide sequence of HK1-Flt3L-E7E6 | ATGACAGTGCTGGCCCCAGCCTGGAGCCCAAATTCCTCCCTGTTGCTGCT<br>GTTGCTGCTGCTGAGTCCTTGCCTGAGGGGACACCTGACTGTTACTTCA<br>GCCACAGTCCCATCTCCTCCAACTTCAAAGTGAAGTTCAGAGAGTTGACT<br>GACCACCTGCTCAAAGATTACCCAGTCACTGTGGCAGTCAATCTTCAGGA<br>TGAGAAGCACTGCAAGGCCTTGTGGAGCCTCTTCCTGGCCCAGAGGTGGA<br>TTGAGCAACTGAAGACTGTGGCAGGGTCAAAGATGCAAACTCTTCTGGAG<br>GATGTCAACACTGAGATCCATTTTGTCACCTCATGCACCTTCCAGCCCCT<br>TCCAGAATGTCTGAGATTTGTCCAGACCAACATCTCCCACCTCCTGAAGG<br>ACACCTGCACACAGCTGCTTGCTCTGAAGCCCTGCATAGGGAAGGCCTGC<br>CAGAATTTCTCCAGGTGCCTGGAGGTGCAGTGCCAGCCAGACTCCTCCAC<br>CCTGCTGCCCCAAGGAGTCCCATTGCCCTGGAAGCCACTGAGCTCCCAG<br>AGCCCAGGCCCAGGCAGCTGTTGCTCCTGCTGCTGCTGCTGCCTCTC<br>ACACTGGTGCTGCTGGCAGCTGCCTGGGGCCTCAGGTGGCAAAGGGCAAG<br>AAGGAGGGGGGAGCTCCACCCTGGGGTGCCCCTCCCCTCCCATCCCATGC<br>ATGGTGACACCCCAACCCTGCATGAGTACATGCTGGACCTGCAGCCAGAG<br>ACAACAGACCTGTATGGCTATGGCCAGCTGAATGACAGCAGTGAGGAAGA<br>GGATGAGATTGATGGCCCTGCTGGACAGGCAGAACCTGACAGAGCCCACT<br>ACAACATTGTGACATTCTGCTGCAAGTGTGACAGCACCCTGAGACTGTGT<br>GTGCAGAGCACCCATGTGGACATCAGAACCCTGGAAGATCTGCTGATGGG<br>CACCCTGGGCATTGTGGGCCCAATCTGCTCTCAGAAGCCCCACCAGAAAA<br>GAACAGCCATGTTCCAGGACCCCCAGGAAAGACCCAGAAAGCTGCCCCAG<br>CTGTGCACAGAGCTGCAGACCACCATCCATGACATCATCCTGGAATGTGT<br>GTACTGCAAGCAGCAGCTGCTGAGAAGAGAGGTGTATGACTTTGCCTTCA<br>GGGACCTGTGCATTGTGTACAGGGATGGCAACCCTTATGCTGTGGGGGAC<br>AAGTGCCTGAAGTTCTACAGCAAGATCAGTGAGTACAGGCACTACTGCTA<br>CAGCCTGTATGGAACCACCCTGGAACAGCAGTACAACAAGCCCCTGTGTG<br>ACCTGCTGATCAGATGCATCAATGGCCAGAAACCCCTGTGCCCTGAGGAA<br>AAGCAGAGACACCTGGACAAGAAGCAGAGGTTCCACAACATCAGAGGCAG<br>ATGGACAGGCAGATGCATGAGCTGTTGCAGAAGCAGCAGAACCAGAAGAG<br>AGACTCAGCTGTGA |
| 28 | Amino acid sequence of Flt3L-E7E6 antigen | MTVLAPAWSPNSSLLLLLLLLSPCLRGTPDCYFSHSPISSNFKVKFRELT<br>DHLLKDYPVTVAVNLQDEKHCKALWSLFLAQRWIEQLKTVAGSKMQTLLE<br>DVNTEIHFVTSCTFQPLPECLRFVQTNISHLLKDTCTQLLALKPCIGKAC<br>QNFSRCLEVQCQPDSSTLLPPRSPIALEATELPEPRPRQLLLLLLLLPL<br>TLVLLAAAWGLRWQRARRGELHPGVPLPSHPMHGDTPTLHEYMLDLQPE<br>TTDLYGYGQLNDSSEEEDEIDGPAGQAEPDRAHYNIVTFCCKCDSTLRLC<br>VQSTHVDIRTLEDLLMGTLGIVGPICSQKPHQKRTAMFQDPQERPRKLPQ<br>LCTELQTTIHDIILECVYCKQQLLRREVYDFAFRDLCIVYRDGNPYAVGD<br>KCLKFYSKISEYRHYCYSLYGTTLEQQYNKPLCDLLIRCINGQKPLCPEE<br>KQRHLDKKQRFHNIRGRWTGRCMSCCRSSRTRRETQL |
| 28 | Nucleotide sequence of HK1-Flt3L-E7E6 shuffle | ATGACAGTGCTGGCACCAGCCTGGAGCCCAAATTCCTCCCTGTTGCTGCT<br>GTTGCTGCTGCTGAGTCCTTGCCTGAGGGGACACCTGACTGTTACTTCA<br>GCCACAGTCCCATCTCCTCCAACTTCAAAGTGAAGTTCAGAGAGTTGACT<br>GACCACCTGCTCAAAGATTACCCAGTCACTGTGGCTGTCAATCTTCAGGA<br>TGAGAAGCACTGCAAGGCCTTGTGGAGCCTCTTCCTGGCCCAGAGATGGA |

TABLE 1-continued

Sequences

| SEQ ID No. | Description | Sequence |
|---|---|---|
| | | TAGAGCAACTGAAGACTGTGGCAGGGTCAAAGATGCAAACACTTCTGGAG GATGTCAACACTGAGATCCATTTTGTCCACCTCATGCACCTTCCAGCCCCT GCCAGAATGTCTGAGATTTGTCCAGACCAACATCTCCCACCTCCTGAAGG ACACCTGCACACAGCTGCTTGCTCTGAAGCCCTGCATTGGGAAGGCCTGC CAGAATTTCTCCAGGTGCCTGGAGGTGCAGTGCCAGCCTGACTCCTCCAC CCTGCTGCCCCCAAGGAGTCCCATAGCCCTGGAAGCCACTGAGCTCCCAG AGCCCAGGCCCAGGCAGCTGTTGCTCCTGCTGCTGCTGCCTCTC ACACTGGTGCTGCTGGCAGCAGCCTGGGGCCTCAGATGGCAAAGGGCAAG AAGGAGGGGGGAGCTCCACCCTGGGGTGCCCCTCCCCTCCCATCCCATGC ACCAAAAGAGAACTGCAATGTTTCAGGACCCACAGGAGAGACCCAGAAAG TTGCCACAGTTGTGCACAGAGCTGCAAACAACCATCCATGACATCATTTT GGAATGTGTGTACTGCAAGCAACAGTTGCTGAGAAGAGAGGTGTATGACT TTGCTTTCAGGGATTTGTGCATAGTGTACAGAGATGGGAATCCATATGCT GTCTGTGACAAATGTTTGAAGTTTTATTCAAAAATCAGTGAGTACAGACA CATGCATGGAGACACACCCACATTGCATGAATACATGTTGGATTTGCAAC CAGAGACAACTGATCTCTACTGTTATGAGCAATTGAATGACAGCTCAGAG GAGGAGGATGAAATAGATGGTCCAGCTGGACAAGCAGAACCAGACAGAGC CCATTACAACATTGTGACCTTTTGTTGCAAGTGTGACTCAACACTTGACA AATGTTTGAAGTTTTATTCCAAAATCAGTGAGTACAGACATTATTGTTAC AGTTTGTATGGAACAACATTGGAACAGCAATACAACAAACCATTGTGTGA TTTGTTGATCAGGTGCATCAACTGTCAAAAGCCACTGTGTCCTGAAGAAA AGCAAAGACATCTGGACAAAAAGCAAAGATTCCACAACATCAGGGGGAGG TGGACAGGCAGATGCATGTCTTGTTGCAGATCATCAAGAACAAGAAGAGA AACCCAGCTGCATTACAACATTGTGACCTTTTGTTGCAAGTGTGACTCCA CCCTCAGGTTGTGTGTCCAAAGCACACATGTTGACATCAGGACTTTGGAA GACCTGTTGATGGGCACACTTGGAATTGTGTGCCCCATCTGTTCTCAGAA ACCATAA |
| 30 | Amino acid sequence of Flt3L-E7E6 shuffle antigen | MTVLAPAWSPNSSLLLLLLLLSPCLRGTPDCYFSHSPISSNFKVKFRELT DHLLKDYPVTVAVNLQDEKHCKALWSLFLAQRWIEQLKTVAGSKMQTLLE DVNTEIHFVTSCTFQPLPECLRFVQTNISHLLKDTCTQLLALKPCIGKAC QNFSRCLEVQCQPDSSTLLPPRSPIALEATELPEPRPRQLLLLLLLLLPL TLVLLAAAWGLRWQRARRRGELHPGVPLPSHPMHQKRTAMFQDPQERPRK LPQLCTELQTTIHDIILECVYCKQQLLRREVYDFAFRDLCIVYRDGNPYA VCDKCLKFYSKISEYRHMHGDTPTLHEYMLDLQPETTDLYCYEQLNDSSE EEDEIDGPAGQAEPDRAHYNIVTFCCKCDSTLDKCLKFYSKISEYRHYCY SLYGTTLEQQYNKPLCDLLIRCINCQKPLCPEEKQRHLDKKQRFHNIRGR WTGRCMSCCRSSRTRRETQLHYNIVTFCCKCDSTLRLCVQSTHVDIRTLE DLLMGTLGIVCPICSQKP |
| 31 | Nucleotide sequence of HK1-mli-E7E6 | ATGGATGACCAAAGGGACCTCATCTCAAACCATGAGCAATTGCCCATCCT GGGCAACAGACCTAGAGAGCCAGAAAGGTGCAGCAGAGGAGCTCTGTACA CAGGTGTTTCTGTCCTGGTGGCTCTGCTCTTGGCTGGGCAGGCCACAACT GCTTACTTCCTGTACCAGCAACAGGGCAGACTAGACAAGCTGACCATCAC CTCCCAGAACCTGCAACTGGAGAGCCTCAGGATGAAGCTTCCCAAATCTG CCAAACCTGTGAGCCAGATGAGGATGGCCACTCCCTTGCTGATGAGGCCA ATGTCCATGGACAACATGCTCCTTGGGCCTGTGAAGAATGTGACCAAGTA TGGCAACATGACCCAGGACCATGTGATGCATCTGCTCACAAGGTCTGGAC CCCTGGAGTACCCTCAGCTGAAGGGGACCTTCCCAGAGAATCTGAAGCAT CTGAAGAACTCCATGGATGGAGTGAACTGGAAGATCTTTGAGAGCTGGAT GAAGCAGTGGCTCTTGTTTGAGATGAGCAAGAACTCCCTGGAGGAGAAGA AGCCCACAGAGGCTCCACCAAAAGAGCCCACTGGACATGGAAGACCTTTCT TCTGGCCTGGGAGTGACCAGGCAGGAACTGGGTCAAGTCACCCTGAGTGA CAGGTATTTGAACAGGAGAGCCATGCATGGAGACACCCCAACCCTGCATG AGTACATGCTGGACCTGCAGCCTGAGACAACTGACCTGTATGGCTATGGC CAGCTGAATGACAGCAGTGAGGAAGAGGATGAGATTGATGGCCCTGCTGG ACAGGCTGAACCTGACAGAGCCCACTACAACATTGTGACATTCTGCTGCA AGTGTGACAGCACCCTGAGACTGTGTGTGCAGAGCACCCATGTGGACATC AGAACCCTGGAAGATCTGCTGATGGGCACCCTGGGCATTGTGGGCCCTAT CTGCTCTCAGAAGCCCCACCAGAAAAGAACAGCCATGTTCCAGGACCCCC AGGAAAGACCCAGAAAGCTGCCCCAGCTGTGCACAGAGCTGCAGACCACC ATCCATGACATCATCCTGGAATGTGTGTACTGCAAGCAGCAGCTGCTGAG AAGAGAGGTGTATGACTTTGCCTTCAGGGACCTGTGCATTGTGTACAGGG ATGGCAACCCTTATGCTGTGGGGACAAGTGCCTGAAGTTCTACAGCAAG ATCAGTGAGTACAGGCACTACTGCTACAGCCTGTATGGAACCACCCTGGA ACAGCAGTACAACAAGCCCCTGTGTGACCTGCTGATCAGATGCATCAATG GCCAGAAACCCCTGTGCCCTGAGGAAAGCAGAGACACCTGGACAAGAAG CAGAGGTTCCACAACATCAGAGGCAGATGGACAGGCAGATGCATGAGCTG TTGCAGAAGCAGCAGAACCAGAAGGGAGACTCAGCTGTGA |
| 32 | Amino acid sequence of mli-E7E6 antigen | MDDQRDLISNHEQLPILGNRPREPERCSRGALYTGVSVLVALLLAGQATT AYFLYQQQGRLDKLTITSQNLQLESLRMKLPKSAKPVSQMRMATPLLMRP MSMDNMLLGPVKNVTKYGNMTQDHVMHLLTRSGPLEYPQLKGTFPENLKH LKNSMDGVNWKIFESWMKQWLLFEMSKNSLEEKKPTEAPPKEPLDMEDLS |

TABLE 1-continued

Sequences

| SEQ ID No. | Description | Sequence |
|---|---|---|
| | | SGLGVTRQELGQVTLSDRYLNRRAMHGDTPTLHEYMLDLQPETTDLYGYG QLNDSSEEEDEIDGPAGQAEPDRAHYNIVTFCCKCDSTLRLCVQSTHVDI RTLEDLLMGTLGIVGPICSQKPHQKRTAMFQDPQERPRKLPQLCTELQTT IHDIILECVYCKQQLLRREVYDFAFRDLCIVYRDGNPYAVGDKCLKFYSK ISEYRHYCYSLYGTTLEQQYNKPLCDLLIRCINGQKPLCPEEKQRHLDKK QRFHNIRGRWTGRCMSCCRSSRTRRETQL |
| 33 | Nucleotide sequence encoding a HPV16E7-HPV18E6 fusion protein having an N-terminal VSVG signal sequence and a C-terminal GSG linker followed by a self-cleaving peptide (2A peptide from Porcine Teschovirus) and the CDS for human GM-CSF | ATGAAATGTCTCCTCTACCTGGCCTTTCTCTTCATTGGTGTGAATTGCAT GCATGGGGACACCCCCACCCTGCATGAATACATGCTGGATCTGCAGCCTG AAACCACTGATCTGTATGGCTATGGCCAGCTGAATGACAGCAGTGAAGAA GAGGATGAAATTGATGGCCCAGCTGGCCAGGCAGAACCTGACAGAGCTCA TTACAACATTGTGACCTTTTGCTGCAAATGTGACAGCACTCTGAGGCTGT GTGTGCAGAGCACCCATGTGGACATCAGAACCCTGGAAGATCTGCTGATG GGCACCCTGGGCATTGTGTGTCCTATTTGCAGTCAGAAACCTGCCAGGTT TGAAGATCCCACCAGGAGTGGCTACAAACTGCCAGACCTGTGCACAGAAC TGAACACCAGCCTGCAGGACATTGAAATCACCTGTGTGTATTGCAAAACA GTGCTGGAACTGACAGAAGTGTTTGAAAAGATCTGTTTGTGGTGTACAG AGACAGCATTCCCCATGCTGCCTGCCACAAATGCATTGATTTTTACAGCA GGATCAGAGAACTGAGACATTACAGTGACAGTGTGTATGGGGACACTCTG GAGAAGCTGACCAACACTGGCCTGTACAATCTGCTGATCAGGTGTCTGAG GTGCCAGAAACCCCTGCTGAGGCATCTGAATGAAAAGAGGAGGTTTCACA ACATTGCTGGCCACTACAGAGGTCAGTGCCACAGCTGCTGCAACAGAGCC AGGCAGGAAAGACTGCAGAGGAGAAGAGAAACTCAGGTGGGCAGTGGTGC AACCAACTTCAGTCTGCTGAAACAGGCAGGTGATGTGGAAGAAAATCCAG GCCCCTGGCTGCAGAGCCTGCTTCTGCTGGGCACTGTGGCCTGCAGCATC AGTGCCCCAGCAAGGAGCCCCAGCCCCAGCACTCAGCCCTGGGAACATGT GAATGCCATTCAGGAGGCAAGGAGACTGCTGAACCTGAGCAGAGACACTG CTGCAGAAATGAATGAAACTGTGGAAGTGATCAGTGAAATGTTTGATCTG CAGGAGCCCACTTGCCTGCAGACCAGGCTGGAACTGTACAAACAGGGCCT GAGAGGAAGCCTGACCAAGCTGAAAGGCCCCCTGACCATGATGGCCAGCC ATTACAAACAGCACTGCCCTCCCACACCTGAAACCAGTTGTGCAACCCAG ATCATCACTTTTGAGAGTTTCAAGGAAAACCTGAAAGATTTTCTGCTGGT GATTCCCTTTGACTGTTGGGAGCCAGTGCAGGAATGA |
| 34 | Amino acid sequence of a HPV16E7-HPV18E6 fusion protein having an N-terminal VSVG signal sequence and a C-terminal GSG linker followed by a self-cleaving peptide (2A peptide from Porcine Teschovirus) and the CDS for human GM-CSF | MKCLLYLAFLFIGVNCMHGDTPTLHEYMLDLQPETTDLYGYGQLNDSSEE EDEIDGPAGQAEPDRAHYNIVTFCCKCDSTLRLCVQSTHVDIRTLEDLLM GTLGIVCPICSQKPARFEDPTRSGYKLPDLCTELNTSLQDIEITCVYCKT VLELTEVFEKDLFVVYRDSIPHAACHKCIDFYSRIRELRHYSDSVYGDTL EKLTNTGLYNLLIRCLRCQKPLLRHLNEKRRFHNIAGHYRGQCHSCCNRA RQERLQRRRETQVGSGATNFSLLKQAGDVEENPGPWLQSLLLLGTVACSI SAPARSPSPSTQPWEHVNAIQEARRLLNLSRDTAAEMNETVEVISEMFDL QEPTCLQTRLELYKQGLRGSLTKLKGPLTMMASHYKQHCPPTPETSCATQ IITFESFKENLKDFLINIPFDCWEPVQE |
| 35 | Nucleotide sequence encoding a HPV18E7-HPV16E6 fusion protein having an N-terminal VSVG signal sequence and a C-terminal GSG linker followed by a self-cleaving peptide (2A peptide from Porcine Teschovirus) and the CDS for human GM-CSF | ATGAAGTGTCTCCTCTACCTGGCCTTTCTCTTCATAGGGGTCAATTGCAT GCATGGCCCTAAAGCTACCCTGCAGGATATTGTGCTCCATCTGGAACCTC AGAATGAAATCCCTGTGGATCTGCTGGGCCATGGCCAGCTGAGTGACAGT GAAGAAGAAATGATGAAATTGATGGAGTGAACCATCAGCATCTGCCAGC CAGAAGGGCAGAGCCTCAGAGGCATACCATGCTGTGCATGTGCTGCAAAT GTGAAGCCAGAATTGAACTGGTGGTGGAAAGCAGTGCAGATGACCTGAGG GCCTTTCAGCAGCTGTTCCTGAACACCCTGAGCTTTGTGTGCCCTTGGTG TGCCAGCCAGCAGCATCAGAAGAACAGCAATGTTTCAGGATCCACAGG AAAGTGGCAGGAAGCTGCCTCAGCTGTGCACTGAACTGCAGACCACCATC CATGACATCATCCTGGAATGTGTGTACTGCAAGCAGCAGCTGCTGAGGAG GGAAGTGTATGATAGAGACCTGTGCATTGTGTACAGGGATGGCAACCCCT ATGCTGTGTGTGATAAATGCCTGAAATTTTATAGCAAGATTAGTGAATAT AGACATTATTGCTACAGCCTGTATGGCACCACCCTGGAACAGCAGTATAA CAAACCACTGTGTGATCTGCTGATTAGGTGCATTAACTGCCAGAAGCCAC TGCAGAGGCACCTGGACAAGAAACAGAGGTTCCATAACATTAGGGGCAGG TGGACAGGCAGATGCATGAGCTGCTGCAGAAGCAGCAGAACCAGAAGGGA AACCCAGCTGGGCAGTGGAGCAACTAACTTCAGCCTGCTGAAACAGGCTG GGGATGTGGAAGAGAACCCAGGCCCATGGCTGCAGAGCCTGCTGCTGCTG GGCACAGTGGCATGCAGCATTAGTGCCCCTGCCAGAAGCCCTAGCCCAAG CACCCAGCCCTGGGAGCATGTGAATGCTATCCAGGAGGCCAGAAGACTGC TGAACCTGAGCAGGGACACTGCAGCAGAAATGAATGAAACTGTGGAGGTG ATTAGTGAAATGTTTGACCTGCAGGAACCCACCTGCCTGCAGACCAGACT GGAACTGTATAAACAGGGGCTGAGAGGCAGCCTGACCAAGCTGAAGGGCC CCCTGACCATGATGGCAAGCCATTATAAACAGCATTGCCCCCCCACCCCT GAAACCAGCTGTGCCACCCAGATCATTACCTTTGAAAGCTTTAAAGAAAA CCTCAAGGATTTTCTGCTGGTGATTCCCTTTGACTGCTGGGAACCAGTGC AGGAATGA |

TABLE 1-continued

Sequences

| SEQ ID No. | Description | Sequence |
|---|---|---|
| 36 | Amino acid sequence of a HPV18E7-HPV16E6 fusion protein having an N-terminal VSVG signal sequence and a C-terminal GSG linker followed by a self-cleaving peptide (2A peptide from Porcine Teschovirus) and the CDS for human GM-CSF | MKCLLYLAFLFIGVNCMHGPKATLQDIVLHLEPQNEIPVDLLGHGQLSDS EEENDEIDGVNHQHLPARRAEPQRHTMLCMCCKCEARIELVVESSADDLR AFQQLFLNTLSFVCPWCASQQHQKRTAMFQDPQESGRKLPQLCTELQTTI HDIILECVYCKQQLLRREVYDRDLCIVYRDGNPYAVCDKCLKFYSKISEY RHYCYSLYGTTLEQQYNKPLCDLLIRCINCQKPLQRHLDKKQRFHNIRGR WTGRCMSCCRSSRTRRETQLGSGATNFSLLKQAGDVEENPGPWLQSLLLL GTVACSISAPARSPSPSTQPWEHVNAIQEARRLLNLSRDTAAEMNETVEV ISEMFDLQEPTCLQTRLELYKQGLRGSLTKLKGPLTMMASHYKQHCPPTP ETSCATQIITFESFKENLKDFLLVIPFDCWEPVQE |
| 37 | Nucleotide sequence encoding a HPV16E7-HPV18E6_HPV16E6-HPV18E7 fusion protein having an N-terminal VSVG signal sequence and a C-terminal GSG linker followed by a self-cleaving peptide (2A peptide from Porcine Teschovirus) and the CDS for human GM-CSF | ATGAAATGCCTCCTCTACCTGGCCTTCCTCTTCATTGGTGTCAATTGCAT GCATGGAGATACCCCTACCCTGCATGAATATATGCTGGATCTGCAGCCTG AAACCACTGACCTGTATGGCCAGCTGAATGATAGCAGTGAGGAG GAAGATGAGATTGATGGCCCTGCAGGCCAGGCAGAACCTGACAGGGCACA TTACAACATTGTGACCTTTTGCTGCAAATGTGATAGCACCCTGAGACTCT GTGTCCAGAGCACCCATGGGATATTAGGACCCTGGAAGATCTGCTGATG GGCACCCTGGGCATTGTGTGCCCAATTTGCAGCCAGAAGCCAGCTAGGTT TGAAGATCCCACCAGAAGTGGCTACAAACTCCCAGATCTCTGCACAGAGC TGAACACCAGCCTGCAGGATATTGAGATCACCTGTGTGTACTGCAAAACA GTGCTAGAACTGACAGAAGTCTTTGAAAAGGATCTGTTTGTGGTGTATAG AGACAGCATTCCTCATGCAGCCTGCCACAAATGCATTGATTTCTATAGCA GGATCAGGGAACTGAGGCATTACAGTGATAGTGTGTATGGTGATACCCTT GAAAAGCTGACCAACACTGGCCTGTACAACCTGCTGATTAGGTGCCTGAG ATGCCAGAAACCACTCCTGAGGCATCTCAATGAAAAAGGAGGTTTCATA ACATTGCAGGCCATTATAGGGGCCAGTGCCATAGCTGCTGCAACAGGGCC AGGCAGGAAAGACTGCAGAGAAGGAGGGAAACCCAGGTGCATCAGAAAAG GACTGCAATGTTCCAGGATCCACAGGAAAGTGGCAGGAAACTGCCACAGC TGTGCACAGAACTGCAGACCACCATCCATGATATTATCCTGGAATGTGTG TATTGCAAACAGCAGCTCCTCAGGAGGGAAGTGTATGATAGGGATCTGTG CATTGTGTATAGAGATGGCAACCCTTATGCAGTGTGTGACAAATGCCTGA AATTTTATAGCAAAATCAGTGAATATAGGCACTACTGCTATAGCCTGTAT GGCACCACCCTGGAACAGCAGTACAACAAACCTCTGTGTGACCTGCTGAT TAGGTGCATCAACTGCCAGAAACCTCTGCAGAGGCATCTGGATAAAAAAC AGAGGTTTCATAACATTAGGGGGAGGTGGACTGGCAGATGCATGAGCTGC TGCAGGAGCAGCAGAACCAGGAGGGAAACCCAGCTGCATGGCCCCAAAGC CACCCTGCAGGATATTGTGCTGCATCTGGAACCACAGAATGAGATTCCAG TGGATCTGCTGGGCCATGGCCAGCTCAGTGATAGTGAAGAGGAAAATGAT GAAATTGATGGGGTCAACCATCAGCACCTGCCAGCCAGGAGAGCAGAGCC CCAGAGACACACCATGCTGTGCATGTGCTGCAAATGTGAGGCCAGGATTG AACTGGTGGTGGAAAGCAGTGCAGATGATCTGAGGGCCTTCCAGCAGCTG TTTCTGAACACCCTGAGCTTTGTGTGCCCTTGGTGTGCCAGCCAGCAGGG GAGTGGTGCAACCAACTTTAGCCTGCTGAAACAGGCAGGTGATGTGGAGG AAAACCCAGGCCCCTGGCTGCAGAGCCTGCTGCTGCTGGGCACAGTGGCA TGCAGCATTAGTGCCCCAGCCAGGAGCCCCAGCCCCAGCACCCAGCCCTG GGAGCATGTGAATGCAATTCAGGAAGCCAGGAGGCTGCTGAACCTGAGCA GGGATACTGCAGCTGAGATGAATGAAACAGTGGAGGTGATTAGTGAGATG TTTGACCTCCAGGAACCCACCTGCCTGCAGACCAGGCTGGAGCTCTACAA ACAGGGCCTGAGAGGCAGCCTCACCAAACTGAAGGGCCCACTGACCATGA TGGCCAGCCATTACAAACAGCATTGCCCTCCCACCCCTGAGACCAGCTGT GCCACCCAGATCATTACCTTTGAAAGCTTTAAAGAAAACCTGAAAGACTT CCTGCTGGTGATTCCATTTGACTGCTGGGAACCTGTGCAGGAATGA |
| 38 | Amino acid sequence of a HPV16E7-HPV18E6_HPV16E6-HPV18E7 fusion protein having an N-terminal VSVG signal sequence and a C-terminal GSG linker followed by a self-cleaving peptide (2A peptide from Porcine Teschovirus) and the CDS for human GM-CSF | MKCLLYLAFLFIGVNCMHGDTPTLHEYMLDLQPETTDLYGYGQLNDSSEE EDEIDGPAGQAEPDRAHYNIVTFCCKCDSTLRLCVQSTHVDIRTLEDLLM GTLGIVCPICSQKPARFEDPTRSGYKLPDLCTELNTSLQDIEITCVYCKT VLELTEVFEKDLFVVYRDSIPHAACHKCIDFYSRIRELRHYSDSVYGDTL EKLTNTGLYNLLIRCLRCQKPLLRHLNEKRRFHNIAGHYRGQCHSCCNRA RQERLQRRRETQVHQKRTAMFQDPQESGRKLPQLCTELQTTIHDIILECV YCKQQLLRREVYDRDLCIVYRDGNPYAVCDKCLKFYSKISEYRHYCYSLY GTTLEQQYNKPLCDLLIRCINCQKPLQRHLDKKQRFHNIRGRWTGRCMSC CRSSRTRRETQLHGPKATLQDIVLHLEPQNEIPVDLLGHGQLSDSEEEND EIDGVNHQHLPARRAEPQRHTMLCMCCKCEARIELVVESSADDLRAFQQL FLNTLSFVCPWCASQQGSGATNFSLLKQAGDVEENPGPWLQSLLLLGTVA CSISAPARSPSPSTQPWEHVNAIQEARRLLNLSRDTAAEMNETVEVISEM FDLQEPTCLQTRLELYKQGLRGSLTKLKGPLTMMASHYKQHCPPTPETSC ATQIITFESFKENLKDFLLVIPFDCWEPVQE |
| 39 | Nucleotide sequence of a tri-segmented r3LCMVart-based vector expressing HPV16 E7E6 fusion protein: S | GCGCACCGGGGATCCTAGGCTTTTTGGATTGCGCTTTCCTCTAGATCAAC TGGGTGTCAGGCCCTATCCTACAGAAGGATGCACGGCGACACCCCTACCC TGCACGAGTACATGCTGGACCTGCAGCCCGAGCAACCGACCTGTACGGC TACGGCCAGCTGAACGACAGCAGCGAGGAAGAGGACGAGATCGACGGCCC TGCTGGACAGGCCGAACCTGACAGAGCCCACTACAACATCGTGACATTCT |

TABLE 1-continued

Sequences

| SEQ ID No. | Description | Sequence |
|---|---|---|
| | segment 1 (containing GP) | GCTGCAAGTGCGACAGCACCCTGAGACTGTGCGTGCAGAGCACCCACGTG GACATCAGAACCCTGGAAGATCTGCTGATGGGCACCCTGGGCATCGTGGG CCCTATCTGCTCTCAGAAGCCCCACCAGAAAAGAACCGCCATGTTCCAGG ACCCCCAGGAAAGACCCAGAAAGCTGCCCCAGCTGTGCACCGAGCTGCAG ACCACCATCCACGACATCATCCTGGAATGCGTGTACTGCAAGCAGCAGCT GCTGAGAAGAGAGGTGTACGACTTCGCCTTCCGGGACCTGTGCATCGTGT ACAGGGACGGCAACCCTTACGCCGTGGGCGACAAGTGCCTGAAGTTCTAC AGCAAGATCAGCGAGTACCGGCACTACTGCTACAGCCTGTACGGAACCAC CCTGGAACAGCAGTACAACAAGCCCCTGTGCGACCTGCTGATCAGATGCA TCAACGGCCAGAAACCCCTGTGCCCCGAGGAAAAGCAGAGACACCTGGAC AAGAAGCAGCGGTTCCACAACATCAGAGGCAGATGGACCGGCAGATGCAT GAGCTGTTGCAGAAGCAGCAGAACCAGACGCGAGACTCAGCTGTGAAGAA CAGCGCCTCCCTGACTCTCCACCTCGAAAGAGGTGGAGAGTCAGGGAGGC CCAGAGGGTCTTAGAGTGTCACAACATTTGGGCCTCTAAAAATTAGGTCA TGTGGCAGAATGTTGTGAACAGTTTTCAGATCTGGGAGCCTTGCTTTGGA GGCGCTTTCAAAAATGATGCAGTCCATGAGTGCACAGTGCGGGGTGATCT CTTTCTTCTTTTTGTCCCTTACTATTCCAGTATGCATCTTACACAACCAG CCATATTTGTCCCACACTTTATCTTCATACTCCCTCGAAGCTTCCCTGGT CATTTCAACATCGATAAGCTTAATGTCCTTCCTATTTTGTGAGTCCAGAA GCTTTCTGATGTCATCGGAGCCTTGACAGCTTAGAACCATCCCCTGCGGA AGAGCACCTATAACTGACGAGGTCAACCCGGGTTGCGCATTGAAGAGGTC GGCAAGATCCATGCCGTGTGAGTACTTGGAATCTTGCTTGAATTGTTTTT GATCAACGGGTTCCCTGTAAAAGTGTATGAACTGCCCGTTCTGTGGTTGG AAAAATTGCTATTTCCACTGGATCATTAAATCTACCCTCAATGTCAATCCA TGTAGGAGCGTTGGGGTCAATTCCTCCCATGAGGTCTTTTAAAAGCATTG TCTGGCTGTAGCTTAAGCCCACCTGAGGTGGACCTGCTGCTCCAGGCGCT GGCCTGGGTGAGTTGACTGCAGGTTTCTCGCTTGTGAGATCAATTGTTGT GTTTTCCCATGCTCTCCCCACAATCGATGTTCTACAAGCTATGTATGGCC ATCCTTCACCTGAAAGGCAAACTTTATAGAGGATGTTTTCATAAGGGTTC CTGTCCCCAACTTGGTCTGAAACAAACATGTTGAGTTTTCTCTTGGCCCC GAGAACTGCCTTCAAGAGATCCTCGCTGTTGCTTGGCTTGATCAAAATTG ACTCTAACATGTTACCCCCATCCAACAGGGCTGCCCCTGCCTTCACGGCA GCACCAAGACTAAAGTTATAGCCAGAAATGTTGATGCTGGACTGCTGTTC AGTGATGACCCCCAGAACTGGGTGCTTGTCTTTCAGCCTTTCAAGATCAT TAAGATTTGGATACTTGACTGTGTAAAGCAAGCCAAGGTCTGTGAGCGCT TGTACAACGTCATTGAGCGGAGTCTGTGACTGTTTGGCCATACAAGCCAT AGTTAGACTTGGCATTGTGCCAAATTGATTGTTCAAAAGTGATGAGTCTT TCACATCCCAAACTCTTACCACACCACTTGCACCCTGCTGAGGCTTTCTC ATCCCAACTATCTGTAGGATCTGAGATCTTTGGTCTAGTTGCTGTGTTGT TAAGTTCCCCATATATACCCCTGAAGCCTGGGGCCTTTCAGACCTCATGA TCTTGGCCTTCAGCTTCTCAAGGTCAGCCGCAAGAGACATCAGTTCTTCT GCACTGAGCCTCCCCACTTTTCAAAACATTCTTCTTTGATGTTGACTTTAA ATCCACAAGAGAATGTACAGTCTGGTTGAGACTTCTGAGTCTCTGTAGGT CTTTGTCATCTCTCTTTTCCTTCCTCATGATCCTCTGAACATTGCTGACC TCAGAGAAGTCCAACCCATTCAGAAGGTTGGTTGCATCCTTAATGACAGC AGCCTTCACATCTGATGTGAAGCTCTGCAATTCTCTTCTCAATGCTTGCG TCCATTGGAAGCTCTTAACTTCCTTAGACAAGGACATCTTGTTGCTCAAT GGTTTCTCAAGACAAATGCGCAATCAAATGCCTAGGATCCACTGTGCG |
| 40 | Nucleotide sequence of a tri-segmented r

TABLE 1-continued

Sequences

| SEQ ID No. | Description | Sequence |
|---|---|---|
| | | GTTTCGCCGGTCTTTGCATGTTCTAGGTACCAAAACTTTGAGTAATTGCA<br>ATATGGCACCCCCATCAGATCTCTCAAGTGGTTCCTCATCAGTAGTTGAT<br>CTGAAATCAAAGAATTCACTGTTGTTTTGAATAAGTGCAAGGCAGATTCT<br>ACGTCCTCTTTGAACTTACTCAAAGCAGCCTTGTTGTAGTCAATTAGTCG<br>CAGCATGTCACAGAATTCTTCATCATGATTTACATTGCATTTCGCAACTG<br>CTGTGTTCCCGAAACACTTAAGCTCTGCAGCAAGAATCATCCATTTGGTC<br>AGGCAATAACCACCTGGATTCTCCACCCCTGAAGAGTCTGACAAAGTCCA<br>GGTGAATGTGCCCGCTAGTCTCCTAGTGGAGAACTTAGTTTTCTCTTGGG<br>AAAGGAGAATCCTGGACATCCCAAAAGGACCTGCATATGTGCAGTGGTTT<br>TCCCAGGTTCTATTTTGTATAATCAGGTATTGGTAACTCGTCTGGCTACA<br>CCAGGTGGTCTTGCCATCTGAGCCTGTCCAGCCCCAGCCACTCCTCATGT<br>ATTTCCCCCCGAAGGCAGTTCTAAACATATCTAGGACTCTACCTCTGAAG<br>GTTCTACACTGGCTCTGAGCACTTTGTGCATCTGAGAATGTCAAGTTGTA<br>TTGGATGGTTATGCCATTGTTGAAGTCGCAGGATACTGCCTTATAGTTGG<br>AGTTCCCTCTGATACTGAGGTGTAGGCTCGAAACTATACTCATGAGTGTG<br>TGGTCAAAGGTCTTTTTGTTGAAGGCAGAGGTCAGATTGCAAAAGTTGTG<br>ACTGATGATGGAATCATTGGTGAAGGTCAATTCTAGTCCAGAAGTCCCCA<br>TACTGATGTAATGGTGGGAGTTGTTGGCTGAACATGCGTTGGGCATGGTC<br>AGGTTCAGATGTGACATATCAAACTCCACTGACTTAAATTGGTAAACTCC<br>TTTGTAAATGTCGGGTCCCTTAAGACCGTACATGCCACAGGACCTGCCAG<br>CCAGAAGTAGGAAACTGATCAATGCGAATATCCCACAGGTGGCAAAATTG<br>TAGACAGCCTTGATACCCGTGATCACGATAAGCACAATAATGACAATGTT<br>GATCACCTCATCGATGATGTGAGGCAGAGCCTCAAACATTGTCACAATCT<br>GACCCATCTTGTTGCTCAATGGTTTCTCAAGACAAATGCGCAATCAAATG<br>CCTAGGATCCACTGTGCG |
| 41 | Nucleotide sequence of a tri-segmented r3LCMVart-based vector expressing HPV16 E7E6 fusion protein: L segment | gCGCACCGGGGATCCTAGGCGTTTAGTTGCGCTGTTTGGTTGCACAACTT<br>TCTTCGTGAGGCTGTCAGAAGTGGACCTGGCTGATAGCGATGGGTCAAGG<br>CAAGTCCAGAGAGGAGAAAGGCACCAATAGTACAAACAGGGCCGAAATCC<br>TACCAGATACCACCTATCTTGGCCCTTTAAGCTGCAAATCTTGCTGGCAG<br>AAATTTGACAGCTTGGTAAGATGCCATGACCACTACCTTTGCAGGCACTG<br>TTTAAACCTTCTGCTGTCAGTATCCGACAGGTGTCCTCTTTGTAAATATC<br>CATTACCAACCAGATTGAAGATATCAACAGCCCCAAGCTCTCCACCTCCC<br>TACGAAGAGTAACACCGTCCGGCCCCGGCCCCGACAAACAGCCCAGCACA<br>AGGGAACCGCACGTCaCCCAACGCACACAGACACAGCACCCAACACAGAA<br>CACGCACACACACACACACACACACCCACACGCACGCGCCCCCACCACCG<br>GGGGGCGCCCCCCCCGGGGGGCGGCCCCCGGGAGCCCGGGCGGAGCCC<br>CACGGAGATGCCCATCAGTCGATGTCCTCGGCCACCGACCCGCCcAGCCA<br>ATCGTCGCAGGACCTCCCCTTGAGTCTAAACCTGCCCCCCACTgTTTCAT<br>ACATCAAAGTGCTCCTAGATTTGCTAAAACAAAGTCTGCAATCCTTAAAG<br>GCGAACCAGTCTGGCAAAAGCGACAGTGGAATCAGCAGAATAGATCTGTC<br>TATACATAGTTCCTGGAGGATTACACTTATCTCTGAACCCAACAAATGTT<br>CACCAGTTCTGAATCGATGCAGGAAGAGGTTCCCAAGGACATCACTAATC<br>TTTTCATAGCCCTCAAGTCCTGCTAGAAAGACTTTCATGTCCTTGGTCTC<br>CAGCTTCACAATGATATTTTGGACAAGGTTTCTTCCTTCAAAAAGGGCAC<br>CCATCTTTACAGTCAGTGGCACAGGCTCCCACTCAGGTCCAACTCTCTCA<br>AAGTCAATAGATCTAATCCCATCCAGTATTCTTTTGGAGCCCAACAACTC<br>AAGCTCAAGAGAATCACCAAGTATCAAGGGATCTTCCATGTAATCCTCAA<br>ACTCTTCAGATCTGATATCAAAGACACCATCGTTCACCTTGAAGACAGAG<br>TCTGTCCTCAGTAAGTGGAGGCATTCATCCAACATTCTTCTATCTATCTC<br>ACCCTTAAAGAGGTGAGAGCATGATAAAAGTTCAGCCACACCTGGATTCT<br>GTAATTGGCACCTAACCAAGAATATCAATGAAAATTTCCTTAAACAGTCA<br>GTATTATTCTGATTGTGCGTAAAGTCCACTGAAATTGAAAACTCCAATAC<br>CCCTTTTGTGTAGTTGAGCATGTAGTCCCACAGATCCTTTAAGGATTTAA<br>ATGCCTTTGGGTTTGTCAGGCCCTGCCTAATCAACATGGCAGCATTACAC<br>ACAACATCTCCCATTCGGTAAGAGAACCACCCAAAACCAAACTGCAAATC<br>ATTCCTAAACATAGGCCTCTCCACATTTTTGTTCACCACCTTTGAGACAA<br>ATGATTGAAAGGGGCCCAGTGCCTCAGCACCATCTTCAGATGGCATCATT<br>TCTTTATGAGGGAACCATGAAAAATTGCCTAATGTCCTGGTTGTTGCAAC<br>AAATTCTCGAACAAATGATTCAAAATACACCTGTTTTAAGAAGTTCTTGC<br>AGACATCCCTCGTGCTAACAACAAATTCATCAACCAGACTGGAGTCAGAT<br>CGCTGATGAGAATTGGCAAGGTCAGAAAACAGAACAGTGTAATGTTCATC<br>CCTTTTCCACTTAACAACATGAGAAATGAGTGACAAGGATTCTGAGTTAA<br>TATCAATTAAAACACAGAGGTCAAGGAATTTAATTCTGGGACTCCACCTC<br>ATGTTTTTTGAGCTCATGTCAGACATAAATGGAAGAAGCTGATCCTCAAA<br>GATCTTGGGATATAGCCGCCTCACAGATTGAATCACTTGGTTCAAATTCA<br>CTTTGTCCTCCAGTAGCCTTGAGCTCTCAGGCTTTCTTGCTACATAATCA<br>CATGGGTTTAAGTGCTTAAGAGTTAGGTTCTCACTGTTATTCTTCCCTTT<br>GGTCGGTTCTGCTAGGACCCAAACACCCAACTCAAAAGAGTTGCTCAATG<br>AAATACAAATGTAGTCCCAAAGAAGAGGCCTTAAAAGGCATATATGATCA<br>CGGTGGGCTTCTGGATGAGACTGTTTGTCACAAATGTACAGCGTTATACC<br>ATCCCGATTGCAAACTCTTGTCACATGATCATCTGTGGTTAGATCCTCAA<br>GCAGCTTTTTGATATACAGATTTTCCCTATTTTTGTTTCTCACACACCTG<br>CTTCCTAGAGTTTTGCAAAGGCCTATAAAGCCAGATGAGATACAACTCTG |

TABLE 1-continued

Sequences

| SEQ ID No. | Description | Sequence |
|---|---|---|
| | | GAAAGCTGACTTGTTGATTGCTTCTGACAGCAGCTTCTGTGCACCCCTTG
TGAATTTACTACAAAGTTTGTTCTGGAGTGTCTTGATCAATGATGGGATT
CTTTCCTCTTGGAAAGTCATCACTGATGGATAAACCACCTTTTGTCTTAA
AACCATCCTTAATGGGAACATTTCATTCAAATTCAACCAGTTAACATCTG
CTAACTGATTCAGATCTTCTTCAAGACCGAGGAGGTCTCCCAATTGAAGA
ATGGCCTCCtTTTTATCTCTGTTAAATAGGTCTAAGAAAAATTCTTCATT
AAATTCACCATTTTTGAGCTTATGATGCAGTTTCCTTACAAGCTTTCTTA
CAACCTTTGTTTCATTAGGACACAGTTCCTCAATGAGTCTTTGTATTCTG
TAACCTCTAGAACCATCCAGCCAATCTTTCACATCAGTGTTGGTATTCAG
TAGAAATGGATCCAAAGGGAAATTGGCATACTTTAGGAGGTCCAGTGTTC
TCCTTTGGATACTATTAACTAGGGAGACTGGGACGCCATTTGCGATGGCT
TGATCTGCAATTGTATCTATTGTTTCACAAAGTTGATGTGGCTCTTTACA
CTTGACATTGTGTAGCGCTGCAGATACAAACTTTGTGAGAAGAGGGACTT
CCTCCCCCCATACATAGAATCTAGATTTAAATTCTGCAGCGAACCTCCCA
GCCACACTTTTTGGGCTGATAAATTTGTTTAACAAGCCGCTCAGATGAGA
TTGGAATTCCAACAGGACAAGGACTTCCTCCGGATCACTTACAACCAGGT
CACTCAGCCTCCTATCAAATAAAGTGATCTGATCATCACTTGATGTGTAA
GCCTCTGGTCTTTCGCCAAAGATAACACCAATGCAGTAGTTGATGAACCT
CTCGCTAAGCAAACCATAGAAGTCAGAAGCATTATGCAAGATTCCCTGCC
CCATATCAATAAGGCTGGATATATGGGATGGCACTATCCCCATTTCAAAA
TATTGTCTGAAAATTCTCTCAGTAACAGTTGTTTCTGAACCCCTGAGAAG
TTTTAGCTTCGACTTGACATATGATTTCATCATTGCATTCACAACAGGAA
AGGGGACCTCGACAAGCTTATGCATGTGCCAAGTTAACAAAGTGCTAACA
TGATCTTTCCCGGAACGCACATACTGGTCATCACCTAGTTTGAGATTTTG
TAGAAACATTAAGAACAAAAATGGGCACATCATTGGTCCCCATTTGCTGT
GATCCATACTATAGTTTAAGAACCCTTCCCGCACATTGATAGTCATTGAC
AAGATTGCATTTTCAAATTCCTTATCATTGTTTAAACAGGAGCCTGAAAA
GAAACTTGAAAAGACTCAAAATAATCTTCTATTAACCTTGTGAACATTT
TTGTCCTCAAATCTCCAATATAGAGTTCTCTATTTCCCCCAACCTGCTCT
TTATAAGATAGTGCAAATTTCAGCCTTCCAGAGTCAGGACCTACTGAGGT
GTATGATGTTGGTGATTCTTCTGAGTAGAAGCACAGATTTTTCAAAGCAG
CACTCATACATTgTGTCAACGACAGAGCTTTACTAAGGGACTCAGAATTA
CTTTCCCTCTCACTGATTCTCACGTCTTCTTCCAGTTTGTCCCAGTCAAA
TTTGAAATTCAAGCCTTGCCTTTGCATATGCCTGTATTTCCCTGAGTACG
CATTTGCATTCATTTGCAACAGAATCATCTTCATGCAAGAAACCAATCA
TTCTCAGAAAAGAACTTTCTACAAAGGTTTTTTGCCATCTCATCGAGGCC
ACACTGATCTTTAATGACTGAGGTGAAATACAAAGGTGACAGCTCTGTGG
AACCCTCAACAGCCTCACAGATAAATTTCATGTCATCATTGGTTAGACAT
GATGGGTCAAAGTCTTCTACTAAATGGAAAGATATTTCTGACAAGATAAC
TTTTCTTAAGTGAGCCATCTTCCCTGTTAGAATAAGCTGTAAATGATGTA
GTCCTTTTGTATTTGTAAGTTTTTCTCCATCTCCTTTGTCATTGGCCCTC
CTACCTCTTCTGTACCGTGCTATTGTGGTGTTGACCTTTTCTTCGAGACT
TTTGAAGAAGCTTGTCTCTTCTTCTCCATCAAAACATATTTCTGCCAGGT
TGTCTTCCGATCTCCCTGTCTCTTCTCCCTTGGAACCGATGACCAATCTA
GAGACTAACTTGGAAACTTTATATTCATAGTCTGAGTGGCTCAACTTATA
CTTTTGTTTTCTTACGAAACTCTCCGTAATTTGACTCACAGCACTAACAA
GCAATTTGTTAAAGTCATATTCCAGAAGTCGTTCTCCATTTAGATGCTTA
TTAACCACCACACTTTTGTTACTAGCAAGATCTAATGCTGTCGCACATCC
AGAGTTAGTCATGGGATCTAGGCTGTTTAGCTTCTTCTCTCCTTTGAAAA
TTAAAGTGCCGTTGTTAAATGAAGACACCATTAGGCTAAAGGCTTCCAGA
TTAACACCTGGAGTTGTATGCTGACAGTCAATTTCTTTACTAGTGAATCT
CTTCATTTGCTCATAGAACACACATTCTTCCTCAGGAGTGATTGCTTCCT
TGGGGTTGACAAAAAAACCAAATTGACTTTTGGGCTCAAAGAACTTTTCA
AAACATTTTATCTGATCTGTTAGCCTGTCAGGGGTCTCCTTTGTGATCAA
ATGACACAGGTATGACACATTCAACATAAATTTAAATTTTGCACTCAACA
ACACCTTCTCACCAGTACCAAAAATAGTTTTTATTAGGAATCTAAGCAGC
TTATACACCACCTTCTCAGCAGGTGTGATCAGATCCTCCCTCAACTTATC
CATTAATGATGTAGATGAAAAATCTGACACTATTGCCATCACCAAATATC
TGACACTCTGTACCTGCTTTTGATTTCTCTTTGTTGGGTTGGTGAGCATT
AGCAACAATAGGGTCCTCAGTGCAACCTCAATGTCGGTGAGACAGTCTTT
CAAATCAGGACATGATCTAATCCATGAAATCATGATGTCTATCATATTGT
ATAAGACCTCATCTGAAAAAATTGGTAAAAAGAACCTTTTAGGATCTGCA
TAGAAGGAAATTAAATGACCATCCGGGCCTTGTATGGAGTAGCACCTTGA
AGATTCTCCAGTCTTCTGGTATAATAGGTGGTATTCTTCAGAGTCCAGTT
TTATTACTTGGCAAAACACTTCTTTGCATTCTACCACTTGATATCTCACA
GACCCTATTTGATTTTGCCTTAGTCTAGCAACTGAGCTAGTTTTCATACT
GTTTGTTAAGGCCAGACAAACAGATGATAATCTTCTCAGGCTCTGTATGT
TCTTCAGCTGCTCTGTGCTGGGTTGGAAATTGTAATCTTCAAACTTCGTA
TAATACATTATCGGGTGAGCTCCAATTTTCATAAAGTTCTCAAATTCAGT
GAATGGTATGTGGCATTCTTGCTCAAGGTGTTCAGACAGTCCGTAATGCT
CGAAACTCAGTCCCACCACTAACAGGCATTTTTGAATTTTGCAATGAAC
TCACTAATAGAtGCCCTAAACAATTCCTCAAAAGACACCTTTCTAAACAC
CTTTGACTTTTTTCTATTCCTCAAAGTCTAATGAACTCCTCTTTAGTGC
TGTGAAAGCTTACCAGCCTATCATTCACACTACTATAGCAACAACCCACC |

TABLE 1-continued

Sequences

| SEQ ID No. | Description | Sequence |
|---|---|---|
| | | CAGTGTTTATCATTTTTTAACCCTTTGAATTTCGACTGTTTTATCAATGA
GGAAAGACACAAAACATCCAGATTTAACAACTGTCTCCTTCTAGTATTCA
ACAGTTTCAAACTCTTGACTTTGTTTAACATAGAGAGGAGCCTCTCATAT
TCAGTGCTAGTCTCACTTCCCCTTTCGTGCCCATGGGTCTCTGCAGTTAT
GAATCTCATCAAAGGACAGGATTCGACTGCCTCCCTGCTTAATGTTAAGA
TATCATCACTATCAGCAAGGTTTTCATAGAGCTCAGAGAATTCCTTGATC
AAGCCTTCAGGGTTTACTTTCTGAAAGTTTCTCTTTAATTTCCCACTTTC
TAAATCTCTTCTAAACCTGCTGAAAAGAGAGTTTATTCCAAAAACCACAT
CATCACAGCTCATGTTGGGGTTGATGCCTTCGTGGCACATCCTCATAATT
TCATCATTGTGAGTTGACCTCGCATCTTTCAGAATTTTCATAGAGTCCAT
ACCGGAGCGCTTGTCGATAGTAGTCTTCAGGGACTCACAGAGTCTAAAAT
ATTCAGACTCTTCAAAGACTTTCTCATTTTGGTTAGAATACTCCAAAAGT
TTGAATAAAAGGTCTCTAAATTTGAAGTTTGCCCACTCTGGCATAAAACT
ATTATCATAATCACAACGACCATCTACTATTGGAACTAATGTGACACCCG
CAACAGCAAGGTCTTCCCTGATGCATGCCAATTTGTTAGTGTCCTCTATA
AATTTCTTCTCAAAACTGGCTGGaGtGCTCCTAACAAAACACTCAAGAAG
AATGAGAGAATTGTCTATCAGCTTGTAACCATCAGGAATGATAAGTGGTA
GTCCTGGGCATACAATTCCAGACTCCACCAAAATTGTTTCCACAGACTTA
TCGTCGTGGTTGTGTGTGCAGCCACTCTTGTCTGCACTGTCTATTTCAAT
GCAGCGTGACAGCAACTTGAGTCCCTCAATCAGAACCATTCTGGGTTCCC
TTTGTCCCAGAAAGTTGAGTTTCTGCCTTGACAACCTCTCATCCTGTTCT
ATATAGTTTAAACATAACTCTCTCAATTCTGAGATGATTTCATCCATTGC
GCATCAAAAAGCCTAGGATCCTCGGTGCG |
| 42 | Nucleotide sequence of a tri-segmented r3JUNVart-based vector expressing the HPV16 E7E6 fusion protein: S segment 1 (containing NP) | GCGCACCG TABLE 1-continued Sequences

| SEQ ID No. | Description | Sequence |
|---|---|---|
| | | ACTTGGTTGAAGTCGATGCTGTCAGCAATTAGCTTGGCGTCCTTCAAAAC<br>ATCTGACTTGACAGTCTGAGTGAATTGGCTCAAACCTCTCCTTAAGGACT<br>GAGTCCATCTAAAGCTTGGAACCTCCTTGGAGTGTGCCATGCCAGAAGTT<br>CTGGTGATTTTGATCTAGAATAGAGTTGCTCAGTGAAAGTGTTAGACACT<br>ATGCCTAGGATCCACTGTGCG |
| 43 | Nucleotide sequence of a tri-segmented r3JUNVart-based vector expressing the HPV16 E7E6 fusion protein: S segment 2 (containing GP) | GCGCACCGGGGATCCTAGGCGATTTTGGTTACGCTATAATTGTAACTGTT<br>TTCTGTTTGGACAACATCAAAAACATCCATTGCACAATGCACGGCGACAC<br>CCCTACCCTGCACGAGTACATGCTGGACCTGCAGCCCGAGACAACCGACC<br>TGTACGGCTACGGCCAGCTGAACGACAGCAGCGAGGAAGAGGACGAGATC<br>GACGGCCCTGCTGGACAGGCCGAACCTGACAGAGCCCACTACAACATCGT<br>GACATTCTGCTGCAAGTGCGACAGCACCCTGAGACTGTGCGTGCAGAGCA<br>CCCACGTGGACATCAGAACCCTGGAAGATCTGCTGATGGGCACCCTGGGC<br>ATCGTGGGCCCTATCTGCTCTCAGAAGCCCCACCAGAAAAGAACCGCCAT<br>GTTCCAGGACCCCCAGGAAAGACCCAGAAAGCTGCCCCAGCTGTGCACCG<br>AGCTGCAGACCACCATCCACGACATCATCCTGGAATGCGTGTACTGCAAG<br>CAGCAGCTGCTGAGAAGAGAGGTGTACGACTTCGCCTTCCGGGACCTGTG<br>CATCGTGTACAGGGACGGCAACCCTTACGCCGTGGGCGACAAGTGCCTGA<br>AGTTCTACAGCAAGATCAGCGAGTACCGGCACTACTGCTACAGCCTGTAC<br>GGAACCACCCTGGAACAGCAGTACAACAAGCCCCTGTGCGACCTGCTGAT<br>CAGATGCATCAACGGCCAGAAACCCCTGTGCCCCGAGGAAAAGCAGAGAC<br>ACCTGGACAAGAAGCAGCGGTTCCACAACATCAGAGGCAGATGGACCGGC<br>AGATGCATGAGCTGTTGCAGAAGCAGCAGAACCAGACGCGAGACTCAGCT<br>GTGAGACCTCCTGAGGGTCCCCACCAGCCCGGGCACTGCCCGGGCTGGTG<br>TGGCCCCCCAGTCCGCGGCCTGGCCGCGGACTGGGGAGGCACTGCTTAGT<br>GTCCTCTACGCCAAACTGTTGGTTTCTTTAGATTGGGGTACTTACCACAT<br>CTGCAACCACCCAAGCTGTTCAACCTGTGTGGCAAAGGGCATGCTTCGCC<br>CCTGATGTGTCTGTGGGAGGGTATACCCACCAAGTGAAGGAAGAGTGACG<br>CTGTGAAGAATACTGTGCTCCAAATACAGATGTCAACTAAAGTCAAAGGA<br>GTTTTACCCTGCCTGTCCGAATACTCTTTGCTTAGCATTTCAGAAATTAA<br>GAAGTCACTTTCTAATATCCAGTCATTACGGAAGTCAGAGATGTTCAAAT<br>AGCTGTTGTTTTTTATTAACCAGCACCTTGGTAATGAGTGTTGTCCTGAA<br>AGTGTGTGGTTGACATACCAAAATTTTGTGTAATTGCAGTAAGGGACACT<br>CATCAGTTCCCTAATTTTGTTTTTCATCAATAAATTGTCAGATATCAGGG<br>CATTGATTGTCTGCCCCATCAGATTTACTTGTTTCTTAGTTTCATCATTT<br>AGGGTTTTGATAGCATTTTTGTTGTAATCAAAGAGCCTCAACATGTCACA<br>GAATTCAGAGTCATGATTCAAATTGCATTTTGCTACAGCAGTATTGCCAA<br>AACACTTCATTTTGGCTGCTACGAGCATCCACTCTTCTAGACAATAGCCT<br>CCAGGGGTATCCTTGCCGGATGAGTCTGTCAAAGACCAGGAGAAGAATGC<br>TTTCAAGGACCTCCTTGGAAGTTGAATGTTTTTACCTCTTGTAAGGAAGT<br>GTAATGTGTTAACGTGGTCGAGTGGACATTGGAGAGGCCAACTGGTAGGT<br>TGTGCCTTCATTAAGCACAGTTTGCCATTCAAGCAAGGGTCAGGATATTC<br>TCTATATAAATGATGCATGCCAGTCTTAAACTTCTTAGCATAATTTCCAT<br>TGACACCAGTCTTGGAGGTGTTGACTTGAAAGATGAAGCCTTCTGTCTTT<br>GCACGGTTCCTACACAGAAATGGTGGGTCTAGATGCCAATCATGTCCCAC<br>AGCATTCATGAACCACTGAGACAACCAAATTTGATCATCACTTTTGGAAC<br>ACCAGCTCATATCTGCTGGATGTTGTATTATAACATCATACTGTGGCAAC<br>AATACTGCAATATCATCAAAGCTGATCTGAAATGAAGCATTGCCCCCCTT<br>AATGTAAAGATGGCTCTTGTTTAAGGTACACAACAAAGGTAGGTCATGTG<br>GATTGTTGGAAAAGAGACCCACCATTGAGAAGGACACAGTCTGGAACTCA<br>GTGTGCAGTCCGATTTTGAAAGCTTCTTCTGTGCAGGATCTTCCTGCAAG<br>CGCTAGGAATACAAAGAATTGGAATAAACCACTTTTGTACAAGTTCACTA<br>TACCCTTAATGATGGCAATGAGACTGACTGCAACAAGAGCAATGTTCAGA<br>GCCTCCTGCAAAAAGGTTGGTATTTCTTGCATGAAGCTAATGAACTGCCC<br>CATGCCAGAAGTTCTGGTGATTTTGATCTAGAATAGAGTTGCTCAGTGAA<br>AGTGTTAGACACTATGCCTAGGGATCCACTGTGCG |
| 44 | Nucleotide sequence of a tri-segmented r3JUNVart-based vector expressing the HPV16 E7E6 fusion protein: L segment | GCGCACCGGGGATCCTAGGCGTAACTTCATCATTAAAATCTCAGATTCTG<br>CTCTGAGTGTGACTTACTGCGAAGAGGCAGACAAATGGGCAACTGCAACG<br>GGGCATCCAAGTCTAACCAGCCAGACTCCTCAAGAGCCACACAGCCAGCC<br>GCAGAATTTAGGAGGGTAGCTCACAGCAGTCTATATGGTAGATATAACTG<br>TAAGTGCTGCTGGTTTGCTGATACCAATTTGATAACCTGTAATGATCACT<br>ACCTTTGTTTAAGGTGCCATCAGGGTATGTTAAGGAATTCAGATCTCTGC<br>AATATCTGCTGGAAGCCCCTGCCCACCACAATCACAGTACCGGTGGAGCC<br>AACAGCACCACCACCATAGGCAGACTGCACAGGGTCAGACCCGACCCCCC<br>GGGGGGCCCCCATGGGGACCCCCCGTGGGGGAACCCCGGGGGTGATGCGC<br>CATTAGTCAATGTCTTTGATCTCGACTTTGTGCTTCAGTGGCCTGCATGT<br>CACCCCTTTCAATCTGAACTGCCCTTGGGGATCTGATATCAGCAGGTCAT<br>TTAAAGATCTGCTGAATGCCACCTTGAAATTTGAGAATTCCAACCAGTCA<br>CCAAATTTATCAAGTGAACGGATCAACTGCTCTTTGTGTAGATCATAAAC<br>GAGGACAAAGTCCTCTTGCTGAAATAATATTGTTTGTGATGTTGTTTTTA<br>GATAAGGCCATAGTTGGCTTAATAAGGTTTCCACACTATCAATGTCCTCT<br>AGTGCTCCAATTGCCTTGACTATGACATCCCCAGACAACTCAACTCTATA<br>TGTTGACAACCTTTCATTACCTCTGTAAAAGATACCCTCTTTCAAGACAA |

TABLE 1-continued

Sequences

| SEQ ID No. | Description | Sequence |
|---|---|---|
| | | GAGGTTCTCCTGGGTTATCTGGCCCAATGAGGTCATATGCATACTTGTTA
CTTAGTTCAGAATAAAAGTCACCAAAGTTGAACTTAACATGGCTCAGAAT
ATTGTCATCATTTGTCGCAGCGTAGCCTGCATCAATAAACAAGCCAGCTA
GGTCAAAGCTCTCATGGCCTGTGAACAATGGTAGGCTAGCGATAACCAGT
GCACCATCCAACAATGAGTGGCTTCCCTCAGACCCAGAAACACATTGACT
CATTGCATCCACATTCAGCTCTAATTCAGGGGTACCGACATCATCCACTC
CTAGTGAACTGACAATGGTGTAACTGTACACCATCTTTCTTCTAAGTTTA
AATTTTGTCGAAACTCGTGTGTGTTCTACTTGAATGATCAATTTTAGTTT
CACAGCTTCTTGGCAAGCAACATTGCGCAACACAGTGTGCAGGTCCATCA
TGTCTTCCTGAGGCAACAAGGAGATGTTGTCAACAGAGACACCCTCAAGG
AAAACCTTGATATTATCAAAGCTAGAAACTACATAACCCATTGCAATGTC
TTCAACAAACATTGCTCTTGATACTTTATTATTCCTAACTGACAAGGTAA
AATCTGTGAGTTCAGCTAGATCTACTTGACTGTCATCTTCTAGATCTAGA
ACTTCATTGAACCAAAAGAAGGATTTGAGACACGATGTTGACATGACTAG
TGGGTTTATCATCGAAGATAAGACAACTTGCACCATGAAGTTCCTGCAAA
CTTGCTGTGGGCTGATGCCAACTTCCCAATTTGTATACTCTGACTGTCTA
ACATGGGCTGAAGCGCAATCACTCTGTTTCACAATATAAACATTATTATC
TCTTACTTTCAATAAGTGACTTATAATCCCTAAGTTTTCATTCATCATGT
CTAGAGCCACACAGACATCTAGAAACTTGAGTCTTCCACTATCCAAAGAT
CTGTTCACTTGAAGATCATTCATAAAGGGTGCCAAATGTTCTTCAAATAG
TTTGGGGTAATTTCTTCGTATAGAATGCAATACATGGTTCATGCCTAATT
GGTCTTCTATCTGTCGTACTGCTTTGGGTTAACAGCCCAGAAGAAATTC
TTATTACATAAGACCAGAGGGGCCTGTGGACTCTTAATAGCAGAAAACAC
CCACTCCCTAACTCACAGGCATTTGTCAGCACCAAAGAGAAGTAATCCC
ACAAAATTGGTTTAGAAAATTGGTTAACTTCTTTAAGTGATTTTTGACAG
TAAATAACTTTAGGCTTTCTCTCACAAATTCCACAAAGACATGGCATTAT
TCGAGTAAATATGTCCTTTATATACAGAAATCCGCCTTTACCATCCCTAA
CACACTTACTCCCCATACTCTTACAAAACCCAATGAAGCCTGAGGCAACA
GAAGACTGAAATGCAGATTTGTTGATTGACTCTGCCAAGATCTTCTTCAC
GCCTTTTGTGAAATTTCTTGACAGCCTGGACTGTATTGTCCTTATCAATG
TTGGCATCTCTTCTTTCTCTAACACTCTTCGACTTGTCATGAGTTTGGTC
CTCAAGACCAACCTCAAGTCCCCAAAGCTCGCTAAATTGACCCATCTGTA
GTCTAGAGTTTGTCTGATTTCATCTTCACTACACCCGGCATATTGCAGGA
ATCCGGATAAAGCCTCATCCCCTCCCCTGCTTATCAAGTTGATAAGGTTT
TCCTCAAAGATTTTGCCTCTCTTAATGTCATTGAACACTTTCCTCGCGCA
GTTCCTTATAAACATTGTCTCCTTATCATCAGAAAAAATAGCTTCAATTT
TCCTCTGTAGACGGTACCCTCTAGACCCATCAACCCAGTCTTTGACATCT
TGTTCTTCAATAGCTCCAAACGGAGTCTCTCTGTATCCAGAGTATCTAAT
CAATTGGTTGACTCTAATGGAAATCTTTGACACTATATGAGTGCTAACCC
CATTAGCAATACATTGATCACAAATTGTGTCTATGGTCTCTGACAGTTGT
GTTGGAGTTTTACACTTAACGTTGTGTAGAGCAGCAGACACAAACTTGGT
GAGTAAAGGAGTCTCTTCACCCATGACAAAAAATCTTGACTTAAACTCAG
CAACAAAAGTTCCTATCACACTCTTTGGGCTGATAAACTTGTTTAATTTA
GAAGATAAGAATTCATGGAAGCACACCATTTCCAGCAGTTCTGTCCTGTC
TTGAAACTTTTCATCACTAAGGCAAGGAATTTTTATAAGGCTAACCTGGT
CATCGCTGGAGGTATAAGTGACAGGTATCACATCATACAATAAGTCAAGT
GCATAACACAGAAATTGTTCAGTAATTAGCCCATATAAATCTGATGTGTT
GTGCAAGATTCCCTGGCCCATGTCCAAGACAGACATTATATGGCTGGGGA
CCTGGTCCCTTGACTGCAGATACTGGTGAAAAAACTCTTCACCAACACTA
GTACAGTCACAACCCATTAAACCTAAAGATCTCTTCAATTTCCCTACACA
GTAGGCTTCTGCAACATTAATTGGAACTTCAACGACCTTATGAAGATGCC
ATTTGAGAATGTTCATTACTGGTTCAAGATTCACCTTTGTTCTATCTCTG
GGATTCTTCAATTCTAATGTGTACAAAAAAGAAAGGAAAAGTGCTGGGCT
CATAGTTGGTCCCCATTTGGAGTGGTCATATGAACAGGACAAGTCACCAT
TGTTAACAGCCATTTTCATATCACAGATTGCACGTTCGAATTCCTTTTCT
GAATTCAAGCATGTGTATTTCATTGAACTACCCACAGCTTCTGAGAAGTC
TTCAACTAACCTGGTCATCAGCTTAGTGTTGAGGTCTCCCACATACAGTT
CTCTATTTGAGCCAACCTGCTCCTTATAACTTAGTCCAAATTTCAAGTTC
CCTGTATTTGAGCTGATGCTTGTGAACTCTGTAGGAGAGTCGTCTGAATA
GAAACATAAATTCCGTAGGGCTGCATTTGTAAAATAACTTTTGTCTAGCT
TATCAGCAATGGCTTCAGAATTGCTTTCCCTGGTACTAAGCCGAACCTCA
TCCTTTAGTCTCAGAACTTCACTGGAAAAGCCCAATCTAGATCTACTTCT
ATGCTCATAACTACCCAATTTCTGATCATAATGTCCTTGAATTAAAAGAT
ACTTGAAGCATTCAAAGAATTCATCTTCTTGGTAGGCTATTGTTGTCAAA
TTTTTTAATAACAAACCCAAAGGGCAGATGTCCTGCGGTGCTTCAAGAAA
ATAAGTCAATTTAAATGGAGATAGATAAACAGCATCACATAACTCTTTAT
ACACATCAGACCTGAGCACATCTGGATCAAAATCCTTCACCTCATGCATT
GACACCTCTGCTTTAATCTCTCTCAACACTCCAAAAGGGGCCCACAATGA
CTCAAGAGACTCTCGCTCATCAACAGATGGATTTTTTGATTTCAACTTGG
TGATCTCAACTTTTGTCCCCTCACTATTAGCCATCTTGGCTAGTGTCATT
TGTACGTCATTTCTAATACCCTCAAAGGCCCTTACTTGATCCTCTGTTAA
ACTCTCATACATCACTGATAATTCTTCTTGATTGGTTCTGGTTCTTGAAC
CGGTGCTCACAAGACCTGTTAGATTTTTTAATATTAAGTAGTCCATGGAA
TCAGGATCAAGATTATACCTGCCTTTTGTTTTAAACCTCTCAGCCATAGT |

TABLE 1-continued

Sequences

| SEQ ID No. | Description | Sequence |
|---|---|---|
| | | AGAAACGCATGTTGAAACAAGTTTCTCCTTATCATAAACAGAAAGAATAT
TTCCAAGTTCGTCGAGCTTGGGGATTACCACACTTTTATTGCTTGACAGA
TCCAGAGCTGTGCTAGTGATGTTAGGCCTGTAGGGATTGCTTTTCAGTTC
ACCTGTAACTTTAAGTCTTCCTCTATTGAAGAGAGAAATGCAGAAGGACA
AAATCTCTTTACACACTCCTGGAATTTGAGTATCTGAGGAAGTCTTAGCC
TCTTTGGAAAAGAATCTGTCCAATCCTCTTATCATGGTGTCCTCTTGTTC
CAGTGTTAGACTCCCACTTAGAGGGGGGTTTACAACAACACAATCAAACT
TGACTTTGGGCTCAATAAACTTCTCAAAACACTTTATTTGATCTGTCAGG
CGATCAGGTGTCTCTTTGGTTACCAAGTGACACAGATAACTAACATTTAA
TAGATATTTAACCCTTCTTGCAAAGTAAAGATCTGCATCTTCCCCTTCAC
CCAAAATTGTCTGGAAAAGTTCCACAGCCATCCTCTGAATCAGCACCTCT
GATCCAGACATGCAGTCGACCCTTAACTTTGACATCAAATCCACATGATG
GATTTGATTTGCATATGCCATCAAGAAATATCTTAGACCTTGTAAAAATG
TCTGGTTCCTTTTGGAAGGGGAACAGAGTACAGCTAACACTAACAATCTT
AATATTGGCCTTGTCATTGTCATGAGTTCGTGGCTAAAATCCAACCAGCT
GGTCATTTCCTCACACATTTCAATTAACACATCCTCCGAAAATATAGGCA
GGAAAAATCTCTTTGGATCACAGTAAAAAGAGCCTTGTTCTTCCAATACC
CCATTGATGGATAGATAGATAGAATAGCACCTTGACTTCTCACCTGTTTT
TTGGTAAAACAAGAGACCAAATGTATTCTTTGTCAGATGAAATCTTTGTA
CATAACACTCTCTTAGTCTAACATTCCCAAAATATCTAGAATACTCTCTT
TCATTGATTAACAATCGGGAGGAAAATGATGTCTTCATCGAGTTGACCAA
TGCAAGGGAAATGGAGGACAAAATCCTAAATAATTTCTTCTGCTCACCTT
CCACTAAGCTGCTGAATGGCTGATGTCTACAGATTTTCTCAAATTCCTTG
TTAATAGTATATCTCATCACTGGTCTGTCAGAAACAAGTGCCTGAGCTAA
AATCATCAAGCTATCCATATCAGGGTGTTTTATTAGTTTTTCCAGCTGTG
ACCAGAGATCTTGATGAGAGTTCTTCAATGTTCTGGAACACGCTTGAACC
CACTTGGGGCTGGTCATCAATTTCTTCCTTATTAGTTTAATCGCCTCCAG
AATATCTAGAAGTCTGTCATTGACTAACATTAACATTTGTCCAACAACTA
TTCCCGCATTTCTTAACCTTACAATTGCATCATCATGCGTTTTGAAAAGA
TCACAAAGTAAATTGAGTAAAACTAAGTCCAGAAACAGTAAAGTGTTTCT
CCTGGTGTTGAAAACTTTTAGACCTTTCACTTTGTTACACACGGAAAGGG
CTTGAAGATAACACCTCTCTACAGCATCAATAGATATAGAATTCTCATCT
GACTGGCTTTCCATGTTGACTTCATCTATTGGATGCAATGCGATAGAGTA
GACTACATCCATCAACTTGTTTGCACAAAAAGGGCAGCTGGGCACATCAC
TGTCTTTGTGGCTTCCTAATAAGATCAAGTCATTTATAAGCTTAGACTTT
TGTGAAAATTTGAATTTCCCCAACTGCTTGTCAAAAATCTCCTTCTTAAA
CCAAAACCTTAACTTTATGAGTTCTTCTCTTATGACAGATTCTCTAATGT
CTCCTCTAACCCCAACAAAGAGGGATTCATTTAACCTCTCATCATAACCC
AAAGAATTCTTTTTCAAGCATTCGATGTTTTCTAATCCCAAGCTCTGGTT
TTTTGTGTTGGACAAACTATGGATCAATCGCTGGTATTCTTGTTCTTCAA
TATTAATCTCTTGCATAAATTTTGATTTCTTTAGGATGTCGATCAGCAAC
CACCGAACTCTTTCAACAACCCAATCAGCAAGGAATCTATTGCTGTAGCT
AGATCTGCCATCAACCACAGGAACCAACGTAATCCCTGCCCTTAGTAGGT
CGGACTTTAGGTTTAAGAGCTTTGACATGTCACTCTTCCATTTTCTCTCA
AACTCATCAGGATTGACCCTAACAAAGGTTTCCAATAGGATGAGTGTTTT
CCCTGTGAGTTTGAAGCCATCCGGAATGACTTTTGGAAGGGTGGGACATA
GTATGCCATAGTCAGACAGGATCACATCAACAAACTTCTGATCTGAATTG
ATCTGACAGGCGTGTGCCTCACAGGACTCAAGCTCTACTAAACTTGACAG
AAGTTTGAACCCTTCCAACAACAGAGAGCTGGGGTGATGTTGAGATAAAA
AGATGTCCCTTTGGTATGCTAGCTCCTGTCTTTCTGGAAAATGCTTTCTA
ATAAGGCTTTTTATTTCATTTACTGATTCCTCCATGCTCAAGTGCCGCCT
AGGATCCTCGGTGCG |

What is claimed is:

1. A method of generating a tri-segmented arenavirus viral vector comprising one L segment and two S segments and a nucleotide sequence encoding a polypeptide comprising an amino acid sequence that is at least 99% identical to SEQ ID NO: 10, wherein the method comprises:

a. transfecting into a host cell one or more complementary deoxyribonucleic acid (cDNA) of the one L segment and two S segments;

b. maintaining the host cell under conditions suitable for virus formation; and c. harvesting the tri-segmented arenavirus viral vector, wherein one of the two S segments is selected from the group consisting of:

(i) an S segment wherein the ORF encoding the NP is under control of an arenavirus 5' UTR, (ii) an S segment wherein the ORF encoding the Z protein is under control of an arenavirus 5' UTR, (iii) an S segment wherein the ORF encoding the L protein is under control of an arenavirus 5' UTR, (iv) an S segment wherein the ORF encoding the GP is under control of an arenavirus 3' UTR, (v) an S segment wherein the ORF encoding the L protein is under control of an arenavirus 3' UTR, and (vi) an S segment wherein the ORF encoding the Z protein is under control of an arenavirus 3' UTR.

2. The method of claim 1, wherein the method further comprises transcribing the one or more cDNAs of the one L segment and two S segments using a promoter.

3. The method of claim 2, wherein the promoter is a bidirectional promoter.

4. The method of claim 1, wherein the method further comprises transfecting into the host cell one or more nucleic acids encoding an arenavirus polymerase.

5. The method of claim 4, wherein the arenavirus polymerase is the L protein.

6. The method of claim 1, wherein the method further comprises transfecting into the host cell one or more nucleic acids encoding the NP protein.

7. The method of claim 2, wherein the promoter is selected from the group consisting of:

an RNA polymerase I promoter;

(ii) an RNA polymerase II promoter; and (iii) a T7 promoter.

8. The method of claim 1, wherein the tri-segmented arenavirus viral vector is derived from a lymphocytic choriomeningitis virus (LCMV) or a Pichinde virus.

9. The method of claim 8, wherein the LCMV is MP strain, WE strain, Armstrong strain, or Armstrong Clone 13 strain.

10. The method of claim 1, wherein the tri-segmented arenavirus viral vector comprises all four arenavirus ORFs, and wherein the tri-segmented arenavirus viral vector is infectious and replication competent.

11. The method of claim 1, wherein the tri-segmented arenavirus viral vector is attenuated.

12. The method of claim 1, wherein one of the two S segments comprises a nucleotide sequence encoding a polypeptide comprising an amino acid sequence that is at least 99% identical to SEQ ID NO: 10.

13. The method of claim 1, wherein one of the two S segments comprises a nucleotide sequence encoding a polypeptide comprising an amino acid sequence that is 100% identical to SEQ ID NO: 10.

14. The method of claim 1, wherein the two S segments each comprise a nucleotide sequence encoding a polypeptide comprising an amino acid sequence that is at least 99% identical to SEQ ID NO: 10.

15. The method of claim 1, wherein the two S segments each comprise a nucleotide sequence encoding a polypeptide comprising an amino acid sequence that is 100% identical to SEQ ID NO: 10.

16. The method of claim 1, wherein inter-segmental recombination of the two S segments, uniting two arenavirus ORFs on only one instead of two separate S segments, abrogates viral promoter activity.

17. A method of generating a tri-segmented arenavirus viral vector comprising one L segment and two S segments, wherein the method comprises:

a. transfecting into a host cell one or more complementary deoxyribonucleic acid (cDNA) of the one L segment and two S segments;

b. maintaining the host cell under conditions suitable for virus formation; and c. harvesting the tri-segmented arenavirus viral vector, wherein a first S segment of the two S segments is engineered to carry an ORF encoding GP in a position under control of an arenavirus 3' UTR and an ORF encoding a polypeptide comprising an amino acid sequence that is at least 99% identical to SEQ ID NO: 10 in a position under control of an arenavirus 5' UTR and a second S segment of the two S segments is engineered to carry an ORF encoding NP in a position under control of an arenavirus 3' UTR and an ORF encoding a polypeptide comprising an amino acid sequence that is at least 99% identical to SEQ ID NO: 10 in a position under control of an arenavirus 5' UTR, wherein the arenavirus 3' UTR is a 3' UTR of an arenavirus S segment and the arenavirus 5' UTR is a 5' UTR of an arenavirus S segment.

18. The method of claim 17, wherein the tri-segmented arenavirus viral vector is attenuated.

19. The method of claim 17, wherein the tri-segmented arenavirus viral vector is derived from a LCMV or a Pichinde virus.

20. The method of claim 17, wherein the polypeptide encoded on the first S segment and the polypeptide encoded on the second S segment each comprise an amino acid sequence that is 100% identical to SEQ ID NO: 10.

* * * * *

SEQUENCE LISTING

<160> NUMBER OF SEQ ID NOS: 44

<210> SEQ ID NO 1
<211> LENGTH: 3376
<212> TYPE: DNA
<213> ORGANISM: Lymphocytic choriomeningitis virus
<220> FEATURE:
<223> OTHER INFORMATION: Lymphocytic choriomeningitis virus segment S

<400> SEQUENCE: 1
cgcaccgggg atcctaggct ttttggattg cgctttcctc tagatcaact gggtgtcagg        60
ccctatccta cagaaggatg ggtcagattg tgacaatgtt tgaggctctg cctcacatca      120

```
tcgatgaggt gatcaacatt gtcattattg tgcttatcgt gatcacgggt atcaaggctg      180
tctacaattt tgccacctgt gggatattcg cattgatcag tttcctactt ctggctggca      240
ggtcctgtgg catgtacggt cttaagggac ccgacattta caaaggagtt taccaattta      300
agtcagtgga gtttgatatg tcacatctga acctgaccat gcccaacgca tgttcagcca      360
acaactccca ccattacatc agtatgggga cttctggact agaattgacc ttcaccaatg      420
attccatcat cagtcacaac ttttgcaatc tgacctctgc cttcaacaaa agacctttg       480 accacacact catgagtata gtttcgagcc tacacctcag tatcagaggg aactccaact      540
ataaggcagt atcctgcgac ttcaacaatg gcataaccat ccaatacaac ttgacattct      600
cagatcgaca aagtgctcag agccagtgta gaaccttcag aggtagagtc ctagatatgt      660
ttagaactgc cttcgggggg aaatacatga ggagtggctg gggctggaca ggctcagatg      720
gcaagaccac ctggtgtagc cagacgagtt accaatacct gattatacaa aatagaacct      780
gggaaaacca ctgcacatat gcaggtcctt ttgggatgtc caggattctc ctttcccaag      840
agaagactaa gttcttcact aggagactag cgggcacatt cacctggact tgtcagact       900 cttcaggggt ggagaatcca ggtggttatt gcctgaccaa atggatgatt cttgctgcag      960
agcttaagtg tttcgggaac acagcagttg cgaaatgcaa tgtaaatcat gatgccgaat     1020
tctgtgacat gctgcgacta attgactaca acaaggctgc tttgagtaag ttcaaagagg     1080
acgtagaatc tgccttgcac ttattcaaaa caacagtgaa ttctttgatt tcagatcaac     1140
tactgatgag gaaccacttg agagatctga tgggggtgcc atattgcaat tactcaaagt     1200
tttggtacct agaacatgca aagaccggcg aaactagtgt ccccaagtgc tggcttgtca     1260
ccaatggttc ttacttaaat gagacccact tcagtgatca aatcgaacag gaagccgata     1320
acatgattac agagatgttg aggaaggatt acataaagag gcagggagt accccctag       1380 cattgatgga ccttctgatg ttttccacat ctgcatatct agtcagcatc ttcctgcacc     1440
ttgtcaaaat accaacacac aggcacataa aaggtggctc atgtccaaag ccacaccgat     1500
taaccaacaa aggaatttgt agttgtggtg catttaaggt gcctggtgta aaaaccgtct     1560
ggaaaagacg ctgaagaaca gcgcctccct gactctccac ctcgaaagag gtggagagtc     1620
agggaggccc agagggtctt agagtgtcac aacatttggg cctctaaaaa ttaggtcatg     1680
tggcagaatg ttgtgaacag ttttcagatc tgggagcctt gctttggagg cgctttcaaa     1740
aatgatgcag tccatgagtg cacagtgcgg ggtgatctct ttcttctttt tgtcccttac     1800
tattccagta tgcatcttac acaaccagcc atatttgtcc cacactttgt cttcatactc     1860
cctcgaagct tccctggtca tttcaacatc gataagctta atgtccttcc tattctgtga     1920
gtccagaagc tttctgatgt catcggagcc ttgacagctt agaaccatcc cctgcggaag     1980
agcacctata actgacgagg tcaacccggg ttgcgcattg aagaggtcgg caagatccat     2040
gccgtgtgag tacttggaat cttgcttgaa ttgtttttga tcaacgggtt ccctgtaaaa     2100
gtgtatgaac tgcccgttct gtggttggaa aattgctatt tccactggat cattaaatct     2160
accctcaatg tcaatccatg taggagcgtt ggggtcaatt cctcccatga ggtctttaa      2220 aagcattgtc tggctgtagc ttaagcccac ctgaggtgga cctgctgctc caggcgctgg     2280
cctgggtgaa ttgactgcag gtttctcgct tgtgagatca attgttgtgt tttcccatgc     2340
tctccccaca atcgatgttc tacaagctat gtatggccat ccttcacctg aaaggcaaac     2400
tttatagagg atgttttcat aagggttcct gtccccaact tggtctgaaa caaacatgtt     2460
```

```
gagttttctc ttggccccga gaactgcctt caagaggtcc tcgctgttgc ttggcttgat    2520
caaaattgac tctaacatgt taccccatc caacagggct gcccctgcct tcacggcagc     2580
accaagacta aagttatagc cagaaatgtt gatgctggac tgctgttcag tgatgacccc   2640
cagaactggg tgcttgtctt tcagccttc aagatcatta agatttggat acttgactgt    2700
gtaaagcaag ccaaggtctg tgagcgcttg tacaacgtca ttgagcggag tctgtgactg   2760
tttggccata caagccatag ttagacttgg cattgtgcca aattgattgt tcaaaagtga   2820
tgagtctttc acatcccaaa ctcttaccac accacttgca ccctgctgag ctttctcat    2880 cccaactatc tgtaggatct gagatctttg gtctagttgc tgtgttgtta agttccccat   2940 ataccct gaagcctggg gcctttcaga cctcatgatc ttggccttca gcttctcaag      3000
gtcagccgca agagacatca gttcttctgc actgagcctc cccactttca aaacattctt   3060
ctttgatgtt gactttaaat ccacaagaga atgtacagtc tggttgagac ttctgagtct   3120
ctgtaggtct ttgtcatctc tcttttcctt cctcatgatc ctctgaacat tgctgacctc   3180
agagaagtcc aacccattca gaaggttggt tgcatcctta atgacagcag ccttcacatc   3240
tgatgtgaag ctctgcaatt ctcttctcaa tgcttgcgtc cattggaagc tcttaacttc   3300
cttagacaag gacatcttgt tgctcaatgg tttctcaaga caaatgcgca atcaaatgcc   3360
taggatccac tgtgcg                                                   3376
```

<210> SEQ ID NO 2
<211> LENGTH: 3377
<212> TYPE: DNA
<213> ORGANISM: Lymphocytic choriomeningitis virus
<220> FEATURE:
<223> OTHER INFORMATION: Lymphocytic choriomeningitis virus clone 13
      segment S, complete sequence (GenBank: DQ361065.2).

<400> SEQUENCE: 2

```
gcgcaccggg gatcctaggc ttttggatt gcgctttcct ctagatcaac tgggtgtcag     60
gccctatcct acagaaggat gggtcagatt gtgacaatgt ttgaggctct gcctcacatc   120
atcgatgagg tgatcaacat tgtcattatt gtgcttatcg tgatcacggg tatcaaggct   180
gtctacaatt ttgccacctg tgggatattc gcattgatca gtttcctact tctggctggc   240
aggtcctgtg gcatgtacgg tcttaaggga cccgacattt acaaggagt ttaccaattt     300 aagtcagtgg agtttgatat gtcacatctg aacctgacca tgcccaacgc atgttcagcc   360
aacaactccc accattacat cagtatgggg acttctggac tagaattgac cttcaccaat   420
gattccatca tcagtcacaa cttttgcaat ctgacctctg ccttcaacaa aaagaccttt   480
gaccacacac tcatgagtat agtttcgagc ctacacctca gtatcagagg gaactccaac   540
tataaggcag tatcctgcga cttcaacaat ggcataacca tccaatacaa cttgacattc   600
tcagatgcac aaagtgctca gagccagtgt agaaccttca gaggtagagt cctagatatg   660
tttagaactg ccttcggggg gaaatacatg aggagtggct ggggctggac aggctcagat   720
ggcaagacca cctggtgtag ccagacgagt taccaatacc tgattataca aaatagaacc   780
tgggaaaacc actgcacata tgcaggtcct tttgggatgt ccaggattct cctttccccaa   840 gagaagacta agttcctcac taggagacta gcgggcacat tcacctggac tttgtcagac   900
tcttcagggg tggagaatcc aggtggttat tgcctgacca atggatgat tcttgctgca    960 gagcttaagt gtttcgggaa cacagcagtt gcgaaatgca atgtaaatca tgatgaagaa   1020
ttctgtgaca tgctgcgact aattgactac aacaaggctg ctttgagtaa gttcaaagag   1080
```

-continued

```
gacgtagaat ctgccttgca cttattcaaa acaacagtga attctttgat ttcagatcaa    1140
ctactgatga ggaaccactt gagagatctg atgggggtgc catattgcaa ttactcaaag    1200
ttttggtacc tagaacatgc aaagaccggc gaaactagtg tccccaagtg ctggcttgtc    1260
accaatggtt cttacttaaa tgagacccac ttcagtgacc aaatcgaaca ggaagccgat    1320
aacatgatta cagagatgtt gaggaaggat tacataaaga ggcaggggag tacccccta    1380
gcattgatgg accttctgat gttttccaca tctgcatatc tagtcagcat cttcctgcac    1440
cttgtcaaaa taccaacaca caggcacata aaaggtggct catgtccaaa gccacaccga    1500
ttaaccaaca aaggaatttg tagttgtggt gcatttaagg tgcctggtgt aaaaaccgtc    1560
tggaaaagac gctgaagaac agcgcctccc tgactctcca cctcgaaaga ggtggagagt    1620
cagggaggcc cagagggtct tagagtgtca caacatttgg gcctctaaaa attaggtcat    1680
gtggcagaat gttgtgaaca gttttcagat ctggagcct tgctttggag gcgctttcaa    1740
aaatgatgca gtccatgagt gcacagtgcg gggtgatctc tttcttcttt ttgtcccta    1800
ctattccagt atgcatctta cacaaccagc catatttgtc ccacactttg tcttcatact    1860
ccctcgaagc ttccctggtc atttcaacat cgataagctt aatgtccttc ctattctgtg    1920
agtccagaag ctttctgatg tcatcggagc cttgacagct tagaaccatc ccctgcggaa    1980
gagcacctat aactgacgag gtcaacccgg gttgcgcatt gaagaggtcg gcaagatcca    2040
tgccgtgtga gtacttggaa tcttgcttga attgttttg atcaacgggt tccctgtaaa    2100
agtgtatgaa ctgcccgttc tgtggttgga aaattgctat ttccactgga tcattaaatc    2160
taccctcaat gtcaatccat gtaggagcgt tggggtcaat tcctcccatg aggtctttta    2220
aaagcattgt ctggctgtag cttaagccca cctgaggtgg acctgctgct ccaggcgctg    2280
gcctgggtga attgactgca ggtttctcgc ttgtgagatc aattgttgtg ttttcccatg    2340
ctctccccac aatcgatgtt ctacaagcta tgtatggcca tccttcacct gaaaggcaaa    2400
ctttatagag gatgttttca taagggttcc tgtcccaac ttggtctgaa acaaacatgt    2460
tgagttttct cttggccccg agaactgcct tcaagaggtc ctcgctgttg cttggcttga    2520
tcaaaattga ctctaacatg ttaccccat ccaacagggc tgccctgcc ttcacggcag    2580
caccaagact aaagttatag ccagaaatgt tgatgctgga ctgctgttca gtgatgaccc    2640
ccagaactgg gtgcttgtct ttcagccttt caagatcatt aagatttgga tacttgactg    2700
tgtaaagcaa gccaaggtct gtgagcgctt gtacaacgtc attgagcgga gtctgtgact    2760
gtttggccat acaagccata gttagacttg gcattgtgcc aaattgattg ttcaaaagtg    2820
atgagtcttt cacatcccaa actcttacca caccacttgc accctgctga ggctttctca    2880
tcccaactat ctgtaggatc tgagatcttt ggtctagttg ctgtgttgtt aagttcccca    2940
tatataccc tgaagcctgg ggcctttcag acctcatgat cttggccttc agcttctcaa    3000
ggtcagccgc aagagacatc agttcttctg cactgagcct ccccactttc aaaacattct    3060
tctttgatgt tgactttaaa tccacaagag aatgtacagt ctggttgaga cttctgagtc    3120
tctgtaggtc tttgtcatct ctctttcct tcctcatgat cctctgaaca ttgctgacct    3180
cagagaagtc caaccattc agaaggttgg ttgcatcctt aatgacagca gccttcacat    3240
ctgatgtgaa gctctgcaat tctcttctca atgcttgcgt ccattggaag ctcttaactt    3300
ccttagacaa ggacatcttg ttgctcaatg gtttctcaag acaaatgcgc aatcaaatgc    3360
ctaggatcca ctgtgcg                                                  3377
```

```
<210> SEQ ID NO 3
<211> LENGTH: 7229
<212> TYPE: DNA
<213> ORGANISM: Lymphocytic choriomeningitis virus
<220> FEATURE:
<223> OTHER INFORMATION: Lymphocytic choriomeningitis virus clone 13
      segment L, complete sequence (GenBank: DQ361066.1)

<400> SEQUENCE: 3
gcgcaccggg gatcctaggc gtttagttgc gctgtttggt tgcacaactt tcttcgtgag     60
gctgtcagaa gtggacctgg ctgatagcga tgggtcaagg caagtccaga gaggagaaag    120
gcaccaatag tacaaacagg gccgaaatcc taccagatac cacctatctt ggccctttaa    180
gctgcaaatc ttgctggcag aaatttgaca gcttggtaag atgccatgac cactaccttt    240
gcaggcactg tttaaacctt ctgctgtcag tatccgacag gtgtcctctt tgtaaatatc    300
cattaccaac cagattgaag atatcaacag ccccaagctc tccacctccc tacgaagagt    360
aacaccgtcc ggccccggcc ccgacaaaca gcccagcaca agggaaccgc acgtcaccca    420
acgcacacag acacagcacc caacacagaa cacgcacaca cacacacaca cacacccaca    480
cgcacgcgcc cccaccaccg gggggcgccc ccccccgggg ggcggccccc cgggagcccg    540
ggcggagccc cacggagatg cccatcagtc gatgtcctcg gccaccgacc cgcccagcca    600
atcgtcgcag gacctcccct tgagtctaaa cctgcccccc actgtttcat acatcaaagt    660
gctcctagat ttgctaaaac aaagtctgca atccttaaag gcgaaccagt ctggcaaaag    720
cgacagtgga atcagcagaa tagatctgtc tatacatagt tcctggagga ttacacttat    780
ctctgaaccc aacaaatgtt caccagttct gaatcgatgc aggaagaggt tcccaaggac    840
atcactaatc ttttcatagc cctcaagtcc tgctagaaag actttcatgt ccttggtctc    900
cagcttcaca atgatatttt ggacaaggtt tcttccttca aaaagggcac ccatctttac    960
agtcagtggc acaggctccc actcaggtcc aactctctca aagtcaatag atctaatccc   1020
atccagtatt cttttggagc ccaacaactc aagctcaaga gaatcaccaa gtatcaaggg   1080
atcttccatg taatcctcaa actcttcaga tctgatatca aagacaccat cgttcacctt   1140
gaagacagag tctgtcctca gtaagtggag gcattcatcc aacattcttc tatctatctc   1200
acccttaaag aggtgagagc atgataaaag ttcagccaca cctggattct gtaattggca   1260
cctaaccaag aatatcaatg aaaatttcct taaacagtca gtattattct gattgtgcgt   1320
aaagtccact gaaattgaaa actccaatac cccttttgtg tagttgagca tgtagtccca   1380
cagatccttt aaggatttaa atgcctttgg gtttgtcagg ccctgcctaa tcaacatggc   1440
agcattacac acaacatctc ccattcggta agagaaccac ccaaaaccaa actgcaaatc   1500
attcctaaac ataggcctct ccacattttt gttcaccacc tttgagacaa atgattgaaa   1560
ggggcccagt gcctcagcac catcttcaga tggcatcatt tctttatgag ggaaccatga   1620
aaaattgcct aatgtcctgg ttgttgcaac aaattctcga acaaatgatt caaaatacac   1680
ctgttttaag aagttcttgc agacatccct cgtgctaaca acaaattcat caaccagact   1740
ggagtcagat cgctgatgag aattggcaag gtcagaaaac agaacagtgt aatgttcatc   1800
ccttttccac ttaacaacat gagaaatgag tgacaaggat tctgagttaa tatcaattaa   1860
aacacagagg tcaaggaatt taattctggg actccacctc atgtttttg agctcatgtc   1920 agacataaat ggaagaagct gatcctcaaa gatcttggga tatagccgcc tcacagattg   1980
aatcacttgg ttcaaattca ctttgtcctc cagtagcctt gagctctcag gctttcttgc   2040
tacataatca catgggttta agtgcttaag agttaggttc tcactgttat tcttcccttt   2100
```

```
ggtcggttct gctaggaccc aaacacccaa ctcaaaagag ttgctcaatg aaatacaaat    2160
gtagtcccaa agaagaggcc ttaaaaggca tatatgatca cggtgggctt ctggatgaga    2220
ctgtttgtca caaatgtaca gcgttatacc atcccgattg caaactcttg tcacatgatc    2280
atctgtggtt agatcctcaa gcagcttttt gatatacaga ttttccctat ttttgtttct    2340
cacacacctg cttcctagag ttttgcaaag gcctataaag ccagatgaga tacaactctg    2400
gaaagctgac ttgttgattg cttctgacag cagcttctgt gcacccttg tgaatttact     2460 acaaagtttg ttctggagtg tcttgatcaa tgatgggatt ctttcctctt ggaaagtcat    2520
cactgatgga taaccacct tttgtcttaa aaccatcctt aatgggaaca tttcattcaa      2580
attcaaccag ttaacatctg ctaactgatt cagatcttct tcaagaccga ggaggtctcc    2640
caattgaaga atggcctcct ttttatctct gttaaatagg tctaagaaaa attcttcatt    2700
aaattcacca ttttgagct tatgatgcag tttccttaca agctttctta caacctttgt      2760
ttcattagga cacagttcct caatgagtct ttgtattctg taacctctag aaccatccag    2820
ccaatctttc acatcagtgt tggtattcag tagaaatgga tccaagggaa aattggcata    2880
ctttaggagg tccagtgttc tcctttggat actattaact agggagactg ggacgccatt    2940
tgcgatggct tgatctgcaa ttgtatctat tgtttcacaa agttgatgtg gctctttaca    3000
cttgacattg tgtagcgctg cagatacaaa ctttgtgaga agggacttt cctcccccca      3060 tacatagaat ctagatttaa attctgcagc gaacctccca gccacacttt ttgggctgat    3120
aaatttgttt aacaagccgc tcagatgaga ttggaattcc aacaggacaa ggacttcctc    3180
cggatcactt acaaccaggt cactcagcct cctatcaaat aaagtgatct gatcatcact    3240
tgatgtgtaa gcctctggtc tttcgccaaa gataacacca atgcagtagt tgatgaacct    3300
ctcgctaagc aaaccataga agtcagaagc attatgcaag attccctgcc ccatatcaat    3360
aaggctggat atatgggatg gcactatccc catttcaaaa tattgtctga aaattctctc    3420
agtaacagtt gtttctgaac ccctgagaag ttttagcttc gacttgacat atgatttcat    3480
cattgcattc acaacaggaa aggggacctc gacaagctta tgcatgtgcc aagttaacaa    3540
agtgctaaca tgatctttcc cggaacgcac atactggtca tcacctagtt tgagattttg    3600
tagaaacatt aagaacaaaa atgggcacat cattggtccc catttgctgt gatccatact    3660
atagtttaag aacccttccc gcacattgat agtcattgac aagattgcat ttcaaattc     3720 cttatcattg tttaaacagg agcctgaaaa gaaacttgaa aaagactcaa ataatcttc     3780 tattaacctt gtgaacattt ttgtcctcaa atctccaata tagagttctc tatttccccc    3840
aacctgctct ttataagata gtgcaaattt cagccttcca gagtcaggac ctactgaggt    3900
gtatgatgtt ggtgattctt ctgagtagaa gcacagattt tcaaagcag cactcataca      3960 ttgtgtcaac gacagagctt tactaaggga ctcagaatta cttccctct cactgattct      4020 cacgtcttct tccagtttgt cccagtcaaa tttgaaattc aagccttgcc tttgcatatg    4080
cctgtatttc cctgagtacg catttgcatt catttgcaac agaatcatct tcatgcaaga    4140
aaaccaatca ttctcagaaa agaactttct acaaaggttt tttgccatct catcgaggcc    4200
acactgatct ttaatgactg aggtgaaata caaaggtgac agctctgtgg aaccctcaac    4260
agcctcacag ataaatttca tgtcatcatt ggttagacat gatgggtcaa agtcttctac    4320
taaatggaaa gatattttctg acaagataac ttttcttaag tgagccatct tccctgttag    4380
aataagctgt aaatgatgta gtccttttgt atttgtaagt ttttctccat ctcctttgtc    4440
```

```
attggccctc ctacctcttc tgtaccgtgc tattgtggtg ttgacctttt cttcgagact    4500
tttgaagaag cttgtctctt cttctccatc aaaacatatt tctgccaggt tgtcttccga    4560
tctccctgtc tcttctccct tggaaccgat gaccaatcta gagactaact tggaaacttt    4620
atattcatag tctgagtggc tcaacttata cttttgtttt cttacgaaac tctccgtaat    4680
ttgactcaca gcactaacaa gcaatttgtt aaagtcatat tccagaagtc gttctccatt    4740
tagatgctta ttaaccacca cacttttgtt actagcaaga tctaatgctg tcgcacatcc    4800
agagttagtc atgggatcta ggctgtttag cttcttctct cctttgaaaa ttaaagtgcc    4860
gttgttaaat gaagacacca ttaggctaaa ggcttccaga ttaacacctg gagttgtatg    4920
ctgacagtca atttctttac tagtgaatct cttcatttgc tcatagaaca cacattcttc    4980
ctcaggagtg attgcttcct tggggttgac aaaaaaacca aattgacttt tgggctcaaa    5040
gaactttttca aaacatttta tctgatctgt tagcctgtca ggggtctcct ttgtgatcaa    5100
atgacacagg tatgacacat tcaacataaa tttaaatttt gcactcaaca acaccttctc    5160
accagtacca aaaatagttt ttattaggaa tctaagcagc ttatacacca ccttctcagc    5220
aggtgtgatc agatcctccc tcaacttatc cattaatgat gtagatgaaa aatctgacac    5280
tattgccatc accaaatatc tgacactctg tacctgcttt tgatttctct ttgttgggtt    5340
ggtgagcatt agcaacaata gggtcctcag tgcaacctca atgtcggtga cacagtcttt    5400
caaatcagga catgatctaa tccatgaaat catgatgtct atcatattgt ataagacctc    5460
atctgaaaaa attggtaaaa agaaccttt aggatctgca tagaaggaaa ttaaatgacc    5520
atccgggcct tgtatggagt agcaccttga agattctcca gtcttctggt ataataggtg    5580
gtattcttca gagtccagtt ttattacttg gcaaaacact tctttgcatt ctaccacttg    5640
atatctcaca gaccctattt gattttgcct tagtctagca actgagctag ttttcatact    5700
gtttgttaag gccagacaaa cagatgataa tcttctcagg ctctgtatgt tcttcagctg    5760
ctctgtgctg ggtggaaat tgtaatcttc aaacttcgta taatacatta tcgggtgagc    5820
tccaatttc ataaagttct caaattcagt gaatggtatg tggcattctt gctcaaggtg    5880
ttcagacagt ccgtaatgct cgaaactcag tcccaccact aacaggcatt tttgaatttt    5940
tgcaatgaac tcactaatag atgccctaaa caattcctca aaagacacct ttctaaacac    6000
ctttgacttt tttctattcc tcaaaagtct aatgaactcc tctttagtgc tgtgaaagct    6060
taccagccta tcattcacac tactatagca acaacccacc cagtgtttat cattttttaa    6120
cccttttgaat ttcgactgtt ttatcaatga ggaaagacac aaaacatcca gatttaacaa    6180
ctgtctcctt ctagtattca acagtttcaa actcttgact ttgtttaaca tagagaggag    6240
cctctcatat tcagtgctag tctcacttcc cctttcgtgc ccatgggtct ctgcagttat    6300
gaatctcatc aaaggacagg attcgactgc ctccctgctt aatgttaaga tatcatcact    6360
atcagcaagg ttttcataga gctcagagaa ttccttgatc aagccttcag ggttacttt    6420
ctgaaagttt ctctttaatt tcccactttc taaatctctt ctaaacctgc tgaaaagaga    6480
gtttattcca aaaaccacat catcacagct catgttgggg ttgatgccctt cgtggcacat    6540
cctcataatt tcatcattgt gagttgacct cgcatctttc agaattttca tagagtccat    6600
accggagcgc ttgtcgatag tagtcttcag ggactcacag agtctaaaat attcagactc    6660
ttcaaagact ttctcatttt ggttagaata ctccaaaagt ttgaataaaa ggtctctaaa    6720
tttgaagttt gcccactctg gcataaaact attatcataa tcacaacgac catctactat    6780
tggaactaat gtgacacccg caacagcaag gtcttccctg atgcatgcca atttgttagt    6840
```

```
gtcctctata aatttcttct caaaactggc tggagtgctc ctaacaaaac actcaagaag      6900
aatgagagaa ttgtctatca gcttgtaacc atcaggaatg ataagtggta gtcctgggca      6960
tacaattcca gactccacca aaattgtttc cacagactta tcgtcgtggt tgtgtgtgca      7020
gccactcttg tctgcactgt ctatttcaat gcagcgtgac agcaacttga gtccctcaat      7080
cagaaccatt ctgggttccc tttgtcccag aaagttgagt ttctgccttg acaacctctc      7140
atcctgttct atatagttta aacataactc tctcaattct gagatgattt catccattgc      7200
gcatcaaaaa gcctaggatc ctcggtgcg                                        7229

<210> SEQ ID NO 4
<211> LENGTH: 7205
<212> TYPE: DNA
<213> ORGANISM: Lymphocytic choriomeningitis virus
<220> FEATURE:
<223> OTHER INFORMATION: Lymphocytic choriomeningitis strain MP segment
      L

<400> SEQUENCE: 4
gcgcaccggg gatcctaggc attttgttg cgcattttgt tgtgttattt gttgcacagc        60
ccttcatcgt gggaccttca caaacaaacc aaaccaccag ccatgggcca aggcaagtcc       120
aaagagggaa gggatgccag caatacgagc agagctgaaa ttctgccaga caccacctat       180
ctcggacctc tgaactgcaa gtcatgctgg cagagatttg acagtttagt cagatgccat       240
gaccactatc tctgcagaca ctgcctgaac ctcctgctgt cagtctccga caggtgccct       300
ctctgcaaac atccattgcc aaccaaactg aaaatatcca cggccccaag ctctccaccc       360
ccttacgagg agtgacgccc cgagccccaa caccgacaca aggaggccac caacacaacg       420
cccaacacgg aacacacaca cacacaccca cacacacatc cacacacacg cgcccccaca       480
acggggggcgc cccccggggg gtggcccccc gggtgctcgg gcggagcccc acggagaggc       540
caattagtcg atcctcctcga ccaccgactt ggtcagccag tcatcacagg acttgccctt      600
aagtctgtac ttgcccacaa ctgtttcata catcaccgtg ttctttgact tactgaaaca       660
tagcctacag tctttgaaag tgaaccagtc aggcacaagt gacagcggta ccagtagaat       720
ggatctatct atacacaact cttggagaat tgtgctaatt ccgaccccct gtagatgctc       780
accagttctg aatcgatgta gaagaaggct cccaaggacg tcatcaaaat ttccataacc       840
ctcgagctct gccaagaaaa ctctcatatc cttggtctcc agtttcacaa cgatgttctg       900
aacaaggctt cttccctcaa aaagagcacc cattctcaca gtcaagggca caggctccca       960
ttcaggccca atcctctcaa aatcaaggga tctgatcccg tccagtattt tccttgagcc      1020
tatcagctca agctcaagag agtcaccgag tatcaggggg tcctccatat agtcctcaaa      1080
ctcttcagac ctaatgtcaa aaacaccatc gttcaccttg aagatagagt ctgatctcaa      1140
caggtggagg cattcgtcca agaaccttct gtccacctca cctttaaaga ggtgagagca      1200
tgataggaac tcagctacac ctggaccttg taactggcac ttcactaaaa agatcaatga      1260
aaacttcctc aaacaatcag tgttattctg gttgtgagtg aaatctactg taattgagaa      1320
ctctagcact ccctctgtat tatttatcat gtaatcccac aagtttctca agacttgaa       1380
tgcctttgga tttgtcaagc cttgtttgat tagcatggca gcattgcaca caatatctcc      1440
caatcggtaa gagaaccatc caaatccaaa ttgcaagtca ttcctaaaca tgggcctctc      1500
catatttttg ttcactactt ttaagatgaa tgattggaaa ggcccaatg cttcagcgcc       1560
atcttcagat ggcatcatgt ctttatgagg gaaccatgaa aaacttccta gagttctgct      1620
```

```
tgttgctaca aattctcgta caaatgactc aaaatacact tgttttaaaa agtttttgca    1680
gacatccctt gtactaacga caaattcatc aacaaggctt gagtcagagc gctgatggga    1740
atttacaaga tcagaaaata gaacagtgta gtgttcgtcc ctcttccact taactacatg    1800
agaaatgagc gataaagatt ctgaattgat atcgatcaat acgcaaaggt caaggaattt    1860
gattctggga ctccatctca tgttttttga gctcatatca gacatgaagg gaagcagctg    1920
atcttcatag attttagggt acaatcgcct cacagattgg attacatggt ttaaacttat    1980
cttgtcctcc agtagccttg aactctcagg cttccttgct acataatcac atgggttcaa    2040
gtgcttgagg cttgagcttc cctcattctt ccctttcaca ggttcagcta agacccaaac    2100
acccaactca aaggaattac tcagtgagat gcaaatatag tcccaaagga ggggcctcaa    2160
gagactgatg tggtcgcagt gagcttctgg atgactttgc ctgtcacaaa tgtacaacat    2220
tatgccatca tgtctgtgga ttgctgtcac atgcgcatcc atagctagat cctcaagcac    2280 tttttctaatg tatagattgt ccctattttt atttctcaca catctacttc ccaaagtttt    2340
gcaaagacct ataaagcctg atgagatgca actttgaaag gctgacttat tgattgcttc    2400
tgacagcaac ttctgtgcac ctcttgtgaa cttactgcag agcttgttct ggagtgtctt    2460
gattaatgat gggattcttt cctcttggaa agtcattact gatggataaa ccactttctg    2520
cctcaagacc attcttaatg ggaacaactc attcaaattc agccaattta tgtttgccaa    2580
ttgacttaga tcctcttcga ggccaaggat gtttcccaac tgaagaatgg cttccttttt    2640
atccctattg aagaggtcta agaagaattc ttcattgaac tcaccattct tgagcttatg    2700
atgtagtctc cttacaagcc ttctcatgac cttcgtttca ctaggacaca attcttcaat    2760
aagcctttgg attctgtaac ctctagagcc atccaaccaa tccttgacat cagtattagt    2820
gttaagcaaa atgggtccaa agggaaagtt ggcatatttt aagaggtcta atgttctctt    2880
ctggatgcag tttaccaatg aaactggaac accatttgca acagcttgat cggcaattgt    2940
atctattgtt tcacagagtt ggtgtggctc tttacactta acgttgtgta atgctgctga    3000
cacaaatttt gttaaaagtg ggacctcttc cccccacaca taaaatctgg atttaaattc    3060
tgcagcaaat cgccccacca cacttttcgg actgatgaac ttgttaagca agccactcaa    3120
atgagaatga aattccagca atacaaggac ttcctcaggg tcactatcaa ccagttcact    3180
caatctccta tcaaataagg tgatctgatc atcacttgat gtgtaagatt ctggtctctc    3240
accaaaaatg acaccgatac aataattaat gaatctctca ctgattaagc cgtaaaagtc    3300
agaggcatta tgtaagattc cctgtcccat gtcaatgaga ctgcttatat gggaaggcac    3360
tattcctaat tcaaaatatt ctcgaaagat tctttcagtc acagttgtct ctgaaccct    3420 aagaagtttc agctttgatt tgatatatga tttcatcatt gcattcacaa caggaaaagg    3480
gacctcaaca agtttgtgca tgtgccaagt taataaggtg ctgatatgat cctttccgga    3540
acgcacatac tggtcatcac ccagtttgag attttgaagg agcattaaaa acaaaaatgg    3600
gcacatcatt ggcccccatt tgctatgatc catactgtag ttcaacaacc cctctcgcac    3660
attgatggtc attgatagaa ttgcattttc aaattctttg tcattgttta agcatgaacc    3720
tgagaagaag ctagaaaaag actcaaaata atcctctatc aatcttgtaa acattttgt    3780 tctcaaatcc ccaatataaa gttctctgtt tcctccaacc tgctctttgt atgataacgc    3840
aaacttcaac cttccggaat caggaccaac tgaagtgtat gacgttggtg actcctctga    3900
gtaaaaacat aaattcttta aagcagcact catgcatttt gtcaatgata gagccttact    3960
```

```
tagagactca gaattacttt cccttteact aattctaaca tettettcta gtttgtccca    4020
gtcaaacttg aaattcagac cttgtctttg catgtgcctg tatttccctg agtatgcatt    4080
tgcattcatt tgcagtagaa tcattttcat acacgaaaac caatcaccct ctgaaaaaaa    4140
cttcctgcag aggttttttg ccatttcatc cagaccacat tgttctttga cagctgaagt    4200
gaaatacaat ggtgacagtt ctgtagaagt ttcaatagcc tcacagataa atttcatgtc    4260
atcattggtg agacaagatg ggtcaaaatc ttccacaaga tgaaaagaaa tttctgataa    4320
gatgaccttc cttaaatatg ccattttacc tgacaatata gtctgaaggt gatgcaatcc    4380
ttttgtattt tcaaacccca cctcattttc cccttcattg gtcttcttgc ttctttcata    4440
ccgctttatt gtggagttga ccttatcttc taaattcttg aagaaacttg tctcttcttc    4500
cccatcaaag catatgtctg ctgagtcacc ttctagtttc ccagcttctg tttctttaga    4560
gccgataacc aatctagaga ccaactttga aaccttgtac tcgtaatctg agtggttcaa    4620
tttgtacttc tgcttttctca tgaagctctc tgtgatctga ctcacagcac taacaagcaa    4680
tttgttaaaa tcatactcta ggagccgttc cccatttaaa tgtttgttaa caaccacact    4740
tttgttgctg gcaaggtcta atgctgttgc acccagag ttagtcatgg gatccaagct    4800
attgagcctc ttctcccctt tgaaaatcaa agtgccattg ttgaatgagg acaccatcat    4860
gctaaaggcc tccagattga cacctggggt tgtgcgctga cagtcaactt ctttcccagt    4920
gaacttcttc atttggtcat aaaaaacaca ctcttcctca ggggtgattg actctttagg    4980
gttaacaaag aagccaaact cacttttagg ctcaaagaat ttctcaaagc atttaatttg    5040
atctgtcagc ctatcagggg tttcctttgt gattaaatga cacaggtatg acacattcaa    5100
catgaacttg aactttgcgc tcaacagtac cttttcacca gtcccaaaaa cagttttgat    5160
caaaaatctg agcaatttgt acactacttt ctcagcaggt gtgatcaaat cctccttcaa    5220
cttgtccatc aatgatgtgg atgagaagtc tgagacaatg gccatcacta aatacctaat    5280
gttttgaacc tgttttttgat tcctctttgt tgggttggtg agcatgagta ataatagggt    5340
tctcaatgca atctcaacat catcaatgct gtccttcaag tcaggacatg atctgatcca    5400
tgagatcatg gtgtcaatca tgttgtgcaa cacttcatct gagaagattg gtaaaaagaa    5460
ccttttttggg tctgcataaa aagagattag atggccattg ggaccttgta tagaataaca    5520
ccttgaggat tctccagtct tttgatacag caggtgatat tcctcagagt ccaattttat    5580
cacttggcaa aatcctctt tacattccac cacttgatac cttacagagc ccaattggtt    5640
ttgtcttaat ctagcaactg aacttgtttt catactgttt gtcaaagcta gacagacaga    5700
tgacaatctt ttcaaactat gcatgttcct taattgttcc gtattaggct ggaaatcata    5760
atcttcaaac tttgtataat acattatagg atgagttccg gacctcatga aattctcaaa    5820
ctcaataaat ggtatgtggc actcatgctc aagatgttca gacagaccat agtgcccaaa    5880
actaagtccc accactgaca agcacctttg aacttttaaa atgaactcat ttatggatgt    5940
tctaaacaaa tcctcaagag ataccttttct atacgccttt gactttctcc tgttccttag    6000
aagtctgatg aactcttcct tggtgctatg aaagctcacc aacctatcat tcacactccc    6060
atagcaacaa ccaacccagt gcttatcatt ttttgaccct tgagtttag actgtttgat    6120
caacgaagag agacacaaga catccaaatt cagtaactgt ctccttctgg tgttcaataa    6180
ttttaaactt ttaactttgt tcaacataga gaggagcctc tcatactcag tgctagtctc    6240
acttcctctc tcataaccat gggtatctgc tgtgataaat ctcatcaaag gacaggattc    6300
aactgcctcc ttgcttagtg ctgaaatgtc atcactgtca gcaagagtct cataaagctc    6360
```

```
agagaattcc ttaattaaat ttccggggtt gattttctga aaactcctct tgagcttccc    6420
agtttccaag tctcttctaa acctgctgta aagggagttt atgccaagaa ccacatcatc    6480
gcagttcatg tttgggttga caccatcatg gcacattttc ataatttcat cattgtgaaa    6540
tgatcttgca tctttcaaga ttttcataga gtctataccg gaacgcttat caacagtggt    6600
cttgagagat tcgcaaagtc tgaagtactc agattcctca aagactttct catcttggct    6660
agaatactct aaaagtttaa acagaaggtc tctgaacttg aaattcaccc actctggcat    6720
aaagctgtta tcataatcac accgaccatc cactattggg accaatgtga tacccgcaat    6780
ggcaaggtct tctttgatac aggctagttt attggtgtcc tctataaatt tcttctcaaa    6840
actagctggt gtgcttctaa cgaagcactc aagaagaatg agggaattgt caatcagttt    6900
ataaccatca ggaatgatca aaggcagtcc cgggcacaca atcccagact ctattagaat    6960
tgcctcaaca gatttatcat catggttgtg tatgcagccg ctcttgtcag cactgtctat    7020
ctctatacaa cgcgacaaaa gtttgagtcc ctctatcaat accattctgg gttctctttg    7080
ccctaaaaag ttgagcttct gccttgacaa cctctcatct tgttctatgt ggtttaagca    7140
caactctctc aactccgaaa tagcctcatc cattgcgcat caaaaagcct aggatcctcg    7200
gtgcg                                                                 7205

<210> SEQ ID NO 5
<211> LENGTH: 3359
<212> TYPE: DNA
<213> ORGANISM: Lymphocytic choriomeningitis virus
<220> FEATURE:
<223> OTHER INFORMATION: Lymphocytic choriomeningitis strain MP segment
      S

<400> SEQUENCE: 5
cgcaccgggg atcctaggct ttttggattg cgctttcctc agctccgtct tgtgggagaa      60
tgggtcaaat tgtgacgatg tttgaggctc tgcctcacat cattgatgag gtcattaaca     120
ttgtcattat cgtgcttatt atcatcacga gcatcaaagc tgtgtacaat ttcgccacct     180 gcggatact tgcattgatc agctttcttt tctggctgg caggtcctgt ggaatgtatg       240
gtcttgatgg gcctgacatt tacaaagggg tttaccgatt caagtcagtg gagtttgaca     300
tgtcttacct taacctgacg atgcccaatg catgttcggc aaacaactcc catcattata     360
taagtatggg gacttctgga ttggagttaa ccttcacaaa tgactccatc atcacccaca     420
acttttgtaa tctgacttcc gccctcaaca gaggacttt tgaccacaca cttatgagta     480
tagtctcaag tctgcacctc agcattagag gggtccccag ctacaaagca gtgtcctgtg     540
attttaacaa tggcatcact attcaataca acctgtcatt ttctaatgca cagagcgctc     600
tgagtcaatg taagaccttc aggggagag tcctggatat gttcagaact gcttttggag     660
gaaagtacat gaggagtggc tggggctgga caggttcaga tggcaagact acttggtgca     720
gccagacaaa ctaccaatat ctgattatac aaaacaggac ttgggaaaac cactgcaggt     780
acgcaggccc tttcggaatg tctagaattc tcttcgctca gaaaagaca aggtttctaa     840 ctagaaggct tgcaggcaca ttcacttgga ctttatcaga ctcatcagga gtggagaatc     900
caggtggtta ctgcttgacc aagtggatga tcctcgctgc agagctcaag tgttttggga     960
acacagctgt tgcaaagtgc aatgtaaatc atgatgaaga gttctgtgat atgctacgac    1020
tgattgatta caacaaggct gctttgagta aattcaaaga gatgtagaa tccgctctac     1080 atctgttcaa gacaacagtg aattctttga tttctgatca gcttttgatg agaaatcacc    1140
```

-continued

```
taagagactt gatgggagtg ccatactgca attactcgaa attctggtat ctagagcatg   1200
caaagactgg tgagactagt gtccccaagt gctggcttgt cagcaatggt tcttatttga   1260
atgaaaccca tttcagcgac caaattgagc aggaagcaga taatatgatc acagaaatgc   1320
tgagaaagga ctacataaaa aggcaaggga gtaccctct  agccttgatg gatctattga   1380
tgttttctac atcagcatat ttgatcagca tctttctgca tcttgtgagg ataccaacac   1440
acagacacat aaagggcggc tcatgcccaa aaccacatcg gttaaccagc aagggaatct   1500
gtagttgtgg tgcatttaaa gtaccaggtg tggaaaccac ctggaaaaga cgctgaacag   1560
cagcgcctcc ctgactcacc acctcgaaag aggtggtgag tcaggaggc  ccagagggtc   1620 ttagagtgtt acgacatttg gacctctgaa gattaggtca tgtggtagga tattgtggac   1680
agttttcagg tcggggagcc ttgccttgga ggcgctttca agatgatac  agtccatgag   1740 tgcacagtgt ggggtgacct ctttcttttt cttgtccctc actattccag tgtgcatctt   1800
gcatagccag ccatatttgt cccagacttt gtcctcatat tctcttgaag cttctttagt   1860
catctcaaca tcgatgagct taatgtctct tctgttttgt gaatctagga gtttcctgat   1920
gtcatcagat ccctgacaac ttaggaccat tccctgtgga agagcaccta ttactgaaga   1980
tgtcagccca ggttgtgcat tgaagaggtc agcaaggtcc atgccatgtg agtatttgga   2040
gtcctgcttg aattgttttt gatcagtggg ttctctatag aaatgtatgt actgcccatt   2100
ctgtggctga atattgcta  tttctaccgg gtcattaaat ctgccctcaa tgtcaatcca   2160
tgtaggagcg ttagggtcaa tacctcccat gaggtccttc agcaacattg tttggctgta   2220
gcttaagccc acctgaggtg ggcccgctgc cccaggcgct ggtttgggtg agttggccat   2280
aggcctctca tttgtcagat caattgttgt gttctcccat gctctcccta caactgatgt   2340
tctacaagct atgtatggcc acccctcccc tgaaagacag actttgtaga ggatgttctc   2400
gtaaggattc ctgtctccaa cctgatcaga aacaaacatg ttgagtttct tcttggcccc   2460
aagaactgct tcaggagat  cctcactgtt gcttggctta attaagatgg attccaacat   2520
gttaccccca tctaacaagg ctgccctgc  tttcacagca gcaccgagac tgaaattgta   2580
gccagatatg ttgatgctag actgctgctc agtgatgact cccaagactg ggtgcttgtc   2640
tttcagcctt tcaaggtcac ttaggttcgg gtacttgact gtgtaaagca gcccaaggtc   2700
tgtgagtgct tgcacaacgt cattgagtga ggttgtgat  tgtttggcca tacaagccat   2760
tgttaagctt ggcattgtgc cgaattgatt gttcagaagt gatgagtcct tcacatccca   2820
gaccctcacc acaccatttg cactctgctg aggtctcctc attccaacca tttgcagaat   2880
ctgagatctt tggtcaagct gttgtgctgt taagttcccc atgtagactc cagaagttag   2940 aggccttca  gacctcatga ttttagcctt cagttttca  aggtcagctg caagggacat   3000
cagttcttct gcactaagcc tccctacttt tagaacattc ttttttgatg ttgactttag   3060
gtccacaagg gaatacacag tttggttgag cttctgagt  ctctgtaaat ctttgtcatc   3120
cctcttctct ttcctcatga tcctctgaac attgctcacc tcagagaagt ctaatccatt   3180
cagaaggctg gtggcatcct tgatcacagc agctttcaca tctgatgtga agccttgaag   3240
ctctctcctc aatgcctggg tccattgaaa gcttttaact tctttggaca gagacatttt   3300
gtcactcagt ggatttccaa gtcaaatgcg caatcaaaat gcctaggatc cactgtgcg    3359
```

<210> SEQ ID NO 6
<211> LENGTH: 558
<212> TYPE: PRT

<213> ORGANISM: Lymphocytic choriomeningitis virus
<220> FEATURE:
<223> OTHER INFORMATION: NP protein of the MP strain of LCMV

<400> SEQUENCE: 6

```
Met Ser Leu Ser Lys Glu Val Lys Ser Phe Gln Trp Thr Gln Ala Leu
1               5                   10                  15

Arg Arg Glu Leu Gln Gly Phe Thr Ser Asp Val Lys Ala Ala Val Ile
            20                  25                  30

Lys Asp Ala Thr Ser Leu Leu Asn Gly Leu Asp Phe Ser Glu Val Ser
        35                  40                  45

Asn Val Gln Arg Ile Met Arg Lys Glu Lys Arg Asp Asp Lys Asp Leu
    50                  55                  60

Gln Arg Leu Arg Ser Leu Asn Gln Thr Val Tyr Ser Leu Val Asp Leu
65                  70                  75                  80

Lys Ser Thr Ser Lys Lys Asn Val Leu Lys Val Gly Arg Leu Ser Ala
                85                  90                  95

Glu Glu Leu Met Ser Leu Ala Ala Asp Leu Lys Leu Lys Ala Lys
            100                 105                 110

Ile Met Arg Ser Glu Arg Pro Leu Thr Ser Gly Val Tyr Met Gly Asn
            115                 120                 125

Leu Thr Ala Gln Gln Leu Asp Gln Arg Ser Gln Ile Leu Gln Met Val
130                 135                 140

Gly Met Arg Arg Pro Gln Gln Ser Ala Asn Gly Val Val Arg Val Trp
145                 150                 155                 160

Asp Val Lys Asp Ser Ser Leu Leu Asn Asn Gln Phe Gly Thr Met Pro
                165                 170                 175

Ser Leu Thr Met Ala Cys Met Ala Lys Gln Ser Gln Thr Ser Leu Asn
            180                 185                 190

Asp Val Val Gln Ala Leu Thr Asp Leu Gly Leu Leu Tyr Thr Val Lys
        195                 200                 205

Tyr Pro Asn Leu Ser Asp Leu Glu Arg Leu Lys Asp Lys His Pro Val
210                 215                 220

Leu Gly Val Ile Thr Glu Gln Gln Ser Ser Ile Asn Ile Ser Gly Tyr
225                 230                 235                 240

Asn Phe Ser Leu Gly Ala Ala Val Lys Ala Gly Ala Ala Leu Leu Asp
                245                 250                 255

Gly Gly Asn Met Leu Glu Ser Ile Leu Ile Lys Pro Ser Asn Ser Glu
            260                 265                 270

Asp Leu Leu Lys Ala Val Leu Gly Ala Lys Lys Lys Leu Asn Met Phe
        275                 280                 285

Val Ser Asp Gln Val Gly Asp Arg Asn Pro Tyr Glu Asn Ile Leu Tyr
290                 295                 300

Lys Val Cys Leu Ser Gly Glu Gly Trp Pro Tyr Ile Ala Cys Arg Thr
305                 310                 315                 320

Ser Val Val Gly Arg Ala Trp Glu Asn Thr Thr Ile Asp Leu Thr Asn
                325                 330                 335

Glu Arg Pro Met Ala Asn Ser Pro Lys Pro Ala Pro Gly Ala Ala Gly
            340                 345                 350

Pro Pro Gln Val Gly Leu Ser Tyr Ser Gln Thr Met Leu Leu Lys Asp
        355                 360                 365

Leu Met Gly Gly Ile Asp Pro Asn Ala Pro Thr Trp Ile Asp Ile Glu
370                 375                 380

Gly Arg Phe Asn Asp Pro Val Glu Ile Ala Ile Phe Gln Pro Gln Asn
```

```
                385                 390                 395                 400
        Gly Gln Tyr Ile His Phe Tyr Arg Glu Pro Thr Asp Gln Lys Gln Phe
                        405                 410                 415

Lys Gln Asp Ser Lys Tyr Ser His Gly Met Asp Leu Ala Asp Leu Phe
                        420                 425                 430

Asn Ala Gln Pro Gly Leu Thr Ser Val Ile Gly Ala Leu Pro Gln
                    435                 440                 445

Gly Met Val Leu Ser Cys Gln Gly Ser Asp Ile Arg Lys Leu Leu
            450                 455                 460

Asp Ser Gln Asn Arg Arg Asp Ile Lys Leu Ile Asp Val Glu Met Thr
        465                 470                 475                 480

Lys Glu Ala Ser Arg Glu Tyr Glu Asp Lys Val Trp Asp Lys Tyr Gly
                        485                 490                 495

Trp Leu Cys Lys Met His Thr Gly Ile Val Arg Asp Lys Lys Lys
                    500                 505                 510

Glu Val Thr Pro His Cys Ala Leu Met Asp Cys Ile Ile Phe Glu Ser
                    515                 520                 525

Ala Ser Lys Ala Arg Leu Pro Asp Leu Lys Thr Val His Asn Ile Leu
            530                 535                 540

Pro His Asp Leu Ile Phe Arg Gly Pro Asn Val Val Thr Leu
        545                 550                 555

<210> SEQ ID NO 7
<211> LENGTH: 498
<212> TYPE: PRT
<213> ORGANISM: Lymphocytic choriomeningitis virus
<220> FEATURE:
<223> OTHER INFORMATION: GP protein of the MP strain of LCMV

<400> SEQUENCE: 7

Met Gly Gln Ile Val Thr Met Phe Glu Ala Leu Pro His Ile Ile Asp
1               5                   10                  15

Glu Val Ile Asn Ile Val Ile Val Leu Ile Ile Ile Thr Ser Ile
            20                  25                  30

Lys Ala Val Tyr Asn Phe Ala Thr Cys Gly Ile Leu Ala Leu Ile Ser
            35                  40                  45

Phe Leu Phe Leu Ala Gly Arg Ser Cys Gly Met Tyr Gly Leu Asp Gly
    50                  55                  60

Pro Asp Ile Tyr Lys Gly Val Tyr Arg Phe Lys Ser Val Glu Phe Asp
65                  70                  75                  80

Met Ser Tyr Leu Asn Leu Thr Met Pro Asn Ala Cys Ser Ala Asn Asn
                85                  90                  95

Ser His His Tyr Ile Ser Met Gly Thr Ser Gly Leu Glu Leu Thr Phe
            100                 105                 110

Thr Asn Asp Ser Ile Ile Thr His Asn Phe Cys Asn Leu Thr Ser Ala
        115                 120                 125

Leu Asn Lys Arg Thr Phe Asp His Thr Leu Met Ser Ile Val Ser Ser
    130                 135                 140

Leu His Leu Ser Ile Arg Gly Val Pro Ser Tyr Lys Ala Val Ser Cys
145                 150                 155                 160

Asp Phe Asn Asn Gly Ile Thr Ile Gln Tyr Asn Leu Ser Phe Ser Asn
                165                 170                 175

Ala Gln Ser Ala Leu Ser Gln Cys Lys Thr Phe Arg Gly Arg Val Leu
            180                 185                 190

Asp Met Phe Arg Thr Ala Phe Gly Gly Lys Tyr Met Arg Ser Gly Trp
```

```
              195                 200                 205
Gly Trp Thr Gly Ser Asp Gly Lys Thr Thr Trp Cys Ser Gln Thr Asn
210                 215                 220

Tyr Gln Tyr Leu Ile Ile Gln Asn Arg Thr Trp Glu Asn His Cys Arg
225                 230                 235                 240

Tyr Ala Gly Pro Phe Gly Met Ser Arg Ile Leu Phe Ala Gln Glu Lys
                245                 250                 255

Thr Arg Phe Leu Thr Arg Arg Leu Ala Gly Thr Phe Thr Trp Thr Leu
            260                 265                 270

Ser Asp Ser Ser Gly Val Glu Asn Pro Gly Gly Tyr Cys Leu Thr Lys
                275                 280                 285

Trp Met Ile Leu Ala Ala Glu Leu Lys Cys Phe Gly Asn Thr Ala Val
            290                 295                 300

Ala Lys Cys Asn Val Asn His Asp Glu Glu Phe Cys Asp Met Leu Arg
305                 310                 315                 320

Leu Ile Asp Tyr Asn Lys Ala Ala Leu Ser Lys Phe Lys Glu Asp Val
                325                 330                 335

Glu Ser Ala Leu His Leu Phe Lys Thr Thr Val Asn Ser Leu Ile Ser
            340                 345                 350

Asp Gln Leu Leu Met Arg Asn His Leu Arg Asp Leu Met Gly Val Pro
                355                 360                 365

Tyr Cys Asn Tyr Ser Lys Phe Trp Tyr Leu Glu His Ala Lys Thr Gly
370                 375                 380

Glu Thr Ser Val Pro Lys Cys Trp Leu Val Ser Asn Gly Ser Tyr Leu
385                 390                 395                 400

Asn Glu Thr His Phe Ser Asp Gln Ile Glu Gln Ala Asp Asn Met
                405                 410                 415

Ile Thr Glu Met Leu Arg Lys Asp Tyr Ile Lys Arg Gln Gly Ser Thr
            420                 425                 430

Pro Leu Ala Leu Met Asp Leu Leu Met Phe Ser Thr Ser Ala Tyr Leu
                435                 440                 445

Ile Ser Ile Phe Leu His Leu Val Arg Ile Pro Thr His Arg His Ile
450                 455                 460

Lys Gly Gly Ser Cys Pro Lys Pro His Arg Leu Thr Ser Lys Gly Ile
465                 470                 475                 480

Cys Ser Cys Gly Ala Phe Lys Val Pro Gly Val Glu Thr Thr Trp Lys
                485                 490                 495

Arg Arg

<210> SEQ ID NO 8
<211> LENGTH: 2209
<212> TYPE: PRT
<213> ORGANISM: Lymphocytic choriomeningitis virus
<220> FEATURE:
<223> OTHER INFORMATION: L protein of the MP strain of LCMV

<400> SEQUENCE: 8

Met Asp Glu Ala Ile Ser Glu Leu Arg Glu Leu Cys Leu Asn His Ile
1               5                   10                  15

Glu Gln Asp Glu Arg Leu Ser Arg Gln Lys Leu Asn Phe Leu Gly Gln
                20                  25                  30

Arg Glu Pro Arg Met Val Leu Ile Glu Gly Leu Lys Leu Leu Ser Arg
            35                  40                  45

Cys Ile Glu Ile Asp Ser Ala Asp Lys Ser Gly Cys Ile His Asn His
        50                  55                  60
```

```
Asp Asp Lys Ser Val Glu Ala Ile Leu Ile Glu Ser Gly Ile Val Cys
 65                  70                  75                  80

Pro Gly Leu Pro Leu Ile Ile Pro Asp Gly Tyr Lys Leu Ile Asp Asn
             85                  90                  95

Ser Leu Ile Leu Leu Glu Cys Phe Val Arg Ser Thr Pro Ala Ser Phe
            100                 105                 110

Glu Lys Lys Phe Ile Glu Asp Thr Asn Lys Leu Ala Cys Ile Lys Glu
        115                 120                 125

Asp Leu Ala Ile Ala Gly Ile Thr Leu Val Pro Ile Val Asp Gly Arg
        130                 135                 140

Cys Asp Tyr Asp Asn Ser Phe Met Pro Glu Trp Val Asn Phe Lys Phe
145                 150                 155                 160

Arg Asp Leu Leu Phe Lys Leu Leu Glu Tyr Ser Ser Gln Asp Glu Lys
            165                 170                 175

Val Phe Glu Glu Ser Glu Tyr Phe Arg Leu Cys Glu Ser Leu Lys Thr
            180                 185                 190

Thr Val Asp Lys Arg Ser Gly Ile Asp Ser Met Lys Ile Leu Lys Asp
        195                 200                 205

Ala Arg Ser Phe His Asn Asp Glu Ile Met Lys Met Cys His Asp Gly
210                 215                 220

Val Asn Pro Asn Met Asn Cys Asp Asp Val Val Leu Gly Ile Asn Ser
225                 230                 235                 240

Leu Tyr Ser Arg Phe Arg Arg Asp Leu Glu Thr Gly Lys Leu Lys Arg
                245                 250                 255

Ser Phe Gln Lys Ile Asn Pro Gly Asn Leu Ile Lys Glu Phe Ser Glu
            260                 265                 270

Leu Tyr Glu Thr Leu Ala Asp Ser Asp Ile Ser Ala Leu Ser Lys
            275                 280                 285

Glu Ala Val Glu Ser Cys Pro Leu Met Arg Phe Ile Thr Ala Asp Thr
290                 295                 300

His Gly Tyr Glu Arg Gly Ser Glu Thr Ser Thr Glu Tyr Glu Arg Leu
305                 310                 315                 320

Leu Ser Met Leu Asn Lys Val Lys Ser Leu Lys Leu Leu Asn Thr Arg
                325                 330                 335

Arg Arg Gln Leu Leu Asn Leu Asp Val Leu Cys Leu Ser Ser Leu Ile
            340                 345                 350

Lys Gln Ser Lys Leu Lys Gly Ser Lys Asn Asp Lys His Trp Val Gly
            355                 360                 365

Cys Cys Tyr Gly Ser Val Asn Asp Arg Leu Val Ser Phe His Ser Thr
370                 375                 380

Lys Glu Glu Phe Ile Arg Leu Leu Arg Asn Arg Lys Ser Lys Ala
385                 390                 395                 400

Tyr Arg Lys Val Ser Leu Glu Asp Leu Phe Arg Thr Ser Ile Asn Glu
            405                 410                 415

Phe Ile Leu Lys Val Gln Arg Cys Leu Ser Val Val Gly Leu Ser Phe
            420                 425                 430

Gly His Tyr Gly Leu Ser Glu His Leu Glu His Glu Cys His Ile Pro
        435                 440                 445

Phe Ile Glu Phe Glu Asn Phe Met Arg Ser Gly Thr His Pro Ile Met
        450                 455                 460

Tyr Tyr Thr Lys Phe Glu Asp Tyr Asp Phe Gln Pro Asn Thr Glu Gln
465                 470                 475                 480
```

```
Leu Arg Asn Met His Ser Leu Lys Arg Leu Ser Ser Val Cys Leu Ala
            485                 490                 495

Leu Thr Asn Ser Met Lys Thr Ser Ser Val Ala Arg Leu Arg Gln Asn
            500                 505                 510

Gln Leu Gly Ser Val Arg Tyr Gln Val Val Glu Cys Lys Glu Val Phe
            515                 520                 525

Cys Gln Val Ile Lys Leu Asp Ser Glu Glu Tyr His Leu Leu Tyr Gln
            530                 535                 540

Lys Thr Gly Glu Ser Ser Arg Cys Tyr Ser Ile Gln Gly Pro Asn Gly
545                 550                 555                 560

His Leu Ile Ser Phe Tyr Ala Asp Pro Lys Arg Phe Phe Leu Pro Ile
            565                 570                 575

Phe Ser Asp Glu Val Leu His Asn Met Ile Asp Thr Met Ile Ser Trp
            580                 585                 590

Ile Arg Ser Cys Pro Asp Leu Lys Asp Ser Ile Asp Asp Val Glu Ile
            595                 600                 605

Ala Leu Arg Thr Leu Leu Leu Met Leu Thr Asn Pro Thr Lys Arg
            610                 615                 620

Asn Gln Lys Gln Val Gln Asn Ile Arg Tyr Leu Val Met Ala Ile Val
625                 630                 635                 640

Ser Asp Phe Ser Ser Thr Ser Leu Met Asp Lys Leu Lys Glu Asp Leu
            645                 650                 655

Ile Thr Pro Ala Glu Lys Val Val Tyr Lys Leu Leu Arg Phe Leu Ile
            660                 665                 670

Lys Thr Val Phe Gly Thr Gly Glu Lys Val Leu Leu Ser Ala Lys Phe
            675                 680                 685

Lys Phe Met Leu Asn Val Ser Tyr Leu Cys His Leu Ile Thr Lys Glu
            690                 695                 700

Thr Pro Asp Arg Leu Thr Asp Gln Ile Lys Cys Phe Glu Lys Phe Phe
705                 710                 715                 720

Glu Pro Lys Ser Glu Phe Gly Phe Phe Val Asn Pro Lys Glu Ser Ile
            725                 730                 735

Thr Pro Glu Glu Glu Cys Val Phe Tyr Asp Gln Met Lys Lys Phe Thr
            740                 745                 750

Gly Lys Glu Val Asp Cys Gln Arg Thr Thr Pro Gly Val Asn Leu Glu
            755                 760                 765

Ala Phe Ser Met Met Val Ser Ser Phe Asn Asn Gly Thr Leu Ile Phe
            770                 775                 780

Lys Gly Glu Lys Arg Leu Asn Ser Leu Asp Pro Met Thr Asn Ser Gly
785                 790                 795                 800

Cys Ala Thr Ala Leu Asp Leu Ala Ser Asn Lys Ser Val Val Val Asn
            805                 810                 815

Lys His Leu Asn Gly Glu Arg Leu Leu Glu Tyr Asp Phe Asn Lys Leu
            820                 825                 830

Leu Val Ser Ala Val Ser Gln Ile Thr Glu Ser Phe Met Arg Lys Gln
            835                 840                 845

Lys Tyr Lys Leu Asn His Ser Asp Tyr Glu Tyr Lys Val Ser Lys Leu
            850                 855                 860

Val Ser Arg Leu Val Ile Gly Ser Lys Glu Thr Glu Ala Gly Lys Leu
865                 870                 875                 880

Glu Gly Asp Ser Ala Asp Ile Cys Phe Asp Gly Glu Glu Thr Ser
            885                 890                 895

Phe Phe Lys Asn Leu Glu Asp Lys Val Asn Ser Thr Ile Lys Arg Tyr
```

```
                900             905             910
Glu Arg Ser Lys Lys Thr Asn Glu Gly Glu Asn Glu Val Gly Phe Glu
            915             920             925
Asn Thr Lys Gly Leu His His Leu Gln Thr Ile Leu Ser Gly Lys Met
        930             935             940
Ala Tyr Leu Arg Lys Val Ile Leu Ser Glu Ile Ser Phe His Leu Val
945             950             955             960
Glu Asp Phe Asp Pro Ser Cys Leu Thr Asn Asp Asp Met Lys Phe Ile
            965             970             975
Cys Glu Ala Ile Glu Thr Ser Thr Glu Leu Ser Pro Leu Tyr Phe Thr
            980             985             990
Ser Ala Val Lys Glu Gln Cys Gly Leu Asp Glu Met Ala Lys Asn Leu
        995             1000            1005
Cys Arg Lys Phe Phe Ser Glu Gly Asp Trp Phe Ser Cys Met Lys Met
        1010            1015            1020
Ile Leu Leu Gln Met Asn Ala Asn Ala Tyr Ser Gly Lys Tyr Arg His
1025            1030            1035            1040
Met Gln Arg Gln Gly Leu Asn Phe Lys Phe Asp Trp Asp Lys Leu Glu
            1045            1050            1055
Glu Asp Val Arg Ile Ser Glu Arg Glu Ser Asn Ser Glu Ser Leu Ser
            1060            1065            1070
Lys Ala Leu Ser Leu Thr Lys Cys Met Ser Ala Ala Leu Lys Asn Leu
            1075            1080            1085
Cys Phe Tyr Ser Glu Glu Ser Pro Thr Ser Tyr Thr Ser Val Gly Pro
            1090            1095            1100
Asp Ser Gly Arg Leu Lys Phe Ala Leu Ser Tyr Lys Glu Gln Val Gly
1105            1110            1115            1120
Gly Asn Arg Glu Leu Tyr Ile Gly Asp Leu Arg Thr Lys Met Phe Thr
            1125            1130            1135
Arg Leu Ile Glu Asp Tyr Phe Glu Ser Phe Ser Ser Phe Phe Ser Gly
            1140            1145            1150
Ser Cys Leu Asn Asn Asp Lys Glu Phe Glu Asn Ala Ile Leu Ser Met
            1155            1160            1165
Thr Ile Asn Val Arg Glu Gly Leu Leu Asn Tyr Ser Met Asp His Ser
        1170            1175            1180
Lys Trp Gly Pro Met Met Cys Pro Phe Leu Phe Leu Met Leu Leu Gln
1185            1190            1195            1200
Asn Leu Lys Leu Gly Asp Asp Gln Tyr Val Arg Ser Gly Lys Asp His
            1205            1210            1215
Ile Ser Thr Leu Leu Thr Trp His Met His Lys Leu Val Glu Val Pro
            1220            1225            1230
Phe Pro Val Val Asn Ala Met Met Lys Ser Tyr Ile Lys Ser Lys Leu
            1235            1240            1245
Lys Leu Leu Arg Gly Ser Glu Thr Thr Val Thr Glu Arg Ile Phe Arg
            1250            1255            1260
Glu Tyr Phe Glu Leu Gly Ile Val Pro Ser His Ile Ser Ser Leu Ile
1265            1270            1275            1280
Asp Met Gly Gln Gly Ile Leu His Asn Ala Ser Asp Phe Tyr Gly Leu
            1285            1290            1295
Ile Ser Glu Arg Phe Ile Asn Tyr Cys Ile Gly Val Ile Phe Gly Glu
            1300            1305            1310
Arg Pro Glu Ser Tyr Thr Ser Ser Asp Asp Gln Ile Thr Leu Phe Asp
            1315            1320            1325
```

```
Arg Arg Leu Ser Glu Leu Val Asp Ser Asp Pro Glu Glu Val Leu Val
        1330                1335                1340

Leu Leu Glu Phe His Ser His Leu Ser Gly Leu Leu Asn Lys Phe Ile
1345                1350                1355                1360

Ser Pro Lys Ser Val Val Gly Arg Phe Ala Ala Glu Phe Lys Ser Arg
            1365                1370                1375

Phe Tyr Val Trp Gly Glu Glu Val Pro Leu Leu Thr Lys Phe Val Ser
        1380                1385                1390

Ala Ala Leu His Asn Val Lys Cys Lys Glu Pro His Gln Leu Cys Glu
            1395                1400                1405

Thr Ile Asp Thr Ile Ala Asp Gln Ala Val Ala Asn Gly Val Pro Val
        1410                1415                1420

Ser Leu Val Asn Cys Ile Gln Lys Arg Thr Leu Asp Leu Leu Lys Tyr
1425                1430                1435                1440

Ala Asn Phe Pro Leu Asp Pro Phe Leu Leu Asn Thr Asn Thr Asp Val
            1445                1450                1455

Lys Asp Trp Leu Asp Gly Ser Arg Gly Tyr Arg Ile Gln Arg Leu Ile
        1460                1465                1470

Glu Glu Leu Cys Pro Ser Glu Thr Lys Val Met Arg Arg Leu Val Arg
    1475                1480                1485

Arg Leu His His Lys Leu Lys Asn Gly Glu Phe Asn Glu Glu Phe Phe
        1490                1495                1500

Leu Asp Leu Phe Asn Arg Asp Lys Lys Glu Ala Ile Leu Gln Leu Gly
1505                1510                1515                1520

Asn Ile Leu Gly Leu Glu Glu Asp Leu Ser Gln Leu Ala Asn Ile Asn
            1525                1530                1535

Trp Leu Asn Leu Asn Glu Leu Phe Pro Leu Arg Met Val Leu Arg Gln
        1540                1545                1550

Lys Val Val Tyr Pro Ser Val Met Thr Phe Gln Glu Glu Arg Ile Pro
        1555                1560                1565

Ser Leu Ile Lys Thr Leu Gln Asn Lys Leu Cys Ser Lys Phe Thr Arg
1570                1575                1580

Gly Ala Gln Lys Leu Leu Ser Glu Ala Ile Asn Lys Ser Ala Phe Gln
1585                1590                1595                1600

Ser Cys Ile Ser Ser Gly Phe Ile Gly Leu Cys Lys Thr Leu Gly Ser
            1605                1610                1615

Arg Cys Val Arg Asn Lys Asn Arg Asp Asn Leu Tyr Ile Arg Lys Val
            1620                1625                1630

Leu Glu Asp Leu Ala Met Asp Ala His Val Thr Ala Ile His Arg His
        1635                1640                1645

Asp Gly Ile Met Leu Tyr Ile Cys Asp Arg Gln Ser His Pro Glu Ala
    1650                1655                1660

His Cys Asp His Ile Ser Leu Leu Arg Pro Leu Leu Trp Asp Tyr Ile
1665                1670                1675                1680

Cys Ile Ser Leu Ser Asn Ser Phe Glu Leu Gly Val Trp Val Leu Ala
            1685                1690                1695

Glu Pro Val Lys Gly Lys Asn Glu Gly Ser Ser Ser Leu Lys His Leu
        1700                1705                1710

Asn Pro Cys Asp Tyr Val Ala Arg Lys Pro Glu Ser Ser Arg Leu Leu
        1715                1720                1725

Glu Asp Lys Ile Ser Leu Asn His Val Ile Gln Ser Val Arg Arg Leu
    1730                1735                1740
```

```
Tyr Pro Lys Ile Tyr Glu Asp Gln Leu Leu Pro Phe Met Ser Asp Met
1745                1750                1755                1760

Ser Ser Lys Asn Met Arg Trp Ser Pro Arg Ile Lys Phe Leu Asp Leu
            1765                1770                1775

Cys Val Leu Ile Asp Ile Asn Ser Glu Ser Leu Ser Leu Ile Ser His
            1780                1785                1790

Val Val Lys Trp Lys Arg Asp Glu His Tyr Thr Val Leu Phe Ser Asp
        1795                1800                1805

Leu Val Asn Ser His Gln Arg Ser Asp Ser Ser Leu Val Asp Glu Phe
        1810                1815                1820

Val Val Ser Thr Arg Asp Val Cys Lys Asn Phe Leu Lys Gln Val Tyr
1825                1830                1835                1840

Phe Glu Ser Phe Val Arg Glu Phe Val Ala Thr Ser Arg Thr Leu Gly
            1845                1850                1855

Ser Phe Ser Trp Phe Pro His Lys Asp Met Met Pro Ser Glu Asp Gly
            1860                1865                1870

Ala Glu Ala Leu Gly Pro Phe Gln Ser Phe Ile Leu Lys Val Val Asn
        1875                1880                1885

Lys Asn Met Glu Arg Pro Met Phe Arg Asn Asp Leu Gln Phe Gly Phe
        1890                1895                1900

Gly Trp Phe Ser Tyr Arg Leu Gly Asp Ile Val Cys Asn Ala Ala Met
1905                1910                1915                1920

Leu Ile Lys Gln Gly Leu Thr Asn Pro Lys Ala Phe Lys Ser Leu Arg
            1925                1930                1935

Asn Leu Trp Asp Tyr Met Ile Asn Asn Thr Glu Gly Val Leu Glu Phe
            1940                1945                1950

Ser Ile Thr Val Asp Phe Thr His Asn Gln Asn Asn Thr Asp Cys Leu
            1955                1960                1965

Arg Lys Phe Ser Leu Ile Phe Leu Val Lys Cys Gln Leu Gln Gly Pro
        1970                1975                1980

Gly Val Ala Glu Phe Leu Ser Cys Ser His Leu Phe Lys Gly Glu Val
1985                1990                1995                2000

Asp Arg Arg Phe Leu Asp Glu Cys Leu His Leu Leu Arg Ser Asp Ser
            2005                2010                2015

Ile Phe Lys Val Asn Asp Gly Val Phe Asp Ile Arg Ser Glu Glu Phe
            2020                2025                2030

Glu Asp Tyr Met Glu Asp Pro Leu Ile Leu Gly Asp Ser Leu Glu Leu
        2035                2040                2045

Glu Leu Ile Gly Ser Arg Lys Ile Leu Asp Gly Ile Arg Ser Leu Asp
        2050                2055                2060

Phe Glu Arg Ile Gly Pro Glu Trp Glu Pro Val Pro Leu Thr Val Arg
2065                2070                2075                2080

Met Gly Ala Leu Phe Glu Gly Arg Ser Leu Val Gln Asn Ile Val Val
            2085                2090                2095

Lys Leu Glu Thr Lys Asp Met Arg Val Phe Leu Ala Glu Leu Glu Gly
            2100                2105                2110

Tyr Gly Asn Phe Asp Asp Val Leu Gly Ser Leu Leu Leu His Arg Phe
        2115                2120                2125

Arg Thr Gly Glu His Leu Gln Gly Ser Glu Ile Ser Thr Ile Leu Gln
        2130                2135                2140

Glu Leu Cys Ile Asp Arg Ser Ile Leu Leu Val Pro Leu Ser Leu Val
2145                2150                2155                2160

Pro Asp Trp Phe Thr Phe Lys Asp Cys Arg Leu Cys Phe Ser Lys Ser
```

```
              2165                2170                2175
Lys Asn Thr Val Met Tyr Glu Thr Val Val Gly Lys Tyr Arg Leu Lys
            2180                2185                2190

Gly Lys Ser Cys Asp Asp Trp Leu Thr Lys Ser Val Val Glu Glu Ile
        2195                2200                2205

Asp

<210> SEQ ID NO 9
<211> LENGTH: 90
<212> TYPE: PRT
<213> ORGANISM: Lymphocytic choriomeningitis virus
<220> FEATURE:
<223> OTHER INFORMATION: Z protein of the MP strain of LCMV

<400> SEQUENCE: 9

Met Gly Gln Gly Lys Ser Lys Glu Gly Arg Asp Ala Ser Asn Thr Ser
1               5                   10                  15

Arg Ala Glu Ile Leu Pro Asp Thr Thr Tyr Leu Gly Pro Leu Asn Cys
            20                  25                  30

Lys Ser Cys Trp Gln Arg Phe Asp Ser Leu Val Arg Cys His Asp His
        35                  40                  45

Tyr Leu Cys Arg His Cys Leu Asn Leu Leu Leu Ser Val Ser Asp Arg
    50                  55                  60

Cys Pro Leu Cys Lys His Pro Leu Pro Thr Lys Leu Lys Ile Ser Thr
65                  70                  75                  80

Ala Pro Ser Ser Pro Pro Tyr Glu Glu
                85                  90

<210> SEQ ID NO 10
<211> LENGTH: 255
<212> TYPE: PRT
<213> ORGANISM: Artificial Sequence
<220> FEATURE:
<223> OTHER INFORMATION: HPV16 E7/E6 fusion protein with mutations in Rb
      binding site and zinc finger motifs

<400> SEQUENCE: 10

Met His Gly Asp Thr Pro Thr Leu His Glu Tyr Met Leu Asp Leu Gln
1               5                   10                  15

Pro Glu Thr Thr Asp Leu Tyr Gly Tyr Gly Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Gly Pro Ile Cys Ser Gln
                85                  90                  95

Lys Pro His Gln Lys Arg Thr Ala Met Phe Gln Asp Pro Gln Glu Arg
            100                 105                 110

Pro Arg Lys Leu Pro Gln Leu Cys Thr Glu Leu Gln Thr Thr Ile His
        115                 120                 125

Asp Ile Ile Leu Glu Cys Val Tyr Cys Lys Gln Gln Leu Leu Arg Arg
    130                 135                 140

Glu Val Tyr Asp Phe Ala Phe Arg Asp Leu Cys Ile Val Tyr Arg Asp
145                 150                 155                 160
```

```
Gly Asn Pro Tyr Ala Val Gly Asp Lys Cys Leu Lys Phe Tyr Ser Lys
            165                 170                 175

Ile Ser Glu Tyr Arg His Tyr Cys Tyr Ser Leu Tyr Gly Thr Thr Leu
        180                 185                 190

Glu Gln Gln Tyr Asn Lys Pro Leu Cys Asp Leu Leu Ile Arg Cys Ile
            195                 200                 205

Asn Gly Gln Lys Pro Leu Cys Pro Glu Glu Lys Gln Arg His Leu Asp
        210                 215                 220

Lys Lys Gln Arg Phe His Asn Ile Arg Gly Arg Trp Thr Gly Arg Cys
225                 230                 235                 240

Met Ser Cys Cys Arg Ser Ser Arg Thr Arg Arg Glu Thr Gln Leu
                245                 250                 255
```

<210> SEQ ID NO 11
<211> LENGTH: 670
<212> TYPE: PRT
<213> ORGANISM: Artificial Sequence
<220> FEATURE:
<223> OTHER INFORMATION: HPV16 E7/E6 fusion protein with mutations in Rb
      binding site and zinc finger motifs, linked to mouse Calreticulin

<400> SEQUENCE: 11

```
Met His Gly Asp Thr Pro Thr Leu His Glu Tyr Met Leu Asp Leu Gln
1               5                   10                  15

Pro Glu Thr Thr Asp Leu Tyr Gly Tyr Gly Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Gly Pro Ile Cys Ser Gln
                85                  90                  95

Lys Pro His Gln Lys Arg Thr Ala Met Phe Gln Asp Pro Gln Glu Arg
            100                 105                 110

Pro Arg Lys Leu Pro Gln Leu Cys Thr Glu Leu Gln Thr Thr Ile His
        115                 120                 125

Asp Ile Ile Leu Glu Cys Val Tyr Cys Lys Gln Gln Leu Leu Arg Arg
    130                 135                 140

Glu Val Tyr Asp Phe Ala Phe Arg Asp Leu Cys Ile Val Tyr Arg Asp
145                 150                 155                 160

Gly Asn Pro Tyr Ala Val Gly Asp Lys Cys Leu Lys Phe Tyr Ser Lys
                165                 170                 175

Ile Ser Glu Tyr Arg His Tyr Cys Tyr Ser Leu Tyr Gly Thr Thr Leu
            180                 185                 190

Glu Gln Gln Tyr Asn Lys Pro Leu Cys Asp Leu Leu Ile Arg Cys Ile
        195                 200                 205

Asn Gly Gln Lys Pro Leu Cys Pro Glu Glu Lys Gln Arg His Leu Asp
    210                 215                 220

Lys Lys Gln Arg Phe His Asn Ile Arg Gly Arg Trp Thr Gly Arg Cys
225                 230                 235                 240

Met Ser Cys Cys Arg Ser Ser Arg Thr Arg Arg Glu Thr Gln Leu Leu
                245                 250                 255

Leu Ser Val Pro Leu Leu Leu Gly Leu Leu Gly Leu Ala Ala Ala Asp
            260                 265                 270
```

Pro Ala Ile Tyr Phe Lys Glu Gln Phe Leu Asp Gly Asp Ala Trp Thr
        275                 280                 285

Asn Arg Trp Val Glu Ser Lys His Lys Ser Asp Phe Gly Lys Phe Val
290                 295                 300

Leu Ser Ser Gly Lys Phe Tyr Gly Asp Leu Glu Lys Asp Lys Gly Leu
305                 310                 315                 320

Gln Thr Ser Gln Asp Ala Arg Phe Tyr Ala Leu Ser Ala Lys Phe Glu
                325                 330                 335

Pro Phe Ser Asn Lys Gly Gln Thr Leu Val Val Gln Phe Thr Val Lys
                340                 345                 350

His Glu Gln Asn Ile Asp Cys Gly Gly Gly Tyr Val Lys Leu Phe Pro
                355                 360                 365

Ser Gly Leu Asp Gln Lys Asp Met His Gly Asp Ser Glu Tyr Asn Ile
        370                 375                 380

Met Phe Gly Pro Asp Ile Cys Gly Pro Gly Thr Lys Lys Val His Val
385                 390                 395                 400

Ile Phe Asn Tyr Lys Gly Lys Asn Val Leu Ile Asn Lys Asp Ile Arg
                    405                 410                 415

Cys Lys Asp Asp Glu Phe Thr His Leu Tyr Thr Leu Ile Val Arg Pro
                420                 425                 430

Asp Asn Thr Tyr Glu Val Lys Ile Asp Asn Ser Gln Val Glu Ser Gly
                435                 440                 445

Ser Leu Glu Asp Asp Trp Asp Phe Leu Pro Pro Lys Lys Ile Lys Asp
        450                 455                 460

Pro Asp Ala Ala Lys Pro Glu Asp Trp Asp Arg Ala Lys Ile Asp
465                 470                 475                 480

Asp Pro Thr Asp Ser Lys Pro Glu Asp Trp Asp Lys Pro Glu His Ile
                    485                 490                 495

Pro Asp Pro Asp Ala Lys Lys Pro Glu Asp Trp Asp Glu Glu Met Asp
                500                 505                 510

Gly Glu Trp Glu Pro Pro Val Ile Gln Asn Pro Glu Tyr Lys Gly Glu
        515                 520                 525

Trp Lys Pro Arg Gln Ile Asp Asn Pro Asp Tyr Lys Gly Thr Trp Ile
        530                 535                 540

His Pro Glu Ile Asp Asn Pro Glu Tyr Ser Pro Asp Ala Asn Ile Tyr
545                 550                 555                 560

Ala Tyr Asp Ser Phe Ala Val Leu Gly Leu Asp Leu Trp Gln Val Lys
                565                 570                 575

Ser Gly Thr Ile Phe Asp Asn Phe Leu Ile Thr Asn Asp Glu Ala Tyr
                580                 585                 590

Ala Glu Glu Phe Gly Asn Glu Thr Trp Gly Val Thr Lys Ala Ala Glu
                595                 600                 605

Lys Gln Met Lys Asp Lys Gln Asp Glu Glu Arg Leu Lys Glu Glu
610                 615                 620

Glu Glu Asp Lys Lys Arg Lys Glu Glu Glu Ala Glu Asp Lys Glu
625                 630                 635                 640

Asp Asp Asp Asp Arg Asp Glu Asp Glu Glu Asp Glu Lys Glu
                645                 650                 655

Glu Asp Glu Glu Glu Ser Pro Gly Gln Ala Lys Asp Glu Leu
                660                 665                 670

<210> SEQ ID NO 12
<211> LENGTH: 330

```
<212> TYPE: PRT
<213> ORGANISM: Artificial Sequence
<220> FEATURE:
<223> OTHER INFORMATION: HPV16 E7/E6 fusion protein with mutations in Rb
      binding site and zinc finger motifs, linked to mouse Ubiquitin

<400> SEQUENCE: 12

Met His Gly Asp Thr Pro Thr Leu His Glu Tyr Met Leu Asp Leu Gln
1               5                   10                  15

Pro Glu Thr Thr Asp Leu Tyr Gly Tyr Gly Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Gly Pro Ile Cys Ser Gln
                85                  90                  95

Lys Pro His Gln Lys Arg Thr Ala Met Phe Gln Asp Pro Gln Glu Arg
            100                 105                 110

Pro Arg Lys Leu Pro Gln Leu Cys Thr Glu Leu Gln Thr Thr Ile His
        115                 120                 125

Asp Ile Ile Leu Glu Cys Val Tyr Cys Lys Gln Leu Leu Arg Arg
130                 135                 140

Glu Val Tyr Asp Phe Ala Phe Arg Asp Leu Cys Ile Val Tyr Arg Asp
145                 150                 155                 160

Gly Asn Pro Tyr Ala Val Gly Asp Lys Cys Leu Lys Phe Tyr Ser Lys
                165                 170                 175

Ile Ser Glu Tyr Arg His Tyr Cys Tyr Ser Leu Tyr Gly Thr Thr Leu
            180                 185                 190

Glu Gln Gln Tyr Asn Lys Pro Leu Cys Asp Leu Leu Ile Arg Cys Ile
        195                 200                 205

Asn Gly Gln Lys Pro Leu Cys Pro Glu Glu Lys Gln Arg His Leu Asp
210                 215                 220

Lys Lys Gln Arg Phe His Asn Ile Arg Gly Arg Trp Thr Gly Arg Cys
225                 230                 235                 240

Met Ser Cys Cys Arg Ser Ser Arg Thr Arg Arg Glu Thr Gln Leu Gln
                245                 250                 255

Ile Phe Val Lys Thr Leu Thr Gly Lys Thr Ile Thr Leu Glu Val Glu
            260                 265                 270

Pro Ser Asp Thr Ile Glu Asn Val Lys Ala Lys Ile Gln Asp Lys Glu
        275                 280                 285

Gly Ile Pro Pro Asp Gln Gln Arg Leu Ile Phe Ala Gly Lys Gln Leu
    290                 295                 300

Glu Asp Gly Arg Thr Leu Ser Asp Tyr Asn Ile Gln Lys Glu Ser Thr
305                 310                 315                 320

Leu His Leu Val Leu Arg Leu Arg Gly Ala
                325                 330

<210> SEQ ID NO 13
<211> LENGTH: 417
<212> TYPE: PRT
<213> ORGANISM: Artificial Sequence
<220> FEATURE:
<223> OTHER INFORMATION: HPV16 E7/E6 fusion protein with mutations in Rb
      binding site and zinc finger motifs, co-expressed with mouse
```

GM-CSF, separated by a nucleotide sequence that encodes a
self-cleaving peptide (2A peptide)

<400> SEQUENCE: 13

```
Met His Gly Asp Thr Pro Thr Leu His Glu Tyr Met Leu Asp Leu Gln
1               5                   10                  15

Pro Glu Thr Thr Asp Leu Tyr Gly Tyr Gly Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Gly Pro Ile Cys Ser Gln
                85                  90                  95

Lys Pro His Gln Lys Arg Thr Ala Met Phe Gln Asp Pro Gln Glu Arg
                100                 105                 110

Pro Arg Lys Leu Pro Gln Leu Cys Thr Glu Leu Gln Thr Thr Ile His
            115                 120                 125

Asp Ile Ile Leu Glu Cys Val Tyr Cys Lys Gln Gln Leu Leu Arg Arg
        130                 135                 140

Glu Val Tyr Asp Phe Ala Phe Arg Asp Leu Cys Ile Val Tyr Arg Asp
145                 150                 155                 160

Gly Asn Pro Tyr Ala Val Gly Asp Lys Cys Leu Lys Phe Tyr Ser Lys
                165                 170                 175

Ile Ser Glu Tyr Arg His Tyr Cys Tyr Ser Leu Tyr Gly Thr Thr Leu
                180                 185                 190

Glu Gln Gln Tyr Asn Lys Pro Leu Cys Asp Leu Leu Ile Arg Cys Ile
            195                 200                 205

Asn Gly Gln Lys Pro Leu Cys Pro Glu Glu Lys Gln Arg His Leu Asp
        210                 215                 220

Lys Lys Gln Arg Phe His Asn Ile Arg Gly Arg Trp Thr Gly Arg Cys
225                 230                 235                 240

Met Ser Cys Cys Arg Ser Ser Arg Thr Arg Arg Glu Thr Gln Leu Gly
                245                 250                 255

Ser Gly Ala Thr Asn Phe Ser Leu Leu Lys Gln Ala Gly Asp Val Glu
                260                 265                 270

Glu Asn Pro Gly Pro Trp Leu Gln Asn Leu Leu Phe Leu Gly Ile Val
            275                 280                 285

Val Tyr Ser Leu Ser Ala Pro Thr Arg Ser Pro Ile Thr Val Thr Arg
290                 295                 300

Pro Trp Lys His Val Glu Ala Ile Lys Glu Ala Leu Asn Leu Leu Asp
305                 310                 315                 320

Asp Met Pro Val Thr Leu Asn Glu Glu Val Glu Val Val Ser Asn Glu
                325                 330                 335

Phe Ser Phe Lys Lys Leu Thr Cys Val Gln Thr Arg Leu Lys Ile Phe
                340                 345                 350

Glu Gln Gly Leu Arg Gly Asn Phe Thr Lys Leu Lys Gly Ala Leu Asn
            355                 360                 365

Met Thr Ala Ser Tyr Tyr Gln Thr Tyr Cys Pro Pro Thr Pro Glu Thr
        370                 375                 380

Asp Cys Glu Thr Gln Val Thr Thr Tyr Ala Asp Phe Ile Asp Ser Leu
385                 390                 395                 400
```

Lys Thr Phe Leu Thr Asp Ile Pro Phe Glu Cys Lys Lys Pro Val Gln
            405                 410                 415

Lys

<210> SEQ ID NO 14
<211> LENGTH: 768
<212> TYPE: DNA
<213> ORGANISM: Artificial Sequence
<220> FEATURE:
<223> OTHER INFORMATION: Nucleotide sequence encoding HPV16 E7/E6 fusion
      protein with mutations in Rb binding site and zinc finger motifs

<400> SEQUENCE: 14

```
atgcacggcg acacccctac cctgcacgag tacatgctgg acctgcagcc cgagacaacc      60
gacctgtacg gctacggcca gctgaacgac agcagcgagg aagaggacga gatcgacggc     120
cctgctggac aggccgaacc tgacagagcc cactacaaca tcgtgacatt ctgctgcaag     180
tgcgacagca ccctgagact gtgcgtgcag agcacccacg tggacatcag aaccctggaa     240
gatctgctga tgggcaccct gggcatcgtg ggcctatct gctctcagaa gccccaccag     300
aaaagaaccg ccatgttcca ggaccccag gaaagaccca gaaagctgcc ccagctgtgc     360
accgagctgc agaccaccat ccacgacatc atcctggaat gcgtgtactg caagcagcag     420
ctgctgagaa gagaggtgta cgacttcgcc ttccgggacc tgtgcatcgt gtacagggac     480
ggcaacccct acgccgtggg cgacaagtgc ctgaagttct acagcaagat cagcgagtac     540
cggcactact gctacagcct gtacggaacc accctggaac agcagtacaa caagcccctg     600
tgcgacctgc tgatcagatg catcaacggc cagaaacccc tgtgccccga ggaaaagcag     660
agacacctgg acaagaagca gcggttccac aacatcagag gcagatggac cggcagatgc     720
atgagctgtt gcagaagcag cagaaccaga cgcgagactc agctgtga               768
```

<210> SEQ ID NO 15
<211> LENGTH: 2016
<212> TYPE: DNA
<213> ORGANISM: Artificial Sequence
<220> FEATURE:
<223> OTHER INFORMATION: Nucleotide sequence encoding HPV16 E7/E6 fusion
      protein with mutations in Rb binding site and zinc finger motifs,
      linked to mouse Calreticulin

<400> SEQUENCE: 15

```
atgcacggcg acacccctac cctgcacgag tacatgctgg acctgcagcc cgagacaacc      60
gacctgtacg gctacggcca gctgaacgac agcagcgagg aagaggacga gatcgacggc     120
cctgctggac aggccgaacc tgacagagcc cactacaaca tcgtgacatt ctgctgcaag     180
tgcgacagca ccctgagact gtgcgtgcag agcacccacg tggacatcag aaccctggaa     240
gatctgctga tgggcaccct gggcatcgtg ggcctatct gctctcagaa gccccaccag     300
aaaagaaccg ccatgttcca ggaccccag gaaagaccca gaaagctgcc ccagctgtgc     360
accgagctgc agaccaccat ccacgacatc atcctggaat gcgtgtactg caagcagcag     420
ctgctgagaa gagaggtgta cgacttcgcc ttccgggacc tgtgcatcgt gtacagggac     480
ggcaacccct acgccgtggg cgacaagtgc ctgaagttct acagcaagat cagcgagtac     540
cggcactact gctacagcct gtacggaacc accctggaac agcagtacaa caagcccctg     600
tgcgacctgc tgatcagatg catcaacggc cagaaacccc tgtgccccga ggaaaagcag     660
agacacctgg acaagaagca gcggttccac aacatcagag gcagatggac cggcagatgc     720
```

| | |
|---|---|
| atgagctgtt gcagaagcag cagaaccaga agagagacac agctgctgct gtccgtgccc | 780 |
| ctgctgctgg gcctgctggg actggctgct gcagatcccg ccatctactt caaagagcag | 840 |
| ttcctggacg gcgacgcctg gaccaacaga tgggtggaaa gcaagcacaa gagcgacttc | 900 |
| ggcaagttcg tgctgagcag cggcaagttt tacggcgacc tggaaaagga caagggcctg | 960 |
| cagacaagcc aggacgccag attctacgcc ctgagcgcca agttcgagcc cttcagcaac | 1020 |
| aagggccaga ccctggtggt gcagttcacc gtgaagcacg agcagaacat cgactgcggc | 1080 |
| ggaggctacg tgaagctgtt ccctagcggc ctggatcaga agacatgca cggggactcc | 1140 |
| gagtacaaca tcatgttcgg ccccgacatc tgcggccctg gcaccaagaa agtgcacgtg | 1200 |
| atcttcaact acaagggcaa gaacgtgctg atcaacaagg acatcaggtg caaggacgac | 1260 |
| gagttcaccc cctgtacac cctgatcgtg cggcccgaca cacctacga agtgaagatc | 1320 |
| gacaacagcc aggtggaatc cggctctctg gaagatgact gggacttcct gccccccaag | 1380 |
| aagatcaagg accccgacgc cgccaagccc gaggactggg atgagagagc caagatcgac | 1440 |
| gaccccaccg acagcaagcc tgaagattgg acaagcctg agcacatccc cgacccagac | 1500 |
| gccaagaagc cagaggattg gacgaagag atggacgggg agtgggagcc ccccgtgatc | 1560 |
| cagaacccag agtacaaggg cgagtggaag cccagacaga tcgataaccc cgactataag | 1620 |
| ggcacctgga tccaccccga aatcgacaac cctgagtact cccctgacgc caacatctac | 1680 |
| gcctacgaca gcttcgccgt gctggggctg gatctgtggc aagtgaagtc cggaacaatc | 1740 |
| ttcgacaact tcctgatcac caacgacgag gcctacgccg aggaattcgg caacgagaca | 1800 |
| tggggcgtga ccaaggccgc cgagaagcag atgaaggaca gcaggatga ggaacagcgc | 1860 |
| ctgaaagagg aagaagagga taagaagcgc aaagaagagg aagaggccga ggacaaagag | 1920 |
| gacgacgacg acagggacga ggacgaggat gaagaagatg agaaagaaga ggacgaagaa | 1980 |
| gagtcccag gccaggccaa ggacgagctg tgatga | 2016 |

<210> SEQ ID NO 16
<211> LENGTH: 993
<212> TYPE: DNA
<213> ORGANISM: Artificial Sequence
<220> FEATURE:
<223> OTHER INFORMATION: Nucleotide sequence encoding HPV16 E7/E6 fusion
       protein with mutations in Rb binding site and zinc finger motifs,
       linked to mouse Ubiquitin

<400> SEQUENCE: 16

| | |
|---|---|
| atgcacggcg acacccctac cctgcacgag tacatgctgg acctgcagcc cgagacaacc | 60 |
| gacctgtacg gctacggcca gctgaacgac agcagcgagg aagaggacga gatcgacggc | 120 |
| cctgctggac aggccgaacc tgacagagcc cactacaaca tcgtgacatt ctgctgcaag | 180 |
| tgcgacagca ccctgagact gtgcgtgcag agcacccacg tggacatcag aaccctggaa | 240 |
| gatctgctga tgggcaccct gggcatcgtg ggccctatct gctctcagaa gccccaccag | 300 |
| aaaagaaccg ccatgttcca ggaccccag gaaagaccca gaaagctgcc ccagctgtgc | 360 |
| accgagctgc agaccaccat ccacgacatc atcctggaat gcgtgtactg caagcagcag | 420 |
| ctgctgagaa gagaggtgta cgacttcgcc ttccgggacc tgtgcatcgt gtacagggac | 480 |
| ggcaaccctt acgccgtggg cgacaagtgc ctgaagttct acagcaagat cagcgagtac | 540 |
| cggcactact gctacagcct gtacggaacc accctggaac agcagtacaa caagcccctg | 600 |
| tgcgacctgc tgatcagatg catcaacggc cagaaccccc tgtgccccga ggaaaagcag | 660 |
| agacacctgg acaagaagca gcggttccac aacatcagag gcagatggac cggcagatgc | 720 |

```
atgagctgtt gcagaagcag cagaaccaga agagagacac agctgcagat ctttgtgaaa      780
accctgaccg caagaccat cacactggaa gtggaaccca gcgacaccat cgagaacgtg       840
aaggccaaga tccaggacaa agagggcatc cccccgacc agcagagact gatcttcgcc       900
ggaaagcagc tggaagatgg caggaccctg agcgattaca acatccagaa agagtccacc      960
ctgcacctgg tgctgagact gagaggcgcc tga                                   993
```

<210> SEQ ID NO 17
<211> LENGTH: 1254
<212> TYPE: DNA
<213> ORGANISM: Artificial Sequence
<220> FEATURE:
<223> OTHER INFORMATION: Nucleotide sequence encoding HPV16 E7/E6 fusion
      protein with mutations in Rb binding site and zinc finger motifs,
      co-expressed with mouse GM-CSF, separated by a nucleotide sequence
      that encodes a self-cleaving peptide (2A peptide)

<400> SEQUENCE: 17

```
atgcacggcg acacccctac cctgcacgag tacatgctgg acctgcagcc cgagacaacc       60
gacctgtacg gctacggcca gctgaacgac agcagcgagg aagaggacga gatcgacggc      120
cctgctggac aggccgaacc tgacagagcc cactacaaca tcgtgacatt ctgctgcaag      180
tgcgacagca ccctgagact gtgcgtgcag agcacccacg tggacatcag aaccctggaa      240
gatctgctga tgggcaccct gggcatcgtg gccctatct gctctcagaa gccccaccag       300
aaaagaaccg ccatgttcca ggaccccag gaaagaccca gaaagctgcc ccagctgtgc      360
accgagctgc agaccaccat ccacgacatc atcctggaat gcgtgtactg caagcagcag      420
ctgctgagaa gagaggtgta cgacttcgcc ttccgggacc tgtgcatcgt gtacagggac      480 ggcaacccctt acgccgtggg cgacaagtgc ctgaagttct acagcaagat cagcgagtac      540
cggcactact gctacagcct gtacggaacc accctggaac agcagtacaa caagcccctg      600
tgcgacctgc tgatcagatg catcaacggc cagaaacccc tgtgccccga ggaaaagcag      660
agacacctgg acaagaagca gcggttccac aacatcagag gcagatggac cggcagatgc      720
atgagctgtt gcagaagcag cagaaccaga agagagactc agctgggcag cggcgccacc      780
aacttcagcc tgctgaaaca ggccggcgac gtggaagaga cccaggccc ttggctgcag       840 aacctgctgt ttctgggaat cgtggtgtac agcctgagcg cccctaccag atccccatc       900 accgtgacca gaccttggaa gcacgtggaa gccatcaaag aggccctgaa tctgctggac      960
gacatgcccg tgaccctgaa cgaagaggtg gaagtggtgt ccaacgagtt cagcttcaag     1020
aaactgacct gtgtgcagac ccggctgaag atctttgagc agggcctgag aggcaacttc     1080
accaagctga agggcgctct gaacatgacc gccagctact accagaccta ctgccccccc     1140
acccccgaga cagattgcga gacacaagtg accacctacg ccgacttcat cgacagcctg     1200
aaaaccttcc tgaccgacat ccccttcgag tgcaagaaac ccgtgcagaa gtga           1254
```

<210> SEQ ID NO 18
<211> LENGTH: 3
<212> TYPE: PRT
<213> ORGANISM: Artificial Sequence
<220> FEATURE:
<223> OTHER INFORMATION: GSG sequence

<400> SEQUENCE: 18

Gly Ser Gly
1

<210> SEQ ID NO 19
<211> LENGTH: 7115
<212> TYPE: DNA
<213> ORGANISM: Junin virus
<220> FEATURE:
<223> OTHER INFORMATION: Junin virus Candid No.1 L segment

<400> SEQUENCE: 19

| | |
|---|---:|
| gcgcaccggg gatcctaggc gtaacttcat cattaaaatc tcagattctg ctctgagtgt | 60 |
| gacttactgc gaagaggcag acaaatgggc aactgcaacg gggcatccaa gtctaaccag | 120 |
| ccagactcct caagagccac acagccagcc gcagaattta ggagggtagc tcacagcagt | 180 |
| ctatatggta gatataactg taagtgctgc tggtttgctg ataccaattt gataacctgt | 240 |
| aatgatcact acctttgttt aaggtgccat cagggtatgt taaggaattc agatctctgc | 300 |
| aatatctgct ggaagcccct gcccaccaca atcacagtac cggtggagcc aacagcacca | 360 |
| ccaccatagg cagactgcac agggtcagac ccgaccccccc gggggcccc catggggacc | 420 |
| ccccgtgggg gaaccccggg ggtgatgcgc cattagtcaa tgtctttgat ctcgactttg | 480 |
| tgcttcagtg gcctgcatgt caccccttc aatctgaact gcccttgggg atctgatatc | 540 |
| agcaggtcat ttaaagatct gctgaatgcc accttgaaat ttgagaattc caaccagtca | 600 |
| ccaaatttat caagtgaacg gatcaactgc tctttgtgta gatcataaac gaggacaaag | 660 |
| tcctcttgct gaaataatat tgtttgtgat gttgtttta gataaggcca tagttggctt | 720 |
| aataaggttt ccacactatc aatgtcctct agtgctccaa ttgccttgac tatgacatcc | 780 |
| ccagacaact caactctata tgttgacaac ctttcattac ctctgtaaaa gatacgctct | 840 |
| ttcaagacaa gaggttctcc tgggttatct ggcccaatga ggtcatatgc atacttgtta | 900 |
| cttagttcag aataaagtc accaaagttg aacttaacat ggctcagaat attgtcatca | 960 |
| tttgtcgcag cgtagcctgc atcaataaac aagccagcta ggtcaaagct ctcatggcct | 1020 |
| gtgaacaatg gtaggctagc gataaccagt gcaccatcca acaatgagtg gcttccctca | 1080 |
| gacccagaaa cacattgact cattgcatcc acattcagct ctaattcagg gtaccgaca | 1140 |
| tcatccactc ctagtgaact gacaatggtg taactgtaca ccatctttct tctaagttta | 1200 |
| aattttgtcg aaactcgtgt gtgttctact tgaatgatca attttagttt cacagcttct | 1260 |
| tggcaagcaa cattgcgcaa cacagtgtgc aggtccatca tgtcttcctg aggcaacaag | 1320 |
| gagatgttgt caacagagac accctcaagg aaaaccttga tattatcaaa gctagaaact | 1380 |
| acataaccca ttgcaatgtc ttcaacaaac attgctcttg atactttatt attcctaact | 1440 |
| gacaaggtaa aatctgtgag ttcagctaga tctacttgac tgtcatcttc tagatctaga | 1500 |
| acttcattga accaaaagaa ggatttgaga cacgatgttg acatgactag tgggtttatc | 1560 |
| atcgaagata agacaacttg caccatgaag ttcctgcaaa cttgctgtgg gctgatgcca | 1620 |
| acttcccaat ttgtatactc tgactgtcta acatgggctg aagcgcaatc actctgtttc | 1680 |
| acaatataaa cattattatc tcttactttc aataagtgac ttataatccc taagttttca | 1740 |
| ttcatcatgt ctagagccac acagacatct agaaacttga gtcttccact atccaaagat | 1800 |
| ctgttcactt gaagatcatt cataaagggt gccaaatgtt cttcaaatag tttggggtaa | 1860 |
| tttcttcgta tagaatgcaa tacatggttc atgcctaatt ggtcttctat ctgtcgtact | 1920 |
| gctttggggtt taacagccca gaagaaattc ttattacata agaccagagg ggcctgtgga | 1980 |
| ctcttaatag cagaaaacac ccactcccct aactcacagg catttgtcag caccaaagag | 2040 |
| aagtaatccc acaaaattgg tttagaaaat tggttaactt cttttaagtga ttttttgacag | 2100 |

-continued

```
taaataactt taggctttct ctcacaaatt ccacaaagac atggcattat tcgagtaaat   2160
atgtccttta tatacagaaa tccgccttta ccatccctaa cacacttact ccccatactc   2220
ttacaaaacc caatgaagcc tgaggcaaca gaagactgaa atgcagattt gttgattgac   2280
tctgccaaga tcttcttcac gccttttgtg aaatttcttg acagcctgga ctgtattgtc   2340
cttatcaatg ttggcatctc ttctttctct aacactcttc gacttgtcat gagtttggtc   2400
ctcaagacca acctcaagtc cccaaagctc gctaaattga cccatctgta gtctagagtt   2460
tgtctgattt catcttcact acacccggca tattgcagga atccggataa agcctcatcc   2520
cctcccctgc ttatcaagtt gataaggttt tcctcaaaga ttttgcctct cttaatgtca   2580
ttgaacactt cctcgcgca gttccttata acattgtct ccttatcatc agaaaaaata    2640
gcttcaattt tcctctgtag acggtaccct ctagacccat caacccagtc tttgacatct   2700
tgttcttcaa tagctccaaa cggagtctct ctgtatccag agtatctaat caattggttg   2760
actctaatgg aaatctttga cactatatga gtgctaaccc cattagcaat acattgatca   2820
caaattgtgt ctatggtctc tgacagttgt gttggagttt tacacttaac gttgtgtaga   2880
gcagcagaca caaacttggt gagtaaagga gtctcttcac ccatgacaaa aaatcttgac   2940
ttaaactcag caacaaaagt tcctatcaca ctctttgggc tgataaactt gtttaattta   3000
gaagataaga attcatggaa gcacaccatt tccagcagtt ctgtcctgtc ttgaaacttt   3060
tcatcactaa ggcaaggaat ttttataagg ctaacctggt catcgctgga ggtataagtg   3120
acaggtatca catcatacaa taagtcaagt gcataacaca gaaattgttc agtaattagc   3180
ccatataaat ctgatgtgtt gtgcaagatt ccctggccca tgtccaagac agacattata   3240
tggctgggga cctggtccct tgactgcaga tactggtgaa aaaactcttc accaacacta   3300
gtacagtcac aacccattaa acctaaagat ctcttcaatt tccctacaca gtaggcttct   3360
gcaacattaa ttggaacttc aacgacctta tgaagatgcc atttgagaat gttcattact   3420
ggttcaagat tcacctttgt tctatctctg ggattcttca attctaatgt gtacaaaaaa   3480
gaaaggaaaa gtgctgggct catagttggt ccccatttgg agtggtcata tgaacaggac   3540
aagtcaccat tgttaacagc cattttcata tcacagattg cacgttcgaa ttccttttct   3600
gaattcaagc atgtgtattt cattgaacta cccacagctt ctgagaagtc ttcaactaac   3660
ctggtcatca gctagtgtt gaggtctccc acatacagtt ctctatttga gccaacctgc    3720
tccttataac ttagtccaaa tttcaagttc cctgtatttg agctgatgct tgtgaactct   3780
gtaggagagt cgtctgaata gaaacataaa ttccgtaggg ctgcatttgt aaaataactt   3840
ttgtctagct tatcagcaat ggcttcagaa ttgctttccc tggtactaag ccgaacctca   3900
tcctttagtc tcagaacttc actggaaaag cccaatctag atctacttct atgctcataa   3960
ctacccaatt tctgatcata atgtccttga attaaaagat acttgaagca ttcaaagaat   4020
tcatcttctt ggtaggctat tgttgtcaaa tttttttaata acaaacccaa agggcagatg   4080
tcctgcggtg cttcaagaaa ataagtcaat ttaaatggag atagataaac agcatcacat   4140
aactctttat acacatcaga cctgagcaca tctggatcaa aatccttcac ctcatgcatt   4200
gacacctctg ctttaatctc tctcaacact ccaaagggg cccacaatga ctcaagagac    4260
tctcgctcat caacagatgg attttttgat ttcaacttgg tgatctcaac ttttgtcccc   4320
tcactattag ccatcttggc tagtgtcatt tgtacgtcat ttctaatacc ctcaaaggcc   4380
cttacttgat cctctgttaa actctcatac atcactgata attcttcttg attggttctg   4440
```

-continued

```
gttcttgaac cggtgctcac aagacctgtt agattttta atattaagta gtccatggaa    4500
tcaggatcaa gattatacct gccttttgtt ttaaacctct cagccatagt agaaacgcat    4560
gttgaaacaa gtttctcctt atcataaaca gaaagaatat ttccaagttc gtcgagcttg    4620
gggattacca cacttttatt gcttgacaga tccagagctg tgctagtgat gttaggcctg    4680
tagggattgc ttttcagttc acctgtaact ttaagtcttc ctctattgaa gagagaaatg    4740
cagaaggaca aaatctcttt acacactcct ggaatttgag tatctgagga agtcttagcc    4800
tctttggaaa agaatctgtc caatcctctt atcatggtgt cctcttgttc cagtgttaga    4860
ctcccactta gagggggggtt tacaacaaca caatcaaact tgactttggg ctcaataaac    4920
ttctcaaaac actttatttg atctgtcagg cgatcaggtg tctctttggt taccaagtga    4980
cacagataac taacatttaa tagatattta aaccttcttg caaagtaaag atctgcatct    5040
tccccttcac ccaaaattgt ctggaaaagt tccacagcca tcctctgaat cagcacctct    5100
gatccagaca tgcagtcgac ccttaacttt gacatcaaat ccacatgatg gatttgattt    5160
gcatatgcca tcaagaaata tcttagacct tgtaaaaatg tctggttcct tttggaaggg    5220
gaacagagta cagctaacac taacaatctt aatattggcc ttgtcattgt catgagttcg    5280
tggctaaaat ccaaccagct ggtcatttcc tcacacattt caattaacac atcctccgaa    5340
aatataggca ggaaaaatct ctttggatca cagtaaaaag agccttgttc ttccaatacc    5400
ccattgatgg atagatagat agaatagcac cttgacttct cacctgtttt ttggtaaaac    5460
aagagaccaa atgtattctt tgtcagatga atctttgta cataacactc tcttagtcta    5520
acattcccaa aatatctaga atactctctt tcattgatta acaatcggga ggaaaatgat    5580
gtcttcatcg agttgaccaa tgcaagggaa atggaggaca aaatcctaaa taatttcttc    5640
tgctcacctt ccactaagct gctgaatggc tgatgtctac agattttctc aaattccttg    5700
ttaatagtat atctcatcac tggtctgtca gaaacaagtg cctgagctaa aatcatcaag    5760
ctatccatat cagggtgttt tattagtttt tccagctgtg accagagatc ttgatgagag    5820
ttcttcaatg ttctggaaca cgcttgaacc cacttggggc tggtcatcaa tttcttcctt    5880
attagtttaa tcgcctccag aatatctaga agtctgtcat tgactaacat taacatttgt    5940
ccaacaacta ttcccgcatt tcttaacctt acaattgcat catcatgcgt tttgaaaaga    6000
tcacaaagta aattgagtaa aactaagtcc agaaacagta aagtgtttct cctggtgttg    6060
aaaactttta gacctttcac tttgttacac acggaaaggg cttgaagata cacctctct    6120
acagcatcaa tagatataga attctcatct gactggcttt ccatgttgac ttcatctatt    6180
ggatgcaatg cgatagagta gactacatcc atcaacttgt ttgcacaaaa agggcagctg    6240
ggcacatcac tgtctttgtg gcttcctaat aagatcaagt catttataag cttagctttt    6300
tgtgaaaatt tgaatttccc caactgcttg tcaaaaatct ccttcttaaa ccaaaacctt    6360
aactttatga gttcttctct tatgacagat tctctaatgt ctcctctaac cccaacaaag    6420
agggattcat ttaacctctc atcataaccc aaagaattct ttttcaagca ttcgatgttt    6480
tctaatccca agctctggtt ttttgtgttg acaaactat ggatcaatcg ctggtattct    6540
tgttcttcaa tattaatctc ttgcataaat tttgatttct ttaggatgtc gatcagcaac    6600
caccgaactc tttcaacaac ccaatcagca aggaatctat tgctgtagct agatctgcca    6660
tcaaccacag gaaccaacgt aatccctgcc cttagtaggt cggactttag gtttaagagc    6720
tttgacatgt cactcttcca ttttctctca aactcatcag gattgaccct aacaaaggtt    6780
tccaatagga tgagtgtttt ccctgtgagt ttgaagccat ccggaatgac ttttggaagg    6840
```

| | |
|---|---|
| gtgggacata gtatgccata gtcagacagg atcacatcaa caaacttctg atctgaattg | 6900 |
| atctgacagg cgtgtgcctc acaggactca agctctacta aacttgacag aagtttgaac | 6960 |
| ccttccaaca acagagagct ggggtgatgt tgagataaaa agatgtccct ttggtatgct | 7020 |
| agctcctgtc tttctggaaa atgctttcta ataaggcttt ttatttcatt tactgattcc | 7080 |
| tccatgctca agtgccgcct aggatcctcg gtgcg | 7115 |

<210> SEQ ID NO 20
<211> LENGTH: 3411
<212> TYPE: DNA
<213> ORGANISM: Junin virus
<220> FEATURE:
<223> OTHER INFORMATION: Junin virus Candid No.1 S segment

<400> SEQUENCE: 20

| | |
|---|---|
| gcgcaccggg gatcctaggc gattttggtt acgctataat tgtaactgtt ttctgtttgg | 60 |
| acaacatcaa aaacatccat tgcacaatgg ggcagttcat tagcttcatg caagaaatac | 120 |
| caacctttt gcaggaggct ctgaacattg ctcttgttgc agtcagtctc attgccatca | 180 |
| ttaagggtat agtgaacttg tacaaaagtg gtttattcca attctttgta ttcctagcgc | 240 |
| ttgcaggaag atcctgcaca gaagaagctt tcaaaatcgg actgcacact gagttccaga | 300 |
| ctgtgtcctt tcaatggtg ggtctctttt ccaacaatcc acatgaccta cctttgttgt | 360 |
| gtaccttaaa caagagccat ctttacatta aggggggcaa tgcttcattt cagatcagct | 420 |
| ttgatgatat tgcagtattg ttgccacagt atgatgttat aatacaacat ccagcagata | 480 |
| tgagctggtg ttccaaaagt gatgatcaaa tttggttgtc tcagtggttc atgaatgctg | 540 |
| tgggacatga ttggcatcta gacccaccat ttctgtgtag gaaccgtgca aagacagaag | 600 |
| gcttcatctt tcaagtcaac acctccaaga ctggtgtcaa tggaaattat gctaagaagt | 660 |
| ttaagactgg catgcatcat ttatatagag aatatcctga cccttgcttg aatggcaaac | 720 |
| tgtgcttaat gaaggcacaa cctaccagtt ggcctctcca atgtccactc gaccacgtta | 780 |
| acacattaca cttccttaca agaggtaaaa acattcaact tccaaggagg tccttgaaag | 840 |
| cattcttctc ctggtctttg acagactcat ccggcaagga taccctgga ggctattgtc | 900 |
| tagaagagtg gatgctcgta gcagccaaaa tgaagtgttt tggcaatact gctgtagcaa | 960 |
| aatgcaattt gaatcatgac tctgaattct gtgacatgtt gaggctcttt gattacaaca | 1020 |
| aaaatgctat caaaacccta aatgatgaaa ctaagaaaca agtaaatctg atggggcaga | 1080 |
| caatcaatgc cctgatatct gacaatttat tgatgaaaaa caaattagg gaactgatga | 1140 |
| gtgtccctta ctgcaattac acaaaatttt ggtatgtcaa ccacacactt tcaggacaac | 1200 |
| actcattacc aagtgctgg ttaataaaaa acaacagcta tttgaacatc tctgacttcc | 1260 |
| gtaatgactg gatattagaa agtgacttct taatttctga aatgctaagc aaagagtatt | 1320 |
| cggacaggca gggtaaaact cctttgactt tagttgacat ctgtatttgg agcacagtat | 1380 |
| tcttcacagc gtcactcttc cttcacttgg tgggtatacc ctcccacaga cacatcaggg | 1440 |
| gcgaagcatg ccctttgcca cacaggttga acagctgggg tggttgcaga tgtggtaagt | 1500 |
| accccaatct aaagaaacca acagtttggc gtagaggaca ctaagacctc ctgagggtcc | 1560 |
| ccaccagccc gggcactgcc cgggctggtg tggcccccca gtccgcggcc tggccgcgga | 1620 |
| ctggggaggc actgcttaca gtgcataggc tgccttcggg aggaacagca agctcggtgg | 1680 |
| taatagaggt gtaggttcct cctcatagag cttcccatct agcactgact gaaacattat | 1740 |

```
gcagtctagc agagcacagt gtggttcact ggaggccaac ttgaagggag tatccttttc    1800
cctctttttc ttattgacaa ccactccatt gtgatatttg cataagtgac catatttctc    1860
ccagacctgt tgatcaaact gcctggcttg ttcagatgtg agcttaacat caaccagttt    1920
aagatctctt cttccatgga ggtcaaacaa cttcctgatg tcatcggatc cttgagtagt    1980
cacaaccatg tctggaggca gcaagccgat cacgtaacta agaactcctg gcattgcatc    2040
ttctatgtcc ttcattaaga tgccgtgaga gtgtctgcta ccattttaa ccctttctc     2100
atcatgtggt tttctgaagc agtgaatgta ctgcttacct gcaggttgga ataatgccat    2160
ctcaacaggg tcagtggctg gtccttcaat gtcgagccaa agggtgttgg tggggtcgag    2220
tttccccact gcctctctga tgacagcttc ttgtatctct gtcaagttag ccaatctcaa    2280
attctgaccg ttttttccg gctgtctagg accagcaact ggtttccttg tcagatcaat     2340
acttgtgttg tcccatgacc tgcctgtgat tgtgatcta gaaccaatat aaggccaacc     2400
atcgccagaa agacaaagtt tgtacaaaag gttttcataa ggatttctat tgcctggttt    2460
ctcatcaata aacatgcctt ctcttcgttt aacctgaatg gttgatttta tgagggaaga    2520
gaagttttct ggggtgactc tgattgtttc aacatgtttt ccaccatcaa gaatagatgc    2580
tccagccttt actgcagctg aaagactgaa gttgtaacca gaaatattga tggagctttc    2640
atctttagtc acaatctgaa ggcagtcatg ttcctgagtc agtctgtcaa ggtcacttaa    2700
gtttggatac ttcacagtgt atagaagccc aagtgaggtt aaagcttgta tgacactgtt    2760
cattgtctca cctccttgaa cagtcatgca tgcaattgtc aatgcaggaa cagagccaaa    2820
ctgattgttt agctttgaag ggtctttaac atcccatatc ctcaccacac catttccccc    2880
agtcccttgc tgttgaaatc ccagtgttct caatatctct gatcttttag caagttgtga    2940
ctgggacaag ttacccatgt aaaccccctg agagcctgtc tctgctcttc ttatcttgtt    3000
ttttaatttc tcaaggtcag acgccaactc catcagttca tccctcccca gatctcccac    3060
cttgaaaact gtgtttcgtt gaacactcct catggacatg agtctgtcaa cctctttatt    3120
caggtccctc aacttgttga ggtcttcttc ccccttttta gtctttctga gtgcccgctg    3180
cacctgtgcc acttggttga agtcgatgct gtcagcaatt agcttggcgt ccttcaaaac    3240
atctgacttg acagtctgag tgaattggct caaacctctc cttaaggact gagtccatct    3300
aaagcttgga acctccttgg agtgtgccat gccagaagtt ctggtgattt tgatctagaa    3360
tagagttgct cagtgaaagt gttagacact atgcctagga tccactgtgc g             3411

<210> SEQ ID NO 21
<211> LENGTH: 1254
<212> TYPE: DNA
<213> ORGANISM: Artificial Sequence
<220> FEATURE:
<223> OTHER INFORMATION: Nucleotide sequence of HK1-E7E6-GMCSF

<400> SEQUENCE: 21
atgcacggcg acaccnctac cctgcacgag tacatgctgg acctgcagcc cgagacaacc      60
gacctgtacg gctacggcca gctgaacgac agcagcgagg aagaggacga gatcgacggc     120
cctgctggac aggccgaacc tgacagagcc cactacaaca tcgtgacatt ctgctgcaag     180
tgcgacagca ccctgagact gtgcgtgcag agcacccacg tggacatcag aaccctggaa     240
gatctgctga tgggcaccct gggcatcgtg ggcccctatct gctctcagaa gcccaccag     300
aaaagaaccg ccatgttcca ggaccccag gaaagaccca gaaagctgcc ccagctgtgc     360
accgagctgc agaccaccat ccacgacatc atcctggaat gcgtgtactg caagcagcag    420
```

```
ctgctgagaa gagaggtgta cgacttcgcc ttccgggacc tgtgcatcgt gtacagggac    480
ggcaacccct tacgccgtgg cgacaagtgc ctgaagttct acagcaagat cagcgagtac    540
cggcactact gctacagcct gtacggaacc accctggaac agcagtacaa caagcccctg    600
tgcgacctgc tgatcagatg catcaacggc agaaacccc tgtgccccga ggaaaagcag     660
agacacctgg acaagaagca gcggttccac aacatcagag gcagatggac cggcagatgc    720
atgagctgtt gcagaagcag cagaaccaga agagagactc agctgggcag cggcgccacc    780
aacttcagcc tgctgaaaca ggccggcgac gtggaagaga cccaggccc ttggctgcag     840 aacctgctgt ttctgggaat cgtggtgtac agcctgagcg cccctaccag atcccccatc    900
accgtgacca gaccttggaa gcacgtggaa gccatcaaag aggccctgaa tctgctggac    960
gacatgcccg tgaccctgaa cgaagaggtg aagtggtgt ccaacgagtt cagcttcaag    1020
aaactgacct gtgtgcagac ccggctgaag atctttgagc agggcctgag aggcaacttc    1080
accaagctga agggcgctct gaacatgacc gccagctact accagaccta ctgccccccc    1140 accccgaga cagattgcga gacacaagtg accacctacg ccgacttcat cgacagcctg    1200
aaaaccttcc tgaccgacat ccccttcgag tgcaagaaac ccgtgcagaa gtga          1254
```

<210> SEQ ID NO 22
<211> LENGTH: 417
<212> TYPE: PRT
<213> ORGANISM: Artificial Sequence
<220> FEATURE:
<223> OTHER INFORMATION: Amino acid sequence of E7E6-GMCSF antigen

<400> SEQUENCE: 22

```
Met His Gly Asp Thr Pro Thr Leu His Glu Tyr Met Leu Asp Leu Gln
1               5                   10                  15

Pro Glu Thr Thr Asp Leu Tyr Gly Tyr Gly Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Gly Pro Ile Cys Ser Gln
                85                  90                  95

Lys Pro His Gln Lys Arg Thr Ala Met Phe Gln Asp Pro Gln Glu Arg
            100                 105                 110

Pro Arg Lys Leu Pro Gln Leu Cys Thr Glu Leu Gln Thr Thr Ile His
        115                 120                 125

Asp Ile Ile Leu Glu Cys Val Tyr Cys Lys Gln Gln Leu Leu Arg Arg
    130                 135                 140

Glu Val Tyr Asp Phe Ala Phe Arg Asp Leu Cys Ile Val Tyr Arg Asp
145                 150                 155                 160

Gly Asn Pro Tyr Ala Val Gly Asp Lys Cys Leu Lys Phe Tyr Ser Lys
                165                 170                 175

Ile Ser Glu Tyr Arg His Tyr Cys Tyr Ser Leu Tyr Gly Thr Thr Leu
            180                 185                 190

Glu Gln Gln Tyr Asn Lys Pro Leu Cys Asp Leu Leu Ile Arg Cys Ile
        195                 200                 205

Asn Gly Gln Lys Pro Leu Cys Pro Glu Glu Lys Gln Arg His Leu Asp
```

```
        210                 215                 220
Lys Lys Gln Arg Phe His Asn Ile Arg Gly Arg Trp Thr Gly Arg Cys
225                 230                 235                 240

Met Ser Cys Cys Arg Ser Ser Arg Thr Arg Arg Glu Thr Gln Leu Gly
                245                 250                 255

Ser Gly Ala Thr Asn Phe Ser Leu Leu Lys Gln Ala Gly Asp Val Glu
                260                 265                 270

Glu Asn Pro Gly Pro Trp Leu Gln Asn Leu Leu Phe Leu Gly Ile Val
            275                 280                 285

Val Tyr Ser Leu Ser Ala Pro Thr Arg Ser Pro Ile Thr Val Thr Arg
        290                 295                 300

Pro Trp Lys His Val Glu Ala Ile Lys Glu Ala Leu Asn Leu Leu Asp
305                 310                 315                 320

Asp Met Pro Val Thr Leu Asn Glu Glu Val Glu Val Val Ser Asn Glu
                325                 330                 335

Phe Ser Phe Lys Lys Leu Thr Cys Val Gln Thr Arg Leu Lys Ile Phe
                340                 345                 350

Glu Gln Gly Leu Arg Gly Asn Phe Thr Lys Leu Lys Gly Ala Leu Asn
            355                 360                 365

Met Thr Ala Ser Tyr Tyr Gln Thr Tyr Cys Pro Pro Thr Pro Glu Thr
        370                 375                 380

Asp Cys Glu Thr Gln Val Thr Thr Tyr Ala Asp Phe Ile Asp Ser Leu
385                 390                 395                 400

Lys Thr Phe Leu Thr Asp Ile Pro Phe Glu Cys Lys Lys Pro Val Gln
                405                 410                 415

Lys

<210> SEQ ID NO 23
<211> LENGTH: 1680
<212> TYPE: DNA
<213> ORGANISM: Artificial Sequence
<220> FEATURE:
<223> OTHER INFORMATION: Nucleotide sequence of HK1-E7E6-VP22

<400> SEQUENCE: 23
atgcatggtg acaccccaac cctgcatgag tacatgctgg acctgcagcc agagacaaca    60
gacctgtatg ctatggcca gctgaatgac agcagtgagg aagaggatga gattgatggc   120
cctgctggac aggcagaacc tgacagagcc cactacaaca ttgtgacatt ctgctgcaag   180
tgtgacagca ccctgagact gtgtgtgcag agcacccatg tggacatcag aaccctggaa   240
gatctgctga tgggcaccct gggcattgtg gccccatct gctctcagaa gccccaccag   300
aaaagaacag ccatgttcca ggaccccag gaaagaccca gaaagctgcc ccagctgtgc   360
actgagctgc agaccaccat ccatgacatc atcctggaat gtgtgtactg caagcagcag   420
ctgctgagaa gagaggtgta tgactttgcc ttcagggacc tgtgcattgt gtacagggat   480 ggcaacccctt atgcagtggg agacaagtgc ctgaagttct acagcaagat cagtgagtac   540
aggcactact gctacagcct gtatggaacc accctggaac agcagtacaa caagcccctg   600
tgtgacctgc tgatcagatg catcaatggc cagaaacccc tgtgccctga ggaaaagcag   660
agacacctgg acaagaagca gaggttccac aacatcagag cagatggac tggcagatgc   720 atgagctgtt gcagaagcag cagaaccaga gggagactc agctgggatc aggaatgacc   780
tcaaggaggt cagtgaagtc tggtccaagg gaggttccca gagatgagta tgaggatctg   840
tactacaccc cttcttcatg catggccagt cctgacagtc ccctgacac tccagaaga    900
```

```
ggtgccctgc agacaagagc cagaccaagg ggggaggtca gatttgtcca gtatgatgag    960
tcagattatg ccctctatgg gggctcatca tctgaagatg atgaacaccc agaggtcccc   1020
aggaccagga gacctgtttc aggggctgtt ttgtcagccc cagggcctgc aagggcccct   1080 ccccccctg ctgggtcagg aggggcagga agaacaccca ccactgcccc cagggccccc    1140
agaacccaga gggtggccac caaggcccct gcagcccctg cagcagagac caccaggggc   1200
aggaaatcag cccagccaga atcagcagca ctcccagatg ccccagcatc aacagctcca   1260
accagatcca agacaccagc acaggggctg ccagaaagc tgcacttcag cacagccccc    1320
ccaaaccctg atgccccatg gaccccagg gtggcaggct tcaacaagag ggtcttctgt    1380
gctgcagttg ggaggctggc agccatgcat gccaggatgg cagctgtcca gctctgggac   1440
atgtcaagac caaggacaga tgaagacctc aatgaactcc ttggcatcac caccatcagg   1500
gtgactgtct gtgagggcaa aaacctgatt cagagggcca atgagttggt gaatccagat   1560
gtggtgcagg atgttgatgc tgccactgca actagaggga ggtctgctgc ctcaagaccc   1620
actgagagac aagagccccc agccaggtct gcttccagac ccagaaggcc agtggagtga   1680
```

<210> SEQ ID NO 24
<211> LENGTH: 559
<212> TYPE: PRT
<213> ORGANISM: Artificial Sequence
<220> FEATURE:
<223> OTHER INFORMATION: Amino acid sequence of E7E6-VP22 antigen

<400> SEQUENCE: 24

```
Met His Gly Asp Thr Pro Thr Leu His Glu Tyr Met Leu Asp Leu Gln
1               5                   10                  15

Pro Glu Thr Thr Asp Leu Tyr Gly Tyr Gly Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Gly Pro Ile Cys Ser Gln
                85                  90                  95

Lys Pro His Gln Lys Arg Thr Ala Met Phe Gln Asp Pro Gln Glu Arg
            100                 105                 110

Pro Arg Lys Leu Pro Gln Leu Cys Thr Glu Leu Gln Thr Thr Ile His
        115                 120                 125

Asp Ile Ile Leu Glu Cys Val Tyr Cys Lys Gln Gln Leu Leu Arg Arg
    130                 135                 140

Glu Val Tyr Asp Phe Ala Phe Arg Asp Leu Cys Ile Val Tyr Arg Asp
145                 150                 155                 160

Gly Asn Pro Tyr Ala Val Gly Asp Lys Cys Leu Lys Phe Tyr Ser Lys
                165                 170                 175

Ile Ser Glu Tyr Arg His Tyr Cys Tyr Ser Leu Tyr Gly Thr Thr Leu
            180                 185                 190

Glu Gln Gln Tyr Asn Lys Pro Leu Cys Asp Leu Leu Ile Arg Cys Ile
        195                 200                 205

Asn Gly Gln Lys Pro Leu Cys Pro Glu Glu Lys Gln Arg His Leu Asp
    210                 215                 220
```

Lys Lys Gln Arg Phe His Asn Ile Arg Gly Arg Trp Thr Gly Arg Cys
225                 230                 235                 240

Met Ser Cys Cys Arg Ser Ser Arg Thr Arg Glu Thr Gln Leu Gly
            245                 250                 255

Ser Gly Met Thr Ser Arg Arg Ser Val Lys Ser Gly Pro Arg Glu Val
            260                 265                 270

Pro Arg Asp Glu Tyr Glu Asp Leu Tyr Tyr Thr Pro Ser Ser Cys Met
            275                 280                 285

Ala Ser Pro Asp Ser Pro Pro Asp Thr Ser Arg Arg Gly Ala Leu Gln
            290                 295                 300

Thr Arg Ala Arg Pro Arg Gly Glu Val Arg Phe Val Gln Tyr Asp Glu
305                 310                 315                 320

Ser Asp Tyr Ala Leu Tyr Gly Gly Ser Ser Glu Asp Glu His
                325                 330                 335

Pro Glu Val Pro Arg Thr Arg Arg Pro Val Ser Gly Ala Val Leu Ser
            340                 345                 350

Ala Pro Gly Pro Ala Arg Ala Pro Pro Pro Ala Gly Ser Gly Gly
            355                 360                 365

Ala Gly Arg Thr Pro Thr Thr Ala Pro Arg Ala Pro Arg Thr Gln Arg
370                 375                 380

Val Ala Thr Lys Ala Pro Ala Ala Pro Ala Ala Glu Thr Thr Arg Gly
385                 390                 395                 400

Arg Lys Ser Ala Gln Pro Glu Ser Ala Ala Leu Pro Asp Ala Pro Ala
                405                 410                 415

Ser Thr Ala Pro Thr Arg Ser Lys Thr Pro Ala Gln Gly Leu Ala Arg
            420                 425                 430

Lys Leu His Phe Ser Thr Ala Pro Pro Asn Pro Asp Ala Pro Trp Thr
            435                 440                 445

Pro Arg Val Ala Gly Phe Asn Lys Arg Val Phe Cys Ala Ala Val Gly
450                 455                 460

Arg Leu Ala Ala Met His Ala Arg Met Ala Ala Val Gln Leu Trp Asp
465                 470                 475                 480

Met Ser Arg Pro Arg Thr Asp Glu Asp Leu Asn Glu Leu Leu Gly Ile
            485                 490                 495

Thr Thr Ile Arg Val Thr Val Cys Glu Gly Lys Asn Leu Ile Gln Arg
            500                 505                 510

Ala Asn Glu Leu Val Asn Pro Asp Val Val Gln Asp Val Asp Ala Ala
            515                 520                 525

Thr Ala Thr Arg Gly Arg Ser Ala Ala Ser Arg Pro Thr Glu Arg Pro
530                 535                 540

Arg Ala Pro Ala Arg Ser Ala Ser Arg Pro Arg Pro Val Glu
545                 550                 555

<210> SEQ ID NO 25
<211> LENGTH: 1416
<212> TYPE: DNA
<213> ORGANISM: Artificial Sequence
<220> FEATURE:
<223> OTHER INFORMATION: Nucleotide sequence of HK1-E7E6-CD40L

<400> SEQUENCE: 25
atgcatggtg acacccctac cctgcatgag tacatgctgg acctgcagcc agagacaaca    60
gacctgtatg ctatggcca gctgaatgac agcagtgagg aagaggatga gattgatggc   120
cctgctggac aggctgaacc tgacagagcc cactacaaca ttgtgacatt ctgctgcaag   180

-continued

```
tgtgacagca ccctgagact gtgtgtgcag agcacccatg tggacatcag aaccctggaa    240
gatctgctga tgggcaccct gggcattgtg ggccccatct gctctcagaa gccccaccag    300
aaaagaactg ccatgttcca ggaccccag gaaagaccca gaaagctgcc ccagctgtgc     360
acagagctgc agaccaccat ccatgacatc atcctggaat gtgtgtactg caagcagcag    420
ctgctgagaa gagaggtgta tgactttgcc ttcagggacc tgtgcatagt gtacagggat    480
ggcaacccct tatgctgtggg ggacaagtgc ctgaagttct acagcaagat cagtgagtac    540
aggcactact gctacagcct gtatggaacc accctggaac agcagtacaa caagcccctg    600
tgtgacctgc tgatcagatg catcaatggc cagaaacccc tgtgccctga ggaaaagcag    660
agacacctgg acaagaagca gaggttccac aacatcagag gcagatggac aggcagatgc    720
atgagctgtt gcagaagcag cagaaccaga gagagactc agctgaatga tgcacaggca    780
ccaaagagtg tggaagagga agtcaacctt catgaagatt ttgttttcat caaaaagctc    840
aagagatgca caaaggaga aggatctttg tccttgctga actgtgagga gatgagaagg    900
caatttgaag accttgtcaa ggacatcact ttgaacaaag aagagaaaaa agaaaacagc    960
tttgaaatgc aaagaggtga tgaggatcct caaattgcag cacatgttgt cagtgaagcc   1020
aacagcaatg cagcatctgt tctgcagtgg gccaagaaag gatattacac catgaaaagc   1080
aacttggtca tgcttgaaaa tgggaaacag ctgactgtga aaagagaagg actctattat   1140
gtctacactc aagtcacctt ctgctcaaac agggagcctt caagtcaaag accattcatt   1200
gtgggcctct ggctgaagcc cagcagtgga tctgagagaa tcttgctcaa ggcagcaaac   1260
acccacagtt cctcccagct ttgtgagcag cagtctgttc acttgggagg agtgtttgaa   1320
ttgcaagctg gtgcttctgt gtttgtcaat gtgactgaag caagccaagt gatccacaga   1380
gttggcttct catctttgg cttgctcaaa ctctga                              1416
```

<210> SEQ ID NO 26
<211> LENGTH: 471
<212> TYPE: PRT
<213> ORGANISM: Artificial Sequence
<220> FEATURE:
<223> OTHER INFORMATION: Amino acid sequence of E7E6-CD40L antigen

<400> SEQUENCE: 26

```
Met His Gly Asp Thr Pro Thr Leu His Glu Tyr Met Leu Asp Leu Gln
1               5                   10                  15

Pro Glu Thr Thr Asp Leu Tyr Gly Tyr Gly Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Gly Pro Ile Cys Ser Gln
                85                  90                  95

Lys Pro His Gln Lys Arg Thr Ala Met Phe Gln Asp Pro Gln Glu Arg
            100                 105                 110

Pro Arg Lys Leu Pro Gln Leu Cys Thr Glu Leu Gln Thr Thr Ile His
        115                 120                 125

Asp Ile Ile Leu Glu Cys Val Tyr Cys Lys Gln Gln Leu Leu Arg Arg
    130                 135                 140
```

```
Glu Val Tyr Asp Phe Ala Phe Arg Asp Leu Cys Ile Val Tyr Arg Asp
145                 150                 155                 160
Gly Asn Pro Tyr Ala Val Gly Asp Lys Cys Leu Lys Phe Tyr Ser Lys
                165                 170                 175
Ile Ser Glu Tyr Arg His Tyr Cys Tyr Ser Leu Tyr Gly Thr Thr Leu
            180                 185                 190
Glu Gln Gln Tyr Asn Lys Pro Leu Cys Asp Leu Leu Ile Arg Cys Ile
        195                 200                 205
Asn Gly Gln Lys Pro Leu Cys Pro Glu Glu Lys Gln Arg His Leu Asp
210                 215                 220
Lys Lys Gln Arg Phe His Asn Ile Arg Gly Arg Trp Thr Gly Arg Cys
225                 230                 235                 240
Met Ser Cys Cys Arg Ser Ser Arg Thr Arg Arg Glu Thr Gln Leu Asn
                245                 250                 255
Asp Ala Gln Ala Pro Lys Ser Val Glu Glu Val Asn Leu His Glu
            260                 265                 270
Asp Phe Val Phe Ile Lys Lys Leu Lys Arg Cys Asn Lys Gly Glu Gly
        275                 280                 285
Ser Leu Ser Leu Leu Asn Cys Glu Glu Met Arg Arg Gln Phe Glu Asp
290                 295                 300
Leu Val Lys Asp Ile Thr Leu Asn Lys Glu Glu Lys Lys Glu Asn Ser
305                 310                 315                 320
Phe Glu Met Gln Arg Gly Asp Glu Asp Pro Gln Ile Ala Ala His Val
                325                 330                 335
Val Ser Glu Ala Asn Ser Asn Ala Ala Ser Val Leu Gln Trp Ala Lys
            340                 345                 350
Lys Gly Tyr Tyr Thr Met Lys Ser Asn Leu Val Met Leu Glu Asn Gly
        355                 360                 365
Lys Gln Leu Thr Val Lys Arg Glu Gly Leu Tyr Tyr Val Tyr Thr Gln
370                 375                 380
Val Thr Phe Cys Ser Asn Arg Glu Pro Ser Ser Gln Arg Pro Phe Ile
385                 390                 395                 400
Val Gly Leu Trp Leu Lys Pro Ser Ser Gly Ser Glu Arg Ile Leu Leu
                405                 410                 415
Lys Ala Ala Asn Thr His Ser Ser Ser Gln Leu Cys Glu Gln Gln Ser
            420                 425                 430
Val His Leu Gly Gly Val Phe Glu Leu Gln Ala Gly Ala Ser Val Phe
        435                 440                 445
Val Asn Val Thr Glu Ala Ser Gln Val Ile His Arg Val Gly Phe Ser
450                 455                 460
Ser Phe Gly Leu Leu Lys Leu
465                 470

<210> SEQ ID NO 27
<211> LENGTH: 1464
<212> TYPE: DNA
<213> ORGANISM: Artificial Sequence
<220> FEATURE:
<223> OTHER INFORMATION: Nucleotide sequence of HK1-Flt3L-E7E6

<400> SEQUENCE: 27
atgacagtgc tggcccccagc ctggagccca aattcctccc tgttgctgct gttgctgctg        60
ctgagtcctt gcctgagggg gacacctgac tgttacttca gccacagtcc catctcctcc       120
aacttcaaag tgaagttcag agagttgact gaccacctgc tcaaagatta cccagtcact       180
```

```
gtggcagtca atcttcagga tgagaagcac tgcaaggcct tgtggagcct cttcctggcc    240
cagaggtgga ttgagcaact gaagactgtg gcagggtcaa agatgcaaac tcttctggag    300
gatgtcaaca ctgagatcca ttttgtcacc tcatgcacct ccagcccct tccagaatgt     360 ctgagatttg ccagaccaa catctcccac ctcctgaagg acacctgcac acagctgctt     420
gctctgaagc cctgcatagg gaaggcctgc agaatttct ccaggtgcct ggaggtgcag     480
tgccagccag actcctccac cctgctgccc caaggagtc ccattgccct ggaagccact     540
gagctcccag agcccaggcc caggcagctg ttgctcctgc tgctgctgct gctgcctctc     600
acactggtgc tgctggcagc tgcctggggc ctcaggtggc aaagggcaag aaggaggggg    660
gagctccacc ctggggtgcc cctcccctcc catcccatgc atggtgacac cccaaccctg    720
catgagtaca tgctggacct gcagccagag acaacagacc tgtatggcta tggccagctg    780
aatgacagca gtgaggaaga ggatgagatt gatggccctg ctggacaggc agaacctgac    840
agagcccact acaacattgt gacattctgc tgcaagtgtg acagcaccct gagactgtgt    900
gtgcagagca cccatgtgga catcagaacc ctggaagatc tgctgatggg caccctgggc    960
attgtgggcc caatctgctc tcagaagccc accagaaaaa gaacagccat gttccaggac    1020
ccccaggaaa gacccagaaa gctgcccag ctgtgcacag agctgcagac caccatccat     1080
gacatcatcc tggaatgtgt gtactgcaag cagcagctgc tgagaagaga ggtgtatgac    1140
tttgccttca gggacctgtg cattgtgtac agggatggca cccttatgc tgtggggac     1200 aagtgcctga agttctacag caagatcagt gagtacaggc actactgcta cagcctgtat    1260
ggaaccaccc tggaacagca gtacaacaag ccctgtgtg acctgctgat cagatgcatc    1320
aatggccaga accctgtg ccctgaggaa aagcagagac acctggacaa gaagcagagg      1380
ttccacaaca tcagaggcag atggacaggc agatgcatga gctgttgcag aagcagcaga    1440
accagaagag agactcagct gtga                                            1464
```

<210> SEQ ID NO 28
<211> LENGTH: 487
<212> TYPE: PRT
<213> ORGANISM: Artificial Sequence
<220> FEATURE:
<223> OTHER INFORMATION: Amino acid sequence of Flt3L-E7E6 antigen

<400> SEQUENCE: 28

```
Met Thr Val Leu Ala Pro Ala Trp Ser Pro Asn Ser Ser Leu Leu Leu
1               5                   10                  15

Leu Leu Leu Leu Ser Pro Cys Leu Arg Gly Thr Pro Asp Cys Tyr
            20                  25                  30

Phe Ser His Ser Pro Ile Ser Ser Asn Phe Lys Val Lys Phe Arg Glu
        35                  40                  45

Leu Thr Asp His Leu Leu Lys Asp Tyr Pro Val Thr Val Ala Val Asn
    50                  55                  60

Leu Gln Asp Glu Lys His Cys Lys Ala Leu Trp Ser Leu Phe Leu Ala
65                  70                  75                  80

Gln Arg Trp Ile Glu Gln Leu Lys Thr Val Ala Gly Ser Lys Met Gln
                85                  90                  95

Thr Leu Glu Asp Val Asn Thr Glu Ile His Phe Val Thr Ser Cys
            100                 105                 110

Thr Phe Gln Pro Leu Pro Glu Cys Leu Arg Phe Val Gln Thr Asn Ile
        115                 120                 125

Ser His Leu Leu Lys Asp Thr Cys Thr Gln Leu Leu Ala Leu Lys Pro
```

| | | | | | | | | | | | | | | |
|---|---|---|---|---|---|---|---|---|---|---|---|---|---|---|
| | | 130 | | | | | 135 | | | | | 140 | | |
| Cys | Ile | Gly | Lys | Ala | Cys | Gln | Asn | Phe | Ser | Arg | Cys | Leu | Glu | Val | Gln |
| 145 | | | | | 150 | | | | | 155 | | | | | 160 |
| Cys | Gln | Pro | Asp | Ser | Ser | Thr | Leu | Leu | Pro | Pro | Arg | Ser | Pro | Ile | Ala |
| | | | | 165 | | | | | 170 | | | | | 175 | |
| Leu | Glu | Ala | Thr | Glu | Leu | Pro | Glu | Pro | Arg | Pro | Arg | Gln | Leu | Leu | Leu |
| | | | 180 | | | | | 185 | | | | | 190 | | |
| Leu | Leu | Leu | Leu | Leu | Leu | Pro | Leu | Thr | Leu | Val | Leu | Leu | Ala | Ala | Ala |
| | | | | 195 | | | | | 200 | | | | | 205 | |
| Trp | Gly | Leu | Arg | Trp | Gln | Arg | Ala | Arg | Arg | Arg | Gly | Glu | Leu | His | Pro |
| | | 210 | | | | | 215 | | | | | 220 | | | |
| Gly | Val | Pro | Leu | Pro | Ser | His | Pro | Met | His | Gly | Asp | Thr | Pro | Thr | Leu |
| 225 | | | | | 230 | | | | | 235 | | | | | 240 |
| His | Glu | Tyr | Met | Leu | Asp | Leu | Gln | Pro | Glu | Thr | Thr | Asp | Leu | Tyr | Gly |
| | | | | 245 | | | | | 250 | | | | | 255 | |
| Tyr | Gly | Gln | Leu | Asn | Asp | Ser | Ser | Glu | Glu | Glu | Asp | Glu | Ile | Asp | Gly |
| | | | 260 | | | | | 265 | | | | | 270 | | |
| Pro | Ala | Gly | Gln | Ala | Glu | Pro | Asp | Arg | Ala | His | Tyr | Asn | Ile | Val | Thr |
| | | | | 275 | | | | | 280 | | | | | 285 | |
| Phe | Cys | Cys | Lys | Cys | Asp | Ser | Thr | Leu | Arg | Leu | Cys | Val | Gln | Ser | Thr |
| | | 290 | | | | | 295 | | | | | 300 | | | |
| His | Val | Asp | Ile | Arg | Thr | Leu | Glu | Asp | Leu | Leu | Met | Gly | Thr | Leu | Gly |
| 305 | | | | | 310 | | | | | 315 | | | | | 320 |
| Ile | Val | Gly | Pro | Ile | Cys | Ser | Gln | Lys | Pro | His | Gln | Lys | Arg | Thr | Ala |
| | | | | 325 | | | | | 330 | | | | | 335 | |
| Met | Phe | Gln | Asp | Pro | Gln | Glu | Arg | Pro | Arg | Lys | Leu | Pro | Gln | Leu | Cys |
| | | | 340 | | | | | 345 | | | | | 350 | | |
| Thr | Glu | Leu | Gln | Thr | Thr | Ile | His | Asp | Ile | Ile | Leu | Glu | Cys | Val | Tyr |
| | | | | 355 | | | | | 360 | | | | | 365 | |
| Cys | Lys | Gln | Gln | Leu | Leu | Arg | Arg | Glu | Val | Tyr | Asp | Phe | Ala | Phe | Arg |
| | | 370 | | | | | 375 | | | | | 380 | | | |
| Asp | Leu | Cys | Ile | Val | Tyr | Arg | Asp | Gly | Asn | Pro | Tyr | Ala | Val | Gly | Asp |
| 385 | | | | | 390 | | | | | 395 | | | | | 400 |
| Lys | Cys | Leu | Lys | Phe | Tyr | Ser | Lys | Ile | Ser | Glu | Tyr | Arg | His | Tyr | Cys |
| | | | | 405 | | | | | 410 | | | | | 415 | |
| Tyr | Ser | Leu | Tyr | Gly | Thr | Thr | Leu | Glu | Gln | Gln | Tyr | Asn | Lys | Pro | Leu |
| | | | 420 | | | | | 425 | | | | | 430 | | |
| Cys | Asp | Leu | Leu | Ile | Arg | Cys | Ile | Asn | Gly | Gln | Lys | Pro | Leu | Cys | Pro |
| | | | | 435 | | | | | 440 | | | | | 445 | |
| Glu | Glu | Lys | Gln | Arg | His | Leu | Asp | Lys | Lys | Gln | Arg | Phe | His | Asn | Ile |
| | | | | 450 | | | | | 455 | | | | | 460 | |
| Arg | Gly | Arg | Trp | Thr | Gly | Arg | Cys | Met | Ser | Cys | Cys | Arg | Ser | Ser | Arg |
| 465 | | | | | 470 | | | | | 475 | | | | | 480 |
| Thr | Arg | Arg | Glu | Thr | Gln | Leu | | | | | | | | | |
| | | | | 485 | | | | | | | | | | | |

<210> SEQ ID NO 29
<211> LENGTH: 1557
<212> TYPE: DNA
<213> ORGANISM: Artificial Sequence
<220> FEATURE:
<223> OTHER INFORMATION: Nucleotide sequence of HK1-Flt3L-E7E6shuffle

<400> SEQUENCE: 29
atgacagtgc tggcaccagc ctggagccca aattcctccc tgttgctgct gttgctgctg    60

```
ctgagtcctt gcctgagggg gacacctgac tgttacttca gccacagtcc catctcctcc    120
aacttcaaag tgaagttcag agagttgact gaccacctgc tcaaagatta cccagtcact    180
gtggctgtca atcttcagga tgagaagcac tgcaaggcct tgtggagcct cttcctggcc    240
cagagatgga tagagcaact gaagactgtg cagggtcaa agatgcaaac acttctggag    300
gatgtcaaca ctgagatcca ttttgtcacc tcatgcacct tccagcccct gccagaatgt    360
ctgagatttg tccagaccaa catctcccac ctcctgaagg acacctgcac acagctgctt    420
gctctgaagc cctgcattgg gaaggcctgc agaatttct ccaggtgcct ggaggtgcag    480
tgccagcctg actcctccac cctgctgccc caaggagtc ccatagccct ggaagccact    540
gagctcccag agcccaggcc caggcagctg ttgctcctgc tgctgctgct gctgcctctc    600
acactggtgc tgctggcagc agcctggggc ctcagatggc aaagggcaag aaggagggg    660 gagctccacc ctggggtgcc cctcccctcc catcccatgc accaaaagag aactgcaatg    720
tttcaggacc cacaggagag acccagaaag ttgccacagt tgtgcacaga gctgcaaaca    780
accatccatg acatcatttt ggaatgtgtg tactgcaagc aacagttgct gagaagagag    840
gtgtatgact ttgctttcag ggatttgtgc atagtgtaca gagatgggaa tccatatgct    900
gtctgtgaca atgtttgaa gttttattca aaaatcagtg agtacagaca catgcatgga    960
gacacaccca cattgcatga atacatgttg gatttgcaac cagagacaac tgatctctac   1020
tgttatgagc aattgaatga cagctcagag gaggaggatg aaatagatgg tccagctgga   1080
caagcagaac cagacagagc ccattacaac attgtgacct tttgttgcaa gtgtgactca   1140
acacttgaca atgtttgaa gttttattcc aaaatcagtg agtacagaca ttattgttac   1200
agtttgtatg gaacaacatt ggaacagcaa tacaacaaac cattgtgtga tttgttgatc   1260
aggtgcatca actgtcaaaa gccactgtgt cctgaagaaa agcaaagaca tctggacaaa   1320
aagcaaagat tccacaacat caggggggagg tggacaggca gatgcatgtc ttgttgcaga   1380
tcatcaagaa caagaagaga aacccagctg cattacaaca ttgtgacctt ttgttgcaag   1440
tgtgactcca ccctcaggtt gtgtgtccaa agcacacatg ttgacatcag gactttggaa   1500
gacctgttga tgggcacact tggaattgtg tgccccatct gttctcagaa accataa      1557
```

<210> SEQ ID NO 30
<211> LENGTH: 518
<212> TYPE: PRT
<213> ORGANISM: Artificial Sequence
<220> FEATURE:
<223> OTHER INFORMATION: Amino acid sequence of Flt3L-E7E6shuffle
     antigen

<400> SEQUENCE: 30

Met Thr Val Leu Ala Pro Ala Trp Ser Pro Asn Ser Ser Leu Leu Leu
1               5                   10                  15

Leu Leu Leu Leu Leu Ser Pro Cys Leu Arg Gly Thr Pro Asp Cys Tyr
            20                  25                  30

Phe Ser His Ser Pro Ile Ser Ser Asn Phe Lys Val Lys Phe Arg Glu
        35                  40                  45

Leu Thr Asp His Leu Leu Lys Asp Tyr Pro Val Thr Val Ala Val Asn
    50                  55                  60

Leu Gln Asp Glu Lys His Cys Lys Ala Leu Trp Ser Leu Phe Leu Ala
65                  70                  75                  80

Gln Arg Trp Ile Glu Gln Leu Lys Thr Val Ala Gly Ser Lys Met Gln
                85                  90                  95

```
Thr Leu Leu Glu Asp Val Asn Thr Glu Ile His Phe Val Thr Ser Cys
            100                 105                 110

Thr Phe Gln Pro Leu Pro Glu Cys Leu Arg Phe Val Gln Thr Asn Ile
            115                 120                 125

Ser His Leu Leu Lys Asp Thr Cys Thr Gln Leu Leu Ala Leu Lys Pro
        130                 135                 140

Cys Ile Gly Lys Ala Cys Gln Asn Phe Ser Arg Cys Leu Glu Val Gln
145                 150                 155                 160

Cys Gln Pro Asp Ser Ser Thr Leu Leu Pro Arg Ser Pro Ile Ala
                165                 170                 175

Leu Glu Ala Thr Glu Leu Pro Glu Pro Arg Pro Arg Gln Leu Leu Leu
            180                 185                 190

Leu Leu Leu Leu Leu Leu Pro Leu Thr Leu Val Leu Leu Ala Ala Ala
            195                 200                 205

Trp Gly Leu Arg Trp Gln Arg Ala Arg Arg Gly Glu Leu His Pro
            210                 215                 220

Gly Val Pro Leu Pro Ser His Pro Met His Gln Lys Arg Thr Ala Met
225                 230                 235                 240

Phe Gln Asp Pro Gln Glu Arg Pro Arg Lys Leu Pro Gln Leu Cys Thr
            245                 250                 255

Glu Leu Gln Thr Thr Ile His Asp Ile Ile Leu Glu Cys Val Tyr Cys
            260                 265                 270

Lys Gln Gln Leu Leu Arg Arg Glu Val Tyr Asp Phe Ala Phe Arg Asp
        275                 280                 285

Leu Cys Ile Val Tyr Arg Asp Gly Asn Pro Tyr Ala Val Cys Asp Lys
    290                 295                 300

Cys Leu Lys Phe Tyr Ser Lys Ile Ser Glu Tyr Arg His Met His Gly
305                 310                 315                 320

Asp Thr Pro Thr Leu His Glu Tyr Met Leu Asp Leu Gln Pro Glu Thr
            325                 330                 335

Thr Asp Leu Tyr Cys Tyr Glu Gln Leu Asn Asp Ser Ser Glu Glu Glu
        340                 345                 350

Asp Glu Ile Asp Gly Pro Ala Gly Gln Ala Glu Pro Asp Arg Ala His
    355                 360                 365

Tyr Asn Ile Val Thr Phe Cys Cys Lys Cys Asp Ser Thr Leu Asp Lys
370                 375                 380

Cys Leu Lys Phe Tyr Ser Lys Ile Ser Glu Tyr Arg His Tyr Cys Tyr
385                 390                 395                 400

Ser Leu Tyr Gly Thr Thr Leu Glu Gln Gln Tyr Asn Lys Pro Leu Cys
            405                 410                 415

Asp Leu Leu Ile Arg Cys Ile Asn Cys Gln Lys Pro Leu Cys Pro Glu
            420                 425                 430

Glu Lys Gln Arg His Leu Asp Lys Lys Gln Arg Phe His Asn Ile Arg
        435                 440                 445

Gly Arg Trp Thr Gly Arg Cys Met Ser Cys Cys Arg Ser Ser Arg Thr
        450                 455                 460

Arg Arg Glu Thr Gln Leu His Tyr Asn Ile Val Thr Phe Cys Cys Lys
465                 470                 475                 480

Cys Asp Ser Thr Leu Arg Leu Cys Val Gln Ser Thr His Val Asp Ile
                485                 490                 495

Arg Thr Leu Glu Asp Leu Leu Met Gly Thr Leu Gly Ile Val Cys Pro
            500                 505                 510
```

Ile Cys Ser Gln Lys Pro
        515

<210> SEQ ID NO 31
<211> LENGTH: 1440
<212> TYPE: DNA
<213> ORGANISM: Artificial Sequence
<220> FEATURE:
<223> OTHER INFORMATION: Nucleotide sequence of HK1-mli-E7E6

<400> SEQUENCE: 31

```
atggatgacc aaagggacct catctcaaac catgagcaat gcccatcct gggcaacaga      60
cctagagagc cagaaaggtg cagcagagga gctctgtaca caggtgtttc tgtcctggtg    120
gctctgctct tggctgggca ggccacaact gcttacttcc tgtaccagca cagggcaga    180
ctagacaagc tgaccatcac ctcccagaac ctgcaactgg agagcctcag gatgaagctt    240
cccaaatctg ccaaacctgt gagccagatg aggatggcca ctcccttgct gatgaggcca    300
atgtccatgg acaacatgct ccttgggcct gtgaagaatg tgaccaagta tggcaacatg    360
acccaggacc atgtgatgca tctgctcaca aggtctggac ccctggagta ccctcagctg    420
aaggggaccct tcccagagaa tctgaagcat ctgaagaact ccatggatgg agtgaactgg    480
aagatctttg agagctggat gaagcagtgg ctcttgtttg agatgagcaa gaactccctg    540
gaggagaaga gcccacaga ggctccacca aaagagccac tggacatgga agacctttct    600
tctggcctgg gagtgaccag gcaggaactg ggtcaagtca ccctgagtga caggtatttg    660
aacaggagag ccatgcatgg agacaccccca accctgcatg agtacatgct ggacctgcag    720
cctgagacaa ctgacctgta tggctatggc cagctgaatg acagcagtga ggaagaggat    780
gagattgatg gccctgctgg acaggctgaa cctgacagag cccactacaa cattgtgaca    840
ttctgctgca gtgtgacag caccctgaga ctgtgtgtgc agagcaccca tgtggacatc    900
agaacccctgg aagatctgct gatgggcacc ctgggcattg tgggcccta ctgctctcag    960
aagcccacc agaaaagaac agccatgttc caggaccccc aggaaagacc agaaagctg     1020
cccccagctgt gcacagagct gcagaccacc atccatgaca tcatcctgga atgtgtgtac    1080
tgcaagcagc agctgctgag aagagaggtg tatgactttg ccttcaggga cctgtgcatt    1140
gtgtacaggg atggcaaccc ttatgctgtg ggggacaagt gcctgaagtt ctacagcaag    1200
atcagtgagt acaggcacta ctgctacagc ctgtatggaa ccaccctgga acagcagtac    1260
aacaagcccc tgtgtgacct gctgatcaga tgcatcaatg ccagaaaccc cctgtgccct    1320
gaggaaaagc agagacacct ggacaagaag cagaggttcc acaacatcag aggcagatgg    1380
acaggcagat gcatgagctg ttgcagaagc agcagaacca aagggagac tcagctgtga    1440
```

<210> SEQ ID NO 32
<211> LENGTH: 479
<212> TYPE: PRT
<213> ORGANISM: Artificial Sequence
<220> FEATURE:
<223> OTHER INFORMATION: Amino acid sequence of mli-E7E6 antigen

<400> SEQUENCE: 32

Met Asp Asp Gln Arg Asp Leu Ile Ser Asn His Glu Gln Leu Pro Ile
1               5                   10                  15

Leu Gly Asn Arg Pro Arg Glu Pro Glu Arg Cys Ser Arg Gly Ala Leu
            20                  25                  30

Tyr Thr Gly Val Ser Val Leu Val Ala Leu Leu Leu Ala Gly Gln Ala
        35                  40                  45

```
Thr Thr Ala Tyr Phe Leu Tyr Gln Gln Gly Arg Leu Asp Lys Leu
     50                  55                  60

Thr Ile Thr Ser Gln Asn Leu Gln Leu Glu Ser Leu Arg Met Lys Leu
65                  70                  75                  80

Pro Lys Ser Ala Lys Pro Val Ser Gln Met Arg Met Ala Thr Pro Leu
                85                  90                  95

Leu Met Arg Pro Met Ser Met Asp Asn Met Leu Leu Gly Pro Val Lys
            100                 105                 110

Asn Val Thr Lys Tyr Gly Asn Met Thr Gln Asp His Val Met His Leu
        115                 120                 125

Leu Thr Arg Ser Gly Pro Leu Glu Tyr Pro Gln Leu Lys Gly Thr Phe
    130                 135                 140

Pro Glu Asn Leu Lys His Leu Lys Asn Ser Met Asp Gly Val Asn Trp
145                 150                 155                 160

Lys Ile Phe Glu Ser Trp Met Lys Gln Trp Leu Leu Phe Glu Met Ser
                165                 170                 175

Lys Asn Ser Leu Glu Glu Lys Lys Pro Thr Glu Ala Pro Pro Lys Glu
            180                 185                 190

Pro Leu Asp Met Glu Asp Leu Ser Ser Gly Leu Gly Val Thr Arg Gln
        195                 200                 205

Glu Leu Gly Gln Val Thr Leu Ser Asp Arg Tyr Leu Asn Arg Arg Ala
    210                 215                 220

Met His Gly Asp Thr Pro Thr Leu His Glu Tyr Met Leu Asp Leu Gln
225                 230                 235                 240

Pro Glu Thr Thr Asp Leu Tyr Gly Tyr Gly Gln Leu Asn Asp Ser Ser
                245                 250                 255

Glu Glu Glu Asp Glu Ile Asp Gly Pro Ala Gly Gln Ala Glu Pro Asp
            260                 265                 270

Arg Ala His Tyr Asn Ile Val Thr Phe Cys Cys Lys Cys Asp Ser Thr
        275                 280                 285

Leu Arg Leu Cys Val Gln Ser Thr His Val Asp Ile Arg Thr Leu Glu
    290                 295                 300

Asp Leu Leu Met Gly Thr Leu Gly Ile Val Gly Pro Ile Cys Ser Gln
305                 310                 315                 320

Lys Pro His Gln Lys Arg Thr Ala Met Phe Gln Asp Pro Gln Glu Arg
                325                 330                 335

Pro Arg Lys Leu Pro Gln Leu Cys Thr Glu Leu Gln Thr Thr Ile His
            340                 345                 350

Asp Ile Ile Leu Glu Cys Val Tyr Cys Lys Gln Gln Leu Leu Arg Arg
        355                 360                 365

Glu Val Tyr Asp Phe Ala Phe Arg Asp Leu Cys Ile Val Tyr Arg Asp
    370                 375                 380

Gly Asn Pro Tyr Ala Val Gly Asp Lys Cys Leu Lys Phe Tyr Ser Lys
385                 390                 395                 400

Ile Ser Glu Tyr Arg His Tyr Cys Tyr Ser Leu Tyr Gly Thr Thr Leu
                405                 410                 415

Glu Gln Gln Tyr Asn Lys Pro Leu Cys Asp Leu Leu Ile Arg Cys Ile
            420                 425                 430

Asn Gly Gln Lys Pro Leu Cys Pro Glu Glu Lys Gln Arg His Leu Asp
        435                 440                 445

Lys Lys Gln Arg Phe His Asn Ile Arg Gly Arg Trp Thr Gly Arg Cys
    450                 455                 460
```

Met Ser Cys Cys Arg Ser Ser Arg Thr Arg Arg Glu Thr Gln Leu
465                 470                 475

<210> SEQ ID NO 33
<211> LENGTH: 1287
<212> TYPE: DNA
<213> ORGANISM: Artificial Sequence
<220> FEATURE:
<223> OTHER INFORMATION: Nucleotide sequence encoding a HPV16E7-HPV18E6
      fusion protein having an N-terminal VSVG signal sequence and a
      C-terminal GSG linker followed by a self-cleaving peptide (2A
      peptide from Porcine Teschovirus) and the CDS for human GM-CSF

<400> SEQUENCE: 33
atgaaatgtc tcctctacct ggcctttctc ttcattggtg tgaattgcat gcatggggac      60 accccaccc tgcatgaata catgctggat ctgcagcctg aaaccactga tctgtatggc     120
tatggccagc tgaatgacag cagtgaagaa gaggatgaaa ttgatggccc agctggccag     180
gcagaacctg acagagctca ttacaacatt gtgaccttt gctgcaaatg tgacagcact     240
ctgaggctgt gtgtgcagag cacccatgtg acatcagaa ccctggaaga tctgctgatg     300
ggcaccctgg gcattgtgtg tcctatttgc agtcagaaac ctgccaggtt tgaagatccc     360
accaggagtg gctacaaact gccagacctg tgcacagaac tgaacaccag cctgcaggac     420
attgaaatca cctgtgtgta ttgcaaaaca gtgctggaac tgacagaagt gtttgaaaaa     480
gatctgtttg tggtgtacag agacagcatt ccccatgctg cctgccacaa atgcattgat     540
ttttacagca ggatcagaga actgagacat tacagtgaca gtgtgtatgg ggacactctg     600
gagaagctga ccaacactgg cctgtacaat ctgctgatca ggtgtctgag gtgccagaaa     660 ccctgctga ggcatctgaa tgaaaagagg aggtttcaca acattgctgg ccactacaga     720
ggtcagtgcc acagctgctg caacagagcc aggcaggaaa gactgcagag gagaagagaa     780
actcaggtgg gcagtggtgc aaccaacttc agtctgctga acaggcagg tgatgtggaa     840 gaaaatccag ccccctggct gcagagcctg cttctgctgg gcactgtggc ctgcagcatc     900
agtgccccag caaggagccc cagccccagc actcagccct gggaacatgt gaatgccatt     960
caggaggcaa ggagactgct gaacctgagc agagacactg ctgcagaaat gaatgaaact    1020
gtggaagtga tcagtgaaat gtttgatctg caggagccca cttgcctgca gaccaggctg    1080
gaactgtaca acagggcct gagaggaagc ctgaccaagc tgaaaggccc cctgaccatg    1140
atggccagcc attacaaaca gcactgccct cccacacctg aaaccagttg tgcaacccag    1200
atcatcactt ttgagagttt caaggaaaac ctgaaagatt ttctgctggt gattcccttt    1260
gactgttggg agccagtgca ggaatga                                        1287

<210> SEQ ID NO 34
<211> LENGTH: 428
<212> TYPE: PRT
<213> ORGANISM: Artificial Sequence
<220> FEATURE:
<223> OTHER INFORMATION: Amino acid sequence of a HPV16E7-HPV18E6 fusion
      protein having an N-terminal VSVG signal sequence and a C-terminal
      GSG linker followed by a self-cleaving peptide (2A peptide from
      Porcine Teschovirus) and the CDS for human GM-CSF

<400> SEQUENCE: 34

Met Lys Cys Leu Leu Tyr Leu Ala Phe Leu Phe Ile Gly Val Asn Cys
1               5                   10                  15

Met His Gly Asp Thr Pro Thr Leu His Glu Tyr Met Leu Asp Leu Gln
                20                  25                  30

```
Pro Glu Thr Thr Asp Leu Tyr Gly Tyr Gly Gln Leu Asn Asp Ser Ser
            35                  40                  45

Glu Glu Glu Asp Glu Ile Asp Gly Pro Ala Gly Gln Ala Glu Pro Asp
 50                  55                  60

Arg Ala His Tyr Asn Ile Val Thr Phe Cys Cys Lys Cys Asp Ser Thr
 65                  70                  75                  80

Leu Arg Leu Cys Val Gln Ser Thr His Val Asp Ile Arg Thr Leu Glu
                 85                  90                  95

Asp Leu Leu Met Gly Thr Leu Gly Ile Val Cys Pro Ile Cys Ser Gln
            100                 105                 110

Lys Pro Ala Arg Phe Glu Asp Pro Thr Arg Ser Gly Tyr Lys Leu Pro
            115                 120                 125

Asp Leu Cys Thr Glu Leu Asn Thr Ser Leu Gln Asp Ile Glu Ile Thr
130                 135                 140

Cys Val Tyr Cys Lys Thr Val Leu Glu Leu Thr Glu Val Phe Glu Lys
145                 150                 155                 160

Asp Leu Phe Val Val Tyr Arg Asp Ser Ile Pro His Ala Ala Cys His
                165                 170                 175

Lys Cys Ile Asp Phe Tyr Ser Arg Ile Arg Glu Leu Arg His Tyr Ser
            180                 185                 190

Asp Ser Val Tyr Gly Asp Thr Leu Glu Lys Leu Thr Asn Thr Gly Leu
            195                 200                 205

Tyr Asn Leu Leu Ile Arg Cys Leu Arg Cys Gln Lys Pro Leu Leu Arg
            210                 215                 220

His Leu Asn Glu Lys Arg Arg Phe His Asn Ile Ala Gly His Tyr Arg
225                 230                 235                 240

Gly Gln Cys His Ser Cys Cys Asn Arg Ala Arg Gln Glu Arg Leu Gln
                245                 250                 255

Arg Arg Arg Glu Thr Gln Val Gly Ser Gly Ala Thr Asn Phe Ser Leu
            260                 265                 270

Leu Lys Gln Ala Gly Asp Val Glu Glu Asn Pro Gly Pro Trp Leu Gln
            275                 280                 285

Ser Leu Leu Leu Gly Thr Val Ala Cys Ser Ile Ser Ala Pro Ala
            290                 295                 300

Arg Ser Pro Ser Pro Ser Thr Gln Pro Trp Glu His Val Asn Ala Ile
305                 310                 315                 320

Gln Glu Ala Arg Arg Leu Leu Asn Leu Ser Arg Asp Thr Ala Ala Glu
                325                 330                 335

Met Asn Glu Thr Val Glu Val Ile Ser Glu Met Phe Asp Leu Gln Glu
            340                 345                 350

Pro Thr Cys Leu Gln Thr Arg Leu Glu Leu Tyr Lys Gln Gly Leu Arg
            355                 360                 365

Gly Ser Leu Thr Lys Leu Lys Gly Pro Leu Thr Met Met Ala Ser His
370                 375                 380

Tyr Lys Gln His Cys Pro Pro Thr Pro Glu Thr Ser Cys Ala Thr Gln
385                 390                 395                 400

Ile Ile Thr Phe Glu Ser Phe Lys Glu Asn Leu Lys Asp Phe Leu Leu
                405                 410                 415

Val Ile Pro Phe Asp Cys Trp Glu Pro Val Gln Glu
            420                 425
```

<210> SEQ ID NO 35
<211> LENGTH: 1308
<212> TYPE: DNA

-continued

<213> ORGANISM: Artificial Sequence
<220> FEATURE:
<223> OTHER INFORMATION: Nucleotide sequence encoding a HPV18E7-HPV16E6
    fusion protein having an N-terminal VSVG signal sequence and a
    C-terminal GSG linker followed by a self-cleaving peptide (2A
    peptide from Porcine Teschovirus) and the CDS for human GM-CSF

<400> SEQUENCE: 35

```
atgaagtgtc tcctctacct ggcctttctc ttcatagggg tcaattgcat gcatggccct    60
aaagctaccc tgcaggatat tgtgctccat ctggaacctc agaatgaaat ccctgtggat   120
ctgctgggcc atggccagct gagtgacagt gaagaagaaa atgatgaaat tgatggagtg   180
aaccatcagc atctgccagc cagaagggca gagcctcaga ggcataccat gctgtgcatg   240
tgctgcaaat gtgaagccag aattgaactg gtggtggaaa gcagtgcaga tgacctgagg   300
gcctttcagc agctgttcct gaacaccctg agctttgtgt gcccttggtg tgccagccag   360
cagcatcaga gagaacagca atgtttcag gatccacagg aaagtggcag aagctgcct    420
cagctgtgca ctgaactgca gaccaccatc catgacatca tcctggaatg tgtgtactgc   480
aagcagcagc tgctgaggag ggaagtgtat gatagagacc tgtgcattgt gtacagggat   540
ggcaacccct atgctgtgtg tgataaatgc ctgaaatttt atagcaagat tagtgaatat   600
agacattatt gctacagcct gtatggcacc accctggaac agcagtataa caaaccactg   660
tgtgatctgc tgattaggtg cattaactgc cagaagccac tgcagaggca cctggacaag   720
aaacagaggt tccataacat taggggcagg tggacaggca gatgcatgag ctgctgcaga   780
agcagcagaa ccagaaggga aacccagctg ggcagtggag caactaactt cagcctgctg   840
aaacaggctg gggatgtgga agagaaccca ggcccatggc tgcagagcct gctgctgctg   900
ggcacagtgg catgcagcat tagtgcccct gccagaagcc ctagcccaag cacccagccc   960
tgggagcatg tgaatgctat ccaggaggcc agaagactgc tgaacctgag cagggacact  1020
gcagcagaaa tgaatgaaac tgtggaggtg attagtgaaa tgtttgacct gcaggaaccc  1080
acctgcctgc agaccagact ggaactgtat aaacaggggc tgagaggcag cctgaccaag  1140
ctgaagggcc ccctgaccat gatggcaagc cattataaac agcattgccc ccccaccccct 1200
gaaaccagct gtgccaccca gatcattacc tttgaaagct taaagaaaaa cctcaaggat  1260
tttctgctgg tgattccctt tgactgctgg gaaccagtgc aggaatga                1308
```

<210> SEQ ID NO 36
<211> LENGTH: 435
<212> TYPE: PRT
<213> ORGANISM: Artificial Sequence
<220> FEATURE:
<223> OTHER INFORMATION: Amino acid sequence of a HPV18E7-HPV16E6 fusion
    protein having an N-terminal VSVG signal sequence and a C-terminal
    GSG linker followed by a self-cleaving peptide (2A peptide from
    Porcine Teschovirus) and the CDS for human GM-CSF

<400> SEQUENCE: 36

Met Lys Cys Leu Leu Tyr Leu Ala Phe Leu Phe Ile Gly Val Asn Cys
1               5                   10                  15

Met His Gly Pro Lys Ala Thr Leu Gln Asp Ile Val Leu His Leu Glu
                20                  25                  30

Pro Gln Asn Glu Ile Pro Val Asp Leu Leu Gly His Gly Gln Leu Ser
            35                  40                  45

Asp Ser Glu Glu Glu Asn Asp Glu Ile Asp Gly Val Asn His Gln His
        50                  55                  60

Leu Pro Ala Arg Arg Ala Glu Pro Gln Arg His Thr Met Leu Cys Met

```
                65                  70                  75                  80
Cys Cys Lys Cys Glu Ala Arg Ile Glu Leu Val Val Glu Ser Ser Ala
                    85                  90                  95

Asp Asp Leu Arg Ala Phe Gln Gln Leu Phe Leu Asn Thr Leu Ser Phe
                    100                 105                 110

Val Cys Pro Trp Cys Ala Ser Gln Gln His Gln Lys Arg Thr Ala Met
                    115                 120                 125

Phe Gln Asp Pro Gln Glu Ser Gly Arg Lys Leu Pro Gln Leu Cys Thr
130                 135                 140

Glu Leu Gln Thr Thr Ile His Asp Ile Ile Leu Glu Cys Val Tyr Cys
145                 150                 155                 160

Lys Gln Gln Leu Leu Arg Arg Glu Val Tyr Asp Arg Asp Leu Cys Ile
                    165                 170                 175

Val Tyr Arg Asp Gly Asn Pro Tyr Ala Val Cys Asp Lys Cys Leu Lys
                    180                 185                 190

Phe Tyr Ser Lys Ile Ser Glu Tyr Arg His Tyr Cys Tyr Ser Leu Tyr
                    195                 200                 205

Gly Thr Thr Leu Glu Gln Gln Tyr Asn Lys Pro Leu Cys Asp Leu Leu
                    210                 215                 220

Ile Arg Cys Ile Asn Cys Gln Lys Pro Leu Gln Arg His Leu Asp Lys
225                 230                 235                 240

Lys Gln Arg Phe His Asn Ile Arg Gly Arg Trp Thr Gly Arg Cys Met
                    245                 250                 255

Ser Cys Cys Arg Ser Ser Arg Thr Arg Arg Glu Thr Gln Leu Gly Ser
                    260                 265                 270

Gly Ala Thr Asn Phe Ser Leu Leu Lys Gln Ala Gly Asp Val Glu Glu
                    275                 280                 285

Asn Pro Gly Pro Trp Leu Gln Ser Leu Leu Leu Gly Thr Val Ala
290                 295                 300

Cys Ser Ile Ser Ala Pro Ala Arg Ser Pro Ser Thr Gln Pro
305                 310                 315                 320

Trp Glu His Val Asn Ala Ile Gln Glu Ala Arg Arg Leu Leu Asn Leu
                    325                 330                 335

Ser Arg Asp Thr Ala Ala Glu Met Asn Glu Thr Val Glu Val Ile Ser
                    340                 345                 350

Glu Met Phe Asp Leu Gln Glu Pro Thr Cys Leu Gln Thr Arg Leu Glu
                    355                 360                 365

Leu Tyr Lys Gln Gly Leu Arg Gly Ser Leu Thr Lys Leu Lys Gly Pro
                    370                 375                 380

Leu Thr Met Met Ala Ser His Tyr Lys Gln His Cys Pro Pro Thr Pro
385                 390                 395                 400

Glu Thr Ser Cys Ala Thr Gln Ile Ile Thr Phe Glu Ser Phe Lys Glu
                    405                 410                 415

Asn Leu Lys Asp Phe Leu Leu Val Ile Pro Phe Asp Cys Trp Glu Pro
                    420                 425                 430

Val Gln Glu
        435

<210> SEQ ID NO 37
<211> LENGTH: 2046
<212> TYPE: DNA
<213> ORGANISM: Artificial Sequence
<220> FEATURE:
<223> OTHER INFORMATION: Nucleotide sequence encoding a
      HPV16E7-HPV18E6_HPV16E6-HPV18E7 fusion protein having an
```

-continued

N-terminal VSVG signal sequence and a C-terminal GSG linker followed by a self-cleaving peptide (2A peptide from Porcine Teschovirus) and the CDS for human GM-CSF

<400> SEQUENCE: 37

```
atgaaatgcc tcctctacct ggccttcctc ttcattggtg tcaattgcat gcatggagat     60
acccctaccc tgcatgaata tatgctggat ctgcagcctg aaaccactga cctgtatggc    120
tatggccagc tgaatgatag cagtgaggag gaagatgaga ttgatggccc tgcaggccag    180
gcagaacctg acagggcaca ttacaacatt gtgacctttt gctgcaaatg tgatagcacc    240
ctgagactct gtgtccagag cacccatgtg gatattagga ccctggaaga tctgctgatg    300
ggcaccctgg gcattgtgtg cccaatttgc agccagaagc cagctaggtt tgaagatccc    360
accagaagtg gctacaaact cccagatctc tgcacagagc tgaacaccag cctgcaggat    420
attgagatca cctgtgtgta ctgcaaaaca gtgctagaac tgacagaagt ctttgaaaag    480
gatctgtttg tggtgtatag agacagcatt cctcatgcag cctgccacaa atgcattgat    540
ttctatagca ggatcaggga actgaggcat tacagtgata gtgtgtatgg tgataccctt    600
gaaaagctga ccaacactgg cctgtacaac ctgctgatta ggtgcctgag atgccagaaa    660
ccactcctga ggcatctcaa tgaaaaaagg aggtttcata acattgcagg ccattatagg    720
ggccagtgcc atagctgctg caacagggcc aggcaggaaa gactgcagag aaggagggaa    780
acccaggtgc atcagaaaag gactgcaatg ttccaggatc cacaggaaag tggcaggaaa    840
ctgccacagc tgtgcacaga actgcagacc accatccatg atattatcct ggaatgtgtg    900
tattgcaaac agcagctcct caggagggaa gtgtatgata gggatctgtg cattgtgtat    960
agagatggca acccttatgc agtgtgtgac aaatgcctga aattttatag caaaatcagt   1020
gaatataggc actactgcta tagcctgtat ggcaccaccc tggaacagca gtacaacaaa   1080
cctctgtgtg acctgctgat taggtgcatc aactgccaga aacctctgca gaggcatctg   1140
gataaaaaac agaggtttca taacattagg gggaggtgga ctggcagatg catgagctgc   1200
tgcaggagca gcagaaccag gagggaaacc cagctgcatg gccccaaagc caccctgcag   1260
gatattgtgc tgcatctgga accacagaat gagattccag tggatctgct gggccatggc   1320
cagctcagtg atagtgaaga ggaaaatgat gaaattgatg ggtcaacca tcagcacctg    1380
ccagccagga gagcagagcc ccagagacac accatgctgt gcatgtgctg caaatgtgag   1440
gccaggattg aactggtggt ggaaagcagt gcagatgatc tgagggcctt ccagcagctg   1500
tttctgaaca ccctgagctt tgtgtgccct tggtgtgcca gccagcaggg gagtggtgca   1560
accaacttta gcctgctgaa acaggcaggt gatgtggagg aaaacccagg cccctggctg   1620
cagagcctgc tgctgctggg cacagtggca tgcagcatta gtgccccagc caggagcccc   1680
agccccagca cccagccctg ggagcatgtg aatgcaattc aggaagccag gaggctgctg   1740
aacctgagca gggatactgc agctgagatg aatgaaacag tggaggtgat tagtgagatg   1800
tttgacctcc aggaacccac ctgcctgcag accaggctgg agctctacaa acagggcctg   1860
agaggcagcc tcaccaaact gaagggccca ctgaccatga tggccagcca ttacaaacag   1920
cattgccctc ccacccctga gaccagctgt gccacccaga tcattacctt tgaaagcttt   1980
aaagaaaacc tgaaagactt cctgctggtg attccatttg actgctggga acctgtgcag   2040
gaatga                                                              2046
```

<210> SEQ ID NO 38
<211> LENGTH: 681

<212> TYPE: PRT
<213> ORGANISM: Artificial Sequence
<220> FEATURE:
<223> OTHER INFORMATION: Amino acid sequence of a
    HPV16E7-HPV18E6_HPV16E6-HPV18E7fusion protein having an N-terminal
    VSVG signal sequence and a C-terminal GSG linker followed by a
    self-cleaving peptide (2A peptide from Porcine Teschovirus) and
    the CDS  for human GM-CSF

<400> SEQUENCE: 38

| | | | | | | | | | | | | | | |
|---|---|---|---|---|---|---|---|---|---|---|---|---|---|---|
| Met | Lys | Cys | Leu | Leu | Tyr | Leu | Ala | Phe | Leu | Phe | Ile | Gly | Val | Asn | Cys |
| 1 | | | | 5 | | | | | 10 | | | | | 15 | |
| Met | His | Gly | Asp | Thr | Pro | Thr | Leu | His | Glu | Tyr | Met | Leu | Asp | Leu | Gln |
| | | | 20 | | | | | 25 | | | | | 30 | | |
| Pro | Glu | Thr | Thr | Asp | Leu | Tyr | Gly | Tyr | Gly | Gln | Leu | Asn | Asp | Ser | Ser |
| | | | 35 | | | | | 40 | | | | | 45 | | |
| Glu | Glu | Glu | Asp | Glu | Ile | Asp | Gly | Pro | Ala | Gly | Gln | Ala | Glu | Pro | Asp |
| | 50 | | | | | 55 | | | | | 60 | | | | |
| Arg | Ala | His | Tyr | Asn | Ile | Val | Thr | Phe | Cys | Cys | Lys | Cys | Asp | Ser | Thr |
| 65 | | | | | 70 | | | | | 75 | | | | | 80 |
| Leu | Arg | Leu | Cys | Val | Gln | Ser | Thr | His | Val | Asp | Ile | Arg | Thr | Leu | Glu |
| | | | | 85 | | | | | 90 | | | | | 95 | |
| Asp | Leu | Leu | Met | Gly | Thr | Leu | Gly | Ile | Val | Cys | Pro | Ile | Cys | Ser | Gln |
| | | | 100 | | | | | 105 | | | | | 110 | | |
| Lys | Pro | Ala | Arg | Phe | Glu | Asp | Pro | Thr | Arg | Ser | Gly | Tyr | Lys | Leu | Pro |
| | | | 115 | | | | | 120 | | | | | 125 | | |
| Asp | Leu | Cys | Thr | Glu | Leu | Asn | Thr | Ser | Leu | Gln | Asp | Ile | Glu | Ile | Thr |
| | 130 | | | | | 135 | | | | | 140 | | | | |
| Cys | Val | Tyr | Cys | Lys | Thr | Val | Leu | Glu | Leu | Thr | Glu | Val | Phe | Glu | Lys |
| 145 | | | | | 150 | | | | | 155 | | | | | 160 |
| Asp | Leu | Phe | Val | Val | Tyr | Arg | Asp | Ser | Ile | Pro | His | Ala | Ala | Cys | His |
| | | | | 165 | | | | | 170 | | | | | 175 | |
| Lys | Cys | Ile | Asp | Phe | Tyr | Ser | Arg | Ile | Arg | Glu | Leu | Arg | His | Tyr | Ser |
| | | | 180 | | | | | 185 | | | | | 190 | | |
| Asp | Ser | Val | Tyr | Gly | Asp | Thr | Leu | Glu | Lys | Leu | Thr | Asn | Thr | Gly | Leu |
| | | | 195 | | | | | 200 | | | | | 205 | | |
| Tyr | Asn | Leu | Leu | Ile | Arg | Cys | Leu | Arg | Cys | Gln | Lys | Pro | Leu | Leu | Arg |
| | 210 | | | | | 215 | | | | | 220 | | | | |
| His | Leu | Asn | Glu | Lys | Arg | Arg | Phe | His | Asn | Ile | Ala | Gly | His | Tyr | Arg |
| 225 | | | | | 230 | | | | | 235 | | | | | 240 |
| Gly | Gln | Cys | His | Ser | Cys | Cys | Asn | Arg | Ala | Arg | Gln | Glu | Arg | Leu | Gln |
| | | | | 245 | | | | | 250 | | | | | 255 | |
| Arg | Arg | Arg | Glu | Thr | Gln | Val | His | Gln | Lys | Arg | Thr | Ala | Met | Phe | Gln |
| | | | 260 | | | | | 265 | | | | | 270 | | |
| Asp | Pro | Gln | Glu | Ser | Gly | Arg | Lys | Leu | Pro | Gln | Leu | Cys | Thr | Glu | Leu |
| | | | 275 | | | | | 280 | | | | | 285 | | |
| Gln | Thr | Thr | Ile | His | Asp | Ile | Ile | Leu | Glu | Cys | Val | Tyr | Cys | Lys | Gln |
| | 290 | | | | | 295 | | | | | 300 | | | | |
| Gln | Leu | Leu | Arg | Arg | Glu | Val | Tyr | Asp | Arg | Asp | Leu | Cys | Ile | Val | Tyr |
| 305 | | | | | 310 | | | | | 315 | | | | | 320 |
| Arg | Asp | Gly | Asn | Pro | Tyr | Ala | Val | Cys | Asp | Lys | Cys | Leu | Lys | Phe | Tyr |
| | | | | 325 | | | | | 330 | | | | | 335 | |
| Ser | Lys | Ile | Ser | Glu | Tyr | Arg | His | Tyr | Cys | Tyr | Ser | Leu | Tyr | Gly | Thr |
| | | | 340 | | | | | 345 | | | | | 350 | | |
| Thr | Leu | Glu | Gln | Gln | Tyr | Asn | Lys | Pro | Leu | Cys | Asp | Leu | Leu | Ile | Arg |
| | | | 355 | | | | | 360 | | | | | 365 | | |

Cys Ile Asn Cys Gln Lys Pro Leu Gln Arg His Leu Asp Lys Lys Gln
            370                 375                 380

Arg Phe His Asn Ile Arg Gly Arg Trp Thr Gly Arg Cys Met Ser Cys
385                 390                 395                 400

Cys Arg Ser Ser Arg Thr Arg Arg Glu Thr Gln Leu His Gly Pro Lys
            405                 410                 415

Ala Thr Leu Gln Asp Ile Val Leu His Leu Glu Pro Gln Asn Glu Ile
            420                 425                 430

Pro Val Asp Leu Leu Gly His Gly Gln Leu Ser Asp Ser Glu Glu Glu
            435                 440                 445

Asn Asp Glu Ile Asp Gly Val Asn His Gln His Leu Pro Ala Arg Arg
            450                 455                 460

Ala Glu Pro Gln Arg His Thr Met Leu Cys Met Cys Cys Lys Cys Glu
465                 470                 475                 480

Ala Arg Ile Glu Leu Val Val Glu Ser Ser Ala Asp Asp Leu Arg Ala
            485                 490                 495

Phe Gln Gln Leu Phe Leu Asn Thr Leu Ser Phe Val Cys Pro Trp Cys
            500                 505                 510

Ala Ser Gln Gln Gly Ser Gly Ala Thr Asn Phe Ser Leu Leu Lys Gln
            515                 520                 525

Ala Gly Asp Val Glu Glu Asn Pro Gly Pro Trp Leu Gln Ser Leu Leu
            530                 535                 540

Leu Leu Gly Thr Val Ala Cys Ser Ile Ser Ala Pro Ala Arg Ser Pro
545                 550                 555                 560

Ser Pro Ser Thr Gln Pro Trp Glu His Val Asn Ala Ile Gln Glu Ala
            565                 570                 575

Arg Arg Leu Leu Asn Leu Ser Arg Asp Thr Ala Ala Glu Met Asn Glu
            580                 585                 590

Thr Val Glu Val Ile Ser Glu Met Phe Asp Leu Gln Glu Pro Thr Cys
            595                 600                 605

Leu Gln Thr Arg Leu Glu Leu Tyr Lys Gln Gly Leu Arg Gly Ser Leu
610                 615                 620

Thr Lys Leu Lys Gly Pro Leu Thr Met Met Ala Ser His Tyr Lys Gln
625                 630                 635                 640

His Cys Pro Pro Thr Pro Glu Thr Ser Cys Ala Thr Gln Ile Ile Thr
            645                 650                 655

Phe Glu Ser Phe Lys Glu Asn Leu Lys Asp Phe Leu Leu Val Ile Pro
            660                 665                 670

Phe Asp Cys Trp Glu Pro Val Gln Glu
            675                 680

<210> SEQ ID NO 39
<211> LENGTH: 2648
<212> TYPE: DNA
<213> ORGANISM: Artificial Sequence
<220> FEATURE:
<223> OTHER INFORMATION: Nucleotide sequence of a tri-segmented
      r3LCMVart-based vector expressing HPV16 E7E6 fusion protein: S
      segment 1 (containing GP)

<400> SEQUENCE: 39
gcgcaccggg gatcctaggc ttttggatt gcgctttcct ctagatcaac tgggtgtcag      60
gccctatcct acagaaggat gcacggcgac accctaccc tgcacgagta catgctggac     120
ctgcagcccg agacaaccga cctgtacggc tacggccagc tgaacgacag cagcgaggaa     180

-continued

```
gaggacgaga tcgacggccc tgctggacag gccgaacctg acagagccca ctacaacatc    240
gtgacattct gctgcaagtg cgacagcacc ctgagactgt gcgtgcagag cacccacgtg    300
gacatcagaa ccctggaaga tctgctgatg gcaccctgg gcatcgtggg ccctatctgc     360
tctcagaagc cccaccagaa aagaaccgcc atgttccagg accccagga agacccaga     420 aagctgcccc agctgtgcac cgagctgcag accaccatcc acgacatcat cctggaatgc    480
gtgtactgca agcagcagct gctgagaaga gaggtgtacg acttcgcctt ccggacctg     540 tgcatcgtgt acagggacgg caacccttac gccgtgggcg caagtgcct gaagttctac     600 agcaagatca gcgagtaccg gcactactgc tacagcctgt acggaaccac cctggaacag    660
cagtacaaca gcccctgtg cgacctgctg atcagatgca tcaacggcca gaaacccctg     720
tgccccgagg aaaagcagag acacctggac aagaagcagc ggttccacaa catcagaggc    780
agatggaccg gcagatgcat gagctgttgc agaagcagca gaaccagacg cgagactcag    840
ctgtgaagaa cagcgcctcc ctgactctcc acctcgaaag aggtggagag tcagggaggc    900
ccagagggtc ttagagtgtc acaacatttg ggcctctaaa aattaggtca tgtggcagaa    960
tgttgtgaac agttttcaga tctgggagcc ttgctttgga ggcgctttca aaaatgatgc   1020
agtccatgag tgcacagtgc ggggtgatct ctttcttctt tttgtccctt actattccag   1080
tatgcatctt acacaaccag ccatatttgt cccacacttt atcttcatac tccctcgaag   1140
cttccctggt catttcaaca tcgataagct taatgtcctt cctatttgt gagtccagaa    1200 gctttctgat gtcatcggag ccttgacagc ttagaaccat cccctgcgga agagcaccta   1260
taactgacga ggtcaacccg ggttgcgcat gaagaggtc ggcaagatcc atgccgtgtg    1320
agtacttgga atcttgcttg aattgttttt gatcaacggg ttccctgtaa agtgtatga    1380 actgcccgtt ctgtggttgg aaaattgcta tttccactgg atcattaaat ctaccctcaa   1440
tgtcaatcca tgtaggagcg ttggggtcaa ttcctcccat gaggtctttt aaaagcattg   1500
tctggctgta gcttaagccc acctgaggtg gacctgctgc tccaggcgct ggcctgggtg   1560
agttgactgc aggttctcg cttgtgagat caattgttgt gttttcccat gctctcccca    1620
caatcgatgt tctacaagct atgtatggcc atccttcacc tgaaaggcaa actttataga   1680
ggatgttttc ataagggttc ctgtcccaa cttggtctga aacaaacatg ttgagttttc    1740
tcttggcccc gagaactgcc ttcaagagat cctcgctgtt gcttggcttg atcaaaattg   1800
actctaacat gttacccca tccaacaggg ctgcccctgc cttcacggca gcaccaagac    1860
taaagttata gccagaaatg ttgatgctgg actgctgttc agtgatgacc cccagaactg   1920
ggtgcttgtc tttcagcctt tcaagatcat taagatttgg atacttgact gtgtaaagca   1980
agccaaggtc tgtgagcgct tgtacaacgt cattgagcgg agtctgtgac tgttttggcca   2040 tacaagccat agttagactt ggcattgtgc caaattgatt gttcaaaagt gatgagtctt   2100
tcacatccca aactcttacc acaccacttg caccctgctg aggctttctc atcccaacta   2160
tctgtaggat ctgagatctt tggtctagtt gctgtgttgt taagttcccc atatatacccc   2220 ctgaagcctg ggcctttca gacctcatga tcttggcctt cagcttctca aggtcagccg    2280
caagagacat cagttcttct gcactgagcc tccccacttt caaaacattc ttctttgatg   2340
ttgactttaa atccacaaga gaatgtacag tctggttgag acttctgagt ctctgtaggt    2400
ctttgtcatc tctctttttcc ttcctgatga tcctctgaac attgctgacc tcagagaagt   2460
ccaacccatt cagaaggttg gttgcatcct taatgacagc agccttcaca tctgatgtga   2520
agctctgcaa ttctcttctc aatgcttgcg tccattggaa gctcttaact tccttagaca   2580
```

```
aggacatctt gttgctcaat ggtttctcaa gacaaatgcg caatcaaatg cctaggatcc   2640
actgtgcg                                                            2648

<210> SEQ ID NO 40
<211> LENGTH: 2468
<212> TYPE: DNA
<213> ORGANISM: Artificial Sequence
<220> FEATURE:
<223> OTHER INFORMATION: Nucleotide sequence of a tri-segmented
      r3LCMVart-based vector expressing HPV16 E7E6 fusion protein: S
      segment 2 (containing GP)

<400> SEQUENCE: 40
gcgcaccggg gatcctaggc ttttttggatt gcgctttcct ctagatcaac tgggtgtcag     60
gccctatcct acagaaggat gcacggcgac accccctaccc tgcacgagta catgctggac   120
ctgcagcccg agacaaccga cctgtacggc tacggccagc tgaacgacag cagcgaggaa   180
gaggacgaga tcgacggccc tgctggacag gccgaacctg acagagccca ctacaacatc   240
gtgacattct gctgcaagtg cgacagcacc ctgagactgt gcgtgcagag cacccacgtg   300
gacatcagaa ccctggaaga tctgctgatg ggcaccctgg catcgtgggg ccctatctgc   360
tctcagaagc cccaccagaa agaaccgcc atgttccagg accccaggaa agacccaga    420 aagctgcccc agctgtgcac cgagctgcag accaccatcc acgacatcat cctggaatgc   480
gtgtactgca agcagcagct gctgagaaga gaggtgtacg acttcgcctt ccgggacctg   540
tgcatcgtgt acagggacgg caaccccttac gccgtgggcg acaagtgcct gaagttctac   600
agcaagatca gcgagtaccg gcactactgc tacagcctgt acggaaccac cctggaacag   660
cagtacaaca gcccctgtg cgacctgctg atcagatgca tcaacggcca gaaacccctg   720
tgccccgagg aaaagcagag cacctggac aagaagcagc ggttccacaa catcagaggc   780
agatggaccg gcagatgcat gagctgttgc agaagcagca gaaccagacg cgagactcag   840
ctgtgaagaa cagcgcctcc ctgactctcc acctcgaaag aggtggagag tcagggaggc   900
ccagagggtc tcagcgtctt ttccagacgg ttttttacacc aggcaccta aatgcaccac   960 aactacaaat tcctttgttg gttaatcggt gtggctttgg acatgagcca cctttatgt   1020 gcctgtgtgt tggtattttg acaaggtgca ggaagatgct gactagatat gcagatgtgg   1080
aaaacatcag aaggtccatc aatgctaggg gggtactccc ctgcctcttt atgtaatcct   1140
tcctcaacat ctctgtaatc atgttatcgg cttcctgttc gatttggtca ctgaagtggg   1200 tctcattta gtaagaacca ttggtgacaa gccagcactt ggggacacta gtttcgccgg   1260
tctttgcatg ttctaggtac caaaactttg agtaattgca atatggcacc cccatcagat   1320
ctctcaagtg gttcctcatc agtagttgat ctgaaatcaa agaattcact gttgttttga   1380
ataagtgcaa ggcagattct acgtcctctt tgaacttact caaagcagcc ttgttgtagt   1440
caattagtcg cagcatgtca cagaattctt catcatgatt tacattgcat tcgcaactg   1500 ctgtgttccc gaaacactta agctctgcag caagaatcat ccatttggtc aggcaataac   1560
cacctggatt ctccacccct gaagagtctg acaaagtcca ggtgaatgtg cccgctagtc   1620
tcctagtgga gaacttagtt ttctcttggg aaaggagaat cctggacatc ccaaaaggac   1680
ctgcatatgt gcagtggttt tcccaggttc tattttgtat aatcaggtat tggtaactcg   1740
tctggctaca ccaggtggtc ttgccatctg agctgtccca gccccagcca ctcctcatgt   1800 atttccccc gaaggcagtt ctaaacatat ctaggactct acctctgaag gttctacact   1860
```

```
ggctctgagc actttgtgca tctgagaatg tcaagttgta ttggatggtt atgccattgt    1920
tgaagtcgca ggatactgcc ttatagttgg agttccctct gatactgagg tgtaggctcg    1980
aaactatact catgagtgtg tggtcaaagg tcttttgtt gaaggcagag gtcagattgc     2040
aaaagttgtg actgatgatg aatcattgg tgaaggtcaa ttctagtcca gaagtcccca    2100
tactgatgta atggtgggag ttgttggctg aacatgcgtt gggcatggtc aggttcagat    2160
gtgacatatc aaactccact gacttaaatt ggtaaactcc tttgtaaatg tcgggtccct    2220
taagaccgta catgccacag acctgccag ccagaagtag gaaactgatc aatgcgaata    2280
tcccacaggt ggcaaaattg tagacagcct tgatacccgt gatcacgata agcacaataa    2340
tgacaatgtt gatcacctca tcgatgatgt gaggcagagc ctcaaacatt gtcacaatct    2400
gacccatctt gttgctcaat ggtttctcaa gacaaatgcg caatcaaatg cctaggatcc    2460
actgtgcg                                                              2468

<210> SEQ ID NO 41
<211> LENGTH: 7229
<212> TYPE: DNA
<213> ORGANISM: Artificial Sequence
<220> FEATURE:
<223> OTHER INFORMATION: Nucleotide sequence of a tri-segmented
      r3LCMVart-based vector expressing HPV16 E7E6 fusion protein: L
      segment

<400> SEQUENCE: 41
gcgcaccggg gatcctaggc gtttagttgc gctgtttggt tgcacaactt tcttcgtgag      60
gctgtcagaa gtggacctgg ctgatagcga tgggtcaagg caagtccaga gaggagaaag     120
gcaccaatag tacaaacagg gccgaaatcc taccagatac cacctatctt ggccctttaa     180
gctgcaaatc ttgctggcag aaatttgaca gcttggtaag atgccatgac cactacctt     240 gcaggcactg tttaaacctt ctgctgtcag tatccgacag gtgtcctctt tgtaaatatc     300
cattaccaac cagattgaag atatcaacag ccccaagctc tccacctccc tacgaagagt     360
aacaccgtcc ggccccggcc ccgacaaaca gcccagcaca agggaaccgc acgtcaccca     420
acgcacacag acacagcacc caacacagaa cacgcacaca cacacacaca cacccaca      480 cgcacgcgcc cccaccaccg gggggcgccc cccccgggg ggcggccccc cgggagcccg      540
ggcggagccc cacggagatg cccatcagtc gatgtcctcg gccaccgacc cgcccagcca     600
atcgtcgcag gacctcccct tgagtctaaa cctgccccc actgtttcat acatcaaagt     660
gctcctagat ttgctaaaac aaagtctgca atccttaaag gcgaaccagt ctggcaaaag     720
cgacagtgga atcagcagaa tagatctgtc tatacatagt tcctggagga ttacacttat     780
ctctgaaccc aacaaatgtt caccagttct gaatcgatgc aggaagaggt tcccaaggac     840
atcactaatc tttttcatagc cctcaagtcc tgctagaaag actttcatgt ccttggtctc     900
cagcttcaca atgatatttt ggacaaggtt tcttccttca aaagggcac ccatctttac       960 agtcagtggc acaggctccc actcaggtcc aactctctca aagtcaatag atctaatccc    1020
atccagtatt cttttggagc ccaacaactc aagctcaaga gaatcaccaa gtatcaaggg    1080
atcttccatg taatcctcaa acttcttcaga tctgatatca aagacaccat cgttcacctt    1140
gaagacagag tctgtcctca gtaagtggag gcattcatcc aacattcttc tatctatctc    1200
accctttaag gaggtgagag catgataaag ttcagccaca cctggattct gtaattggca    1260
cctaaccaag aatatcaatg aaaatttcct taaacagtca gtattattct gattgtgcgt    1320
aaagtccact gaaattgaaa actccaatac ccctttgtg tagttgagca tgtagtccca    1380
```

```
cagatccttt aaggatttaa atgcctttgg gtttgtcagg ccctgcctaa tcaacatggc   1440
agcattacac acaacatctc ccattcggta agagaaccac ccaaaaccaa actgcaaatc   1500
attcctaaac ataggcctct ccacatttt gttcaccacc tttgagacaa atgattgaaa    1560
ggggcccagt gcctcagcac catcttcaga tggcatcatt tctttatgag ggaaccatga   1620
aaaattgcct aatgtcctgg ttgttgcaac aaattctcga acaaatgatt caaaatacac   1680
ctgttttaag aagttcttgc agacatccct cgtgctaaca acaaattcat caaccagact   1740
ggagtcagat cgctgatgag aattggcaag gtcagaaaac agaacagtgt aatgttcatc   1800 cctttccac ttaacaacat gagaaatgag tgacaaggat tctgagttaa tatcaattaa    1860
aacacagagg tcaaggaatt taattctggg actccacctc atgtttttg agctcatgtc    1920 agacataaat ggaagaagct gatcctcaaa gatcttggga tatagccgcc tcacagattg   1980
aatcacttgg ttcaaattca ctttgtcctc cagtagcctt gagctctcag gctttcttgc   2040
tacataatca catgggttta agtgcttaag agttaggttc tcactgttat tcttcccttt   2100
ggtcggttct gctaggaccc aaacacccaa ctcaaaagag ttgctcaatg aaatacaaat   2160
gtagtcccaa agaagaggcc ttaaaaggca tatatgatca cggtgggctt ctggatgaga   2220
ctgtttgtca caaatgtaca gcgttatacc atcccgattg caaactcttg tcacatgatc   2280
atctgtggtt agatcctcaa gcagcttttt gatatacaga ttttccctat ttttgtttct   2340
cacacacctg cttcctagag ttttgcaaag gcctataaag ccagatgaga tacaactctg   2400
gaaagctgac ttgttgattg cttctgacag cagcttctgt gcaccccttg tgaatttact   2460
acaaagtttg ttctggagtg tcttgatcaa tgatgggatt ctttcctctt ggaaagtcat   2520
cactgatgga taaccacct tttgtcttaa aaccatcctt aatgggaaca tttcattcaa    2580
attcaaccag ttaacatctg ctaactgatt cagatcttct tcaagaccga ggaggtctcc   2640
caattgaaga atggcctcct ttttatctct gttaaatagg tctaagaaaa attcttcatt   2700
aaattcacca ttttttgagct tatgatgcag tttccttaca agctttctta caacctttgt   2760
ttcattagga cacagttcct caatgagtct ttgtattctg taacctctag aaccatccag   2820
ccaatctttc acatcagtgt tggtattcag tagaaatgga tccaaaggga aattggcata   2880
ctttaggagg tccagtgttc tccttttggat actattaact agggagactg ggacgccatt   2940
tgcgatggct tgatctgcaa ttgtatctat tgtttcacaa agttgatgtg gctctttaca   3000
cttgacattg tgtagcgctg cagatacaaa cttttgtgaga agagggactt cctcccccca   3060
tacatagaat ctagatttaa attctgcagc gaacctccca gccacacttt ttgggctgat   3120
aaatttgttt aacaagccgc tcagatgaga ttggaattcc aacaggacaa ggacttcctc   3180
cggatcactt acaaccaggt cactcagcct cctatcaaat aaagtgatct gatcatcact   3240
tgatgtgtaa gcctctggtc tttcgccaaa gataacacca atgcagtagt tgatgaacct   3300
ctcgctaagc aaaccataga agtcagaagc attatgcaag attccctgcc ccatatcaat   3360
aaggctggat atatgggatg gcactatccc catttcaaaa tattgtctga aaattctctc   3420
agtaacagtt gtttctgaac ccctgagaag ttttagcttc gacttgacat atgatttcat   3480
cattgcattc acaacaggaa aggggacctc gacaagctta tgcatgtgcc aagttaacaa   3540
agtgctaaca tgatctttcc cggaacgcac atactggtca tcacctagtt tgagattttg   3600
tagaaacatt aagaacaaaa atgggcacat cattggtccc catttgctgt gatccatact   3660
atagtttaag aacccttccc gcacattgat agtcattgac aagattgcat tttcaaattc   3720
```

```
cttatcattg tttaaacagg agcctgaaaa gaaacttgaa aaagactcaa aataatcttc    3780
tattaacctt gtgaacattt ttgtcctcaa atctccaata tagagttctc tatttcccc     3840 aacctgctct ttataagata gtgcaaattt cagccttcca gagtcaggac ctactgaggt    3900
gtatgatgtt ggtgattctt ctgagtagaa gcacagattt ttcaaagcag cactcataca    3960
ttgtgtcaac gacagagctt tactaaggga ctcagaatta ctttccctct cactgattct    4020
cacgtcttct tccagtttgt cccagtcaaa tttgaaattc aagccttgcc tttgcatatg    4080
cctgtatttc cctgagtacg catttgcatt catttgcaac agaatcatct tcatgcaaga    4140
aaaccaatca ttctcagaaa agaactttct acaaaggttt tttgccatct catcgaggcc    4200
acactgatct ttaatgactg aggtgaaata caaaggtgac agctctgtgg aaccctcaac    4260
agcctcacag ataaatttca tgtcatcatt ggttagacat gatgggtcaa agtcttctac    4320
taaatggaaa gatatttctg acaagataac ttttcttaag tgagccatct tccctgttag    4380
aataagctgt aaatgatgta gtccttttgt atttgtaagt ttttctccat ctcctttgtc    4440 attgccctc ctacctcttc tgtaccgtgc tattgtggtg ttgaccttt cttcgagact      4500 tttgaagaag cttgtctctt cttctccatc aaaacatatt tctgccaggt tgtcttccga    4560
tctccctgtc tcttctccct tggaaccgat gaccaatcta gagactaact tggaaacttt    4620
atattcatag tctgagtggc tcaacttata cttttgtttt cttacgaaac tctccgtaat    4680
ttgactcaca gcactaacaa gcaatttgtt aaagtcatat tccagaagtc gttctccatt    4740
tagatgctta ttaaccacca cacttttgtt actagcaaga tctaatgctg tcgcacatcc    4800
agagttagtc atgggatcta ggctgtttag cttcttctct cctttgaaaa ttaaagtgcc    4860
gttgttaaat gaagacacca ttaggctaaa ggcttccaga ttaacacctg gagttgtatg    4920
ctgacagtca atttctttac tagtgaatct cttcatttgc tcatagaaca cacattcttc    4980
ctcaggagtg attgcttcct tggggttgac aaaaaaacca aattgacttt tgggctcaaa    5040
gaacttttca aaacatttta tctgatctgt tagcctgtca ggggtctcct ttgtgatcaa    5100
atgacacagg tatgacacat tcaacataaa tttaaatttt gcactcaaca acaccttctc    5160
accagtacca aaaatagttt ttattaggaa tctaagcagc ttatacacca ccttctcagc    5220
aggtgtgatc agatcctccc tcaacttatc cattaatgat gtagatgaaa aatctgacac    5280
tattgccatc accaaaatatc tgacactctg tacctgcttt tgatttctct ttgttgggtt    5340
ggtgagcatt agcaacaata gggtcctcag tgcaacctca atgtcggtga gacagtcttt    5400
caaatcagga catgatctaa tccatgaaat catgatgtct atcatattgt ataagacctc    5460
atctgaaaaa attggtaaaa agaaccttt aggatctgca tagaaggaaa ttaaatgacc     5520
atccgggcct tgtatggagt agcaccttga agattctcca gtcttctggt ataataggtg    5580
gtattcttca gagtccagtt ttattacttg gcaaacact tctttgcatt ctaccacttg      5640
atatctcaca gacccattt gattttgcct tagtctagca actgagctag ttttcatact      5700
gtttgttaag gccagacaaa cagatgataa tcttctcagg ctctgtatgt tcttcagctg    5760
ctctgtgctg ggttggaaat tgtaatcttc aaacttcgta taatacatta tcgggtgagc    5820
tccaattttc ataagttct caattcagt gaatggtatg tggcattctt gctcaaggtg        5880
ttcagacagt ccgtaatgct cgaaactcag tcccaccact aacaggcatt tttgaatttt    5940
tgcaatgaac tcactaatag atgccctaaa caattcctca aaagacacct ttctaaacac    6000
ctttgacttt tttctattcc tcaaaagtct aatgaactcc tctttagtgc tgtgaaagct    6060
taccagccta tcattcacac tactatagca acaacccacc cagtgtttat catttttta    6120
```

```
cccctttgaat tcgactgtt ttatcaatga ggaaagacac aaaacatcca gatttaacaa     6180
ctgtctcctt ctagtattca acagtttcaa actcttgact ttgtttaaca tagagaggag     6240
cctctcatat tcagtgctag tctcacttcc cctttcgtgc ccatgggtct ctgcagttat     6300
gaatctcatc aaaggacagg attcgactgc ctccctgctt aatgttaaga tatcatcact     6360
atcagcaagg ttttcataga gctcagagaa ttccttgatc aagccttcag ggtttacttt     6420
ctgaaagttt ctctttaatt tcccactttc taaatctctt ctaaacctgc tgaaaagaga     6480
gtttattcca aaaccacat catcacagct catgttgggg ttgatgcctt cgtggcacat      6540
cctcataatt tcatcattgt gagttgacct cgcatctttc agaattttca tagagtccat     6600
accggagcgc ttgtcgatag tagtcttcag ggactcacag agtctaaaat attcagactc     6660
ttcaaagact ttctcatttt ggttagaata ctccaaaagt ttgaataaaa ggtctctaaa     6720
tttgaagttt gcccactctg gcataaaact attatcataa tcacaacgac catctactat     6780
tggaactaat gtgacacccg caacagcaag gtcttccctg atgcatgcca atttgttagt     6840
gtcctctata aatttcttct caaaactggc tggagtgctc ctaacaaaac actcaagaag     6900
aatgagagaa ttgtctatca gcttgtaacc atcaggaatg ataagtggta gtcctgggca     6960
tacaattcca gactccacca aaattgtttc cacagactta tcgtcgtggt tgtgtgtgca     7020
gccactcttg tctgcactgt ctatttcaat gcagcgtgac agcaacttga gtccctcaat     7080
cagaaccatt ctgggttccc tttgtcccag aaagttgagt ttctgccttg acaacctctc     7140
atcctgttct atatagttta aacataactc tctcaattct gagatgattt catccattgc     7200
gcatcaaaaa gcctaggatc ctcggtgcg                                      7229

<210> SEQ ID NO 42
<211> LENGTH: 2721
<212> TYPE: DNA
<213> ORGANISM: Artificial Sequence
<220> FEATURE:
<223> OTHER INFORMATION: Nucleotide sequence of a tri-segmented
      r3JUNVart-based vector expressing the HPV16 E7E6 fusion protein: S
      segment 1 (containing NP)

<400> SEQUENCE: 42
gcgcaccggg gatcctaggc gattttggtt acgctataat tgtaactgtt ttctgtttgg      60
acaacatcaa aaacatccat tgcacaatgc acggcgacac ccctaccctg cacgagtaca     120
tgctggacct gcagcccgag acaaccgacc tgtacggcta cggccagctg aacgacagca     180
gcgaggaaga ggacgagatc gacggccctg ctggacaggc cgaacctgac agagcccact     240
acaacatcgt gacattctgc tgcaagtgcg acagcaccct gagactgtgc gtgcagagca     300
cccacgtgga catcagaacc ctggaagatc tgctgatggg cacctgggc atcgtgggcc      360 ctatctgctc tcagaagccc accagaaaa gaaccgccat gttccaggac cccaggaaa      420 gacccagaaa gctgccccag ctgtgcaccg agctgcagac caccatccac gacatcatcc     480
tggaatgcgt gtactgcaag cagcagctgc tgagaagaga ggtgtacgac ttcgccttcc     540
gggacctgtg catcgtgtac agggacggca acccttacgc cgtgggcgac aagtgcctga     600
agttctacag caagatcagc gagtaccggc actactgcta cagcctgtac ggaaccaccc     660
tggaacagca gtacaacaag ccctgtgcg acctgctgat cagatgcatc aacggccaga     720 aaccctgtg ccccgaggaa aagcagagac acctggacaa gaagcagcgg ttccacaaca     780
tcagaggcag atggaccggc agatgcatga gctgttgcag aagcagcaga accagacgcg     840
```

| | |
|---|---|
| agactcagct gtgagacctc ctgagggtcc ccaccagccc gggcactgcc cgggctggtg | 900 |
| tggcccccca gtccgcggcc tggccgcgga ctggggaggc actgcttaca gtgcataggc | 960 |
| tgccttcggg aggaacagca agctcggtgg taatagaggt gtaggttcct cctcatagag | 1020 |
| cttcccatct agcactgact gaaacattat gcagtctagc agagcacagt gtggttcact | 1080 |
| ggaggccaac ttgaagggag tatccttttc cctcttttc ttattgacaa ccactccatt | 1140 |
| gtgatatttg cataagtgac catatttctc ccagacctgt tgatcaaact gcctggcttg | 1200 |
| ttcagatgtg agcttaacat caaccagttt aagatctctt cttccatgga ggtcaaacaa | 1260 |
| cttcctgatg tcatcggatc cttgagtagt cacaaccatg tctggaggca gcaagccgat | 1320 |
| cacgtaacta agaactcctg gcattgcatc ttctatgtcc ttcattaaga tgccgtgaga | 1380 |
| gtgtctgcta ccattttaa acccttctc atcatgtggt tttctgaagc agtgaatgta | 1440 |
| ctgcttacct gcaggttgga ataatgccat ctcaacaggg tcagtggctg gtccttcaat | 1500 |
| gtcgagccaa agggtgttgg tggggtcgag tttccccact gcctctctga tgacagcttc | 1560 |
| ttgtatctct gtcaagttag ccaatctcaa attctgaccg ttttttccg gctgtctagg | 1620 |
| accagcaact ggtttccttg tcagatcaat acttgtgttg tcccatgacc tgcctgtgat | 1680 |
| ttgtgatcta gaaccaatat aaggccaacc atcgccagaa agacaaagtt tgtacaaaag | 1740 |
| gttttcataa ggatttctat tgcctggttt ctcatcaata aacatgcctt ctcttcgttt | 1800 |
| aacctgaatg gttgatttta tgagggaaga gaagttttct ggggtgactc tgattgtttc | 1860 |
| caacatgttt ccaccatcaa gaatagatgc tccagccttt actgcagctg aaagactgaa | 1920 |
| gttgtaacca gaaatattga tggagctttc atctttagtc acaatctgaa ggcagtcatg | 1980 |
| ttcctgagtc agtctgtcaa ggtcacttaa gtttggatac ttcacagtgt atagaagccc | 2040 |
| aagtgaggtt aaagcttgta tgacactgtt cattgtctca cctccttgaa cagtcatgca | 2100 |
| tgcaattgtc aatgcaggaa cagagccaaa ctgattgttt agctttgaag ggtctttaac | 2160 |
| atcccatatc ctcaccacac catttccccc agtcccttgc tgttgaaatc ccagtgttct | 2220 |
| caatatctct gatcttttag caagttgtga ctgggacaag ttacccatgt aaaccccctg | 2280 |
| agagcctgtc tctgctcttc ttatcttgtt ttttaatttc tcaaggtcag acgccaactc | 2340 |
| catcagttca tccctcccca gatctcccac cttgaaaact gtgtttcgtt gaacactcct | 2400 |
| catggacatg agtctgtcaa cctctttatt caggtccctc aacttgttga gatcttcttc | 2460 |
| cccctttta gtctttctga gtgcccgctg cacctgtgcc acttggttga agtcgatgct | 2520 |
| gtcagcaatt agcttggcgt ccttcaaaac atctgacttg acagtctgag tgaattggct | 2580 |
| caaacctctc cttaaggact gagtccatct aaagcttgga acctccttgg agtgtgccat | 2640 |
| gccagaagtt ctggtgattt tgatctagaa tagagttgct cagtgaaagt gttagacact | 2700 |
| atgcctagga tccactgtgc g | 2721 |

<210> SEQ ID NO 43
<211> LENGTH: 2485
<212> TYPE: DNA
<213> ORGANISM: Artificial Sequence
<220> FEATURE:
<223> OTHER INFORMATION: Nucleotide sequence of a tri-segmented
      r3JUNVart-based vector expressing the HPV16 E7E6 fusion protein: S
      segment 2 (containing GP)

<400> SEQUENCE: 43

| | |
|---|---|
| gcgcaccggg gatcctaggc gattttggtt acgctataat tgtaactgtt ttctgtttgg | 60 |
| acaacatcaa aaacatccat tgcacaatgc acggcgacac ccctaccctg cacgagtaca | 120 |

```
tgctggacct gcagcccgag acaaccgacc tgtacggcta cggccagctg aacgacagca      180
gcgaggaaga ggacgagatc gacggccctg ctggacaggc cgaacctgac agagcccact      240
acaacatcgt gacattctgc tgcaagtgcg acagcaccct gagactgtgc gtgcagagca      300
cccacgtgga catcagaacc ctggaagatc tgctgatggg caccctgggc atcgtgggcc      360
ctatctgctc tcagaagccc caccagaaaa gaaccgccat gttccaggac ccccaggaaa      420
gacccagaaa gctgccccag ctgtgcaccg agctgcagac caccatccac gacatcatcc      480
tggaatgcgt gtactgcaag cagcagctgc tgagaagaga ggtgtacgac ttcgccttcc      540
gggacctgtg catcgtgtac agggacggca acccttacgc cgtgggcgac aagtgcctga      600
agttctacag caagatcagc gagtaccggc actactgcta cagcctgtac ggaaccaccc      660
tggaacagca gtacaacaag cccctgtgcg acctgctgat cagatgcatc aacgccaga       720 aaccctgtg ccccgaggaa aagcagagac acctggacaa gaagcagcgg ttccacaaca       780
tcagaggcag atggaccggc agatgcatga gctgttgcag aagcagcaga accagacgcg      840
agactcagct gtgagacctc ctgagggtcc ccaccagccc gggcactgcc cgggctggtg      900
tggcccccca gtccgcggcc tggccgcgga ctggggaggc actgcttagt gtcctctacg      960
ccaaactgtt ggtttcttta gattggggta cttaccacat ctgcaaccac ccaagctgtt     1020
caacctgtgt ggcaaagggc atgcttcgcc cctgatgtgt ctgtgggagg gtatacccac     1080
caagtgaagg aagagtgacg ctgtgaagaa tactgtgctc caaatacaga tgtcaactaa     1140
agtcaaagga gttttaccct gcctgtccga atactctttg cttagcattt cagaaattaa     1200
gaagtcactt tctaatatcc agtcattacg gaagtcagag atgttcaaat agctgttgtt     1260
ttttattaac cagcaccttg gtaatgagtg ttgtcctgaa agtgtgtggt tgacatacca     1320
aaattttgtg taattgcagt aagggacact catcagttcc ctaattttgt ttttcatcaa     1380
taaattgtca gatatcaggg cattgattgt ctgccccatc agatttactt gtttcttagt     1440
ttcatcattt agggttttga tagcattttt gttgtaatca aagagcctca acatgtcaca     1500
gaattcagag tcatgattca aattgcattt tgctacagca gtattgccaa acacttcat      1560 tttggctgct acgagcatcc actcttctag acaatagcct ccaggggtat ccttgccgga     1620
tgagtctgtc aaagaccagg agaagaatgc tttcaaggac ctccttggaa gttgaatgtt     1680
tttacctctt gtaaggaagt gtaatgtgtt aacgtggtcg agtggacatt ggagaggcca     1740
actggtaggt tgtgccttca ttaagcacag tttgccattc aagcaagggt caggatattc     1800
tctatataaa tgatgcatgc cagtcttaaa cttcttagca taatttccat tgacaccagt     1860
cttggaggtg ttgacttgaa agatgaagcc ttctgtcttt gcacggttcc tacacagaaa     1920
tggtgggtct agatgccaat catgtcccac agcattcatg aaccactgag acaaccaaat     1980
ttgatcatca cttttggaac accagctcat atctgctgga tgttgtatta taacatcata     2040
ctgtggcaac aatactgcaa tatcatcaaa gctgatctga aatgaagcat tgccccccttt    2100 aatgtaaaga tggctcttgt ttaaggtaca caacaaaggt aggtcatgtg gattgttgga     2160
aaagagaccc accattgaga aggacacagt ctggaactca gtgtgcagtc cgattttgaa     2220
agcttcttct gtgcaggatc ttcctgcaag cgctaggaat acaaagaatt ggaataaacc     2280
acttttgtac aagttcacta tacccttaat gatggcaatg agactgactg caacaagagc     2340
aatgttcaga gcctcctgca aaaggttgg tatttcttgc atgaagctaa tgaactgccc      2400
catgccagaa gttctggtga ttttgatcta gaatagagtt gctcagtgaa agtgttagac     2460
```
actatgccta gggatccact gtgcg 2485

<210> SEQ ID NO 44
<211> LENGTH: 7115
<212> TYPE: DNA
<213> ORGANISM: Artificial Sequence
<220> FEATURE:
<223> OTHER INFORMATION: Nucleotide sequence of a tri-segmented r3JUNVart-based vector expressing the HPV16 E7E6 fusion protein: L segment

<400> SEQUENCE: 44

```
gcgcaccggg gatcctaggc gtaacttcat cattaaaatc tcagattctg ctctgagtgt    60
gacttactgc gaagaggcag acaaatgggc aactgcaacg gggcatccaa gtctaaccag   120
ccagactcct caagagccac acagccagcc gcagaattta ggagggtagc tcacagcagt   180
ctatatggta gatataactg taagtgctgc tggtttgctg ataccaattt gataacctgt   240
aatgatcact acctttgttt aaggtgccat cagggtatgt taaggaattc agatctctgc   300
aatatctgct ggaagcccct gcccaccaca atcacagtac cggtggagcc aacagcacca   360
ccaccatagg cagactgcac agggtcagac ccgaccccce ggggggcccc catggggacc   420
ccccgtgggg aaccccggg ggtgatgcgc cattagtcaa tgtctttgat ctcgactttg    480
tgcttcagtg gcctgcatgt caccccttc aatctgaact gcccttgggg atctgatatc   540
agcaggtcat ttaaagatct gctgaatgcc accttgaaat tgagaattc caaccagtca   600
ccaaatttat caagtgaacg gatcaactgc tctttgtgta gatcataaac gaggacaaag   660
tcctcttgct gaaataatat tgtttgtgat gttgttttta gataaggcca tagttggctt   720
aataaggttt ccacactatc aatgtcctct agtgctccaa ttgccttgac tatgacatcc   780
ccagacaact caactctata tgttacaac ctttcattac ctctgtaaaa gatccctct    840
ttcaagacaa gaggttctcc tgggttatct ggcccaatga ggtcatatgc atacttgtta   900
cttagttcag aataaaagtc accaaagttg aacttaacat ggctcagaat attgtcatca   960
tttgtcgcag cgtagcctgc atcaataaac aagccagcta ggtcaaagct ctcatggcct  1020
gtgaacaatg gtaggctagc gataaccagt gcaccatcca acaatgagtg gcttccctca  1080
gacccagaaa cacattgact cattgcatcc acattcagct ctaattcagg ggtaccgaca  1140
tcatccactc ctagtgaact gacaatggtg taactgtaca ccatctttct tctaagttta  1200
aattttgtcg aaactcgtgt gtgttctact tgaatgatca attttagttt cacagcttct  1260
tggcaagcaa cattgcgcaa cacagtgtgc aggtccatca tgtcttcctg aggcaacaag  1320
gagatgttgt caacagagac accctcaagg aaaaccttga tattatcaaa gctagaaact  1380
acataaccca ttgcaatgtc ttcaacaaac attgctcttg atactttatt attcctaact  1440
gacaaggtaa aatctgtgag ttcagctaga tctacttgac tgtcatcttc tagatctaga  1500
acttcattga accaaaagaa ggatttgaga cacgatgttg acatgactag tgggtttatc  1560
atcgaagata agacaacttg caccatgaag ttcctgcaaa cttgctgtgg gctgatgcca  1620
acttcccaat ttgtatactc tgactgtcta acatgggctg aagcgcaatc actctgtttc  1680
acaatataaa cattattatc tcttactttc aataagtgac ttataatccc taagttttca  1740
ttcatcatgt ctagagccac acagacatct agaaacttga gtcttccact atccaaagat  1800
ctgttcactt gaagatcatt cataaagggt gccaaatgtt cttcaaatag tttggggtaa  1860
tttcttcgta tagaatgcaa tacatggttc atgcctaatt ggtcttctat ctgtcgtact  1920
gctttgggtt taacagccca gaagaaattc ttattacata agaccagagg ggcctgtgga  1980
```

```
ctcttaatag cagaaaacac ccactcccct aactcacagg catttgtcag caccaaagag    2040
aagtaatccc acaaaattgg tttagaaaat tggttaactt ctttaagtga tttttgacag    2100
taaataactt taggctttct ctcacaaatt ccacaaagac atggcattat tcgagtaaat    2160
atgtccttta tatacagaaa tccgccttta ccatccctaa cacacttact ccccatactc    2220
ttacaaaacc caatgaagcc tgaggcaaca gaagactgaa atgcagattt gttgattgac    2280
tctgccaaga tcttcttcac gccttttgtg aaatttcttg acagcctgga ctgtattgtc    2340
cttatcaatg ttggcatctc ttcttttctct aacactcttc gacttgtcat gagtttggtc    2400
ctcaagacca acctcaagtc cccaaagctc gctaaattga cccatctgta gtctagagtt    2460
tgtctgattt catcttcact acacccggca tattgcagga atccggataa agcctcatcc    2520
cctcccctgc ttatcaagtt gataaggttt tcctcaaaga ttttgcctct cttaatgtca    2580 ttgaacacctt cctcgcgca gttccttata acattgtct ccttatcatc agaaaaaata    2640
gcttcaattt tcctctgtag acggtaccct ctagacccat caacccagtc tttgacatct    2700
tgttcttcaa tagctccaaa cggagtctct ctgtatccag agtatctaat caattggttg    2760
actctaatgg aaatctttga cactatatga gtgctaaccc cattagcaat acattgatca    2820
caaattgtgt ctatggtctc tgacagttgt gttggagttt tacacttaac gttgtgtaga    2880
gcagcagaca caaacttggt gagtaaagga gtctcttcac ccatgacaaa aaatcttgac    2940
ttaaactcag caacaaaagt tcctatcaca ctctttgggc tgataaactt gtttaattta    3000
gaagataaga attcatggaa gcacaccatt tccagcagtt ctgtcctgtc ttgaaacttt    3060
tcatcactaa ggcaaggaat ttttataagg ctaacctggt catcgctgga ggtataagtg    3120
acaggtatca catcatacaa taagtcaagt gcataacaca gaaattgttc agtaattagc    3180
ccatataaat ctgatgtgtt gtgcaagatt ccctggccca tgtccaagac agacattata    3240
tggctgggga cctggtccct tgactgcaga tactggtgaa aaaactcttc accaacacta    3300
gtacagtcac aacccattaa acctaaagat ctcttcaatt tccctacaca gtaggcttct    3360
gcaacattaa ttggaacttc aacgacctta tgaagatgcc atttgagaat gttcattact    3420
ggttcaagat tcacctttgt tctatctctg ggattcttca attctaatgt gtacaaaaaa    3480
gaaaggaaaa gtgctgggct catagttggt ccccatttgg agtggtcata tgaacaggac    3540
aagtcaccat tgttaacagc catttttcata tcacagattg cacgttcgaa ttccttttct    3600
gaattcaagc atgtgtattt cattgaacta cccacagctt ctgagaagtc ttcaactaac    3660
ctggtcatca gcttagtgtt gaggtctccc acatacagtt ctctatttga gccaacctgc    3720
tccttataac ttagtccaaa tttcaagttc cctgtatttg agctgatgct tgtgaactct    3780
gtaggagagt cgtctgaata gaaacataaa ttccgtaggg ctgcatttgt aaaataactt    3840
ttgtctagct tatcagcaat ggcttcagaa ttgctttccc tggtactaag ccgaacctca    3900
tcctttagtc tcagaacttc actggaaaag cccaatctag atctacttct atgctcataa    3960
ctacccaatt tctgatcata atgtccttga attaaaagat acttgaagca ttcaaagaat    4020
tcatcttctt ggtaggctat tgttgtcaaa tttttttaata acaaacccaa agggcagatg    4080
tcctgcggtg cttcaagaaa ataagtcaat ttaaatggaa atagataaac agcatcacat    4140
aactctttat acacatcaga cctgagcaca tctggatcaa aatccttcac ctcatgcatt    4200
gacacctctg ctttaatctc tctcaacact ccaaaagggg cccacaatga ctcaagagac    4260
tctcgctcat caacagatgg atttttttgat ttcaacttgg tgatctcaac ttttgtcccc    4320
```

-continued

```
tcactattag ccatcttggc tagtgtcatt tgtacgtcat ttctaatacc ctcaaaggcc    4380
cttacttgat cctctgttaa actctcatac atcactgata attcttcttg attggttctg    4440
gttcttgaac cggtgctcac aagacctgtt agattttta atattaagta gtccatggaa     4500
tcaggatcaa gattatacct gccttttgtt ttaaacctct cagccatagt agaaacgcat    4560
gttgaaacaa gtttctcctt atcataaaca gaaagaatat ttccaagttc gtcgagcttg    4620
gggattacca cacttttatt gcttgacaga tccagagctg tgctagtgat gttaggcctg    4680
tagggattgc ttttcagttc acctgtaact ttaagtcttc ctctattgaa gagagaaatg    4740
cagaaggaca aaatctcttt acacactcct ggaatttgag tatctgagga agtcttagcc    4800
tctttggaaa agaatctgtc caatcctctt atcatggtgt cctcttgttc cagtgttaga    4860
ctcccactta gagggggtt tacaacaaca caatcaaact tgactttggg ctcaataaac     4920
ttctcaaaac actttatttg atctgtcagg cgatcaggtg tctctttggt taccaagtga    4980
cacagataac taacatttaa tagatattta aaccttcttg caaagtaaag atctgcatct    5040
tccccttcac ccaaaattgt ctggaaaagt tccacagcca tcctctgaat cagcacctct    5100
gatccagaca tgcagtcgac ccttaacttt gacatcaaat ccacatgatg gatttgattt    5160
gcatatgcca tcaagaaata tcttagacct tgtaaaaatg tctggttcct tttggaaggg    5220
gaacagagta cagctaacac taacaatctt aatattggcc ttgtcattgt catgagttcg    5280
tggctaaaat ccaaccagct ggtcatttcc tcacacattt caattaacac atcctccgaa    5340
aatataggca ggaaaaatct ctttggatca cagtaaaaag agccttgttc ttccaatacc    5400
ccattgatgg atagatagat agaatagcac cttgacttct cacctgtttt ttggtaaaac    5460
aagagaccaa atgtattctt tgtcagatga aatctttgta cataacactc tcttagtcta    5520
acattcccaa aatatctaga atactctctt tcattgatta acaatcggga ggaaaatgat    5580
gtcttcatcg agttgaccaa tgcaagggaa atggaggaca aaatcctaaa taatttcttc    5640
tgctcacctt ccactaagct gctgaatggc tgatgtctac agattttctc aaattccttg    5700
ttaatagtat atctcatcac tggtctgtca gaaacaagtg cctgagctaa aatcatcaag    5760
ctatccatat cagggtgttt tattagtttt tccagctgtg accagagatc ttgatgagag    5820
ttcttcaatg ttctggaaca cgcttgaacc cacttggggc tggtcatcaa tttcttcctt    5880
attagtttaa tcgcctccag aatatctaga agtctgtcat tgactaacat taacatttgt    5940
ccaacaacta ttcccgcatt tcttaacctt acaattgcat catcatgcgt tttgaaaaga    6000
tcacaaagta aattgagtaa aactaagtcc agaaacagta aagtgtttct cctggtgttg    6060
aaaactttta gacctttcac tttgttacac acggaaaggg cttgaagata cacctctct    6120
acagcatcaa tagatataga attctcatct gactggcttt ccatgttgac ttcatctatt    6180
ggatgcaatg cgatagagta gactacatcc atcaacttgt ttgcacaaaa agggcagctg    6240
ggcacatcac tgtctttgtg gcttcctaat aagatcaagt catttataag cttagacttt    6300
tgtgaaaatt tgaatttccc caactgcttg tcaaaaatct ccttcttaaa ccaaaaccttt   6360
aactttatga gttcttctct tatgacagat tctctaatgt ctcctctaac cccaacaaag    6420
agggattcat ttaacctctc atcataaccc aaagaattc ttttcaagca ttcgatgttt     6480
tctaatccca agctctggtt ttttgtgttg acaaactat ggatcaatcg ctggtattct     6540
tgttcttcaa tattaatctc ttgcataaat tttgatttct ttaggatgtc gatcagcaac    6600
caccgaactc tttcaacaac ccaatcagca aggaatctat tgctgtagct agatctgcca    6660
tcaaccacag gaaccaacgt aatccctgcc cttagtaggt cggactttag gtttaagagc    6720
```

-continued

```
tttgacatgt cactcttcca ttttctctca aactcatcag gattgaccct aacaaaggtt   6780
tccaatagga tgagtgtttt ccctgtgagt ttgaagccat ccggaatgac ttttggaagg   6840
gtgggacata gtatgccata gtcagacagg atcacatcaa caaacttctg atctgaattg   6900
atctgacagg cgtgtgcctc acaggactca agctctacta aacttgacag aagtttgaac   6960
ccttccaaca acagagagct ggggtgatgt tgagataaaa agatgtccct ttggtatgct   7020
agctcctgtc tttctggaaa atgctttcta ataaggcttt ttatttcatt tactgattcc   7080
tccatgctca agtgccgcct aggatcctcg gtgcg                              7115
```